(12) United States Patent
Cheng et al.

(10) Patent No.: US 11,168,322 B2
(45) Date of Patent: *Nov. 9, 2021

(54) CRISPR RNA TARGETING ENZYMES AND SYSTEMS AND USES THEREOF

(71) Applicant: Arbor Biotechnologies, Inc., Cambridge, MA (US)

(72) Inventors: David R. Cheng, Boston, MA (US); David A. Scott, Cambridge, MA (US); Winston X. Yan, Brookline, MA (US); Shaorong Chong, Somerville, MA (US)

(73) Assignee: Arbor Biotechnologies, Inc., Cambridge, MA (US)

(*) Notice: Subject to any disclaimer, the term of this patent is extended or adjusted under 35 U.S.C. 154(b) by 529 days.

This patent is subject to a terminal disclaimer.

(21) Appl. No.: 15/916,274

(22) Filed: Mar. 8, 2018

(65) Prior Publication Data
US 2019/0002889 A1    Jan. 3, 2019

Related U.S. Application Data

(60) Provisional application No. 62/635,443, filed on Feb. 26, 2018, provisional application No. 62/628,921, filed on Feb. 9, 2018, provisional application No. 62/626,679, filed on Feb. 5, 2018, provisional application No. 62/619,691, filed on Jan. 19, 2018, provisional application No. 62/587,381, filed on Nov. 16, 2017, provisional application No. 62/580,880, filed on Nov. 2, 2017, provisional application No. 62/572,367, filed on Oct. 13, 2017, provisional application No. 62/527,957, filed on Jun. 30, 2017.

(51) Int. Cl.
| | | |
|---|---|---|
| C12N 15/11 | (2006.01) | |
| C12N 9/22 | (2006.01) | |
| C12N 15/62 | (2006.01) | |
| C12N 15/113 | (2010.01) | |
| C07K 14/195 | (2006.01) | |

(52) U.S. Cl.
CPC ............ *C12N 15/11* (2013.01); *C07K 14/195* (2013.01); *C12N 9/22* (2013.01); *C12N 15/111* (2013.01); *C12N 15/113* (2013.01); *C12N 15/62* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 10,392,616 | B2 | 8/2019 | Cheng et al. |
| 2018/0274017 | A1* | 9/2018 | Abudayyeh .......... C12Q 1/6895 |
| 2018/0298445 | A1 | 10/2018 | Abudayyeh et al. |
| 2018/0305689 | A1 | 10/2018 | Saetrom et al. |
| 2018/0362944 | A1 | 12/2018 | Hanewich-Hollatz et al. |
| 2019/0002875 | A1 | 1/2019 | Cheng et al. |
| 2019/0062724 | A1 | 2/2019 | Hsu et al. |

FOREIGN PATENT DOCUMENTS

| | | | | |
|---|---|---|---|---|
| WO | WO 2013/176772 | | 11/2013 | ............ C12N 15/11 |
| WO | WO 2016/161207 | | 10/2016 | ............... C12N 9/22 |
| WO | WO2016/205764 | | 12/2016 | |
| WO | WO 2017/070605 | | 4/2017 | ............... C12N 9/22 |
| WO | WO 2017/137768 | | 8/2017 | ............ C12N 15/90 |
| WO | WO 2018/035250 | | 2/2018 | ............ G06F 19/22 |
| WO | WO-2018/183403 | A1 | 10/2018 | |
| WO | WO-2019/006471 | A2 | 1/2019 | |

OTHER PUBLICATIONS

Omar O. Abudayyeh et al., "C2c2 is a single-component programmable RNA-guided RNA-targeting CRISPR effector," Science, pp. 1-17 (2016).
Anantharaman et al., "Comprehensive analysis of the HEPN superfamily: identification of novel roles in intra-genomic conflicts, defense, pathogenesis and RNA processing," Biology Direct, (8(1): 15, 28 pages (Jun. 2013).
Alexis C. Komor et al., "Programmable editing of a target base in genomic DNA without double-stranded DNA cleavage," Nature, 533(7603): 1-25 (2016).
Omar O. Abudayyeh et al., "RNA targeting with CRISPR-Cas13," Letter—Nature, pp. 1-20 (2017).
Jonathan S. Gootenberg et al., "Nucleic acid detection with CRISPR-Cas13a/C2c2," Science, pp. 1-9 (2017).
Aaron A. Smargon et al., "Cas13b Is a Type VI-B CRISPR-Associated RNA-Guided RNase Differentially Regulated by Accessory Proteins Csx27 and Csx28," Molecular Cell, 65:1-13 (2017).
Jonathan S. Gootenberg et al., "Multiplexed and portable nucleic acid detection platform with Cas13, Cas12a and Csm6," Science, pp. 1-10 (Feb. 15, 2018).
Alexandra East-Seletsky et al., "Two distinct RNase activities of CRISPR-C2c2 enable guide-RNA processing and RNA detection," Nature, vol. 538:270-286 (2016).
David B.T. Cox et al., "RNA editing with CRISPR-Cas13," Science, pp. 1-15 (2017).
Sergey Shmakov et al., "Diversity and evolution of class 2 CRISPR-Cas systems," Nature Reviews, Microbiology, vol. 15:169-182 (2017).
Patrick Hsu, "Mining novel CRISPR systems for new genome engineering tools," Cellular Technologies, 1 page (Feb. 5, 2018).
Hein et al., "Adaptation and modification of three CRISPR loci in two closely related cyanobacteria," RNA Biol. 10(5):852-864 (2013).
International Search Report and Written Opinion for International Application No. PCT/US2018/040649, dated Apr. 2, 2019 (22 pages).
Konermann et al., "Transcriptome engineering with RNA-targeting type VI-D CRISPR effectors," Cell 173(3):665-676.e14 (2018) (26 pages).

(Continued)

*Primary Examiner* — Channing S Mahatan
(74) *Attorney, Agent, or Firm* — Clark & Elbing LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of a nucleic acid.

21 Claims, 60 Drawing Sheets
(58 of 60 Drawing Sheet(s) Filed in Color)
Specification includes a Sequence Listing.

(56) References Cited

OTHER PUBLICATIONS

Sequence Alignment of SEQ ID No. 151 with SEQ ID No. 697272 of USPGPUB 20190048337, Search conducted on May 9, 2019 (1 page).
Shmakov et al. "Discovery and functional characterization of diverse class 2 CRISPR-Cas systems," Mol Cell. 60(3):385-397 (2015).
Yan et al. "Cas13d is a compact RNA-targeting type VI CRISPR effector positively modulated by a WYL domain-containing accessory protein," available in PMC Apr. 19, 2019, published in final edited form as: Mol Cell. 70(2):327-339.e5 (2018) (32 pages).
The International Search Report and Written Opinion of the International Searching Authority for International Application No. PCT/US2018/059089 dated Mar. 1, 2019
Gao et al., "CRISPR/Cas9-based Pten knock-out and Sleeping Beauty Transposon-mediated Nras knock-in induces hepatocellular carcinoma and hepatic lipid accumulation in mice", *Cancer Biology & Therapy*, vol. 18, No. 7, pp. 505-512 (May 17, 2017)
Nishirnasu et al, "Crystal Structure of Cas9 in Complex with Guide RNA and Target DNA", *Cell*, vol. 156. No. 5. page 935 (Feb. 13, 2014)
Nishirnasu et al, "Crystal Structure of *Staphylococcus aureus* Cas9", *cell*, vol. 162, No. 5, pp. 1113-1126 (Aug. 27, 2015)
Peters et al, "Recruitment of CRISPR-Cas systems by Tn7-like transposons", *Proceedings of the National Academy of Sciences of the United States of America*, vol. 114, No. 35, pp. E7358-E7366 (Aug. 15, 2017)
Xu et al., "piggyBac mediates efficient in Vivo CRISPR library screening for tumorigenesis in mice", *Proceedings of the National Academy of Sciences of the United States of America*, vol. 114, No. 4, pp. 722-727 (Jan. 24, 2017)

\* cited by examiner

SEQUENCE LISTING

```
<160> NUMBER OF SEQ ID NOS: 173

<210> SEQ ID NO 1
<211> LENGTH: 954
<212> TYPE: PRT
<213> ORGANISM: Eubacterium siraeum

<400> SEQUENCE: 1

Met Gly Lys Lys Ile His Ala Arg Asp Leu Arg Glu Gln Arg Lys Thr
1               5                   10                  15

Asp Arg Thr Glu Lys Phe Ala Asp Gln Asn Lys Lys Arg Glu Ala Glu
            20                  25                  30

Arg Ala Val Pro Lys Lys Asp Ala Ala Val Ser Val Lys Ser Val Ser
        35                  40                  45

Ser Val Ser Ser Lys Lys Asp Asn Val Thr Lys Ser Met Ala Lys Ala
    50                  55                  60

Ala Gly Val Lys Ser Val Phe Ala Val Gly Asn Thr Val Tyr Met Thr
65                  70                  75                  80

Ser Phe Gly Arg Gly Asn Asp Ala Val Leu Glu Gln Lys Ile Val Asp
                85                  90                  95

Thr Ser His Glu Pro Leu Asn Ile Asp Asp Pro Ala Tyr Gln Leu Asn
            100                 105                 110

Val Val Thr Met Asn Gly Tyr Ser Val Thr Gly His Arg Gly Glu Thr
        115                 120                 125

Val Ser Ala Val Thr Asp Asn Pro Leu Arg Arg Phe Asn Gly Arg Lys
    130                 135                 140

Lys Asp Glu Pro Glu Gln Ser Val Pro Thr Asp Met Leu Cys Leu Lys
145                 150                 155                 160

Pro Thr Leu Glu Lys Lys Phe Phe Gly Lys Glu Phe Asp Asp Asn Ile
                165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
        195                 200                 205

Glu Asn Ile Glu Asn Ser Asp Phe Phe Met Lys Arg Thr Thr Asp Glu
    210                 215                 220

Thr Phe Asp Asp Phe Glu Lys Lys Lys Glu Ser Thr Asn Ser Arg Glu
225                 230                 235                 240

Lys Ala Asp Phe Asp Ala Phe Glu Lys Phe Ile Gly Asn Tyr Arg Leu
                245                 250                 255

Ala Tyr Phe Ala Asp Ala Phe Tyr Val Asn Lys Lys Asn Pro Lys Gly
            260                 265                 270

Lys Ala Lys Asn Val Leu Arg Glu Asp Lys Glu Leu Tyr Ser Val Leu
```

```
                275                 280                 285
Thr Leu Ile Gly Lys Leu Arg His Trp Cys Val His Ser Glu Glu Gly
            290                 295                 300
Arg Ala Glu Phe Trp Leu Tyr Lys Leu Asp Glu Leu Lys Asp Asp Phe
305                 310                 315                 320
Lys Asn Val Leu Asp Val Val Tyr Asn Arg Pro Val Glu Glu Ile Asn
                325                 330                 335
Asn Arg Phe Ile Glu Asn Asn Lys Val Asn Ile Gln Ile Leu Gly Ser
            340                 345                 350
Val Tyr Lys Asn Thr Asp Ile Ala Glu Leu Val Arg Ser Tyr Tyr Glu
                355                 360                 365
Phe Leu Ile Thr Lys Lys Tyr Lys Asn Met Gly Phe Ser Ile Lys Lys
            370                 375                 380
Leu Arg Glu Ser Met Leu Glu Gly Lys Gly Tyr Ala Asp Lys Glu Tyr
385                 390                 395                 400
Asp Ser Val Arg Asn Lys Leu Tyr Gln Met Thr Asp Phe Ile Leu Tyr
                405                 410                 415
Thr Gly Tyr Ile Asn Glu Asp Ser Asp Arg Ala Asp Asp Leu Val Asn
            420                 425                 430
Thr Leu Arg Ser Ser Leu Lys Glu Asp Asp Lys Thr Thr Val Tyr Cys
                435                 440                 445
Lys Glu Ala Asp Tyr Leu Trp Lys Lys Tyr Arg Glu Ser Ile Arg Glu
450                 455                 460
Val Ala Asp Ala Leu Asp Gly Asp Asn Ile Lys Lys Leu Ser Lys Ser
465                 470                 475                 480
Asn Ile Glu Ile Gln Glu Asp Lys Leu Arg Lys Cys Phe Ile Ser Tyr
                485                 490                 495
Ala Asp Ser Val Ser Glu Phe Thr Lys Leu Ile Tyr Leu Leu Thr Arg
            500                 505                 510
Phe Leu Ser Gly Lys Glu Ile Asn Asp Leu Val Thr Thr Leu Ile Asn
            515                 520                 525
Lys Phe Asp Asn Ile Arg Ser Phe Leu Glu Ile Met Asp Glu Leu Gly
            530                 535                 540
Leu Asp Arg Thr Phe Thr Ala Glu Tyr Ser Phe Glu Gly Ser Thr
545                 550                 555                 560
Lys Tyr Leu Ala Glu Leu Val Glu Leu Asn Ser Phe Val Lys Ser Cys
                565                 570                 575
Ser Phe Asp Ile Asn Ala Lys Arg Thr Met Tyr Arg Asp Ala Leu Asp
            580                 585                 590
Ile Leu Gly Ile Glu Ser Asp Lys Thr Glu Glu Asp Ile Glu Lys Met
            595                 600                 605
Ile Asp Asn Ile Leu Gln Ile Asp Ala Asn Gly Asp Lys Lys Leu Lys
            610                 615                 620
Lys Asn Asn Gly Leu Arg Asn Phe Ile Ala Ser Asn Val Ile Asp Ser
625                 630                 635                 640
Asn Arg Phe Lys Tyr Leu Val Arg Tyr Gly Asn Pro Lys Lys Ile Arg
                645                 650                 655
Glu Thr Ala Lys Cys Lys Pro Ala Val Arg Phe Val Leu Asn Glu Ile
            660                 665                 670
Pro Asp Ala Gln Ile Glu Arg Tyr Tyr Glu Ala Cys Cys Pro Lys Asn
            675                 680                 685
Thr Ala Leu Cys Ser Ala Asn Lys Arg Arg Glu Lys Leu Ala Asp Met
            690                 695                 700
```

Ile Ala Glu Ile Lys Phe Glu Asn Phe Ser Asp Ala Gly Asn Tyr Gln
705                 710                 715                 720

Lys Ala Asn Val Thr Ser Arg Thr Ser Glu Ala Ile Lys Arg Lys
            725                 730                 735

Asn Gln Ala Ile Ile Arg Leu Tyr Leu Thr Val Met Tyr Ile Met Leu
            740                 745                 750

Lys Asn Leu Val Asn Val Asn Ala Arg Tyr Val Ile Ala Phe His Cys
            755                 760                 765

Val Glu Arg Asp Thr Lys Leu Tyr Ala Glu Ser Gly Leu Glu Val Gly
    770                 775                 780

Asn Ile Glu Lys Asn Lys Thr Asn Leu Thr Met Ala Val Met Gly Val
785                 790                 795                 800

Lys Leu Glu Asn Gly Ile Ile Lys Thr Glu Phe Asp Lys Ser Phe Ala
                805                 810                 815

Glu Asn Ala Ala Asn Arg Tyr Leu Arg Asn Ala Arg Trp Tyr Lys Leu
                820                 825                 830

Ile Leu Asp Asn Leu Lys Lys Ser Glu Arg Ala Val Val Asn Glu Phe
                835                 840                 845

Arg Asn Thr Val Cys His Leu Asn Ala Ile Arg Asn Ile Asn Ile Asn
850                 855                 860

Ile Lys Glu Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895

Arg Asp Thr Gly Asp Phe Ile Ser Lys Leu Glu His Lys Thr Tyr
                900                 905                 910

Cys Lys Asp Phe Val Lys Ala Tyr Cys Thr Pro Phe Gly Tyr Asn Leu
                915                 920                 925

Val Arg Tyr Lys Asn Leu Thr Ile Asp Gly Leu Phe Asp Lys Asn Tyr
    930                 935                 940

Pro Gly Lys Asp Asp Ser Asp Glu Gln Lys
945                 950

<210> SEQ ID NO 2
<211> LENGTH: 919
<212> TYPE: PRT
<213> ORGANISM: Ruminococcus sp.

<400> SEQUENCE: 2

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
            35                  40                  45

Glu Lys Lys Lys Ser Ser Val Ala Ala Gly Met Lys Ser Ile Leu
        50                  55                  60

Val Ser Lys Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Gln Thr Gln
                85                  90                  95

Leu Ser Ser Lys Gly Ser Ser Asn Ile Glu Leu Arg Gly Val Asn Glu
            100                 105                 110

Val Asn Ile Thr Phe Ser Ser Lys His Gly Phe Glu Ser Gly Val Glu

-continued

```
            115                 120                 125
Ile Asn Thr Ser Asn Pro Thr His Arg Ser Gly Glu Ser Ser Pro Val
            130                 135                 140
Arg Gly Asp Met Leu Gly Leu Lys Ser Glu Leu Glu Lys Arg Phe Phe
145                 150                 155                 160
Gly Lys Thr Phe Asp Asn Ile His Ile Gln Leu Ile Tyr Asn Ile
                    165                 170                 175
Leu Asp Ile Glu Lys Ile Leu Ala Val Tyr Val Thr Asn Ile Val Tyr
                180                 185                 190
Ala Leu Asn Asn Met Leu Ser Ile Lys Asp Ser Glu Ser Tyr Asp Asp
            195                 200                 205
Phe Met Gly Tyr Leu Ser Ala Arg Asn Thr Tyr Glu Val Phe Thr His
    210                 215                 220
Pro Asp Lys Ser Asn Leu Ser Asp Lys Ala Lys Gly Asn Ile Lys Lys
225                 230                 235                 240
Ser Phe Ser Thr Phe Asn Asp Leu Leu Lys Thr Lys Arg Leu Gly Tyr
                    245                 250                 255
Phe Gly Leu Glu Glu Pro Lys Thr Lys Asp Thr Arg Val Ser Gln Ala
                260                 265                 270
Tyr Lys Lys Arg Val Tyr His Met Leu Ala Ile Val Gly Gln Ile Arg
            275                 280                 285
Gln Ser Val Phe His Asp Lys Ser Ser Lys Leu Asp Glu Asp Leu Tyr
    290                 295                 300
Ser Phe Ile Asp Ile Ile Asp Ser Glu Tyr Arg Glu Thr Leu Asp Tyr
305                 310                 315                 320
Leu Val Asp Glu Arg Phe Asp Ser Ile Asn Lys Gly Phe Ile Gln Gly
                    325                 330                 335
Asn Lys Val Asn Ile Ser Leu Leu Ile Asp Met Met Lys Gly Tyr Glu
                340                 345                 350
Ala Asp Asp Ile Ile Arg Leu Tyr Tyr Asp Phe Ile Val Leu Lys Ser
            355                 360                 365
Gln Lys Asn Leu Gly Phe Ser Ile Lys Lys Leu Arg Glu Lys Met Leu
    370                 375                 380
Asp Glu Tyr Gly Phe Arg Phe Lys Asp Lys Gln Tyr Asp Ser Val Arg
385                 390                 395                 400
Ser Lys Met Tyr Lys Leu Met Asp Phe Leu Leu Phe Cys Asn Tyr Tyr
                    405                 410                 415
Arg Asn Asp Val Val Ala Gly Glu Ala Leu Val Arg Lys Leu Arg Phe
                420                 425                 430
Ser Met Thr Asp Asp Glu Lys Glu Gly Ile Tyr Ala Asp Glu Ala Ser
            435                 440                 445
Lys Leu Trp Gly Lys Phe Arg Asn Asp Phe Glu Asn Ile Ala Asp His
    450                 455                 460
Met Asn Gly Asp Val Ile Lys Glu Leu Gly Lys Ala Asp Met Asp Phe
465                 470                 475                 480
Asp Glu Lys Ile Leu Asp Ser Glu Lys Lys Asn Ala Ser Asp Leu Leu
                    485                 490                 495
Tyr Phe Ser Lys Met Ile Tyr Met Leu Thr Tyr Phe Leu Asp Gly Lys
                500                 505                 510
Glu Ile Asn Asp Leu Leu Thr Thr Leu Ile Ser Lys Phe Asp Asn Ile
            515                 520                 525
Lys Glu Phe Leu Lys Ile Met Lys Ser Ser Ala Val Asp Val Glu Cys
    530                 535                 540
```

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
            565                 570                 575

Ser Ser Ala Lys Leu Thr Met Phe Arg Asp Ala Leu Thr Ile Leu Gly
        580                 585                 590

Ile Asp Asp Asn Ile Thr Asp Asp Arg Ile Ser Glu Ile Leu Lys Leu
        595                 600                 605

Lys Glu Lys Gly Lys Gly Ile His Gly Leu Arg Asn Phe Ile Thr Asn
610                 615                 620

Asn Val Ile Glu Ser Ser Arg Phe Val Tyr Leu Ile Lys Tyr Ala Asn
625                 630                 635                 640

Ala Gln Lys Ile Arg Lys Val Ala Lys Asn Glu Lys Val Val Met Phe
            645                 650                 655

Val Leu Gly Gly Ile Pro Asp Thr Gln Ile Glu Arg Tyr Tyr Lys Ser
        660                 665                 670

Cys Val Glu Phe Pro Asp Met Asn Ser Ser Leu Glu Val Lys Arg Ser
        675                 680                 685

Glu Leu Ala Arg Met Ile Lys Asn Ile Ser Phe Asp Asp Phe Lys Asn
690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
            725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
        770                 775                 780

Leu Cys Asp Lys Ser Pro Asn Leu Phe Leu Lys Asn Glu Arg Leu
785                 790                 795                 800

Arg Lys Cys Val Glu Val Asp Ile Asn Asn Ala Asp Ser Ser Met Thr
            805                 810                 815

Arg Lys Tyr Arg Asn Cys Ile Ala His Leu Thr Val Val Arg Glu Leu
            820                 825                 830

Lys Glu Tyr Ile Gly Asp Ile Arg Thr Val Asp Ser Tyr Phe Ser Ile
        835                 840                 845

Tyr His Tyr Val Met Gln Arg Cys Ile Thr Lys Arg Glu Asn Asp Thr
850                 855                 860

Lys Gln Glu Glu Lys Ile Lys Tyr Glu Asp Asp Leu Leu Lys Asn His
865                 870                 875                 880

Gly Tyr Thr Lys Asp Phe Val Lys Ala Leu Asn Ser Pro Phe Gly Tyr
            885                 890                 895

Asn Ile Pro Arg Phe Lys Asn Leu Ser Ile Glu Gln Leu Phe Asp Arg
        900                 905                 910

Asn Glu Tyr Leu Thr Glu Lys
        915

<210> SEQ ID NO 3
<211> LENGTH: 981
<212> TYPE: PRT
<213> ORGANISM: Unknown
<220> FEATURE:

<223> OTHER INFORMATION: Description of Unknown:
    Animal-digestive system-orangutan individual fecal sequence

<400> SEQUENCE: 3

Met Gly Lys Lys Ile His Ala Arg Asp Leu Arg Glu Gln Arg Lys Asn
1               5                   10                  15

Asp Arg Thr Thr Lys Phe Ala Glu Gln Asn Lys Lys Arg Glu Ala Gln
            20                  25                  30

Met Ala Val Gln Lys Lys Asp Ala Ala Val Ser Ala Lys Ser Val Ser
        35                  40                  45

Ser Val Ser Ser Lys Lys Gly Asn Val Thr Lys Ser Met Ala Lys Ala
    50                  55                  60

Ala Gly Val Lys Ser Val Phe Ala Val Gly Lys Asn Thr Val Tyr Met
65                  70                  75                  80

Thr Ser Phe Gly Arg Gly Asn Asp Ala Val Leu Glu Gln Lys Ile Val
                85                  90                  95

Asp Thr Ser His Glu Pro Leu Asn Ile Asp Asp Pro Ala Tyr Gln Leu
            100                 105                 110

Asn Val Val Thr Met Asn Gly Tyr Ser Val Thr Gly His Arg Gly Glu
        115                 120                 125

Thr Val Ser Ala Ile Thr Asp Asn Pro Leu Arg Arg Phe Asn Gly Gly
    130                 135                 140

Lys Lys Asp Lys Pro Glu Gln Ser Val Pro Ala Asp Met Leu Cys Leu
145                 150                 155                 160

Lys Pro Thr Leu Glu Lys Lys Phe Phe Gly Lys Glu Phe Asp Asp Asn
                165                 170                 175

Ile His Ile Gln Leu Ile Tyr Asn Ile Leu Asp Ile Glu Lys Ile Leu
            180                 185                 190

Ala Val Tyr Ser Thr Asn Ala Val Tyr Ala Leu Asn Asn Thr Ile Ala
        195                 200                 205

Asp Glu Asn Asn Glu Asn Trp Asp Leu Phe Ala Asn Phe Ser Thr Asp
    210                 215                 220

Asn Thr Tyr Gly Glu Leu Ile Asn Ala Ala Thr Tyr Lys Glu Ser Thr
225                 230                 235                 240

Asp Asp Val Ser Thr Asp Glu Lys Arg Arg Glu Ala Glu Lys Lys
                245                 250                 255

Lys Arg Glu Ala Lys Ile Ala Gly Lys Ile Leu Ala Asp Tyr Glu Lys
            260                 265                 270

Phe Arg Lys Asn Asn Arg Leu Ala Tyr Phe Ala Asp Ala Phe Tyr Ile
        275                 280                 285

Glu Lys Asn Lys Ser Lys Ser Lys Ser Gln Asn Lys Ala Glu Gly Ile
    290                 295                 300

Lys Arg Gly Lys Lys Glu Ile Tyr Ser Ile Leu Ala Leu Ile Ala Lys
305                 310                 315                 320

Leu Arg His Trp Cys Val His Ser Glu Asp Gly Arg Ala Glu Phe Trp
                325                 330                 335

Leu Tyr Lys Leu Asp Glu Leu Glu Asp Asp Phe Lys Asn Val Leu Asp
            340                 345                 350

Val Val Tyr Asn Arg Pro Val Glu Glu Ile Asn Asp Asp Phe Val Glu
        355                 360                 365

Arg Asn Lys Val Asn Ile Gln Ile Leu His Ser Lys Cys Glu Asn Ser
    370                 375                 380

Asp Ile Ala Glu Leu Thr Arg Ser Tyr Tyr Glu Phe Leu Ile Thr Lys
385                 390                 395                 400

-continued

Lys Tyr Lys Asn Met Gly Phe Ser Ile Lys Lys Leu Arg Glu Ile Ile
                405             410             415

Leu Glu Gly Thr Glu Tyr Asn Asp Asn Lys Tyr Asp Thr Val Arg Asn
            420             425             430

Lys Leu Tyr Gln Met Val Asp Phe Ile Leu Tyr Arg Gly Tyr Ile Asn
        435             440             445

Glu Asn Ser Glu Arg Ala Glu Ala Leu Val Asn Ala Leu Arg Ser Thr
    450             455             460

Leu Asn Glu Asp Asp Lys Thr Lys Leu Tyr Ser Ser Glu Ala Ala Phe
465             470             475             480

Leu Lys Arg Lys Tyr Met Lys Ile Ile Arg Glu Val Thr Asp Ser Leu
            485             490             495

Asp Val Lys Lys Leu Lys Glu Leu Lys Lys Asn Ala Phe Thr Ile Pro
        500             505             510

Asp Asn Glu Leu Arg Lys Cys Phe Ile Ser Tyr Ala Asp Ser Val Ser
    515             520             525

Glu Phe Thr Lys Leu Ile Tyr Leu Leu Thr Arg Phe Leu Ser Gly Lys
    530             535             540

Glu Ile Asn Asp Leu Val Thr Thr Leu Ile Asn Lys Phe Asp Asn Ile
545             550             555             560

Arg Ser Phe Leu Glu Ile Met Asp Glu Leu Gly Leu Glu Arg Thr Phe
            565             570             575

Thr Asp Glu Tyr Ser Phe Phe Glu Gly Ser Thr Lys Tyr Leu Ala Glu
            580             585             590

Leu Ile Glu Leu Asn Ser Phe Val Lys Ser Cys Ser Phe Asp Met Ser
        595             600             605

Ala Lys Arg Pro Met Tyr Arg Asp Ala Leu Asp Ile Leu Gly Ile Glu
    610             615             620

Ser Asp Lys Ser Glu Asp Asp Ile Lys Arg Met Ile Asp Asn Ile Leu
625             630             635             640

Gln Val Asp Ala Asn Gly Lys Lys Leu Pro Asn Lys Asn His Gly Leu
            645             650             655

Arg Asn Phe Ile Ala Ser Asn Val Val Glu Ser Asn Arg Phe Glu Tyr
            660             665             670

Leu Val Arg Tyr Gly Asn Pro Lys Lys Ile Arg Glu Thr Ala Lys Cys
        675             680             685

Lys Pro Ala Val Arg Phe Val Leu Asn Glu Ile Pro Asp Ala Gln Ile
    690             695             700

Glu Arg Tyr Tyr Lys Ala Tyr Tyr Leu Asp Glu Lys Ser Leu Cys Leu
705             710             715             720

Ala Asn Met Gln Arg Asp Lys Leu Ala Gly Val Ile Ala Asp Ile Lys
            725             730             735

Phe Asp Asp Phe Ser Asp Ala Gly Ser Tyr Gln Lys Ala Asn Ala Thr
        740             745             750

Ser Thr Lys Ile Thr Ser Glu Ala Glu Ile Lys Arg Lys Asn Gln Ala
    755             760             765

Ile Ile Arg Leu Tyr Leu Thr Val Met Tyr Ile Met Leu Lys Asn Leu
    770             775             780

Val Asn Val Asn Ala Arg Tyr Val Ile Ala Phe His Cys Leu Glu Arg
785             790             795             800

Asp Thr Lys Leu Tyr Ala Glu Ser Gly Leu Glu Val Gly Asn Ile Glu
            805             810             815

```
Lys Asn Lys Thr Asn Leu Thr Met Ala Val Met Gly Val Lys Leu Glu
            820                 825                 830

Asn Gly Ile Ile Lys Thr Glu Phe Asp Lys Ser Leu Ala Glu Asn Ala
        835                 840                 845

Ala Asn Arg Tyr Leu Arg Asn Ala Arg Trp Tyr Lys Leu Ile Leu Asp
850                 855                 860

Asn Leu Lys Met Ser Glu Arg Ala Val Val Asn Glu Phe Arg Asn Thr
865                 870                 875                 880

Val Cys His Leu Asn Ala Ile Arg Asn Ile Asn Ile Asn Ile Asp Gly
                885                 890                 895

Ile Lys Glu Val Glu Asn Tyr Phe Ala Leu Tyr His Tyr Leu Ile Gln
            900                 905                 910

Lys His Leu Glu Asn Arg Phe Ala Asp Asn Gly Gly Ser Thr Gly Asp
            915                 920                 925

Tyr Ile Gly Lys Leu Glu Glu His Lys Thr Tyr Cys Lys Asp Phe Val
        930                 935                 940

Lys Ala Tyr Cys Thr Pro Phe Gly Tyr Asn Leu Val Arg Tyr Lys Asn
945                 950                 955                 960

Leu Thr Ile Asp Gly Leu Phe Asp Lys Asn Tyr Pro Gly Lys Asp Asp
                965                 970                 975

Ser Asp Lys Gln Lys
            980

<210> SEQ ID NO 4
<211> LENGTH: 1054
<212> TYPE: PRT
<213> ORGANISM: Unknown
<220> FEATURE:
<223> OTHER INFORMATION: Description of Unknown:
      Arthropoda-digestive system-cubitermes and nasutitermes
      termite gut sequence

<400> SEQUENCE: 4

Met Ser Gln Ser Thr Lys Thr Lys Ala Lys Arg Met Gly Val Lys Ser
1               5                   10                  15

Val Leu Ala His Gly Lys Asp Glu Lys Gly His Ile Lys Leu Ala Ile
            20                  25                  30

Thr Ala Phe Gly Lys Gly Asn Lys Ala Glu Leu Ala Ile Gln Thr Asp
        35                  40                  45

Glu Lys Gly Ser Asn Leu Ala Lys Thr Tyr Lys Glu Arg Asn Ile Thr
    50                  55                  60

Ala Asn Lys Ile Val Ser Glu Gly Ile Gln Thr Ser Gly Thr Ile Ala
65                  70                  75                  80

Gly Glu Gly His Ala Thr Phe Leu Asn Asn Pro Ala Glu His Val Gly
                85                  90                  95

Thr Asp Tyr Leu Lys Leu Lys Glu Thr Leu Glu Met Glu Phe Phe Gly
            100                 105                 110

Lys Ser Phe Pro Gly Asp Ser Val Arg Ile Gln Ile His Gln Ile
            115                 120                 125

Leu Asp Ile Gln Lys Leu Leu Gly Ile Tyr Ile Thr Asp Ile Ile Tyr
            130                 135                 140

Cys Ile Asn Asn Leu Arg Asp Glu Thr His Leu Asp His Glu Ser Asp
145                 150                 155                 160

Ile Val Gly Leu Ser Met Ser Asn Thr Asn Val Asn Leu Ala Leu Asn
                165                 170                 175

Gln Met Arg Pro Tyr Phe Gly Phe Phe Gly Glu Ala Phe Arg Pro Val
```

```
                180                 185                 190
Gly Asp Asp Lys Val Lys Glu Ile Thr Leu Ser Asp Glu Val Arg Lys
            195                 200                 205
Asn Ile Glu Lys Ile Ile Ala Leu Glu Glu Gln Lys Arg Asn Pro Ser
            210                 215                 220
Thr Pro Arg Phe Lys Gln Glu Asn Ile Asn Leu Glu Ile Glu Asn Ala
225                 230                 235                 240
Met Gly Lys Phe Lys Ser Lys Asp Ala Phe Glu Thr Ala Lys Lys Lys
                245                 250                 255
Tyr Asn Arg Ile Val Ala Asp Glu Thr Asn Ala Lys Thr Leu Arg Ile
            260                 265                 270
Leu Gly Ala Met Arg Gln Ile Thr Ala His Phe Lys Asp Gln Ala Thr
            275                 280                 285
Leu Phe Met Ser Asp Val Glu Leu Pro Lys Ile Leu Lys Lys Glu Phe
            290                 295                 300
Ser Lys Ala Asp Trp Gln Thr Val Glu Asp Tyr Tyr Ala Lys Leu Val
305                 310                 315                 320
Asp Arg Ile Asn Glu Gly Phe Cys Lys Asn Ala Ala Thr Asn Val His
                325                 330                 335
Phe Leu Thr Glu Leu Leu Pro Glu Glu Ser Lys Lys Gln Leu Thr Glu
            340                 345                 350
Asp Tyr Phe Arg Phe Ala Ile Leu Lys Glu Gly Lys Asn Leu Gly Val
            355                 360                 365
Asn Met Lys Arg Leu Arg Glu Val Met Phe Ala Leu Phe Val Pro Glu
            370                 375                 380
Leu Thr Ala Pro Glu Thr Lys Lys Arg Tyr Asp Ser Tyr Arg Ala Lys
385                 390                 395                 400
Ile Tyr Gly Leu Thr Asp Phe Leu Leu Phe Lys His Ile His Asn Thr
                405                 410                 415
Lys Gln Leu Glu Glu Trp Val Ala Val Leu Arg Glu Thr Ser Asn Glu
            420                 425                 430
Asp Ala Lys Glu Asn Leu Tyr Asp Glu Phe Ala Arg Thr Ala Trp Asn
            435                 440                 445
Thr Val Gly Asp Ser Ala Lys Gln Leu Ile Glu Asn Met Gln Ser Tyr
            450                 455                 460
Phe Thr Lys Lys Glu Lys Glu Ile Thr Lys Thr Ala Gln Pro Val Leu
465                 470                 475                 480
Ser Thr Ser Ser Ile Ala His Thr Ser Lys Lys Ile Thr Gln Phe Ser
                485                 490                 495
Ser Phe Ala Lys Leu Leu Ala Phe Leu Cys Asn Phe Trp Glu Gly Lys
            500                 505                 510
Glu Ile Asn Glu Leu Leu Ser Ala Tyr Ile His Lys Phe Glu Asn Ile
            515                 520                 525
Gln Glu Phe Ile Asn Leu Leu Glu Lys Leu Gly Lys Lys Pro Gln
            530                 535                 540
Phe Thr Glu Asn Tyr Ala Leu Phe Asn Glu Ala Ala Gly Gln Arg Ala
545                 550                 555                 560
Gly Glu Ile Ala Gln Asn Leu Arg Ile Leu Ala Ser Ile Gly Lys Met
                565                 570                 575
Lys Pro Asp Leu Gly Asp Ala Lys Arg Gln Leu Tyr Lys Ala Ala Ile
            580                 585                 590
Glu Met Leu Gly Ile Asp Thr Glu Glu Tyr Ile Ser Asp Glu Trp Leu
            595                 600                 605
```

```
Glu Pro Asn Met Leu Ala Gln Pro Pro Lys Pro Lys Lys Asp
    610                 615                 620

Asn Glu Lys Tyr Arg Lys Glu Pro His Lys Tyr Ser Tyr Glu Lys Asp
625                 630                 635                 640

Met Glu Thr Tyr Arg Lys Lys Leu Arg Glu Tyr Glu Thr Trp Arg
                    645                 650                 655

Ser Leu Ile Asp Tyr Glu Tyr Leu Met Pro Glu Thr Asn Pro Phe Arg
                    660                 665                 670

Asn Phe Val Ala Lys Gln Val Ile Glu Ser Arg Arg Phe Met Tyr Leu
        675                 680                 685

Val Arg Tyr Thr Lys Pro Lys Thr Val Arg Ala Leu Met Ser Asn Arg
    690                 695                 700

Ala Ile Val His Tyr Val Leu Ser Arg Ile Ala Asp Ile Gln Asp His
705                 710                 715                 720

His Met Thr Glu Ser Gln Ile Asp Arg Tyr Tyr Gln Asn Leu Pro Gln
                    725                 730                 735

Tyr Asn Glu Gln Gln His Lys Asn Val Ser Leu Glu Thr Lys Ile Asp
                740                 745                 750

Ala Leu Ala Asp Tyr Leu Cys Lys Tyr Thr Phe Glu Lys Asn Val Leu
                755                 760                 765

Lys Gln Lys Asn Gly Ile Val Leu Asn Thr Lys Ser Ala Thr Lys Asn
770                 775                 780

Val Glu Ile Glu His Leu Lys Ala Leu Thr Gly Leu Tyr Leu Thr Val
785                 790                 795                 800

Ala Tyr Ile Ala Val Lys Asn Leu Val Lys Ala Asn Ala Arg Tyr Tyr
                805                 810                 815

Ile Ala Phe Ser Ile Phe Glu Arg Asp Tyr Ala Leu Phe Glu Lys Lys
                820                 825                 830

Leu Gly Lys Asp Thr Leu Glu Lys Tyr Val Lys Pro Phe Lys Tyr Ile
        835                 840                 845

Asp Lys Gly Glu Glu Lys Glu Gly Lys Asn Asn Phe Phe Ala Leu Thr
        850                 855                 860

Glu Tyr Leu Leu Asp Lys Asp Asn Ser Leu Arg Tyr Gln Trp Asn Asn
865                 870                 875                 880

Asp Leu Ser Asp Glu Glu Asn Lys Gln Ala Leu Arg Lys His Leu Asp
                885                 890                 895

Lys Lys Glu Ile Arg Ser Gln Arg His Phe Ser Gln Tyr Trp Leu Asp
                900                 905                 910

Ile Phe Ala Arg Gln Ile Glu Asn Ala Lys Lys Thr Ser Glu Ser Gly
        915                 920                 925

Tyr Leu Leu Thr Ala Ala Arg Asn Cys Ala Leu His Leu Asn Val Leu
930                 935                 940

Thr Ala Leu Pro Glu Phe Val Gly Glu Phe Arg Lys Thr Gly Asp Lys
945                 950                 955                 960

Met Thr Ser Tyr Phe Glu Leu Tyr His Phe Leu Leu Gln Lys Leu Met
                965                 970                 975

Leu Ala Glu Ala Gly Leu Asn Leu Asp Glu Tyr Arg Glu Arg Ile Asp
                980                 985                 990

Thr Tyr Gln Thr Ala Cys Lys Asp Leu Ile Asn Ile Thr Tyr Val Ser
        995                 1000                1005

Leu Gly Tyr Asn Leu Pro Arg Tyr Lys Asn Leu Thr Cys Glu Pro
    1010                1015                1020
```

-continued

```
Leu Phe Asp Glu Glu Ser Ala Thr Gly Lys Glu Arg Gln Thr Arg
    1025                1030                1035

Leu Asp Glu Lys Ser Lys Glu Lys Lys Gln Arg Lys Gly Gly Gln
    1040                1045                1050

Lys

<210> SEQ ID NO 5
<211> LENGTH: 1006
<212> TYPE: PRT
<213> ORGANISM: Eubacterium sp.

<400> SEQUENCE: 5

Met Ser Lys Lys Gln Arg Pro Lys Asp Ile Arg Lys Arg Gln Glu Glu
1               5                   10                  15

Glu Lys Arg Glu Lys Tyr Lys Lys Gln Glu Glu Leu Arg Lys Lys Gln
            20                  25                  30

Glu Glu Leu Arg Lys Glu Gln Glu Gln Arg Arg Glu Asp Gln Lys Glu
        35                  40                  45

Leu Glu Lys Ile Lys Lys Glu Val Gly Glu Gly Glu Lys Lys Lys
    50                  55                  60

Ser Arg Ala Lys Ala Leu Gly Leu Lys Ser Thr Phe Ile Leu Asp Arg
65                  70                  75                  80

Asp Glu Gln Lys Val Leu Met Thr Ser Phe Gly Gln Gly Asn Lys Ala
                85                  90                  95

Val Arg Asp Lys Tyr Ile Ile Gly Asp Lys Val Ser Asp Ile Asn Asp
            100                 105                 110

Asp Arg Lys Asn Lys Lys Ala Ala Leu Leu Val Glu Val Cys Gly Lys
        115                 120                 125

Ser Phe Asn Ile Ser Lys Lys Glu Asn Asp Asp Cys Asp Pro Val Lys
    130                 135                 140

Val Asn Asn Pro Val Val Ser Arg Asn Lys Lys Asp Asp Leu Ile
145                 150                 155                 160

His Cys Arg Lys Lys Leu Glu Glu Leu Tyr Phe Gly Glu Gln Phe Lys
                165                 170                 175

Asp Asn Ile His Ile Gln Leu Ile Tyr Asn Ile Leu Asp Ile Glu Lys
            180                 185                 190

Ile Leu Ala Val Gln Val Asn Asn Ile Val Phe Ala Leu Asn Asn Leu
        195                 200                 205

Leu Ser Trp Ser Gly Glu Glu Lys Phe Asp Leu Ile Gly Tyr Leu Gly
    210                 215                 220

Val Asn Asp Thr Tyr Glu Lys Phe Arg Asp Ala Lys Gly Lys Arg Lys
225                 230                 235                 240

Gly Leu Tyr Glu Lys Phe Ser Thr Leu Ile Glu Lys Lys Arg Met Arg
                245                 250                 255

Tyr Phe Gly Ser Thr Phe Tyr Pro Leu Asn Glu Lys Gly Glu Glu Ile
            260                 265                 270

Thr Ser Asn Asp Lys Lys Glu Trp Glu Gln Phe Glu Lys Lys Cys Tyr
        275                 280                 285

His Leu Leu Ala Val Leu Gly Met Met Arg Gln Ala Thr Ala His Gly
    290                 295                 300

Asp Ser Lys Arg Arg Ala Glu Ile Tyr Lys Leu Gly Lys Glu Phe Asp
305                 310                 315                 320

Lys Ser Glu Ala Arg Gly Cys Arg Gln Glu Ala Arg Lys Glu Leu Asp
                325                 330                 335
```

```
Asp Leu Tyr Arg Lys Lys Ile His Glu Met Asn Gln Ser Phe Leu Lys
            340                 345                 350

Asn Ser Lys Arg Asp Ile Leu Met Leu Phe Arg Ile Tyr Asp Ala Glu
        355                 360                 365

Ser Lys Glu Ala Lys Arg Lys Leu Ala Gln Glu Tyr Tyr Glu Phe Ile
    370                 375                 380

Met Leu Lys Ser Tyr Lys Asn Thr Gly Phe Ser Ile Lys His Leu Arg
385                 390                 395                 400

Glu Thr Val Ile Asp Lys Met Asp Glu Asp Ile Lys Glu Lys Ile Lys
                405                 410                 415

Asp Asp Lys Tyr Asn Pro Ile Arg Arg Lys Leu Tyr Arg Ile Met Asp
            420                 425                 430

Phe Val Ile Tyr Gln Tyr Tyr Gln Glu Ser Glu Gln Gln Glu Glu Ala
        435                 440                 445

Met Glu Leu Val Arg Lys Leu Arg Asn Ala Glu Thr Lys Val Glu Lys
    450                 455                 460

Glu Leu Thr Tyr Arg Lys Glu Ala Glu Lys Leu Lys Glu Glu Leu Glu
465                 470                 475                 480

Lys Ile Ile Arg Asn Ser Ile Leu Ser Val Cys Asp Arg Ile Leu Ala
                485                 490                 495

Glu Met Asn Glu Lys Arg His Lys Lys Val Asn Gln Glu Ser Ser Asp
            500                 505                 510

Thr Asp Ser Glu Glu Pro Leu Asp Pro Glu Ile Ser Glu Gly Ile Thr
        515                 520                 525

Phe Ile Lys Glu Thr Ala His Ser Phe Ser Glu Met Ile Tyr Leu Leu
    530                 535                 540

Thr Val Phe Leu Asp Gly Lys Glu Ile Asn Ile Leu Leu Thr Gln Leu
545                 550                 555                 560

Ile His Cys Phe Asp Asn Ile Ser Ser Phe Met Asp Thr Met Lys Glu
                565                 570                 575

Glu Asn Leu Leu Thr Lys Leu Lys Glu Asp Tyr Glu Ile Phe Glu Glu
            580                 585                 590

Ser Lys Glu Ile Ser Lys Glu Leu Arg Ile Ile Asn Ser Phe Ala Arg
        595                 600                 605

Met Thr Glu Pro Val Pro Lys Thr Glu Lys Thr Met Phe Ile Asp Ala
    610                 615                 620

Ala Gln Ile Leu Gly Tyr Ser Asn Asp Glu Lys Leu Glu Gly Tyr
625                 630                 635                 640

Val Asp Ala Leu Leu Asp Thr Lys Asn Lys Thr Lys Asp Lys Glu Arg
                645                 650                 655

Lys Gly Phe Glu Lys Tyr Ile Trp Asn Asn Val Ile Lys Ser Thr Arg
            660                 665                 670

Phe Arg Tyr Leu Val Arg Tyr Ala Asp Pro Lys Lys Val Arg Ala Phe
        675                 680                 685

Ala Ala Asn Lys Lys Val Val Ala Phe Val Leu Lys Asp Ile Pro Asp
    690                 695                 700

Glu Gln Ile Lys Ala Tyr Tyr Asn Ser Cys Phe Ser Gln Asn Ser Asp
705                 710                 715                 720

Ser Ser Ser Asn Met Ser Ile Ala Phe Gln Asp Gly Asp Ser Asn Lys
                725                 730                 735

Lys Gly Thr Ser Val His Asp Met Met Arg Lys Ala Leu Thr Glu Lys
            740                 745                 750

Ile Thr Gly Leu Asn Phe Gly Asp Phe Glu Glu Glu Ser Lys Lys Gly
```

```
            755                 760                 765
Ile Arg Arg Glu Glu Ser Asp Lys Asn Ile Ile Arg Leu Tyr Leu Thr
    770                 775                 780

Val Leu Tyr Leu Val Gln Lys Asn Leu Ile Tyr Val Asn Ser Arg Tyr
785                 790                 795                 800

Phe Leu Ala Phe His Cys Ala Glu Arg Asp Glu Val Leu Tyr Asn Gly
                805                 810                 815

Glu Thr Ile Asp Asn Asn Lys Glu Lys Gly Ser Glu Lys Asp Trp Lys
                820                 825                 830

Lys Phe Ala Lys Glu Phe Ile Ile Glu His Pro Pro Lys Lys Lys Val
                835                 840                 845

Lys Asp Tyr Leu Ala Lys Asn Phe Glu Tyr Ser Asn Lys Trp Ser Leu
    850                 855                 860

Arg Val Phe Arg Asn Ser Val Gln His Leu Asn Val Ile Arg Asp Ala
865                 870                 875                 880

Tyr Lys Tyr Ile Lys Cys Ile Asp Asp Asn Lys Asp Val Gln Ser Tyr
                885                 890                 895

Phe Ala Leu Tyr His Tyr Leu Val Gln Arg Tyr Ile Ser Glu Met Ala
                900                 905                 910

Glu Asn Leu Thr Asp Lys Gly Glu Leu Ser Glu Gly Arg Leu Gln Tyr
                915                 920                 925

Tyr Leu Ser Gln Val Glu Asn Tyr Arg Thr Tyr Cys Lys Asp Phe Val
    930                 935                 940

Lys Ala Leu Asn Val Pro Phe Ala Tyr Asn Leu Pro Arg Tyr Lys Asn
945                 950                 955                 960

Leu Ser Ile Asp Glu Leu Phe Asp Arg Asn Asn Tyr Leu Pro Asn Lys
                965                 970                 975

Ala Lys Lys Trp Ile Ser Glu Lys Glu Asn Gly Glu Tyr Val Met
                980                 985                 990

Glu Asp Cys Gly Asn Lys Gly Ala Gly Gln Val Glu Asn Ala
                995                 1000                1005

<210> SEQ ID NO 6
<211> LENGTH: 1001
<212> TYPE: PRT
<213> ORGANISM: Eubacterium sp.

<400> SEQUENCE: 6

Met Ala Lys Lys Leu Arg Pro Lys Glu Leu Arg Glu Lys Arg Arg Met
1               5                   10                  15

Ala Glu Lys Glu Glu His Lys Lys Gln Glu Lys Leu Arg Lys Glu Gln
                20                  25                  30

Glu Glu Leu Arg Lys Lys Gln Glu Lys Gln Arg Glu Asp Gln Lys Glu
            35                  40                  45

Leu Glu Lys Ile Lys Lys Glu Glu Gly Gly Glu Gly Glu Lys Lys Lys
        50                  55                  60

Ser Gly Ala Lys Ala Leu Gly Leu Lys Ser Thr Phe Ile Leu Asp Arg
65                  70                  75                  80

Asp Glu Gln Lys Met Leu Met Thr Ser Phe Gly Arg Gly Asn Lys Ala
                85                  90                  95

Val Arg Asp Lys Tyr Ile Ile Gly Asp Lys Val Ser Asp Ile Asp Asp
                100                 105                 110

Ser Trp Glu Asn Lys Lys Ala Ala Leu Ser Val Glu Val Cys Gly Lys
            115                 120                 125
```

Ser Phe Asn Ile Ser Lys Lys Glu Asn Asp Asp Cys Glu Pro Val Lys
130                 135                 140

Val Asn Asn Pro Val Leu Ser Gly Asn Lys Lys Asp Asp Asp Leu Ile
145                 150                 155                 160

His Cys Arg Lys Asn Leu Glu Glu Met Tyr Phe Gly Gln Gln Phe Lys
            165                 170                 175

Asp Asn Ile His Ile Gln Leu Ile Tyr Asn Ile Leu Asp Ile Glu Lys
            180                 185                 190

Ile Leu Ala Val Gln Ile Asn Asn Ile Val Phe Ile Leu Asn Asn Leu
            195                 200                 205

Leu Arg Trp Ser Gly Glu Glu Phe Asp Leu Ile Gly Ser Leu Gly
210                 215                 220

Val Asn His Thr Tyr Glu Glu Phe Arg Gly Arg Asn Lys Asn Tyr Gly
225                 230                 235                 240

Lys Phe Ser Glu Leu Ile Lys Gln Ser Gln Met Arg Tyr Phe Gly Ser
            245                 250                 255

Thr Phe Cys Leu Phe Asn Glu Asn Glu Glu Arg Ile Thr Ser Glu Asn
            260                 265                 270

Lys Lys Glu Trp Lys Arg Phe Glu Lys Lys Cys Tyr His Leu Leu Ala
            275                 280                 285

Val Leu Gly Met Met Arg Gln Ala Thr Ala His Gly Asp Ser Lys Arg
290                 295                 300

Arg Ala Glu Ile Tyr Lys Leu Gly Lys Glu Phe Asp Arg Leu Glu Ala
305                 310                 315                 320

Arg Gly Cys Arg Pro Glu Ala Arg Lys Glu Leu Asp Glu Leu Tyr Lys
            325                 330                 335

Lys Lys Ile His Glu Met Asn Gln Gly Phe Leu Lys Asn Ser Lys Ser
            340                 345                 350

Asp Ile Leu Met Leu Phe Arg Ile Tyr Asn Ala Glu Ser Lys Glu Ala
            355                 360                 365

Lys Arg Lys Leu Ala Gln Glu Tyr Tyr Glu Phe Ile Met Leu Lys Ser
            370                 375                 380

Tyr Lys Asn Thr Gly Phe Ser Ile Lys His Leu Arg Glu Thr Met Ile
385                 390                 395                 400

Asp Lys Met Asp Glu Asp Lys Lys Glu Lys Leu Lys Asp Asp Lys Tyr
            405                 410                 415

Asn Pro Ile Arg Arg Lys Ile Tyr Arg Ile Met Asp Phe Met Ile Tyr
            420                 425                 430

Gln Tyr Tyr Gln Glu Pro Glu His Gln Glu Glu Ala Glu Glu Leu Val
            435                 440                 445

Arg Lys Leu Arg Asn Ala Glu Ile Glu Ala Lys Lys Glu Leu Ala Tyr
450                 455                 460

Arg Lys Glu Ala Glu Lys Leu Lys Lys Glu Leu Glu Lys Ile Ile Phe
465                 470                 475                 480

Asn Ser Val Leu Pro Ser Cys Asp Arg Ile Leu Ser Glu Met Asp Glu
            485                 490                 495

Arg Arg Asn Lys Lys Val Asn Gln Glu Ser Ser Asp Thr Asp Lys Glu
            500                 505                 510

Glu Pro Leu Asp Ser Glu Ile Ala Glu Gly Ile Thr Phe Ile Lys Glu
            515                 520                 525

Thr Ala His Ser Phe Ser Glu Met Ile Tyr Leu Leu Thr Val Phe Leu
            530                 535                 540

Asp Gly Lys Glu Ile Asn Ile Leu Leu Thr Gln Leu Ile His Cys Phe

-continued

```
            545                 550                 555                 560
        Asp Asn Ile Ser Ser Phe Met Asp Thr Met Glu Glu Asn Leu Leu
                            565                 570                 575
        Thr Lys Leu Lys Glu Asp Tyr Glu Ile Phe Glu Glu Ser Lys Glu Ile
                            580                 585                 590
        Ser Arg Glu Leu Arg Ile Ile Asn Ser Phe Ala Arg Met Thr Glu Pro
                            595                 600                 605
        Val Pro Lys Thr Glu Arg Ile Met Phe Ile Glu Ala Ala Gln Ile Leu
                            610                 615                 620
        Gly Tyr Ser Asn Gly Glu Lys Glu Leu Glu Gly Tyr Val Asp Ala Leu
        625                 630                 635                 640
        Leu Asp Thr Lys Asn Lys Thr Asn Asp Lys Lys Lys Gly Phe Val
                            645                 650                 655
        Arg Tyr Ile Trp Asn Asn Val Ile Lys Ser Thr Arg Phe Arg Tyr Leu
                            660                 665                 670
        Val Arg Tyr Ala Asp Pro Lys Lys Val Arg Ala Phe Ala Ala Asn Lys
                            675                 680                 685
        Lys Val Val Ala Phe Val Leu Lys Asp Ile Pro Asp Asp Gln Ile Arg
        690                 695                 700
        Ala Tyr Tyr Asn Ser Cys Phe Arg Gln Asn Ser Asp Ser Ser Ser Asn
        705                 710                 715                 720
        Asn Ser Asn Ala Ser Trp Asp Ala Asp Ser Asn Lys Arg Asp Ile Ser
                            725                 730                 735
        Val Ser Asp Met Arg Lys Ala Leu Thr Glu Lys Ile Thr Gly Leu Asn
                            740                 745                 750
        Phe Gly Asp Phe Glu Glu Ser Lys Lys Gly Ile Arg Lys Glu Glu
                            755                 760                 765
        Ser Asp Lys Asn Ile Ile Arg Leu Tyr Leu Thr Val Leu Tyr Leu Val
                            770                 775                 780
        Gln Lys Asn Leu Ile Tyr Val Asn Ser Arg Tyr Phe Leu Ala Phe His
        785                 790                 795                 800
        Cys Ala Glu Arg Asp Glu Met Leu Tyr Asn Gly Glu Thr Ile Asp Asn
                            805                 810                 815
        Asn Lys Glu Lys Gly Ser Glu Lys Asp Trp Arg Lys Phe Ala Lys Gln
                            820                 825                 830
        Phe Ile Met Glu His Ser Pro Lys Lys Val Lys Asp Tyr Leu Ala
                            835                 840                 845
        Lys Asn Phe Glu Tyr Ser Asn Lys Trp Ser Leu Lys Glu Phe Arg Asn
        850                 855                 860
        Ser Val Gln His Leu Asn Val Ile Arg Asp Ala His Lys Tyr Ile Lys
        865                 870                 875                 880
        Tyr Ile Asn Asp Asn Lys Asp Val Gln Ser Tyr Phe Ala Leu Tyr His
                            885                 890                 895
        Tyr Leu Val Gln Arg Tyr Ile Ser Glu Arg Ala Ala Asn Arg Thr Asp
                            900                 905                 910
        Lys Glu Ser Leu Ser Glu Gly Arg Leu Gln Tyr Tyr Leu Ser Gln Val
                            915                 920                 925
        Lys Glu Tyr Arg Thr Tyr Cys Lys Asp Phe Val Lys Ala Leu Asn Val
                            930                 935                 940
        Pro Phe Ala Tyr Asn Leu Pro Arg Tyr Lys Asn Leu Ser Ile Asp Glu
        945                 950                 955                 960
        Leu Phe Asp Arg Asn Asn Tyr Leu Pro Asn Lys Ala Lys Lys Trp Ile
                            965                 970                 975
```

Pro Glu Lys Lys Glu Asn Gly Glu Tyr Val Met Glu Asp Cys Gly Asn
            980                 985                 990

Lys Asp Ala Gly Gln Val Glu Asn Ala
        995                 1000

<210> SEQ ID NO 7
<211> LENGTH: 906
<212> TYPE: PRT
<213> ORGANISM: Unknown
<220> FEATURE:
<223> OTHER INFORMATION: Description of Unknown:
      Gut metagenome sequence

<400> SEQUENCE: 7

Met Glu Arg Glu Val Lys Lys Pro Lys Lys Ser Leu Ala Lys Ala
1               5                   10                  15

Ala Gly Leu Lys Ser Thr Phe Val Ile Ser Pro Gln Glu Lys Glu Leu
            20                  25                  30

Ala Met Thr Ala Phe Gly Arg Gly Asn Asp Ala Leu Leu Gln Lys Arg
            35                  40                  45

Ile Val Asp Gly Val Val Arg Asp Val Ala Gly Glu Lys Gln Gln Phe
50                  55                  60

Gln Val Gln Arg Gln Asp Glu Ser Arg Phe Arg Leu Gln Asn Ser Arg
65                  70                  75                  80

Leu Ala Asp Arg Thr Val Thr Ala Asp Pro Leu His Arg Ala Glu
                85                  90                  95

Thr Pro Arg Arg Gln Pro Leu Gly Ala Gly Met Asp Gln Leu Arg Arg
            100                 105                 110

Lys Ala Ile Leu Glu Gln Lys Tyr Phe Gly Arg Thr Phe Asp Asp Asn
            115                 120                 125

Ile His Ile Gln Leu Ile Tyr Asn Ile Leu Asp Ile His Lys Met Leu
            130                 135                 140

Ala Val Pro Ala Asn His Ile Val His Thr Leu Asn Leu Leu Gly Gly
145                 150                 155                 160

Tyr Gly Glu Thr Asp Phe Val Gly Met Leu Pro Ala Gly Leu Pro Tyr
                165                 170                 175

Asp Lys Leu Arg Val Val Lys Lys Asn Gly Asp Thr Val Asp Ile
            180                 185                 190

Lys Ala Asp Ile Ala Ala Tyr Ala Lys Arg Pro Gln Leu Ala Tyr Leu
            195                 200                 205

Gly Ala Ala Phe Tyr Asp Val Thr Pro Gly Lys Ser Lys Arg Asp Ala
    210                 215                 220

Ala Arg Gly Arg Val Lys Arg Glu Gln Asp Val Tyr Thr Ile Leu Ser
225                 230                 235                 240

Leu Met Ser Leu Leu Arg Gln Phe Cys Ala His Asp Ser Val Arg Ile
                245                 250                 255

Trp Gly Gln Asn Thr Pro Ala Ala Leu Tyr Gly Leu Gln Ala Leu Pro
            260                 265                 270

Gln Asp Met Lys Asp Leu Leu Asp Asp Gly Trp Arg Arg Ala Leu Gly
            275                 280                 285

Gly Val Asn Asp His Phe Leu Asp Thr Asn Lys Val Asn Leu Leu Thr
    290                 295                 300

Leu Phe Glu Tyr Tyr Gly Ala Glu Thr Lys Gln Glu Arg Val Ala Leu
305                 310                 315                 320

Thr Gln Asp Phe Tyr Arg Phe Val Val Leu Lys Glu Gln Lys Asn Met

-continued

```
                325                 330                 335
Gly Phe Ser Leu Arg Arg Leu Arg Glu Glu Leu Leu Lys Leu Pro Asp
                340                 345                 350

Ala Ala Tyr Leu Thr Gly Gln Glu Tyr Asp Ser Val Arg Gln Lys Leu
                355                 360                 365

Tyr Met Leu Leu Asp Phe Leu Leu Cys Arg Leu Tyr Ala Gln Glu Arg
            370                 375                 380

Ala Asp Arg Cys Glu Glu Leu Val Ser Ala Leu Arg Cys Ala Leu Ser
385                 390                 395                 400

Asp Glu Glu Lys Asp Ala Val Tyr Gln Ala Glu Ala Ala Leu Trp
                405                 410                 415

Gln Ala Leu Gly Asp Thr Leu Arg Arg Glu Leu Leu Pro Leu Leu Lys
                420                 425                 430

Gly Lys Lys Leu Gln Asp Lys Asp Lys Lys Leu Asp Glu Leu Gly
                435                 440                 445

Leu Ser Arg Asp Val Leu Asp Gly Val Leu Phe Arg Pro Ala Gln Gln
            450                 455                 460

Gly Ser Arg Ala Asn Ala Asp Tyr Phe Cys Arg Leu Met His Leu Ser
465                 470                 475                 480

Thr Trp Phe Met Asp Gly Lys Glu Ile Asn Thr Leu Thr Thr Leu
                485                 490                 495

Ile Ser Lys Leu Glu Asn Ile Asp Ser Leu Arg Ser Val Leu Glu Ser
            500                 505                 510

Met Gly Leu Ala Tyr Ser Phe Val Pro Ala Tyr Ala Met Phe Asp His
                515                 520                 525

Ser Arg Tyr Ile Ala Gly Gln Leu Arg Val Val Asn Asn Ile Ala Arg
            530                 535                 540

Met Arg Lys Pro Ala Ile Gly Ala Lys Arg Glu Met Tyr Arg Ala Ala
545                 550                 555                 560

Val Val Leu Leu Gly Val Asp Ser Pro Glu Ala Ala Ala Ile Thr
                565                 570                 575

Asp Asp Leu Leu Gln Ile Asp Pro Glu Thr Gly Lys Val Arg Pro Arg
            580                 585                 590

Gly Asp Ser Ala Arg Asp Thr Gly Leu Arg Asn Phe Val Ala Asn Asn
                595                 600                 605

Val Val Glu Ser Arg Arg Phe Thr Tyr Leu Leu Arg Tyr Met Thr Pro
            610                 615                 620

Glu Gln Ala Arg Val Leu Ala Gln Asn Glu Lys Leu Ile Ala Phe Val
625                 630                 635                 640

Leu Ser Thr Val Pro Ser Ala Gln Leu Glu Arg Tyr Cys Arg Thr Cys
                645                 650                 655

Gly Arg Glu Asp Ile Thr Gly Arg Pro Ala Gln Ile Arg Tyr Leu Thr
            660                 665                 670

Ala Gln Ile Met Gly Val Arg Tyr Glu Ser Phe Thr Asp Val Glu Gln
            675                 680                 685

Arg Gly Arg Gly Asp Asn Pro Lys Lys Glu Arg Tyr Lys Ala Leu Ile
            690                 695                 700

Gly Leu Tyr Leu Thr Val Leu Tyr Leu Ala Val Lys Asn Met Val Asn
705                 710                 715                 720

Cys Asn Ala Arg Tyr Val Ile Ala Phe Tyr Cys Arg Asp Arg Asp Thr
                725                 730                 735

Ala Leu Tyr Gln Lys Glu Val Cys Trp Tyr Asp Leu Glu Glu Asp Lys
            740                 745                 750
```

-continued

Lys Ser Gly Lys Gln Arg Gln Val Glu Asp Tyr Thr Ala Leu Thr Arg
            755                 760                 765

Tyr Phe Val Ser Gln Gly Tyr Leu Asn Arg His Ala Cys Gly Tyr Leu
        770                 775                 780

Arg Ser Asn Met Asn Gly Ile Ser Asn Gly Leu Leu Ala Ala Tyr Arg
785                 790                 795                 800

Asn Ala Val Asp His Leu Asn Val Ile Pro Pro Leu Gly Ser Leu Cys
            805                 810                 815

Arg Asp Ile Gly Arg Val Asp Ser Tyr Phe Ala Leu Tyr His Tyr Ala
        820                 825                 830

Val Gln Gln Tyr Leu Asn Gly Arg Tyr Tyr Arg Lys Thr Pro Arg Glu
            835                 840                 845

Gln Glu Leu Phe Ala Ala Met Ala Gln His Arg Thr Trp Cys Ser Asp
        850                 855                 860

Leu Val Lys Ala Leu Asn Thr Pro Phe Gly Tyr Asn Leu Ala Arg Tyr
865                 870                 875                 880

Lys Asn Leu Ser Ile Asp Gly Leu Phe Asp Arg Glu Gly Asp His Val
            885                 890                 895

Val Arg Glu Asp Gly Glu Lys Pro Ala Glu
        900                 905

<210> SEQ ID NO 8
<211> LENGTH: 925
<212> TYPE: PRT
<213> ORGANISM: Unknown
<220> FEATURE:
<223> OTHER INFORMATION: Description of Unknown:
      Gut metagenome sequence

<400> SEQUENCE: 8

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Lys Asn Asn Ala Val
            20                  25                  30

Pro Ala Ile Ala Ala Met Pro Ala Ala Glu Ala Ala Ala Pro Ala Val
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65              70                  75                  80

Ala Val Leu Glu Tyr Glu Val Asp Lys Val Asp Asn Asn Tyr Asn
            85                  90                  95

Lys Thr Gln Leu Ser Ser Lys Asp Asn Ser Ile Glu Leu Gly Asp
            100                 105                 110

Val Asn Glu Val Asn Ile Thr Phe Ser Ser Lys Arg Gly Asn Glu Ser
            115                 120                 125

Gly Val Glu Ile Asn Thr Ser Asn Pro Thr His Arg Ser Gly Glu Ser
    130                 135                 140

Ser Pro Val Arg Trp Asp Met Leu Gly Leu Lys Ser Glu Leu Glu Lys
145                 150                 155                 160

Arg Phe Phe Gly Lys Thr Phe Asp Asp Asn Ile His Ile Gln Leu Ile
                165                 170                 175

Tyr Asn Ile Leu Asp Ile Glu Lys Ile Leu Ala Val Tyr Val Thr Asn
            180                 185                 190

Ile Val Tyr Ala Leu Asn Asn Met Leu Gly Ile Lys Gly Ser Glu Ser

```
            195                 200                 205
Tyr Asp Asp Phe Met Gly Tyr Leu Ser Ala Arg Asn Thr Tyr Glu Val
210                 215                 220

Phe Thr His Pro Asp Lys Ser Asn Leu Ser Asp Lys Val Lys Gly Asn
225                 230                 235                 240

Ile Lys Lys Ser Leu Ser Lys Phe Asn Asp Leu Leu Lys Thr Lys Arg
                245                 250                 255

Leu Gly Tyr Phe Gly Leu Glu Glu Pro Lys Thr Lys Asp Thr Arg Val
                260                 265                 270

Ser Gln Ala Tyr Lys Lys Arg Val Tyr His Met Leu Ala Ile Val Gly
            275                 280                 285

Gln Ile Arg Gln Cys Val Phe His Asp Lys Ser Gly Ala Lys Arg Phe
290                 295                 300

Asp Leu Tyr Ser Phe Ile Asn Asn Ile Asp Pro Glu Tyr Arg Asp Thr
305                 310                 315                 320

Leu Asp Tyr Leu Val Glu Glu Arg Leu Lys Ser Ile Asn Lys Asp Phe
                325                 330                 335

Ile Glu Gly Asn Lys Val Asn Ile Ser Leu Leu Ile Asp Met Met Lys
                340                 345                 350

Gly Tyr Glu Ala Asp Asp Ile Ile Arg Leu Tyr Tyr Asp Phe Ile Val
            355                 360                 365

Leu Lys Ser Gln Lys Asn Leu Gly Phe Ser Ile Lys Lys Leu Arg Glu
370                 375                 380

Lys Met Leu Glu Glu Tyr Gly Tyr Arg Phe Lys Asp Lys Gln Tyr Asp
385                 390                 395                 400

Ser Val Arg Ser Lys Met Tyr Lys Leu Met Asp Phe Leu Leu Phe Cys
                405                 410                 415

Asn Tyr Tyr Arg Asn Asp Val Val Ala Gly Glu Ala Leu Val Arg Lys
                420                 425                 430

Leu Arg Phe Ser Met Thr Asp Asp Glu Lys Glu Gly Ile Tyr Ala Asp
            435                 440                 445

Glu Ala Ser Lys Leu Trp Gly Lys Phe Arg Asn Asp Phe Glu Asn Ile
450                 455                 460

Ala Asp His Met Asn Gly Asp Val Ile Lys Glu Leu Gly Lys Ala Asp
465                 470                 475                 480

Met Asp Phe Asp Glu Lys Ile Leu Asp Ser Lys Lys Asn Ala Ser
                485                 490                 495

Asp Leu Leu Tyr Phe Ser Lys Met Ile Tyr Met Leu Thr Tyr Phe Leu
            500                 505                 510

Asp Gly Lys Glu Ile Asn Asp Leu Leu Thr Thr Leu Ile Ser Lys Phe
            515                 520                 525

Asp Asn Ile Lys Glu Phe Leu Lys Ile Met Lys Ser Ser Ala Val Asp
530                 535                 540

Val Glu Cys Glu Leu Thr Ala Gly Tyr Lys Leu Phe Asn Asp Ser Gln
545                 550                 555                 560

Arg Ile Thr Asn Glu Leu Phe Ile Val Lys Asn Ile Ala Ser Met Arg
                565                 570                 575

Lys Pro Ala Ala Ser Ala Lys Leu Thr Met Phe Arg Asp Ala Leu Thr
                580                 585                 590

Ile Leu Gly Ile Asp Asp Lys Ile Thr Asp Asp Arg Ile Ser Glu Ile
            595                 600                 605

Leu Lys Leu Lys Glu Lys Gly Lys Gly Ile His Gly Leu Arg Asn Phe
            610                 615                 620
```

```
Ile Thr Asn Asn Val Ile Glu Ser Ser Arg Phe Val Tyr Leu Ile Lys
625                 630                 635                 640

Tyr Ala Asn Ala Gln Lys Ile Arg Glu Val Ala Lys Asn Glu Lys Val
            645                 650                 655

Val Met Phe Val Leu Gly Gly Ile Pro Asp Thr Gln Ile Glu Arg Tyr
        660                 665                 670

Tyr Lys Ser Cys Val Glu Phe Pro Asp Met Asn Ser Ser Leu Glu Ala
    675                 680                 685

Lys Arg Ser Glu Leu Ala Arg Met Ile Lys Asn Ile Arg Phe Asp Asp
690                 695                 700

Phe Lys Asn Val Lys Gln Gln Ala Lys Gly Arg Glu Asn Val Ala Lys
705                 710                 715                 720

Glu Arg Ala Lys Ala Val Ile Gly Leu Tyr Leu Thr Val Met Tyr Leu
            725                 730                 735

Leu Val Lys Asn Leu Val Asn Val Asn Ala Arg Tyr Val Ile Ala Ile
            740                 745                 750

His Cys Leu Glu Arg Asp Phe Gly Leu Tyr Lys Glu Ile Ile Pro Glu
        755                 760                 765

Leu Ala Ser Lys Asn Leu Lys Asn Asp Tyr Arg Ile Leu Ser Gln Thr
770                 775                 780

Leu Cys Glu Leu Cys Asp Asp Arg Asp Glu Ser Pro Asn Leu Phe Leu
785                 790                 795                 800

Lys Lys Asn Lys Arg Leu Arg Lys Cys Val Glu Val Asp Ile Asn Asn
            805                 810                 815

Ala Asp Ser Ser Met Thr Arg Lys Tyr Arg Asn Cys Ile Ala His Leu
            820                 825                 830

Thr Val Val Arg Glu Leu Lys Glu Tyr Ile Gly Asp Ile Arg Thr Val
        835                 840                 845

Asp Ser Tyr Phe Ser Ile Tyr His Tyr Val Met Gln Arg Cys Ile Thr
    850                 855                 860

Lys Arg Glu Asp Asp Thr Lys Gln Glu Glu Lys Ile Lys Tyr Glu Asp
865                 870                 875                 880

Asp Leu Leu Lys Asn His Gly Tyr Thr Lys Asp Phe Val Lys Ala Leu
            885                 890                 895

Asn Ser Pro Phe Gly Tyr Asn Ile Pro Arg Phe Lys Asn Leu Ser Ile
            900                 905                 910

Glu Gln Leu Phe Asp Arg Asn Glu Tyr Leu Thr Glu Lys
        915                 920                 925

<210> SEQ ID NO 9
<211> LENGTH: 923
<212> TYPE: PRT
<213> ORGANISM: Unknown
<220> FEATURE:
<223> OTHER INFORMATION: Description of Unknown:
      Gut metagenome sequence

<400> SEQUENCE: 9

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Val
            20                  25                  30

Pro Ala Ile Ala Ala Met Pro Ala Ala Glu Val Ile Ala Pro Ala Ala
        35                  40                  45

Glu Lys Lys Lys Ser Ser Val Lys Ala Ala Gly Met Lys Ser Ile Leu
```

-continued

```
            50                  55                  60
Val Ser Glu Asn Lys Met Tyr Ile Thr Ser Phe Gly Lys Gly Asn Ser
 65                  70                  75                  80

Ala Val Leu Glu Tyr Glu Val Asp Lys Val Asp Asn Asp Tyr Asn
                 85                  90                  95

Lys Thr Gln Leu Ser Ser Lys Asp Asn Ser Asn Ile Glu Leu Gly Asn
                100                 105                 110

Val Asn Glu Val Asn Ile Thr Phe Ser Ser Arg Arg Gly Phe Glu Ser
                115                 120                 125

Gly Val Glu Ile Asn Thr Ser Asn Pro Thr His Arg Ser Gly Glu Ser
                130                 135                 140

Ser Ser Val Arg Gly Asp Met Leu Gly Leu Lys Ser Glu Leu Glu Lys
145                 150                 155                 160

Arg Phe Phe Gly Lys Thr Phe Asp Asp Asn Ile His Ile Gln Leu Ile
                165                 170                 175

Tyr Asn Ile Leu Asp Ile Glu Lys Ile Leu Ala Val Tyr Val Thr Asn
                180                 185                 190

Ile Val Tyr Ala Leu Asn Asn Met Leu Gly Val Lys Gly Ser Glu Ser
                195                 200                 205

Tyr Asp Asp Phe Met Gly Tyr Leu Ser Ala Gln Asn Thr Tyr Tyr Ile
                210                 215                 220

Phe Thr His Pro Asp Lys Ser Asn Leu Ser Asp Lys Val Lys Gly Asn
225                 230                 235                 240

Ile Lys Lys Ser Leu Ser Lys Phe Asn Asp Leu Leu Lys Thr Lys Arg
                245                 250                 255

Leu Gly Tyr Phe Gly Leu Glu Glu Pro Lys Thr Lys Asp Lys Arg Val
                260                 265                 270

Ser Glu Ala Tyr Lys Lys Arg Val Tyr His Met Leu Ala Ile Val Gly
                275                 280                 285

Gln Ile Arg Gln Ser Val Phe His Asp Lys Ser Asn Glu Leu Asp Glu
                290                 295                 300

Tyr Leu Tyr Ser Phe Ile Asp Ile Ile Asp Ser Glu Tyr Arg Asp Thr
305                 310                 315                 320

Leu Asp Tyr Leu Val Asp Glu Arg Phe Asp Ser Ile Asn Lys Gly Phe
                325                 330                 335

Ile Gln Gly Asn Lys Val Asn Ile Ser Leu Leu Ile Asp Met Met Lys
                340                 345                 350

Asp Asp Tyr Glu Ala Asp Asp Ile Ile Arg Leu Tyr Tyr Asp Phe Ile
                355                 360                 365

Val Leu Lys Ser Gln Lys Asn Leu Gly Phe Ser Ile Lys Lys Leu Arg
                370                 375                 380

Glu Lys Met Leu Glu Glu Tyr Gly Phe Arg Phe Lys Asp Lys Gln Tyr
385                 390                 395                 400

Asp Ser Val Arg Ser Lys Met Tyr Lys Ile Met Asp Phe Leu Leu Phe
                405                 410                 415

Cys Asn Tyr Tyr Arg Asn Asp Val Val Ala Gly Glu Ala Leu Val Arg
                420                 425                 430

Lys Leu Arg Phe Ser Met Thr Asp Asp Glu Lys Glu Gly Ile Tyr Ala
                435                 440                 445

Asp Glu Ala Ala Lys Leu Trp Gly Lys Phe Arg Asn Asp Phe Glu Asn
                450                 455                 460

Ile Ala Asp His Met Asn Gly Asp Val Ile Lys Glu Leu Gly Lys Ala
465                 470                 475                 480
```

```
Asp Met Asp Phe Asp Glu Lys Ile Leu Asp Ser Glu Lys Lys Asn Ala
            485                 490                 495

Ser Asp Leu Leu Tyr Phe Ser Lys Met Ile Tyr Met Leu Thr Tyr Phe
            500                 505                 510

Leu Asp Gly Lys Glu Ile Asn Asp Leu Leu Thr Thr Leu Ile Ser Lys
            515                 520                 525

Phe Asp Asn Ile Lys Glu Phe Leu Lys Ile Met Lys Ser Ser Ala Val
            530                 535                 540

Asp Val Glu Cys Glu Leu Thr Ala Gly Tyr Lys Leu Phe Asn Asp Ser
545                 550                 555                 560

Gln Arg Ile Thr Asn Glu Leu Phe Ile Val Lys Asn Ile Ala Ser Met
            565                 570                 575

Arg Lys Pro Ala Ala Ser Ala Lys Leu Thr Met Phe Arg Asp Ala Leu
            580                 585                 590

Thr Ile Leu Gly Ile Asp Asp Asn Ile Thr Asp Asp Arg Ile Ser Glu
            595                 600                 605

Ile Leu Lys Leu Lys Glu Lys Gly Lys Gly Ile His Gly Leu Arg Asn
            610                 615                 620

Phe Ile Thr Asn Asn Val Ile Glu Ser Ser Arg Phe Val Tyr Leu Ile
625                 630                 635                 640

Lys Tyr Ala Asn Ala Gln Lys Ile Arg Glu Val Ala Lys Asn Glu Lys
            645                 650                 655

Val Val Met Phe Val Leu Gly Gly Ile Pro Asp Thr Gln Ile Glu Arg
            660                 665                 670

Tyr Tyr Lys Ser Cys Val Glu Phe Pro Asp Met Asn Ser Ser Leu Glu
            675                 680                 685

Val Lys Arg Ser Glu Leu Ala Arg Met Ile Lys Asn Ile Cys Phe Asp
            690                 695                 700

Asp Phe Lys Asn Val Lys Gln Gln Ala Lys Gly Arg Glu Asn Val Ala
705                 710                 715                 720

Lys Glu Arg Ala Lys Ala Val Ile Gly Leu Tyr Leu Thr Val Met Tyr
            725                 730                 735

Leu Leu Val Lys Asn Leu Val Asn Val Asn Ala Arg Tyr Val Ile Ala
            740                 745                 750

Ile His Cys Leu Glu Arg Asp Phe Gly Leu Tyr Lys Glu Ile Val Ser
            755                 760                 765

Glu Leu Ala Ser Lys Asn Leu Lys Asn Asp Tyr Arg Ile Leu Ser Gln
            770                 775                 780

Thr Leu Cys Glu Leu Cys Asp Lys Ser Pro Asn Leu Phe Leu Lys Lys
785                 790                 795                 800

Asn Glu Arg Leu Arg Lys Cys Val Glu Val Asp Ile Asn Asn Ala Asp
            805                 810                 815

Ser Ser Met Thr Arg Lys Tyr Arg Asn Cys Ile Ala His Leu Thr Val
            820                 825                 830

Val Arg Glu Leu Lys Glu Tyr Ile Gly Asp Ile Arg Ala Val Asp Ser
            835                 840                 845

Tyr Phe Ser Ile Tyr His Tyr Val Met Gln Arg Cys Ile Thr Lys Arg
            850                 855                 860

Gly Asn Asp Thr Lys Gln Glu Asp Lys Ile Lys Tyr Glu Asp Asp Leu
865                 870                 875                 880

Leu Lys Asn His Gly Tyr Thr Lys Asp Phe Val Lys Ala Leu Asn Ser
            885                 890                 895
```

```
Pro Phe Gly Tyr Asn Ile Pro Arg Phe Lys Asn Leu Ser Ile Glu Gln
                895                 900                 905                 910

Leu Phe Asp Arg Asn Glu Tyr Leu Thr Glu Lys
            915                 920

<210> SEQ ID NO 10
<211> LENGTH: 906
<212> TYPE: PRT
<213> ORGANISM: Unknown
<220> FEATURE:
<223> OTHER INFORMATION: Description of Unknown:
      Gut metagenome sequence

<400> SEQUENCE: 10

Met Glu Arg Glu Val Lys Lys Pro Lys Lys Ser Leu Ala Lys Ala
1               5                   10                  15

Ala Gly Leu Lys Ser Thr Phe Val Ile Ser Pro Gln Glu Lys Glu Leu
                20                  25                  30

Ala Met Thr Ala Phe Gly Arg Gly Asn Asp Ala Leu Leu Gln Lys Arg
            35                  40                  45

Ile Val Asp Gly Val Val Arg Asp Val Ala Gly Glu Lys Gln Gln Phe
50                  55                  60

Gln Val Gln Arg Gln Asp Glu Ser Arg Phe Arg Leu Gln Asn Ser Arg
65                  70                  75                  80

Leu Ala Asp Arg Thr Val Thr Ala Asp Asp Pro Leu His Arg Ala Glu
                85                  90                  95

Thr Pro Arg Arg Gln Pro Leu Gly Ala Gly Met Asp Gln Leu Arg Arg
            100                 105                 110

Lys Ala Ile Leu Glu Gln Lys Tyr Phe Gly Arg Thr Phe Asp Asp Asn
        115                 120                 125

Ile His Ile Gln Leu Ile Tyr Asn Ile Leu Asp Ile His Lys Met Leu
130                 135                 140

Ala Val Pro Ala Asn His Ile Val His Thr Leu Asn Leu Leu Gly Gly
145                 150                 155                 160

Tyr Gly Glu Thr Asp Phe Val Gly Met Leu Pro Ala Gly Leu Pro Tyr
                165                 170                 175

Asp Lys Leu Arg Val Val Lys Lys Asn Gly Asp Thr Val Asp Ile
            180                 185                 190

Lys Ala Asp Ile Ala Ala Tyr Ala Lys Arg Pro Gln Leu Ala Tyr Leu
        195                 200                 205

Gly Ala Ala Phe Tyr Asp Val Thr Pro Gly Lys Ser Lys Arg Asp Ala
    210                 215                 220

Ala Arg Gly Arg Val Lys Arg Glu Gln Asp Val Tyr Ala Ile Leu Ser
225                 230                 235                 240

Leu Met Ser Leu Leu Arg Gln Phe Cys Ala His Asp Ser Val Arg Ile
                245                 250                 255

Trp Gly Gln Asn Thr Thr Ala Ala Leu Tyr His Leu Gln Ala Leu Pro
            260                 265                 270

Gln Asp Met Lys Asp Leu Leu Asp Asp Gly Trp Arg Arg Ala Leu Gly
        275                 280                 285

Gly Val Asn Asp His Phe Leu Asp Thr Asn Lys Val Asn Leu Leu Thr
    290                 295                 300

Leu Phe Glu Tyr Tyr Gly Ala Glu Thr Lys Gln Ala Arg Val Ala Leu
305                 310                 315                 320

Thr Gln Asp Phe Tyr Arg Phe Val Val Leu Lys Glu Gln Lys Asn Met
                325                 330                 335
```

```
Gly Phe Ser Leu Arg Arg Leu Arg Glu Glu Leu Leu Lys Leu Pro Asp
            340                 345                 350

Ala Ala Tyr Leu Thr Gly Gln Glu Tyr Asp Ser Val Arg Gln Lys Leu
            355                 360                 365

Tyr Met Leu Leu Asp Phe Leu Leu Cys Arg Leu Tyr Ala Gln Glu Arg
            370                 375                 380

Ala Asp Arg Cys Glu Glu Leu Val Ser Ala Leu Arg Cys Ala Leu Ser
385                 390                 395                 400

Asp Glu Glu Lys Asp Thr Val Tyr Gln Ala Glu Ala Ala Leu Trp
                405                 410                 415

Gln Ala Leu Gly Asp Thr Leu Arg Arg Lys Leu Leu Pro Leu Leu Lys
            420                 425                 430

Gly Lys Lys Leu Gln Asp Lys Asp Lys Lys Ser Asp Glu Leu Gly
            435                 440                 445

Leu Ser Arg Asp Val Leu Asp Gly Val Leu Phe Arg Pro Ala Gln Gln
450                 455                 460

Gly Ser Arg Ala Asn Ala Asp Tyr Phe Cys Arg Leu Met His Leu Ser
465                 470                 475                 480

Thr Trp Phe Met Asp Gly Lys Glu Ile Asn Thr Leu Leu Thr Thr Leu
                485                 490                 495

Ile Ser Lys Leu Glu Asn Ile Asp Ser Leu Arg Ser Val Leu Glu Ser
            500                 505                 510

Met Gly Leu Ala Tyr Ser Phe Val Pro Ala Tyr Ala Met Phe Asp His
            515                 520                 525

Ser Arg Tyr Ile Ala Gly Gln Leu Arg Val Val Asn Asn Ile Ala Arg
            530                 535                 540

Met Arg Lys Pro Ala Ile Gly Ala Lys Arg Glu Met Tyr Arg Ala Ala
545                 550                 555                 560

Val Val Leu Leu Gly Val Asp Ser Pro Glu Ala Ala Ala Ile Thr
                565                 570                 575

Asp Asp Leu Leu Gln Ile Asp Pro Glu Thr Gly Lys Val Arg Pro Arg
            580                 585                 590

Ser Asp Ser Ala Arg Asp Thr Gly Leu Arg Asn Phe Ile Ala Asn Asn
            595                 600                 605

Val Val Glu Ser Arg Arg Phe Thr Tyr Leu Leu Arg Tyr Met Thr Pro
            610                 615                 620

Glu Gln Ala Arg Val Leu Ala Gln Asn Glu Lys Leu Ile Ala Phe Val
625                 630                 635                 640

Leu Ser Thr Val Pro Asp Thr Gln Leu Glu Arg Tyr Cys Arg Thr Cys
                645                 650                 655

Gly Arg Glu Asp Ile Thr Gly Arg Pro Ala Gln Ile Arg Tyr Leu Thr
            660                 665                 670

Ala Gln Ile Met Gly Val Arg Tyr Glu Ser Phe Thr Asp Val Glu Gln
            675                 680                 685

Arg Gly Arg Gly Asp Asn Pro Lys Lys Glu Arg Tyr Lys Ala Leu Ile
            690                 695                 700

Gly Leu Tyr Leu Thr Val Leu Tyr Leu Ala Val Lys Asn Met Val Asn
705                 710                 715                 720

Cys Asn Ala Arg Tyr Val Ile Ala Phe Tyr Cys Arg Asp Arg Asp Thr
                725                 730                 735

Ala Leu Tyr Gln Lys Glu Val Cys Trp Tyr Asp Leu Glu Glu Asp Lys
            740                 745                 750
```

-continued

```
Lys Ser Gly Lys Gln Arg Gln Val Glu Asp Tyr Thr Ala Leu Thr Arg
            755                 760                 765

Tyr Phe Val Ser Gln Gly Tyr Leu Asn Arg His Ala Cys Gly Tyr Leu
    770                 775                 780

Arg Ser Asn Met Asn Gly Ile Ser Asn Ser Leu Leu Thr Ala Tyr Arg
785                 790                 795                 800

Asn Ala Val Asp His Leu Asn Ala Ile Pro Pro Leu Gly Ser Leu Cys
                805                 810                 815

Arg Asp Ile Gly Arg Val Asp Ser Tyr Phe Ala Leu Tyr His Tyr Ala
                820                 825                 830

Val Gln Gln Tyr Leu Asn Gly Arg Tyr Tyr Arg Lys Thr Pro Arg Glu
            835                 840                 845

Gln Glu Leu Phe Ala Ala Met Ala Gln His Arg Thr Trp Cys Ser Asp
        850                 855                 860

Leu Val Lys Ala Leu Asn Thr Pro Phe Gly Tyr Asn Leu Ala Arg Tyr
865                 870                 875                 880

Lys Asn Leu Ser Ile Asp Gly Leu Phe Asp Arg Glu Gly Asp His Val
                885                 890                 895

Val Arg Glu Asp Gly Glu Lys Pro Ala Glu
            900                 905

<210> SEQ ID NO 11
<211> LENGTH: 929
<212> TYPE: PRT
<213> ORGANISM: Unknown
<220> FEATURE:
<223> OTHER INFORMATION: Description of Unknown:
      Gut metagenome sequence

<400> SEQUENCE: 11

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Gln Val Ile Ala Pro Ala Ala
        35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Lys Val Asp Asn Asn Tyr Asn
                85                  90                  95

Lys Thr Gln Leu Ser Ser Lys Asp Asn Ser Asn Ile Glu Leu Gly Asp
            100                 105                 110

Val Asn Glu Val Asn Ile Thr Phe Ser Ser Lys His Gly Phe Glu Ser
        115                 120                 125

Gly Val Glu Ile Asn Thr Ser Asn Pro Thr His Arg Ser Gly Glu Ser
    130                 135                 140

Ser Pro Val Arg Trp Asp Met Leu Gly Leu Lys Ser Glu Leu Glu Lys
145                 150                 155                 160

Arg Phe Phe Gly Lys Thr Phe Asp Asp Asn Ile His Ile Gln Leu Ile
                165                 170                 175

Tyr Asn Ile Leu Asp Ile Glu Lys Ile Leu Ala Val Tyr Val Thr Asn
            180                 185                 190

Ile Val Tyr Ala Leu Asn Asn Met Leu Gly Ile Lys Gly Ser Glu Ser
        195                 200                 205
```

Tyr Asp Asp Phe Met Gly Tyr Leu Ser Ala Arg Asn Thr Tyr Glu Val
210                 215                 220

Phe Thr His Pro Asp Lys Ser Asn Leu Ser Asp Lys Val Lys Gly Asn
225                 230                 235                 240

Ile Lys Lys Ser Phe Ser Thr Phe Asn Asp Leu Leu Lys Thr Lys Arg
            245                 250                 255

Leu Gly Tyr Phe Gly Leu Glu Glu Pro Lys Thr Lys Asp Thr Arg Val
            260                 265                 270

Ser Glu Ala Tyr Lys Lys Arg Val Tyr His Met Leu Ala Ile Val Gly
        275                 280                 285

Gln Ile Arg Gln Cys Val Phe His Asp Leu Ser Glu His Ser Glu Tyr
290                 295                 300

Asp Leu Tyr Ser Phe Ile Asp Asn Ser Lys Lys Val Tyr Arg Glu Cys
305                 310                 315                 320

Arg Glu Thr Leu Asn Tyr Leu Val Asp Glu Arg Phe Asp Ser Ile Asn
            325                 330                 335

Lys Gly Phe Ile Gln Gly Asn Lys Val Asn Ile Ser Leu Leu Ile Asp
            340                 345                 350

Met Met Lys Asp Asp Tyr Glu Ala Asp Asp Ile Ile His Leu Tyr Tyr
        355                 360                 365

Asp Phe Ile Val Leu Lys Ser Gln Lys Asn Leu Gly Phe Ser Ile Lys
370                 375                 380

Lys Leu Arg Glu Lys Met Leu Asp Glu Tyr Gly Phe Arg Phe Lys Asp
385                 390                 395                 400

Lys Gln Tyr Asp Ser Val Arg Ser Lys Met Tyr Lys Leu Met Asp Phe
            405                 410                 415

Leu Leu Phe Cys Asn Tyr Tyr Arg Asn Asp Val Val Ala Gly Glu Ala
            420                 425                 430

Leu Val Arg Lys Leu Arg Phe Ser Met Thr Asp Asp Glu Lys Glu Gly
        435                 440                 445

Ile Tyr Ala Asp Glu Ala Glu Lys Leu Trp Gly Lys Phe Arg Asn Asp
450                 455                 460

Phe Glu Asn Ile Ala Asp His Met Asn Gly Asp Val Ile Lys Glu Leu
465                 470                 475                 480

Gly Lys Ala Asp Met Asp Phe Asp Glu Lys Ile Leu Asp Ser Glu Lys
            485                 490                 495

Lys Asn Ala Ser Asp Leu Leu Tyr Phe Ser Lys Met Ile Tyr Met Leu
            500                 505                 510

Thr Tyr Phe Leu Asp Gly Lys Glu Ile Asn Asp Leu Leu Thr Thr Leu
        515                 520                 525

Ile Ser Lys Phe Asp Asn Ile Lys Glu Phe Leu Lys Ile Met Lys Ser
530                 535                 540

Ser Ala Val Asp Val Glu Cys Glu Leu Thr Ala Gly Tyr Lys Leu Phe
545                 550                 555                 560

Asn Asp Ser Gln Arg Ile Thr Asn Glu Leu Phe Ile Val Lys Asn Ile
            565                 570                 575

Ala Ser Met Arg Lys Pro Ala Ala Ser Ala Lys Leu Thr Met Phe Arg
            580                 585                 590

Asp Ala Leu Thr Ile Leu Gly Ile Asp Asp Lys Ile Thr Asp Asp Arg
        595                 600                 605

Ile Ser Glu Ile Leu Lys Leu Lys Glu Lys Gly Lys Gly Ile His Gly
610                 615                 620

-continued

Leu Arg Asn Phe Ile Thr Asn Asn Val Ile Glu Ser Ser Arg Phe Val
625                 630                 635                 640

Tyr Leu Ile Lys Tyr Ala Asn Ala Gln Lys Ile Arg Glu Val Ala Lys
            645                 650                 655

Asn Glu Lys Val Val Met Phe Val Leu Gly Gly Ile Pro Asp Thr Gln
        660                 665                 670

Ile Glu Arg Tyr Tyr Lys Ser Cys Val Glu Phe Pro Asp Met Asn Ser
    675                 680                 685

Ser Leu Lys Val Lys Arg Ser Glu Leu Ala Arg Met Ile Lys Asn Ile
690                 695                 700

Arg Phe Asp Asp Phe Lys Asn Val Lys Gln Gln Ala Lys Gly Arg Glu
705                 710                 715                 720

Asn Val Ala Lys Glu Arg Ala Lys Ala Val Ile Gly Leu Tyr Leu Thr
                725                 730                 735

Val Met Tyr Leu Leu Val Lys Asn Leu Val Asn Val Asn Ala Arg Tyr
            740                 745                 750

Val Ile Ala Ile His Cys Leu Glu Arg Asp Phe Gly Leu Tyr Lys Glu
        755                 760                 765

Ile Ile Pro Glu Leu Ala Ser Lys Asn Leu Lys Asn Asp Tyr Arg Ile
    770                 775                 780

Leu Ser Gln Thr Leu Cys Glu Leu Cys Asp Asp Arg Asp Glu Ser Pro
785                 790                 795                 800

Asn Leu Phe Leu Lys Lys Asn Arg Arg Leu Arg Lys Cys Val Glu Val
                805                 810                 815

Asp Ile Asn Asn Ala Asp Ser Ser Met Thr Arg Lys Tyr Arg Asn Cys
            820                 825                 830

Ile Ala His Leu Thr Val Val Arg Glu Leu Lys Glu Tyr Ile Gly Asp
        835                 840                 845

Ile Arg Thr Val Asp Ser Tyr Phe Ser Ile Tyr His Tyr Val Met Gln
    850                 855                 860

Arg Cys Ile Thr Lys Arg Glu Asp Asp Thr Lys Gln Glu Glu Lys Ile
865                 870                 875                 880

Lys Tyr Glu Asp Asp Leu Leu Lys Asn His Gly Tyr Thr Lys Asp Phe
                885                 890                 895

Val Lys Ala Leu Asn Ser Pro Phe Gly Tyr Asn Ile Pro Arg Phe Lys
            900                 905                 910

Asn Leu Ser Ile Glu Gln Leu Phe Asp Arg Asn Glu Tyr Leu Thr Glu
        915                 920                 925

Lys

<210> SEQ ID NO 12
<211> LENGTH: 919
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 12

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Ala Ala
        35                  40                  45

-continued

```
Glu Lys Lys Lys Ser Ser Val Lys Ala Ala Gly Met Lys Ser Ile Leu
 50                  55                  60
Val Ser Glu Asn Lys Met Tyr Ile Thr Ser Phe Gly Lys Gly Asn Ser
 65                  70                  75                  80
Ala Val Leu Glu Tyr Glu Val Asp Asn Asp Tyr Asn Lys Thr Gln
                 85                  90                  95
Leu Ser Ser Lys Asp Ser Ser Asn Ile Glu Leu Arg Gly Val Asn Glu
                100                 105                 110
Val Asn Ile Thr Phe Ser Ser Lys His Gly Phe Gly Ser Gly Val Glu
                115                 120                 125
Ile Asn Thr Ser Asn Pro Thr His Arg Ser Gly Glu Ser Ser Pro Val
130                 135                 140
Arg Trp Asp Met Leu Gly Leu Lys Ser Glu Leu Glu Lys Arg Phe Phe
145                 150                 155                 160
Gly Lys Thr Phe Asp Asp Asn Ile His Ile Gln Leu Ile Tyr Asn Ile
                165                 170                 175
Leu Asp Ile Glu Lys Ile Leu Ala Val Tyr Val Thr Asn Ile Val Tyr
                180                 185                 190
Ala Leu Asn Asn Met Leu Gly Ile Lys Lys Ser Glu Ser His Asp Asp
                195                 200                 205
Phe Met Gly Tyr Leu Ser Ala Lys Asn Thr Tyr Asp Val Phe Thr Asn
210                 215                 220
Pro Asn Gly Ser Thr Leu Ser Asp Asp Lys Lys Asn Ile Arg Lys
225                 230                 235                 240
Ser Leu Arg Lys Phe Asn Asp Leu Leu Lys Thr Lys Arg Leu Gly Tyr
                245                 250                 255
Phe Gly Leu Glu Glu Pro Lys Thr Lys Asp Thr Arg Val Ser Gln Ala
                260                 265                 270
Tyr Lys Lys Arg Val Tyr His Met Leu Ala Ile Val Gly Gln Ile Arg
                275                 280                 285
Gln Ser Val Phe His Asp Lys Ser Ser Lys Leu His Glu Asp Leu Tyr
290                 295                 300
Ser Phe Ile Asp Ile Ile Asp Ser Glu Tyr Arg Glu Thr Leu Asp Tyr
305                 310                 315                 320
Leu Val Asp Glu Arg Phe Asp Ser Ile Asn Lys Gly Phe Ile Gln Gly
                325                 330                 335
Asn Lys Val Asn Ile Ser Leu Leu Ile Asp Met Met Lys Gly Tyr Glu
                340                 345                 350
Ala Asp Asp Ile Ile Arg Leu Tyr Tyr Asp Phe Ile Val Leu Lys Ser
                355                 360                 365
Gln Lys Asn Leu Gly Phe Ser Ile Lys Lys Leu Arg Glu Lys Met Leu
                370                 375                 380
Asp Glu Tyr Gly Phe Arg Phe Lys Asp Lys Gln Tyr Asp Ser Val Arg
385                 390                 395                 400
Ser Lys Met Tyr Lys Leu Met Asp Phe Leu Phe Cys Asn Tyr Tyr
                405                 410                 415
Arg Asn Asp Val Ala Ala Gly Glu Ala Leu Val Arg Lys Leu Arg Phe
                420                 425                 430
Ser Met Thr Asp Asp Glu Lys Glu Gly Ile Tyr Ala Asp Glu Ala Ala
                435                 440                 445
Lys Leu Trp Gly Lys Phe Arg Asn Asp Phe Glu Asn Ile Ala Asp His
450                 455                 460
Met Asn Gly Asp Val Ile Lys Glu Leu Gly Lys Ala Asp Met Asp Phe
```

```
        465                 470                 475                 480
Asp Glu Lys Ile Ile Asp Ser Glu Lys Asn Ala Ser Asp Leu Leu
                485                 490                 495
Tyr Phe Ser Lys Met Ile Tyr Met Leu Thr Tyr Phe Leu Asp Gly Lys
                500                 505                 510
Glu Ile Asn Asp Leu Leu Thr Thr Leu Ile Ser Lys Phe Asp Asn Ile
                515                 520                 525
Lys Glu Phe Leu Lys Ile Met Lys Ser Ser Ala Val Asp Val Glu Cys
                530                 535                 540
Glu Leu Thr Ala Gly Tyr Lys Leu Phe Asn Asp Ser Gln Arg Ile Thr
545                 550                 555                 560
Asn Glu Leu Phe Ile Val Lys Asn Ile Ala Ser Met Arg Lys Pro Ala
                565                 570                 575
Ala Ser Ala Lys Leu Thr Met Phe Arg Asp Ala Leu Thr Ile Leu Gly
                580                 585                 590
Ile Asp Asp Asn Ile Thr Asp Asp Arg Ile Ser Glu Ile Leu Lys Leu
                595                 600                 605
Lys Glu Lys Gly Lys Gly Ile His Gly Leu Arg Asn Phe Ile Thr Asn
610                 615                 620
Asn Val Ile Glu Ser Ser Arg Phe Val Tyr Leu Ile Lys Tyr Ala Asn
625                 630                 635                 640
Ala Gln Lys Ile Arg Lys Val Ala Lys Asn Glu Lys Val Val Met Phe
                645                 650                 655
Val Leu Gly Gly Ile Pro Asp Thr Gln Ile Glu Arg Tyr Tyr Lys Ser
                660                 665                 670
Cys Val Glu Phe Pro Asp Met Asn Ser Ser Leu Glu Val Lys Arg Ser
                675                 680                 685
Glu Leu Ala Arg Met Ile Lys Asn Ile Ser Phe Asp Asp Phe Lys Asn
                690                 695                 700
Val Lys Gln Gln Ala Lys Gly Arg Glu Asn Val Ala Lys Glu Arg Ala
705                 710                 715                 720
Lys Ala Val Ile Gly Leu Tyr Leu Thr Val Met Tyr Leu Leu Val Lys
                725                 730                 735
Asn Leu Val Asn Val Asn Ala Arg Tyr Val Ile Ala Ile His Cys Leu
                740                 745                 750
Glu Arg Asp Phe Gly Leu Tyr Lys Glu Ile Ile Pro Glu Leu Ala Ser
                755                 760                 765
Lys Asn Leu Lys Asn Asp Tyr Arg Ile Leu Ser Gln Thr Leu Cys Glu
                770                 775                 780
Leu Cys Asp Lys Ser Pro Asn Leu Phe Leu Lys Lys Asn Arg Arg Leu
785                 790                 795                 800
Arg Lys Cys Val Glu Val Asp Ile Asn Asn Ala Asp Ser Ser Met Thr
                805                 810                 815
Arg Lys Tyr Arg Asn Cys Ile Ala His Leu Thr Val Val Arg Glu Leu
                820                 825                 830
Lys Glu Tyr Ile Gly Asp Ile Arg Thr Val Asp Ser Tyr Phe Ser Ile
                835                 840                 845
Tyr His Tyr Val Met Gln Arg Cys Ile Thr Lys Arg Glu Asn Asp Thr
                850                 855                 860
Lys Gln Glu Glu Lys Ile Lys Tyr Glu Asp Asp Leu Leu Lys Asn His
865                 870                 875                 880
Gly Tyr Thr Lys Asp Phe Val Lys Ala Leu Asn Ser Pro Phe Gly Tyr
                885                 890                 895
```

-continued

```
Asn Ile Pro Arg Phe Lys Asn Leu Ser Ile Glu Gln Leu Phe Asp Arg
                900                 905                 910

Asn Glu Tyr Leu Thr Glu Lys
        915

<210> SEQ ID NO 13
<211> LENGTH: 924
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 13

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Ala Ala
        35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Glu Asp Ser Ser Asn Ile Glu Leu Cys Gly Val Asn Lys
            100                 105                 110

Val Asn Ile Thr Phe Ser Ser Lys His Gly Phe Glu Ser Gly Val Glu
        115                 120                 125

Ile Asn Thr Ser Asn Pro Thr His Arg Ser Gly Glu Ser Ser Pro Val
130                 135                 140

Arg Trp Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Glu Gly Asp Glu Ser Asn Tyr Asp Phe
        195                 200                 205

Met Gly Tyr Leu Ser Thr Phe Asn Thr Tyr Lys Val Phe Thr Asn Pro
210                 215                 220

Asn Gly Ser Thr Leu Ser Asp Asp Lys Lys Glu Asn Ile Arg Lys Ser
225                 230                 235                 240

Leu Ser Lys Phe Asn Ala Leu Leu Lys Thr Lys Arg Leu Gly Tyr Phe
                245                 250                 255

Gly Leu Glu Glu Pro Lys Thr Lys Asp Thr Asn Ala Leu Glu Ala Tyr
            260                 265                 270

Lys Lys Arg Val Tyr Tyr Met Leu Ala Ile Val Gly Gln Ile Arg Gln
        275                 280                 285

Cys Val Phe His Asp Leu Ser Glu His Ser Glu Tyr Asp Leu Tyr Ser
290                 295                 300

Phe Ile Asp Asn Ser Lys Lys Val Tyr Arg Glu Cys Arg Glu Thr Leu
305                 310                 315                 320

Asp Tyr Leu Val Asp Glu Arg Phe Asp Ser Ile Asn Lys Gly Phe Ile
```

```
                  325                 330                 335
Gln Gly Asn Lys Val Asn Ile Ser Leu Leu Ile Asp Met Met Lys Gly
                340                 345                 350
Tyr Glu Ala Asp Asp Ile Ile Arg Leu Tyr Tyr Asp Phe Ile Val Leu
                355                 360                 365
Lys Ser Gln Lys Asn Leu Gly Phe Ser Ile Lys Lys Leu Arg Glu Lys
                370                 375                 380
Met Leu Asp Glu Tyr Gly Phe Arg Phe Lys Asp Lys Gln Tyr Asp Pro
385                 390                 395                 400
Val Arg Ser Lys Met Tyr Lys Leu Met Asp Phe Leu Leu Phe Cys Asn
                405                 410                 415
Tyr Tyr Arg Asn Asp Val Val Ala Gly Glu Ala Leu Val Arg Lys Leu
                420                 425                 430
Arg Phe Ser Met Thr Asp Asp Glu Lys Glu Gly Ile Tyr Ala Asp Glu
                435                 440                 445
Ala Ala Lys Leu Trp Gly Lys Phe Arg Asn Asp Phe Glu Asn Ile Ala
                450                 455                 460
Asp His Met Asn Gly Asp Val Ile Lys Glu Leu Gly Lys Ala Asp Met
465                 470                 475                 480
Asp Phe Asp Glu Lys Ile Leu Asp Ser Glu Lys Lys Asn Ala Ser Asp
                485                 490                 495
Leu Leu Tyr Phe Ser Lys Met Ile Tyr Met Leu Thr Tyr Phe Leu Asp
                500                 505                 510
Gly Lys Glu Ile Asn Asp Leu Leu Thr Thr Leu Ile Ser Lys Phe Asp
                515                 520                 525
Asn Ile Lys Glu Phe Leu Lys Ile Met Lys Ser Ser Ala Val Asn Val
                530                 535                 540
Glu Cys Glu Leu Thr Ala Gly Tyr Lys Leu Phe Asn Asp Ser Gln Arg
545                 550                 555                 560
Ile Thr Asn Glu Leu Phe Ile Val Lys Asn Ile Ala Ser Met Arg Lys
                565                 570                 575
Pro Ala Ala Ser Ala Lys Leu Thr Met Phe Arg Asp Ala Leu Thr Ile
                580                 585                 590
Leu Gly Ile Asp Asp Lys Ile Thr Asp Asp Arg Ile Ser Glu Ile Leu
                595                 600                 605
Lys Leu Lys Glu Lys Gly Lys Gly Ile His Gly Leu Arg Asn Phe Ile
                610                 615                 620
Thr Asn Asn Val Ile Glu Ser Ser Arg Phe Val Tyr Leu Ile Lys Tyr
625                 630                 635                 640
Ala Asn Ala Gln Lys Ile Arg Glu Val Ala Lys Asn Glu Lys Val Val
                645                 650                 655
Met Phe Val Leu Gly Gly Ile Pro Asp Thr Gln Ile Glu Arg Tyr Tyr
                660                 665                 670
Lys Ser Cys Val Glu Phe Pro Asp Met Asn Ser Ser Leu Glu Ala Lys
                675                 680                 685
Arg Ser Glu Leu Ala Arg Met Ile Lys Asn Ile Ser Phe Asp Asp Phe
                690                 695                 700
Lys Asn Val Lys Gln Gln Ala Lys Gly Arg Glu Asn Val Ala Lys Glu
705                 710                 715                 720
Arg Ala Lys Ala Val Ile Gly Leu Tyr Leu Thr Val Met Tyr Leu Leu
                725                 730                 735
Val Glu Asn Leu Val Asn Val Asn Ala Arg Tyr Val Ile Ala Ile His
                740                 745                 750
```

```
Cys Leu Glu Arg Asp Phe Gly Leu Tyr Lys Glu Ile Ile Ser Glu Leu
        755                 760                 765

Ala Ser Lys Asn Leu Lys Asn Asp Tyr Arg Ile Leu Ser Gln Thr Leu
770                 775                 780

Cys Glu Leu Cys Asp Asn Cys Asp Glu Ser Pro Asn Leu Phe Leu Lys
785                 790                 795                 800

Lys Asn Glu Arg Leu Arg Lys Cys Val Glu Val Asp Ile Asn Asn Ala
                805                 810                 815

Asp Ser Asn Met Thr Arg Lys Tyr Arg Asn Cys Ile Ala His Leu Thr
                820                 825                 830

Val Val Arg Glu Leu Asn Lys Tyr Ile Lys Asp Ile Arg Thr Val Asp
                835                 840                 845

Ser Tyr Phe Ser Ile Tyr His Tyr Val Met Gln Arg Cys Ile Thr Lys
        850                 855                 860

Arg Glu Asp Asp Lys Lys Gln Glu Gly Lys Ile Lys Tyr Glu Asp Asp
865                 870                 875                 880

Leu Leu Lys Asn His Gly Tyr Thr Lys Asp Phe Val Lys Ala Leu Asn
                885                 890                 895

Ser Pro Phe Gly Tyr Asn Ile Pro Arg Phe Lys Asn Leu Ser Ile Glu
        900                 905                 910

Gln Leu Phe Asp Arg Asn Glu Tyr Leu Thr Glu Lys
        915                 920
```

<210> SEQ ID NO 14
<211> LENGTH: 922
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 14

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Ala Ala Pro Ala Ala
        35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asp Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
    130                 135                 140

Arg Trp Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
```

-continued

```
            180                 185                 190
Ala Leu Asn Asn Met Leu Gly Glu Gly Gly Asp Glu Ser His Asp Asp
            195                 200                 205
Ile Met Gly Tyr Leu Ser Ala Lys Asn Thr Tyr Asp Val Phe Thr Asp
            210                 215                 220
Pro Asp Glu Ser Asp Leu Ser Lys Asn Ile Lys Gly Asn Ile Lys Lys
225                 230                 235                 240
Ser Leu Ser Lys Phe Asn Asp Leu Leu Lys Thr Lys Arg Leu Gly Tyr
                245                 250                 255
Phe Gly Leu Glu Glu Pro Lys Thr Lys Asp Lys Arg Ala Ser Glu Ala
                260                 265                 270
Tyr Lys Lys Arg Val Tyr His Met Leu Ala Ile Val Gly Gln Ile Arg
                275                 280                 285
Gln Ser Val Phe His Asp Lys Ser Asn Glu Leu Asp Glu Tyr Leu Tyr
            290                 295                 300
Ser Phe Ile Asp Ile Ile Asp Ser Glu Tyr Arg Asp Thr Leu Asp Tyr
305                 310                 315                 320
Leu Val Asp Glu Arg Phe Asp Ser Ile Asn Lys Gly Phe Ile Gln Gly
                325                 330                 335
Asn Lys Val Asn Ile Ser Leu Leu Ile Asp Met Met Lys Gly Tyr Glu
            340                 345                 350
Ala Asp Asp Ile Ile Arg Leu Tyr Tyr Asp Phe Ile Val Leu Lys Ser
            355                 360                 365
Gln Lys Asn Leu Gly Phe Ser Ile Lys Lys Leu Arg Glu Lys Met Leu
            370                 375                 380
Asp Glu Tyr Gly Phe Arg Phe Lys Asp Lys Gln Tyr Asp Ser Val Arg
385                 390                 395                 400
Ser Lys Met Tyr Lys Leu Met Asp Phe Leu Leu Phe Cys Asn Tyr Tyr
                405                 410                 415
Arg Asn Asp Val Ile Ala Gly Glu Ala Leu Val Arg Lys Leu Arg Phe
                420                 425                 430
Ser Met Thr Asp Asp Glu Lys Glu Gly Ile Tyr Ala Asp Glu Ala Ala
                435                 440                 445
Lys Leu Trp Gly Lys Phe Arg Asn Asp Phe Glu Asn Ile Ala Asp His
            450                 455                 460
Met Asn Gly Asp Val Ile Lys Glu Leu Gly Lys Ala Asp Met Asp Phe
465                 470                 475                 480
Asp Glu Lys Ile Leu Asp Ser Glu Lys Lys Asn Ala Ser Asp Leu Leu
                485                 490                 495
Tyr Phe Ser Lys Met Ile Tyr Met Leu Thr Tyr Phe Leu Asp Gly Lys
                500                 505                 510
Glu Ile Asn Asp Leu Leu Thr Thr Leu Ile Ser Lys Phe Asp Asn Ile
            515                 520                 525
Lys Glu Phe Leu Lys Ile Met Lys Ser Ser Ala Val Asp Val Glu Cys
            530                 535                 540
Glu Leu Thr Ala Gly Tyr Lys Leu Phe Asn Asp Ser Gln Arg Ile Thr
545                 550                 555                 560
Asn Glu Leu Phe Ile Val Lys Asn Ile Ala Ser Met Arg Lys Pro Ala
                565                 570                 575
Ala Ser Ala Lys Leu Thr Met Phe Arg Asp Ala Leu Thr Ile Leu Gly
                580                 585                 590
Ile Asp Asp Asn Ile Thr Asp Asp Arg Ile Ser Glu Ile Leu Lys Leu
                595                 600                 605
```

```
Lys Glu Lys Gly Lys Gly Ile His Gly Leu Arg Asn Phe Ile Thr Asn
        610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
            645                 650                 655

Val Leu Gly Gly Ile Pro Asp Thr Gln Ile Glu Arg Tyr Tyr Lys Ser
        660                 665                 670

Cys Val Glu Phe Pro Asp Met Asn Ser Ser Met Gly Ala Lys Arg Arg
            675                 680                 685

Glu Leu Ala Lys Met Ile Lys Ser Ile Ser Phe Glu Asp Phe Lys Asp
        690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
            725                 730                 735

Asn Leu Val Asn Val Asn Ala Arg Tyr Val Ile Ala Ile His Cys Leu
        740                 745                 750

Glu Arg Asp Phe Gly Leu Tyr Lys Glu Ile Pro Glu Leu Ala Ser
        755                 760                 765

Lys Asn Leu Lys Asn Asp Tyr Arg Ile Leu Ser Gln Thr Leu Cys Glu
770                 775                 780

Leu Cys Asp Asn Gly Asp Glu Ser Pro Asn Leu Phe Leu Lys Lys Asn
785                 790                 795                 800

Lys Arg Leu Arg Lys Cys Val Glu Val Asp Ile Asn Asn Ala Asp Ser
            805                 810                 815

Asn Met Thr Arg Lys Tyr Arg Asn Cys Ile Ala His Leu Thr Val Val
        820                 825                 830

Arg Glu Leu Asn Lys Tyr Ile Lys Asp Ile Arg Thr Val Asp Ser Tyr
        835                 840                 845

Phe Ser Ile Tyr His Tyr Val Met Gln Arg Cys Ile Thr Lys Arg Glu
850                 855                 860

Asn Asp Thr Lys Gln Glu Lys Ile Asn Tyr Glu Asp Asp Leu Leu
865                 870                 875                 880

Lys Asn His Gly Tyr Thr Lys Asp Phe Val Lys Ala Leu Asn Ser Pro
            885                 890                 895

Phe Gly Tyr Asn Ile Pro Arg Phe Lys Asn Leu Ser Ile Glu Gln Leu
        900                 905                 910

Phe Asp Arg Asn Glu Tyr Leu Thr Glu Lys
        915                 920

<210> SEQ ID NO 15
<211> LENGTH: 923
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 15

Met Phe Met Ala Lys Lys Asn Lys Met Lys Pro Arg Glu Arg Glu
1               5                   10                  15

Ala Gln Lys Lys Ala Arg Gln Leu Lys Ala Ala Glu Ile Asn Asn Asn
            20                  25                  30

Ala Val Pro Ala Ile Ala Ala Met His Ala Ala Glu Val Ile Ala Pro
```

```
                    35                  40                  45
Ala Ala Glu Lys Lys Lys Ser Ser Val Lys Ala Ala Gly Met Lys Ser
 50                  55                  60

Ile Leu Val Ser Glu Asn Lys Met Tyr Ile Thr Ser Phe Gly Lys Gly
 65                  70                  75                  80

Asn Ser Ala Val Leu Glu Tyr Glu Val Asp Asn Asp Tyr Asn Gln
                 85                  90                  95

Thr Gln Leu Ser Ser Lys Asp Asn Ser Asn Ile Glu Leu Cys Gly Val
                100                 105                 110

Thr Lys Val Asn Ile Thr Phe Ser Ser Lys His Gly Phe Glu Ser Gly
                115                 120                 125

Val Glu Ile Asn Thr Ser Asn Pro Thr His Arg Ser Gly Glu Ser Ser
        130                 135                 140

Pro Val Arg Gly Asp Met Leu Gly Leu Lys Ser Glu Leu Glu Lys Arg
145                 150                 155                 160

Phe Phe Gly Lys Thr Phe Asp Asp Asn Ile His Ile Gln Leu Ile Tyr
                165                 170                 175

Asn Ile Leu Asp Ile Glu Lys Ile Leu Ala Val Tyr Val Thr Asn Ile
                180                 185                 190

Val Tyr Ala Leu Asn Asn Met Leu Gly Glu Gly Asp Glu Ser Asn Tyr
        195                 200                 205

Asp Phe Met Gly Tyr Leu Ser Thr Phe Asn Thr Tyr Lys Val Phe Thr
        210                 215                 220

Asn Pro Asn Gly Ser Thr Leu Ser Asp Asp Lys Lys Glu Asn Ile Arg
225                 230                 235                 240

Lys Ser Leu Ser Lys Phe Asn Ala Leu Leu Lys Thr Lys Arg Leu Gly
                245                 250                 255

Tyr Phe Gly Leu Glu Glu Pro Lys Thr Lys Asp Thr Arg Ala Ser Glu
                260                 265                 270

Ala Tyr Lys Lys Arg Val Tyr His Met Leu Ala Ile Val Gly Gln Ile
        275                 280                 285

Arg Gln Cys Val Phe His Asp Lys Ser Gly Ala Lys Arg Phe Asp Leu
        290                 295                 300

Tyr Ser Phe Ile Asn Asn Ile Tyr Pro Glu Tyr Arg Asp Thr Leu Asp
305                 310                 315                 320

Tyr Leu Val Glu Glu Arg Leu Lys Ser Ile Asn Lys Asp Phe Ile Gln
                325                 330                 335

Gly Asn Lys Val Asn Ile Ser Leu Leu Ile Asp Met Met Lys Gly Tyr
                340                 345                 350

Glu Ala Asp Asp Ile Ile Arg Leu Tyr Tyr Asp Phe Ile Val Leu Lys
        355                 360                 365

Ser Gln Lys Asn Leu Gly Phe Ser Ile Lys Lys Leu Arg Glu Lys Met
        370                 375                 380

Leu Asp Glu Tyr Gly Phe Arg Phe Lys Asp Lys Gln Tyr Asp Ser Val
385                 390                 395                 400

Arg Ser Lys Met Tyr Lys Leu Met Asp Phe Leu Leu Phe Cys Asn Tyr
                405                 410                 415

Tyr Arg Asn Asp Val Val Ala Gly Glu Ala Leu Val Arg Lys Leu Arg
                420                 425                 430

Phe Ser Met Thr Asp Asp Glu Lys Glu Gly Ile Tyr Ala Asp Glu Ala
        435                 440                 445

Ala Lys Leu Trp Gly Lys Phe Arg Asn Asp Phe Glu Asn Ile Ala Asp
        450                 455                 460
```

```
His Met Asn Gly Asp Val Ile Lys Glu Leu Gly Lys Ala Asp Met Asp
465                 470                 475                 480

Phe Asp Glu Lys Ile Leu Asp Ser Glu Lys Lys Asn Ala Ser Asp Leu
                485                 490                 495

Leu Tyr Phe Ser Lys Met Ile Tyr Met Leu Thr Tyr Phe Leu Asp Gly
            500                 505                 510

Lys Glu Ile Asn Asp Leu Leu Thr Thr Leu Ile Ser Lys Phe Asp Asn
                515                 520                 525

Ile Lys Glu Phe Leu Lys Ile Met Lys Ser Ser Ala Val Asp Val Glu
            530                 535                 540

Cys Glu Leu Thr Ala Gly Tyr Lys Leu Phe Asn Asp Ser Gln Arg Ile
545                 550                 555                 560

Thr Asn Glu Leu Phe Ile Val Lys Asn Ile Ala Ser Met Arg Lys Pro
                565                 570                 575

Ala Ala Ser Ala Lys Leu Thr Met Phe Arg Asp Ala Leu Thr Ile Leu
            580                 585                 590

Gly Ile Asp Asp Lys Ile Thr Asp Arg Ile Ser Glu Ile Leu Lys
                595                 600                 605

Leu Lys Glu Lys Gly Lys Gly Ile His Gly Leu Arg Asn Phe Ile Thr
610                 615                 620

Asn Asn Val Ile Glu Ser Ser Arg Phe Val Tyr Leu Ile Lys Tyr Ala
625                 630                 635                 640

Asn Ala Gln Lys Ile Arg Glu Val Ala Lys Asn Glu Lys Val Val Met
            645                 650                 655

Phe Val Leu Gly Gly Ile Pro Asp Thr Gln Ile Glu Arg Tyr Tyr Lys
            660                 665                 670

Ser Cys Val Glu Phe Pro Asp Met Asn Ser Ser Leu Glu Ala Lys Arg
            675                 680                 685

Ser Glu Leu Ala Arg Met Ile Lys Asn Ile Ser Phe Asp Asp Phe Lys
690                 695                 700

Asn Val Lys Gln Gln Ala Lys Gly Arg Glu Asn Val Ala Lys Glu Arg
705                 710                 715                 720

Ala Lys Ala Val Ile Gly Leu Tyr Leu Thr Val Met Tyr Leu Leu Val
            725                 730                 735

Lys Asn Leu Val Asn Val Asn Ala Arg Tyr Val Ile Ala Ile His Cys
            740                 745                 750

Leu Glu Arg Asp Phe Gly Leu Tyr Lys Glu Ile Ile Pro Glu Leu Ala
            755                 760                 765

Ser Lys Asn Leu Lys Asn Asp Tyr Arg Ile Leu Ser Gln Thr Leu Cys
            770                 775                 780

Glu Leu Cys Asp Asp Arg Asp Glu Ser Pro Asn Leu Phe Leu Lys Lys
785                 790                 795                 800

Asn Lys Arg Leu Arg Lys Cys Val Glu Val Asp Ile Asn Asn Ala Asp
                805                 810                 815

Ser Ser Met Thr Arg Lys Tyr Arg Asn Cys Ile Ala His Leu Thr Val
            820                 825                 830

Val Arg Glu Leu Lys Lys Tyr Ile Gly Asp Ile Arg Thr Val Asp Ser
            835                 840                 845

Tyr Phe Ser Ile Tyr His Tyr Val Met Gln Arg Cys Ile Thr Lys Arg
            850                 855                 860

Glu Asp Asp Thr Lys Gln Glu Glu Lys Ile Lys Tyr Glu Asp Asp Leu
865                 870                 875                 880
```

```
Leu Lys Asn His Gly Tyr Thr Lys Asp Phe Val Lys Ala Leu Asn Ser
            885                 890                 895

Pro Phe Gly Tyr Asn Ile Pro Arg Phe Lys Asn Leu Ser Ile Glu Gln
            900                 905                 910

Leu Phe Asp Arg Asn Glu Tyr Leu Thr Glu Lys
            915                 920

<210> SEQ ID NO 16
<211> LENGTH: 963
<212> TYPE: PRT
<213> ORGANISM: Unknown
<220> FEATURE:
<223> OTHER INFORMATION: Description of Unknown:
      Mammals-digestive system-asian elephant fecal-elephas
      maximus sequence

<400> SEQUENCE: 16

Met Tyr Asn Ile Asp Lys Leu Trp Leu Thr His Ile Leu Phe Val Ser
1               5                   10                  15

Leu Thr Ala Gly Lys Lys Asn Glu Thr Ile Leu Glu Gln Glu Ile Asn
            20                  25                  30

Lys Asp Ser Asn Lys Lys Asn Ile Leu Val Asn Pro Thr Lys Phe Asp
            35                  40                  45

Ala Asn Ile Lys Glu Val Arg Met Val Ser Ile Lys Pro Glu Lys Tyr
        50                  55                  60

Asn Glu Thr Val Val Asn Asn Pro Tyr Tyr Val Lys Asp Gly Gln Val
65                  70                  75                  80

Val Gly Gln Asp Tyr Leu Gly Ile Lys Asp Lys Leu Glu Asp Thr Phe
            85                  90                  95

Phe Gly Lys Thr Tyr Asp Asp Asn Ile His Ile Gln Ile Ala Tyr Lys
            100                 105                 110

Leu Leu Asp Ile Arg Lys Ile Met Gly Met Ser Val Gly Ser Ala Val
            115                 120                 125

Phe Ser Leu Asn Asn Leu Gln Gln Arg Pro Val Gly Glu Asn Pro Asn
        130                 135                 140

Asp Ile Val Gly Gln Ile Lys Thr Asp Thr Ser Phe Asp Glu Ile Pro
145                 150                 155                 160

Asp Asn Tyr Ala Lys Ala Asp Lys Phe Ile Asp Ile Leu Leu Asp
            165                 170                 175

Tyr Thr Arg Tyr Phe Asp Asn Val Phe Glu Lys Gln Ser Ile Ser Val
            180                 185                 190

Asp Asp Lys Thr Lys Asp Ile Leu Asn Asn Leu Lys Glu Cys Glu Thr
            195                 200                 205

Val Ser Val Lys Thr Val Gly Thr Ile Asp Arg Ile Asn Lys Asn Asp
        210                 215                 220

Pro Asn Asn Asn Asn Tyr Thr Ile Phe Lys Ile Gly Gly Leu Lys Ile
225                 230                 235                 240

Lys Leu Lys Gly Ile Leu Ser Asn Val Asp Val Gly Thr Lys Leu Asn
            245                 250                 255

Ile Glu Gly Gln Ile Arg Arg Asn Asn Asp Tyr Arg Asp Lys Lys Gly
            260                 265                 270

Lys Leu Cys Arg Ser Tyr Ser Leu Leu Thr Gly Ala Lys Tyr Ser Ile
            275                 280                 285

Ser His Glu Val Tyr Asn Pro Asp Thr Tyr Thr Phe Asn Tyr Asp Ile
        290                 295                 300

Leu Arg Leu Val Ser Tyr Leu Arg Gln Ala Val Val His Asn Asn Asn
```

```
            305                 310                 315                 320
Asp Asp Tyr Ile Asp Trp Leu Tyr Ser Ile Asp Asn Lys Lys Glu Thr
                    325                 330                 335

Lys Asp Ile Leu Asn Ala Ala Asn Lys Val Phe Glu Ser Gln Leu Glu
                    340                 345                 350

Ala Phe Asn Lys Asp Phe Asn Ala Asn Ala Gln Lys Asn Val Tyr Met
                    355                 360                 365

Ile Ala Ser Val Leu Asn Asp Ser Pro Lys Thr Met Phe Lys Glu Glu
    370                 375                 380

Ile Lys Asp Ile Tyr Glu Lys Tyr Asn Phe Val Leu Phe Lys Glu
385                 390                 395                 400

Asn Arg Asn Val Gly Ile Asn Leu Arg Asn Ile Arg Asn Asn Ile Phe
                    405                 410                 415

Tyr Glu Asp Ile Lys Pro Asn Tyr Asp Glu Lys Glu Leu Ser Arg Glu
                    420                 425                 430

Arg Ala Lys Ile Asn Thr Leu Leu Asp Tyr Phe Ile Tyr Gln Asp Phe
                    435                 440                 445

Asn Asn Asn Glu Lys Leu Ala Glu Asp Val Ile Ala Arg Leu Gln Pro
                    450                 455                 460

Thr Lys Gln Glu Val Asp Lys Val Gln Val Tyr Ala Asp Val Thr Lys
465                 470                 475                 480

Glu Phe Lys Val Arg Asn Pro Lys Leu Val Asp Arg Ile Leu Ser Thr
                    485                 490                 495

Val Lys Asn Thr Ile Glu Ala Lys Ile Glu Asn Phe Ile Pro Asp Asn
                    500                 505                 510

Cys Val Pro Ser Ser Ile Lys Val Ser Ser Leu Ala Lys Tyr Val
                    515                 520                 525

Tyr Val Leu Ala Lys Phe Leu Asp Thr Lys Glu Val Asn Asn Leu Leu
                    530                 535                 540

Thr Ser Leu Ile Asn Ser Phe Glu Asn Ile Gly Ser Leu Val Lys Val
545                 550                 555                 560

Leu Lys Asp Glu Lys Gly Tyr Ser Ile Tyr Lys Asp Arg Phe Ala Leu
                    565                 570                 575

Leu Asn Gln Lys Asn Pro Phe Asp Leu Ala Asn Asp Phe Ile Leu Val
                    580                 585                 590

Lys Asn Leu Ala Thr Met Lys Thr Lys Leu Ala Lys Ala Asn Val Lys
                    595                 600                 605

Asp Val Lys Asn Lys Val Gly Lys Arg Leu Tyr Cys Ser Ala Ile Asn
                    610                 615                 620

Leu Phe Lys Asp Lys Asn Asp Glu Val Ile Leu Asp Asn Gln Glu Phe
625                 630                 635                 640

Glu Asp Ile Met Ser Glu Phe Ser Ser Asn Val Gly Asn Lys Lys Asn
                    645                 650                 655

Arg Arg Gly Thr Ala Gly Ser Lys Ile Arg Asn Phe Leu Ile Asn Asn
                    660                 665                 670

Val Ile Asp Ser Arg Arg Phe Tyr Phe Ile Ile Lys Tyr Tyr Asp Thr
                    675                 680                 685

Arg Arg Cys His Glu Ile Gln Asn Glu Asn Leu Val Arg Phe Ile
                    690                 695                 700

Leu Gly Arg Glu Asp Met Pro Thr Asp Gln Leu Ile Arg Tyr Tyr Lys
705                 710                 715                 720

Thr Ile Thr Gly Asn Glu Cys Asn Asn Arg Asn Gln Ile Ile Asp Thr
                    725                 730                 735
```

```
Leu Val Lys Lys Leu Lys Glu Val Ser Phe Arg Lys Leu Leu Leu Lys
            740                 745                 750

Gly Glu Arg Leu Lys Glu Ile Gly Asn Asp Gln Asp Asn Gln Glu Val
            755                 760                 765

Glu Ser Leu Lys Ser Leu Ile Gly Leu Tyr Leu Thr Ile Cys Tyr Leu
            770                 775                 780

Ile Val Lys Gly Ile Val Asn Val Asn Ser Val Tyr Leu Leu Ala Trp
785                 790                 795                 800

Ser Ala Tyr Glu Arg Asp Met Tyr Tyr Leu Tyr Asn Glu Asp Met Glu
            805                 810                 815

Asp Lys Asn Thr Asn His Asp Tyr Leu Lys Ala Ala Thr Asp Phe Tyr
            820                 825                 830

Asn Asn Lys Ser Cys Tyr Gln Lys Arg His Lys Tyr Leu Ile Lys Asp
            835                 840                 845

Ile Glu Glu Ala Arg Gln Asn Ser Asn Asn Leu Asn Tyr Lys Asp Tyr
850                 855                 860

Arg Asn Lys Val Cys His Tyr Asn Ile Cys Thr Ser Phe Met Asp Tyr
865                 870                 875                 880

Ala Asn Asn Ile Gly Lys Val Ser Cys Tyr Phe Asp Ile Tyr Asn Tyr
            885                 890                 895

Cys Phe Gln Arg Tyr Phe Ala Lys Lys Asn Asp Asn Leu Ser Thr Leu
            900                 905                 910

Leu Asp Thr Tyr Asn Cys Tyr Asn Lys Asp Tyr Leu Lys Leu Leu Asn
            915                 920                 925

Met Pro Phe Ala Tyr Asn Met Ala Arg Tyr Lys Asn Leu Thr Ile Ala
            930                 935                 940

Asp Leu Phe Asn Asp Lys Tyr Pro Ser Glu Asn Lys Glu Ala Thr Ala
945                 950                 955                 960

Ser Asn Asp

<210> SEQ ID NO 17
<211> LENGTH: 1057
<212> TYPE: PRT
<213> ORGANISM: Unknown
<220> FEATURE:
<223> OTHER INFORMATION: Description of Unknown:
      Mammals-digestive system-asian elephant fecal-elephas
      maximus sequence

<400> SEQUENCE: 17

Met Glu Glu Thr Lys Val Thr Lys Glu Thr Thr Ile Glu Lys Gln Ser
1               5                   10                  15

Thr Lys Arg His Lys Gln Lys Ser Lys Lys Thr Ala Thr Lys Met Ser
            20                  25                  30

Gly Leu Lys Ser Ala Leu Val Ile Asn Asn His Glu Met Leu Leu Thr
        35                  40                  45

Ser Phe Gly Lys Gly Asn Asn Ala Ile Ala Glu Lys Arg Tyr Ile Leu
    50                  55                  60

Asp Gly Asp Ile Glu Thr Ile Asn Asn Lys Lys Phe Asp Ala
65                  70                  75                  80

Asn Asn Asp Ser Lys Val Val Ile Lys Gly Ile Ser Asn Pro Asn
            85                  90                  95

Gly Gln Leu Thr Asn Pro Leu Phe Asp Gln Ser Pro Thr Ala Ile Gln
            100                 105                 110

Pro Asn Arg Thr Ser Gly Asn Asp Met Ile Gly Ile Arg Arg Met Leu
```

```
                115                 120                 125
Glu Arg Lys Tyr Phe Val His Asn Glu Glu Asn Lys Glu Phe Gln Asp
    130                 135                 140

Asn Ile Arg Ile Gln Ile Ala Tyr Cys Ile Leu Asp Ile Glu Lys Ile
145                 150                 155                 160

Leu Met Pro His Ile Asn Asn Ile Cys Phe Glu Ile Asn Asn Met Leu
                    165                 170                 175

Arg Leu Glu Gly Tyr Gln Glu Asp Ser Phe Met Gly Ser Phe Asn Leu
                180                 185                 190

Tyr Lys Pro Tyr Asp Ala Phe Ile Ala Thr Thr Asp Lys Glu Ser
            195                 200                 205

Ser Arg Arg Asp Asn Phe Ala Lys Leu Met Thr Ser Lys Gln Val Arg
    210                 215                 220

Tyr Leu Gly Asn Ala Leu Tyr Ser Asp Ser Leu Ser Asn Leu Thr Lys
225                 230                 235                 240

Asp Glu Ile Leu Asp Gly Lys Arg Ser Lys Glu Leu Lys Lys Tyr Tyr
                245                 250                 255

Gln Glu Leu Cys Leu Leu Gly Met Val Arg Gln Ser Met Ile His Ser
                260                 265                 270

Asn Gln Phe Asn Ser Ser Ile Tyr Thr Leu Asp Ser Ser Tyr Asp Ser
            275                 280                 285

Thr Met Asn Thr Ala Glu Leu Leu Gly Lys Gly Asp Asp Ser Ser Leu
    290                 295                 300

Val Ala Leu Ala Thr Asp Ala Arg Val Glu Ala Arg Ala Ile Leu Asp
305                 310                 315                 320

Glu Ile Tyr Lys Lys Gly Val Asp Ser Ile Asn Asn Ser Phe Leu Ser
                325                 330                 335

Asn Ser Ile Asn Asp Leu Glu Asn Leu Phe Lys Ile Tyr Lys Cys Asp
                340                 345                 350

Ser Ser Glu Lys Lys Thr Glu Leu Ile Lys Gln Tyr Tyr Asp Phe Cys
            355                 360                 365

Ile Arg Lys Pro Gln Met Asn Met Gly Phe Ser Ile Thr Thr Ile Arg
    370                 375                 380

Glu Gly Met Phe Thr Arg Cys Ser Glu Ala Asn Thr Leu Leu Leu Cys
385                 390                 395                 400

Asp Glu Gly Ser Thr Val Lys Leu Asn Val His Asp Thr Met Lys Ser
                405                 410                 415

Lys Phe Tyr Lys Asn Leu Asp Phe Met Ile Tyr Lys Tyr Tyr Lys Tyr
                420                 425                 430

Glu Asn Pro Glu Lys Gly Glu Lys Leu Ile Glu Asp Leu Arg Ser Lys
            435                 440                 445

Ile Lys Gly Lys Lys Glu Asp Glu Lys Lys Gln Arg Tyr Ala
    450                 455                 460

Glu Glu Ser Ala Cys Ile Leu Lys Ala Lys Arg Asp Ile Ile Lys Lys
465                 470                 475                 480

Asp Leu Thr Glu Ala Ala Asn Lys Asp Leu Phe Ala Asp Leu Val Lys
                485                 490                 495

Ser Asn Lys Asn Glu Lys Gln Lys Phe Lys Asn Glu Tyr Glu Leu
            500                 505                 510

Leu Lys Pro Phe Met Ile Pro Val Lys Val Asp Tyr Phe Ser Glu Leu
    515                 520                 525

Ile Tyr Leu Val Thr Arg Phe Leu Ser Gly Lys Glu Ile Asn Asp Leu
    530                 535                 540
```

```
Leu Thr Gln Leu Ile Asn Lys Phe Glu Asn Ile Ala Ala Phe Ile Arg
545                 550                 555                 560

Met Tyr Gln Asn Asp Gln Gly Lys Leu Glu Phe Thr Ala Asn Tyr Lys
                565                 570                 575

Met Phe Glu Ile Asp Pro Gln Lys Asp Ile Pro Lys Asp Gly Lys Arg
                580                 585                 590

Val Leu Ser Gly Ser Ala Lys Ile Ala Tyr Tyr Leu Arg Thr Ile Asn
                595                 600                 605

Tyr Ile Ala Arg Met Glu Ser Phe Glu Ile Lys Ser Asp Lys Thr Ala
                610                 615                 620

Ile Asn Asp Ala Ile Ser Leu Leu Gly Tyr Asn Ser Asn Glu His Arg
625                 630                 635                 640

Asp Glu Phe Ile Thr Tyr Thr Met Ala Lys His Val Val Asp Lys Tyr
                645                 650                 655

Gln Asn Thr Asp Tyr Gln Lys Ile Val Lys Asp Phe Leu Ser Ala Asn
                660                 665                 670

Lys Thr Leu Asp Cys Lys Ser Lys Asn Met Gln Ala Phe Val Ser Glu
                675                 680                 685

Leu Lys Asn Ala His Leu Ser Glu Asn Tyr Glu Gln Arg Glu Lys Glu
690                 695                 700

Ile Tyr Glu Leu Ala Asp Thr Asn Leu Pro Ala Tyr Phe Ser Glu Glu
705                 710                 715                 720

Asp Lys Glu Lys Leu Ala Arg Tyr Ile Val His Ser Asp Gly Thr Tyr
                725                 730                 735

Lys Lys Phe Leu Lys Glu Ser Phe Tyr Ala Ile Glu Glu Leu Pro Asn
                740                 745                 750

Glu Gly Phe Arg Asn Phe Ile Ser Asn Asn Val Ile Asn Ser Arg Arg
                755                 760                 765

Phe Asn Tyr Ile Met Arg Phe Cys Asn Pro Glu Lys Ile Ala Asn Ile
                770                 775                 780

Gly Lys Asn Lys Val Leu Ile Ser Phe Ala Leu Ser Ser Leu Ala Glu
785                 790                 795                 800

Lys Thr Asp Met Ile Ala Lys Tyr Tyr Arg Val Phe Cys Asp Arg Ile
                805                 810                 815

Asp Asp Gln Lys Thr Met Glu Asp Tyr Leu Val Asn Lys Leu Thr Lys
                820                 825                 830

Ile Ser Tyr Thr Glu Phe Leu Asn Val Asn Gln Lys Ala Asn Ala Glu
                835                 840                 845

Lys Asn Lys Glu Lys Asp Arg Ser Gln Lys Leu Ile Gly Leu Tyr Ile
                850                 855                 860

Thr Leu Leu Tyr Glu Ile Val Lys Asn Leu Val Asn Ile Asn Ser Arg
865                 870                 875                 880

Tyr Asn Ile Ala Phe Gln Arg Cys Asp Asn Asp Ser Ile Met Ile Leu
                885                 890                 895

Gln Gly Gln Tyr Asp Glu Arg Ala Val Gln Ser Lys Leu Thr Lys
                900                 905                 910

Lys Phe Ile Ser Asn Gln Lys Leu Asn Ser Tyr Ser Cys Arg Tyr Leu
                915                 920                 925

Thr His Asn Ile Ser Gln Leu Asp Arg Cys Asn Asp Phe Ile Arg Gln
                930                 935                 940

Tyr Arg Asn Lys Val Ala His Leu Glu Val Val Ser Asn Ile Asp Glu
945                 950                 955                 960
```

-continued

```
Tyr Leu Ser Gly Ile Lys His Ile Glu Ser Tyr Tyr Ala Leu Tyr His
                965                 970                 975
Tyr Leu Met Gln Lys Cys Leu Leu Lys Asn Tyr Arg Ile Glu Asp His
            980                 985                 990
Ser Gln Asn Glu Tyr Lys Asn Leu Asn Asp Phe Ser Ser Lys Leu Asp
        995                 1000                1005
Lys His Gly Thr Tyr Val Lys Asp Phe Val Lys Ala Leu Asn Val
    1010                1015                1020
Pro Phe Gly Tyr Asn Leu Pro Arg Tyr Lys Asn Leu Ser Ile Asp
    1025                1030                1035
Glu Leu Phe Asp Arg Asn Lys Leu Lys Thr Gly Gly Thr Ile Glu
    1040                1045                1050
Met Lys Gly Glu
    1055

<210> SEQ ID NO 18
<211> LENGTH: 977
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 18

Met Lys Glu Arg Ile Asp Met Ile Glu Lys Lys Ser Tyr Ala Lys
1               5                   10                  15
Gly Met Gly Leu Lys Ser Thr Leu Val Ser Asp Ser Lys Val Tyr Met
            20                  25                  30
Thr Ser Phe Gly Asn Gly Asn Asp Ala Arg Leu Glu Lys Val Val Glu
        35                  40                  45
Asn Asn Ala Ile Ser Cys Leu Val Asp Lys Lys Glu Ala Phe Val Ala
    50                  55                  60
Glu Ile Thr Asp Lys Asn Ala Gly Tyr Lys Ile Ile Asn Lys Lys Phe
65                  70                  75                  80
Gly His Pro Lys Gly Tyr Asp Val Val Ala Asn Asn Pro Leu Tyr Thr
                85                  90                  95
Gly Pro Val Gln Gln Asp Met Leu Gly Leu Lys Glu Thr Leu Glu Lys
            100                 105                 110
Arg Tyr Phe Gly Ser Ser Val Ser Gly Asn Asp Asn Ile Cys Ile Gln
        115                 120                 125
Val Ile His Asn Ile Leu Asp Ile Glu Lys Ile Leu Ala Glu Tyr Ile
    130                 135                 140
Thr Asn Ala Ala Tyr Ala Val Asn Asn Ile Ala Gly Leu Asp Lys Asp
145                 150                 155                 160
Ile Ile Gly Phe Gly Lys Phe Ser Thr Val Tyr Thr Phe Asp Glu Phe
                165                 170                 175
Ala Glu Pro Asp Arg His Lys Glu Arg Phe Ile Lys Asp Gly Lys Leu
            180                 185                 190
Asp Thr Lys Leu Ile Asn Gln Leu Lys Asn Gln Tyr Asp Glu Phe Asp
        195                 200                 205
Ala Phe Leu Asp Asp Thr Arg Phe Gly Tyr Phe Gly Lys Ala Phe Phe
    210                 215                 220
Cys Lys Glu Gly Asp Lys Tyr Leu Asn Lys Gln Asp Asn Glu Arg Tyr
225                 230                 235                 240
His Ile Leu Ala Leu Leu Ser Gly Leu Arg Asn Trp Val Val His Asn
                245                 250                 255
```

-continued

Asn Glu Val Glu Ser Lys Ile Asp Arg Lys Trp Leu Tyr Asn Leu Asp
            260                 265                 270

Lys Asn Leu Asp Lys Glu Tyr Ile Thr Thr Leu Asp Tyr Met Tyr Ser
            275                 280                 285

Asp Ile Ala Asp Glu Leu Thr Lys Ser Phe Ser Lys Asn Ser Ala Ala
            290                 295                 300

Asn Val Asn Tyr Ile Ala Glu Ile Leu Asn Ile Asp Ser Lys Thr Phe
305                 310                 315                 320

Ala Glu Gln Tyr Phe Arg Phe Ser Ile Met Lys Gln Lys Asn Leu
                325                 330                 335

Gly Phe Thr Leu Thr Lys Leu Arg Glu Cys Met Leu Asp Arg Glu Glu
            340                 345                 350

Leu Ser Asp Ile Arg Asp Asn His Lys Val Phe Asp Ser Ile Arg Ser
            355                 360                 365

Lys Leu Tyr Thr Met Met Asp Phe Val Ile Tyr Arg Tyr Tyr Ile Glu
            370                 375                 380

Glu Ala Lys Lys Ile Glu Asn Glu Asn Lys Thr Leu Ser Asp Asp Lys
385                 390                 395                 400

Lys Lys Leu Ser Glu Lys Asp Ile Phe Ile Ser Leu Arg Gly Ser
            405                 410                 415

Phe Ser Glu Glu Gln Lys Asp Lys Leu Tyr Ser Asp Glu Ala Glu Arg
            420                 425                 430

Leu Trp Ala Lys Leu Gly Lys Leu Met Leu Glu Ile Lys Lys Phe Arg
            435                 440                 445

Gly Gln Met Thr Arg Asp Tyr Lys Lys Ser Asp Thr Pro Thr Leu Asn
            450                 455                 460

Arg Ile Leu Pro Glu Ser Glu Asp Val Ser Thr Phe Ser Lys Leu Met
465                 470                 475                 480

Tyr Ala Leu Thr Met Phe Leu Asp Gly Lys Glu Ile Asn Glu Leu Leu
                485                 490                 495

Thr Thr Leu Ile Asn Lys Phe Asp Asn Ile Gln Ser Met Leu Lys Ile
            500                 505                 510

Met Pro Leu Ile Gly Val Asn Ala Lys Phe Ser Ser Asp Tyr Ala Phe
            515                 520                 525

Phe Asn Asn Ser Glu Lys Ile Ala Asp Glu Leu Lys Leu Ile Lys Ser
            530                 535                 540

Phe Ala Arg Met Gly Glu Pro Val Ala Asn Ala Lys Arg Asp Met Met
545                 550                 555                 560

Ile Asp Ala Ile Lys Ile Leu Gly Thr Asp Leu Asp Asn Glu Ile
            565                 570                 575

Lys Lys Leu Ala Asp Ser Phe Phe Lys Asp Ser Asn Gly Lys Leu Leu
            580                 585                 590

His Lys Gly Lys His Gly Met Arg Asn Phe Ile Ile Asn Asn Val Val
            595                 600                 605

Asn Asn Lys Arg Phe His Tyr Ile Ile Arg Tyr Gly Asp Pro Ala His
            610                 615                 620

Leu His Glu Ile Ala Lys Asn Glu Val Val Arg Phe Val Leu Gly
625                 630                 635                 640

Arg Ile Ala Asp Ile Gln Lys Lys Gln Gly Lys Gly Lys Asn Gln
                645                 650                 655

Ile Asp Arg Tyr Tyr Glu Ile Cys Ile Gly Asn Gly Tyr Gly Lys Ser
            660                 665                 670

```
Val Ser Glu Lys Ile Asp Ala Leu Thr Lys Val Ile Ile Asn Met Asn
            675                 680                 685

Tyr Asp Gln Phe Glu Ala Lys Arg Lys Val Ile Glu Asn Thr Gly Arg
        690                 695                 700

Asp Asn Ala Glu Arg Glu Lys Tyr Lys Ile Ile Ser Leu Tyr Leu
705                 710                 715                 720

Thr Val Ile Tyr Gln Ile Leu Lys Asn Leu Asn Val Asn Ser Arg
                725                 730                 735

Tyr Val Ile Gly Phe His Cys Val Glu Arg Asp Ala Gln Leu Tyr Lys
                740                 745                 750

Glu Lys Gly Tyr Asp Ile Asn Thr Asn Asn Leu Glu Ser Lys Gly Phe
            755                 760                 765

Thr Ser Val Thr Lys Leu Cys Val Gly Ile Ala Asp Asp Pro Val
            770                 775                 780

Lys Tyr Lys Asn Val Glu Ile Glu Leu Lys Glu Arg Ala Leu Ala Ser
785                 790                 795                 800

Phe Asp Ala Leu Glu Lys Glu Asn Pro Glu Leu Tyr Glu Lys Tyr Asn
                805                 810                 815

Met Tyr Ser Glu Lys Gln Lys Glu Ala Glu Leu Glu Lys Gln Ile Asn
            820                 825                 830

Arg Glu Lys Ala Lys Thr Ala Leu Asn Ala His Leu Arg Asn Thr Lys
                835                 840                 845

Trp Asn Val Ile Ile Arg Glu Asn Ile Arg Asn Thr Glu Lys Asp Ala
            850                 855                 860

Cys Lys Gln Phe Arg Asn Lys Ala Asp His Leu Glu Val Ala Arg Tyr
865                 870                 875                 880

Ala Tyr Lys Tyr Ile Asn Asp Ile Ser Glu Val Asn Ser Tyr Phe Gln
                885                 890                 895

Leu Tyr His Tyr Ile Met Gln Arg Ile Ile Asp Ser Ser Gly Asn
                900                 905                 910

Asn Ala Asn Gly Met Ile Lys Lys Tyr Glu Ser Val Ile Ser Asp
            915                 920                 925

Lys Lys Tyr Asn Asp Arg Leu Leu Lys Leu Leu Cys Val Pro Phe Gly
930                 935                 940

Tyr Cys Ile Pro Arg Phe Lys Asn Leu Ser Ile Glu Ala Leu Phe Asp
945                 950                 955                 960

Lys Asn Glu Ala Ala Lys Tyr Asp Lys Ile Lys Lys Val Ala Val
                965                 970                 975

Arg

<210> SEQ ID NO 19
<211> LENGTH: 971
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 19

Met Ile Glu Lys Lys Ser Tyr Ala Lys Gly Met Gly Leu Lys Ser
1               5                   10                  15

Thr Leu Val Ser Asp Ser Lys Val Tyr Met Thr Ser Phe Gly Asn Gly
                20                  25                  30

Asn Asp Ala Arg Leu Glu Lys Val Val Glu Asn Asn Ala Ile Ser Cys
            35                  40                  45
```

```
Leu Val Asp Lys Lys Glu Ala Phe Val Ala Glu Ile Thr Asp Lys Asn
    50              55                  60

Ala Gly Tyr Lys Ile Ile Asn Lys Lys Phe Gly His Pro Lys Gly Tyr
65              70                  75                  80

Asp Val Val Ala Asn Asn Pro Leu Tyr Thr Gly Pro Val Gln Gln Asp
                85                  90                  95

Met Leu Gly Leu Lys Glu Thr Leu Glu Lys Arg Tyr Phe Gly Ser Ser
            100                 105                 110

Val Ser Gly Asn Asp Asn Ile Cys Ile Gln Val Ile His Asn Ile Leu
            115                 120                 125

Asp Ile Glu Lys Ile Leu Ala Glu Tyr Ile Thr Asn Ala Ala Tyr Ala
    130                 135                 140

Val Asn Asn Ile Ala Gly Leu Asp Lys Asp Ile Ile Gly Phe Gly Lys
145                 150                 155                 160

Phe Ser Thr Val Tyr Thr Phe Asp Glu Phe Ala Glu Pro Asp Arg His
                165                 170                 175

Lys Glu Arg Phe Ile Lys Asp Gly Lys Leu Asp Thr Lys Leu Ile Asn
            180                 185                 190

Gln Leu Lys Asn Gln Tyr Asp Glu Phe Asp Ala Phe Leu Asp Asp Thr
    195                 200                 205

Arg Phe Gly Tyr Phe Gly Lys Ala Phe Phe Cys Lys Glu Gly Asp Lys
210                 215                 220

Tyr Leu Asn Lys Gln Asp Asn Glu Arg Tyr His Ile Leu Ala Leu Leu
225                 230                 235                 240

Ser Gly Leu Arg Asn Trp Val Val His Asn Asn Glu Val Glu Ser Lys
                245                 250                 255

Ile Asp Arg Lys Trp Leu Tyr Asn Leu Asp Lys Asn Leu Asp Lys Glu
            260                 265                 270

Tyr Ile Thr Thr Leu Asp Tyr Met Tyr Ser Asp Ile Ala Asp Glu Leu
    275                 280                 285

Thr Lys Ser Phe Ser Lys Asn Ser Ala Ala Asn Val Asn Tyr Ile Ala
290                 295                 300

Glu Ile Leu Asn Ile Asp Ser Lys Thr Phe Ala Glu Gln Tyr Phe Arg
305                 310                 315                 320

Phe Ser Ile Met Lys Glu Gln Lys Asn Leu Gly Phe Thr Leu Thr Lys
                325                 330                 335

Leu Arg Glu Cys Met Leu Asp Arg Glu Glu Leu Ser Asp Ile Arg Asp
            340                 345                 350

Asn His Lys Val Phe Asp Ser Ile Arg Ser Lys Leu Tyr Thr Met Met
    355                 360                 365

Asp Phe Val Ile Tyr Arg Tyr Tyr Ile Glu Glu Ala Lys Lys Ile Glu
370                 375                 380

Asn Glu Asn Lys Thr Leu Ser Asp Asp Lys Lys Lys Leu Ser Glu Lys
385                 390                 395                 400

Asp Ile Phe Ile Ile Ser Leu Arg Gly Ser Phe Ser Glu Glu Gln Lys
                405                 410                 415

Asp Lys Leu Tyr Ser Asp Glu Ala Glu Arg Leu Trp Ala Lys Leu Gly
            420                 425                 430

Lys Leu Met Leu Glu Ile Lys Lys Phe Arg Gly Gln Met Thr Arg Asp
    435                 440                 445

Tyr Lys Lys Ser Asp Thr Pro Thr Leu Asn Arg Ile Leu Pro Glu Ser
450                 455                 460

Glu Asp Val Ser Thr Phe Ser Lys Leu Met Tyr Ala Leu Thr Met Phe
```

```
                465                 470                 475                 480
            Leu Asp Gly Lys Glu Ile Asn Glu Leu Leu Thr Thr Leu Ile Asn Lys
                            485                 490                 495
            Phe Asp Asn Ile Gln Ser Met Leu Lys Ile Met Pro Leu Ile Gly Val
                        500                 505                 510
            Asn Ala Lys Phe Ser Ser Asp Tyr Ala Phe Asn Asn Ser Glu Lys
                        515                 520                 525
            Ile Ala Asp Glu Leu Lys Leu Ile Lys Ser Phe Ala Arg Met Gly Glu
                        530                 535                 540
            Pro Val Ala Asn Ala Lys Arg Asp Met Met Ile Asp Ala Ile Lys Ile
            545                 550                 555                 560
            Leu Gly Thr Asp Leu Asp Asn Glu Ile Lys Lys Leu Ala Asp Ser
                            565                 570                 575
            Phe Phe Lys Asp Ser Asn Gly Lys Leu Leu His Lys Gly Lys His Gly
                        580                 585                 590
            Met Arg Asn Phe Ile Ile Asn Asn Val Val Asn Asn Lys Arg Phe His
                        595                 600                 605
            Tyr Ile Ile Arg Tyr Gly Asp Pro Ala His Leu His Glu Ile Ala Lys
            610                 615                 620
            Asn Glu Val Val Val Arg Phe Val Leu Gly Arg Ile Ala Asp Ile Gln
            625                 630                 635                 640
            Lys Lys Gln Gly Lys Gly Gly Lys Asn Gln Ile Asp Arg Tyr Tyr Glu
                            645                 650                 655
            Ile Cys Ile Gly Asn Gly Tyr Gly Lys Ser Val Ser Glu Lys Ile Asp
                        660                 665                 670
            Ala Leu Thr Lys Val Ile Ile Asn Met Asn Tyr Asp Gln Phe Glu Ala
                        675                 680                 685
            Lys Arg Lys Val Ile Glu Asn Thr Gly Arg Asp Asn Ala Glu Arg Glu
                        690                 695                 700
            Lys Tyr Lys Lys Ile Ile Ser Leu Tyr Leu Thr Val Ile Tyr Gln Ile
            705                 710                 715                 720
            Leu Lys Asn Leu Val Asn Val Asn Ser Arg Tyr Val Ile Gly Phe His
                            725                 730                 735
            Cys Val Glu Arg Asp Ala Gln Leu Tyr Lys Glu Lys Gly Tyr Asp Ile
                        740                 745                 750
            Asn Thr Asn Asn Leu Glu Ser Lys Gly Phe Thr Ser Val Thr Lys Leu
                        755                 760                 765
            Cys Val Gly Ile Ala Asp Asp Pro Val Lys Tyr Lys Asn Val Glu
                        770                 775                 780
            Ile Glu Leu Lys Glu Arg Ala Leu Ala Ser Phe Asp Ala Leu Glu Lys
            785                 790                 795                 800
            Glu Asn Pro Glu Leu Tyr Glu Lys Tyr Asn Met Tyr Ser Glu Lys Gln
                            805                 810                 815
            Lys Glu Ala Glu Leu Glu Lys Gln Ile Asn Arg Glu Lys Ala Lys Thr
                        820                 825                 830
            Ala Leu Asn Ala His Leu Arg Asn Thr Lys Trp Asn Val Ile Ile Arg
                        835                 840                 845
            Glu Asn Ile Arg Asn Thr Glu Lys Asp Ala Cys Lys Gln Phe Arg Asn
            850                 855                 860
            Lys Ala Asp His Leu Glu Val Ala Arg Tyr Ala Tyr Lys Tyr Ile Asn
            865                 870                 875                 880
            Asp Ile Ser Glu Val Asn Ser Tyr Phe Gln Leu Tyr His Tyr Ile Met
                            885                 890                 895
```

Gln Arg Ile Ile Ile Asp Ser Ser Gly Asn Asn Ala Asn Gly Met Ile
                900                 905                 910

Lys Lys Tyr Tyr Glu Ser Val Ile Ser Asp Lys Lys Tyr Asn Asp Arg
        915                 920                 925

Leu Leu Lys Leu Leu Cys Val Pro Phe Gly Tyr Cys Ile Pro Arg Phe
        930                 935                 940

Lys Asn Leu Ser Ile Glu Ala Leu Phe Asp Lys Asn Glu Ala Ala Lys
945                 950                 955                 960

Tyr Asp Lys Ile Lys Lys Val Ala Val Arg
                965                 970

<210> SEQ ID NO 20
<211> LENGTH: 900
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 20

Met Ser Thr Lys Lys Arg Phe Arg Tyr Ser Val Ala Ala Lys Ala Ala
1               5                   10                  15

Gly Leu Lys Ser Ser Leu Ala Val Asp Thr Asp Arg Thr Val Met Thr
                20                  25                  30

Ser Phe Gly His Gly Asn Ala Ala Ile Leu Glu Lys Glu Ile Val Asp
            35                  40                  45

Gly Glu Ile Ser Val Leu Asn Ile Glu Asn Pro Ala Phe Asp Ala Val
        50                  55                  60

Ile Asn Asp Lys Lys Tyr Ala Leu Thr Gly His His Ala Gly Val His
65                  70                  75                  80

Ala Leu Val Asp Gln Pro Gln Asn Arg Ser Asp Ala Val His Ile Arg
                85                  90                  95

Gly Ala Leu Glu Lys Lys Tyr Phe Gly Asp Thr Phe Ala Asp Asn Ile
                100                 105                 110

His Val Gln Ile Ala Tyr Asn Ile Leu Asp Ile Thr Lys Ile Leu Thr
            115                 120                 125

Val Tyr Ala Asn Asn Val Val Tyr Ala Leu Asn Asn Leu Val His Ala
        130                 135                 140

Asp Asp Asp Thr Gln Ala Asp Glu Leu Asp Ser Leu Gly Asn Phe Ser
145                 150                 155                 160

Ala Gly Thr Ser Tyr Ala Lys Ser Lys Ser Lys Ser Lys Ser Lys Gln
                165                 170                 175

Gln Asp Phe Val Glu Leu Phe Ile Lys Lys Glu Ile His Gly Tyr
            180                 185                 190

Phe Gly Asp Thr Phe Ala Phe Leu Asp Lys Arg Ile Ala Asp Ala Asp
        195                 200                 205

Lys Glu Lys Gln Val Tyr Ala Met Leu Ala Cys Leu Gly Ser Leu Arg
                210                 215                 220

Gln Ala Cys Ser His Tyr Arg Ile Arg Tyr Ser Val Asn Gly Lys Asn
225                 230                 235                 240

Val Asp Ala Asp Ala Asp Thr Trp Leu Phe Ser Ser Ala Gln Leu Asp
                245                 250                 255

Gln Thr Asp Pro Leu Phe Ser Glu Met Leu Asn Arg Ile Tyr Ser His
            260                 265                 270

Lys Ile Lys Thr Val Asn Gln Asn Phe Phe Glu Asn Asn Arg Lys Ala

-continued

```
                275                 280                 285
Asn Phe Pro Ile Leu Lys Lys Met Tyr Pro Glu Thr Thr Leu Lys Val
            290                 295                 300
Leu Met Asn Glu Tyr Tyr Asp Phe Ser Ile Arg Lys Gly Tyr Lys Asn
305                 310                 315                 320
Phe Gly Phe Ser Ile Lys Ser Leu Arg Glu Ala Leu Leu Ser Pro Gln
                325                 330                 335
Tyr Glu Ser Leu Ile Gly Val Gln Ile Lys Asp Asn Lys Glu Tyr Asp
                340                 345                 350
Thr Val Arg Ser Lys Leu Tyr Gln Leu Phe Asp Phe Ala Leu Thr Arg
                355                 360                 365
Tyr Phe Asn Gln His Pro Asp Met Val Asp Ala Phe Val Glu Leu
370                 375                 380
Arg Ser Leu Ala Lys Asp Glu Asp Ala Lys Asn Ala Val Tyr Glu Lys
385                 390                 395                 400
Tyr Ala Lys Ala Val Trp Asn Asp Val Lys Gln Pro Ile Ala Val Met
                405                 410                 415
Leu Ser Tyr Met Asn Gly Ser Ala Ile Lys Asn Ile Lys Ala Phe Glu
                420                 425                 430
Leu Lys Pro Asp Gln Lys Glu Leu Asn Gly Ile Met Asn Ser Asn Ala
                435                 440                 445
Leu Asp Val Pro His Phe Cys Lys Leu Val Tyr Phe Leu Thr Arg Phe
                450                 455                 460
Leu Asp Gly Lys Glu Ile Asn Asp Leu Leu Thr Thr Leu Val Asn Lys
465                 470                 475                 480
Phe Asp Asn Ile His Ser Phe Asn Gln Val Leu Thr Ala Leu Gly Leu
                485                 490                 495
Ser Ala Ser Tyr Glu Ala Asp Tyr Lys Ile Phe Glu Asp Ser Gly Arg
                500                 505                 510
Val Val Glu Tyr Leu Arg Glu Ile Asn Ser Phe Ala Arg Met Thr Val
                515                 520                 525
Asp Met Glu Lys Ile Lys Arg Ser Ala Tyr Lys Lys Ala Leu Leu Ile
                530                 535                 540
Leu Gly Ser Ser Lys Tyr Ser Asp Glu Asp Leu Asp Ala Arg Val Asp
545                 550                 555                 560
Glu Met Leu Gly Val Asp Tyr Asn Gln Asn Gly Glu Lys Ile Lys Val
                565                 570                 575
Arg Val Asp Thr Gly Phe Arg Asn Phe Ile Ala Asn Asn Val Val Glu
                580                 585                 590
Ser Ser Arg Phe His Tyr Leu Ile Arg Tyr Cys His Pro Arg Lys Ile
                595                 600                 605
Arg Asn Leu Ala Gly Asn Ala Ala Leu Ile Glu Tyr Gln Leu Arg Arg
                610                 615                 620
Leu Pro Glu Leu Gln Ile Leu Arg Tyr Glu Ala Cys Thr Glu Pro
625                 630                 635                 640
Ile Lys Arg Thr Ala Arg Thr Met Asp Glu Lys Ile Gly Thr Leu Ile
                645                 650                 655
Asp Leu Ile Val Lys Met Asp Phe Ser Gln Phe Glu Asp Val Gln Gln
                660                 665                 670
Asn Asp Arg Val Arg Val Phe Ser Asp Ala Glu Lys Lys Glu Lys Ile
                675                 680                 685
Arg Lys Met Arg Glu Lys Gln Arg Tyr Gln Ser Ile Ile Ser Leu Tyr
                690                 695                 700
```

```
Leu Thr Met Leu Tyr Leu Ile Val Lys Asn Leu Val Asn Ile Asn Ala
705                 710                 715                 720

Arg Tyr Val Met Ala Phe Gln Ala Trp Glu Arg Asp Asn Tyr Leu Leu
            725                 730                 735

Leu Gln Leu Ser Gly Lys Glu Ala Glu Ala Glu Tyr Leu Asn Leu Thr
        740                 745                 750

Arg His Phe Ile Glu Pro Leu Asp Gly Ala Lys Pro Tyr Leu Lys Lys
    755                 760                 765

Arg Pro Val Glu Tyr Leu Lys Lys Asp Met Ala Met Val Gly Asn Ser
770                 775                 780

Ser Ile Arg His Phe Arg Asn Ala Thr Val His Leu Asn Val Ile Met
785                 790                 795                 800

Glu Ala His Arg Tyr Thr Lys Asp Ile Lys Tyr Ile Gly Ser Tyr Tyr
            805                 810                 815

Ala Leu Tyr His Tyr Ile Leu Gln Arg His Leu Leu Asp Lys Ile Glu
        820                 825                 830

Glu Asp Ser Tyr Ala Glu Lys Thr Val Ser Glu Lys Leu Trp Glu Ser
    835                 840                 845

Gln Ile Ser Gln Tyr Gly Thr Tyr Ser Lys Asp Phe Val Lys Ala Leu
850                 855                 860

Cys Cys Pro Phe Gly Tyr Asn Leu Pro Arg Phe Lys Asn Leu Ser Ile
865                 870                 875                 880

Glu Gln Leu Phe Asp Arg Asn Glu Ser Lys Glu Ile Thr Asp Ala Thr
            885                 890                 895

Ala Pro Arg Gln
            900

<210> SEQ ID NO 21
<211> LENGTH: 927
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 21

Met Ala Lys Lys Lys Ala Lys Gln Arg Arg Glu Gln Glu Ala
1               5                   10                  15

Ala Arg Met Asn Lys Ile Gln Ser Ala Val Lys Ala Lys Ala Glu Thr
            20                  25                  30

Ala Pro Ala Val Ser Ser Ala Phe Val Glu Lys Arg Lys Asp Lys Gln
        35                  40                  45

Ser Lys Lys Thr Phe Ala Lys Ala Ser Gly Leu Lys Ser Thr Leu Ala
    50                  55                  60

Val Asp Asn Ser Ala Val Met Thr Val Phe Gly Arg Gly Asn Glu Ala
65                  70                  75                  80

Lys Leu Asp His Arg Ile Asn Ala Asp Leu Gln Ser Glu Ser Leu His
            85                  90                  95

Pro Gln Ala Ala Leu Lys Asn Val His Ala Pro Asn Lys Gln Lys Ile
        100                 105                 110

His Phe Ile Gly Arg Met Gln Asp Met Asn Leu Thr Ala Asp His Pro
    115                 120                 125

Leu His Ser His Asp Gly Glu Arg Ala Val Gly Ala Asp Leu Leu Cys
130                 135                 140

Ala Lys Asp Lys Leu Glu Gln Leu Tyr Phe Gly Arg Thr Phe Asn Asp
```

```
            145                 150                 155                 160
Asn Ile His Ile Gln Leu Ile Tyr Gln Ile Leu Asp Ile Gln Lys Ile
                    165                 170                 175

Leu Ala Leu His Ala Asn Asn Ile Ile Phe Ala Leu Asp Asn Leu Leu
                    180                 185                 190

His Lys Lys Asn Asp Glu Leu Ser Asp Asp Phe Val Gly Met Gly Arg
                    195                 200                 205

Met Arg Ala Thr Ile Gly Tyr Asp Ala Phe Arg Asn Ser Thr Asn Gln
            210                 215                 220

Lys Val Gln Glu Thr Tyr Arg Glu Phe Gln Glu Phe Val Arg Arg Lys
225                 230                 235                 240

Glu Leu Leu Tyr Phe Gly Ser Ala Phe Tyr Asn Gly Asp Thr Arg Arg
                    245                 250                 255

Asp Glu Lys Val Ile Tyr His Ile Leu Ser Leu Ala Ala Ser Val Arg
                    260                 265                 270

Gln Phe Cys Phe His Asn Asp Tyr Thr Ser Asp Asp Gly Lys Gly Phe
                    275                 280                 285

Ile Lys Ala Asp Trp Met Tyr Arg Leu Glu Glu Ala Leu Pro Ala Glu
                    290                 295                 300

Tyr Lys Asp Thr Leu Asp Ala Leu Tyr Leu Glu Gly Val Glu Gly Leu
305                 310                 315                 320

Asp Gln Ser Phe Leu Lys Asn Asn Thr Val Asn Ile Gln Ile Leu Cys
                    325                 330                 335

Ser Ile Phe Asn His Asp Asp Pro Asn Lys Ile Ala Glu Glu Tyr Tyr
                    340                 345                 350

Gly Phe Leu Met Thr Lys Glu Tyr Lys Asn Met Gly Phe Ser Ile Lys
                    355                 360                 365

Lys Leu Arg Glu Cys Met Leu Glu Leu Pro Glu Leu Ser Gly Tyr Lys
                    370                 375                 380

Glu Asp Gln Tyr Asn Ser Val Arg Ser Lys Leu Tyr Lys Leu Phe Asp
385                 390                 395                 400

Phe Ile Ile Ala His Tyr Phe Arg Lys His Pro Glu Lys Gly Glu Glu
                    405                 410                 415

Met Val Asp Cys Leu Arg Leu Cys Met Thr Glu Asp Glu Lys Asp Ser
                    420                 425                 430

His Tyr Glu Gly Thr Ala Lys Lys Leu Val Arg Glu Leu Ala Tyr Asp
                    435                 440                 445

Met Gln Glu Ala Ala Glu Gln Ala Asn Gly Ser Asn Ile Thr Gln Met
            450                 455                 460

Gln Lys Asn Glu Gln Gln Gly Lys Thr Lys Gly Met Phe Ala Ile Arg
465                 470                 475                 480

Asp Glu Ile Arg Val Ser Arg Lys Pro Val Ser Tyr Phe Ser Lys Val
                    485                 490                 495

Ile Tyr Val Met Thr Leu Leu Leu Asp Gly Lys Glu Ile Asn Asp Leu
                    500                 505                 510

Leu Thr Thr Leu Ile Asn Lys Phe Glu Asn Ile Val Ser Phe Glu Asp
                    515                 520                 525

Val Leu Arg Gln Leu Asn Val Asp Cys Thr Phe Lys Pro Glu Phe Ala
                    530                 535                 540

Phe Phe Gly Tyr Asp Arg Cys Arg Asn Ile Ser Gly Glu Leu Arg Leu
545                 550                 555                 560

Ile Asn Ser Phe Ala Arg Met Gln Lys Pro Ser Ala Lys Ala Lys His
                    565                 570                 575
```

-continued

```
Val Met Tyr Arg Asp Ala Leu Arg Ile Leu Gly Leu Asp Asn Gly Met
            580                 585                 590

Ser Glu Glu Ala Leu Asp Gln Glu Val Arg Arg Ile Leu Gln Ile Gly
        595                 600                 605

Ala Asp Gly Lys Pro Ile Lys Asn Ala Asn Lys Gly Phe Arg Asn Phe
    610                 615                 620

Ile Ala Ser Asn Val Ile Glu Ser Ser Arg Phe Arg Tyr Leu Val Arg
625                 630                 635                 640

Tyr Asn Asn Pro His Lys Thr Arg Met Ile Ala Gln Asn Glu Ala Ile
                645                 650                 655

Val Arg Phe Val Leu Ser Glu Ile Pro Asp Glu Gln Ile Arg Arg Tyr
            660                 665                 670

Tyr Asp Val Cys Arg Asp Pro Lys Leu Pro Arg Ser Ser Arg Glu
        675                 680                 685

Ala Gln Val Asp Ile Leu Thr Gly Ile Ile Thr Asp Val Asn Tyr Arg
    690                 695                 700

Ile Phe Glu Asp Val Pro Gln Ser Lys Lys Ile Asn Lys Asp Arg Pro
705                 710                 715                 720

Asp Ala Asn Asp Arg Met Thr Leu Lys Lys Gln Arg Tyr Gln Ala Ile
                725                 730                 735

Val Ser Leu Tyr Leu Thr Val Met Tyr Leu Val Thr Lys Asn Leu Val
            740                 745                 750

Tyr Val Asn Ser Arg Tyr Val Met Ala Phe His Ala Leu Glu Arg Asp
        755                 760                 765

Ala Tyr Leu Tyr Gly Ile Thr Asn Ile Lys Gly Asp Tyr Arg Lys Leu
    770                 775                 780

Thr Asp Asn Leu Leu Ala Asp Glu Asn Tyr Lys Lys Phe Gly His Phe
785                 790                 795                 800

Lys Asn Lys Lys Trp Arg Gly Ile Ala Glu Gln Asn Leu Arg Asn Ser
                805                 810                 815

Asp Val Pro Val Ile Lys Ser Phe Arg Asn Met Ala Ala His Ile Ser
            820                 825                 830

Val Ile Arg Asn Ile Asp Leu Tyr Ile Gly Asp Ile Gln Lys Val Asp
        835                 840                 845

Ser Tyr Phe Ala Leu Tyr His Phe Leu Met Gln Lys Leu Ile Gln Arg
    850                 855                 860

Val Val Pro Glu Asn Thr Lys Gly Leu Ser Asp Gln Thr Lys Lys Tyr
865                 870                 875                 880

Tyr Asp Ala Leu Glu Gln Tyr Asn Thr Tyr Cys Lys Asp Phe Val Lys
                885                 890                 895

Ala Tyr Cys Thr Pro Phe Ala Tyr Val Thr Pro Arg Tyr Lys Asn Leu
            900                 905                 910

Thr Ile Asp Gly Leu Phe Asp Arg Asn Arg Pro Gly Glu Asp Lys
        915                 920                 925

<210> SEQ ID NO 22
<211> LENGTH: 1141
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 22

Met Gly Val Glu Lys Asn Lys Val Phe Glu Ser Val Ile Met Asn Phe
```

-continued

```
1               5                   10                  15
Asp Gln Glu Arg Lys Tyr Gly Phe Ile Glu Tyr Lys Glu Thr Asn Asn
                20                  25                  30
Leu Phe Phe His Met Glu Asn Val Lys Asn Pro Lys Glu Ile Val Lys
                35                  40                  45
Gly Ala Lys Val Arg Phe Glu Ile Tyr Glu Asn Pro Lys Pro Lys Lys
                50                  55                  60
Gln Asn Gln Arg Phe Ser Ala Ile Asn Val Glu Val Ile Thr Asp Glu
 65                 70                  75                  80
Thr His Lys Glu Ala Lys Ile Gln Lys Asn Glu Phe Lys Thr Phe Asp
                85                  90                  95
Gln Phe Thr Lys Glu Leu Gln Glu Thr Gln Lys Val Asn Gly Glu Thr
                100                 105                 110
Lys Lys Glu His Ile Thr Lys Asn Lys His Thr Asn Val Lys Ala Ala
                115                 120                 125
Gly Val Lys Ser Val Phe Ala Val Asp Asp Gly Asn Val Leu Ile Thr
                130                 135                 140
Ser Phe Gly Arg Gly Asn Ala Ala Asp Ile Glu Thr Leu Lys Ser Asp
145                 150                 155                 160
Asp Asp Lys Thr Ile Asn Leu Thr Glu Thr Glu Asn Gln Lys Lys Tyr
                165                 170                 175
Val Val Thr Asn Lys Arg Ser Asn Val Lys Gly Leu Ala Asp Asn Pro
                180                 185                 190
Thr Lys Val Glu Ser Ile Ile Pro Gly Glu Thr Gln Ile Gly Phe Lys
                195                 200                 205
Ser Ile Leu Glu Lys His Phe Phe Gly Arg Thr Phe Asn Asp Asn Ile
                210                 215                 220
His Ile Gln Ile Ile His Asn Ile Leu Asp Ile Lys Lys Ile Leu Ala
225                 230                 235                 240
Val His Thr Asn Asn Ile Val Tyr Ala Leu Asp Asn Ile His Glu Arg
                245                 250                 255
Gly Arg Glu Asn Ser Ala Glu Lys Pro Ile Asp Met Ile Gly Ala Gly
                260                 265                 270
Gly Ile Ser Thr Ser Lys Glu Tyr Glu Gln Tyr Cys Ser Glu Lys Ser
                275                 280                 285
Asp Tyr Glu Asp Asn Phe Leu Lys Gln Leu Ile Asn Asn Glu Arg Ile
                290                 295                 300
Ala Tyr Phe Gly Asn Ala Phe Phe Lys Asp Glu Gly Asn Lys Lys Val
305                 310                 315                 320
Met Arg Thr Glu Lys Glu Ile Tyr Tyr Ile Leu Gly Met Leu Asn Glu
                325                 330                 335
Val Arg Asn Val Ser Thr His Phe Thr Glu Glu Asp Asn Arg Asp Trp
                340                 345                 350
Ala Lys Ala Asn Leu Tyr Asn Leu Ser Asn Arg Leu Lys Val Gly Ser
                355                 360                 365
Lys Glu Val Leu Asn Gln Leu Tyr Lys Glu Lys Ile Asp Lys Ile Asp
                370                 375                 380
Ala Asn Gly Phe Val Asn Lys Gly Cys Lys Arg Asp Phe Ser Ile Leu
385                 390                 395                 400
Phe Lys Ser Leu Asn Leu Thr Thr Asp Lys Asp Lys Gly Glu Leu Val
                405                 410                 415
Val Gly Phe Tyr Asp Phe Ser Ile Arg Lys Asn Tyr Lys Asn Ile Gly
                420                 425                 430
```

```
Phe Ser Ile Lys Thr Leu Arg Glu Tyr Met Leu Lys Ile Ser Asn Ser
    435                 440                 445

Thr Leu Cys Ala Asp Thr Ile Ser Asn Asn Ala Ile Arg Pro Lys Ala
450                 455                 460

Tyr Lys Leu Tyr Asp Phe Ile Ile Trp His Tyr Tyr Met Asn Lys Pro
465                 470                 475                 480

Asp Lys Ile Asn Asp Phe Val Glu Lys Leu Arg Thr Gln Asn Lys Asn
            485                 490                 495

Asp Glu Lys Ile Lys Leu Tyr Tyr Asp Glu Ala Val Cys Leu Leu Ser
            500                 505                 510

Glu Leu Gly Arg Glu Ile His Thr Met Thr Ser Cys Val His Asn Ile
            515                 520                 525

Glu Asn Thr Ser Tyr Glu Ile Thr Asp Lys Lys Gln Lys Glu Tyr Tyr
            530                 535                 540

Lys Met Gln Ile Asn Ser Leu Asn Ser Ala Asp Lys Val Ser Asp Phe
545                 550                 555                 560

Ser Lys Val Ile Tyr Leu Val Thr Leu Phe Leu Asp Gly Lys Glu Ile
                565                 570                 575

Asn Asp Leu Leu Thr Thr Leu Ile Asn Lys Phe Asp Asn Ile Ala Ser
            580                 585                 590

Leu Leu Ser Val Leu Glu Lys Gln Ser Gly Lys Lys Val Glu Phe Val
            595                 600                 605

Glu Asn Tyr Ser Phe Phe Asn Ser Ser Asn Leu Leu Lys Glu Lys Thr
            610                 615                 620

Leu Asn Lys Ser Glu Asn Tyr Thr Cys Lys Ile Val Glu Glu Leu Arg
625                 630                 635                 640

Glu Ile Asn Ser Phe Ala Arg Met Thr Gly Asp Cys Lys Ile Arg Lys
                645                 650                 655

Ser Ala Phe Glu Asp Ala Ser Gln Leu Leu Gly Tyr His Asp Lys Thr
            660                 665                 670

Val Asn Asn Leu Phe Glu Val Leu Arg Leu Lys Glu Leu Glu Ser Lys
            675                 680                 685

Asp Trp Lys Lys Arg Thr Asp Asp Glu Gln Gln Glu Tyr Asp Arg Leu
            690                 695                 700

Leu Asn Lys His His Tyr Phe Lys Ser Gly Lys Lys Leu Pro Asp Thr
705                 710                 715                 720

Gly Leu Arg Asn Phe Ile Ile Asn Asn Val Ile Glu Ser Arg Arg Phe
                725                 730                 735

Asn Tyr Ile Val Arg Tyr Ala Asp Pro Lys Lys Ile Arg Lys Cys Thr
            740                 745                 750

Glu Asn Asn Glu Leu Leu Lys Phe Ala Phe Lys Asp Val Pro Asp Ser
            755                 760                 765

Gln Val Asp Arg Tyr Tyr Asn Ile Cys Val Thr Asn Lys Ile Thr Asn
            770                 775                 780

Ala Thr Arg Glu Glu Lys Ile Glu Arg Leu Val Asp Ile Ile Lys Ser
785                 790                 795                 800

Met Asn Leu Ser Lys Val Ala Thr Val Lys Gln Arg Asp Lys Gln Asp
                805                 810                 815

Asn Val Glu Lys Gln Lys Gln Leu Ala Ile Met Ser Leu Tyr Leu Asn
            820                 825                 830

Ile Leu Tyr Gln Ile Ala Lys Asn Leu Val Tyr Val Asn Ser Arg Tyr
            835                 840                 845
```

Val Met Ala Phe His Ser Leu Glu Arg Asp Ser Gln Met Leu Phe Asp
850                 855                 860

Ala Tyr Tyr Asp Val Lys Arg Gly Tyr Cys Asp Leu Ser Thr Val Leu
865                 870                 875                 880

Leu Phe Gly Val Asp Asp Leu Gln Asn Arg Asn Arg Gly Ser Tyr Lys
            885                 890                 895

Tyr Leu Arg Asp Asn Arg Arg Ser Asn Lys Asp Val Ile Glu Thr Phe
        900                 905                 910

Gly Asp Phe Lys Gly Lys Val Ser Lys Val Val Glu Lys Asn Gln
    915                 920                 925

Gly Leu Thr Asn Glu Ile Tyr Asp Ser Leu Cys Asn Val Ala Gly Thr
930                 935                 940

Thr Lys Thr Glu Val Gln Asn Glu Ile Lys Ser Ile Leu Lys Ser Asn
945                 950                 955                 960

Gly Leu Asp Glu Ser Ala Ser Ser Tyr Leu Ser His Lys Leu Val Asn
            965                 970                 975

Lys Val His Ser Tyr Lys Tyr Leu Lys Gln Asn Leu Asp Cys Ala Asp
        980                 985                 990

Asn Thr Met Ile Asn Gln Phe Arg Asn Asn Val Ala His Leu Asn Thr
    995                 1000                1005

Ile Arg Asn Met Asp Gly Ile Glu Asn Val Thr Gly Ile Thr Ser
1010                1015                1020

Tyr Phe Gln Ile Tyr His Tyr Leu Met Gln Lys Ala Leu Tyr Lys
1025                1030                1035

Glu Phe Lys Lys Cys Arg Glu Asn Ala Val Arg Lys Trp Ile Pro
1040                1045                1050

Tyr Ile Thr Glu Asn Ala Glu Pro Lys Tyr Val Tyr Trp Asn Lys
1055                1060                1065

Lys Glu Gln Gln Glu Val Glu Val Ser Phe Asn Pro Lys Ile Phe
1070                1075                1080

Gly Tyr Met Glu Asn Ile Lys Asn His Ser Asn Thr Tyr Cys Lys
1085                1090                1095

Asp Phe Val Lys Ala Leu Cys Ala Pro Phe Ala Tyr Asn Leu Pro
1100                1105                1110

Arg Phe Lys Asn Leu Ser Ile Glu Glu Leu Phe Asp Met His Glu
1115                1120                1125

Leu Ser Glu Glu Pro Lys Glu Ser Met Lys Leu Thr Asp
1130                1135                1140

<210> SEQ ID NO 23
<211> LENGTH: 944
<212> TYPE: PRT
<213> ORGANISM: Ruminococcus albus

<400> SEQUENCE: 23

Met Ala Lys Lys Ser Lys Gly Met Ser Leu Arg Glu Lys Arg Glu Leu
1               5                   10                  15

Glu Lys Gln Lys Arg Ile Gln Lys Ala Ala Val Asn Ser Val Asn Asp
            20                  25                  30

Thr Pro Glu Lys Thr Glu Ala Asn Val Val Ser Val Asn Val Arg
        35                  40                  45

Thr Ser Ala Glu Asn Lys His Ser Lys Lys Ser Ala Ala Lys Ala Leu
    50                  55                  60

Gly Leu Lys Ser Gly Leu Val Ile Gly Asp Glu Leu Tyr Leu Thr Ser
65                  70                  75                  80

```
Phe Gly Arg Gly Asn Glu Ala Lys Leu Glu Lys Ile Ser Gly Asp
                85                  90                  95
Thr Val Glu Lys Leu Gly Ile Gly Ala Phe Glu Val Ala Glu Arg Asp
            100                 105                 110
Glu Ser Thr Leu Thr Leu Glu Ser Gly Arg Ile Lys Asp Lys Thr Ala
            115                 120                 125
Arg Pro Lys Asp Pro Arg His Ile Thr Val Asp Thr Gln Gly Lys Phe
130                 135                 140
Lys Glu Asp Met Leu Gly Ile Arg Ser Val Leu Glu Lys Lys Ile Phe
145                 150                 155                 160
Gly Lys Thr Phe Asp Asp Asn Ile His Val Gln Leu Ala Tyr Asn Ile
                165                 170                 175
Leu Asp Val Glu Lys Ile Met Ala Gln Tyr Val Ser Asp Ile Val Tyr
            180                 185                 190
Met Leu His Asn Thr Asp Lys Thr Glu Arg Asn Asp Asn Leu Met Gly
            195                 200                 205
Tyr Met Ser Ile Arg Asn Thr Tyr Lys Thr Phe Cys Asp Thr Ser Asn
            210                 215                 220
Leu Pro Asp Asp Thr Lys Gln Lys Val Glu Asn Gln Lys Arg Glu Phe
225                 230                 235                 240
Asp Lys Ile Ile Lys Ser Gly Arg Leu Gly Tyr Phe Gly Glu Ala Phe
                245                 250                 255
Met Val Asn Ser Gly Asn Ser Thr Lys Leu Arg Pro Glu Lys Glu Ile
            260                 265                 270
Tyr His Ile Phe Ala Leu Met Ala Ser Leu Arg Gln Ser Tyr Phe His
            275                 280                 285
Gly Tyr Val Lys Asp Thr Asp Tyr Gln Gly Thr Thr Trp Ala Tyr Thr
290                 295                 300
Leu Glu Asp Lys Leu Lys Gly Pro Ser His Glu Phe Arg Glu Thr Ile
305                 310                 315                 320
Asp Lys Ile Phe Asp Glu Gly Phe Ser Lys Ile Ser Lys Asp Phe Gly
                325                 330                 335
Lys Met Asn Lys Val Asn Leu Gln Ile Leu Glu Gln Met Ile Gly Glu
            340                 345                 350
Leu Tyr Gly Ser Ile Glu Arg Gln Asn Leu Thr Cys Asp Tyr Tyr Asp
            355                 360                 365
Phe Ile Gln Leu Lys Lys His Lys Tyr Leu Gly Phe Ser Ile Lys Arg
            370                 375                 380
Leu Arg Glu Thr Met Leu Glu Thr Thr Pro Ala Glu Cys Tyr Lys Ala
385                 390                 395                 400
Glu Cys Tyr Asn Ser Glu Arg Gln Lys Leu Tyr Lys Leu Ile Asp Phe
                405                 410                 415
Leu Ile Tyr Asp Leu Tyr Tyr Asn Arg Lys Pro Ala Arg Ile Glu Glu
            420                 425                 430
Ile Val Asp Lys Leu Arg Glu Ser Val Asn Asp Glu Lys Glu Ser
            435                 440                 445
Ile Tyr Ser Val Glu Ala Lys Tyr Val Tyr Glu Ser Leu Ser Lys Val
450                 455                 460
Leu Asp Lys Ser Leu Lys Asn Ser Val Ser Gly Glu Thr Ile Lys Asp
465                 470                 475                 480
Leu Gln Lys Arg Tyr Asp Asp Glu Thr Ala Asn Arg Ile Trp Asp Ile
                485                 490                 495
```

```
Ser Gln His Ser Ile Ser Gly Asn Val Asn Cys Phe Cys Lys Leu Ile
            500             505             510

Tyr Ile Met Thr Leu Met Leu Asp Gly Lys Glu Ile Asn Asp Leu Leu
            515             520             525

Thr Thr Leu Val Asn Lys Phe Asp Asn Ile Ala Ser Phe Ile Asp Val
        530             535             540

Met Asp Glu Leu Gly Leu Glu His Ser Phe Thr Asp Asn Tyr Lys Met
545             550             555             560

Phe Ala Asp Ser Lys Ala Ile Cys Leu Asp Leu Gln Phe Ile Asn Ser
            565             570             575

Phe Ala Arg Met Ser Lys Ile Asp Asp Glu Lys Ser Lys Arg Gln Leu
            580             585             590

Phe Arg Asp Ala Leu Val Ile Leu Asp Ile Gly Asn Lys Asp Glu Thr
            595             600             605

Trp Ile Asn Asn Tyr Leu Asp Ser Asp Ile Phe Lys Leu Asp Lys Glu
            610             615             620

Gly Asn Lys Leu Lys Gly Ala Arg His Asp Phe Arg Asn Phe Ile Ala
625             630             635             640

Asn Asn Val Ile Lys Ser Ser Arg Phe Lys Tyr Leu Val Lys Tyr Ser
            645             650             655

Ser Ala Asp Gly Met Ile Lys Leu Lys Thr Asn Glu Lys Leu Ile Gly
            660             665             670

Phe Val Leu Asp Lys Leu Pro Glu Thr Gln Ile Asp Arg Tyr Tyr Glu
            675             680             685

Ser Cys Gly Leu Asp Asn Ala Val Val Asp Lys Lys Val Arg Ile Glu
            690             695             700

Lys Leu Ser Gly Leu Ile Arg Asp Met Lys Phe Asp Asp Phe Ser Gly
705             710             715             720

Val Lys Thr Ser Asn Lys Ala Gly Asp Asn Asp Lys Gln Asp Lys Ala
            725             730             735

Lys Tyr Gln Ala Ile Ile Ser Leu Tyr Leu Met Val Leu Tyr Gln Ile
            740             745             750

Val Lys Asn Met Ile Tyr Val Asn Ser Arg Tyr Val Ile Ala Phe His
            755             760             765

Cys Leu Glu Arg Asp Phe Gly Met Tyr Gly Lys Asp Phe Gly Lys Tyr
            770             775             780

Tyr Gln Gly Cys Arg Lys Leu Thr Asp His Phe Ile Glu Glu Lys Tyr
785             790             795             800

Met Lys Glu Gly Lys Leu Gly Cys Asn Lys Val Gly Arg Tyr Leu
            805             810             815

Lys Asn Asn Ile Ser Cys Cys Thr Asp Gly Leu Ile Asn Thr Tyr Arg
            820             825             830

Asn Gln Val Asp His Phe Ala Val Arg Lys Ile Gly Asn Tyr Ala
            835             840             845

Ala Tyr Ile Lys Ser Ile Gly Ser Trp Phe Glu Leu Tyr His Tyr Val
            850             855             860

Ile Gln Arg Ile Val Phe Asp Glu Tyr Arg Phe Ala Leu Asn Thr
865             870             875             880

Glu Ser Asn Tyr Lys Asn Ser Ile Ile Lys His His Thr Tyr Cys Lys
            885             890             895

Asp Met Val Lys Ala Leu Asn Thr Pro Phe Gly Tyr Asp Leu Pro Arg
            900             905             910

Tyr Lys Asn Leu Ser Ile Gly Asp Leu Phe Asp Arg Asn Asn Tyr Leu
```

915                 920                 925
Asn Lys Thr Lys Glu Ser Ile Asp Ala Asn Ser Ser Ile Asp Ser Gln
        930                 935                 940

<210> SEQ ID NO 24
<211> LENGTH: 918
<212> TYPE: PRT
<213> ORGANISM: Ruminococcus bicirculans

<400> SEQUENCE: 24

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Val
            20                  25                  30

Pro Ala Ile Ala Ala Met Pro Ala Ala Glu Ala Ala Pro Ala Ala
        35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asp Tyr Asn Lys Thr Gln
            85                  90                  95

Leu Ser Ser Lys Asp Asn Ser Asn Ile Glu Leu Cys Asp Val Gly Lys
            100                 105                 110

Val Asn Ile Thr Phe Ser Ser Arg Arg Gly Phe Glu Ser Gly Val Glu
            115                 120                 125

Ile Asn Thr Ser Asn Pro Thr His Arg Ser Gly Glu Ser Ser Ser Val
        130                 135                 140

Arg Gly Asp Met Leu Gly Leu Lys Ser Glu Leu Glu Lys Arg Phe Phe
145                 150                 155                 160

Gly Lys Asn Phe Asp Asp Asn Ile His Ile Gln Leu Ile Tyr Asn Ile
            165                 170                 175

Leu Asp Ile Glu Lys Ile Leu Ala Val Tyr Val Thr Asn Ile Val Tyr
            180                 185                 190

Ala Leu Asn Asn Met Leu Gly Glu Gly Asp Ser Asn Tyr Asp Phe
            195                 200                 205

Met Gly Tyr Leu Ser Thr Phe Asn Thr Tyr Lys Val Phe Thr Asn Pro
        210                 215                 220

Asn Gly Ser Thr Leu Ser Asp Asp Lys Lys Glu Asn Ile Arg Lys Ser
225                 230                 235                 240

Leu Ser Lys Phe Asn Ala Leu Leu Lys Thr Lys Arg Leu Gly Tyr Phe
            245                 250                 255

Gly Leu Glu Glu Pro Lys Thr Lys Asp Thr Arg Ala Ser Glu Ala Tyr
            260                 265                 270

Lys Lys Arg Val Tyr His Met Leu Ala Ile Val Gly Gln Ile Arg Gln
        275                 280                 285

Cys Val Phe His Asp Lys Ser Gly Ala Lys Arg Phe Asp Leu Tyr Ser
        290                 295                 300

Phe Ile Asn Asn Ile Asp Pro Glu Tyr Arg Glu Thr Leu Asp Tyr Leu
305                 310                 315                 320

Val Asp Glu Arg Phe Asp Ser Ile Asn Lys Gly Phe Ile Gln Gly Asn
            325                 330                 335

Lys Val Asn Ile Ser Leu Leu Ile Asp Met Met Lys Gly Tyr Glu Ala
            340                 345                 350

```
Asp Asp Ile Ile Arg Leu Tyr Tyr Asp Phe Ile Val Leu Lys Ser Gln
            355                 360                 365

Lys Asn Leu Gly Phe Ser Ile Lys Lys Leu Arg Glu Lys Met Leu Asp
    370                 375                 380

Glu Tyr Gly Phe Arg Phe Lys Asp Lys Gln Tyr Asp Ser Val Arg Ser
385                 390                 395                 400

Lys Met Tyr Lys Leu Met Asp Phe Leu Leu Phe Cys Asn Tyr Tyr Arg
                405                 410                 415

Asn Asp Ile Ala Ala Gly Glu Ser Leu Val Arg Lys Leu Arg Phe Ser
            420                 425                 430

Met Thr Asp Asp Glu Lys Glu Gly Ile Tyr Ala Asp Glu Ala Ala Lys
        435                 440                 445

Leu Trp Gly Lys Phe Arg Asn Asp Phe Glu Asn Ile Ala Asp His Met
    450                 455                 460

Asn Gly Asp Val Ile Lys Glu Leu Gly Lys Ala Asp Met Asp Phe Asp
465                 470                 475                 480

Glu Lys Ile Leu Asp Ser Glu Lys Lys Asn Ala Ser Asp Leu Leu Tyr
                485                 490                 495

Phe Ser Lys Met Ile Tyr Met Leu Thr Tyr Phe Leu Asp Gly Lys Glu
            500                 505                 510

Ile Asn Asp Leu Leu Thr Thr Leu Ile Ser Lys Phe Asp Asn Ile Lys
        515                 520                 525

Glu Phe Leu Lys Ile Met Lys Ser Ser Ala Val Asp Val Glu Cys Glu
    530                 535                 540

Leu Thr Ala Gly Tyr Lys Leu Phe Asn Asp Ser Gln Arg Ile Thr Asn
545                 550                 555                 560

Glu Leu Phe Ile Val Lys Asn Ile Ala Ser Met Arg Lys Pro Ala Ala
                565                 570                 575

Ser Ala Lys Leu Thr Met Phe Arg Asp Ala Leu Thr Ile Leu Gly Ile
            580                 585                 590

Asp Asp Lys Ile Thr Asp Asp Arg Ile Ser Glu Ile Leu Lys Leu Lys
        595                 600                 605

Glu Lys Gly Lys Gly Ile His Gly Leu Arg Asn Phe Ile Thr Asn Asn
    610                 615                 620

Val Ile Glu Ser Ser Arg Phe Val Tyr Leu Ile Lys Tyr Ala Asn Ala
625                 630                 635                 640

Gln Lys Ile Arg Glu Val Ala Lys Asn Glu Lys Val Val Met Phe Val
                645                 650                 655

Leu Gly Gly Ile Pro Asp Thr Gln Ile Glu Arg Tyr Tyr Lys Ser Cys
            660                 665                 670

Val Glu Phe Pro Asp Met Asn Ser Ser Leu Gly Val Lys Arg Ser Glu
        675                 680                 685

Leu Ala Arg Met Ile Lys Asn Ile Ser Phe Asp Phe Lys Asn Val
    690                 695                 700

Lys Gln Gln Ala Lys Gly Arg Glu Asn Val Ala Lys Glu Arg Ala Lys
705                 710                 715                 720

Ala Val Ile Gly Leu Tyr Leu Thr Val Met Tyr Leu Leu Val Lys Asn
                725                 730                 735

Leu Val Asn Val Asn Ala Arg Tyr Val Ile Ala Ile His Cys Leu Glu
            740                 745                 750

Arg Asp Phe Gly Leu Tyr Lys Glu Ile Ile Pro Glu Leu Ala Ser Lys
        755                 760                 765

Asn Leu Lys Asn Asp Tyr Arg Ile Leu Ser Gln Thr Leu Cys Glu Leu
```

```
                770             775             780
Cys Asp Lys Ser Pro Asn Leu Phe Leu Lys Lys Asn Glu Arg Leu Arg
785             790             795             800

Lys Cys Val Glu Val Asp Ile Asn Asn Ala Asp Ser Ser Met Thr Arg
            805             810             815

Lys Tyr Arg Asn Cys Ile Ala His Leu Thr Val Val Arg Glu Leu Lys
            820             825             830

Glu Tyr Ile Gly Asp Ile Cys Thr Val Asp Ser Tyr Phe Ser Ile Tyr
            835             840             845

His Tyr Val Met Gln Arg Cys Ile Thr Lys Arg Glu Asn Asp Thr Lys
            850             855             860

Gln Glu Glu Lys Ile Lys Tyr Glu Asp Asp Leu Leu Lys Asn His Gly
865             870             875             880

Tyr Thr Lys Asp Phe Val Lys Ala Leu Asn Ser Pro Phe Gly Tyr Asn
            885             890             895

Ile Pro Arg Phe Lys Asn Leu Ser Ile Glu Gln Leu Phe Asp Arg Asn
            900             905             910

Glu Tyr Leu Thr Glu Lys
            915

<210> SEQ ID NO 25
<211> LENGTH: 958
<212> TYPE: PRT
<213> ORGANISM: Ruminococcus flavefaciens

<400> SEQUENCE: 25

Met Lys Lys Lys Ile Lys Ala Arg Asp Leu Arg Glu Ala Lys Lys Gln
1               5                   10                  15

Glu Lys Leu Ala Ala Phe Ser Ala Lys Ala Asn Thr Val Tyr Glu Asn
            20                  25                  30

Glu Asp Lys Asn Val Glu Ala Phe Pro Glu Ala Leu Asn Leu Arg Ser
            35                  40                  45

Ile Lys Lys Ser Met Asn Lys Ala Ala Gly Leu Lys Ser Thr Leu Ile
        50                  55                  60

Asp Gly Lys Ser Leu Tyr Leu Thr Ala Phe Gly Lys Gly Asn Asn Ala
65                  70                  75                  80

Val Val Glu His Met Ile Ala Thr Asp Ser Tyr Ser Leu Lys Thr
            85                  90                  95

Leu Glu Asn Glu Pro Ser Leu Lys Val Lys Ala Ala Asp Glu Leu Lys
            100                 105                 110

Val Thr Phe Met Ser Arg Arg Pro Phe Val Gln Glu Ser Glu Leu Ser
            115                 120                 125

Ala Val Asn Pro Leu His Ser Gly Lys Asp Lys Pro Asn Lys Ser Ala
        130                 135                 140

Gly Gln Asp Met Leu Gly Leu Lys Ser Glu Leu Glu Lys Arg Tyr Phe
145                 150                 155                 160

Gly Lys Ile Phe Asp Asp Asn Leu His Ile Gln Ile His Asn Ile
            165                 170                 175

Leu Asp Ile Glu Lys Ile Ile Ala Val Tyr Ala Thr Asn Ile Thr Ala
            180                 185                 190

Ala Ile Asp His Met Val Asp Asp Asn Glu Gln Tyr Leu Gln Gly
        195                 200                 205

Asp Phe Ile Gly Tyr Met Asn Thr Leu Asn Thr Tyr Glu Val Phe Met
        210                 215                 220
```

```
Glu Pro Ser Lys Asn Pro Arg Leu Asp Ser Asn Ala Arg Lys Asn Ile
225                 230                 235                 240

Glu Asn Ser Arg Glu Lys Phe Glu Tyr Leu Leu Asp Thr Gln Arg Leu
            245                 250                 255

Gly Tyr Leu Ser Leu Glu Tyr Asp Lys Arg Ser Lys Asp Lys Arg Lys
            260                 265                 270

Ser Glu Glu Ile Lys Lys Arg Leu Tyr His Leu Val Ala Phe Ala Gly
        275                 280                 285

Gln Leu Arg Gln Trp Ser Phe His Ser Val Glu Gly Leu Pro Arg Thr
    290                 295                 300

Trp Ile Tyr Gln Leu Asp Asn Pro Lys Leu Ala Gln Glu Tyr Arg Asp
305                 310                 315                 320

Thr Leu Asp Tyr Phe Phe Asn Glu Arg Phe Asp Ala Ile Asn Lys Asp
                325                 330                 335

Phe Ile Glu Thr Asn Asn Ile Asn Leu His Ile Leu Lys Glu Val Phe
            340                 345                 350

Pro Ala Glu Asp Phe Gln Lys Leu Ala Ala Leu Tyr Tyr Asp Phe Ile
        355                 360                 365

Val Lys Lys Thr Phe Lys Asn Ile Gly Phe Ser Ile Lys Asn Leu Arg
    370                 375                 380

Glu Gln Met Leu Glu Cys Asp Glu Ala Glu Lys Ile Arg Ser Lys Asp
385                 390                 395                 400

Met Asn Ser Val Arg Ser Lys Leu Tyr Lys Leu Phe Asp Phe Cys Ile
                405                 410                 415

Phe Tyr Gln Tyr Phe Ile Asp Glu Glu Arg Ser Arg Glu Asn Val Asn
            420                 425                 430

Tyr Leu Arg Ser Thr Leu Asn Asp Glu Gln Lys Asp Ala Phe Tyr Glu
        435                 440                 445

Glu Glu Gly Lys Arg Leu Trp Ser Glu Asn Arg Lys Lys Phe Ile Tyr
    450                 455                 460

Phe Cys Asp Asn Ile Asn Lys Trp Val Lys Asn Asp Tyr Ser Asp Glu
465                 470                 475                 480

Val Ala Lys Cys Ile Asp Leu Asn Glu Phe Arg Val Asn Ser Asn Val
                485                 490                 495

Ser Tyr Phe Ser Lys Leu Leu Tyr Ala Met Ser Phe Phe Leu Asp Gly
            500                 505                 510

Lys Glu Ile Asn Asp Leu Leu Thr Thr Leu Ile Asn Lys Phe Asp Asn
        515                 520                 525

Ile Arg Ser Phe Ile Asp Thr Ala Asn Phe Leu Asn Ile Asp Val Lys
    530                 535                 540

Phe Thr Lys Asp Tyr Asp Phe Phe Asn Ile Ile Cys Asp Tyr Ala Gly
545                 550                 555                 560

Glu Leu Asn Ile Ile Lys Asn Ile Ala Arg Met Lys Lys Pro Ser Pro
                565                 570                 575

Ser Ala Lys Lys Asn Met Tyr Arg Asp Ala Leu Thr Ile Leu Gly Ile
            580                 585                 590

Pro Thr Glu Met Ser Asp Glu Gln Leu Asp Ala Glu Ile Asp Lys Ile
        595                 600                 605

Leu Glu Lys Lys Ile Asn Pro Val Thr Gly Lys Thr Glu Lys Gly Lys
    610                 615                 620

Asn Pro Phe Arg Asn Phe Ile Ala Asn Val Ile Glu Asn Lys Arg
625                 630                 635                 640

Phe Ile Tyr Val Ile Lys Phe Cys Asn Pro Lys Asn Val Arg Lys Leu
```

```
                    645                 650                 655
    Val Asn Asn Thr Lys Val Thr Glu Phe Val Leu Lys Arg Met Pro Glu
                660                 665                 670

Thr Gln Ile Asp Arg Tyr Phe Glu Ser Cys Ile Glu Gly Asn Leu Asn
                675                 680                 685

Pro Thr Thr Glu Lys Lys Ile Glu Lys Leu Ala Glu Met Ile Lys Asn
            690                 695                 700

Ile Lys Phe Glu Glu Phe Arg Asn Val Lys Gln Lys Val Arg Asp Asn
    705                 710                 715                 720

Ser Gln Glu Ala Val Glu Lys Glu Arg Phe Lys Ala Ile Ile Gly Leu
                    725                 730                 735

Tyr Leu Thr Val Ile Tyr Leu Leu Val Lys Asn Leu Val Asn Val Asn
                740                 745                 750

Ser Arg Tyr Val Met Ala Phe His Cys Leu Glu Arg Asp Ala Lys Leu
                755                 760                 765

Tyr Gly Val Gln Asn Ile Gly Gly Asp Tyr Leu Ala Leu Thr Ala Lys
                770                 775                 780

Leu Cys Ala Glu Gly Asp Asp Tyr Gly Lys Lys Leu Ser Glu Ala Lys
    785                 790                 795                 800

Gln Asn Ile Asn Gln Asp Lys Val Gln Met Pro Lys Asn Tyr Phe Leu
                    805                 810                 815

Ala Arg Asn Lys Arg Trp Arg Glu Ala Ile Glu Gln Asp Ile Asp Asn
                820                 825                 830

Ala Lys Lys Trp Phe Ile Gly Glu Lys Phe Asn Asn Val Lys Asn Tyr
                835                 840                 845

Arg Asn Asn Val Ala His Leu Thr Ala Ile Arg Asn Cys Ala Glu Phe
            850                 855                 860

Ile Gly Glu Ile Thr Lys Ile Asp Ser Tyr Phe Ala Leu Tyr His Tyr
    865                 870                 875                 880

Leu Ile Gln Arg Gln Leu Ala Gly Arg Leu Asp Pro Asn His Pro Gly
                    885                 890                 895

Phe Glu Lys Asn Tyr Pro Gln Tyr Ala Pro Leu Phe Lys Trp Asn Thr
                900                 905                 910

Tyr Val Lys Asp Met Val Lys Ala Leu Asn Ser Pro Phe Gly Tyr Asn
                915                 920                 925

Ile Pro Arg Phe Lys Asp Leu Ser Ile Asp Ala Leu Phe Asp Arg Asn
                930                 935                 940

Glu Met Lys Glu Glu Thr Asp Asp Glu Lys Lys Ile Gln Thr
    945                 950                 955

<210> SEQ ID NO 26
<211> LENGTH: 967
<212> TYPE: PRT
<213> ORGANISM: Ruminococcus flavefaciens

<400> SEQUENCE: 26

Met Ile Glu Lys Lys Lys Ser Phe Ala Lys Gly Met Gly Val Lys Ser
    1               5                   10                  15

Thr Leu Val Ser Gly Ser Lys Val Tyr Met Thr Thr Phe Ala Glu Gly
                20                  25                  30

Ser Asp Ala Arg Leu Glu Lys Ile Val Glu Gly Asp Ser Ile Arg Ser
                35                  40                  45

Val Asn Glu Gly Glu Ala Phe Ser Ala Glu Met Ala Asp Lys Asn Ala
        50                  55                  60
```

-continued

```
Gly Tyr Lys Ile Gly Asn Ala Lys Phe Ser His Pro Lys Gly Tyr Ala
 65                  70                  75                  80

Val Val Ala Asn Asn Pro Leu Tyr Thr Gly Pro Val Gln Gln Asp Met
                 85                  90                  95

Leu Gly Leu Lys Glu Thr Leu Glu Lys Arg Tyr Phe Gly Glu Ser Ala
            100                 105                 110

Asp Gly Asn Asp Asn Ile Cys Ile Gln Val Ile His Asn Ile Leu Asp
        115                 120                 125

Ile Glu Lys Ile Leu Ala Glu Tyr Ile Thr Asn Ala Ala Tyr Ala Val
    130                 135                 140

Asn Asn Ile Ser Gly Leu Asp Lys Asp Ile Ile Gly Phe Gly Lys Phe
145                 150                 155                 160

Ser Thr Val Tyr Thr Tyr Asp Glu Phe Lys Asp Pro Glu His His Arg
                165                 170                 175

Ala Ala Phe Asn Asn Asn Asp Lys Leu Ile Asn Ala Ile Lys Ala Gln
            180                 185                 190

Tyr Asp Glu Phe Asp Asn Phe Leu Asp Asn Pro Arg Leu Gly Tyr Phe
        195                 200                 205

Gly Gln Ala Phe Phe Ser Lys Glu Gly Arg Asn Tyr Ile Ile Asn Tyr
    210                 215                 220

Gly Asn Glu Cys Tyr Asp Ile Leu Ala Leu Leu Ser Gly Leu Arg His
225                 230                 235                 240

Trp Val Val His Asn Glu Glu Glu Ser Arg Ile Ser Arg Thr Trp
                245                 250                 255

Leu Tyr Asn Leu Asp Lys Asn Leu Asp Asn Glu Tyr Ile Ser Thr Leu
            260                 265                 270

Asn Tyr Leu Tyr Asp Arg Ile Thr Asn Glu Leu Thr Asn Ser Phe Ser
        275                 280                 285

Lys Asn Ser Ala Ala Asn Val Asn Tyr Ile Ala Glu Thr Leu Gly Ile
    290                 295                 300

Asn Pro Ala Glu Phe Ala Glu Gln Tyr Phe Arg Phe Ser Ile Met Lys
305                 310                 315                 320

Glu Gln Lys Asn Leu Gly Phe Asn Ile Thr Lys Leu Arg Glu Val Met
                325                 330                 335

Leu Asp Arg Lys Asp Met Ser Glu Ile Arg Lys Asn His Lys Val Phe
            340                 345                 350

Asp Ser Ile Arg Thr Lys Val Tyr Thr Met Met Asp Phe Val Ile Tyr
        355                 360                 365

Arg Tyr Tyr Ile Glu Glu Asp Ala Lys Val Ala Ala Ala Asn Lys Ser
    370                 375                 380

Leu Pro Asp Asn Glu Lys Ser Leu Ser Glu Lys Asp Ile Phe Val Ile
385                 390                 395                 400

Asn Leu Arg Gly Ser Phe Asn Asp Asp Gln Lys Asp Ala Leu Tyr Tyr
                405                 410                 415

Asp Glu Ala Asn Arg Ile Trp Arg Lys Leu Glu Asn Ile Met His Asn
            420                 425                 430

Ile Lys Glu Phe Arg Gly Asn Lys Thr Arg Glu Tyr Lys Lys Lys Asp
        435                 440                 445

Ala Pro Arg Leu Pro Arg Ile Leu Pro Ala Gly Arg Asp Val Ser Ala
    450                 455                 460

Phe Ser Lys Leu Met Tyr Ala Leu Thr Met Phe Leu Asp Gly Lys Glu
465                 470                 475                 480

Ile Asn Asp Leu Leu Thr Thr Leu Ile Asn Lys Phe Asp Asn Ile Gln
```

```
                485                 490                 495
Ser Phe Leu Lys Val Met Pro Leu Ile Gly Val Asn Ala Lys Phe Val
            500                 505                 510

Glu Glu Tyr Ala Phe Phe Lys Asp Ser Ala Lys Ile Ala Asp Glu Leu
            515                 520                 525

Arg Leu Ile Lys Ser Phe Ala Arg Met Gly Glu Pro Ile Ala Asp Ala
            530                 535                 540

Arg Arg Ala Met Tyr Ile Asp Ala Ile Arg Ile Leu Gly Thr Asn Leu
545                 550                 555                 560

Ser Tyr Asp Glu Leu Lys Ala Leu Ala Asp Thr Phe Ser Leu Asp Glu
            565                 570                 575

Asn Gly Asn Lys Leu Lys Lys Gly Lys His Gly Met Arg Asn Phe Ile
            580                 585                 590

Ile Asn Asn Val Ile Ser Asn Lys Arg Phe His Tyr Leu Ile Arg Tyr
            595                 600                 605

Gly Asp Pro Ala His Leu His Glu Ile Ala Lys Asn Glu Ala Val Val
610                 615                 620

Lys Phe Val Leu Gly Arg Ile Ala Asp Ile Gln Lys Lys Gln Gly Gln
625                 630                 635                 640

Asn Gly Lys Asn Gln Ile Asp Arg Tyr Tyr Glu Thr Cys Ile Gly Lys
            645                 650                 655

Asp Lys Gly Lys Ser Val Ser Glu Lys Val Asp Ala Leu Thr Lys Ile
            660                 665                 670

Ile Thr Gly Met Asn Tyr Asp Gln Phe Asp Lys Lys Arg Ser Val Ile
            675                 680                 685

Glu Asp Thr Gly Arg Glu Asn Ala Glu Arg Glu Lys Phe Lys Lys Ile
            690                 695                 700

Ile Ser Leu Tyr Leu Thr Val Ile Tyr His Ile Leu Lys Asn Ile Val
705                 710                 715                 720

Asn Ile Asn Ala Arg Tyr Val Ile Gly Phe His Cys Val Glu Arg Asp
            725                 730                 735

Ala Gln Leu Tyr Lys Glu Lys Gly Tyr Asp Ile Asn Leu Lys Lys Leu
            740                 745                 750

Glu Glu Lys Gly Phe Ser Ser Val Thr Lys Leu Cys Ala Gly Ile Asp
            755                 760                 765

Glu Thr Ala Pro Asp Lys Arg Lys Asp Val Gly Lys Glu Met Ala Glu
            770                 775                 780

Arg Ala Lys Glu Ser Ile Asp Ser Leu Glu Ser Ala Asn Pro Lys Leu
785                 790                 795                 800

Tyr Ala Asn Tyr Ile Lys Tyr Ser Asp Glu Lys Lys Ala Glu Glu Phe
            805                 810                 815

Thr Arg Gln Ile Asn Arg Glu Lys Ala Lys Thr Ala Leu Asn Ala Tyr
            820                 825                 830

Leu Arg Asn Thr Lys Trp Asn Val Ile Arg Glu Asp Leu Leu Arg
            835                 840                 845

Ile Asp Asn Lys Thr Cys Thr Leu Phe Arg Asn Lys Ala Val His Leu
            850                 855                 860

Glu Val Ala Arg Tyr Val His Ala Tyr Ile Asn Asp Ile Ala Glu Val
865                 870                 875                 880

Asn Ser Tyr Phe Gln Leu Tyr His Tyr Ile Met Gln Arg Ile Ile Met
            885                 890                 895

Asn Glu Arg Tyr Glu Lys Ser Ser Gly Lys Val Ser Glu Tyr Phe Asp
            900                 905                 910
```

-continued

Ala Val Asn Asp Glu Lys Lys Tyr Asn Asp Arg Leu Leu Lys Leu Leu
            915                 920                 925

Cys Val Pro Phe Gly Tyr Cys Ile Pro Arg Phe Lys Asn Leu Ser Ile
930                 935                 940

Glu Ala Leu Phe Asp Arg Asn Glu Ala Ala Lys Phe Asp Lys Glu Lys
945                 950                 955                 960

Lys Lys Val Ser Gly Asn Ser
                965

<210> SEQ ID NO 27
<211> LENGTH: 933
<212> TYPE: PRT
<213> ORGANISM: Ruminococcus flavefaciens

<400> SEQUENCE: 27

Met Lys Lys Lys Met Ser Leu Arg Glu Lys Arg Glu Ala Glu Lys Gln
1               5                   10                  15

Ala Lys Lys Ala Ala Tyr Ser Ala Ala Ser Lys Asn Thr Asp Ser Lys
            20                  25                  30

Pro Ala Glu Lys Lys Ala Glu Thr Pro Lys Pro Ala Glu Ile Ile Ser
        35                  40                  45

Asp Asn Ser Arg Asn Lys Thr Ala Val Lys Ala Gly Leu Lys Ser
    50                  55                  60

Thr Ile Ile Ser Gly Asp Lys Leu Tyr Met Thr Ser Phe Gly Lys Gly
65                  70                  75                  80

Asn Ala Ala Val Ile Glu Gln Lys Ile Asp Ile Asn Asp Tyr Ser Phe
                85                  90                  95

Ser Ala Met Lys Asp Thr Pro Ser Leu Glu Val Asp Lys Ala Glu Ser
            100                 105                 110

Lys Glu Ile Ser Phe Ser Ser His Pro Phe Val Lys Asn Asp Lys
        115                 120                 125

Leu Thr Thr Tyr Asn Pro Leu Tyr Gly Gly Lys Asp Asn Pro Glu Lys
    130                 135                 140

Pro Val Gly Arg Asp Met Leu Gly Leu Lys Asp Lys Leu Glu Glu Arg
145                 150                 155                 160

Tyr Phe Gly Cys Thr Phe Asn Asp Asn Leu His Ile Gln Ile Tyr
                165                 170                 175

Asn Ile Leu Asp Ile Glu Lys Ile Leu Ala Val His Ser Ala Asn Ile
            180                 185                 190

Thr Thr Ala Leu Asp His Met Val Asp Glu Asp Glu Lys Tyr Leu
        195                 200                 205

Asn Ser Asp Tyr Ile Gly Tyr Met Asn Thr Ile Asn Thr Tyr Asp Val
    210                 215                 220

Phe Met Asp Pro Ser Lys Asn Ser Ser Leu Ser Pro Lys Asp Arg Lys
225                 230                 235                 240

Asn Ile Asp Asn Ser Arg Ala Lys Phe Glu Lys Leu Leu Ser Thr Lys
                245                 250                 255

Arg Leu Gly Tyr Phe Gly Phe Asp Tyr Asp Ala Asn Gly Lys Asp Lys
            260                 265                 270

Lys Lys Asn Glu Glu Ile Lys Lys Arg Leu Tyr His Leu Thr Ala Phe
        275                 280                 285

Ala Gly Gln Leu Arg Gln Trp Ser Phe His Ser Ala Gly Asn Tyr Pro
    290                 295                 300

Arg Thr Trp Leu Tyr Lys Leu Asp Ser Leu Asp Lys Glu Tyr Leu Asp

```
            305                 310                 315                 320
        Thr Leu Asp His Tyr Phe Asp Lys Arg Phe Asn Asp Ile Asn Asp Asp
                        325                 330                 335
        Phe Val Thr Lys Asn Ala Thr Asn Leu Tyr Ile Leu Lys Glu Val Phe
                        340                 345                 350
        Pro Glu Ala Asn Phe Lys Asp Ile Ala Asp Leu Tyr Tyr Asp Phe Ile
                        355                 360                 365
        Val Ile Lys Ser His Lys Asn Met Gly Phe Ser Ile Lys Lys Leu Arg
                        370                 375                 380
        Glu Lys Met Leu Glu Cys Asp Gly Ala Asp Arg Ile Lys Glu Gln Asp
        385                 390                 395                 400
        Met Asp Ser Val Arg Ser Lys Leu Tyr Lys Leu Ile Asp Phe Cys Ile
                        405                 410                 415
        Phe Lys Tyr Tyr His Glu Phe Pro Glu Leu Ser Glu Lys Asn Val Asp
                        420                 425                 430
        Ile Leu Arg Ala Ala Val Ser Asp Thr Lys Lys Asp Asn Leu Tyr Ser
                        435                 440                 445
        Asp Glu Ala Ala Arg Leu Trp Ser Ile Phe Lys Glu Lys Phe Leu Gly
        450                 455                 460
        Phe Cys Asp Lys Ile Val Val Trp Val Thr Gly Glu His Glu Lys Asp
        465                 470                 475                 480
        Ile Thr Ser Val Ile Asp Lys Asp Ala Tyr Arg Asn Arg Ser Asn Val
                        485                 490                 495
        Ser Tyr Phe Ser Lys Leu Met Tyr Ala Met Cys Phe Phe Leu Asp Gly
                        500                 505                 510
        Lys Glu Ile Asn Asp Leu Leu Thr Thr Leu Ile Asn Lys Phe Asp Asn
                        515                 520                 525
        Ile Ala Asn Gln Ile Lys Thr Ala Lys Glu Leu Gly Ile Asn Thr Ala
                        530                 535                 540
        Phe Val Lys Asn Tyr Asp Phe Phe Asn His Ser Glu Lys Tyr Val Asp
        545                 550                 555                 560
        Glu Leu Asn Ile Val Lys Asn Ile Ala Arg Met Lys Lys Pro Ser Ser
                        565                 570                 575
        Asn Ala Lys Lys Ala Met Tyr His Asp Ala Leu Thr Ile Leu Gly Ile
                        580                 585                 590
        Pro Glu Asp Met Asp Glu Lys Ala Leu Asp Glu Glu Leu Asp Leu Ile
                        595                 600                 605
        Leu Glu Lys Lys Thr Asp Pro Val Thr Gly Lys Pro Leu Lys Gly Lys
                        610                 615                 620
        Asn Pro Leu Arg Asn Phe Ile Ala Asn Asn Val Ile Glu Asn Ser Arg
        625                 630                 635                 640
        Phe Ile Tyr Leu Ile Lys Phe Cys Asn Pro Glu Asn Val Arg Lys Ile
                        645                 650                 655
        Val Asn Asn Thr Lys Val Thr Glu Phe Val Leu Lys Arg Ile Pro Asp
                        660                 665                 670
        Ala Gln Ile Glu Arg Tyr Tyr Lys Ser Cys Thr Asp Ser Glu Met Asn
                        675                 680                 685
        Pro Pro Thr Glu Lys Lys Ile Thr Glu Leu Ala Gly Lys Leu Lys Asp
                        690                 695                 700
        Met Asn Phe Gly Asn Phe Arg Asn Val Arg Gln Ser Ala Lys Glu Asn
        705                 710                 715                 720
        Met Glu Lys Glu Arg Phe Lys Ala Val Ile Gly Leu Tyr Leu Thr Val
                        725                 730                 735
```

```
Val Tyr Arg Val Val Lys Asn Leu Val Asp Val Asn Ser Arg Tyr Ile
            740                 745                 750

Met Ala Phe His Ser Leu Glu Arg Asp Ser Gln Leu Tyr Asn Val Ser
            755                 760                 765

Val Asp Asn Asp Tyr Leu Ala Leu Thr Asp Thr Leu Val Lys Glu Gly
            770                 775                 780

Asp Asn Ser Arg Ser Arg Tyr Leu Ala Gly Asn Lys Arg Leu Arg Asp
785                 790                 795                 800

Cys Val Lys Gln Asp Ile Asp Asn Ala Lys Lys Trp Phe Val Ser Asp
                805                 810                 815

Lys Tyr Asn Ser Ile Thr Lys Tyr Arg Asn Asn Val Ala His Leu Thr
            820                 825                 830

Ala Val Arg Asn Cys Ala Glu Phe Ile Gly Asp Ile Thr Lys Ile Asp
            835                 840                 845

Ser Tyr Phe Ala Leu Tyr His Tyr Leu Ile Gln Arg Gln Leu Ala Lys
            850                 855                 860

Gly Leu Asp His Glu Arg Ser Gly Phe Asp Arg Asn Tyr Pro Gln Tyr
865                 870                 875                 880

Ala Pro Leu Phe Lys Trp His Thr Tyr Val Lys Asp Val Val Lys Ala
                885                 890                 895

Leu Asn Ala Pro Phe Gly Tyr Asn Ile Pro Arg Phe Lys Asn Leu Ser
            900                 905                 910

Ile Asp Ala Leu Phe Asp Arg Asn Glu Ile Lys Lys Asn Asp Gly Glu
            915                 920                 925

Lys Lys Ser Asp Asp
    930

<210> SEQ ID NO 28
<211> LENGTH: 922
<212> TYPE: PRT
<213> ORGANISM: Ruminococcus sp.

<400> SEQUENCE: 28

Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Glu Val Ile Ala Pro Val Ala
            35                  40                  45

Glu Lys Lys Lys Ser Ser Val Lys Ala Ala Gly Met Lys Ser Ile Leu
    50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
            115                 120                 125

Ile Asn Thr Ser Asn Pro Thr His Arg Ser Gly Glu Ser Ser Pro Val
            130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
```

```
            165                 170                 175
Leu Asp Ile Glu Lys Ile Leu Ala Val Tyr Val Thr Asn Ile Val Tyr
            180                 185                 190
Ala Leu Asn Asn Met Leu Gly Ile Lys Asp Ser Glu Ser Tyr Asp Asp
            195                 200                 205
Phe Met Gly Tyr Leu Ser Ala Arg Asn Thr Tyr Glu Val Phe Thr His
            210                 215                 220
Pro Asp Lys Ser Asn Leu Ser Asp Lys Val Lys Gly Asn Ile Lys Lys
225                 230                 235                 240
Ser Leu Ser Lys Phe Asn Asp Leu Leu Lys Thr Lys Arg Leu Gly Tyr
                245                 250                 255
Phe Gly Leu Glu Glu Pro Lys Thr Lys Asp Thr Arg Ala Ser Glu Ala
            260                 265                 270
Tyr Lys Lys Arg Val Tyr His Met Leu Ala Ile Val Gly Gln Ile Arg
            275                 280                 285
Gln Cys Val Phe His Asp Lys Ser Gly Ala Lys Arg Phe Asp Leu Tyr
            290                 295                 300
Ser Phe Ile Asn Asn Ile Asp Pro Glu Tyr Arg Asp Thr Leu Asp Tyr
305                 310                 315                 320
Leu Val Glu Glu Arg Leu Lys Ser Ile Asn Lys Asp Phe Ile Glu Gly
                325                 330                 335
Asn Lys Val Asn Ile Ser Leu Leu Ile Asp Met Met Lys Gly Tyr Glu
            340                 345                 350
Ala Asp Asp Ile Ile Arg Leu Tyr Tyr Asp Phe Ile Val Leu Lys Ser
            355                 360                 365
Gln Lys Asn Leu Gly Phe Ser Ile Lys Lys Leu Arg Glu Lys Met Leu
            370                 375                 380
Glu Glu Tyr Gly Phe Arg Phe Lys Asp Lys Gln Tyr Asp Ser Val Arg
385                 390                 395                 400
Ser Lys Met Tyr Lys Leu Met Asp Phe Leu Leu Phe Cys Asn Tyr Tyr
                405                 410                 415
Arg Asn Asp Val Ala Ala Gly Glu Ala Leu Val Arg Lys Leu Arg Phe
            420                 425                 430
Ser Met Thr Asp Asp Glu Lys Glu Gly Ile Tyr Ala Asp Glu Ala Ala
            435                 440                 445
Lys Leu Trp Gly Lys Phe Arg Asn Asp Phe Glu Asn Ile Ala Asp His
            450                 455                 460
Met Asn Gly Asp Val Ile Lys Glu Leu Gly Lys Ala Asp Met Asp Phe
465                 470                 475                 480
Asp Glu Lys Ile Leu Asp Ser Glu Lys Lys Asn Ala Ser Asp Leu Leu
                485                 490                 495
Tyr Phe Ser Lys Met Ile Tyr Met Leu Thr Tyr Phe Leu Asp Gly Lys
            500                 505                 510
Glu Ile Asn Asp Leu Leu Thr Thr Leu Ile Ser Lys Phe Asp Asn Ile
            515                 520                 525
Lys Glu Phe Leu Lys Ile Met Lys Ser Ser Ala Val Asp Val Glu Cys
            530                 535                 540
Glu Leu Thr Ala Gly Tyr Lys Leu Phe Asn Asp Ser Gln Arg Ile Thr
545                 550                 555                 560
Asn Glu Leu Phe Ile Val Lys Asn Ile Ala Ser Met Arg Lys Pro Ala
                565                 570                 575
Ala Ser Ala Lys Leu Thr Met Phe Arg Asp Ala Leu Thr Ile Leu Gly
            580                 585                 590
```

```
Ile Asp Asp Asn Ile Thr Asp Arg Ile Ser Glu Ile Leu Lys Leu
            595                 600                 605

Lys Glu Lys Gly Lys Gly Ile His Gly Leu Arg Asn Phe Ile Thr Asn
610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asp Glu Lys Val Val Met Phe
            645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Glu Ala Lys Arg Ser
            675                 680                 685

Glu Leu Ala Arg Met Ile Lys Asn Ile Ser Phe Asp Asp Phe Lys Asn
            690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Pro Glu Leu Ala Ser
            755                 760                 765

Lys Asn Leu Lys Asn Asp Tyr Arg Ile Leu Ser Gln Thr Leu Cys Glu
            770                 775                 780

Leu Cys Asp Asp Arg Asn Glu Ser Ser Asn Leu Phe Leu Lys Lys Asn
785                 790                 795                 800

Lys Arg Leu Arg Lys Cys Val Glu Val Asp Ile Asn Asn Ala Asp Ser
                805                 810                 815

Ser Met Thr Arg Lys Tyr Arg Asn Cys Ile Ala His Leu Thr Val Val
            820                 825                 830

Arg Glu Leu Lys Glu Tyr Ile Gly Asp Ile Arg Thr Val Asp Ser Tyr
            835                 840                 845

Phe Ser Ile Tyr His Tyr Val Met Gln Arg Cys Ile Thr Lys Arg Gly
            850                 855                 860

Asp Asp Thr Lys Gln Glu Lys Ile Lys Tyr Glu Asp Asp Leu Leu
865                 870                 875                 880

Lys Asn His Gly Tyr Thr Lys Asp Phe Val Lys Ala Leu Asn Ser Pro
            885                 890                 895

Phe Gly Tyr Asn Ile Pro Arg Phe Lys Asn Leu Ser Ile Glu Gln Leu
            900                 905                 910

Phe Asp Arg Asn Glu Tyr Leu Thr Glu Lys
            915                 920

<210> SEQ ID NO 29
<211> LENGTH: 877
<212> TYPE: PRT
<213> ORGANISM: Ruminococcus sp.

<400> SEQUENCE: 29

Met Lys Lys Gln Lys Ser Lys Lys Thr Val Ser Lys Thr Ser Gly Leu
1               5                   10                  15

Lys Glu Ala Leu Ser Val Gln Gly Thr Val Ile Met Thr Ser Phe Gly
                20                  25                  30

Lys Gly Asn Met Ala Asn Leu Ser Tyr Lys Ile Pro Ser Ser Gln Lys
```

-continued

```
                35                  40                  45
Pro Gln Asn Leu Asn Ser Ser Ala Gly Leu Lys Asn Val Glu Val Ser
 50                  55                  60
Gly Lys Lys Ile Lys Phe Gln Gly Arg His Pro Lys Ile Ala Thr Thr
 65                  70                  75                  80
Asp Asn Pro Leu Phe Lys Pro Gln Pro Gly Met Asp Leu Leu Cys Leu
                 85                  90                  95
Lys Asp Lys Leu Glu Met His Tyr Phe Gly Lys Thr Phe Asp Asp Asn
                100                 105                 110
Ile His Ile Gln Leu Ile Tyr Gln Ile Leu Asp Ile Glu Lys Ile Leu
                115                 120                 125
Ala Val His Val Asn Asn Ile Val Phe Thr Leu Asp Asn Val Leu His
130                 135                 140
Pro Gln Lys Glu Glu Leu Thr Glu Asp Phe Ile Gly Ala Gly Gly Trp
145                 150                 155                 160
Arg Ile Asn Leu Asp Tyr Gln Thr Leu Arg Gly Gln Thr Asn Lys Tyr
                165                 170                 175
Asp Arg Phe Lys Asn Tyr Ile Lys Arg Lys Glu Leu Leu Tyr Phe Gly
                180                 185                 190
Glu Ala Phe Tyr His Glu Asn Glu Arg Arg Tyr Glu Glu Asp Ile Phe
                195                 200                 205
Ala Ile Leu Thr Leu Leu Ser Ala Leu Arg Gln Phe Cys Phe His Ser
210                 215                 220
Asp Leu Ser Ser Asp Glu Ser Asp His Val Asn Ser Phe Trp Leu Tyr
225                 230                 235                 240
Gln Leu Glu Asp Gln Leu Ser Asp Glu Phe Lys Glu Thr Leu Ser Ile
                245                 250                 255
Leu Trp Glu Glu Val Thr Glu Arg Ile Asp Ser Glu Phe Leu Lys Thr
                260                 265                 270
Asn Thr Val Asn Leu His Ile Leu Cys His Val Phe Pro Lys Glu Ser
                275                 280                 285
Lys Glu Thr Ile Val Arg Ala Tyr Tyr Glu Phe Leu Ile Lys Lys Ser
290                 295                 300
Phe Lys Asn Met Gly Phe Ser Ile Lys Lys Leu Arg Glu Ile Met Leu
305                 310                 315                 320
Glu Gln Ser Asp Leu Lys Ser Phe Lys Glu Asp Lys Tyr Asn Ser Val
                325                 330                 335
Arg Ala Lys Leu Tyr Lys Leu Phe Asp Phe Ile Ile Thr Tyr Tyr Tyr
                340                 345                 350
Asp His His Ala Phe Glu Lys Glu Ala Leu Val Ser Ser Leu Arg Ser
                355                 360                 365
Ser Leu Thr Glu Glu Asn Lys Glu Glu Ile Tyr Ile Lys Thr Ala Arg
370                 375                 380
Thr Leu Ala Ser Ala Leu Gly Ala Asp Phe Lys Lys Ala Ala Ala Asp
385                 390                 395                 400
Val Asn Ala Lys Asn Ile Arg Asp Tyr Gln Lys Lys Ala Asn Asp Tyr
                405                 410                 415
Arg Ile Ser Phe Glu Asp Ile Lys Ile Gly Asn Thr Gly Ile Gly Tyr
                420                 425                 430
Phe Ser Glu Leu Ile Tyr Met Leu Thr Leu Leu Leu Asp Gly Lys Glu
                435                 440                 445
Ile Asn Asp Leu Leu Thr Thr Leu Ile Asn Lys Phe Asp Asn Ile Ile
450                 455                 460
```

```
Ser Phe Ile Asp Ile Leu Lys Lys Leu Asn Leu Glu Phe Lys Phe Lys
465                 470                 475                 480

Pro Glu Tyr Ala Asp Phe Phe Asn Met Thr Asn Cys Arg Tyr Thr Leu
                485                 490                 495

Glu Glu Leu Arg Val Ile Asn Ser Ile Ala Arg Met Gln Lys Pro Ser
            500                 505                 510

Ala Asp Ala Arg Lys Ile Met Tyr Arg Asp Ala Leu Arg Ile Leu Gly
        515                 520                 525

Met Asp Asn Arg Pro Asp Glu Glu Ile Asp Arg Glu Leu Glu Arg Thr
    530                 535                 540

Met Pro Val Gly Ala Asp Gly Lys Phe Ile Lys Gly Lys Gln Gly Phe
545                 550                 555                 560

Arg Asn Phe Ile Ala Ser Asn Val Ile Glu Ser Ser Arg Phe His Tyr
                565                 570                 575

Leu Val Arg Tyr Asn Asn Pro His Lys Thr Arg Thr Leu Val Lys Asn
            580                 585                 590

Pro Asn Val Val Lys Phe Val Leu Glu Gly Ile Pro Glu Thr Gln Ile
        595                 600                 605

Lys Arg Tyr Phe Asp Val Cys Lys Gly Gln Glu Ile Pro Pro Thr Ser
610                 615                 620

Asp Lys Ser Ala Gln Ile Asp Val Leu Ala Arg Ile Ile Ser Ser Val
625                 630                 635                 640

Asp Tyr Lys Ile Phe Glu Asp Val Pro Gln Ser Ala Lys Ile Asn Lys
                645                 650                 655

Asp Asp Pro Ser Arg Asn Phe Ser Asp Ala Leu Lys Lys Gln Arg Tyr
            660                 665                 670

Gln Ala Ile Val Ser Leu Tyr Leu Thr Val Met Tyr Leu Ile Thr Lys
        675                 680                 685

Asn Leu Val Tyr Val Asn Ser Arg Tyr Val Ile Ala Phe His Cys Leu
    690                 695                 700

Glu Arg Asp Ala Phe Leu His Gly Val Thr Leu Pro Lys Met Asn Lys
705                 710                 715                 720

Lys Ile Val Tyr Ser Gln Leu Thr Thr His Leu Leu Thr Asp Lys Asn
                725                 730                 735

Tyr Thr Thr Tyr Gly His Leu Lys Asn Gln Lys Gly His Arg Lys Trp
            740                 745                 750

Tyr Val Leu Val Lys Asn Asn Leu Gln Asn Ser Asp Ile Thr Ala Val
        755                 760                 765

Ser Ser Phe Arg Asn Ile Val Ala His Ile Ser Val Val Arg Asn Ser
770                 775                 780

Asn Glu Tyr Ile Ser Gly Ile Gly Glu Leu His Ser Tyr Phe Glu Leu
785                 790                 795                 800

Tyr His Tyr Leu Val Gln Ser Met Ile Ala Lys Asn Asn Trp Tyr Asp
                805                 810                 815

Thr Ser His Gln Pro Lys Thr Ala Glu Tyr Leu Asn Asn Leu Lys Lys
            820                 825                 830

His His Thr Tyr Cys Lys Asp Phe Val Lys Ala Tyr Cys Ile Pro Phe
        835                 840                 845

Gly Tyr Val Val Pro Arg Tyr Lys Asn Leu Thr Ile Asn Glu Leu Phe
    850                 855                 860

Asp Arg Asn Asn Pro Asn Pro Glu Pro Lys Glu Glu Val
865                 870                 875
```

<210> SEQ ID NO 30
<211> LENGTH: 922
<212> TYPE: PRT
<213> ORGANISM: Ruminococcus sp.

<400> SEQUENCE: 30

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Ala Glu Val Ile Ala Pro Val Ala
        35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
370                 375                 380
```

-continued

```
Glu Glu Tyr Gly Phe Arg Phe Lys Asp Lys Gln Tyr Asp Ser Val Arg
385                 390                 395                 400
Ser Lys Met Tyr Lys Leu Met Asp Phe Leu Leu Phe Cys Asn Tyr Tyr
            405                 410                 415
Arg Asn Asp Val Ala Ala Gly Glu Ala Leu Val Arg Lys Leu Arg Phe
                420                 425                 430
Ser Met Thr Asp Asp Glu Lys Glu Gly Ile Tyr Ala Asp Glu Ala Ala
            435                 440                 445
Lys Leu Trp Gly Lys Phe Arg Asn Asp Phe Glu Asn Ile Ala Asp His
        450                 455                 460
Met Asn Gly Asp Val Ile Lys Glu Leu Gly Lys Ala Asp Met Asp Phe
465                 470                 475                 480
Asp Glu Lys Ile Leu Asp Ser Glu Lys Lys Asn Ala Ser Asp Leu Leu
                485                 490                 495
Tyr Phe Ser Lys Met Ile Tyr Met Leu Thr Tyr Phe Leu Asp Gly Lys
            500                 505                 510
Glu Ile Asn Asp Leu Leu Thr Thr Leu Ile Ser Lys Phe Asp Asn Ile
        515                 520                 525
Lys Glu Phe Leu Lys Ile Met Lys Ser Ala Val Asp Val Glu Cys
530                 535                 540
Glu Leu Thr Ala Gly Tyr Lys Leu Phe Asn Asp Ser Gln Arg Ile Thr
545                 550                 555                 560
Asn Glu Leu Phe Ile Val Lys Asn Ile Ala Ser Met Arg Lys Pro Ala
                565                 570                 575
Ala Ser Ala Lys Leu Thr Met Phe Arg Asp Ala Leu Thr Ile Leu Gly
            580                 585                 590
Ile Asp Asp Asn Ile Thr Asp Asp Arg Ile Ser Glu Ile Leu Lys Leu
        595                 600                 605
Lys Glu Lys Gly Lys Gly Ile His Gly Leu Arg Asn Phe Ile Thr Asn
610                 615                 620
Asn Val Ile Glu Ser Ser Arg Phe Val Tyr Leu Ile Lys Tyr Ala Asn
625                 630                 635                 640
Ala Gln Lys Ile Arg Glu Val Ala Lys Asn Glu Lys Val Val Met Phe
                645                 650                 655
Val Leu Gly Gly Ile Pro Asp Thr Gln Ile Glu Arg Tyr Tyr Lys Ser
            660                 665                 670
Cys Val Glu Phe Pro Asp Met Asn Ser Ser Leu Glu Ala Lys Arg Ser
        675                 680                 685
Glu Leu Ala Arg Met Ile Lys Asn Ile Ser Phe Asp Asp Phe Lys Asn
690                 695                 700
Val Lys Gln Gln Ala Lys Gly Arg Glu Asn Val Ala Lys Glu Arg Ala
705                 710                 715                 720
Lys Ala Val Ile Gly Leu Tyr Leu Thr Val Met Tyr Leu Leu Val Lys
                725                 730                 735
Asn Leu Val Asn Val Asn Ala Arg Tyr Val Ile Ala Ile His Cys Leu
            740                 745                 750
Glu Arg Asp Phe Gly Leu Tyr Lys Glu Ile Ile Pro Glu Leu Ala Ser
        755                 760                 765
Lys Asn Leu Lys Asn Asp Tyr Arg Ile Leu Ser Gln Thr Leu Cys Glu
770                 775                 780
Leu Cys Asp Asp Arg Asn Glu Ser Ser Asn Leu Phe Leu Lys Lys Asn
785                 790                 795                 800
```

```
Lys Arg Leu Arg Lys Cys Val Glu Val Asp Ile Asn Asn Ala Asp Ser
                805             810                 815

Ser Met Thr Arg Lys Tyr Arg Asn Cys Ile Ala His Leu Thr Val Val
        820             825                 830

Arg Glu Leu Lys Glu Tyr Ile Gly Asp Ile Arg Thr Val Asp Ser Tyr
        835             840                 845

Phe Ser Ile Tyr His Tyr Val Met Gln Arg Cys Ile Thr Lys Arg Gly
    850             855                 860

Asp Asp Thr Lys Gln Glu Lys Ile Lys Tyr Glu Asp Leu Leu
865             870              875             880

Lys Asn His Gly Tyr Thr Lys Asp Phe Val Lys Ala Leu Asn Ser Pro
            885             890                 895

Phe Gly Tyr Asn Ile Pro Arg Phe Lys Asn Leu Ser Ile Glu Gln Leu
        900             905                 910

Phe Asp Arg Asn Glu Tyr Leu Thr Glu Lys
        915             920
```

<210> SEQ ID NO 31
<211> LENGTH: 919
<212> TYPE: PRT
<213> ORGANISM: Ruminococcus sp.

<400> SEQUENCE: 31

```
Met Ala Lys Lys Asn Lys Met Lys Pro Arg Glu Leu Arg Glu Ala Gln
1               5                   10                  15

Lys Lys Ala Arg Gln Leu Lys Ala Ala Glu Ile Asn Asn Asn Ala Ala
            20                  25                  30

Pro Ala Ile Ala Ala Met Pro Ala Glu Val Ile Ala Pro Ala Ala
            35                  40                  45

Glu Lys Lys Lys Ser Ser Val Lys Ala Ala Gly Met Lys Ser Ile Leu
50                  55                  60

Val Ser Glu Asn Lys Met Tyr Ile Thr Ser Phe Gly Lys Gly Asn Ser
65                  70                  75                  80

Ala Val Leu Glu Tyr Glu Val Asp Asn Asn Asp Tyr Asn Gln Thr Gln
                85                  90                  95

Leu Ser Ser Lys Asp Asn Ser Asn Ile Gln Leu Gly Val Asn Glu
            100                 105                 110

Val Asn Ile Thr Phe Ser Ser Lys His Gly Phe Glu Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Val Lys Gly Ser Glu Ser His Asp Asp
        195                 200                 205

Phe Ile Gly Tyr Leu Ser Thr Asn Asn Ile Tyr Asp Val Phe Ile Asp
    210                 215                 220

Pro Asp Asn Ser Ser Leu Ser Asp Asp Lys Ala Asn Val Arg Lys
225                 230                 235                 240

Ser Leu Ser Lys Phe Asn Ala Leu Leu Lys Thr Lys Arg Leu Gly Tyr
                245                 250                 255
```

```
Phe Gly Leu Glu Glu Pro Lys Thr Lys Asp Asn Arg Val Ser Gln Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Asp
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Leu Arg Glu Lys Met Leu
    370                 375                 380

Asp Glu Tyr Gly Phe Arg Phe Lys Asp Lys Gln Tyr Asp Ser Val Arg
385                 390                 395                 400

Ser Lys Met Tyr Lys Leu Met Asp Phe Leu Phe Cys Asn Tyr Tyr
                405                 410                 415

Arg Asn Asp Ile Ala Ala Gly Glu Ser Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
            500                 505                 510

Glu Ile Asn Asp Leu Leu Thr Thr Leu Ile Ser Lys Phe Asp Asn Ile
        515                 520                 525

Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Lys Ile Thr Asp Asp Arg Ile Ser Gly Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
                645                 650                 655

Val Leu Gly Gly Ile Pro Asp Thr Gln Ile Glu Arg Tyr Tyr Lys Ser
            660                 665                 670
```

```
Cys Val Glu Phe Pro Asp Met Asn Ser Ser Leu Gly Val Lys Arg Ser
            675                 680                 685

Glu Leu Ala Arg Met Ile Lys Asn Ile Ser Phe Asp Asp Phe Lys Asn
        690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
770                 775                 780

Leu Cys Asp Lys Ser Pro Asn Leu Phe Leu Lys Lys Asn Glu Arg Leu
785                 790                 795                 800

Arg Lys Cys Val Glu Val Asp Ile Asn Asn Ala Asp Ser Ser Met Thr
                805                 810                 815

Arg Lys Tyr Arg Asn Cys Ile Ala His Leu Thr Val Val Arg Glu Leu
            820                 825                 830

Lys Glu Tyr Ile Gly Asp Ile Cys Thr Val Asp Ser Tyr Phe Ser Ile
        835                 840                 845

Tyr His Tyr Val Met Gln Arg Cys Ile Thr Lys Arg Glu Asn Asp Thr
    850                 855                 860

Lys Gln Glu Glu Lys Ile Lys Tyr Glu Asp Asp Leu Leu Lys Asn His
865                 870                 875                 880

Gly Tyr Thr Lys Asp Phe Val Lys Ala Leu Asn Ser Pro Phe Gly Tyr
                885                 890                 895

Asn Ile Pro Arg Phe Lys Asn Leu Ser Ile Glu Gln Leu Phe Asp Arg
            900                 905                 910

Asn Glu Tyr Leu Thr Glu Lys
        915

<210> SEQ ID NO 32
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 32
gaactacacc cgtgcaaaaa tgcaggggtc taaaac                              36

<210> SEQ ID NO 33
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 33
gaattacacc cgtgcaaaaa tgcaggggtc taaaac                              36

<210> SEQ ID NO 34
<211> LENGTH: 36
<212> TYPE: DNA
<213> ORGANISM: Unknown
```

```
<220> FEATURE:
<223> OTHER INFORMATION: Description of Unknown:
      Direct repeat nucleotide sequence

<400> SEQUENCE: 34
gaactacacc cgtgcaaaat tgcaggggtc taaaac                              36

<210> SEQ ID NO 35
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 35
gaactacacc cctgcagaaa tgctggggtc tgaaac                              36

<210> SEQ ID NO 36
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 36
ggacaataac ctgcgaattt tggcaggttc tatgac                              36

<210> SEQ ID NO 37
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 37
gtgcagtagc cttacagatt cgtagggttc tgagac                              36

<210> SEQ ID NO 38
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 38
ctactacact ggtgcgaatt tgcactagtc taaaac                              36

<210> SEQ ID NO 39
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 39
ctactacact agtgcaaatt tgcactagtc taaaac                              36

<210> SEQ ID NO 40
<211> LENGTH: 36
<212> TYPE: DNA
<213> ORGANISM: Unknown
<220> FEATURE:
```

```
<223> OTHER INFORMATION: Description of Unknown:
      Direct repeat nucleotide sequence

<400> SEQUENCE: 40
ctactacaca ggtgcaattt tgcactagtc taaaac                              36

<210> SEQ ID NO 41
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 41
ctactacact ggtgcgaatt tgcactagtc taaaac                              36

<210> SEQ ID NO 42
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 42
ctactatact ggtgcgaatt tgcactagtc taaaac                              36

<210> SEQ ID NO 43
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 43
gaactacacc cgtgcaaaaa tgcaggggtc taaaac                              36

<210> SEQ ID NO 44
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 44
catgtaaacc cctaacaaat gataggggt tgaaac                               36

<210> SEQ ID NO 45
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 45
ctactactac cctgttattt gacagggttc aaaaac                              36

<210> SEQ ID NO 46
<211> LENGTH: 36
<212> TYPE: DNA
<213> ORGANISM: Unknown
<220> FEATURE:
<223> OTHER INFORMATION: Description of Unknown:
```

-continued

Direct repeat nucleotide sequence

<400> SEQUENCE: 46
gaactacagc cctgtgaaat aacggggttc taaaac                              36

<210> SEQ ID NO 47
<211> LENGTH: 36
<212> TYPE: DNA
<213> ORGANISM: Unknown
<220> FEATURE:
<223> OTHER INFORMATION: Description of Unknown:
       Direct repeat nucleotide sequence

<400> SEQUENCE: 47
gaactacagc cctgtgaaat aacagggttc taaaac                              36

<210> SEQ ID NO 48
<211> LENGTH: 36
<212> TYPE: DNA
<213> ORGANISM: Unknown
<220> FEATURE:
<223> OTHER INFORMATION: Description of Unknown:
       Direct repeat nucleotide sequence

<400> SEQUENCE: 48
gaacgacgtc actacacacc gagaggtgtc taaaac                              36

<210> SEQ ID NO 49
<211> LENGTH: 36
<212> TYPE: DNA
<213> ORGANISM: Unknown
<220> FEATURE:
<223> OTHER INFORMATION: Description of Unknown:
       Direct repeat nucleotide sequence

<400> SEQUENCE: 49
caactactac cctgccaaat ggcagggttc agaaac                              36

<210> SEQ ID NO 50
<211> LENGTH: 36
<212> TYPE: DNA
<213> ORGANISM: Unknown
<220> FEATURE:
<223> OTHER INFORMATION: Description of Unknown:
       Direct repeat nucleotide sequence

<400> SEQUENCE: 50
gaccaacacc tctgcaaaac tgcaggggtc taaaac                              36

<210> SEQ ID NO 51
<211> LENGTH: 35
<212> TYPE: DNA
<213> ORGANISM: Unknown
<220> FEATURE:
<223> OTHER INFORMATION: Description of Unknown:
       Direct repeat nucleotide sequence

<400> SEQUENCE: 51
gaactacact ctggctgaaa gtcagggtct aaaac                               35

<210> SEQ ID NO 52
<211> LENGTH: 35
<212> TYPE: DNA
<213> ORGANISM: Unknown
<220> FEATURE:
<223> OTHER INFORMATION: Description of Unknown:
       Direct repeat nucleotide sequence

```
<400> SEQUENCE: 52
gaactacact ctggctgaaa gtcagggtct aaaac                                  35

<210> SEQ ID NO 53
<211> LENGTH: 35
<212> TYPE: DNA
<213> ORGANISM: Unknown
<220> FEATURE:
<223> OTHER INFORMATION: Description of Unknown:
      Direct repeat nucleotide sequence

<400> SEQUENCE: 53
gaactacacc ctggctgaaa gtcagggtct aaaac                                  35

<210> SEQ ID NO 54
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 54
ctactacact ggtgcaaatt tgcactagtc taaaac                                 36

<210> SEQ ID NO 55
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 55
ctactacact agtgcgaatt tgcactagtc taaaac                                 36

<210> SEQ ID NO 56
<211> LENGTH: 38
<212> TYPE: DNA
<213> ORGANISM: Unknown
<220> FEATURE:
<223> OTHER INFORMATION: Description of Unknown:
      Direct repeat nucleotide sequence

<400> SEQUENCE: 56
cagcactaca cccccctgaa acaggagggg tctaaaac                               38

<210> SEQ ID NO 57
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 57
ctactacact agtgcgaatt tgcactagtc taaaat                                 36

<210> SEQ ID NO 58
<211> LENGTH: 36
<212> TYPE: DNA
<213> ORGANISM: Unknown
<220> FEATURE:
<223> OTHER INFORMATION: Description of Unknown:
      Direct repeat nucleotide sequence
```

<400> SEQUENCE: 58
ctactacact agtgcgaatt tgcgctagtc taaaac                                    36

<210> SEQ ID NO 59
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 59
ctactatact ggtgcgaatt tgcactagtc taaaat                                    36

<210> SEQ ID NO 60
<211> LENGTH: 37
<212> TYPE: DNA
<213> ORGANISM: Unknown
<220> FEATURE:
<223> OTHER INFORMATION: Description of Unknown:
      Direct repeat nucleotide sequence

<400> SEQUENCE: 60
ccctttgtac tatacctgtt ttacacaggt ctaaaac                                   37

<210> SEQ ID NO 61
<211> LENGTH: 37
<212> TYPE: DNA
<213> ORGANISM: Unknown
<220> FEATURE:
<223> OTHER INFORMATION: Description of Unknown:
      Direct repeat nucleotide sequence

<400> SEQUENCE: 61
gtactatacc tgttttacac aggataataa ccaaaat                                   37

<210> SEQ ID NO 62
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 62
ctactacact ggtgcgaatt tgcactagtc taaaac                                    36

<210> SEQ ID NO 63
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 63
ctactacact agtgcgaatt tgcactagtc taaaac                                    36

<210> SEQ ID NO 64
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 64
gaactatacc cctaccaaat ggtcggggtc tgaaac                                      36

<210> SEQ ID NO 65
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 65
caagtaaacc cctaccaact ggtcggggtt tgaaac                                      36

<210> SEQ ID NO 66
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 66
caagtaaacc cttaccaact ggtcggggtt tgaaac                                      36

<210> SEQ ID NO 67
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 67
gaactatagt agtgtaaatt tgcactacta taaaac                                      36

<210> SEQ ID NO 68
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 68
ctactacact agtgcgaatt tgcactagtc taaaac                                      36

<210> SEQ ID NO 69
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 69
ctactacact agtgcgaatt tgcgctagtc taaaac                                      36

<210> SEQ ID NO 70
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 70
ctactacact agtgcgaatt tgcactagtc taaaac       36

<210> SEQ ID NO 71
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 71
ctactacact ggtgcaaatt tgcactagtc taaaac       36

<210> SEQ ID NO 72
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 72
ctactacact ggtgcaaatt tgcactagtc taaaac       36

<210> SEQ ID NO 73
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 73
caactacaac cccgtaaaaa tacggggttc tgaaac       36

<210> SEQ ID NO 74
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 74
ctactacact agtgcgaatt tgcactagtc taaaac       36

<210> SEQ ID NO 75
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 75
ctactacact ggtgcaaatt tgcactagtc taaaac       36

<210> SEQ ID NO 76
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 76
ctactacact ggtgcaaatt agcactagtc taaaac       36

<210> SEQ ID NO 77
<211> LENGTH: 36
<212> TYPE: DNA
<213> ORGANISM: Unknown
<220> FEATURE:
<223> OTHER INFORMATION: Description of Unknown:
      Direct repeat nucleotide sequence

<400> SEQUENCE: 77
ctactacact ggtgcaaatt agcactagtc taaaac                              36

<210> SEQ ID NO 78
<211> LENGTH: 392
<212> TYPE: PRT
<213> ORGANISM: Ruminococcus sp.

<400> SEQUENCE: 78

Met Leu Ile Pro Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Glu Trp Gln Ile Glu Glu
                85                  90                  95

Ile Asp Asp Ser Leu Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Leu Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Gly His
        275                 280                 285

Val Lys Ser Val Lys His Leu Leu Ser Asp Pro Arg Phe Gly Ser Asp
    290                 295                 300

```
Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Thr Val Asn Glu Phe Ile Ser Pro Ile Gln Val
            340                 345                 350

Lys Tyr Tyr Phe Asn Lys Phe Gly Lys Asp Gly Val Ile Leu Ser Pro
                355                 360                 365

Ser Asp Ser Phe Glu Glu Met Arg Thr Leu Tyr Val Glu Gly Ala Glu
            370                 375                 380

Ala Tyr Asn Arg Glu Val Glu Met
385                 390
```

<210> SEQ ID NO 79
<211> LENGTH: 389
<212> TYPE: PRT
<213> ORGANISM: Ruminococcus sp.

<400> SEQUENCE: 79

```
Met Leu Ile Leu Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
                20                  25                  30

Ser Val Ile Ile Lys Asp Lys Ser Ile Phe Glu Thr Ser Leu Ser Pro
            35                  40                  45

Asn Gly Ser Val Ser Met Ser Ser Phe Leu Thr Ser Ile Phe Asp Ser
        50                  55                  60

Ala Tyr Ile Ala Ser Leu Lys Tyr Lys Ser Glu Lys Tyr Asn Gly Ile
65                  70                  75                  80

Pro Leu Leu Asn Ala Phe Val Lys Trp Gln Ile Glu Glu Ile Asn Asp
                85                  90                  95

Gly Leu Asp Asp Lys Ser Lys Glu Ile Ile Lys Ser Tyr Leu Ile Ser
            100                 105                 110

Lys Leu Ser Ala Lys Tyr Glu Lys Thr Lys Thr Glu Asn Ala Val Arg
        115                 120                 125

Val Arg Leu Ser Ile Cys Arg Asp Leu Tyr Asp Thr Leu Ser Ser Asp
130                 135                 140

Asp Leu Tyr Tyr Glu Asn Lys Val Tyr Ser Ser Thr Leu Arg Arg Phe
145                 150                 155                 160

Leu Lys Ala Val Tyr Glu Asp Tyr Ala Leu Leu Ser Asp Cys Glu Arg
                165                 170                 175

Glu Arg Leu Ile Phe Ala Asp Asn Ile Ile Lys Ile Asn Glu Val Ile
            180                 185                 190

Lys Gln Asn Gly Ser Arg Tyr Tyr Ser Phe Ile Tyr Ala Tyr Ser Asn
        195                 200                 205

Met Tyr Ser Arg Glu Lys Arg Arg Ile Arg Leu Ile Pro Tyr Arg Ile
210                 215                 220

Val Ser Asp Glu Tyr Lys Met Tyr Asn Tyr Leu Val Cys Leu Ser Asp
225                 230                 235                 240

Glu Lys Ser Ala Gly Lys Glu Phe Lys Ala Asp Ser Tyr Arg Ile Ser
                245                 250                 255

Arg Leu Ser Gly Leu Ser Ile Ala Glu Lys Leu Ser Gln Lys Glu Tyr
            260                 265                 270

Ser Ser Val Thr Glu Tyr Glu Arg Leu Lys Glu Gly His Val Lys Ser
        275                 280                 285
```

```
Val Lys His Leu Leu Ser Asp Pro Arg Phe Gly Ser Asp Glu Ser Asp
    290                 295                 300

Ile Ser Lys Val Tyr Leu Thr Glu Lys Gly Val Glu Met Phe Gly Lys
305                 310                 315                 320

Ile Leu Tyr Gln Arg Pro Ile Leu Lys Gly Asn Glu Lys Pro Lys Pro
                325                 330                 335

Asn Ala Val Asn Glu Phe Ile Ser Pro Pro Ile Gln Val Lys Tyr Tyr
                340                 345                 350

Phe Asn Lys Phe Gly Lys Asp Gly Val Ile Leu Ser Pro Ser Asp Ser
                355                 360                 365

Phe Glu Glu Met Arg Thr Leu Tyr Val Glu Gly Ala Glu Ala Tyr Asn
370                 375                 380

Arg Glu Val Glu Met
385

<210> SEQ ID NO 80
<211> LENGTH: 392
<212> TYPE: PRT
<213> ORGANISM: Ruminococcus bicirculans

<400> SEQUENCE: 80

Met Ser Met Thr Pro Ser Thr Phe Leu Pro Lys Arg Glu Asp Gly Val
1               5                   10                  15

Pro Tyr Ile Ala Glu Val Gln Ser Ile Pro Leu Ser Pro Ser Ala Tyr
                20                  25                  30

Ser Val Ile Ile Lys Asp Lys Ser Ile Phe Glu Thr Ser Leu Ser Pro
                35                  40                  45

Asn Gly Ser Val Ser Met Ser Ser Phe Leu Thr Ser Ile Phe Asp Ser
50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Lys Trp Gln Ile Glu Glu
                85                  90                  95

Ile Asp Asp Ser Leu Asp Asp Lys Ser Lys Glu Ile Ile Lys Ser Tyr
                100                 105                 110

Leu Ile Ser Lys Leu Ser Ala Lys Tyr Glu Lys Thr Lys Thr Glu Asn
                115                 120                 125

Ala Val Arg Val Arg Leu Ser Ile Cys Arg Asp Leu Tyr Asp Thr Leu
                130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
                180                 185                 190

Glu Val Ile Lys Gln Asn Gly Ser Arg Tyr Tyr Ser Phe Ile Tyr Ala
                195                 200                 205

Tyr Ser Asn Met Tyr Ser Arg Glu Lys Arg Ile Arg Leu Ile Pro
210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
```

```
              260                 265                 270
Lys Glu Tyr Ser Ser Val Thr Glu Tyr Glu Arg Leu Lys Glu Gly His
            275                 280                 285

Val Lys Ser Val Lys His Leu Leu Ser Asp Pro Arg Phe Gly Ser Asp
        290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Ala Val Asn Glu Phe Ile Ser Pro Ile Gln Val
            340                 345                 350

Lys Tyr Tyr Phe Asn Lys Phe Gly Lys Asp Gly Val Ile Leu Ser Pro
                355                 360                 365

Ser Asp Ser Phe Glu Glu Met Arg Thr Leu Tyr Val Glu Gly Ala Glu
            370                 375                 380

Ala Tyr Asn Arg Glu Val Glu Met
385                 390

<210> SEQ ID NO 81
<211> LENGTH: 392
<212> TYPE: PRT
<213> ORGANISM: Ruminococcus sp.

<400> SEQUENCE: 81

Met Leu Ile Pro Pro Ser Thr Phe Leu Pro Lys Arg Asp Lys Asn Val
1               5                   10                  15

Pro Tyr Ile Ala Glu Val Gln Ser Ile Pro Leu Ser Pro Ser Ala Tyr
            20                  25                  30

Ser Val Ile Ile Lys Asp Lys Ser Ile Phe Glu Thr Ser Leu Ser Pro
        35                  40                  45

Asn Gly Ser Val Ser Met Ser Ser Phe Leu Thr Ser Ile Phe Asp Ser
    50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Lys Trp Gln Ile Glu Glu
                85                  90                  95

Ile Asp Asp Gly Leu Asp Lys Ser Lys Glu Ile Ile Lys Ser Tyr
            100                 105                 110

Leu Ile Ser Lys Leu Ser Ala Lys Tyr Glu Lys Thr Lys Thr Glu Asn
        115                 120                 125

Ala Val Arg Val Arg Leu Ser Ile Cys Arg Asp Leu Tyr Asp Thr Leu
    130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
            180                 185                 190

Glu Val Ile Lys Gln Asn Gly Ser Arg Tyr Tyr Ser Phe Ile Tyr Ala
        195                 200                 205

Tyr Ser Asn Met Tyr Ser Arg Glu Lys Arg Arg Ile Arg Leu Ile Pro
    210                 215                 220

Tyr Arg Ile Val Ser Asp Glu Tyr Lys Met Tyr Asn Tyr Leu Val Cys
225                 230                 235                 240
```

Leu Ser Asp Glu Lys Ser Ala Gly Lys Glu Phe Lys Ala Asp Ser Cys
                245                 250                 255

Arg Ile Ser Arg Leu Ser Gly Leu Ser Ile Ala Glu Lys Leu Ser Gln
            260                 265                 270

Lys Glu Tyr Ser Ser Val Thr Glu Tyr Glu Arg Leu Lys Glu Val His
            275                 280                 285

Val Lys Ser Val Lys His Leu Leu Ser Asp Pro Arg Phe Gly Ser Asp
            290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Ala Val Asn Glu Phe Ile Ser Pro Ile Gln Val
                340                 345                 350

Lys Tyr Tyr Phe Asn Lys Phe Gly Lys Asp Gly Val Ile Leu Ser Pro
                355                 360                 365

Ser Asp Ser Phe Glu Glu Met Arg Thr Leu Tyr Val Glu Gly Ala Glu
                370                 375                 380

Ala Tyr Asn Arg Glu Val Glu Met
385                 390

<210> SEQ ID NO 82
<211> LENGTH: 389
<212> TYPE: PRT
<213> ORGANISM: Unknown
<220> FEATURE:
<223> OTHER INFORMATION: Description of Unknown:
    Gut metagenome sequence

<400> SEQUENCE: 82

Met Ser Met Thr Pro Ser Thr Phe Leu Pro Lys Arg Asp Lys Asn Ala
1               5                   10                  15

Thr Tyr Ile Ala Glu Val Gln Ser Ile Pro Leu Ser Pro Ser Ala Tyr
                20                  25                  30

Ser Val Ile Ile Lys Asp Lys Ser Ile Phe Glu Thr Ser Leu Ser Pro
            35                  40                  45

Asn Gly Ser Val Ser Met Ser Ser Phe Leu Thr Ser Ile Phe Asp Ser
50                  55                  60

Ala Tyr Ile Ala Ser Leu Lys Tyr Lys Ser Glu Lys Tyr Asn Gly Ile
65                  70                  75                  80

Pro Leu Leu Asn Ala Phe Val Lys Trp Gln Ile Glu Glu Ile Asp Asp
                85                  90                  95

Gly Leu Asp Asp Lys Ser Lys Glu Ile Ile Lys Ser Tyr Leu Ile Ser
                100                 105                 110

Lys Leu Ser Ala Lys Tyr Glu Lys Thr Lys Thr Glu Asn Ala Val Arg
            115                 120                 125

Val Arg Leu Ser Ile Cys Arg Asp Leu Tyr Asp Thr Leu Ser Ser Asp
            130                 135                 140

Asp Leu Tyr Tyr Glu Asn Lys Val Tyr Ser Ser Thr Leu Arg Arg Phe
145                 150                 155                 160

Leu Lys Ala Val Tyr Glu Asp Tyr Ala Leu Leu Ser Asp Cys Glu Arg
                165                 170                 175

Glu Arg Leu Ile Phe Ala Asp Asn Ile Lys Ile Asn Glu Ile Ile
            180                 185                 190

Lys Gln Asn Gly Ser Arg Tyr Tyr Ser Phe Ile Tyr Ala Tyr Ser Asn
            195                 200                 205

-continued

```
Met Tyr Ser Arg Glu Lys Arg Ile Arg Leu Ile Pro Tyr Arg Ile
    210                 215                 220

Val Ser Asp Glu Tyr Lys Met Tyr Asn Tyr Leu Val Cys Leu Ser Asp
225                 230                 235                 240

Glu Lys Ser Ala Gly Lys Glu Phe Lys Ala Asp Ser Tyr Arg Ile Ser
                245                 250                 255

Arg Leu Ser Gly Leu Ser Ile Ala Glu Lys Leu Ser Gln Lys Glu Tyr
                260                 265                 270

Ser Ser Val Thr Glu Tyr Glu Arg Leu Lys Glu Gly His Val Lys Ser
            275                 280                 285

Val Lys His Leu Leu Ser Asp Pro Arg Phe Gly Ser Asp Glu Ser Asp
    290                 295                 300

Ile Ser Lys Val Tyr Leu Thr Glu Lys Gly Val Glu Met Phe Gly Lys
305                 310                 315                 320

Ile Leu Tyr Gln Arg Pro Ile Leu Lys Gly Asn Glu Lys Pro Lys Pro
                325                 330                 335

Asn Thr Val Asn Glu Phe Ile Ser Pro Ile Gln Val Lys Tyr Tyr
                340                 345                 350

Phe Asn Lys Phe Gly Lys Asp Gly Val Ile Leu Ser Pro Ser Asp Ser
                355                 360                 365

Phe Glu Glu Met Arg Thr Leu Tyr Val Glu Gly Ala Glu Ala Tyr Asn
                370                 375                 380

Arg Glu Val Glu Met
385
```

<210> SEQ ID NO 83
<211> LENGTH: 392
<212> TYPE: PRT
<213> ORGANISM: Unknown
<220> FEATURE:
<223> OTHER INFORMATION: Description of Unknown:
      Gut metagenome sequence

<400> SEQUENCE: 83

```
Met Phe Ile Pro Pro Ser Thr Phe Leu Pro Lys Arg Glu Gly Gly Val
1               5                   10                  15

Pro Tyr Ile Ala Glu Val Gln Ser Ile Pro Leu Ser Pro Ser Ala Tyr
                20                  25                  30

Ser Val Ile Ile Lys Asp Lys Ser Ile Phe Glu Thr Ser Leu Ser Pro
            35                  40                  45

Asn Gly Ser Val Ser Met Ser Ser Phe Leu Thr Ser Ile Phe Asp Ser
50                  55                  60

Ala Tyr Ile Ala Ser Leu Lys Tyr Lys Thr Asp Asp Asn Tyr Lys Tyr
65                  70                  75                  80

Ile Gly Ile Pro Leu Leu Asn Ala Phe Ile Lys Trp Gln Ile Glu Glu
                85                  90                  95

Ile Asp Asp Gly Leu Asp Lys Ser Lys Glu Ile Ile Lys Ser Tyr
                100                 105                 110

Leu Ile Ser Lys Phe Ser Ala Lys Tyr Glu Lys Thr Lys Thr Glu Asn
            115                 120                 125

Ala Val Arg Val Arg Leu Ser Ile Cys Arg Asp Leu Tyr Asp Thr Leu
        130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
```

```
                165                 170                 175
Cys Glu Arg Glu Arg Leu Ile Phe Ala Asp Asn Ile Ile Lys Ile Asn
            180                 185                 190
Glu Val Ile Lys Gln Asn Gly Asn Arg Tyr Tyr Ser Phe Ile Tyr Ala
            195                 200                 205
Tyr Ser Asn Met Tyr Ser Arg Glu Lys Arg Ile Arg Leu Ile Pro
        210                 215                 220
Tyr Arg Ile Ile Ser Asp Glu Tyr Lys Met Tyr Asn Tyr Leu Val Cys
225                 230                 235                 240
Leu Ser Asp Glu Lys Ser Ala Gly Lys Glu Phe Lys Ala Asp Ser Cys
                245                 250                 255
Arg Ile Ser Arg Leu Ser Gly Leu Ser Ile Ala Glu Lys Leu Ser Gln
            260                 265                 270
Lys Glu Tyr Ser Ser Val Thr Glu Tyr Glu Arg Leu Lys Glu Gly His
            275                 280                 285
Val Lys Ser Val Lys His Leu Leu Ser Asp Pro Arg Phe Gly Ser Asp
        290                 295                 300
Glu Ser Asp Ile Ser Lys Val Tyr Leu Thr Glu Lys Gly Val Glu Met
305                 310                 315                 320
Phe Gly Lys Ile Leu Tyr Gln Arg Pro Ile Leu Lys Gly Asn Glu Lys
                325                 330                 335
Pro Lys Pro Asn Ala Val Asn Glu Phe Ile Ser Pro Ile Gln Val
            340                 345                 350
Lys Tyr Tyr Phe Asn Lys Phe Gly Lys Asp Gly Val Ile Leu Ser Pro
            355                 360                 365
Ser Asp Ser Phe Glu Glu Met Arg Thr Leu Tyr Val Glu Gly Ala Glu
        370                 375                 380
Ala Tyr Asn Arg Glu Val Glu Met
385                 390

<210> SEQ ID NO 84
<211> LENGTH: 390
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 84

Met Ser Met Thr Pro Ser Thr Phe Leu Pro Lys Arg Asp Thr Asn Ile
1               5                   10                  15
Pro Tyr Ile Ala Glu Val Gln Ser Ile Pro Leu Ser Pro Ser Ala Tyr
            20                  25                  30
Ala Val Ile Val Lys Asp Lys Ser Ile Phe Glu Thr Ser Leu Phe Pro
        35                  40                  45
Asn Gly Gly Ser Val Ser Met Ser Ser Phe Leu Thr Arg Ile Phe Asp
    50                  55                  60
Ser Ala Tyr Ile Ala Ser Leu Lys Tyr Lys Ser Glu Glu Tyr Asn Gly
65                  70                  75                  80
Ile Pro Leu Leu Asn Ala Phe Val Gln Trp Gln Ile Glu Glu Ile Asp
                85                  90                  95
Asp Ser Leu Asp Asp Lys Ser Lys Glu Ile Ile Lys Ser Tyr Leu Ile
            100                 105                 110
Ser Lys Leu Ser Ala Lys Tyr Glu Lys Thr Lys Thr Glu Asn Ala Val
        115                 120                 125
```

Arg Val Arg Leu Ser Ile Cys Arg Asp Leu Tyr Asp Thr Leu Ser Ser
130                 135                 140

Asp Asp Leu Tyr Tyr Glu Asn Lys Val Tyr Ser Ser Thr Leu Arg Arg
145                 150                 155                 160

Phe Leu Lys Ala Val Tyr Glu Asp Tyr Ala Leu Leu Ser Asp Cys Glu
                165                 170                 175

Arg Glu Arg Leu Ile Phe Ala Asp Asn Ile Ile Lys Ile Asn Glu Val
                180                 185                 190

Ile Lys Gln Asn Gly Ser Arg Tyr Tyr Ser Phe Ile Tyr Ala Tyr Ser
            195                 200                 205

Asn Met Tyr Ser Arg Glu Lys Arg Arg Ile Arg Leu Ile Pro Tyr Arg
210                 215                 220

Ile Val Ser Asp Glu Tyr Lys Met Tyr Asn Tyr Leu Val Cys Leu Ser
225                 230                 235                 240

Asp Glu Lys Ser Ala Gly Lys Glu Phe Lys Ala Asp Ser Tyr Arg Ile
                245                 250                 255

Ser Arg Leu Ser Gly Leu Ser Ile Ala Glu Lys Leu Ser Gln Lys Glu
                260                 265                 270

Tyr Ser Ser Val Thr Glu Tyr Glu Arg Leu Lys Glu Gly His Val Lys
            275                 280                 285

Ser Val Lys His Leu Leu Ser Asp Pro Arg Phe Gly Ser Asp Glu Ser
290                 295                 300

Asp Ile Ser Lys Val Tyr Leu Thr Glu Lys Gly Val Glu Met Phe Gly
305                 310                 315                 320

Lys Ile Leu Tyr Gln Arg Pro Ile Leu Lys Gly Asn Glu Lys Pro Lys
                325                 330                 335

Pro Asn Ala Val Asn Glu Phe Ile Ser Pro Ile Gln Val Lys Tyr
                340                 345                 350

Tyr Phe Asn Lys Phe Gly Lys Asp Gly Val Ile Leu Ser Pro Ser Asp
            355                 360                 365

Ser Phe Glu Glu Met Arg Thr Leu Tyr Val Gly Ala Glu Ala Tyr
370                 375                 380

Asn Arg Glu Val Glu Met
385                 390

<210> SEQ ID NO 85
<211> LENGTH: 392
<212> TYPE: PRT
<213> ORGANISM: Unknown
<220> FEATURE:
<223> OTHER INFORMATION: Description of Unknown:
    Human-digestive system-homo sapiens sequence

<400> SEQUENCE: 85

Met Leu Ile Pro Pro Ser Thr Phe Leu Pro Lys Arg Glu Gly Gly Val
1               5                   10                  15

Pro Tyr Ile Ala Glu Val Gln Ser Ile Pro Leu Ser Pro Ser Ala Tyr
                20                  25                  30

Ser Val Ile Ile Lys Asp Lys Ser Ile Phe Glu Thr Ser Leu Phe Pro
            35                  40                  45

Asn Gly Ser Val Ser Met Ser Ser Phe Leu Thr Ser Ile Phe Asp Ser
50                  55                  60

Ala Tyr Ile Ala Ser Leu Lys Tyr Lys Ser Asp Asp Asn Tyr Lys Tyr
65                  70                  75                  80

Ile Gly Ile Pro Leu Leu Asn Ala Phe Val Lys Trp Gln Ile Glu Glu
                85                  90                  95

Ile Asp Asp Gly Leu Asp Asp Lys Ser Lys Glu Ile Ile Lys Ser Tyr
                100                 105                 110

Leu Ile Ser Lys Leu Ser Ala Lys Tyr Lys Thr Lys Thr Glu Asn
        115                 120                 125

Ala Val Arg Val Arg Leu Ser Ile Cys Arg Asp Leu Tyr Asp Thr Leu
130                 135                 140

Ser Ser Asp Asp Leu Tyr Tyr Glu Asn Lys Val Tyr Ser Ser Thr Leu
145                 150                 155                 160

Arg Arg Phe Leu Lys Ala Val Tyr Glu Asp Tyr Ala Leu Leu Ser Asp
                165                 170                 175

Cys Glu Arg Glu Arg Leu Ile Phe Ala Asp Asn Ile Ile Lys Ile Asn
                180                 185                 190

Glu Val Ile Lys Gln Asn Gly Ser Arg Tyr Tyr Ser Phe Ile Tyr Ala
                195                 200                 205

Tyr Ser Asn Met Tyr Ser Arg Glu Lys Arg Ile Arg Leu Ile Pro
        210                 215                 220

Tyr Arg Ile Val Ser Asp Glu Tyr Lys Met Tyr Asn Tyr Leu Val Cys
225                 230                 235                 240

Leu Ser Asp Glu Lys Ser Ala Gly Lys Glu Phe Lys Ala Asp Ser Tyr
                245                 250                 255

Arg Ile Ser Arg Leu Ser Gly Leu Ser Ile Ala Glu Lys Leu Ser Gln
                260                 265                 270

Lys Glu Tyr Ser Ser Val Thr Glu Tyr Glu Arg Leu Lys Glu Val His
                275                 280                 285

Val Lys Ser Val Lys His Leu Leu Ser Asp Pro Arg Phe Gly Ser Asp
                290                 295                 300

Glu Ser Asp Ile Ser Lys Val Tyr Leu Thr Glu Lys Gly Val Glu Met
305                 310                 315                 320

Phe Gly Lys Ile Leu Tyr Gln Arg Pro Ile Leu Lys Gly Asn Glu Lys
                325                 330                 335

Pro Lys Pro Asn Ala Val Asn Glu Phe Ile Ser Pro Ile Gln Val
                340                 345                 350

Lys Tyr Tyr Phe Asn Lys Phe Gly Lys Asp Gly Val Ile Leu Ser Pro
                355                 360                 365

Ser Asp Ser Phe Glu Glu Met Arg Thr Leu Tyr Val Glu Gly Ala Glu
370                 375                 380

Ala Tyr Asn Arg Glu Val Glu Met
385                 390

<210> SEQ ID NO 86
<211> LENGTH: 389
<212> TYPE: PRT
<213> ORGANISM: Unknown
<220> FEATURE:
<223> OTHER INFORMATION: Description of Unknown:
      Human-digestive system-homo sapiens sequence

<400> SEQUENCE: 86

Met Leu Ile Pro Pro Ser Thr Phe Leu Pro Lys Arg Lys Asp Gly Val
1               5                   10                  15

Pro Tyr Ile Ala Glu Val Gln Ser Ile Pro Leu Ser Pro Ser Ala Tyr
                20                  25                  30

Ala Val Ile Val Lys Asp Lys Ser Ile Phe Glu Thr Ser Leu Ser Pro
            35                  40                  45

Asn Ser Ser Val Ser Met Ser Ser Phe Leu Thr Arg Ile Phe Asp Ser

```
                50                  55                  60
    Ala Tyr Arg Ala Ser Leu Lys Tyr Lys Ser Glu Glu Tyr Asn Gly Ile
    65                  70                  75                  80

Pro Leu Leu Asn Ala Phe Val Gln Trp Gln Ile Glu Ile Asp Gly
                        85                  90                  95

Ser Leu Asp Asp Lys Ser Lys Glu Ile Ile Arg Ser Tyr Leu Ile Ser
                    100                 105                 110

Lys Leu Ser Ala Lys Tyr Lys Lys Thr Lys Thr Glu Asn Ala Val Arg
                    115                 120                 125

Val Arg Leu Ser Ile Cys Arg Asp Leu Tyr Asp Thr Leu Ser Arg Val
                130                 135                 140

Asp Leu Cys Tyr Glu Asn Lys Val Tyr Gly Ser Thr Leu Arg Arg Phe
    145                 150                 155                 160

Leu Lys Ala Val Tyr Glu Asp Tyr Ala Leu Leu Ser Asp Cys Glu Arg
                    165                 170                 175

Glu Arg Leu Ile Phe Ala Asp Asn Ile Ile Lys Ile Asn Glu Val Ile
                    180                 185                 190

Lys Gln Asn Ser Asn Arg Tyr Asp Asn Phe Ile Tyr Ala Tyr Ser Ser
                    195                 200                 205

Met Tyr Ser Arg Glu Lys Cys Arg Ile Arg Leu Ile Pro Tyr Arg Ile
    210                 215                 220

Val Ser Asp Glu Tyr Lys Met Tyr Asn Tyr Leu Val Cys Leu Ser Asp
    225                 230                 235                 240

Glu Lys Ser Val Gly Lys Glu Phe Lys Ala Asp Ser Tyr Arg Ile Ser
                    245                 250                 255

Arg Leu Ser Gly Leu Ser Ile Ala Glu Lys Leu Ser Gln Lys Glu Tyr
                    260                 265                 270

Ser Ser Val Thr Glu Tyr Glu Arg Leu Lys Glu Gly His Val Lys Ser
                    275                 280                 285

Val Lys His Leu Leu Ser Asp Pro Arg Phe Gly Ser Asp Glu Ser Asp
                    290                 295                 300

Ile Ser Lys Val Tyr Leu Thr Glu Lys Gly Val Glu Met Phe Gly Lys
    305                 310                 315                 320

Ile Leu Tyr Gln Arg Pro Ile Leu Lys Gly Asn Glu Lys Pro Lys Pro
                    325                 330                 335

Asn Ala Val Asn Glu Phe Ile Ser Pro Pro Ile Gln Val Lys Tyr Tyr
                    340                 345                 350

Phe Asn Lys Phe Gly Lys Asp Gly Val Ile Leu Ser Pro Ser Asp Ser
                    355                 360                 365

Phe Glu Glu Met Arg Thr Leu Tyr Val Glu Gly Ala Glu Ala Tyr Asn
    370                 375                 380

Arg Glu Val Glu Met
    385

<210> SEQ ID NO 87
<211> LENGTH: 359
<212> TYPE: PRT
<213> ORGANISM: Unknown
<220> FEATURE:
<223> OTHER INFORMATION: Description of Unknown:
      Gut metagenome sequence

<400> SEQUENCE: 87

Met Gly Thr Glu Asn Ser Ser Asn Glu Tyr Gln Glu Ala Arg Gln His
    1               5                   10                  15
```

```
Leu Ser Leu Ser Asp Ala Ala Trp Ala Val Leu Gln Asp Arg Gln
             20                  25                  30

Asp Phe Gly Gly Gly Arg Ser Trp Ala Gly Ile Leu Asn Tyr Val Phe
         35                  40                  45

Ala Glu Tyr Arg Asp Lys Ala Asp Ala Ser Ile Ser Val Ala Val Glu
     50                  55                  60

Arg Arg Arg Ala Gln Tyr Glu Glu Lys Leu Val Gly Val Ala Ala Pro
 65                  70                  75                  80

Ala Val Arg Lys Ala Val Leu Glu Ala Leu Ala Asp Tyr Thr Glu
                 85                  90                  95

Glu Leu Ile Lys Lys Ala Ala Gln Asn Gly Ala Thr Pro Pro Asp Lys
                100                 105                 110

Glu Ser Phe Lys Phe Arg Leu Asp Arg Asp Asn Tyr Ala Phe Arg Glu
            115                 120                 125

Gln Trp Leu Asp Ser Pro Asp Ala Gln Tyr Tyr Gly Gly Arg Phe Ser
        130                 135                 140

Arg Tyr Leu Arg Ala Val Leu Glu Glu Tyr Ala Ala Lys Thr Val Tyr
145                 150                 155                 160

Gln Arg Glu Ala Ile Tyr Phe Asp Pro Gln Met Arg Leu Ile Gln Ala
                165                 170                 175

Ser Ala Ala Asn Gly Glu Leu Leu Arg Ile Arg Leu Lys Lys Gly Ser
            180                 185                 190

Glu Phe Glu Val Arg Pro Tyr Gly Val Leu Gly Asp Arg Gln Glu Thr
        195                 200                 205

Tyr His Tyr Leu Val Gly Leu Ser Arg Pro Gly Thr Arg Glu Pro
210                 215                 220

Glu Lys Ala Ser Ser Phe Arg Leu Ser Asn Ile Val Lys Leu Glu Val
225                 230                 235                 240

Ser Phe Arg Arg Ser Gly Arg Leu Thr Glu Lys Glu Arg Thr Asp Ile
                245                 250                 255

Glu Ser Ser Ile Arg Gly Lys Gly Val Gln Phe Leu Val Gln Gln Arg
            260                 265                 270

Glu Thr Ile Arg Ile Arg Leu Thr Glu Asp Gly Arg Gln Asn Tyr Gly
        275                 280                 285

Arg Gln Leu His Leu Arg Pro Ala Ala Arg Glu Arg Ala Glu Val Asp
    290                 295                 300

Asp Gly Leu Tyr Arg Trp Glu Tyr Thr Phe Tyr Cys Thr Glu Phe Gln
305                 310                 315                 320

Ala Lys Ala Tyr Phe Leu Lys Phe Cys Gly Asp Ala Lys Val Val Glu
                325                 330                 335

Pro Gln Ser Leu Arg Glu Thr Phe Ala Gln Glu Tyr Arg Ser Gly Leu
            340                 345                 350

Arg Ala Cys Gly Glu Glu Pro
        355

<210> SEQ ID NO 88
<211> LENGTH: 360
<212> TYPE: PRT
<213> ORGANISM: Unknown
<220> FEATURE:
<223> OTHER INFORMATION: Description of Unknown:
      Gut metagenome sequence

<400> SEQUENCE: 88

Met Gly Thr Glu Asn Ser Ser Asn Glu Tyr Gln Glu Ala Arg Gln His
 1               5                  10                  15
```

Leu Ser Leu Ser Asp Ala Ala Trp Ala Val Leu Gln Asp Arg Arg
        20                  25                  30

Asp Phe Gly Gly Gly Arg Ser Trp Ala Gly Ile Leu Asn Tyr Val Phe
        35                  40                  45

Thr Met Tyr Arg Asp Lys Ala Asp Ala Ser Val Ser Val Ala Val Ser
50                  55                  60

Arg Arg Arg Glu Gln Leu Glu Glu Gln Leu Gly Gly Val Val Ser Pro
65                  70                  75                  80

Ala Ala Arg Asp Ala Val Leu Asp Arg Leu Met Glu Val Tyr Ala Gly
                85                  90                  95

Glu Leu Ala Glu Lys Ala Met Ser Asp Gly Ala Val Ala Gln Gln Lys
            100                 105                 110

Glu Val Phe Lys Phe Arg Leu Asp Arg Asp Asn Tyr Ala Phe Arg Glu
        115                 120                 125

Gln Trp Leu Asp Ser Pro Asp Ala Ala Arg Tyr Tyr Gly Asn Arg Phe
    130                 135                 140

Ser Arg Tyr Leu Arg Ala Val Leu Glu Glu Tyr Ala Ala Lys Thr Val
145                 150                 155                 160

Tyr Gln Arg Glu Ala Ile Tyr Phe Asp Pro Gln Met Arg Leu Ile Arg
                165                 170                 175

Ala Ala Ala Ala Asn Gly Glu Leu Leu Arg Ile Arg Met Lys Thr Gly
            180                 185                 190

Ser Ser Phe Glu Val Arg Pro Tyr Gly Val Leu Gly Asp Arg Gln Glu
        195                 200                 205

Thr Tyr His Tyr Leu Val Gly Leu Ser Arg Pro Asp Gly Thr Arg Gly
    210                 215                 220

Pro Glu Lys Glu Phe Asn Phe Arg Leu Ser Lys Ile Ile Lys Leu Asp
225                 230                 235                 240

Val Ser Phe Arg Arg Ser Gly Arg Leu Thr Glu Lys Glu Arg Thr Asp
                245                 250                 255

Ile Glu Ser Ser Ile Arg Gly Lys Gly Val Gln Phe Leu Ala Gln Gln
            260                 265                 270

Arg Glu Thr Ile Arg Ile Arg Leu Thr Glu Glu Gly Arg Arg Asp Tyr
        275                 280                 285

Gly Ser Gln Met His Leu Arg Pro Pro Ala Gly Thr Arg Thr Ala Val
    290                 295                 300

Asp Asp Gly Ala Tyr Arg Trp Glu Tyr Thr Phe Phe Cys Thr Glu Phe
305                 310                 315                 320

Gln Ala Arg Ala Tyr Phe Leu Lys Phe Cys Gly Glu Ala Lys Val Val
                325                 330                 335

Glu Pro Gln Ser Leu Arg Asp Thr Leu Ala Gln Glu Tyr Arg Ser Gly
            340                 345                 350

Leu Arg Ala Cys Gly Glu Glu Pro
        355                 360

<210> SEQ ID NO 89
<211> LENGTH: 412
<212> TYPE: PRT
<213> ORGANISM: Ruminococcus flavefaciens

<400> SEQUENCE: 89

Met Glu Asn Lys Gly Lys Gln Arg Glu Phe Ile Lys Asp Tyr Asn Lys
1               5                   10                  15

Ile Val Pro Phe Leu Glu Lys Val Phe Tyr Tyr Gly Thr Phe Ser Ser

```
                  20                  25                  30
Glu Asp Tyr Glu Lys Met Asp Met Met Lys Lys Ser Lys Tyr Ser Asp
                 35                  40                  45

Tyr Lys Arg Ile Leu Glu Phe Ala Phe Arg Asp Val Leu Tyr Glu Lys
 50                  55                  60

Lys Asn Ile Asn Gly Lys Ala Leu Gly Leu Arg Ile Asp His Phe
 65                  70                  75                  80

Tyr Asp Pro His Arg Ala Phe Leu Arg Phe Thr Leu Lys Ser Phe
                 85                  90                  95

Val Ser Ile Glu Arg Leu Phe Leu Thr Cys Tyr Ile Leu Lys Arg Ile
                100                 105                 110

Ser Lys Lys Gly Lys Cys Thr Ile Asn Asp Ile Cys Ile Gly Leu Asp
                115                 120                 125

Glu Val Ser Val Asp Asp Glu Val Lys Asp Arg Lys Ser Thr Ile Ser
130                 135                 140

Arg Ile Ile Lys Asn Met Val Asp Tyr Gly Phe Leu Ile Lys Lys Gly
145                 150                 155                 160

Ser Ala Tyr Ser Ile Asn Thr Gly Ala Lys Thr Leu Asn Asn Val Ala
                165                 170                 175

Leu Leu Asn Leu Ile Asp Ile Cys Thr Asn Ala Tyr Pro Ile Ser Ile
                180                 185                 190

Cys Gly Ser Cys Ile Gln Asn Lys Ile Asp Gln Asn Tyr Gln Ser Pro
                195                 200                 205

Phe Leu Ile Lys His Leu His Leu Gly Gln Ile Phe Asn Asp Glu Leu
                210                 215                 220

Ile Trp Lys Leu Leu Ile Tyr Ala Asn Glu Lys Lys Gln Leu Cys Ile
225                 230                 235                 240

Glu Leu Lys Lys Gly Ile Lys Leu Arg Glu Leu Leu Pro Tyr Arg Ile
                245                 250                 255

Ile Thr Asn Arg Glu Thr Gly Arg Gln Tyr Leu Phe Ala Ile Tyr Val
                260                 265                 270

Gly Thr Asn Asn Phe Asp Glu Tyr Leu Met Leu Arg Leu Asp Lys Ile
                275                 280                 285

Ser Asp Ile Lys Ile Glu Ala Ser Glu Cys Glu Ile Pro Asp Asp Thr
                290                 295                 300

Val Leu Lys Glu Lys Tyr Asp Thr Ala Phe Arg Tyr Ser Phe Asn Gly
305                 310                 315                 320

Thr Thr Phe Leu Lys Arg Asp Gln Gln Pro Glu Ser Gly Ile Leu Val
                325                 330                 335

Tyr Asp Lys Ser Phe Glu Trp Asn Ile Lys Lys His Phe Pro Tyr Ser
                340                 345                 350

Asp Ala Val Ser Val Asp Glu Lys His Asn Lys Val Ser Ile Lys Val
                355                 360                 365

Asn Thr Leu Thr Glu Leu Lys Pro Trp Leu Arg Arg Asn Tyr Asp Lys
                370                 375                 380

Val Ser Leu Val Glu Ser Ser Asp Asp Thr Val Asp Lys Met Cys Asp
385                 390                 395                 400

Glu Leu Lys Lys Trp Arg Lys Met Tyr Gly Ile Ile
                405                 410

<210> SEQ ID NO 90
<211> LENGTH: 412
<212> TYPE: PRT
<213> ORGANISM: Ruminococcus flavefaciens
```

<400> SEQUENCE: 90

Met Ala Asn Glu Glu Lys Asn Arg Ser Phe Phe Lys Ile Thr Thr Tyr
1               5                   10                  15

Glu Asn Phe Arg Arg Phe Leu Lys Thr Asn Phe Tyr Tyr Cys Ser Leu
            20                  25                  30

Ser Gln Gly Gln Gln Gly Met Phe Ile Lys Ser Ile Gly Thr Thr Lys
        35                  40                  45

Tyr Asn Glu Tyr Lys Asn Ile Ile Glu Leu Ile Ala Gly Gly Lys Ile
    50                  55                  60

Glu Phe Pro Lys Ile Asn Lys Arg Leu Ala Phe Arg Tyr Asn Ile Ser
65                  70                  75                  80

Gln Leu Glu Ser Asp Tyr Asn Glu Leu Ala Asn Ser Phe Gln Leu Arg
                85                  90                  95

Thr Leu Thr Ser Leu Asp Ala Cys Leu Thr Leu Tyr Ile Leu Leu Phe
            100                 105                 110

Leu Ser Asp Lys Glu Met Gly Ser Ser Asp Ile Tyr Asn Arg Ile Gly
        115                 120                 125

Asp Ile Asp Phe Asp Ile Asp Glu Lys Thr Ile Arg Gly Lys Leu Lys
130                 135                 140

Asn Met Cys Glu Tyr Gly Met Ile Ser Tyr Lys Asn Lys Lys Tyr Ser
145                 150                 155                 160

Leu Asn Glu Cys Ser Leu Tyr Ser Val Asp Thr Ser Ile Met Leu Ser
                165                 170                 175

Leu Leu Asn Met Ala Asp Phe Met Lys Asn Leu Val Tyr Pro Glu Val
            180                 185                 190

Leu Gly Tyr Asp Leu Phe Ala Ala Leu Lys Lys Ile Tyr Glu Glu Arg
        195                 200                 205

Thr Gly Asn Glu Tyr Ile Ser Pro Phe Gln Phe Lys Tyr Ser His Leu
210                 215                 220

Ala Asn Ile Leu Asp Asp Asn Val Leu Trp Thr Leu Ile Glu Ala Ile
225                 230                 235                 240

Asp Asn Arg Gln His Val Ala Phe Glu Tyr Gly Gly Lys Ile Lys Glu
                245                 250                 255

Arg Leu Ile Pro Val Lys Ile Phe Thr Glu Asn Glu Tyr Asn Arg Cys
            260                 265                 270

Tyr Leu Phe Ala Val Lys Arg Phe Arg Asn Lys Leu Lys Phe Phe Val
        275                 280                 285

Phe Arg Leu Ser Lys Ile Tyr Asn Leu Lys Ile Thr Asn Ser Asp Glu
290                 295                 300

Asp Ile Thr Glu Ala Asp Phe Lys Glu Tyr Ser Glu Leu Tyr Asp Ser
305                 310                 315                 320

Glu Lys Lys Cys Ser Phe Phe Gly Lys Ile Asp Ser Ser Ala Gln Asn
                325                 330                 335

Asp Thr Val Glu Leu Lys Tyr Lys Arg Gly Ile Arg Ser Gln Leu Glu
            340                 345                 350

Arg Asp Phe Ser Cys Ile Glu Phe Arg Lys Asn Tyr Thr Ala Ile Val
        355                 360                 365

Thr Val Lys Ser Lys Lys Met Met Ile Pro Tyr Leu Arg Ala Asn Met
370                 375                 380

Gly Leu Ile Arg Thr Thr Asp Asp Glu Leu Ser Gly Ile Leu Asn Glu
385                 390                 395                 400

Asp Ile Glu Glu Met Lys Lys Asn Tyr Gly Ile Ile 405 410

<210> SEQ ID NO 91
<211> LENGTH: 420
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 91

Met Asn Val Ile Ile Lys Gln Gly Asp Ile Phe Met Gly Asn Glu Glu
1               5                   10                  15

Arg Asn Arg Ser Phe Phe Lys Glu Asp Thr Tyr Glu Thr Phe Arg Lys
            20                  25                  30

Phe Leu Lys Thr Asn Phe Tyr Tyr Cys Thr Leu Ser Gln Lys Gln Gln
        35                  40                  45

Ser Glu Tyr Val Lys Tyr Ile Gly Thr Thr Gln Tyr Asn His Tyr Arg
    50                  55                  60

Gly Ile Ile Glu Arg Ile Ser Glu Gly Lys Ile Ser Phe Lys Lys Tyr
65                  70                  75                  80

Asn Lys Lys Ala Phe Lys Tyr Asp Val Ser Gln Phe Ala Ser Asp
                85                  90                  95

Tyr Asn Val Leu Ala Asn Ser Phe Gln Leu Lys Thr Ile Thr Ala Ser
            100                 105                 110

Gln Thr Cys Leu Thr Ile Tyr Ile Leu Cys Val Leu Ala Lys Ser Ser
        115                 120                 125

Leu Thr Arg Lys Gly Ile Val Ala Ala Ile Ala Asp Gly Ile Asp Glu
130                 135                 140

Lys Thr Ile Val Ser Arg Ile Lys Ser Met Lys Glu Ala Gly Leu Ile
145                 150                 155                 160

Ser Tyr Asp Gly Glu Lys Tyr Phe Ile Glu Glu Ser Ile Phe Tyr Ser
                165                 170                 175

Met Asp Glu Ser Leu Leu Leu Arg Leu Leu Asn Met Val Asp Phe Met
            180                 185                 190

Lys Asn Leu Val Tyr Pro Glu Ala Leu Gly Tyr Asn Leu Phe Asp Ile
        195                 200                 205

Ile Lys Lys Ile Tyr Asp Asp Arg Leu Cys Val Asp Tyr Tyr Ser Pro
    210                 215                 220

Phe Gln Leu Lys Tyr Ser His Leu Ala Asn Ile Leu Asp Asp Asn Val
225                 230                 235                 240

Leu Trp Ser Leu Ile Glu Ala Ile Glu Arg Gln Tyr Ile Ser Phe
                245                 250                 255

Ile Tyr Lys Asn Glu Lys Lys Glu Arg Ile Ile Pro Lys Leu Phe
            260                 265                 270

Thr Glu Asn Glu Tyr Ala Arg Arg Tyr Leu Phe Ala Val Lys Lys Phe
        275                 280                 285

Gly Asn Asn Tyr Lys Lys Phe Ile Phe Arg Leu Ser Glu Ile Tyr Asn
    290                 295                 300

Ile Lys Val Met Glu Lys Glu Val Ser Val Ser Lys Glu Glu Phe Gly
305                 310                 315                 320

Lys Leu Leu Glu Met Tyr Glu Thr Glu Ser Gly Tyr Ser Phe Ser Gly
                325                 330                 335

Lys Ile Ala Pro Ser Ser Lys Thr Val Ser Ile Lys Leu Arg Tyr Lys
            340                 345                 350

```
Gly Arg Leu Lys Asn Gln Ile Glu Arg Asp Phe Ser Asn Val Lys Phe
            355                 360                 365

Glu Lys Gly Asn Thr Ala Glu Ile Leu Ile Lys Asn Lys Lys Met Ile
        370                 375                 380

Ile Pro Tyr Leu Arg Ser Asn Met Gln Leu Ile Gln Ser Thr Asp Glu
385                 390                 395                 400

Glu Leu Ser Gln Lys Ile Asn Ser Glu Ile Met Glu Met Lys Lys Leu
                405                 410                 415

Tyr Gly Ile Ile
            420

<210> SEQ ID NO 92
<211> LENGTH: 314
<212> TYPE: PRT
<213> ORGANISM: Ruminococcus flavefaciens

<400> SEQUENCE: 92

Met Glu Leu Phe Asn Glu Tyr Arg Asn Lys Ser Leu Arg Ala Phe Leu
1               5                   10                  15

Lys Leu Ala Glu Arg Ile Ser Tyr Gly Glu Leu Ser Ile Asp Glu
            20                  25                  30

Phe Glu Ala Glu Tyr Tyr Arg Leu Ser Gly Asp Asn Lys Lys Ile Thr
            35                  40                  45

Ser Val Phe Tyr Lys Asn Thr Leu Tyr Asn Asp Lys Leu Pro Ile Phe
    50                  55                  60

Asp Thr Arg Glu Gly Lys Val Arg Leu Phe Gly Glu Pro Asp Lys Cys
65                  70                  75                  80

Ser Asn Lys His Ile Ser Asp Thr Leu Leu Lys Ser Glu Ile Thr Trp
                85                  90                  95

Leu His Asn Ala Leu Asn Asp Lys Leu Ser Lys Leu Phe Leu Ser Asp
            100                 105                 110

Glu Glu Arg Ile Ser Ile Asp Ala Lys Leu Ser Asp Tyr Thr Glu Tyr
            115                 120                 125

Tyr Lys Asn Ile Asp Asp Met Trp Arg Ser Asn Glu Asp Ile Ser Glu
    130                 135                 140

Glu Val Glu Lys Asn Phe Lys Ile Ile Leu Lys Ala Ile Asn Glu Lys
145                 150                 155                 160

Gln Ala Leu Ser Tyr Thr Phe Leu Asn Lys Asn Cys Glu Gly Phe Pro
                165                 170                 175

Val Arg Ile Glu Tyr Asp Glu Arg Thr Cys Arg Ile Tyr Met Ile Ile
            180                 185                 190

Tyr Asp Gly Asn Arg Phe Val Lys Ser Asp Ile Ser Lys Leu Ser Asp
        195                 200                 205

Ile Tyr Ile Thr Glu Asn Ser Ile Asp Thr Ile Pro Glu Ile Lys Asp
    210                 215                 220

Asp Met Leu Asn Lys Lys Ala Tyr Leu Pro Val Val Phe Thr Val Thr
225                 230                 235                 240

Asp Asp Lys Asn Arg Lys Ala Ile Asp Arg Ala Leu Leu Ala Phe Ser
                245                 250                 255

Val Tyr Asp His Val Val Glu Pro Ile Asp Glu Lys Thr Ala Arg Phe
            260                 265                 270

Thr Ile Gln Tyr Tyr Thr Met Asp Leu Asp Leu Leu Ile Lys Asp Ile
        275                 280                 285

Leu Ala Phe Gly Ser Asp Ile Lys Val Glu Ser Pro Arg Tyr Val Val
    290                 295                 300
```

Lys Arg Ile Thr Asp Ile Leu Arg Lys Val
305                 310

<210> SEQ ID NO 93
<211> LENGTH: 318
<212> TYPE: PRT
<213> ORGANISM: Unknown
<220> FEATURE:
<223> OTHER INFORMATION: Description of Unknown:
      Mammals-digestive system-feces sequence

<400> SEQUENCE: 93

Met Glu Leu Phe Asn Glu Phe Arg Asn Lys Ser Phe Asn Ala Phe Ile
1               5                   10                  15

Thr Leu Ala Glu Arg Ile Ala Asn Asp Asn Ala Val Phe Ser Lys Thr
            20                  25                  30

Glu Phe Glu Thr Glu Tyr Tyr Arg Leu Ser Gly Asp Glu Asn Arg Ile
        35                  40                  45

Thr Ser Ile Phe Tyr Asn Asn Val Ile Asn Asn Glu Lys Tyr Gln Ile
    50                  55                  60

Phe Thr Ile Pro Lys Asp Ser Lys Asp Lys Val Gln Leu Ser Ile Glu
65                  70                  75                  80

Phe Asp Asn Lys Asp Asp Ile Asn Ile Ala Asn Ile Pro Ile Thr Ser
                85                  90                  95

Glu Lys Lys Trp Leu His Ser Ala Leu His Asp Lys Leu Ser Lys Leu
            100                 105                 110

Phe Leu Ser Asp Glu Glu Ile Ser Tyr Ile Asp Glu Thr Ile Ser Glu
        115                 120                 125

Phe Pro Leu Tyr Tyr Glu His Ile Asp Asp Ser Trp Arg Lys Gly Glu
    130                 135                 140

Asn Ile Ser Glu Glu Ser Val Ile Asn Phe Arg Ile Ile Leu Gln Ala
145                 150                 155                 160

Ile Asn Glu Lys Lys Ser Leu Ser Tyr Lys Tyr Asn Gly Lys Asp Ser
                165                 170                 175

Glu Gly Ser Pro Val Lys Ile Glu Tyr Asp Glu Arg Thr Cys Lys Ile
            180                 185                 190

Tyr Met Ile Leu Tyr Asn Gly Ser Arg Phe Ile Lys Ser Asp Ile Ser
        195                 200                 205

Gly Leu Ser Asp Ile Cys Ile Lys Glu Gln Leu Tyr Glu Lys Ile Pro
    210                 215                 220

Asp Ile Lys Glu Gly Met Leu Glu Lys Lys Ala Arg His Pro Ile Val
225                 230                 235                 240

Phe Thr Val Thr Asp Asn Lys Asn Arg Lys Ser Ile Glu Arg Ala Leu
                245                 250                 255

Leu Ala Phe Ser Val Tyr Glu His Tyr Val Glu Pro Ile Asp Lys Asn
            260                 265                 270

Thr Ala Lys Phe Thr Ile His Tyr Tyr Thr Met Asp Leu Asp Ile Leu
        275                 280                 285

Ile Lys Asp Ile Leu Ala Phe Gly Ala Asp Ile Lys Val Glu Ala Pro
    290                 295                 300

Gln Phe Val Val Lys Lys Ile Ile Asn Ile Leu Glu Asn Val
305                 310                 315

<210> SEQ ID NO 94
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid

<400> SEQUENCE: 94

Arg Xaa Xaa Xaa Xaa His
1               5

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (11)..(11)
<223> OTHER INFORMATION: Leu or Ile
<220> FEATURE:
<221> NAME/KEY: MOD_RES
<222> LOCATION: (14)..(15)
<223> OTHER INFORMATION: Any amino acid

<400> SEQUENCE: 95

Asp Xaa Xaa Xaa Xaa Gln Xaa Xaa Xaa Xaa Leu Asp Xaa Xaa Lys
1               5                   10                  15

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (17)..(17)
<223> OTHER INFORMATION: Leu or Ile

<400> SEQUENCE: 96

Phe Xaa Xaa Xaa Xaa Xaa Xaa Xaa Xaa Xaa Gly Xaa Xaa Xaa Xaa Xaa
1               5                   10                  15

Xaa Arg

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(15)
<223> OTHER INFORMATION: Any amino acid

<400> SEQUENCE: 97

Lys Glu Xaa Asn Xaa Xaa Xaa Xaa Xaa Xaa Xaa Xaa Xaa Xaa Asn
1               5                   10                  15

Ile

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(13)
<223> OTHER INFORMATION: Any amino acid

<400> SEQUENCE: 98

Tyr Xaa Xaa Xaa Arg Xaa Lys Asx Leu Xaa Xaa Xaa Xaa Leu Phe
1               5                   10                  15

<210> SEQ ID NO 99
<211> LENGTH: 102
<212> TYPE: RNA
<213> ORGANISM: Artificial Sequence
<220> FEATURE:
<223> OTHER INFORMATION: Description of Artificial Sequence: Synthetic
      cr_F1 polynucleotide

<400> SEQUENCE: 99
gaacuacacc cgugcaaaau ugcagggguc uaaaacucau ccgcuuauua ucacuuauuc    60
aggcgugaac uacacccgug caaaauugca gggucuaaa ac                      102

<210> SEQ ID NO 100
<211> LENGTH: 102
<212> TYPE: RNA
<213> ORGANISM: Artificial Sequence
<220> FEATURE:
<223> OTHER INFORMATION: Description of Artificial Sequence: Synthetic
      cr_F4 polynucleotide

<400> SEQUENCE: 100
gaacuacacc cgugcaaaau ugcaggggguc uaaaacauag guacauugag caacugacug   60
aaaugcgaac uacacccgug caaaauugca gggucuaaa ac                      102

<210> SEQ ID NO 101
<211> LENGTH: 103
<212> TYPE: RNA
<213> ORGANISM: Artificial Sequence
<220> FEATURE:
```

<223> OTHER INFORMATION: Description of Artificial Sequence: Synthetic
      cr_F7 polynucleotide

<400> SEQUENCE: 101
cuacuacacu ggugcaaauu ugcacuaguc uaaaaccaag ggugaacacu aucccauauc    60
accagcucua cuacacuggu gcgaauuugc acuagcuaa aac                      103

<210> SEQ ID NO 102
<211> LENGTH: 103
<212> TYPE: RNA
<213> ORGANISM: Artificial Sequence
<220> FEATURE:
<223> OTHER INFORMATION: Description of Artificial Sequence: Synthetic
      cr_F10 polynucleotide

<400> SEQUENCE: 102
cuacuacacu ggugcaaauu ugcacuaguc uaaaacccug uggaacaccu acaucuguau    60
uaacgaacua cuacacuggu gcgaauuugc acuagcuaa aac                      103

<210> SEQ ID NO 103
<211> LENGTH: 100
<212> TYPE: RNA
<213> ORGANISM: Artificial Sequence
<220> FEATURE:
<223> OTHER INFORMATION: Description of Artificial Sequence: Synthetic
      cr_3 polynucleotide

<400> SEQUENCE: 103
gauuuagacu accccaaaaa cgaagggggac uaaaacauuu uuuucuccau uuuagcuucc   60
uuaggauuua gacuaccccca aaaacgaagg ggacuaaaac                        100

<210> SEQ ID NO 104
<211> LENGTH: 100
<212> TYPE: RNA
<213> ORGANISM: Artificial Sequence
<220> FEATURE:
<223> OTHER INFORMATION: Description of Artificial Sequence: Synthetic
      cr_4 polynucleotide

<400> SEQUENCE: 104
gauuuagacu accccaaaaa cgaagggggac uaaaacagaa ucauaauggg gaaggccauc   60
cagcgauuua gacuaccccca aaaacgaagg ggacuaaaac                        100

<210> SEQ ID NO 105
<211> LENGTH: 130
<212> TYPE: RNA
<213> ORGANISM: Artificial Sequence
<220> FEATURE:
<223> OTHER INFORMATION: Description of Artificial Sequence: Synthetic
      sub_F1 polynucleotide

<400> SEQUENCE: 105
auacgcugug guucgccaag ucccaauggc aucguaaaga acauuuugag gcauuucagu    60
caguugcuca auguaccuau aaccagaccg uucagcugga uauuacggcc aagagagcac   120
gaaaguguug                                                          130

<210> SEQ ID NO 106
<211> LENGTH: 130
<212> TYPE: RNA
<213> ORGANISM: Artificial Sequence
<220> FEATURE:
<223> OTHER INFORMATION: Description of Artificial Sequence: Synthetic
      sub_F4 polynucleotide

```
<400> SEQUENCE: 106
auacgcugug guucgccaag aguuauuggu gcccuuaaac gccuggugcu acgccugaau      60
aagugauaau aagcggauga auggcagaaa uucgaaagca aauucgaccc aagagagcac    120
gaaaguguug                                                           130

<210> SEQ ID NO 107
<211> LENGTH: 131
<212> TYPE: RNA
<213> ORGANISM: Artificial Sequence
<220> FEATURE:
<223> OTHER INFORMATION: Description of Artificial Sequence: Synthetic
      sub_F7 polynucleotide

<400> SEQUENCE: 107
auacgcugug guucgccaag cggaauuccg uauggcaaug aaagacggug agcuggugau      60
augggauagu guucacccuu guuacaccgu uuccaugag caaacugaaa caagagagca     120
cgaaaguguu g                                                         131

<210> SEQ ID NO 108
<211> LENGTH: 131
<212> TYPE: RNA
<213> ORGANISM: Artificial Sequence
<220> FEATURE:
<223> OTHER INFORMATION: Description of Artificial Sequence: Synthetic
      sub_F10 polynucleotide

<400> SEQUENCE: 108
auacgcugug guucgccaag cucccagagc cugauaaaaa cgguuagcgc uucguuaaua      60
cagauguagg uguuccacag gguagccagc agcauccugc gaugcagauc aagagagca     120 cgaaaguguu g                                                         131

<210> SEQ ID NO 109
<211> LENGTH: 880
<212> TYPE: RNA
<213> ORGANISM: Artificial Sequence
<220> FEATURE:
<223> OTHER INFORMATION: Description of Artificial Sequence: Synthetic
      GFP polynucleotide

<400> SEQUENCE: 109
gggaauugug agcggauaac aauuccccuc uagaaauaau uuuguuuaac uuuaagaagg      60
agauuuaaau augaaaaucg aagaagguaa aggucaccau caccaucacc acggauccau     120
gacggcauug acgaaggug caaaacuguu ugagaaagag aucccguaua ucaccgaacu     180
ggaaggcgac gucgaaggua ugaaauuuau cauuaaaggc gagguaccg gugacgcgac     240 cacggguacc auuaaagcga aauacaucug cacuacgggc gaccugccgg ucccgugggc     300
aacccuggug agcacccuga gcuacgguga ucaguguuuc gccaaguacc cgagccacau     360
caaggauuuc uuuaagagcg ccaugccgga agguuauacc caagagcgua ccaucagcuu     420
cgaaggcgac ggcguguaca agacgcgugc uaugguuacc uacgaacgcg guucuaucua     480
caaucguguc acgcugacug gugagaacuu uaagaaagac ggucacauuc ugcguaagaa     540
cguugcauuc caaugcccgc caagcauucu guauauucug ccugacaccg uuaacaaugg     600 caucccgcguu gaguucaacc aggcugacga uauugaaggu gugaccgaaa aacugguuac     660
caaaugcagc caaaugaauc guccguuggc gggcuccgcg gcagugcaua ucccgcguua     720
ucaucacauu accuaccaca ccaaacugag caaagaccgc gacgagcgcc gugaucacau     780
```
gugucuggua gaggucguga aagcgguuga ucuggacacg uaucaguaau aaaaagcccg    840
aaaggaagcu gaguuggcug cugccaccgc ugagcaauaa    880

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
      T7_primer

<400> SEQUENCE: 110
cctcgagtaa tacgactcac tataggg    27

<210> SEQ ID NO 111
<211> LENGTH: 145
<212> TYPE: DNA
<213> ORGANISM: Artificial Sequence
<220> FEATURE:
<223> OTHER INFORMATION: Description of Artificial Sequence: Synthetic
      cr_F1_IVT_rev polynucleotide

<400> SEQUENCE: 111
gttttagacc cctgcaattt tgcacgggtg tagttcgcat ttcagtcagt tgctcaatgt    60
acctatgttt tagaccsctg caattttgca cgggtgtagt tccsctatag tgagtcgtat    120
tactcgagga attcttatta tttct    145

<210> SEQ ID NO 112
<211> LENGTH: 145
<212> TYPE: DNA
<213> ORGANISM: Artificial Sequence
<220> FEATURE:
<223> OTHER INFORMATION: Description of Artificial Sequence: Synthetic
      cr_F4_IVT_rev polynucleotide

<400> SEQUENCE: 112
gttttagacc cctgcaattt tgcacgggtg tagttcacgc ctgaataagt gataataagc    60
ggatgagttt tagacccctg caattttgca cgggtgtagt tcccctatag tgagtcgtat    120
tactcgagga attcttatta tttct    145

<210> SEQ ID NO 113
<211> LENGTH: 146
<212> TYPE: DNA
<213> ORGANISM: Artificial Sequence
<220> FEATURE:
<223> OTHER INFORMATION: Description of Artificial Sequence: Synthetic
      cr_F7_IVT_rev polynucleotide

<400> SEQUENCE: 113
gttttagact agtgcaaatt cgcaccagtg tagtagagct ggtgatatgg gatagtgttc    60
acccttggtt ttagactagt gcaaatttgc accagtgtag tagccctata gtgagtcgta    120
ttactcgagg gatccttatt acattt    146

<210> SEQ ID NO 114
<211> LENGTH: 146
<212> TYPE: DNA
<213> ORGANISM: Artificial Sequence
<220> FEATURE:
<223> OTHER INFORMATION: Description of Artificial Sequence: Synthetic
      cr_F10_IVT_rev polynucleotide

<400> SEQUENCE: 114

```
gttttagact agtgcaaatt cgcaccagtg tagtagttcg ttaatacaga tgtaggtgtt    60
ccacagggtt ttagactagt gcaaatttgc accagtgtag tagccctata gtgagtcgta   120
ttactcgagg gatccttatt acattt                                        146
```

<210> SEQ ID NO 115
<211> LENGTH: 143
<212> TYPE: DNA
<213> ORGANISM: Artificial Sequence
<220> FEATURE:
<223> OTHER INFORMATION: Description of Artificial Sequence: Synthetic
      cr_3_IVT_rev polynucleotide

<400> SEQUENCE: 115

```
gttttagtcc ccttcgtttt tggggtagtc taaatcctaa ggaagctaaa atggagaaaa    60
aaatgtttta gtccccttcg tttttggggt agtctaaatc ccctatagtg agtcgtatta   120
ctcgagggat ccttattaca ttt                                           143
```

<210> SEQ ID NO 116
<211> LENGTH: 143
<212> TYPE: DNA
<213> ORGANISM: Artificial Sequence
<220> FEATURE:
<223> OTHER INFORMATION: Description of Artificial Sequence: Synthetic
      cr_4_IVT_rev polynucleotide

<400> SEQUENCE: 116

```
gttttagtcc ccttcgtttt tggggtagtc taaatcgctg gatggccttc cccattatga    60
ttctgtttta gtccccttcg tttttggggt agtctaaatc ccctatagtg agtcgtatta   120
ctcgagggat ccttattaca ttt                                           143
```

<210> SEQ ID NO 117
<211> LENGTH: 130
<212> TYPE: DNA
<213> ORGANISM: Artificial Sequence
<220> FEATURE:
<223> OTHER INFORMATION: Description of Artificial Sequence: Synthetic
      sub_F1_rev polynucleotide

<400> SEQUENCE: 117

```
atacgctgtg gttcgccaag tcccaatggc atcgtaaaga acattttgag gcatttcagt    60
cagttgctca atgtacctat aaccagaccg ttcagctgga tattacggcc aagagagcac   120
gaaagtgttg                                                          130
```

<210> SEQ ID NO 118
<211> LENGTH: 130
<212> TYPE: DNA
<213> ORGANISM: Artificial Sequence
<220> FEATURE:
<223> OTHER INFORMATION: Description of Artificial Sequence: Synthetic
      sub_F4_rev polynucleotide

<400> SEQUENCE: 118

```
atacgctgtg gttcgccaag agttattggt gcccttaaac gcctggtgct acgcctgaat    60
aagtgataat aagcggatga atggcagaaa ttcgaaagca aattcgaccc aagagagcac   120
gaaagtgttg                                                          130
```

<210> SEQ ID NO 119
<211> LENGTH: 131
<212> TYPE: DNA

```
<213> ORGANISM: Artificial Sequence
<220> FEATURE:
<223> OTHER INFORMATION: Description of Artificial Sequence: Synthetic
      sub_F7_rev polynucleotide

<400> SEQUENCE: 119
atacgctgtg gttcgccaag cggaattccg tatggcaatg aaagacggtg agctggtgat      60
atgggatagt gttcaccctt gttacaccgt tttccatgag caaactgaaa caagagagca     120
cgaaagtgtt g                                                          131

<210> SEQ ID NO 120
<211> LENGTH: 131
<212> TYPE: DNA
<213> ORGANISM: Artificial Sequence
<220> FEATURE:
<223> OTHER INFORMATION: Description of Artificial Sequence: Synthetic
      sub_F10_rev polynucleotide

<400> SEQUENCE: 120
atacgctgtg gttcgccaag ctcccagagc ctgataaaaa cggttagcgc ttcgttaata      60
cagatgtagg tgttccacag ggtagccagc agcatcctgc gatgcagatc caagagagca     120
cgaaagtgtt g                                                          131

<210> SEQ ID NO 121
<211> LENGTH: 46
<212> TYPE: DNA
<213> ORGANISM: Artificial Sequence
<220> FEATURE:
<223> OTHER INFORMATION: Description of Artificial Sequence: Synthetic
      PT7_Sub_fw oligonucleotide

<400> SEQUENCE: 121
cgaaattaat acgactcact atagggatac gctgtggttc gccaag                     46

<210> SEQ ID NO 122
<211> LENGTH: 48
<212> TYPE: DNA
<213> ORGANISM: Artificial Sequence
<220> FEATURE:
<223> OTHER INFORMATION: Description of Artificial Sequence: Synthetic
      Sub_ rv oligonucleotide

<400> SEQUENCE: 122
cgaaattatt tcgactgaga ttattcccca acactttcgt gctctctt                   48

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      GFP_PCR_fwd oligonucleotide

<400> SEQUENCE: 123
gatgcgtccg gcgtagagga tcgagatctc                                       30

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

```
Glu Ala Ala Ala Lys
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Ser Gly Gly Gly Gly Ser
1               5

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Gly Gly Ser Gly Gly Gly Gly Ser Gly Gly Gly Gly Ser
1               5                   10                  15

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ser Gly Gly Ser Gly Gly Ser Gly Gly Ser Gly Gly Ser Gly
1               5                   10                  15

Gly Ser

<210> SEQ ID NO 128
<211> LENGTH: 336
<212> TYPE: PRT
<213> ORGANISM: Homo sapiens

<400> SEQUENCE: 128

Ser Leu Gly Thr Gly Asn Arg Cys Val Lys Gly Asp Ser Leu Ser Leu
1               5                   10                  15

Lys Gly Glu Thr Val Asn Asp Cys His Ala Glu Ile Ile Ser Arg Arg
                20                  25                  30

Gly Phe Ile Arg Phe Leu Tyr Ser Glu Leu Met Lys Tyr Asn Ser Gln
            35                  40                  45

Thr Ala Lys Asp Ser Ile Phe Glu Pro Ala Lys Gly Gly Glu Lys Leu
        50                  55                  60

Gln Ile Lys Lys Thr Val Ser Phe His Leu Tyr Ile Ser Thr Ala Pro
65                  70                  75                  80

Cys Gly Asp Gly Ala Leu Phe Asp Lys Ser Cys Ser Asp Arg Ala Met
                85                  90                  95

Glu Ser Thr Glu Ser Arg His Tyr Pro Val Phe Glu Asn Pro Lys Gln
                100                 105                 110

Gly Lys Leu Arg Thr Lys Val Glu Asn Gly Glu Gly Thr Ile Pro Val
            115                 120                 125
```

```
Glu Ser Ser Asp Ile Val Pro Thr Trp Asp Gly Ile Arg Leu Gly Glu
        130                 135                 140

Arg Leu Arg Thr Met Ser Cys Ser Asp Lys Ile Leu Arg Trp Asn Val
145                 150                 155                 160

Leu Gly Leu Gln Gly Ala Leu Leu Thr His Phe Leu Gln Pro Ile Tyr
                165                 170                 175

Leu Lys Ser Val Thr Leu Gly Tyr Leu Phe Ser Gln Gly His Leu Thr
                180                 185                 190

Arg Ala Ile Cys Cys Arg Val Thr Arg Asp Gly Ser Ala Phe Glu Asp
                195                 200                 205

Gly Leu Arg His Pro Phe Ile Val Asn His Pro Lys Val Gly Arg Val
        210                 215                 220

Ser Ile Tyr Asp Ser Lys Arg Gln Ser Gly Lys Thr Lys Glu Thr Ser
225                 230                 235                 240

Val Asn Trp Cys Leu Ala Asp Gly Tyr Asp Leu Glu Ile Leu Asp Gly
                245                 250                 255

Thr Arg Gly Thr Val Asp Gly Pro Arg Asn Glu Leu Ser Arg Val Ser
                260                 265                 270

Lys Lys Asn Ile Phe Leu Leu Phe Lys Lys Leu Cys Ser Phe Arg Tyr
        275                 280                 285

Arg Arg Asp Leu Leu Arg Leu Ser Tyr Gly Glu Ala Lys Lys Ala Ala
290                 295                 300

Arg Asp Tyr Glu Thr Ala Lys Asn Tyr Phe Lys Lys Gly Leu Lys Asp
305                 310                 315                 320

Met Gly Tyr Gly Asn Trp Ile Ser Lys Pro Gln Glu Glu Lys Asn Phe
                325                 330                 335

<210> SEQ ID NO 129
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Leu Gly Thr Gly Asn Arg Cys Val Lys Gly Asp Ser Leu Ser Leu
1               5                   10                  15

Lys Gly Glu Thr Val Asn Asp Cys His Ala Glu Ile Ile Ser Arg Arg
                20                  25                  30

Gly Phe Ile Arg Phe Leu Tyr Ser Glu Leu Met Lys Tyr Asn Ser Gln
            35                  40                  45

Thr Ala Lys Asp Ser Ile Phe Glu Pro Ala Lys Gly Gly Glu Lys Leu
50                  55                  60

Gln Ile Lys Lys Thr Val Ser Phe His Leu Tyr Ile Ser Thr Ala Pro
65                  70                  75                  80

Cys Gly Asp Gly Ala Leu Phe Asp Lys Ser Cys Ser Asp Arg Ala Met
                85                  90                  95

Glu Ser Thr Glu Ser Arg His Tyr Pro Val Phe Glu Asn Pro Lys Gln
                100                 105                 110

Gly Lys Leu Arg Thr Lys Val Glu Asn Gly Gln Gly Thr Ile Pro Val
            115                 120                 125

Glu Ser Ser Asp Ile Val Pro Thr Trp Asp Gly Ile Arg Leu Gly Glu
        130                 135                 140

Arg Leu Arg Thr Met Ser Cys Ser Asp Lys Ile Leu Arg Trp Asn Val
```

```
145                 150                 155                 160
Leu Gly Leu Gln Gly Ala Leu Leu Thr His Phe Leu Gln Pro Ile Tyr
                165                 170                 175

Leu Lys Ser Val Thr Leu Gly Tyr Leu Phe Ser Gln Gly His Leu Thr
            180                 185                 190

Arg Ala Ile Cys Cys Arg Val Thr Arg Asp Gly Ser Ala Phe Glu Asp
        195                 200                 205

Gly Leu Arg His Pro Phe Ile Val Asn His Pro Lys Val Gly Arg Val
    210                 215                 220

Ser Ile Tyr Asp Ser Lys Arg Gln Ser Gly Lys Thr Lys Glu Thr Ser
225                 230                 235                 240

Val Asn Trp Cys Leu Ala Asp Gly Tyr Asp Leu Glu Ile Leu Asp Gly
                245                 250                 255

Thr Arg Gly Thr Val Asp Gly Pro Arg Asn Glu Leu Ser Arg Val Ser
            260                 265                 270

Lys Lys Asn Ile Phe Leu Leu Phe Lys Lys Leu Cys Ser Phe Arg Tyr
        275                 280                 285

Arg Arg Asp Leu Leu Arg Leu Ser Tyr Gly Glu Ala Lys Lys Ala Ala
    290                 295                 300

Arg Asp Tyr Glu Thr Ala Lys Asn Tyr Phe Lys Lys Gly Leu Lys Asp
305                 310                 315                 320

Met Gly Tyr Gly Asn Trp Ile Ser Lys Pro Gln Glu Glu Lys Asn Phe
                325                 330                 335

<210> SEQ ID NO 130
<211> LENGTH: 385
<212> TYPE: PRT
<213> ORGANISM: Homo sapiens

<400> SEQUENCE: 130

Gln Leu His Leu Pro Gln Val Leu Ala Asp Ala Val Ser Arg Leu Val
1               5                   10                  15

Leu Gly Lys Phe Gly Asp Leu Thr Asp Asn Phe Ser Ser Pro His Ala
            20                  25                  30

Arg Arg Lys Val Leu Ala Gly Val Val Met Thr Thr Gly Thr Asp Val
        35                  40                  45

Lys Asp Ala Lys Val Ile Ser Val Ser Thr Gly Thr Lys Cys Ile Asn
    50                  55                  60

Gly Glu Tyr Met Ser Asp Arg Gly Leu Ala Leu Asn Asp Cys His Ala
65                  70                  75                  80

Glu Ile Ile Ser Arg Arg Ser Leu Leu Arg Phe Leu Tyr Thr Gln Leu
                85                  90                  95

Glu Leu Tyr Leu Asn Asn Lys Asp Asp Gln Lys Arg Ser Ile Phe Gln
            100                 105                 110

Lys Ser Glu Arg Gly Gly Phe Arg Leu Lys Glu Asn Val Gln Phe His
        115                 120                 125

Leu Tyr Ile Ser Thr Ser Pro Cys Gly Asp Ala Arg Ile Phe Ser Pro
    130                 135                 140

His Glu Pro Ile Leu Glu Glu Pro Ala Asp Arg His Pro Asn Arg Lys
145                 150                 155                 160

Ala Arg Gly Gln Leu Arg Thr Lys Ile Glu Ser Gly Glu Gly Thr Ile
                165                 170                 175

Pro Val Arg Ser Asn Ala Ser Ile Gln Thr Trp Asp Gly Val Leu Gln
            180                 185                 190
```

```
Gly Glu Arg Leu Leu Thr Met Ser Cys Ser Asp Lys Ile Ala Arg Trp
            195                 200                 205
Asn Val Val Gly Ile Gln Gly Ser Leu Leu Ser Ile Phe Val Glu Pro
        210                 215                 220
Ile Tyr Phe Ser Ser Ile Ile Leu Gly Ser Leu Tyr His Gly Asp His
225                 230                 235                 240
Leu Ser Arg Ala Met Tyr Gln Arg Ile Ser Asn Ile Glu Asp Leu Pro
                245                 250                 255
Pro Leu Tyr Thr Leu Asn Lys Pro Leu Leu Ser Gly Ile Ser Asn Ala
            260                 265                 270
Glu Ala Arg Gln Pro Gly Lys Ala Pro Asn Phe Ser Val Asn Trp Thr
        275                 280                 285
Val Gly Asp Ser Ala Ile Glu Val Ile Asn Ala Thr Thr Gly Lys Asp
290                 295                 300
Glu Leu Gly Arg Ala Ser Arg Leu Cys Lys His Ala Leu Tyr Cys Arg
305                 310                 315                 320
Trp Met Arg Val His Gly Lys Val Pro Ser His Leu Leu Arg Ser Lys
                325                 330                 335
Ile Thr Lys Pro Asn Val Tyr His Glu Ser Lys Leu Ala Ala Lys Glu
            340                 345                 350
Tyr Gln Ala Ala Lys Ala Arg Leu Phe Thr Ala Phe Ile Lys Ala Gly
        355                 360                 365
Leu Gly Ala Trp Val Glu Lys Pro Thr Glu Gln Asp Gln Phe Ser Leu
    370                 375                 380
Thr
385

<210> SEQ ID NO 131
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Leu His Leu Pro Gln Val Leu Ala Asp Ala Val Ser Arg Leu Val
1               5                   10                  15
Leu Gly Lys Phe Gly Asp Leu Thr Asp Asn Phe Ser Ser Pro His Ala
            20                  25                  30
Arg Arg Lys Val Leu Ala Gly Val Val Met Thr Thr Gly Thr Asp Val
        35                  40                  45
Lys Asp Ala Lys Val Ile Ser Val Ser Thr Gly Thr Lys Cys Ile Asn
50                  55                  60
Gly Glu Tyr Met Ser Asp Arg Gly Leu Ala Leu Asn Asp Cys His Ala
65                  70                  75                  80
Glu Ile Ile Ser Arg Arg Ser Leu Leu Arg Phe Leu Tyr Thr Gln Leu
                85                  90                  95
Glu Leu Tyr Leu Asn Asn Lys Asp Asp Gln Lys Arg Ser Ile Phe Gln
            100                 105                 110
Lys Ser Glu Arg Gly Gly Phe Arg Leu Lys Glu Asn Val Gln Phe His
        115                 120                 125
Leu Tyr Ile Ser Thr Ser Pro Cys Gly Asp Ala Arg Ile Phe Ser Pro
    130                 135                 140
His Glu Pro Ile Leu Glu Glu Pro Ala Asp Arg His Pro Asn Arg Lys
145                 150                 155                 160
```

```
Ala Arg Gly Gln Leu Arg Thr Lys Ile Glu Ser Gly Gln Gly Thr Ile
                165                 170                 175

Pro Val Arg Ser Asn Ala Ser Ile Gln Thr Trp Asp Gly Val Leu Gln
            180                 185                 190

Gly Glu Arg Leu Leu Thr Met Ser Cys Ser Asp Lys Ile Ala Arg Trp
        195                 200                 205

Asn Val Val Gly Ile Gln Gly Ser Leu Leu Ser Ile Phe Val Glu Pro
    210                 215                 220

Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
                245                 250                 255

Pro Leu Tyr Thr Leu Asn Lys Pro Leu Leu Ser Gly Ile Ser Asn Ala
            260                 265                 270

Glu Ala Arg Gln Pro Gly Lys Ala Pro Asn Phe Ser Val Asn Trp Thr
        275                 280                 285

Val Gly Asp Ser Ala Ile Glu Val Ile Asn Ala Thr Thr Gly Lys Asp
    290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
                325                 330                 335

Ile Thr Lys Pro Asn Val Tyr His Glu Ser Lys Leu Ala Ala Lys Glu
            340                 345                 350

Tyr Gln Ala Ala Lys Ala Arg Leu Phe Thr Ala Phe Ile Lys Ala Gly
        355                 360                 365

Leu Gly Ala Trp Val Glu Lys Pro Thr Glu Gln Asp Gln Phe Ser Leu
    370                 375                 380

Thr
385

<210> SEQ ID NO 132
<211> LENGTH: 198
<212> TYPE: PRT
<213> ORGANISM: Homo sapiens

<400> SEQUENCE: 132

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
```

```
            130                 135                 140
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
                195
```

<210> SEQ ID NO 133
<211> LENGTH: 208
<212> TYPE: PRT
<213> ORGANISM: Petromyzon marinus

<400> SEQUENCE: 133

```
Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
                20                  25                  30

Cys Tyr Val Leu Phe Glu Leu Lys Arg Arg Gly Glu Arg Arg Ala Cys
            35                  40                  45

Phe Trp Gly Tyr Ala Val Asn Lys Pro Gln Ser Gly Thr Glu Arg Gly
50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205
```

<210> SEQ ID NO 134
<211> LENGTH: 229
<212> TYPE: PRT
<213> ORGANISM: Unknown
<220> FEATURE:
<223> OTHER INFORMATION: Description of Unknown:
      APOBEC1_BE1 sequence

<400> SEQUENCE: 134

```
Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
```

```
                 35                  40                  45
Ser Ile Trp Arg His Thr Ser Gln Asn Thr Asn Lys His Val Glu Val
 50                  55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Trp Ser Pro Cys Gly Glu Cys
                 85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
                115                 120                 125

Gln Gly Leu Arg Asp Leu Ile Ser Ser Gly Val Thr Ile Gln Ile Met
                130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Phe Phe Thr Ile
                195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 135
<211> LENGTH: 7
<212> TYPE: PRT
<213> ORGANISM: Simian virus 40

<400> SEQUENCE: 135

Pro Lys Lys Lys Arg Lys Val
1               5

<210> SEQ ID NO 136
<211> LENGTH: 16
<212> TYPE: PRT
<213> ORGANISM: Unknown
<220> FEATURE:
<223> OTHER INFORMATION: Description of Unknown:
      Nuclear Localization Signal from nucleoplasmin sequence

<400> SEQUENCE: 136

Lys Arg Pro Ala Ala Thr Lys Lys Ala Gly Gln Ala Lys Lys Lys Lys
1               5                   10                  15

<210> SEQ ID NO 137
<211> LENGTH: 9
<212> TYPE: PRT
<213> ORGANISM: Unknown
<220> FEATURE:
<223> OTHER INFORMATION: Description of Unknown:
      c-myc Nuclear Localization Signal sequence

<400> SEQUENCE: 137

Pro Ala Ala Lys Arg Val Lys Leu Asp
1               5

<210> SEQ ID NO 138
```

```
<211> LENGTH: 11
<212> TYPE: PRT
<213> ORGANISM: Unknown
<220> FEATURE:
<223> OTHER INFORMATION: Description of Unknown:
      c-myc Nuclear Localization Signal sequence

<400> SEQUENCE: 138

Arg Gln Arg Arg Asn Glu Leu Lys Arg Ser Pro
1               5                   10

<210> SEQ ID NO 139
<211> LENGTH: 38
<212> TYPE: PRT
<213> ORGANISM: Homo sapiens

<400> SEQUENCE: 139

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20              25                  30

Arg Asn Gln Gly Gly Tyr
        35

<210> SEQ ID NO 140
<211> LENGTH: 42
<212> TYPE: PRT
<213> ORGANISM: Unknown
<220> FEATURE:
<223> OTHER INFORMATION: Description of Unknown:
      IBB domain from importin-alpha nuclear localization
      signal sequence

<400> SEQUENCE: 140

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20              25                  30

Asp Glu Gln Ile Leu Lys Arg Arg Asn Val
        35                  40

<210> SEQ ID NO 141
<211> LENGTH: 8
<212> TYPE: PRT
<213> ORGANISM: Unknown
<220> FEATURE:
<223> OTHER INFORMATION: Description of Unknown:
      Myoma T protein nuclear localization signal sequence

<400> SEQUENCE: 141

Val Ser Arg Lys Arg Pro Arg Pro
1               5

<210> SEQ ID NO 142
<211> LENGTH: 8
<212> TYPE: PRT
<213> ORGANISM: Unknown
<220> FEATURE:
<223> OTHER INFORMATION: Description of Unknown:
      Myoma T protein nuclear localization signal sequence

<400> SEQUENCE: 142

Pro Pro Lys Lys Ala Arg Glu Asp
1               5
```

```
<210> SEQ ID NO 143
<211> LENGTH: 8
<212> TYPE: PRT
<213> ORGANISM: Homo sapiens

<400> SEQUENCE: 143

Pro Gln Pro Lys Lys Lys Pro Leu
1               5

<210> SEQ ID NO 144
<211> LENGTH: 12
<212> TYPE: PRT
<213> ORGANISM: Mus musculus

<400> SEQUENCE: 144

Ser Ala Leu Ile Lys Lys Lys Lys Lys Met Ala Pro
1               5                   10

<210> SEQ ID NO 145
<211> LENGTH: 5
<212> TYPE: PRT
<213> ORGANISM: Influenza virus

<400> SEQUENCE: 145

Asp Arg Leu Arg Arg
1               5

<210> SEQ ID NO 146
<211> LENGTH: 7
<212> TYPE: PRT
<213> ORGANISM: Influenza virus

<400> SEQUENCE: 146

Pro Lys Gln Lys Lys Arg Lys
1               5

<210> SEQ ID NO 147
<211> LENGTH: 10
<212> TYPE: PRT
<213> ORGANISM: Hepatitis virus

<400> SEQUENCE: 147

Arg Lys Leu Lys Lys Lys Ile Lys Lys Leu
1               5                   10

<210> SEQ ID NO 148
<211> LENGTH: 10
<212> TYPE: PRT
<213> ORGANISM: Mus musculus

<400> SEQUENCE: 148

Arg Glu Lys Lys Lys Phe Leu Lys Arg Arg
1               5                   10

<210> SEQ ID NO 149
<211> LENGTH: 20
<212> TYPE: PRT
<213> ORGANISM: Homo sapiens

<400> SEQUENCE: 149

Lys Arg Lys Gly Asp Glu Val Asp Gly Val Asp Glu Val Ala Lys Lys
1               5                   10                  15

Lys Ser Lys Lys
            20
```

<210> SEQ ID NO 150
<211> LENGTH: 17
<212> TYPE: PRT
<213> ORGANISM: Homo sapiens

<400> SEQUENCE: 150

Arg Lys Cys Leu Gln Ala Gly Met Asn Leu Glu Ala Arg Lys Thr Lys
1               5                   10                  15

Lys

<210> SEQ ID NO 151
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
vkrbtytraa ac                                                              12

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cacccgtgca aaattgcagg ggtctaaaac                                           30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cactggtgca aatttgcact agtctaaaac                                           30

<210> SEQ ID NO 154
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 154 tntnaaac                                                                    8

<210> SEQ ID NO 155
<211> LENGTH: 128
<212> TYPE: PRT
<213> ORGANISM: Bacteriophage PP7

<400> SEQUENCE: 155

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Val
            100                 105                 110

Gln Ala Thr Ser Glu Asp Leu Val Val Asn Leu Val Pro Leu Gly Arg
        115                 120                 125

<210> SEQ ID NO 156
<211> LENGTH: 1437
<212> TYPE: PRT
<213> ORGANISM: Unknown
<220> FEATURE:
<223> OTHER INFORMATION: Description of Unknown:
      LbaCas13a sequence

<400> SEQUENCE: 156

Met Lys Ile Ser Lys Val Arg Glu Glu Asn Arg Gly Ala Lys Leu Thr
1               5                   10                  15

Val Asn Ala Lys Thr Ala Val Val Ser Glu Asn Arg Ser Gln Glu Gly
            20                  25                  30

Ile Leu Tyr Asn Asp Pro Ser Arg Tyr Gly Lys Ser Arg Lys Asn Asp
        35                  40                  45

Glu Asp Arg Asp Arg Tyr Ile Glu Ser Arg Leu Lys Ser Ser Gly Lys
    50                  55                  60

Leu Tyr Arg Ile Phe Asn Glu Asp Lys Asn Lys Arg Glu Thr Asp Glu
65                  70                  75                  80

Leu Gln Trp Phe Leu Ser Glu Ile Val Lys Lys Ile Asn Arg Arg Asn
                85                  90                  95

Gly Leu Val Leu Ser Asp Met Leu Ser Val Asp Asp Arg Ala Phe Glu
            100                 105                 110

Lys Ala Phe Glu Lys Tyr Ala Glu Leu Ser Tyr Thr Asn Arg Arg Asn
        115                 120                 125

Lys Val Ser Gly Ser Pro Ala Phe Glu Thr Cys Gly Val Asp Ala Ala
    130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
            180                 185                 190

Lys Arg Gly Leu Lys Lys Leu Leu Met Asn Ala Phe Asp Leu Pro Tyr
        195                 200                 205

Ser Asp Pro Asp Ile Asp Val Gln Arg Asp Phe Ile Asp Tyr Val Leu
    210                 215                 220

```
Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
            245                 250                 255

Ile Thr Val Ser Lys Gly Gly Thr Glu Ser Gly Asn Lys Arg Ser Ala
            260                 265                 270

Glu Lys Glu Ala Phe Lys Lys Phe Leu Ser Asp Tyr Ala Ser Leu Asp
            275                 280                 285

Glu Arg Val Arg Asp Asp Met Leu Arg Arg Met Arg Leu Val Val
    290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
                340                 345                 350

Asp Lys Asp Ala Glu Arg Ile Arg Lys Asn Thr Val Lys Glu Leu Tyr
            355                 360                 365

Arg Asn Gln Asn Ile Gly Cys Tyr Arg Gln Ala Val Lys Ala Val Glu
370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
                405                 410                 415

Lys Gln Val Thr Glu Phe Lys Ala Arg Thr Gly Tyr Leu Ser Glu Lys
            420                 425                 430

Ile Trp Lys Asp Leu Ile Asn Tyr Ile Ser Ile Lys Tyr Ile Ala Met
            435                 440                 445

Gly Lys Ala Val Tyr Asn Tyr Ala Met Asp Glu Leu Asn Ala Ser Asp
    450                 455                 460

Lys Lys Glu Ile Glu Leu Gly Lys Ile Ser Glu Glu Tyr Leu Ser Gly
465                 470                 475                 480

Ile Ser Ser Phe Asp Tyr Glu Leu Ile Lys Ala Glu Glu Met Leu Gln
            485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
        515                 520                 525

Pro Lys Gly Thr Met Asp Lys Asn Asp Lys Asn Lys Leu Ala Ser Asn
    530                 535                 540

Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
                565                 570                 575

Lys Tyr Leu Ala Gly Gly Lys Asp Val Asp Phe Leu Thr Asp Leu
            580                 585                 590

Lys Asp Val Ile Tyr Ser Met Arg Asn Asp Ser Phe His Tyr Ala Thr
            595                 600                 605

Glu Asn His Asn Asn Gly Lys Trp Asn Lys Glu Leu Ile Ser Ala Met
            610                 615                 620

Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Asp Leu Lys Lys
```

```
                645                 650                 655
Leu Leu Ile Asp Leu Tyr Lys Asp Asn Val Glu Arg Ala Ser Gln Val
            660                 665                 670

Pro Ser Phe Asn Lys Val Phe Val Arg Lys Asn Phe Pro Ala Leu Val
            675                 680                 685

Arg Asp Lys Asp Asn Leu Gly Ile Glu Leu Asp Leu Lys Ala Asp Ala
690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
            725                 730                 735

Glu Arg Phe Ile Thr Lys Ala Thr Lys Val Ala Asp Asn Tyr Asp Arg
            740                 745                 750

Asn Lys Glu Arg Asn Leu Lys Asp Arg Ile Lys Ser Ala Gly Ser Asp
            755                 760                 765

Glu Lys Lys Lys Leu Arg Glu Gln Leu Gln Asn Tyr Ile Ala Glu Asn
770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Lys Ser Ala Ala Arg Lys Asp Ile Asn
            820                 825                 830

Lys Asp Ser Tyr Gln His Tyr Lys Met Leu Leu Leu Val Asn Leu Arg
            835                 840                 845

Lys Ala Phe Leu Glu Phe Ile Lys Glu Asn Tyr Ala Phe Val Leu Lys
850                 855                 860

Pro Tyr Lys His Asp Leu Cys Asp Lys Ala Asp Phe Val Pro Asp Phe
865                 870                 875                 880

Ala Lys Tyr Val Lys Pro Tyr Ala Gly Leu Ile Ser Arg Val Ala Gly
            885                 890                 895

Ser Ser Glu Leu Gln Lys Trp Tyr Ile Val Ser Arg Phe Leu Ser Pro
            900                 905                 910

Ala Gln Ala Asn His Met Leu Gly Phe Leu His Ser Tyr Lys Gln Tyr
            915                 920                 925

Val Trp Asp Ile Tyr Arg Arg Ala Ser Glu Thr Gly Thr Glu Ile Asn
            930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
                965                 970                 975

Glu Ile Ser Asp Tyr Phe Lys Asp Glu Val Tyr Ala Glu Tyr Ile
            980                 985                 990

Ser Ser Tyr Leu Asp Phe Glu Tyr  Asp Gly Gly Asn Tyr  Lys Asp Ser
            995                 1000                1005

Leu Asn  Arg Phe Cys Asn Ser  Asp Ala Val Asn Asp  Gln Lys Val
            1010                1015                1020

Ala Leu  Tyr Tyr Asp Gly Glu  His Pro Lys Leu Asn  Arg Asn Ile
            1025                1030                1035

Ile Leu  Ser Lys Leu Tyr Gly  Glu Arg Arg Phe Leu  Glu Lys Ile
            1040                1045                1050

Thr Asp  Arg Val Ser Arg Ser  Asp Ile Val Glu Tyr  Tyr Lys Leu
            1055                1060                1065
```

Lys Lys Glu Thr Ser Gln Tyr Gln Thr Lys Gly Ile Phe Asp Ser
1070            1075            1080

Glu Asp Glu Gln Lys Asn Ile Lys Lys Phe Gln Glu Met Lys Asn
1085            1090            1095

Ile Val Glu Phe Arg Asp Leu Met Asp Tyr Ser Glu Ile Ala Asp
1100            1105            1110

Glu Leu Gln Gly Gln Leu Ile Asn Trp Ile Tyr Leu Arg Glu Arg
1115            1120            1125

Asp Leu Met Asn Phe Gln Leu Gly Tyr His Tyr Ala Cys Leu Asn
1130            1135            1140

Asn Asp Ser Asn Lys Gln Ala Thr Tyr Val Thr Leu Asp Tyr Gln
1145            1150            1155

Gly Lys Lys Asn Arg Lys Ile Asn Gly Ala Ile Leu Tyr Gln Ile
1160            1165            1170

Cys Ala Met Tyr Ile Asn Gly Leu Pro Leu Tyr Tyr Val Asp Lys
1175            1180            1185

Asp Ser Ser Glu Trp Thr Val Ser Asp Gly Lys Glu Ser Thr Gly
1190            1195            1200

Ala Lys Ile Gly Glu Phe Tyr Arg Tyr Ala Lys Ser Phe Glu Asn
1205            1210            1215

Thr Ser Asp Cys Tyr Ala Ser Gly Leu Glu Ile Phe Glu Asn Ile
1220            1225            1230

Ser Glu His Asp Asn Ile Thr Glu Leu Arg Asn Tyr Ile Glu His
1235            1240            1245

Phe Arg Tyr Tyr Ser Ser Phe Asp Arg Ser Phe Leu Gly Ile Tyr
1250            1255            1260

Ser Glu Val Phe Asp Arg Phe Phe Thr Tyr Asp Leu Lys Tyr Arg
1265            1270            1275

Lys Asn Val Pro Thr Ile Leu Tyr Asn Ile Leu Leu Gln His Phe
1280            1285            1290

Val Asn Val Arg Phe Glu Phe Val Ser Gly Lys Lys Met Ile Gly
1295            1300            1305

Ile Asp Lys Lys Asp Arg Lys Ile Ala Lys Glu Lys Glu Cys Ala
1310            1315            1320

Arg Ile Thr Ile Arg Glu Lys Asn Gly Val Tyr Ser Glu Gln Phe
1325            1330            1335

Thr Tyr Lys Leu Lys Asn Gly Thr Val Tyr Val Asp Ala Arg Asp
1340            1345            1350

Lys Arg Tyr Leu Gln Ser Ile Ile Arg Leu Leu Phe Tyr Pro Glu
1355            1360            1365

Lys Val Asn Met Asp Glu Met Ile Glu Val Lys Glu Lys Lys Lys
1370            1375            1380

Pro Ser Asp Asn Asn Thr Gly Lys Gly Tyr Ser Lys Arg Asp Arg
1385            1390            1395

Gln Gln Asp Arg Lys Glu Tyr Asp Lys Tyr Lys Glu Lys Lys Lys
1400            1405            1410

Lys Glu Gly Asn Phe Leu Ser Gly Met Gly Gly Asn Ile Asn Trp
1415            1420            1425

Asp Glu Ile Asn Ala Gln Leu Lys Asn
1430            1435

<210> SEQ ID NO 157
<211> LENGTH: 1159

```
<212> TYPE: PRT
<213> ORGANISM: Unknown
<220> FEATURE:
<223> OTHER INFORMATION: Description of Unknown:
      LbuCas13a sequence

<400> SEQUENCE: 157
```

| | | | | | | | | | | | | | | | |
|---|---|---|---|---|---|---|---|---|---|---|---|---|---|---|---|
| Met | Lys | Val | Thr | Lys | Val | Gly | Gly | Ile | Ser | His | Lys | Lys | Tyr | Thr | Ser |
| 1 | | | | 5 | | | | | 10 | | | | | 15 | |
| Glu | Gly | Arg | Leu | Val | Lys | Ser | Glu | Ser | Glu | Glu | Asn | Arg | Thr | Asp | Glu |
| | | | 20 | | | | | 25 | | | | | 30 | | |
| Arg | Leu | Ser | Ala | Leu | Leu | Asn | Met | Arg | Leu | Asp | Met | Tyr | Ile | Lys | Asn |
| | | | 35 | | | | 40 | | | | | 45 | | | |
| Pro | Ser | Ser | Thr | Glu | Thr | Lys | Glu | Asn | Gln | Lys | Arg | Ile | Gly | Lys | Leu |
| | 50 | | | | | 55 | | | | | 60 | | | | |
| Lys | Lys | Phe | Phe | Ser | Asn | Lys | Met | Val | Tyr | Leu | Lys | Asp | Asn | Thr | Leu |
| 65 | | | | | 70 | | | | | 75 | | | | | 80 |
| Ser | Leu | Lys | Asn | Gly | Lys | Lys | Glu | Asn | Ile | Asp | Arg | Glu | Tyr | Ser | Glu |
| | | | | 85 | | | | | 90 | | | | | 95 | |
| Thr | Asp | Ile | Leu | Glu | Ser | Asp | Val | Arg | Asp | Lys | Lys | Asn | Phe | Ala | Val |
| | | | 100 | | | | | 105 | | | | | 110 | | |
| Leu | Lys | Lys | Ile | Tyr | Leu | Asn | Glu | Asn | Val | Asn | Ser | Glu | Glu | Leu | Glu |
| | 115 | | | | | 120 | | | | | 125 | | | | |
| Val | Phe | Arg | Asn | Asp | Ile | Lys | Lys | Lys | Leu | Asn | Lys | Ile | Asn | Ser | Leu |
| | 130 | | | | | 135 | | | | | 140 | | | | |
| Lys | Tyr | Ser | Phe | Glu | Lys | Asn | Lys | Ala | Asn | Tyr | Gln | Lys | Ile | Asn | Glu |
| 145 | | | | | 150 | | | | | 155 | | | | | 160 |
| Asn | Asn | Ile | Glu | Lys | Val | Glu | Gly | Lys | Ser | Lys | Arg | Asn | Ile | Ile | Tyr |
| | | | | 165 | | | | | 170 | | | | | 175 | |
| Asp | Tyr | Tyr | Arg | Glu | Ser | Ala | Lys | Arg | Asp | Ala | Tyr | Val | Ser | Asn | Val |
| | | | 180 | | | | | 185 | | | | | 190 | | |
| Lys | Glu | Ala | Phe | Asp | Lys | Leu | Tyr | Lys | Glu | Glu | Asp | Ile | Ala | Lys | Leu |
| | | 195 | | | | | 200 | | | | | 205 | | | |
| Val | Leu | Glu | Ile | Glu | Asn | Leu | Thr | Lys | Leu | Glu | Lys | Tyr | Lys | Ile | Arg |
| | 210 | | | | | 215 | | | | | 220 | | | | |
| Glu | Phe | Tyr | His | Glu | Ile | Ile | Gly | Arg | Lys | Asn | Asp | Lys | Glu | Asn | Phe |
| 225 | | | | | 230 | | | | | 235 | | | | | 240 |
| Ala | Lys | Ile | Ile | Tyr | Glu | Glu | Ile | Gln | Asn | Val | Asn | Asn | Met | Lys | Glu |
| | | | | 245 | | | | | 250 | | | | | 255 | |
| Leu | Ile | Glu | Lys | Val | Pro | Asp | Met | Ser | Glu | Leu | Lys | Lys | Ser | Gln | Val |
| | | | 260 | | | | | 265 | | | | | 270 | | |
| Phe | Tyr | Lys | Tyr | Tyr | Leu | Asp | Lys | Glu | Glu | Leu | Asn | Asp | Lys | Asn | Ile |
| | | 275 | | | | | 280 | | | | | 285 | | | |
| Lys | Tyr | Ala | Phe | Cys | His | Phe | Val | Glu | Ile | Glu | Met | Ser | Gln | Leu | Leu |
| | 290 | | | | | 295 | | | | | 300 | | | | |
| Lys | Asn | Tyr | Val | Tyr | Lys | Arg | Leu | Ser | Asn | Ile | Ser | Asn | Asp | Lys | Ile |
| 305 | | | | | 310 | | | | | 315 | | | | | 320 |
| Lys | Arg | Ile | Phe | Glu | Tyr | Gln | Asn | Leu | Lys | Lys | Leu | Ile | Glu | Asn | Lys |
| | | | | 325 | | | | | 330 | | | | | 335 | |
| Leu | Leu | Asn | Lys | Leu | Asp | Thr | Tyr | Val | Arg | Asn | Cys | Gly | Lys | Tyr | Asn |
| | | | 340 | | | | | 345 | | | | | 350 | | |
| Tyr | Tyr | Leu | Gln | Asp | Gly | Glu | Ile | Ala | Thr | Ser | Asp | Phe | Ile | Ala | Arg |
| | | 355 | | | | | 360 | | | | | 365 | | | |
| Asn | Arg | Gln | Asn | Glu | Ala | Phe | Leu | Arg | Asn | Ile | Ile | Gly | Val | Ser | Ser |
| | 370 | | | | | 375 | | | | | 380 | | | | |

```
Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
            405                 410                 415

Glu Glu Lys Tyr Val Ser Gly Glu Val Asp Lys Ile Tyr Asn Glu Asn
                420                 425                 430

Lys Lys Asn Glu Val Lys Glu Asn Leu Lys Met Phe Tyr Ser Tyr Asp
        435                 440                 445

Phe Asn Met Asp Asn Lys Asn Glu Ile Glu Asp Phe Phe Ala Asn Ile
    450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
        515                 520                 525

Leu Glu Lys Tyr Lys Ile Leu Asn Tyr Leu Lys Arg Thr Arg Phe Glu
530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
            580                 585                 590

Ile Tyr Leu Leu Lys Asn Ile Tyr Tyr Gly Glu Phe Leu Asn Tyr Phe
        595                 600                 605

Met Ser Asn Asn Gly Asn Phe Phe Glu Ile Ser Lys Glu Ile Ile Glu
    610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
            660                 665                 670

Glu Lys Asp Thr Tyr Ile Asp Phe Ile Gln Lys Ile Phe Leu Lys Gly
        675                 680                 685

Phe Met Thr Tyr Leu Ala Asn Asn Gly Arg Leu Ser Leu Ile Tyr Ile
    690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
                725                 730                 735

Pro Tyr Glu Ile Asn Glu Phe Leu Arg Glu Ile Lys Leu Gly Asn Ile
            740                 745                 750

Leu Lys Tyr Thr Glu Arg Leu Asn Met Phe Tyr Leu Ile Leu Lys Leu
        755                 760                 765

Leu Asn His Lys Glu Leu Thr Asn Leu Lys Gly Ser Leu Glu Lys Tyr
770                 775                 780

Gln Ser Ala Asn Lys Glu Glu Ala Phe Ser Asp Gln Leu Glu Leu Ile
785                 790                 795                 800
```

```
Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
        820                 825                 830

Lys Asp Asn Lys Glu Leu Lys Lys Phe Asp Thr Asn Lys Ile Tyr Phe
835                 840                 845

Asp Gly Glu Asn Ile Ile Lys His Arg Ala Phe Tyr Asn Ile Lys Lys
    850                 855                 860

Tyr Gly Met Leu Asn Leu Glu Lys Ile Ala Asp Lys Ala Gly Tyr
865                 870                 875                 880

Lys Ile Ser Ile Glu Glu Leu Lys Lys Tyr Ser Asn Lys Asn Glu
            885                 890                 895

Ile Glu Lys Asn His Lys Met Gln Glu Asn Leu His Arg Lys Tyr Ala
                900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
930                 935                 940

Val Glu Phe Asn Glu Leu Asn Leu Leu Gln Gly Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Ile
            980                 985                 990

Phe Asn Phe Glu Asn Lys Lys Asn  Val Lys Tyr Lys Gly  Gly Gln Ile
        995                 1000                1005

Val Glu  Lys Tyr Ile Lys Lys Phe  Tyr Lys Glu Leu His  Gln Asn Asp
    1010                1015                1020

Glu Val  Lys Ile Asn Lys Tyr  Ser Ser Ala Asn Ile  Lys Val Leu
    1025                1030                1035

Lys Gln  Glu Lys Lys Asp Leu  Tyr Ile Arg Asn Tyr  Ile Ala His
    1040                1045                1050

Phe Asn  Tyr Ile Pro His Ala  Glu Ile Ser Leu Leu  Glu Val Leu
    1055                1060                1065

Glu Asn  Leu Arg Lys Leu Leu  Ser Tyr Asp Arg Lys  Leu Lys Asn
    1070                1075                1080

Ala Val  Met Lys Ser Val Val  Asp Ile Leu Lys Glu  Tyr Gly Phe
    1085                1090                1095

Val Ala  Thr Phe Lys Ile Gly  Ala Asp Lys Lys Ile  Gly Ile Gln
    1100                1105                1110

Thr Leu  Glu Ser Glu Lys Ile  Val His Leu Lys Asn  Leu Lys Lys
    1115                1120                1125

Lys Lys  Leu Met Thr Asp Arg  Asn Ser Glu Glu Leu  Cys Lys Leu
    1130                1135                1140

Val Lys  Ile Met Phe Glu Tyr  Lys Met Glu Glu Lys  Lys Ser Glu
    1145                1150                1155

Asn

<210> SEQ ID NO 158
<211> LENGTH: 1389
<212> TYPE: PRT
<213> ORGANISM: Unknown
<220> FEATURE:
<223> OTHER INFORMATION: Description of Unknown:
      LshCas13a sequence
```

<400> SEQUENCE: 158

```
Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
                20                  25                  30

Gly Asn Lys Tyr Ile Leu Asn Ile Asn Glu Asn Asn Lys Glu Lys
                35                  40                  45

Ile Asp Asn Asn Lys Phe Ile Arg Lys Tyr Ile Asn Tyr Lys Lys Asn
50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
                100                 105                 110

Gly Lys Ser Glu Lys Leu Lys Ala Leu Gly Ile Thr Lys Lys Lys Ile
                115                 120                 125

Ile Asp Glu Ala Ile Arg Gln Gly Ile Thr Lys Asp Asp Lys Lys Ile
130                 135                 140

Glu Ile Lys Arg Gln Glu Asn Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Gly Thr Lys Lys Ser Ile Tyr Glu Ile
                180                 185                 190

Phe Lys Asn Ile Asn Met Ser Leu Tyr Lys Ile Ile Glu Lys Ile Ile
                195                 200                 205

Glu Asn Glu Thr Glu Lys Val Phe Glu Asn Arg Tyr Tyr Glu Glu His
210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
                260                 265                 270

Lys Asn Lys Lys Met Leu Val Glu Lys Ile Leu Asn Ile Asn Val Asp
                275                 280                 285

Leu Thr Val Glu Asp Ile Ala Asp Phe Val Ile Lys Glu Leu Glu Phe
                290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
                340                 345                 350

Lys Ile Val Lys Phe Phe Val Glu Asn Ile Lys Asn Asn Ser Ile Lys
                355                 360                 365

Glu Lys Ile Glu Lys Ile Leu Ala Glu Phe Lys Ile Asp Glu Leu Ile
                370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
```

-continued

```
                405                 410                 415
Phe Ser Lys Lys Ser Asp Glu Glu Lys Glu Leu Tyr Lys Ile Ile Tyr
            420                 425                 430
Arg Tyr Leu Lys Gly Arg Ile Glu Lys Ile Leu Val Asn Glu Gln Lys
            435                 440                 445
Val Arg Leu Lys Lys Met Glu Lys Ile Glu Ile Glu Lys Ile Leu Asn
450                 455                 460
Glu Ser Ile Leu Ser Glu Lys Ile Leu Lys Arg Val Lys Gln Tyr Thr
465                 470                 475                 480
Leu Glu His Ile Met Tyr Leu Gly Lys Leu Arg His Asn Asp Ile Asp
                485                 490                 495
Met Thr Thr Val Asn Thr Asp Asp Phe Ser Arg Leu His Ala Lys Glu
            500                 505                 510
Glu Leu Asp Leu Glu Leu Ile Thr Phe Phe Ala Ser Thr Asn Met Glu
            515                 520                 525
Leu Asn Lys Ile Phe Ser Arg Glu Asn Ile Asn Asn Asp Glu Asn Ile
            530                 535                 540
Asp Phe Phe Gly Gly Asp Arg Glu Lys Asn Tyr Val Leu Asp Lys Lys
545                 550                 555                 560
Ile Leu Asn Ser Lys Ile Lys Ile Ile Arg Asp Leu Asp Phe Ile Asp
                565                 570                 575
Asn Lys Asn Asn Ile Thr Asn Asn Phe Ile Arg Lys Phe Thr Lys Ile
            580                 585                 590
Gly Thr Asn Glu Arg Asn Arg Ile Leu His Ala Ile Ser Lys Glu Arg
            595                 600                 605
Asp Leu Gln Gly Thr Gln Asp Tyr Asn Lys Val Ile Asn Ile Ile
            610                 615                 620
Gln Asn Leu Lys Ile Ser Asp Glu Glu Val Ser Lys Ala Leu Asn Leu
625                 630                 635                 640
Asp Val Val Phe Lys Asp Lys Lys Asn Ile Ile Thr Lys Ile Asn Asp
                645                 650                 655
Ile Lys Ile Ser Glu Glu Asn Asn Asp Ile Lys Tyr Leu Pro Ser
            660                 665                 670
Phe Ser Lys Val Leu Pro Glu Ile Leu Asn Leu Tyr Arg Asn Asn Pro
            675                 680                 685
Lys Asn Glu Pro Phe Asp Thr Ile Glu Thr Lys Ile Val Leu Asn
            690                 695                 700
Ala Leu Ile Tyr Val Asn Lys Glu Leu Tyr Lys Lys Leu Ile Leu Glu
705                 710                 715                 720
Asp Asp Leu Glu Glu Asn Glu Ser Lys Asn Ile Phe Leu Gln Glu Leu
                725                 730                 735
Lys Lys Thr Leu Gly Asn Ile Asp Glu Ile Asp Glu Asn Ile Ile Glu
            740                 745                 750
Asn Tyr Tyr Lys Asn Ala Gln Ile Ser Ala Ser Lys Gly Asn Asn Lys
            755                 760                 765
Ala Ile Lys Lys Tyr Gln Lys Lys Val Ile Glu Cys Tyr Ile Gly Tyr
            770                 775                 780
Leu Arg Lys Asn Tyr Glu Glu Leu Phe Asp Phe Ser Asp Phe Lys Met
785                 790                 795                 800
Asn Ile Gln Glu Ile Lys Lys Gln Ile Lys Asp Ile Asn Asp Asn Lys
                805                 810                 815
Thr Tyr Glu Arg Ile Thr Val Lys Thr Ser Asp Lys Thr Ile Val Ile
            820                 825                 830
```

Asn Asp Asp Phe Glu Tyr Ile Ile Ser Ile Phe Ala Leu Leu Asn Ser
            835                 840                 845

Asn Ala Val Ile Asn Lys Ile Arg Asn Arg Phe Phe Ala Thr Ser Val
        850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
            915                 920                 925

Tyr Tyr Glu Asp Ile Lys Asn Asn Ile Leu Thr Glu Phe Lys Asp Asp
        930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys Asp Lys Asp Gln Glu Ile Lys Ser
        995                 1000                1005

Lys Ile Leu Cys Arg Ile Ile Phe Asn Ser Asp Phe Leu Lys Lys
    1010                1015                1020

Tyr Lys Lys Glu Ile Asp Asn Leu Ile Glu Asp Met Glu Ser Glu
    1025                1030                1035

Asn Glu Asn Lys Phe Gln Glu Ile Tyr Tyr Pro Lys Glu Arg Lys
    1040                1045                1050

Asn Glu Leu Tyr Ile Tyr Lys Lys Asn Leu Phe Leu Asn Ile Gly
    1055                1060                1065

Asn Pro Asn Phe Asp Lys Ile Tyr Gly Leu Ile Ser Asn Asp Ile
    1070                1075                1080

Lys Met Ala Asp Ala Lys Phe Leu Phe Asn Ile Asp Gly Lys Asn
    1085                1090                1095

Ile Arg Lys Asn Lys Ile Ser Glu Ile Asp Ala Ile Leu Lys Asn
    1100                1105                1110

Leu Asn Asp Lys Leu Asn Gly Tyr Ser Lys Glu Tyr Lys Glu Lys
    1115                1120                1125

Tyr Ile Lys Lys Leu Lys Glu Asn Asp Asp Phe Phe Ala Lys Asn
    1130                1135                1140

Ile Gln Asn Lys Asn Tyr Lys Ser Phe Glu Lys Asp Tyr Asn Arg
    1145                1150                1155

Val Ser Glu Tyr Lys Lys Ile Arg Asp Leu Val Glu Phe Asn Tyr
    1160                1165                1170

Leu Asn Lys Ile Glu Ser Tyr Leu Ile Asp Ile Asn Trp Lys Leu
    1175                1180                1185

Ala Ile Gln Met Ala Arg Phe Glu Arg Asp Met His Tyr Ile Val
    1190                1195                1200

Asn Gly Leu Arg Glu Leu Gly Ile Ile Lys Leu Ser Gly Tyr Asn
    1205                1210                1215

Thr Gly Ile Ser Arg Ala Tyr Pro Lys Arg Asn Gly Ser Asp Gly
    1220                1225                1230

```
Phe Tyr Thr Thr Thr Ala Tyr Tyr Lys Phe Phe Asp Glu Glu Ser
    1235                1240                1245

Tyr Lys Lys Phe Glu Lys Ile Cys Tyr Gly Phe Gly Ile Asp Leu
    1250                1255                1260

Ser Glu Asn Ser Glu Ile Asn Lys Pro Glu Asn Glu Ser Ile Arg
    1265                1270                1275

Asn Tyr Ile Ser His Phe Tyr Ile Val Arg Asn Pro Phe Ala Asp
    1280                1285                1290

Tyr Ser Ile Ala Glu Gln Ile Asp Arg Val Ser Asn Leu Leu Ser
    1295                1300                1305

Tyr Ser Thr Arg Tyr Asn Asn Ser Thr Tyr Ala Ser Val Phe Glu
    1310                1315                1320

Val Phe Lys Lys Asp Val Asn Leu Asp Tyr Asp Glu Leu Lys Lys
    1325                1330                1335

Lys Phe Lys Leu Ile Gly Asn Asn Asp Ile Leu Glu Arg Leu Met
    1340                1345                1350

Lys Pro Lys Lys Val Ser Val Leu Glu Leu Glu Ser Tyr Asn Ser
    1355                1360                1365

Asp Tyr Ile Lys Asn Leu Ile Ile Glu Leu Leu Thr Lys Ile Glu
    1370                1375                1380

Asn Thr Asn Asp Thr Leu
    1385

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Val Ile Leu Pro Phe Tyr Met Trp
1               5

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164
<211> LENGTH: 11
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: a, c, u, g, unknown or other

<400> SEQUENCE: 164
cuaaaacnnn n                                                                11

<210> SEQ ID NO 165
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: a, c, u, g, unknown or other

<400> SEQUENCE: 165
cuaaaacnnn n                                                                11

<210> SEQ ID NO 166
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: a, c, u, g, unknown or other

<400> SEQUENCE: 166
cuaaaacnnn n                                                                11

<210> SEQ ID NO 167
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: a, c, u, g, unknown or other

<400> SEQUENCE: 167
cuaaaacnnn n                                                                11

<210> SEQ ID NO 168
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(60)
<223> OTHER INFORMATION: a, c, t, g, unknown or other

<400> SEQUENCE: 168
``` caccccgtgca aaattgcagg ggtctaaaac nnnnnnnnnn nnnnnnnnnn nnnnnnnnnn    60

<210> SEQ ID NO 169
<211> LENGTH: 36
<212> TYPE: RNA
<213> ORGANISM: Unknown
<220> FEATURE:
<223> OTHER INFORMATION: Description of Unknown:
      MS2 binding loop

<400> SEQUENCE: 169
ggcccaacau gaggaucacc caugucugca ggggcc    36

<210> SEQ ID NO 170
<211> LENGTH: 29
<212> TYPE: RNA
<213> ORGANISM: Unknown
<220> FEATURE:
<223> OTHER INFORMATION: Description of Unknown:
      QBeta binding loop sequence

<400> SEQUENCE: 170
ggcccaugcu gucuaagaca gcaugggcc    29

<210> SEQ ID NO 171
<211> LENGTH: 130
<212> TYPE: PRT
<213> ORGANISM: Bacteriophage MS2

<400> SEQUENCE: 171

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 172
<211> LENGTH: 133
<212> TYPE: PRT
<213> ORGANISM: Bacteriophage Qbeta

<400> SEQUENCE: 172

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

```
Val Thr Val Ser Val Ser Gln Pro Ser Arg Asn Arg Lys Asn Tyr Lys
    50              55                  60

Val Gln Val Lys Ile Gln Asn Pro Thr Ala Cys Thr Ala Asn Gly Ser
65              70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 173
<211> LENGTH: 34
<212> TYPE: RNA
<213> ORGANISM: Unknown
<220> FEATURE:
<223> OTHER INFORMATION: Description of Unknown:
      PP7 binding loop sequence

<400> SEQUENCE: 173
ggcccuaagg guuuauaugg aaacccuuag ggcc                           34
```

CRISPR RNA TARGETING ENZYMES AND SYSTEMS AND USES THEREOF

CROSS REFERENCE TO RELATED APPLICATIONS

This application claims the benefit of priority of U.S. Application No. 62/527,957, filed Jun. 30, 2017; U.S. Application No. 62/572,367, filed Oct. 13, 2017; U.S. Application No. 62/580,880, filed Nov. 2, 2017; U.S. Application No. 62/587,381, filed Nov. 16, 2017; U.S. Application No. 62/619,691, filed Jan. 19, 2018; U.S. Application No. 62/626,679, filed Feb. 5, 2018; U.S. Application No. 62/628,921, filed Feb. 9, 2018; and U.S. Application No. 62/635,443, filed Feb. 26, 2018. The content of each of the foregoing applications is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 1, 2018, is named 45138-0008002_SL.txt and is 396,110 bytes in size.

FIELD OF THE INVENTION

The present disclosure relates to novel CRISPR systems and components, systems for detecting CRISPR systems, and methods and compositions for use of the CRISPR systems in, for example, nucleic acid targeting and manipulation.

BACKGROUND

Recent advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantity of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the systems involved in host defense include one or more effector proteins capable of modifying DNA or RNA and a RNA guide element that is responsible to target these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat (DR) responsible for protein binding to the crRNA and a spacer sequence, which may be engineered to be complementary to a desired nucleic acid target sequence. In this way, CRISPR systems can be programmed to target DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems that consist of a single effector protein that complexes with the crRNA to target DNA or RNA substrates. The single-subunit effector compositions of the Class 2 systems provide a simpler component set for engineering and application translation, and has thus far been important sources of programmable effectors. The discovery, engineering, and optimization of novel Class 2 systems may lead to widespread and powerful programmable technologies for genome engineering and beyond.

SUMMARY

CRISPR-Cas systems are adaptive immune systems in archaea and bacteria that defend the species against foreign genetic elements. The characterization and engineering of Class 2 CRISPR-Cas systems, exemplified by CRISPR-Cas9, have paved the way for a diverse array of biotechnology applications in genome editing and beyond. Nevertheless, there remains a need for additional programmable effectors and systems for modifying nucleic acids and polynucleotides (i.e., DNA, RNA, or any hybrid, derivative, or modification) beyond the current CRISPR-Cas systems that enable novel applications through their unique properties.

The present disclosure provides methods for computational identification of new single-effector CRISPR Class 2 systems from genomic databases, together with the development of the natural loci into an engineered system, and experimental validation and application translation.

In another aspect, the disclosure provides engineered, non-naturally occurring Clustered Regularly Interspaced Short Palindromic Repeat (CRISPR)-associated (Cas) systems that include: i) an RNA guide or a nucleic acid encoding the RNA guide, wherein the RNA guide comprises a direct repeat sequence and a spacer sequence capable of hybridizing to a target nucleic acid; ii) a CRISPR-associated protein or a nucleic acid encoding the CRISPR-associated protein; and an accessory protein or a nucleic acid encoding the accessory protein, wherein the accessory protein comprises at least one WYL domain, and wherein the accessory protein comprises an amino acid sequence having at least 85% sequence identity to an amino acid sequence provided in any one of Tables 4, 5, and 6; wherein the CRISPR-associated protein is capable of binding to the RNA guide and of targeting the target nucleic acid sequence complementary to the spacer sequence, and wherein the accessory protein modulates an activity of the CRISPR-associated protein.

In some embodiments, the activity is a nuclease activity (e.g., a DNAse activity or an RNAse activity). In some embodiments, the RNAse activity is targeted RNAse activity or a collateral RNAse activity.

In some embodiments, the accessory protein increases the activity of the CRISPR-associated protein. In some embodiments, the accessory protein decreases the activity of the CRISPR-associated protein.

In some embodiments, the accessory protein comprises one WYL domain. In some embodiments, the accessory protein comprises two WYL domains. In some embodiments, the accessory protein further comprises a helix-turnhelix (HTH) fold. In some embodiments, the accessory protein further comprises a ribbon-helix-helix (RHH) fold.

In some embodiments, the accessory protein comprises or consists of an amino acid sequence having at least 80% (e.g., 81%, 82%, 83%, 84%, 85%, 86%, 87% 88%, 89%, 90%, 91%, 92%, 93%, 94%, 95%, 96%, 97%, 98%, 99%, or 100%) sequence identity to an amino acid sequence provided in any one of Tables 4, 5, and 6. In some embodiments, the accessory protein comprises or consists of an amino acid sequence provided in any one of Tables 4, 5, and 6. In some embodiments, the accessory protein is RspWYL1 (SEQ ID NO: 81).

In some embodiments, the target nucleic acid is an RNA. In some embodiments, the target nucleic acid is a DNA.

In some embodiments, the targeting of the target nucleic acid results in a modification (e.g., a cleavage event) of the target nucleic acid. In some embodiments, the modification results in cell toxicity. In some embodiments, the modification results in decreased transcription and/or decreased translation of the target nucleic acid. In some embodiments, the modification results in increased transcription and/or increased translation of the target nucleic acid.

In some embodiments, the CRISPR-associated protein is a Class 2 CRISPR-Cas system protein. In some embodiments, the CRISPR-associated protein comprises a RuvC domain. In some embodiments, the CRISPR-associated protein is selected from the group consisting of a Type VI Cas protein, a Type V Cas protein, and a Type II Cas protein. In some embodiments, the CRISPR-associated protein is a Cas13a protein, a Cas13b protein, a Cas13c protein, a Cas12a protein, or a Cas9 protein.

In some embodiments, the CRISPR-associated protein is a Type VI-D CRISPR-Cas effector protein comprising at least two HEPN domains (e.g., two, three, four, or more HEPN domains). In some embodiments, the Type VI-D CRISPR-Cas effector protein comprises two HEPN domains.

In some embodiments, the Type VI-D CRISPR-Cas effector protein comprises or consists of an amino acid sequence having at least 80% (e.g., 81%, 82%, 83%, 84%, 85%, 86%, 87% 88%, 89%, 90%, 91%, 92%, 93%, 94%, 95%, 96%, 97%, 98%, 99%, or 100%) sequence identity to an amino acid sequence provided in Table 2. In some embodiments, the Type VI-D CRISPR-Cas effector protein comprises or consists of an amino acid sequence provided in Table 2. In some embodiments, the Type VI-D CRISPR-Cas effector protein is RspCas13d (SEQ ID NO: 2) or EsCas13d (SEQ ID NO: 1).

In some embodiments, the Type VI-D CRISPR-Cas effector protein comprises one or more (e.g., two, three, four, five or six) amino acid substitutions within at least one of the HEPN domains. In some embodiments, the Type VI-D CRISPR-Cas effector protein comprises six or less (e.g., five, four, three, two or or) amino acid substitutions within at least one of the HEPN domains. In some embodiments, the one or more one amino acid substitutions comprise an alanine substitution at an amino acid residue corresponding to R295, H300, R849, or H854 of SEQ ID NO: 1, or R288, H293, R820, or H825 of SEQ ID NO: 2. In some embodiments, the one or more amino acid substitutions result in a reduction of an RNAse activity of the Type VI-D CRISPR-Cas effector protein, as compared to the RNAse activity of the Type VI-D CRISPR-Cas effector protein without the one or more acid substitutions.

In some embodiments, the CRISPR-associated proteins include at least one (e.g., two, three, four, five, six or more) nuclear localization signal (NLS). In some embodiments, the CRISPR-associated protein comprises at least one (e.g., two, three, four, five, six, or more) nuclear export signal (NES). In some embodiments, the CRISPR-associated protein comprises at least one (e.g., two, three, four, five, six, or more) NLS and at least one (e.g., two, three, four, five, six, or more) NES.

In some embodiments, the direct repeat sequence includes 5'-$X_1X_2X_3X_4TX_5TX_6$AAAC-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G. In some embodiments, the direct repeat sequence comprises or consists of a nucleotide sequence provided in Table 3. In some embodiments, the direct repeat sequence comprises or consists of either 5'-CACCCGTGCAAAATTGCAGGGGTCTAAAAC-3' (SEQ ID NO: 152) or 5'-CACTGGTGCAAAT-TTGCACTAGTCTAAAAC-3' (SEQ ID NO: 153).

In some embodiments, the spacer includes from about 15 to about 42 nucleotides. In some embodiments, the RNA guide includes a trans-activating CRISPR RNA (tracrRNA).

In some embodiments of the systems described herein, the systems include a single-stranded donor template or a double-stranded donor template (e.g., a single-stranded DNA, a double stranded DNA, a single-stranded RNA, or a double stranded RNA).

In another aspect, the disclosure provides engineered, non-naturally occurring Clustered Regularly Interspaced Short Palindromic Repeat (CRISPR)-associated (Cas) systems that include: i) an RNA guide or a nucleic acid encoding the RNA guide, wherein the RNA guide comprises a direct repeat sequence and a spacer sequence capable of hybridizing to a target nucleic acid, wherein the direct repeat sequence comprises 5'-$X_1X_2X_3X_4TX_5TX_6$AAAC-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G; and ii) a Type VI-D CRISPR-Cas effector protein or a nucleic acid encoding the effector protein, wherein the effector protein is capable of binding to and of targeting the target nucleic acid sequence complementary to the RNA guide spacer sequence, and wherein the target nucleic acid is an RNA.

In some embodiments, the Type VI-D CRISPR-Cas effector protein comprises at least two HEPN domains. In some embodiments, the protein is about 1200 amino acids or less (e.g., 1100, 1000, 1050, 900, 950, 800 amino acids) in length.

In other embodiments, the targeting of the target nucleic acid results in a modification of the target nucleic acid. In some embodiments, the modification of the target nucleic acid is a cleavage event. In some embodiments, the modification results in cell toxicity.

In some embodiments, the modification results in decreased transcription and/or decreased translation of the target nucleic acid. In some embodiments, the modification results in increased transcription and/or increased translation of the target nucleic acid.

In various embodiments, the systems further include a donor template nucleic acid. In some embodiments, the donor template nucleic acid is a DNA or an RNA.

In some embodiments, the Type VI-D CRISPR-Cas effector protein comprises one or more (e.g., two, three, four, five or six) amino acid substitutions within at least one of the HEPN domains. In some embodiments, the one or more amino acid substitutions comprise an alanine substitution at an amino acid residue corresponding to R295, H300, R849, or H854 of SEQ ID NO: 1, or R288, H293, R820, or H825 of SEQ ID NO: 2. In some embodiments, the one or more amino acid substitutions result in a reduction of an RNAse activity of the Type VI-D CRISPR-Cas effector protein, as compared to the RNAse activity of the Type VI-D CRISPR-Cas effector protein without the one or more amino acid substitutions.

In some embodiments, the Type VI-D CRISPR-Cas effector protein comprises or consists of an amino acid sequence having at least 80% (e.g., 81%, 82%, 83%, 84%, 85%, 86%, 87% 88%, 89%, 90%, 91%, 92%, 93%, 94%, 95%, 96%, 97%, 98%, 99%, or 100%) sequence identity to an amino acid sequence provided in Table 2. In some embodiments, the Type VI-D CRISPR-Cas effector protein comprises or consists of an amino acid sequence provided in Table 2. In some embodiments, the Type VI-D CRISPR-Cas effector protein is RspCas13d (SEQ ID NO: 2) or EsCas13d (SEQ ID NO: 1).

In some embodiments, the systems include an accessory protein or a nucleic acid encoding the accessory protein, wherein the accessory protein comprises at least one WYL domain, and wherein the accessory protein comprises or consists of an amino acid sequence having at least 80% (e.g., 81%, 82%, 83%, 84%, 85%, 86%, 87% 88%, 89%, 90%, 91%, 92%, 93%, 94%, 95%, 96%, 97%, 98%, 99%, or 100%) sequence identity to an amino acid sequence provided in any one of Tables 4, 5, and 6. In some embodiments, the accessory protein comprises two WYL domains. In some embodiments, the accessory protein further comprises a helix-turn-helix (HTH) fold or a ribbon-helix-helix (RHH) fold. In some embodiments, the accessory protein is RspWYL1 (SEQ ID NO: 81).

In some embodiments, the accessory protein modulates (e.g., increases or decreases) an activity of the Type VI-D CRISPR-Cas effector protein. In some embodiments, the activity is an RNAse activity, an RNA-binding activity, or both. In some embodiments, the RNAse activity is a targeted RNAse activity or a collateral RNAse activity.

In some embodiments, the CRISPR-associated protein comprises at least one (e.g., two, three, four, five, six, or more) nuclear localization signal (NLS). In some embodiments, the CRISPR-associated protein comprises at least one (e.g., two, three, four, five, six, or more) nuclear export signal (NES). In some embodiments, the CRISPR-associated protein comprises at least one (e.g., two, three, four, five, six, or more) NLS and at least one (e.g., two, three, four, five, six, or more) NES.

In some embodiments, the direct repeat sequence comprises or consists of a nucleotide sequence provided in Table 3. In some embodiments, the direct repeat sequence comprises either 5'-CACCCGTGCAAAAT-TGCAGGGGTCTAAAAC-3' (SEQ ID NO: 152) or 5'-CACTGGTGCAAATTTGCACTAGTCTAAAAC-3' (SEQ ID NO: 153).

In some embodiments, the spacer sequence comprises from about 15 to about 42 nucleotides.

In some embodiments, the systems provided herein include a single-stranded donor template or a double-stranded donor template (e.g., an RNA or a DNA molecule).

In some embodiments, the systems provided herein include a target RNA or a nucleic acid encoding the target RNA, wherein the target RNA comprises a sequence that is capable of hybridizing to the spacer sequence of the RNA guide.

In another aspect, the disclosure provides engineered, non-naturally occurring Clustered Regularly Interspaced Short Palindromic Repeat (CRISPR)-associated (Cas) systems that include: i) an RNA guide or a nucleic acid encoding the RNA guide, wherein the RNA guide comprise a direct repeat sequence and a spacer sequence capable of hybridizing to a target nucleic acid, wherein the direct repeat sequence comprises 5'-$X_1X_2X_3X_4TX_5TX_6AAAC$-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G; and ii) a Type VI-D CRISPR-Cas effector protein and/or a nucleic acid encoding the effector protein, wherein the effector protein is about 1200 or fewer amino acids or less, and wherein the effector protein is capable of binding to the RNA guide and of targeting the target nucleic acid sequence complementary to the spacer sequence.

In another aspect, the disclosure provides engineered, non-naturally occurring Clustered Regularly Interspaced Short Palindromic Repeat (CRISPR)-associated (Cas) systems that include: i) an RNA guide or a nucleic acid encoding the RNA guide, wherein the RNA guide comprises a direct repeat sequence and a spacer sequence capable of hybridizing to a target nucleic acid, wherein the direct repeat sequence comprises 5'-$X_1X_2X_3X_4TX_5TX_6AAAC$-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G; and ii) a Type VI-D CRISPR-Cas effector protein or a nucleic acid encoding the effector protein, wherein the effector protein is about 950 or fewer amino acids, and wherein the effector protein is capable of binding to the RNA guide and of targeting the target nucleic acid sequence complementary to the spacer sequence.

In another aspect, the disclosure provides engineered, non-naturally occurring Clustered Regularly Interspaced Short Palindromic Repeat (CRISPR)-associated (Cas) systems that include: i) an RNA guide (e.g., a crRNA) or a nucleic acid encoding the RNA guide, wherein the RNA guide comprises a direct repeat sequence and a spacer sequence capable of hybridizing to a target nucleic acid, wherein the direct repeat sequence comprises 5'-$X_1X_2X_3X_4TX_5TX_6AAAC$-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G; ii) a Type VI-D CRISPR-Cas effector protein or a nucleic acid encoding the effector protein, wherein the effector protein is capable of binding to the RNA guide and of targeting the target nucleic acid sequence complementary to the spacer sequence; and iii) an accessory protein, wherein the accessory protein comprises at least one WYL domain, wherein the accessory protein comprises or consists of an amino acid sequence having at least 85% sequence identity to an amino acid sequence provided in any one of Tables 4, 5, and 6, and wherein the accessory protein is capable of regulating an activity of the effector protein.

In some embodiments, the accessory protein is RspWYL1 (SEQ ID NO: 81).

In some embodiments, the effector protein comprises at least two HEPN domains. In some embodiments, the effector protein comprises or consists of an amino acid sequence having at least 85% sequence identity to an amino acid sequence provided in Table 2. In some embodiments, the effector protein is RspCas13d (SEQ ID NO: 2) or EsCas13d (SEQ ID NO: 1).

In some embodiments, the CRISPR-associated protein (e.g., Type VI-D CRISPR-Cas effector protein) is fused to a base-editing domain (e.g., Adenosine Deaminase Acting on RNA (ADAR) 1; ADAR2; apolipoprotein B mRNA editing enzyme, catalytic polypeptide-like (APOBEC); and activation-induced cytidine deaminase (AID)). In some embodiments, the base-editing domain is further fused to an RNA-binding domain.

In some embodiments, the CRISPR associated protein (e.g., a Type VI-D CRISPR-Cas effector protein) is fused to a RNA methyltransferase, a RNA demethylase, a splicing modifier, a localization factor, or a translation modification factor.

In some embodiments, the CRISPR-associated (e.g., a Type VI-D CRISPR-Cas effector protein) further comprises a linker sequence. In some embodiments, the CRISPR-associated protein (e.g., a Type VI-D CRISPR-Cas effector protein) includes one or more mutations or amino acid substitutions that render the CRISPR-associated protein unable to cleave RNA.

In some embodiments, the systems described herein also include an RNA-binding fusion polypeptide that comprises an RNA-binding domain and a base-editing domain (e.g., ADAR1, ADAR2, APOBEC, and AID). In some embodiments, the RNA-binding domain is MS2, PP7 or Qbeta.

In some embodiments, the systems described herein include a nucleic acid encoding the CRISPR-associated protein (e.g., a Type VI-D CRISPR-Cas effector protein). In some embodiments, the nucleic acid encoding the CRISPR-associated protein is operably linked to a promoter (e.g., a constitutive promoter or an inducible promoter). In some embodiments, the nucleic acid encoding the CRISPR-associated protein is codon-optimized for expression in a cell (e.g., a mammalian cell or a bacterial cell).

In some embodiments, the systems described herein include a nucleic acid encoding the accessory protein. In some embodiments, the nucleic acid encoding the accessory protein is operably linked to a promoter (e.g., a constitutive promoter or an inducible promoter). In some embodiments, the nucleic acid encoding the accessory protein is codon-optimized for expression in a cell.

In some embodiments, the systems described herein include a nucleic acid encoding one or more RNA guides (e.g., crRNAs). In some embodiments, the nucleic acid encoding the one or more RNA guides is operably linked to a promoter (e.g., a constitutive promoter or an inducible promoter).

In some embodiments, the systems described herein include a nucleic acid encoding a target nucleic acid (e.g., a target RNA). In some embodiments, the nucleic acid encoding the target nucleic acid is operably linked to a promoter (e.g., a constitutive promoter or an inducible promoter).

In some embodiments, the systems described herein include a nucleic acid encoding a CRISPR-associated protein and a nucleic acid encoding an accessory protein in a vector. In some embodiments, the system further includes one or more nucleic acids encoding an RNA guide present in the vector.

In some embodiments, the systems provided herein include a nucleic acid encoding a Type VI-D CRISPR-Cas effector protein in a vector.

In some embodiments, the systems provided herein include a nucleic acid encoding the Type VI-D CRISPR-Cas effector protein and a nucleic acid encoding the accessory protein in a vector. In some embodiments, the system further includes one or more nucleic acids encoding one or more RNA guides (e.g., crRNAs) in the vector.

In some embodiments, the vectors included in the systems are viral vectors (e.g., retroviral vectors, lentiviral vectors, adenoviral vectors, adeno-associated vectors, and herpes simplex vectors. In some embodiments, the vectors included in the system are phage vectors.

In some embodiments, the systems provided herein are in a delivery system. In some embodiments, the delivery system comprises a delivery vehicle selected from the group consisting of a nanoparticle, a liposome, an exosome, a microvesicle, and a gene-gun.

The disclosure also provides a cell (e.g., a eukaryotic cell or a prokaryotic cell (e.g., a bacterial cell)) comprising a system described herein. In some embodiments, the eukaryotic cell is a mammalian cell (e.g., a human cell) or a plant cell. The disclosure also provides animal models (e.g., rodent or rabbit models) and plant model that include the cells.

In another aspect, the disclosure provides methods of cleaving a target nucleic acid, wherein the methods include contacting the target nucleic acid with a system described herein, wherein the spacer sequence is complementary to at least 15 nucleotides of the target nucleic acid, wherein the CRISPR-associated protein or the Type VI-D CRISPR effector protein associates with the RNA guide to form a complex, wherein the complex binds to a target nucleic acid sequence that is complementary to the at least 15 nucleotides of the spacer sequence; and wherein upon binding of the complex to the target nucleic acid sequence the CRISPR-associated protein or the Type VI-D CRISPR effector protein cleaves the target nucleic acid. In some embodiments of the methods, the target nucleic acid is within a cell.

In another aspect, the disclosure also provides methods of inducing dormancy or death of a cell, wherein the methods include contacting the cell with a system described herein, wherein the spacer sequence is complementary to at least 15 nucleotides of the target nucleic acid, wherein the Type VI-D CRISPR effector protein associates with the RNA guide to form a complex, wherein the complex binds to a target nucleic acid sequence that is complementary to the at least 15 nucleotides of the spacer sequence, and wherein upon binding of the complex to the target nucleic acid sequence the Type VI-D CRISPR-Cas effector protein cleaves a non-target nucleic acid within the cell, thereby inducing dormancy or death of the cell. In some embodiments of the methods described herein the death of the cell is via apoptosis, necrosis, necroptosis, or a combination thereof.

In some embodiments, the target nucleic acid is an RNA molecule (e.g., an mRNA, a tRNA, a ribosomal RNA, a non-coding RNA, a lncRNA, or a nuclear RNA). In some embodiments, the target nucleic acid is a DNA molecule (e.g., chromosomal DNA, mitochondrial DNA, single-stranded DNA, or plasmid DNA).

In some embodiments of the methods described herein, upon binding of the complex to the target nucleic acid, the CRISPR-associated protein or the Type VI-D CRISPR-Cas effector protein exhibits collateral RNAse activity.

In some embodiments, the cell is a cancer cell (e.g., a tumor cell). In some embodiments, the cell is an infectious agent cell or a cell infected with an infectious agent. In some embodiments, the cell is a bacterial cell, a cell infected with a virus, a cell infected with a prion, a fungal cell, a protozoan, or a parasite cell.

In another aspect, the disclosure provides methods of treating a condition or disease in a subject in need thereof, the methods include administering to the subject a system described herein, wherein the spacer sequence is complementary to at least 15 nucleotides of a target nucleic acid associated with the condition or disease, wherein the CRISPR-associated protein or the Type VI-D CRISPR-Cas effector protein associates with the RNA guide to form a complex, wherein the complex binds to a target nucleic acid sequence that is complementary to the at least 15 nucleotides of the spacer sequence; and wherein upon binding of the complex to the target nucleic acid sequence the CRISPR-associated protein or the Type VI-D CRISPR-Cas effector protein cleaves the target nucleic acid, thereby treating the condition or disease in the subject.

In some embodiments, the condition or disease is a cancer or an infectious disease. In some embodiments, the condition or disease is cancer, and wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In another aspect, the disclosure provides the use of a system described herein in a method selected from the group consisting of RNA sequence specific interference; RNA sequence-specific gene regulation; screening of RNA, RNA products, lncRNA, non-coding RNA, nuclear RNA, or mRNA; mutagenesis; inhibition of RNA splicing; fluorescence in situ hybridization; breeding; induction of cell dormancy; induction of cell cycle arrest; reduction of cell growth and/or cell proliferation; induction of cell anergy; induction of cell apoptosis; induction of cell necrosis; induction of cell death; or induction of programmed cell death.

In some embodiments, the methods described herein are performed either in vitro, in vivo, or ex vivo.

The disclosure also provides methods of modifying an RNA molecule, comprising contacting the RNA molecule with a system described herein. In some embodiments, the spacer sequence is complementary to at least 15 nucleotides of the RNA molecule.

The disclosure also provides methods of detecting a target RNA (e.g., a single-stranded RNA or a double-stranded RNA) in a sample, the methods including: a) contacting the sample with: (i) an RNA guide or a nucleic acid encoding the RNA guide, wherein the RNA guide comprises a direct repeat sequence and a spacer sequence capable of hybridizing to the target RNA; (ii) a Type VI-D CRISPR-Cas effector protein or a nucleic acid encoding the effector protein; and (iii) a labeled detector RNA; wherein the effector protein associates with the RNA guide to form a complex; wherein the RNA guide hybridizes to the target RNA; and wherein upon binding of the complex to the target RNA, the effector protein exhibits collateral RNAse activity and cleaves the labeled detector RNA; and b) measuring a detectable signal produced by cleavage of the labeled detector RNA, wherein said measuring provides for detection of the single-stranded target RNA in the sample.

In some embodiments, the Type VI-D CRISPR-Cas effector protein comprises at least two HEPN domains. In some embodiments, the Type VI-D CRISPR-Cas effector protein is about 1200 amino acids or less in length.

In some embodiments, the Type VI-D CRISPR-Cas effector protein comprises or consists of an amino acid sequence having at least 80% (e.g., 81%, 82%, 83%, 84%, 85%, 86%, 87% 88%, 89%, 90%, 91%, 92%, 93%, 94%, 95%, 96%, 97%, 98%, 99%, or 100%) sequence identity to an amino acid sequence provided in Table 2. In some embodiments, the Type VI-D CRISPR-Cas effector protein comprises or consists of an amino acid sequence provided in Table 2. In some embodiments, the Type VI-D CRISPR-Cas effector protein is RspCas13d (SEQ ID NO: 2) or EsCas13d (SEQ ID NO: 1).

In some embodiments, the effector protein includes one or more amino acid substitutions within at least one of the HEPN domains. In some embodiments, the one or more amino acid substitutions include an alanine substitution at an amino acid residue corresponding to R295, H300, R849, or H854 of SEQ ID NO: 1, or R288, H293, R820, or H825 of SEQ ID NO: 2.

In some embodiments, the methods further include comparing the detectable signal with a reference signal and determining the amount of target RNA in the sample.

In some embodiments, the measuring is performed using gold nanoparticle detection, fluorescence polarization, colloid phase transition/dispersion, electrochemical detection, and semiconductor based-sensing.

In some embodiments, the labeled detector RNA comprises a fluorescence-emitting dye pair. In some embodiments, the labeled detector RNA comprises a fluorescence resonance energy transfer (FRET) pair. In some embodiments, the labeled detector RNA comprises a quencher/fluor pair.

In some embodiments, upon cleavage of the labeled detector RNA by the effector protein, an amount of detectable signal produced by the labeled detector RNA is decreased. In some embodiments, upon cleavage of the labeled detector RNA by the effector protein, an amount of detectable signal produced by the labeled detector RNA is increased. In some embodiments, the labeled detector RNA produces a first detectable signal prior to cleavage by the effector protein and a second detectable signal after cleavage by the effector protein.

In some embodiments, a detectable signal is produced when the labeled detector RNA is cleaved by the effector protein.

In some embodiments, the labeled detector RNA comprises a modified nucleobase, a modified sugar moiety, a modified nucleic acid linkage, or a combination thereof.

In one aspect, the disclosure relates to engineered, non-naturally occurring Clustered Regularly Interspaced Short Palindromic Repeat (CRISPR)-associated (Cas) systems that include: an RNA guide or a nucleic acid encoding the RNA guide, wherein the RNA guide comprises a direct repeat sequence and a spacer sequence capable of hybridizing to a target nucleic acid, wherein the direct repeat sequence comprises 5'-X1X2X3X4TX5TX6AAAC-3' (SEQ ID NO: 151) at the 3' terminal end of the RNA guide, and wherein X1 is A or C or G, X2 is G or T, X3 is A or G, X4 is C or G or T, X5 is C or T, and X6 is A or G; and a Type VI-D CRISPR-Cas effector protein or a nucleic acid encoding the effector protein, wherein the effector protein is capable of binding to the RNA guide and of targeting the target nucleic acid sequence complementary to the spacer sequence, and wherein the target nucleic acid is an RNA.

In some embodiments of these systems, the Type VI-D CRISPR-Cas effector proteins include at least two HEPN domains. In some embodiments, the Type VI-D CRISPR-Cas effector proteins include an amino acid sequence having at least 90% identity to an amino acid sequence selected from the group consisting of SEQ ID NO: 12, SEQ ID NO: 1, and SEQ ID NO: 10. In other embodiments, the Type VI-D CRISPR-Cas effector proteins include an amino acid sequence having at least 95% sequence identity to an amino acid sequence provided in Table 2, or they can include an amino acid sequence provided in Table 2.

In various embodiments, the direct repeat sequence can include a nucleotide sequence provided in Table 3.

In some embodiments, the targeting of the target nucleic acid results in a modification of the target nucleic acid. For example, the modification of the target nucleic acid can be a cleavage event.

In the new systems, the Type VI-D CRISPR-Cas effector proteins can include one or more amino acid substitutions within at least one of the HEPN domains resulting in a reduction of an RNAse activity of the Type VI-D CRISPR-Cas effector protein, as compared to the RNAse activity of the Type VI-D CRISPR-Cas effector protein without the one or more amino acid substitutions, e.g., 2, 3, 4, 5, 6, 7, or 8 amino acid substitutions. In some embodiments, the one or more amino acid substitutions include an alanine substitution at an amino acid residue corresponding to R295, H300, R849, or H854 of SEQ ID NO: 1, or R288, H293, R820, or H825 of SEQ ID NO: 2.

In some embodiments, the Type VI-D CRISPR-Cas effector protein is fused to a base-editing domain, e.g., to an RNA methyltransferase, a RNA demethylase, a splicing modifier, a localization factor, or a translation modification factor.

In various embodiments, the Type VI-D CRISPR-Cas effector protein includes at least one nuclear localization signal (NLS), at least one nuclear export signal (NES), or both. In some embodiments, the direct repeat sequence includes either 5'-CACCCGTGCAAAAT-TGCAGGGGTCTAAAAC-3' (SEQ ID NO: 152) or 5'-CACTGGTGCAAATTTGCACTAGTCTAAAAC-3' (SEQ ID NO: 153). In some embodiments, the spacer consists of from about 15 to about 42 nucleotides.

In another aspect of the disclosure, the systems include the nucleic acid encoding the Type VI-D CRISPR-Cas effector protein, operably linked to a promoter. For example, the promoter can be a constitutive promoter.

In some embodiments, the nucleic acid encoding the Type VI-D CRISPR-Cas effector protein is codon-optimized for expression in a cell. In various embodiments, the nucleic acids encoding the Type VI-D CRISPR-Cas effector protein are operably linked to a promoter within in a vector, e.g., selected from the group consisting of a retroviral vector, a lentiviral vector, a phage vector, an adenoviral vector, an adeno-associated vector, and a herpes simplex vector.

In another aspect, the system is present in a delivery system selected from the group consisting of a nanoparticle, a liposome, an exosome, a microvesicle, and a gene-gun.

In some embodiments, the systems can further include a target RNA or a nucleic acid encoding the target RNA, wherein the target RNA comprises a sequence that is capable of hybridizing to the spacer sequence of the RNA guide.

In another aspect, the disclosure includes one or more cells that include the systems described herein.

In another aspect, the disclosure provides methods of cleaving a target nucleic acid. The methods include contacting the target nucleic acid with a system as described herein; wherein the spacer sequence is complementary to at least 15 nucleotides of the target nucleic acid; wherein the Type VI-D CRISPR-Cas effector protein associates with the RNA guide to form a complex; wherein the complex binds to a target nucleic acid sequence that is complementary to the at least 15 nucleotides of the spacer sequence; and wherein upon binding of the complex to the target nucleic acid sequence, the Type VI-D CRISPR-Cas effector protein cleaves the target nucleic acid.

In another aspect, the disclosure provides methods of inducing dormancy or death of a cell, the method comprising contacting the cell with a system as described herein; wherein the spacer sequence is complementary to at least 15 nucleotides of the target nucleic acid within the cell; wherein the Type VI-D CRISPR-Cas effector protein associates with the RNA guide to form a complex; wherein the complex binds to the target nucleic acid sequence that is complementary to the at least 15 nucleotides of the spacer sequence; and wherein after binding of the complex to the target nucleic acid sequence, the Type VI-D CRISPR-Cas effector protein cleaves a non-target nucleic acid within the cell, thereby inducing dormancy or death of the cell.

In these methods, the cell can be a bacterial cell, a cell infected with a virus, a cell infected with a prion, a fungal cell, a protozoan, or a parasite cell.

In other embodiments, the disclosure provides methods of modifying a target nucleic acid in a sample, in which the methods include contacting the sample with a system as described herein, e.g., with fusion proteins; wherein the spacer sequence is complementary to at least 15 nucleotides of the target nucleic acid within the sample; wherein the Type VI-D CRISPR-Cas effector protein fused to the base editing domain associates with the RNA guide to form a complex; wherein the complex binds to the target nucleic acid sequence that is complementary to the at least 15 nucleotides of the spacer sequence; and wherein after binding of the complex to the target nucleic acid sequence, the Type VI-D CRISPR-Cas effector protein fused to the base-editing domain modifies at least one nucleobase of the target nucleic acid.

In another aspect, the disclosure provides methods of detecting a single-stranded target RNA in a sample. These methods include: a) contacting the sample with: (i) a RNA guide or a nucleic acid encoding the RNA guide, wherein the RNA guide comprises a direct repeat sequence and a spacer sequence capable of hybridizing to the target RNA; (ii) a Type VI-D CRISPR-Cas effector protein or a nucleic acid encoding the effector protein; and (iii) a labeled detector RNA; wherein the effector protein associates with the RNA guide to form a complex; wherein the RNA guide hybridizes to the target RNA; and wherein upon binding of the complex to the target RNA, the Type VI-D CRISPR-Cas effector protein exhibits collateral RNAse activity and cleaves the labeled detector RNA; and b) measuring a detectable signal produced by cleavage of the labeled detector RNA, wherein said measuring provides for detection of the single-stranded target RNA in the sample.

In these methods, the effector protein includes an amino acid sequence having at least 90% sequence identity to an amino acid sequence provided in Table 2. These methods can further include comparing the detectable signal with a reference signal and determining the amount of target RNA in the sample.

The term "cleavage event," as used herein, refers to a break in a target nucleic acid created by a nuclease (e.g., a Type VI-D CRISPR-Cas effector protein) of a CRISPR system described herein. In some embodiments, the cleavage event is a single-stranded RNA break. In some embodiments, the cleavage event is a double-stranded RNA break. In some embodiments, the cleavage event is a double-stranded DNA break. In some embodiments, the cleavage event is a single-stranded DNA break.

The term "CRISPR system" or "Clustered Interspaced Short Palindromic Repeat (CRISPR)-associated (Cas) system" as used herein refers to nucleic acids and/or proteins involved in the expression of, or directing the activity of, CRISPR-effectors, including sequences encoding CRISPR effectors, RNA guides, and other sequences and transcripts from a CRISPR locus. In some embodiments, the CRISPR system is an engineered, non-naturally occurring CRISPR system. In some embodiments, the components of a CRISPR system may include a nucleic acid(s) (e.g., a vector) encoding one or more components of the system, a component(s) in protein form, or a combination thereof.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The terms "CRISPR repeat," or "CRISPR direct repeat," or "direct repeat," as used herein, refer to multiple short direct repeating sequences, which show very little or no sequence variation within a CRISPR array.

The term "CRISPR RNA" or "crRNA" as used herein refers to a RNA molecule comprising a guide sequence used by a CRISPR effector to target a specific nucleic acid sequence. Typically, crRNAs contains a sequence that mediates target recognition and a sequence that forms a duplex with a tracrRNA. In some embodiments, the crRNA:tracrRNA duplex binds to a CRISPR effector.

The term "donor template nucleic acid," as used herein refers to a nucleic acid molecule that can be used by one or more cellular proteins to modify the sequence of a target nucleic acid after a CRISPR-associated protein described herein has altered the target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome). In some embodiments the donor template is a DNA molecule. In some embodiments, the donor template is an RNA molecule.

The term "CRISPR effector," "effector," "CRISPR-associated protein," or "CRISPR enzyme" as used herein refers to a protein that carries out an enzymatic activity or that binds to a target site on a nucleic acid specified by a RNA guide. In some embodiments, a CRISPR effector has endonuclease activity, nickase activity, exonuclease activity, transposase activity, and/or excision activity. In some embodiments, the CRISPR-associated protein is a Type VI Cas protein, a Type V Cas protein, or a Type II Cas protein. In some embodiments, the CRISPR-associated protein is a Cas13a protein, a Cas13b protein, a Cas13c protein, a Cas13d protein, or a Cas12a protein, or a Cas9 protein. In some embodiments, the CRISPR-associated protein is a Type VI-D CRISPR-Cas effector protein described herein.

The term "guide RNA" or "gRNA" as used herein refers to a RNA molecule capable of directing a CRISPR effector having nuclease activity to target and cleave a specified target nucleic acid.

The term "RNA guide" as used herein refers to any RNA molecule that facilitates the targeting of a protein described herein to a target nucleic acid. Exemplary "RNA guides" include, but are not limited to, tracrRNAs and crRNAs. In some embodiments the RNA guide is an engineered RNA guide.

The term "origin of replication," as used herein, refers to a nucleic acid sequence in a replicating nucleic acid molecule (e.g., a plasmid or a chromosome) that is recognized by a replication initiation factor or a DNA replicase.

As used herein, the term "targeting" refers to the ability of a complex comprising a CRISPR-associated protein and a RNA guide such as crRNA to bind to a specific target nucleic acid and not to other nucleic acids that do not have the same sequence as the target nucleic acid.

As used herein, the term "target nucleic acid" refers to a specific nucleic acid sequence that is to be targeted by a CRISPR system described herein. In some embodiments, the target nucleic acid comprises a gene. In some embodiments, the target nucleic acid comprises a non-coding region (e.g., a promoter). In some embodiments, the target nucleic acid is single-stranded. In some embodiments, the target nucleic acid is double-stranded.

The terms "trans-activating crRNA" or "tracrRNA" as used herein refer to a RNA including a sequence that forms a structure required for a CRISPR-associated protein to bind to a specified target nucleic acid.

The term "collateral RNAse activity," as used herein in reference to a CRISPR-associated protein, refers to non-specific RNAse activity of a CRISPR-associated protein after the enzyme has bound to and/or modified a specifically-targeted nucleic acid. In some embodiments, a CRISPR-associated protein (e.g., a Type VI-D CRISPR-Cas effector protein) exhibits collateral RNAse activity after binding to a target nucleic acid (e.g., a target RNA). A nucleic acid that is cleaved or degraded by a CRISPR-associated protein in a non-specific manner (i.e., when the protein exhibits collateral RNAse activity) is referred to herein as a "non-target nucleic acid."

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Citation or identification of any document in this application is not an admission that such document is available as prior art to the present invention.

Other features and advantages of the invention will be apparent from the following detailed description, and from the claims.

BRIEF FIGURE DESCRIPTION

The patent or application file contains at least one drawing executed in color. Copies of this patent or patent application publication with color drawing(s) will be provided by the Office upon request and payment of the necessary fee.

FIG. 1 depicts a schematic representation of a maximum likelihood tree topology for an exemplary subset of Cas13d, with the genomic arrangement of the genes encoding predicted protein components of Type VI-D system components shown to the right. Each locus sequence is identified by a protein accession or gene number, with the species name provided where available. Key proteins and CRISPR arrays are color-coded as follows: blue—Cas13d, light orange—WYL domain containing protein, light blue—Cas1, green—Cas2, dark gray/gray—CRISPR array.

FIG. 2A depicts a schematic tree comparing the different type VI subtype locus structures. Gene arrows are shown roughly proportional to size. Labels denote the following, HTH—helix-turn-helix domain, WYL—WYL domain, HEPN—HEPN nuclease domain, TM—transmembrane domains of Csx27-28. Key proteins and CRISPR arrays are color-coded as follows: blue—Cas13d, gray—Csx accessory proteins (differentiated by colored domains), light blue—Cas1, green—Cas2, dark gray/gray—CRISPR array.

FIG. 2B depicts a size comparison for Cas13 proteins from the 4 type VI subtypes; error bars specify the mean and standard deviation.

FIG. 3 depicts a phylogenetic tree of Cas1 proteins from type II and type VI CRISPR-Cas systems. The tree was constructed for a non-redundant set of Cas1 proteins associated with Cas13d and type II and type VI CRISPR-Cas systems as described previously (see (Peters et al., 2017)). Several Cas1 proteins associated with subtype I-E systems were selected for an outgroup. Each sequence is denoted by a local numeric identifier, CRISPR-Cas type and species name (if available). Cas1 proteins associated with Cas13d are denoted by blue, and those associated with Cas13a by purple. Several branches were collapsed and are shown by triangles with CRISPR-Cas system indicated on the right. Support values are indicated for each branch, and the support value for Cas13d is shown in red.

FIGS. 4A and 4B depict a phylogenetic tree constructed for a combined set of Cas13d sequences described (blue) and previously described Cas13a sequences. Each sequence is denoted by a protein locus tag and species name (if available). Bootstrap support values (percentage points) are shown for each internal branch. Cas13d proteins form a clade with a 100% support (shown in red).

FIGS. 5A, 5B and 5C depict a multiple sequence alignment of Cas13d protein sequences (RspCas13d (SEQ ID NO: 2) and EsCas13d (SEQ ID NO: 1) and Cas13a protein sequences (LbaCas13a (SEQ ID NO: 156), LbuCas13a (SEQ ID NO: 157), LshCas13a (SEQ ID NO: 158)). Conserved amino acid residues are highlighted as follows: yellow, hydrophobic (CVILPFYMW (SEQ ID NO: 159)); green, small non-polar (GAST); blue, polar (NQH); black, negatively charged (DE); red, positively charged (KR). Previously identified domains of Cas13a are highlighted in color (NTD, N-terminal domain). Note the nearly complete absence of a counterpart to the Helical-1 domain of Cas13a in Cas13d (the alignment in this region cannot be considered reliable).

FIG. 6 depicts a phylogenetic tree of the WYL1 protein family. Exemplary WYL1 proteins associated with Cas13d are denoted by blue. In cases when a CRISPR array and/or other cas genes are present in the vicinity of the respective WYL1 gene (within 10 kb up- and downstream), the description includes "CRISPR". Several branches were collapsed and are indicated by triangles. Domain organization is schematically shown next to each branch. Abbreviation: WYL—WYL domain (usually fused to a characteristic C-terminal subdomain); RHH—ribbon helix superfamily DNA binding domain.

FIG. 7 depicts a multiple sequence alignment of exemplary WYL1 protein sequences. The RHH domain is denoted by 'r' and the WYL domain fused to the characteristic C-terminal subdomain is denoted by 'y' underneath the alignment. The predicted secondary structure elements are shown (E, extended conformation (β-strand), H, α-helix).

Figure 10:
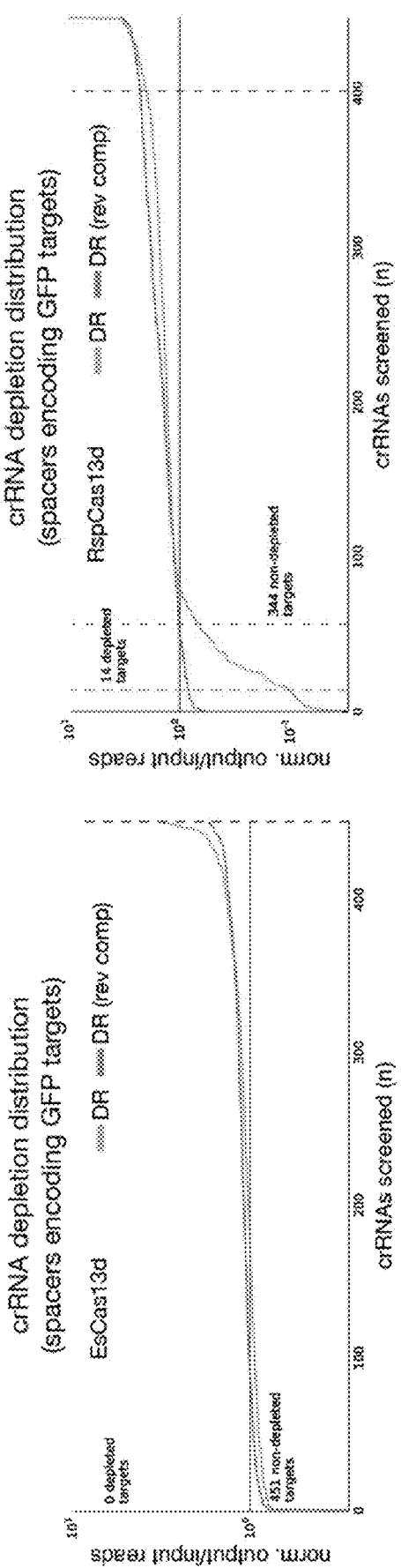

FIG. 10 depicts a negative control condition from bacterial screens for EsCas13d and RspCas13d systems. Blue and orange represent both possible direct repeat (DR) orientations cloned into the screening library. Non-targeting CRISPR arrays (with spacers matching a GFP open reading frame) inserted into EsCas13d and RspCas13d screening systems showed minimal levels of depletion in bacterial negative selection screens (no GFP open reading frame was included in our screen system).

Figure 11:
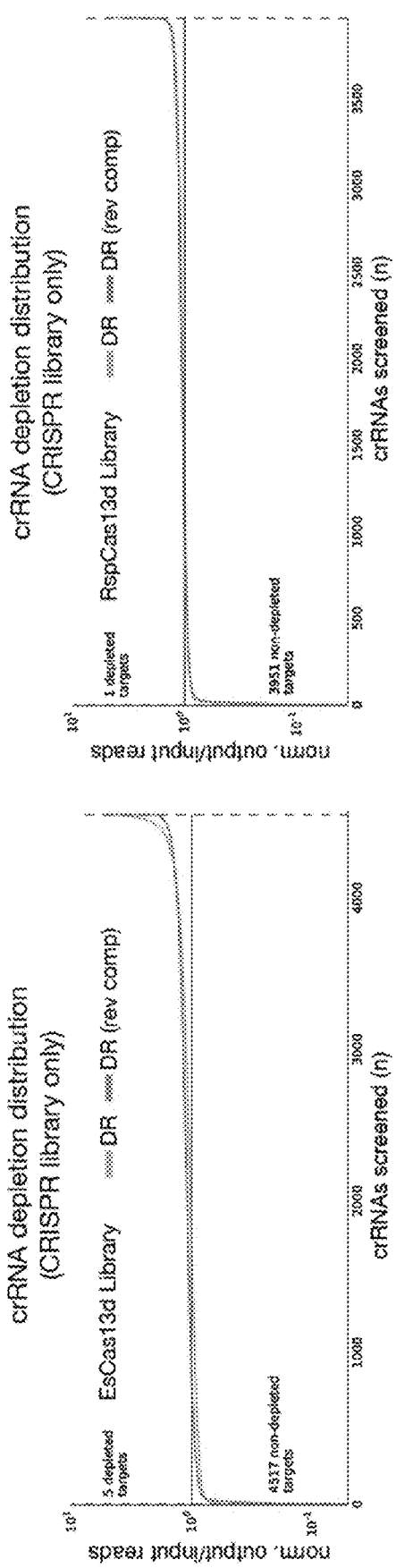

FIG. 11 depicts a negative control condition from bacterial screens for EsCas13d and RspCas13d systems. Deletion of EsCas13d and RspCas13d-RspWYL1 open reading frames from the EsCas13d and RspCas13d screening systems resulted in minimal depletion of library CRISPR array elements in bacterial negative selection screens.

Figure 12A:
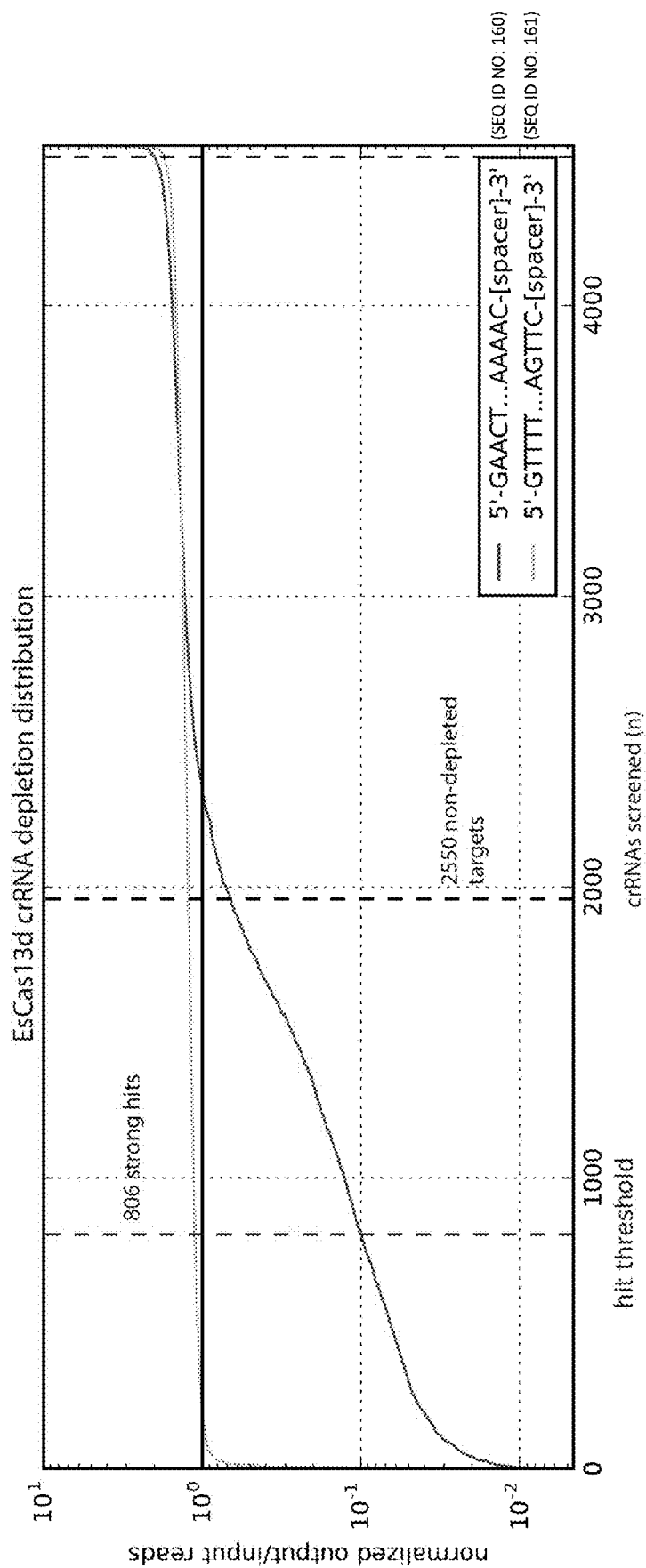
Figure 12B:
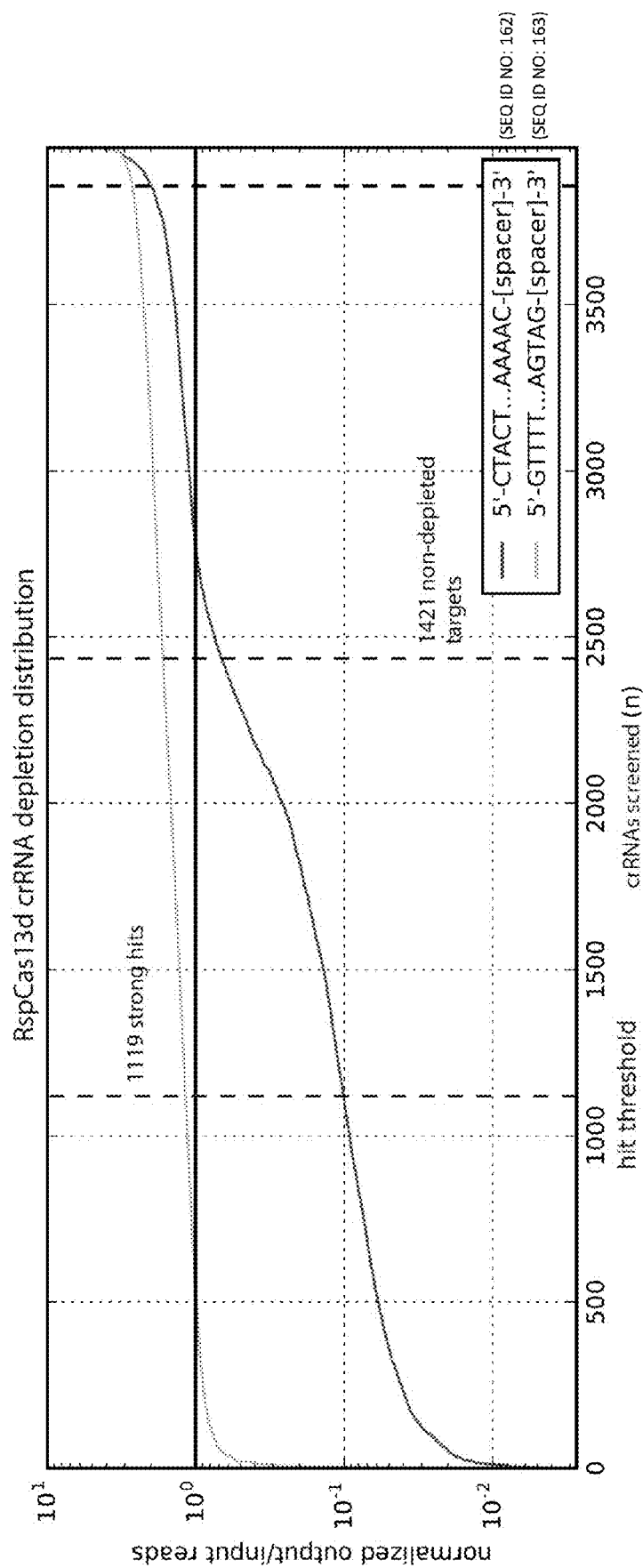

FIGS. 12A and 12B depict the distribution and magnitude of crRNA depletion from bacterial screens for EsCas13d and RspCas13d, respectively. Depletion value was calculated by normalized sequencing reads from the screen output divided by normalized reads from the pre-transformation screen input library for each crRNA spacer and orientation. Blue and orange represent both possible direct repeat (DR) orientations cloned into the screening library. The blue dashed lines demarcate the intersection of the ranked screen hits with the depletion fraction of 0.1, below which we define as strongly depleted.

Figure 13A:
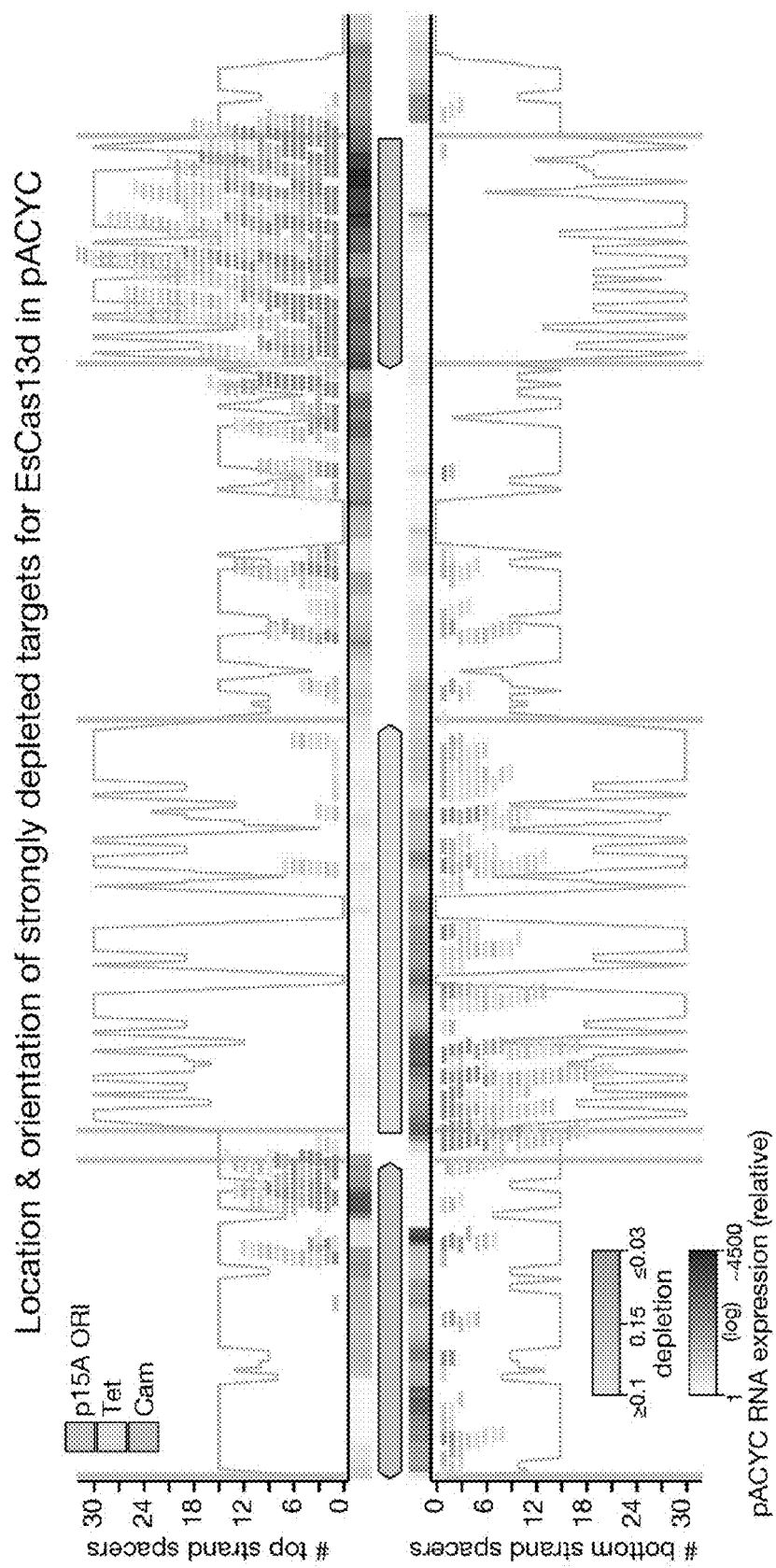
Figure 13B:
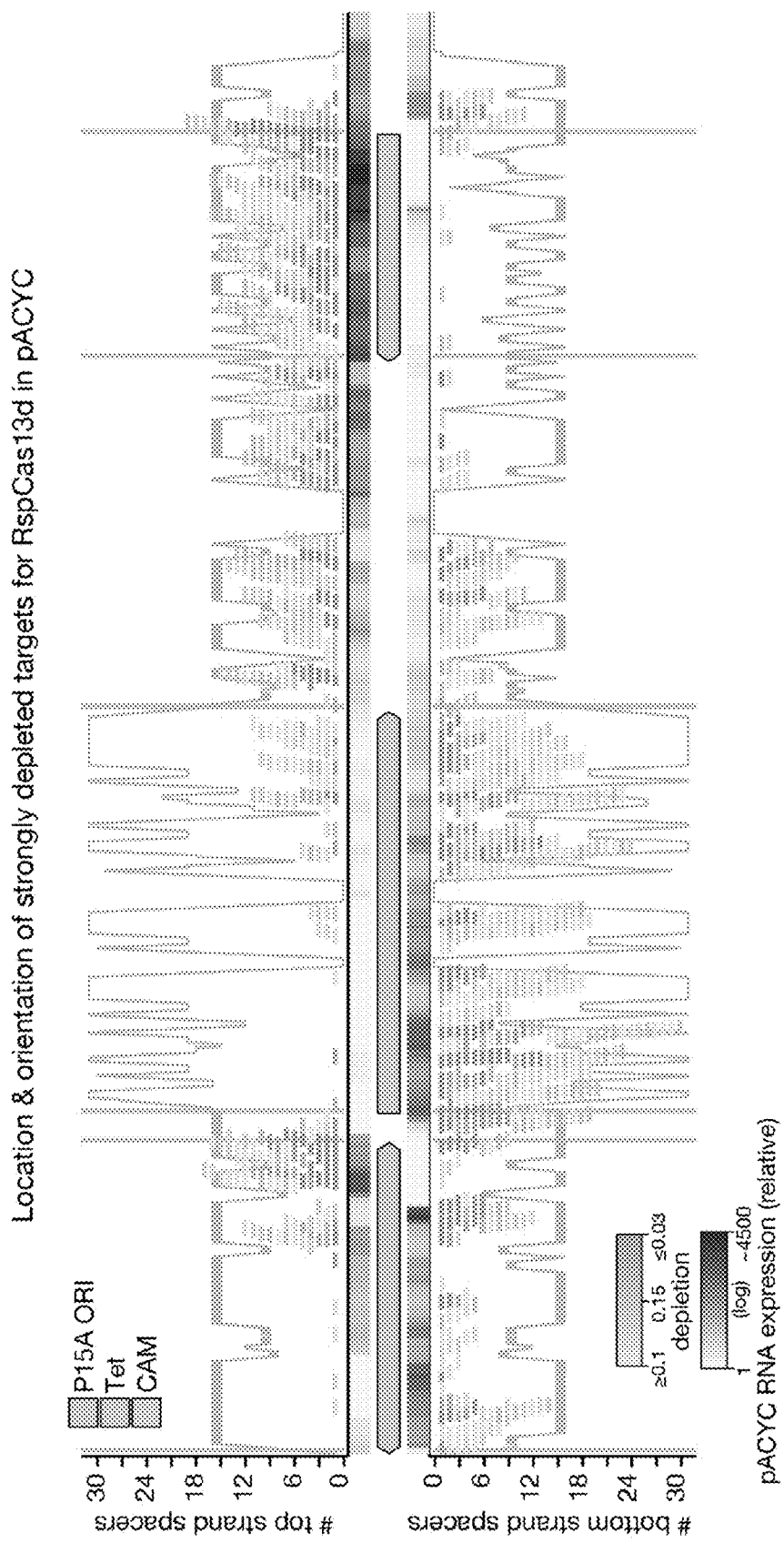

FIGS. 13A and 13B depict the location of strongly depleted targets of the active DR orientation over the strands and genetic features of the pACYC184 plasmid for EsCas13d and RspCas13d systems, respectively. Gray outlines represent the total number of spacers (y-axis) targeting a location, while red bars depict the locations of strongly depleted spacers with heatmap color proportional to magnitude of depletion. Directional expression data for pACYC184 is plotted as a heatmap in blue under the corresponding strand.

Figure 14A:
Figure 14B:

FIGS. 14A and 14B depict web logos for the 5' and 3' 30 nt regions flanking strongly depleted targets for EsCas13d and RspCas13d systems, and show no evidence of PFS or PAM requirements.

Figure 14C:
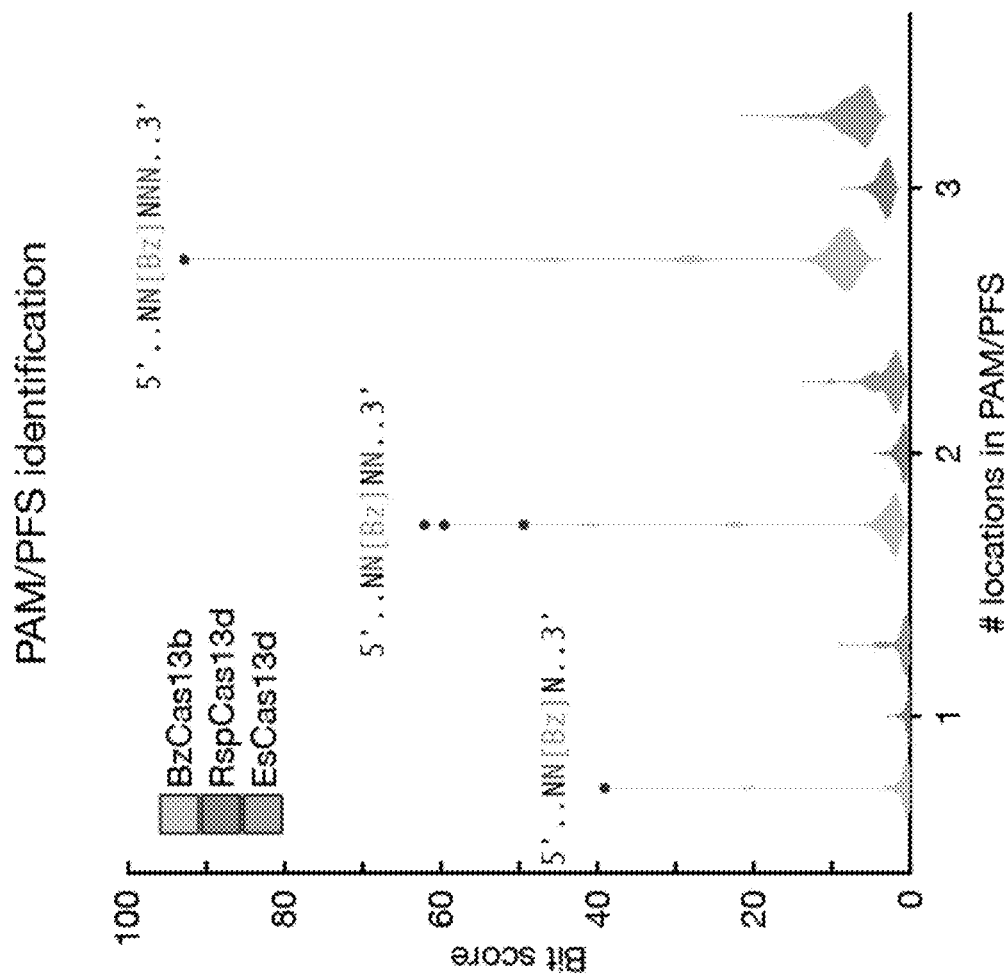

FIG. 14C depicts violin plots of bit scores of all possible PFS targeting rules of up to length 3 involving the target site and +/−15 nt flanking region, for BzCas13b, RspCas13d, and EsCas13d systems. Dots represent data points outside of the discernable density of the violin plot. These dots accurately recapitulate the known PFS positions of BzCas13b, as shown above the dots.

Figure 15:
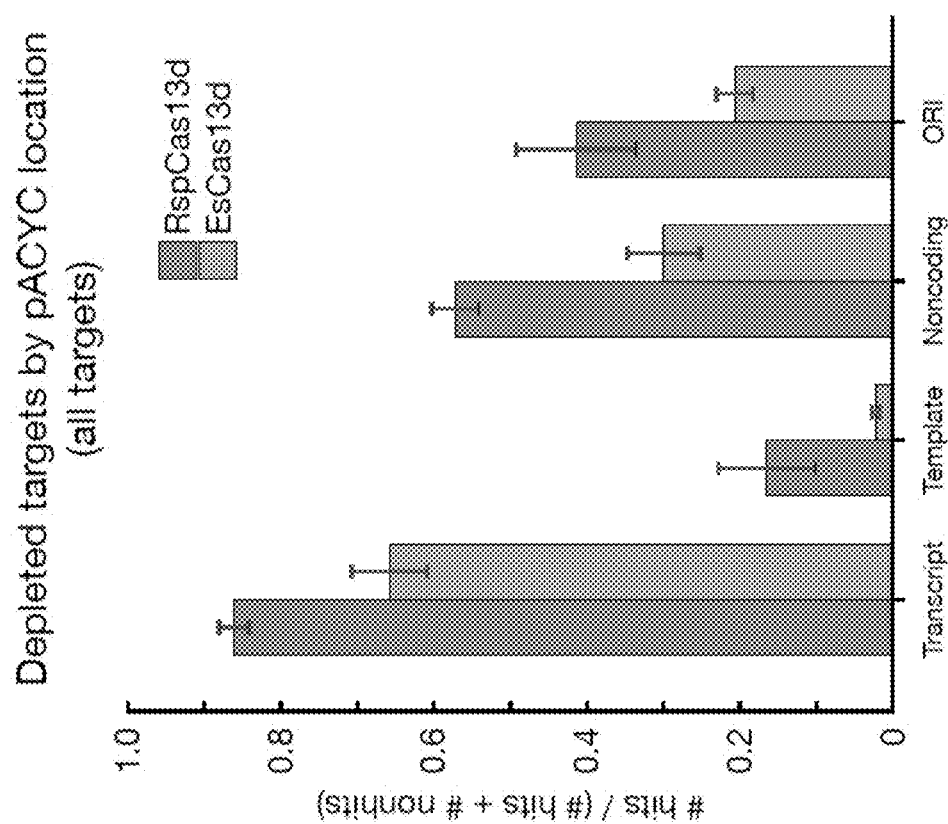

FIG. 15 depicts bar charts showing the fraction of hits for RspCas13d and EsCas13d systems according to features of the plasmid for all targets.

Figure 16A:
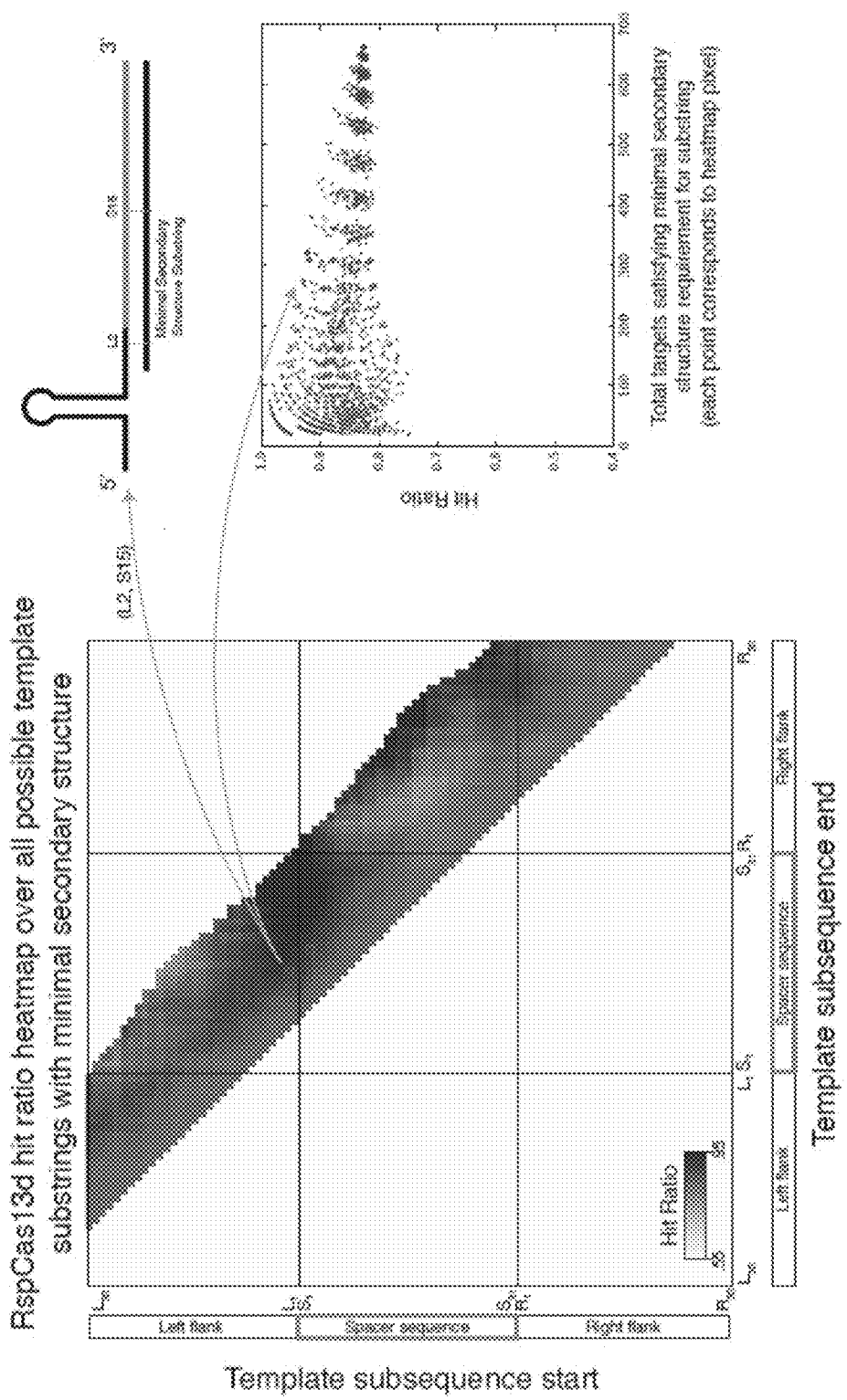
Figure 16B:
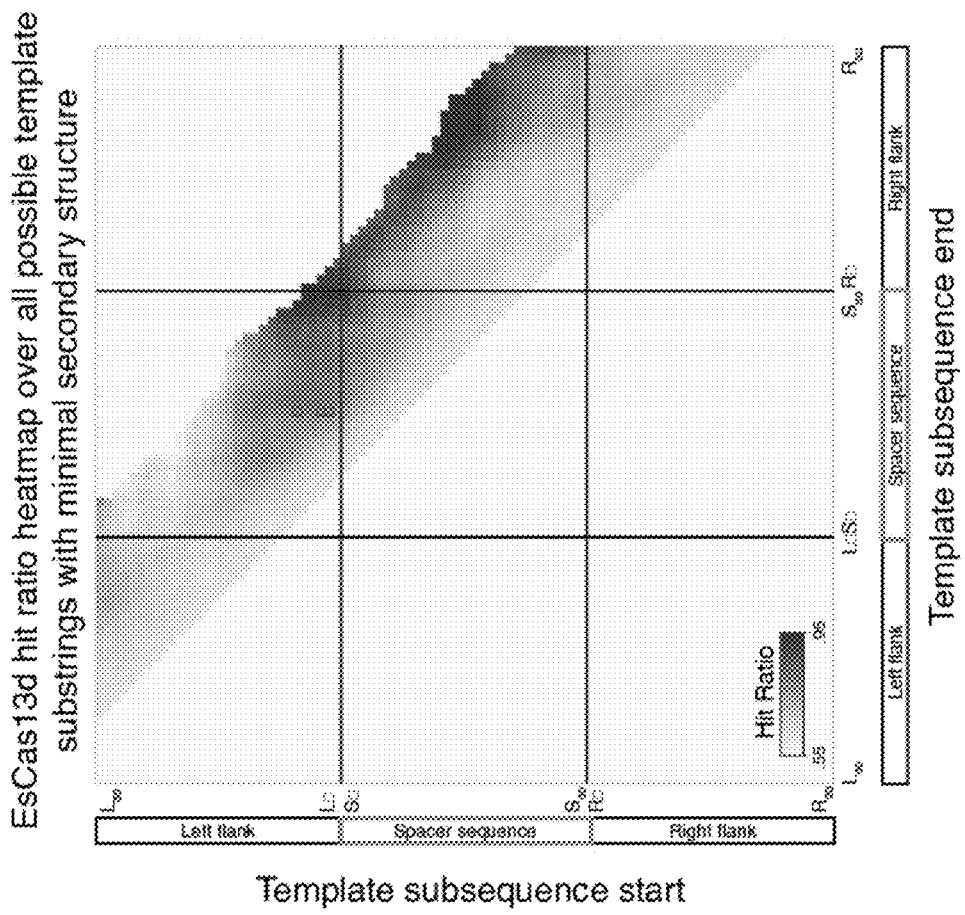

FIGS. 16A and 16B depict heatmaps of the fraction (#strongly depleted spacers)/(#strongly depleted spacers+ #non-depleted spacers) for all target regions (CRISPR arrays with active direct repeat orientation only) with no predicted secondary structure between specific start (x-axis) and end (y-axis) locations. Red boxes indicate specific target regions (bounded by start (x-axis) and end (y-axis) locations), where selection of spacers with no predicted secondary structure maximized targeting efficacy, while minimizing the number of screen spacers eliminated due to the presence of predicted secondary structure. Targets these spacer populations are referred to as "low secondary structure targets" for RspCas13d and EsCas13d respectively.

Figure 16C:
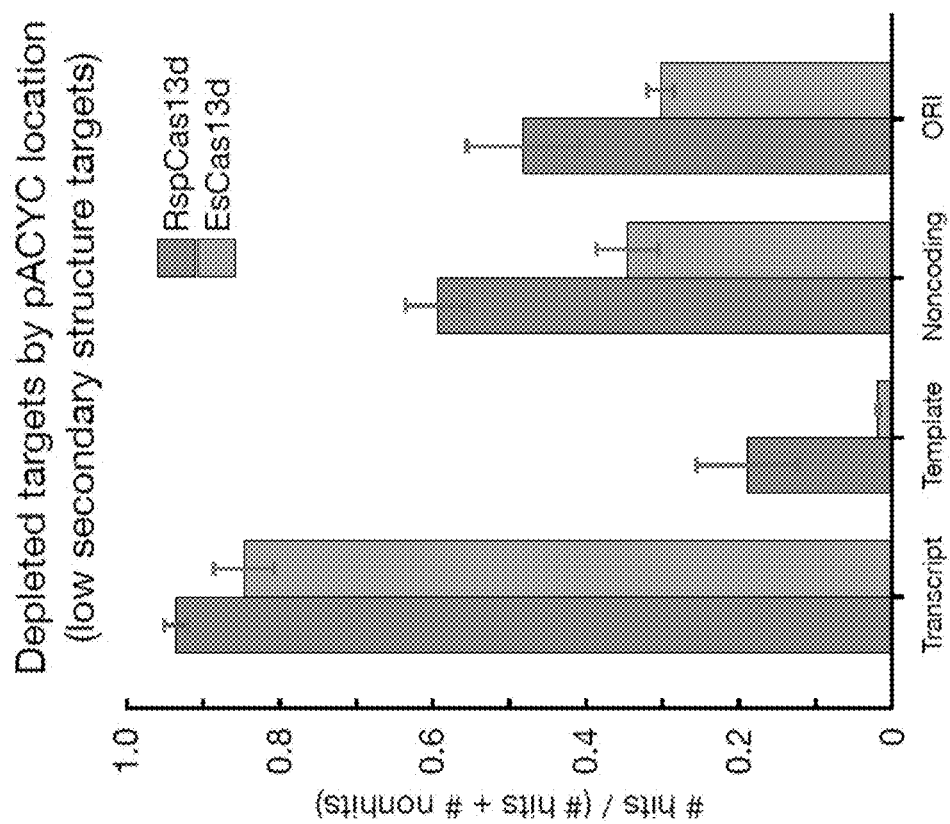

FIG. 16C depicts bar charts showing the fraction of hits for RspCas13d and EsCas13d systems according to features of the plasmid for low secondary structure targets.

Figure 17:
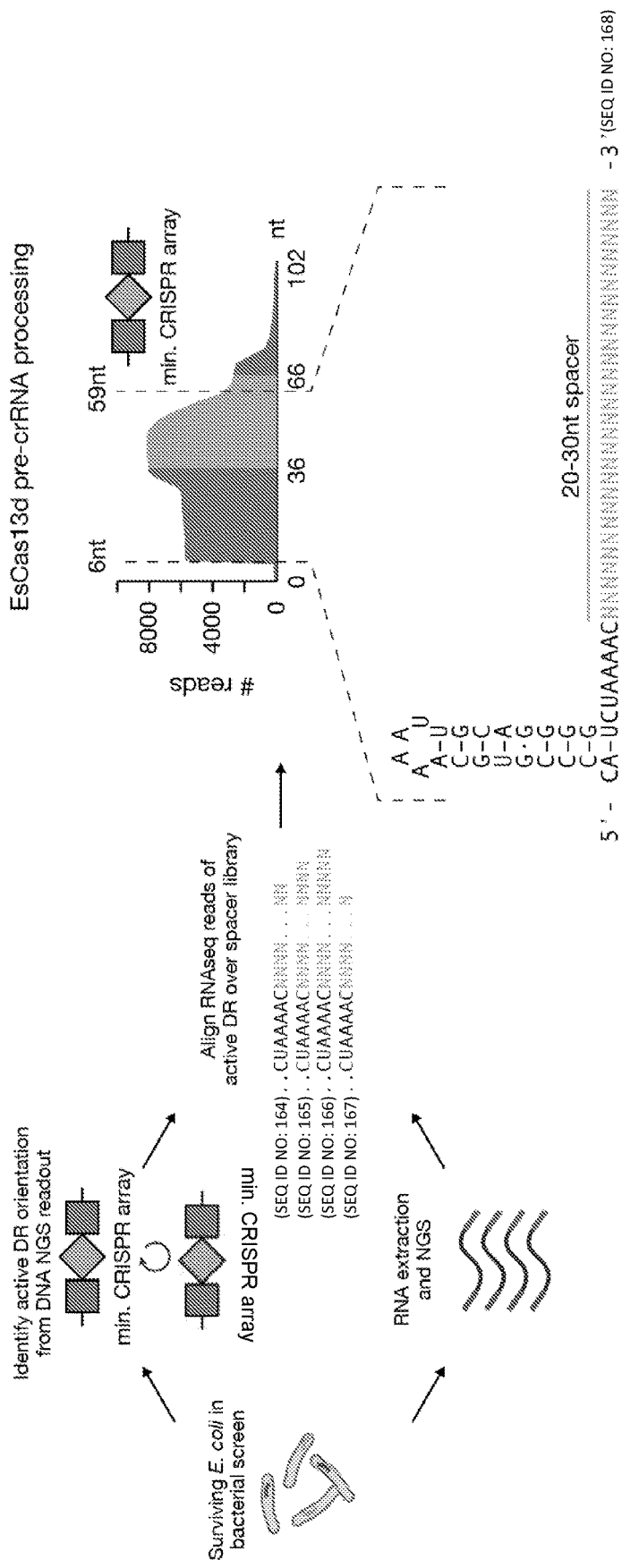

FIG. 17 depicts a schematic of the RNA extraction from bacterial screen, next-generation sequencing (NGS), and alignment to determine the mature crRNA for EsCas13d. Distribution of read counts by crRNA sequence location is depicted on the right, and the predicted EsCas13d mature crRNA secondary structure is shown.

Figure 18:
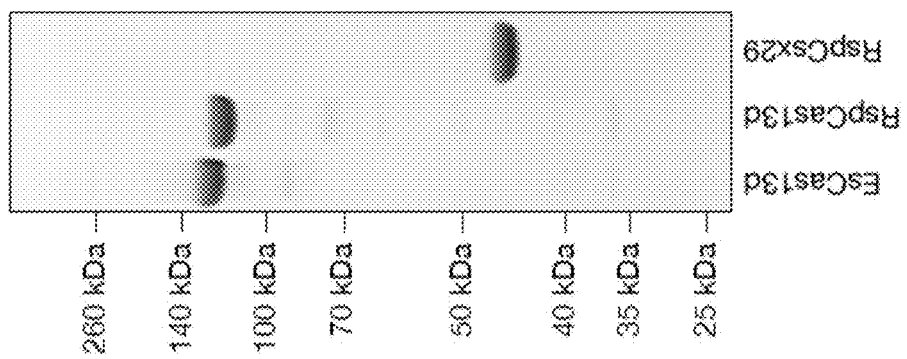

FIG. 18 depicts a coomassie blue stained polyacrylamide gel of purified recombinant proteins EsCas13d, RspCas13d, and RspWYL1 respectively.

Figure 19:
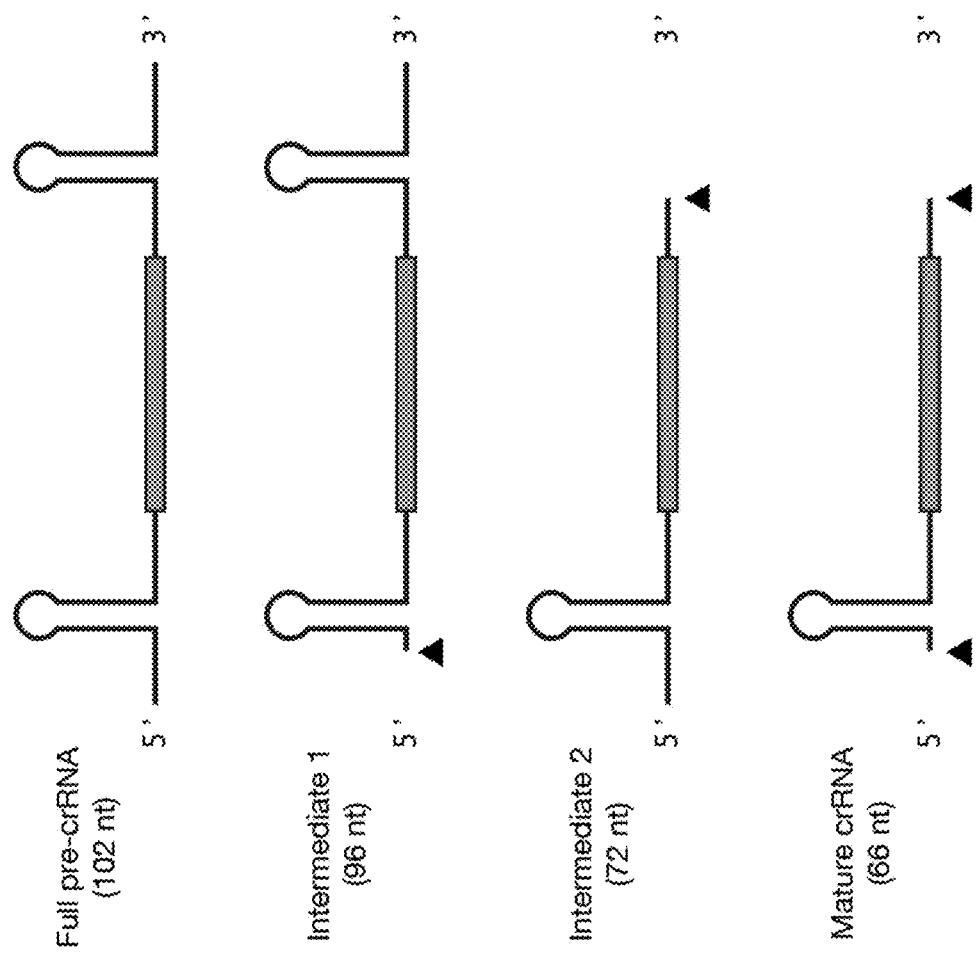
Figure 20A:
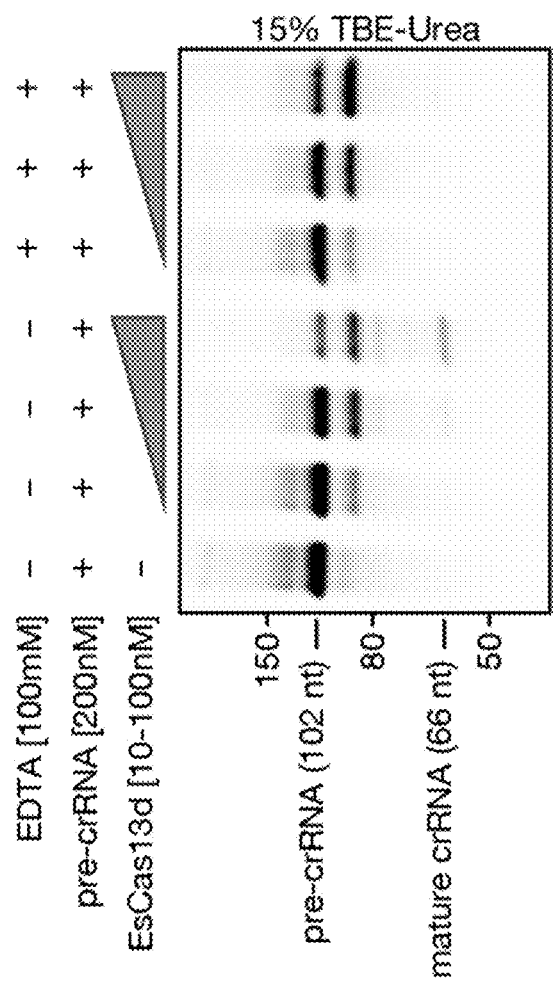
Figure 20B:
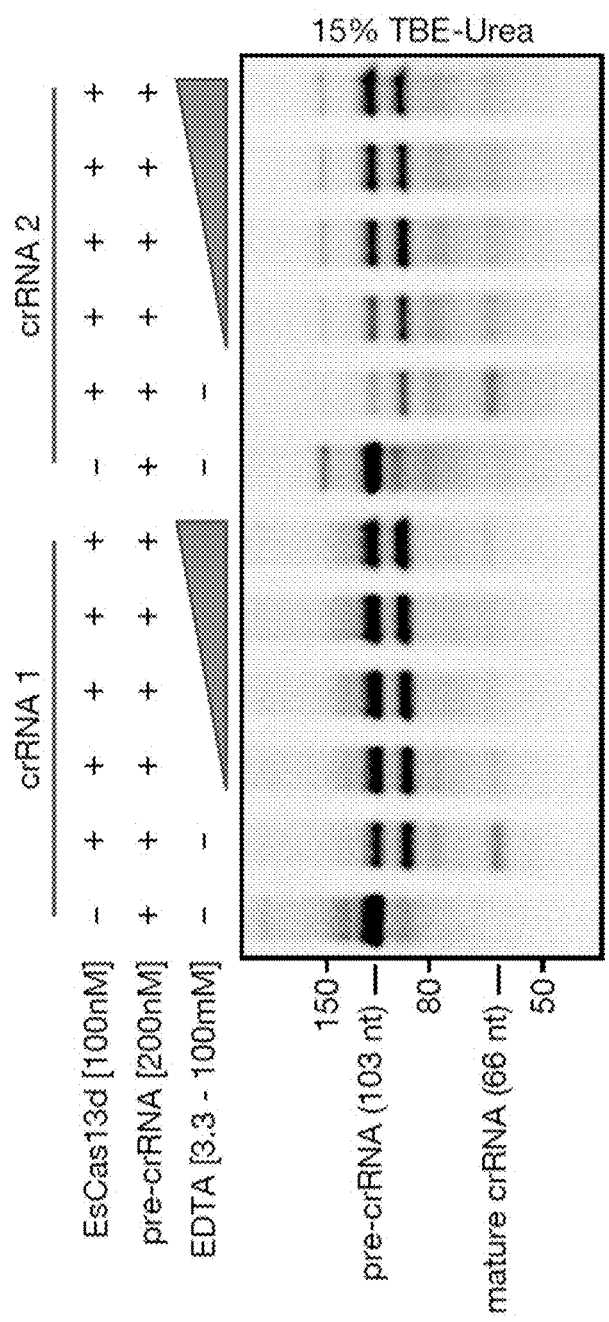
Figure 20C:
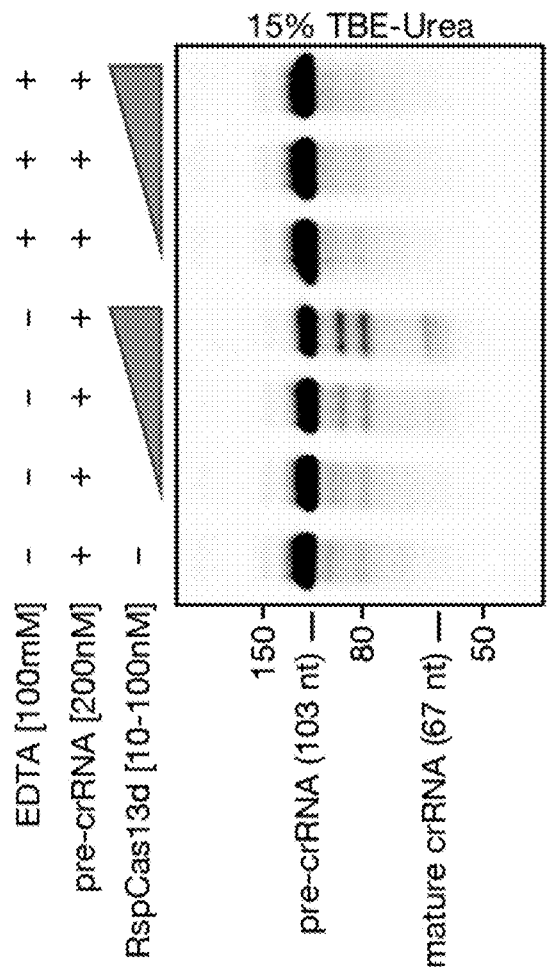
Figure 20D:
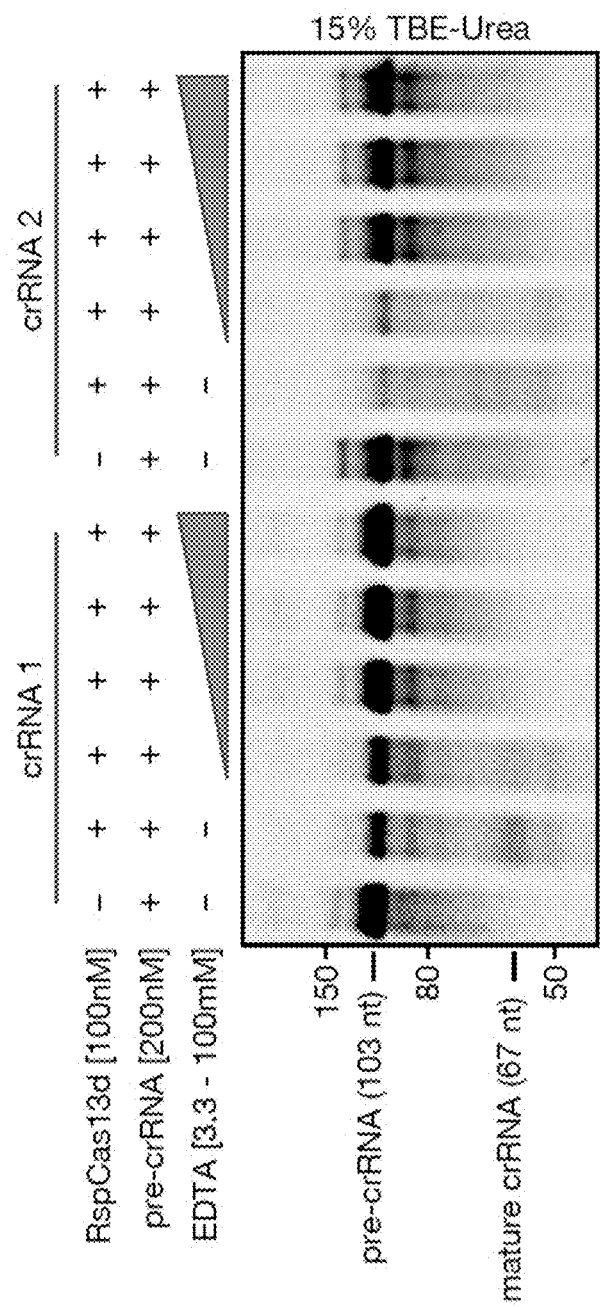

FIG. 19 depicts schematic representations of the major products identified from next-generation sequencing of in vitro cleaved RNA fragments from the pre-crRNA processing with EsCas13d and RspCas13d. The black line represents the direct repeats and associated secondary structure, blue box the full-length spacer, and filled triangle the cleavage sites. The lengths described are for processed EsCas13d crRNAs, with RspCas13d having one extra nucleotide due to the 31 nt natural length spacer used for instead of 30. Not depicted are the 3-4 nt at the 5' end of the pre-crRNA from T7 in vitro transcription.

FIGS. 20A, 20B, 20C, and 20D depict denaturing gels displaying Cas13d mediated cleavage of their cognate pre-crRNAs over a dose titration of effector concentration. The dependence of Cas13d crRNA biogenesis on divalent metal cations was evaluated with the introduction of 100 mM EDTA to the standard reaction conditions.

Figure 21:
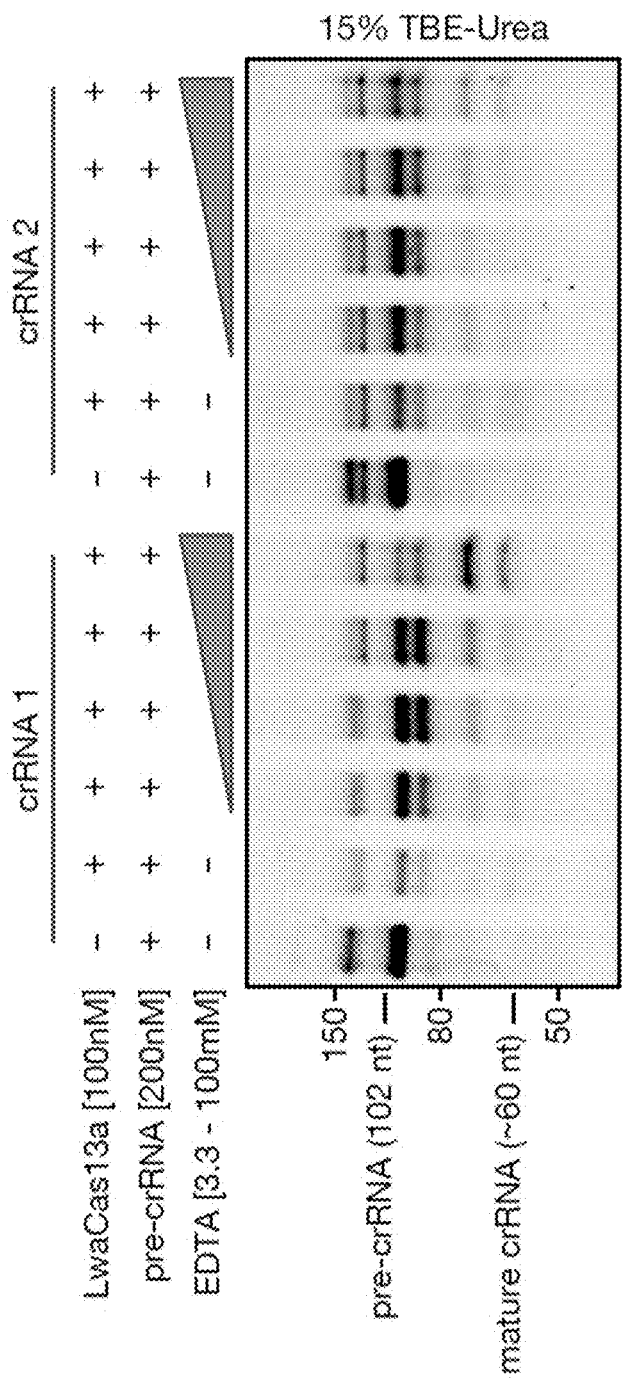

FIG. 21 depicts a denaturing gel displaying LwaCas13a at a final concentration of 100 nM processing of pre-crRNA (200 nM) without the presence of EDTA, and under reaction conditions supplemented with increasing concentrations of EDTA (3.3-100 mM).

Figure 22A:
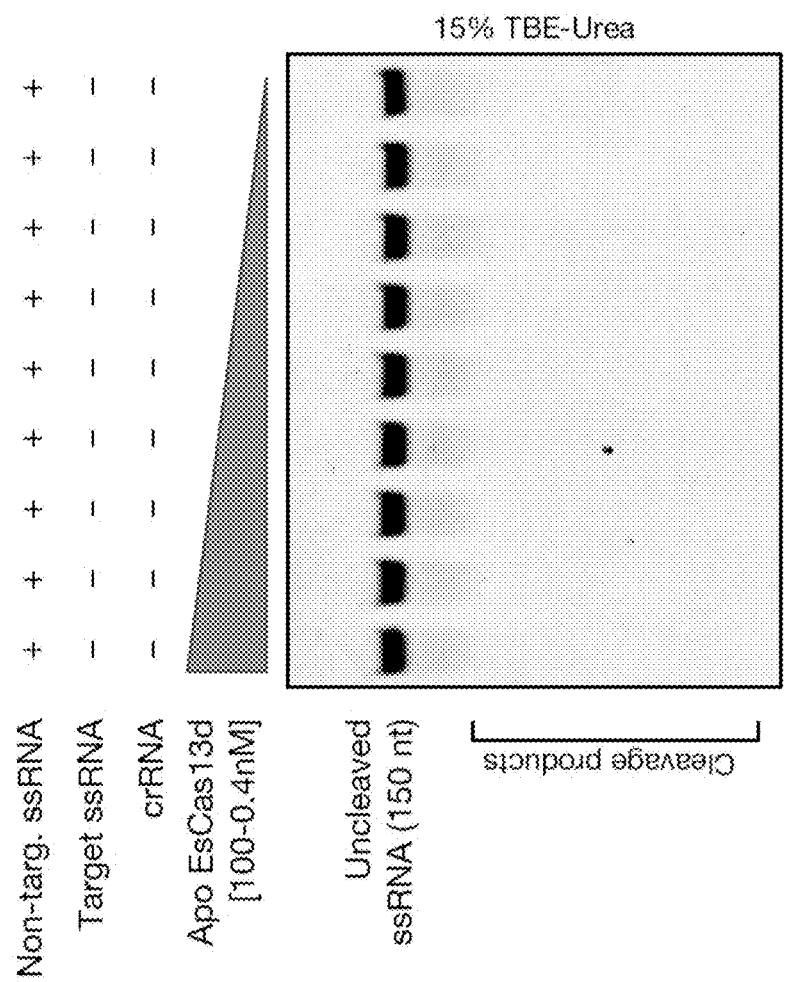
Figure 22B:
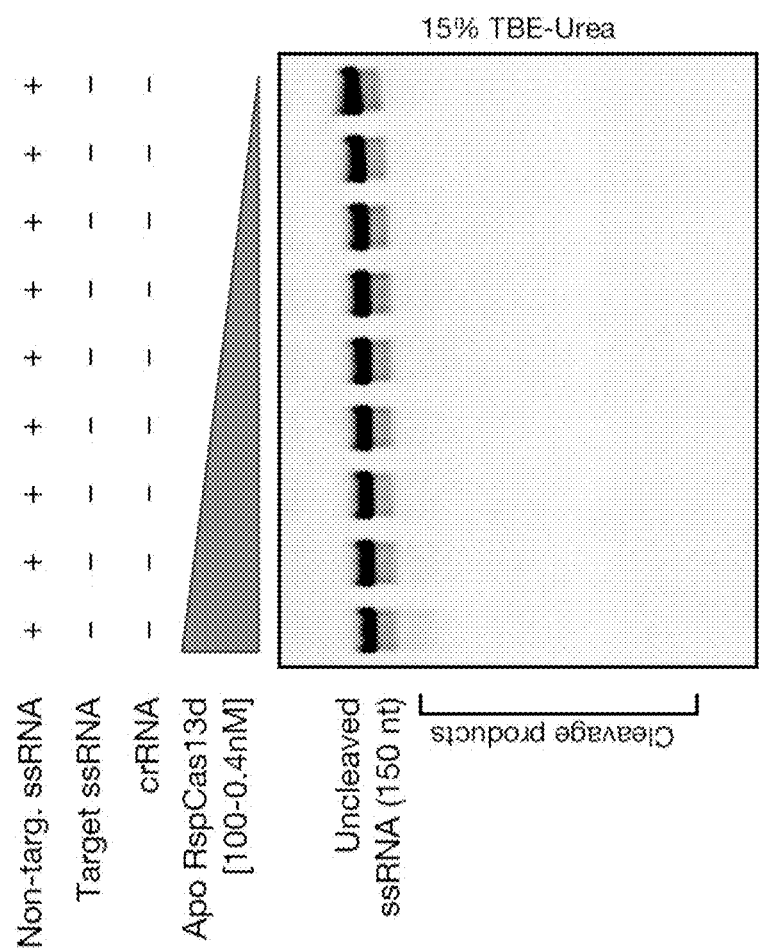

FIGS. 22A and 22B depict a titration of Apo EsCas13d and RspCas13d (100-0.4 nM) over a non-targeted ssDNA substrate (100 nM).

Figure 23A:
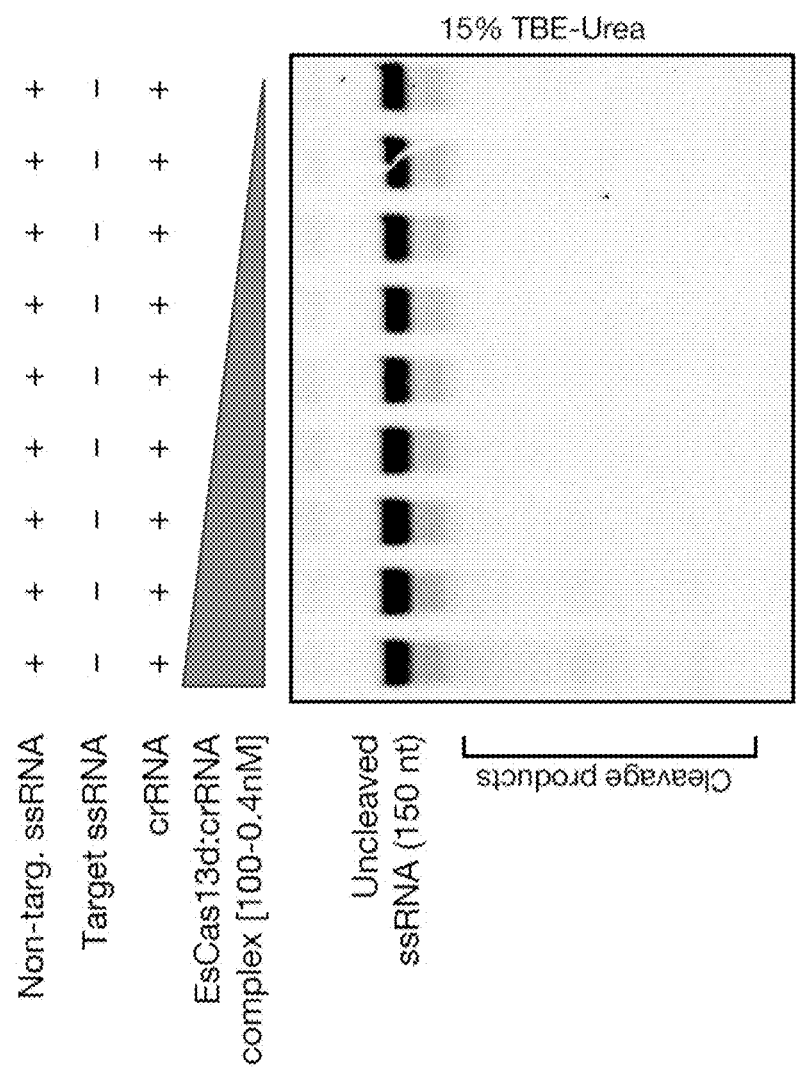
Figure 23B:
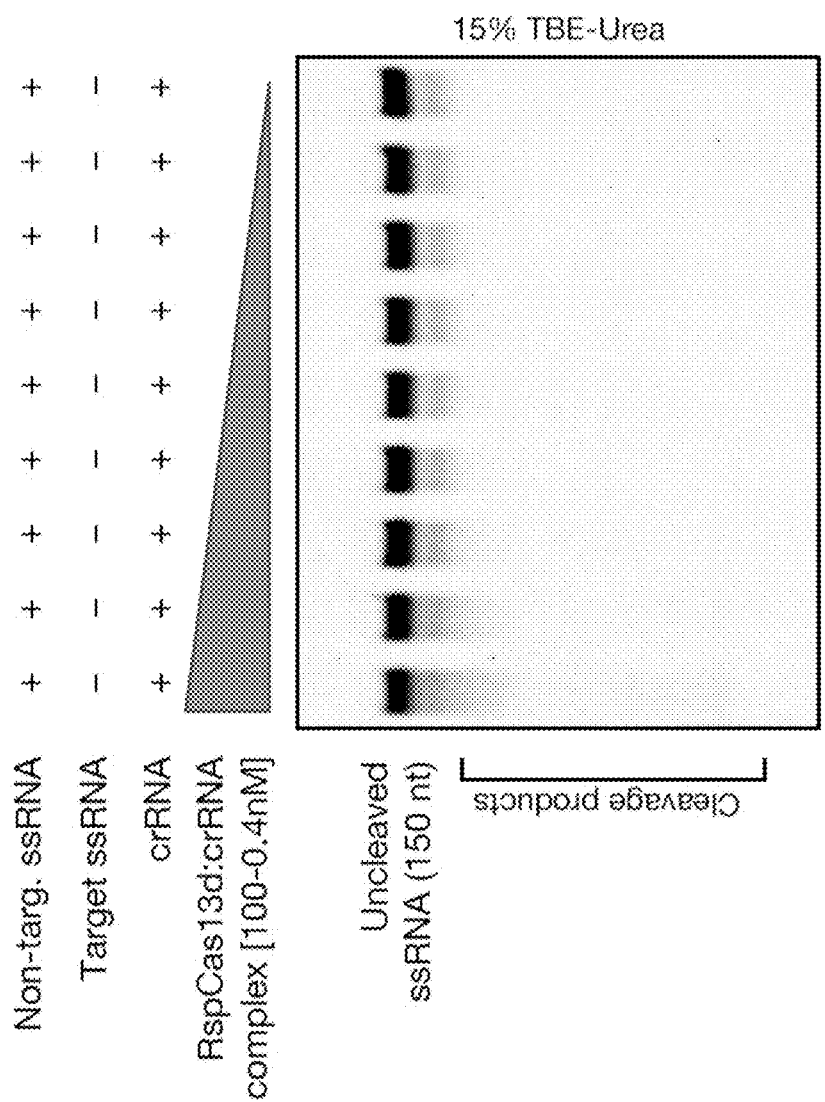

FIGS. 23A and 23B depict a titration of EsCas13d and RspCas13d in complex with crRNA (100-0.4 nM) over non-targeted ssDNA substrates (100 nM).

Figure 24A:
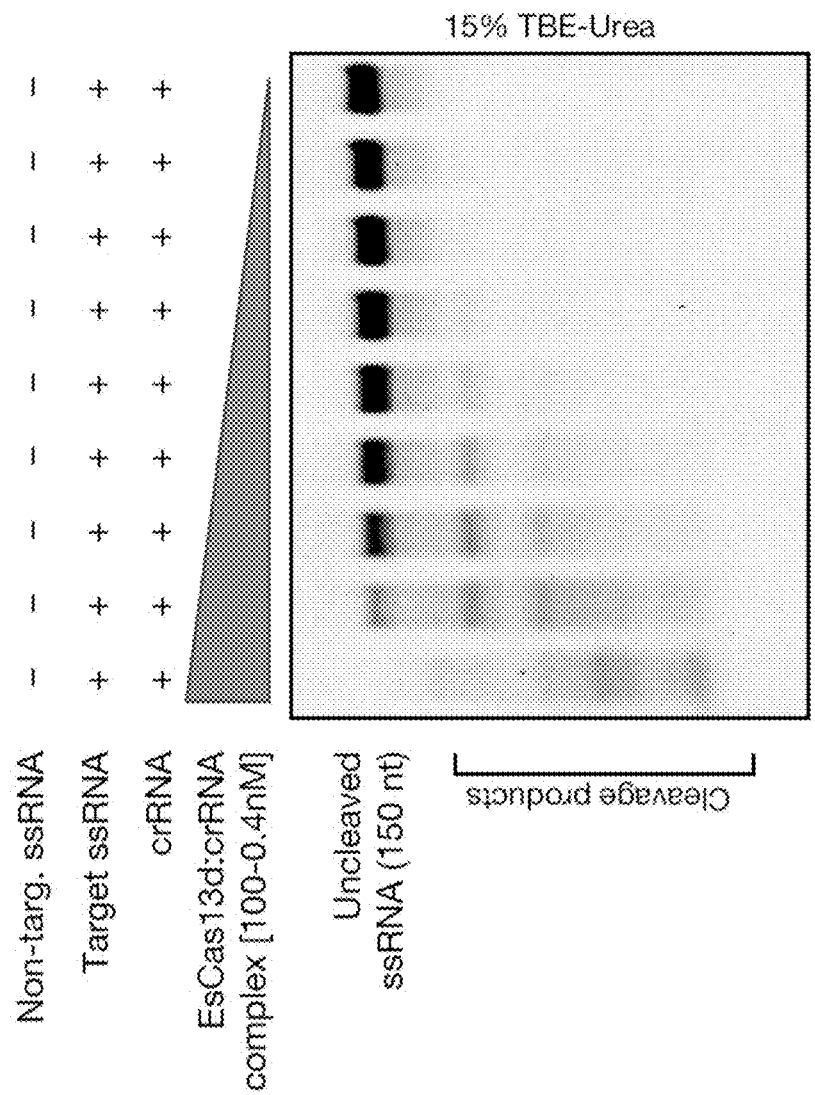
Figure 24B:
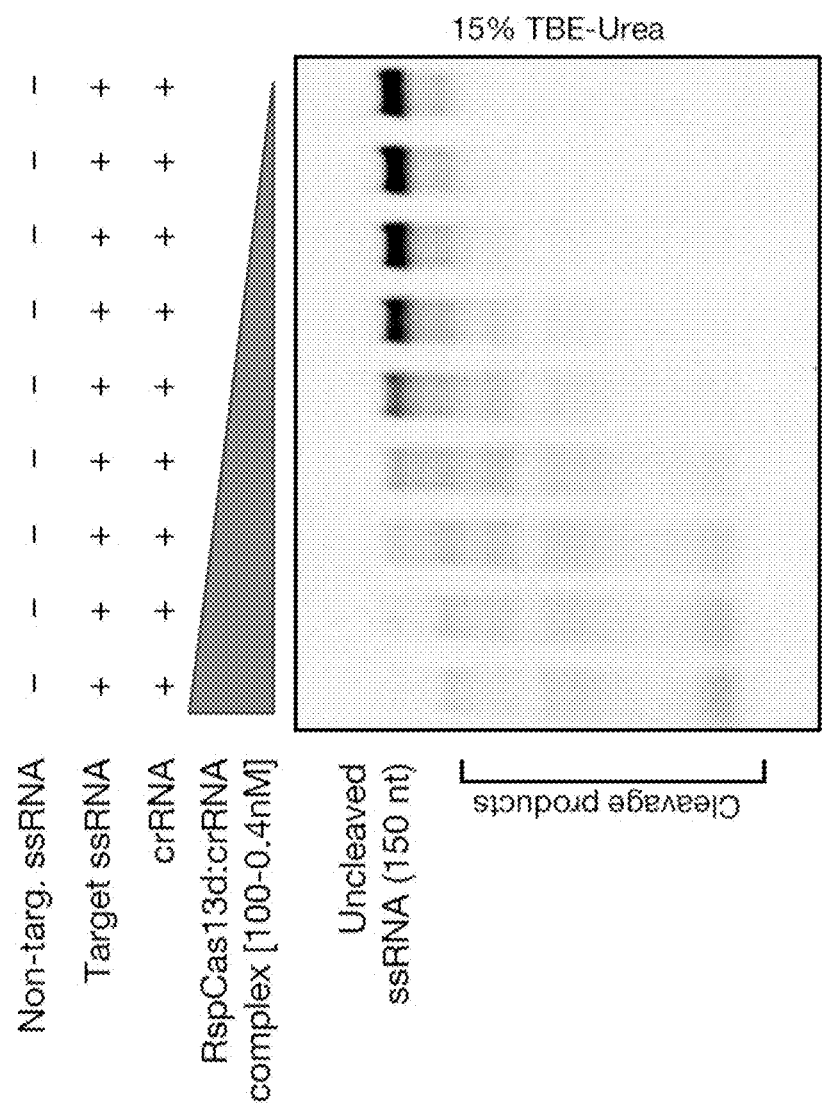
Figure 25A:
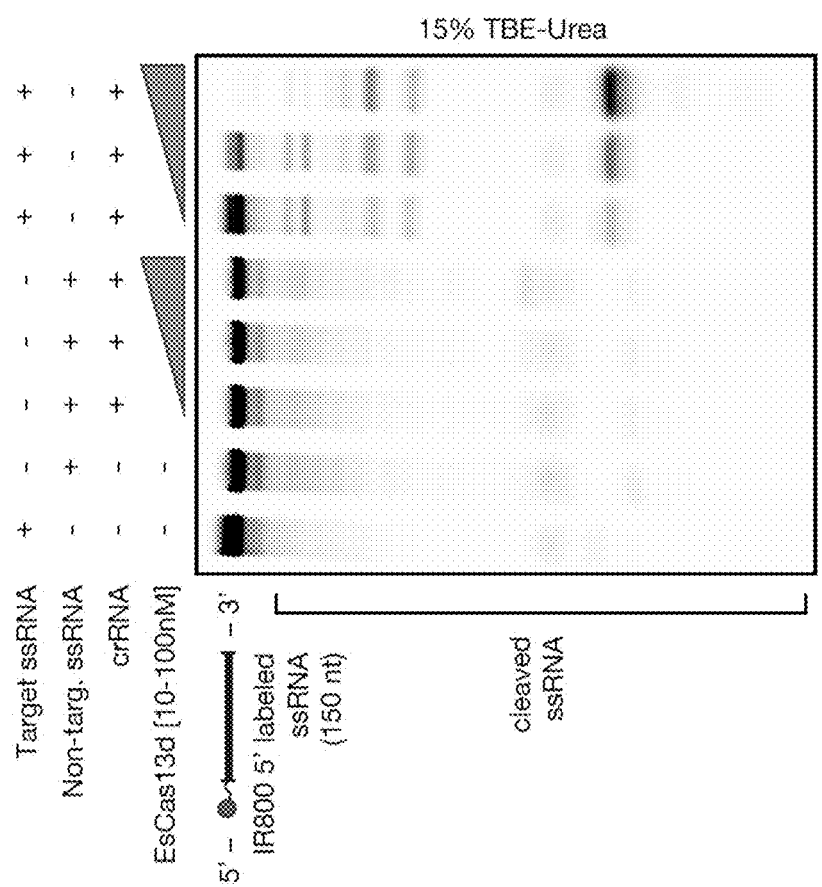
Figure 25B:
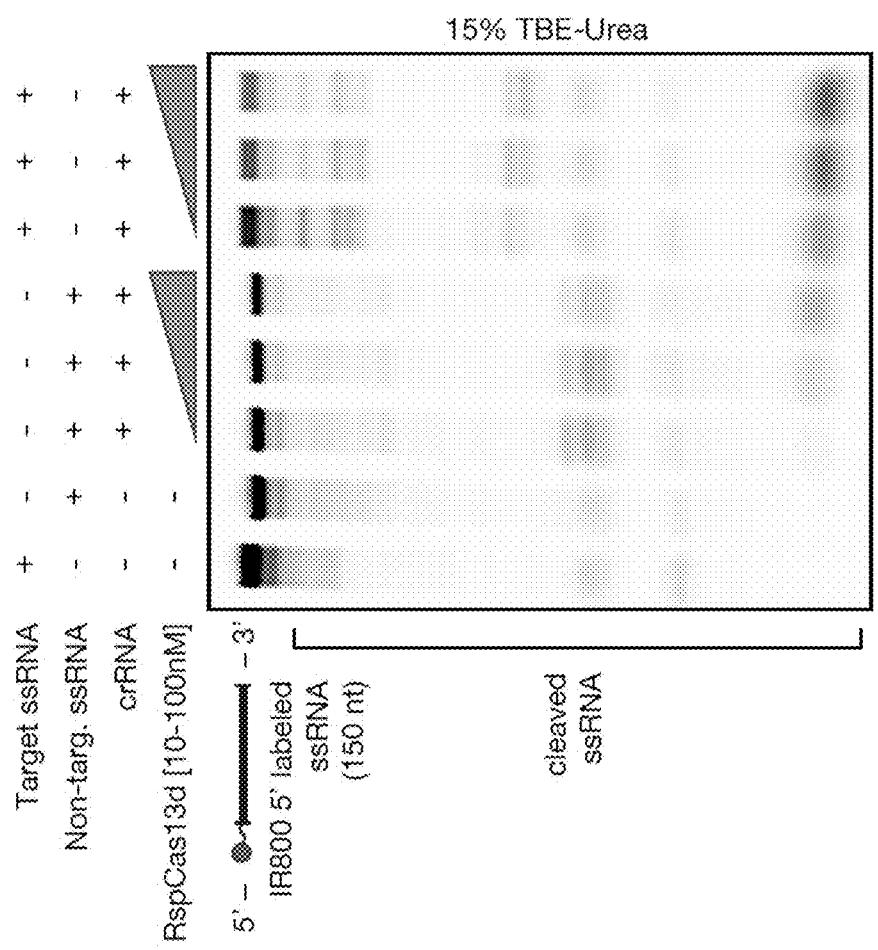

FIGS. 24A and 24B depict a titration of EsCas13d and RspCas13d in complex with crRNA (100-0.4 nM) over targeted ssDNA substrates (100 nM). Saturation of target cleavage activity was observed at approx. 50 nM RspCas13d-crRNA complex and 100 nM EsCas13d-crRNA complex FIGS. 25A and 25B depict representative denaturing gels displaying the targeted RNase activity of EsCas13d and RspCas13d effector proteins, with substrate RNA cleavage occurring when the crRNA matches its complementary target ssRNA. RNA substrates are 5' labeled with IRDye 800.

Figure 26A:
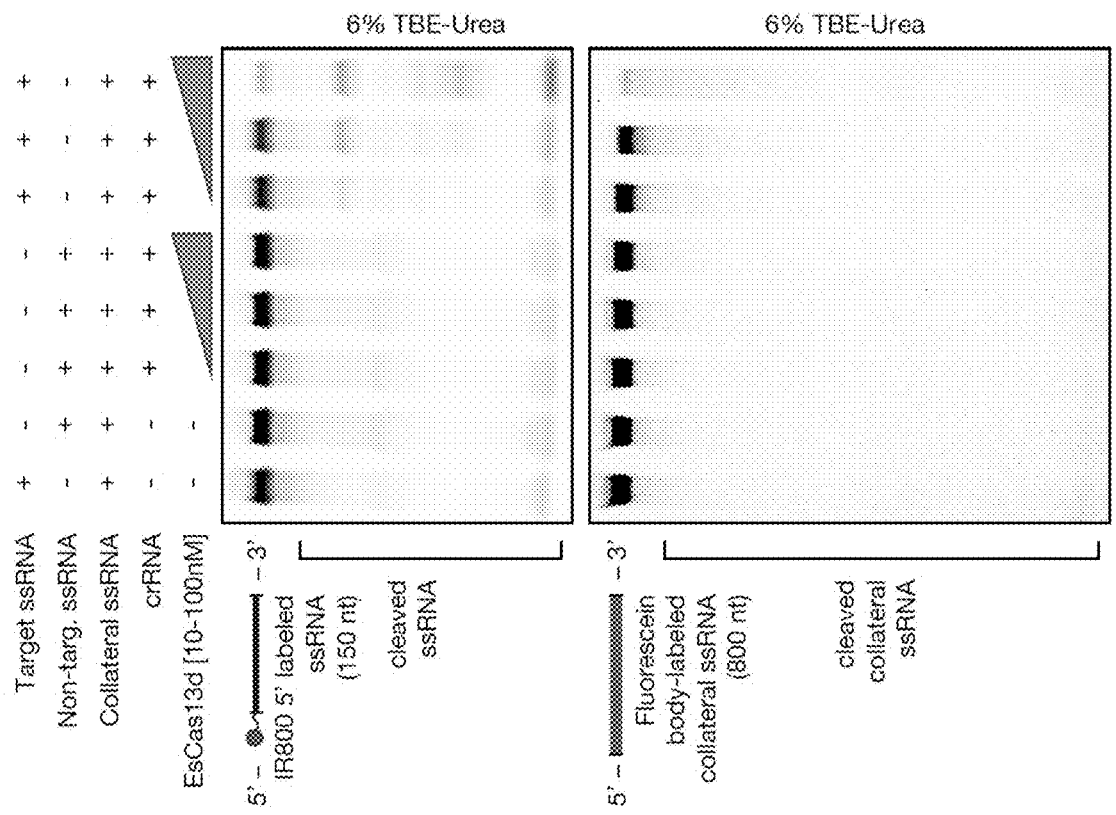
Figure 26B:
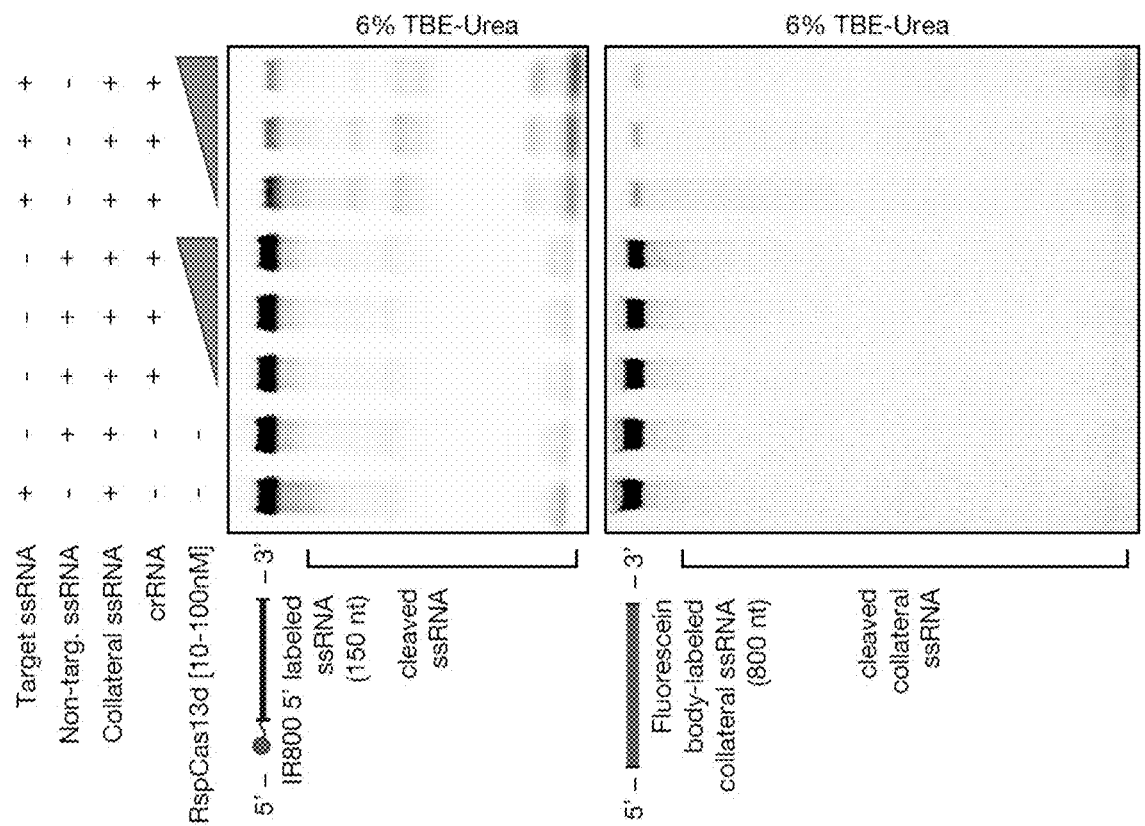

FIGS. 26A and 26B depict representative denaturing gels displaying non-specific RNase activity of the Cas13d effectors upon targeted substrate recognition, demonstrated by the cleavage of fluorescein dUTP body-labeled collateral RNA upon activation of the target nuclease activity. For all reactions, EsCas13d-crRNA and RspCas13d-crRNA complexes were formed by pre-incubating Cas13d and cognate crRNA for 5 minutes at 37° C., prior to adding target and/or collateral ssRNA and incubating the reaction for 30 minutes.

Figure 26C:
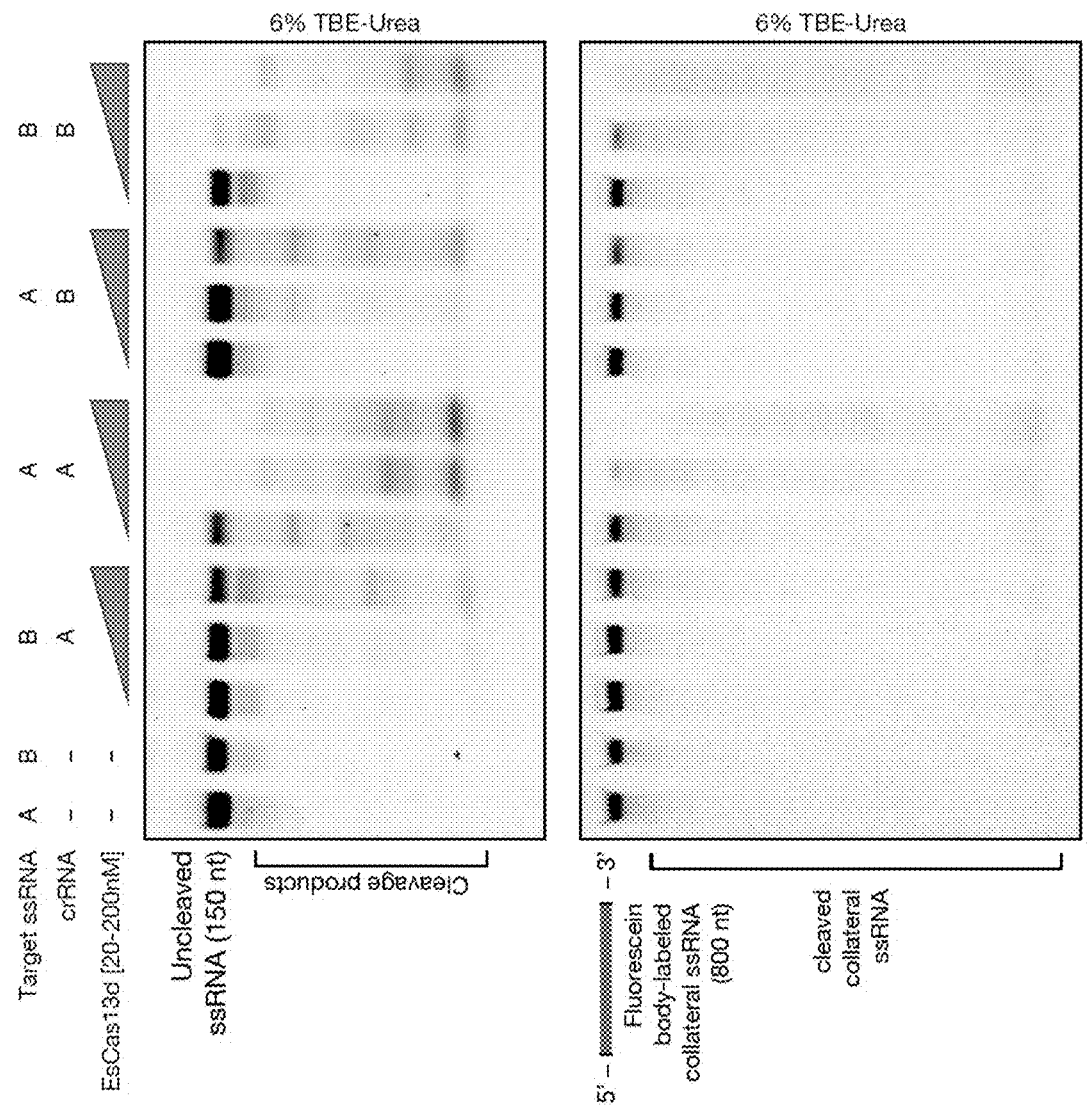
Figure 26D:
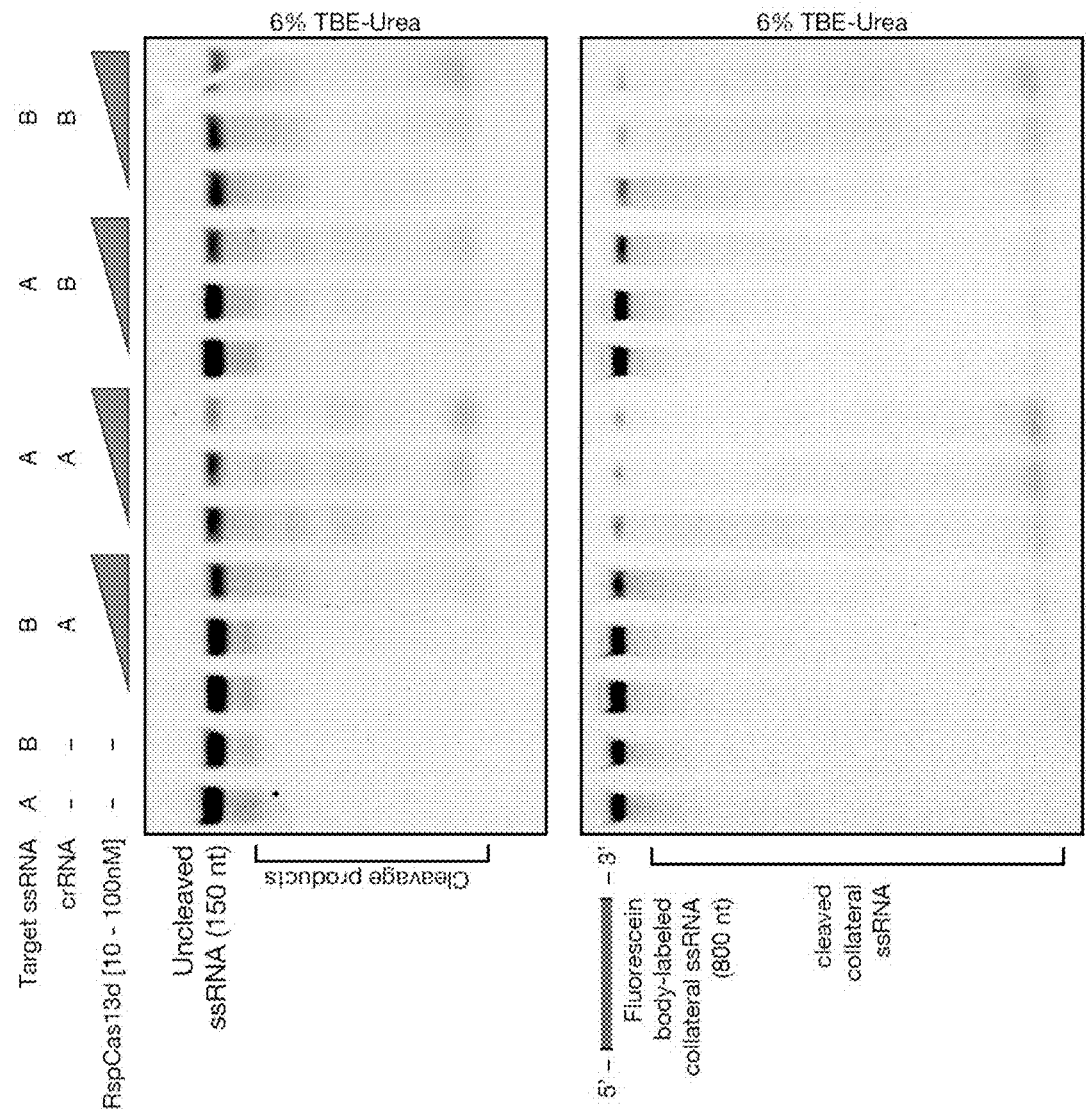

FIGS. 26C and 26D depict denaturing gels displaying cleavage reactions of the Cas13d-crRNA complex over two distinct ssRNA substrates, short 150 nt target RNAs (top) and longer 800 nt fluorescent body-labeled ssRNA substrates (bottom) for EsCas13d and RspCas13d. The labels A and B correspond to matching crRNA/substrate pairs.

Figure 27A:
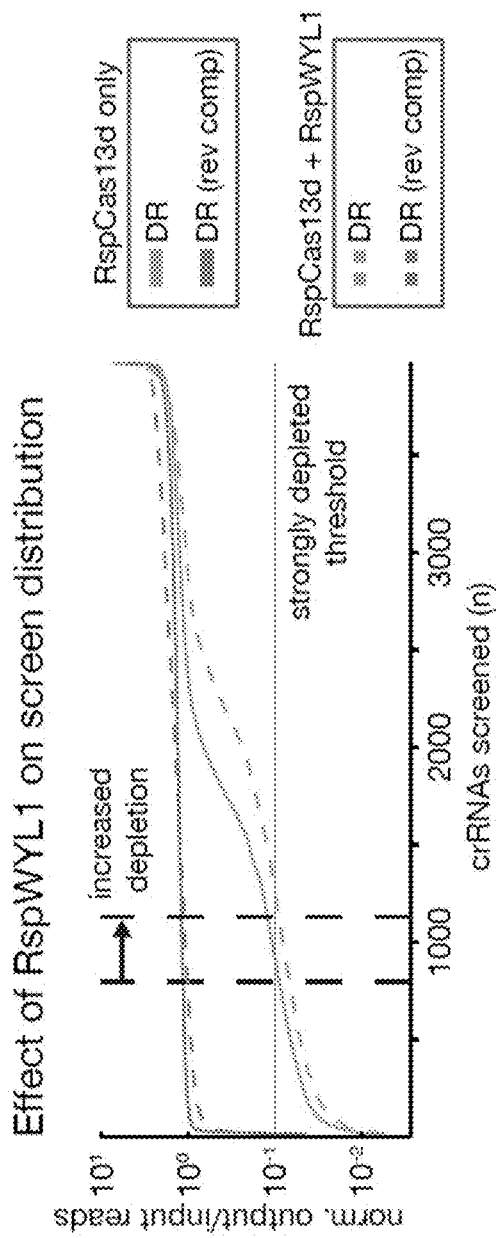

FIG. 27A depicts a comparative depletion plot of bacterial screens performed on RspCas13d only (solid line) versus RspCas13d with RspWYL1 (dotted line). The blue dashed lines demarcate the intersection of the ranked screen hits with the depletion fraction of 0.1, below which we define as strongly depleted.

Figure 27B:
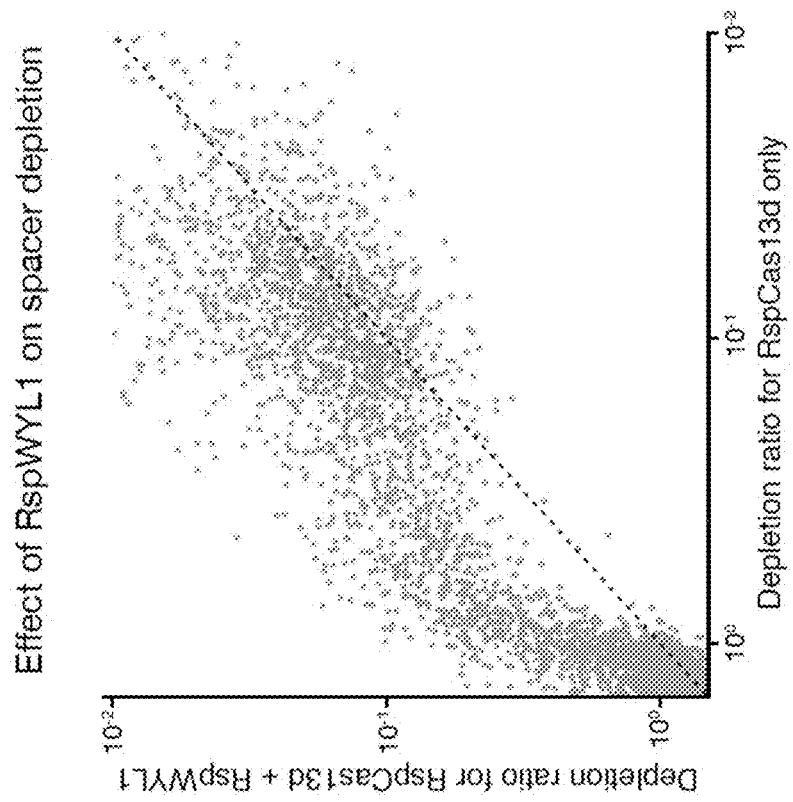

FIG. 27B depicts spacer depletion ratios for RspCas13d with and without RspWYL1.

Figure 28:
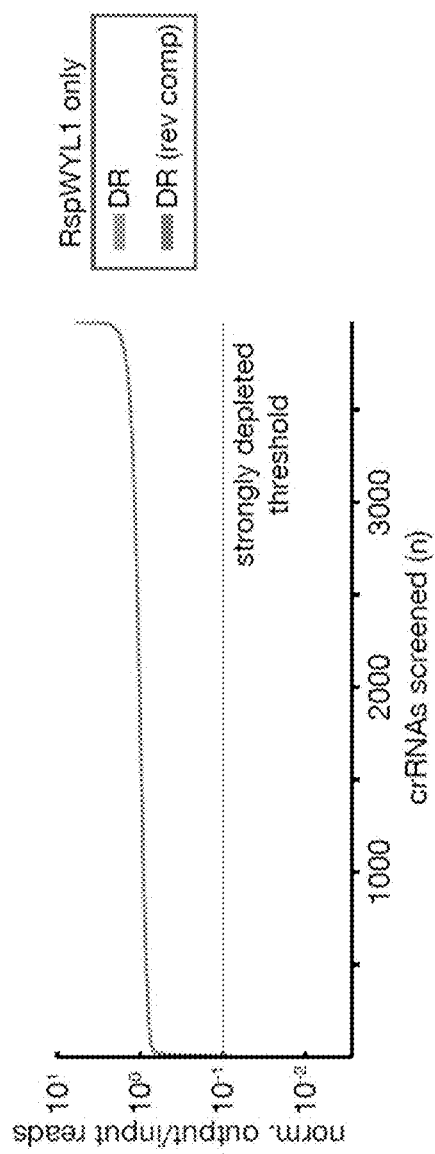

FIG. 28 depicts a depletion plot of bacterial screens using only RspWYL1 and the repeat-spacer-repeat library associated with RspCas13d.

Figure 29A:
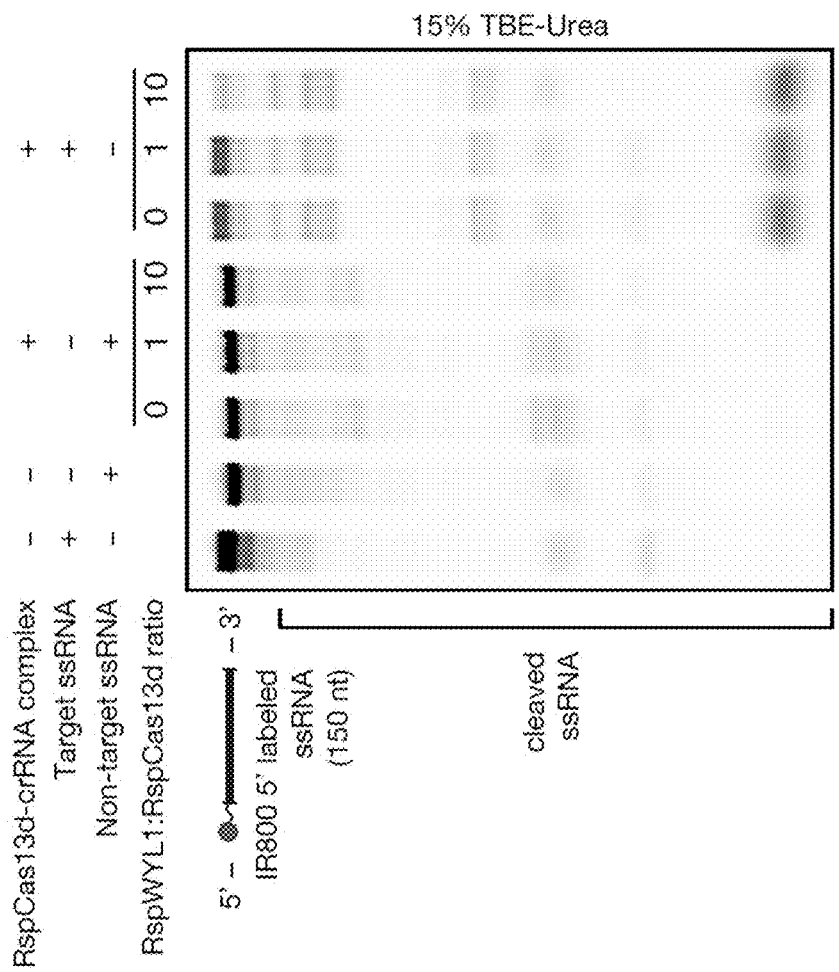
Figure 29B:
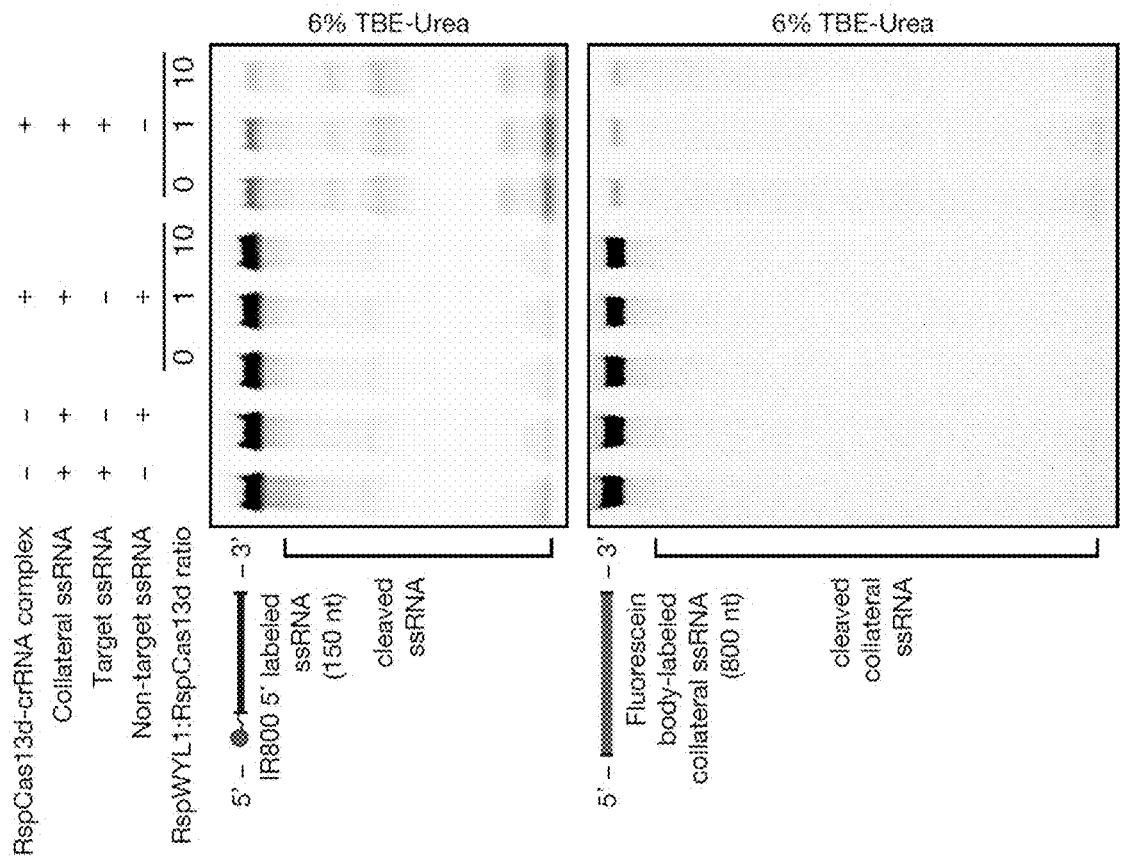

FIGS. 29A and 29B depict representative activity of titrating different molar ratios of purified RspWYL1 to a fixed dose of RspCas13d. FIG. 29A is an ssRNA substrate cleavage assay, and FIG. 29B evaluate the effect of RspWYL1 on collateral activity.

Figure 29C:
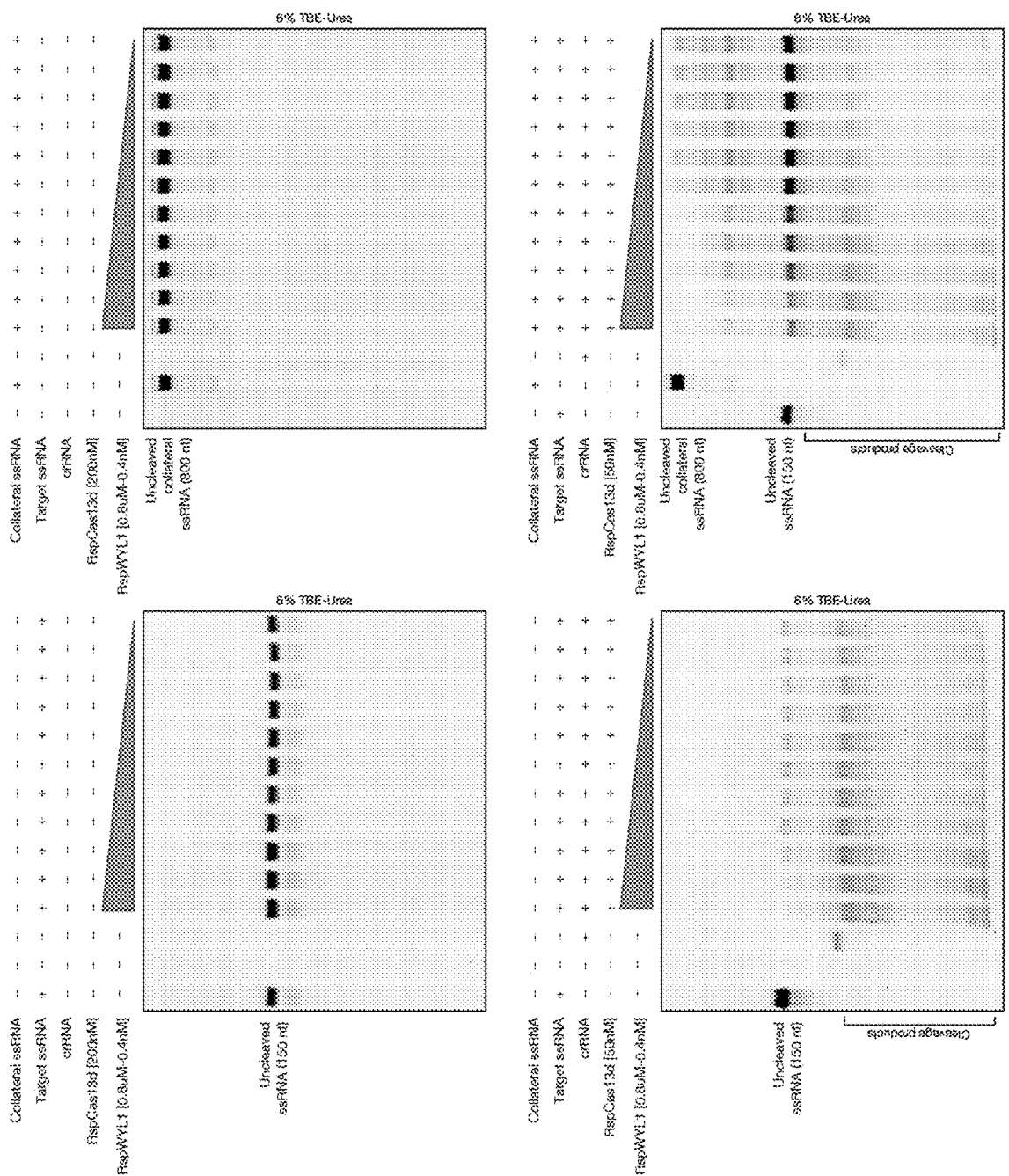

FIG. 29C depicts the effect on RNA cleavage of titrating RspWYL1 (800 to 0.4 nM) while holding fixed the concentration of Apo RspCas13d (200 nM) for (A) target ssRNA and (B) collateral ssRNA activity, and of RspCas13d-crRNA complex (50 nM) for (C) target ssRNA and (D) collateral ssRNA activity.

Figure 30A:
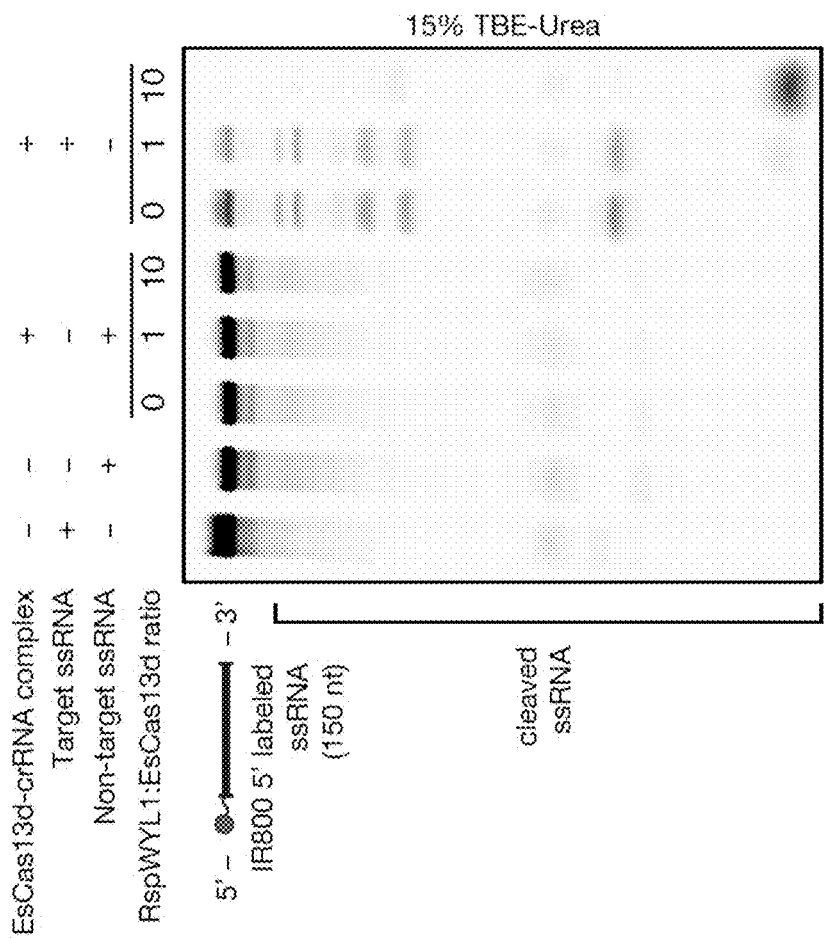
Figure 30B:
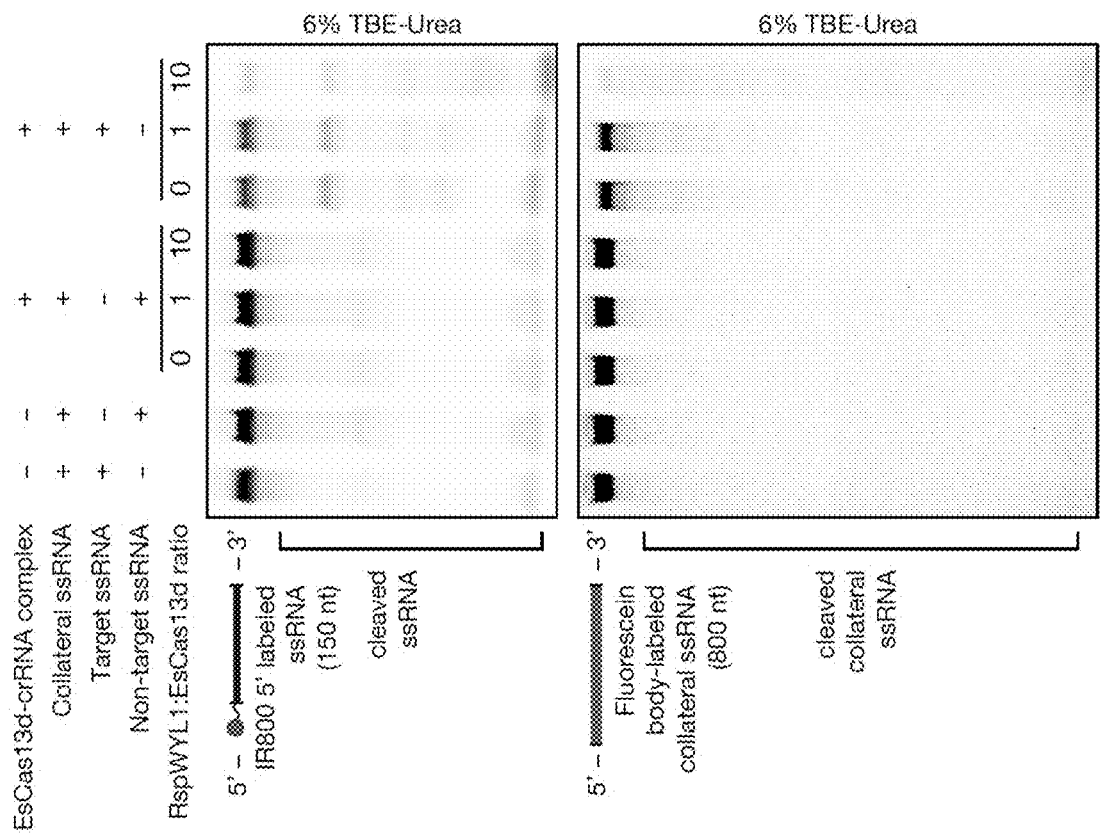

FIGS. 30A and 30B depict representative activity of titrating different molar ratios of purified RspWYL1 to a fixed dose of EsCas13d. FIG. 30A is an ssRNA substrate cleavage assay, and FIG. 30B evaluate the effect of RspWYL1 on collateral activity of EsCas13d. In both of these reactions, RspWYL1 was pre-incubated along with the pre-crRNA and Cas13d effector for 5 minutes at 37° C. before incubation with substrate RNA. The final concentration of Cas13d in the reaction is 33 nM with a 2:1 ratio of Cas13d to pre-crRNA.

Figure 31:
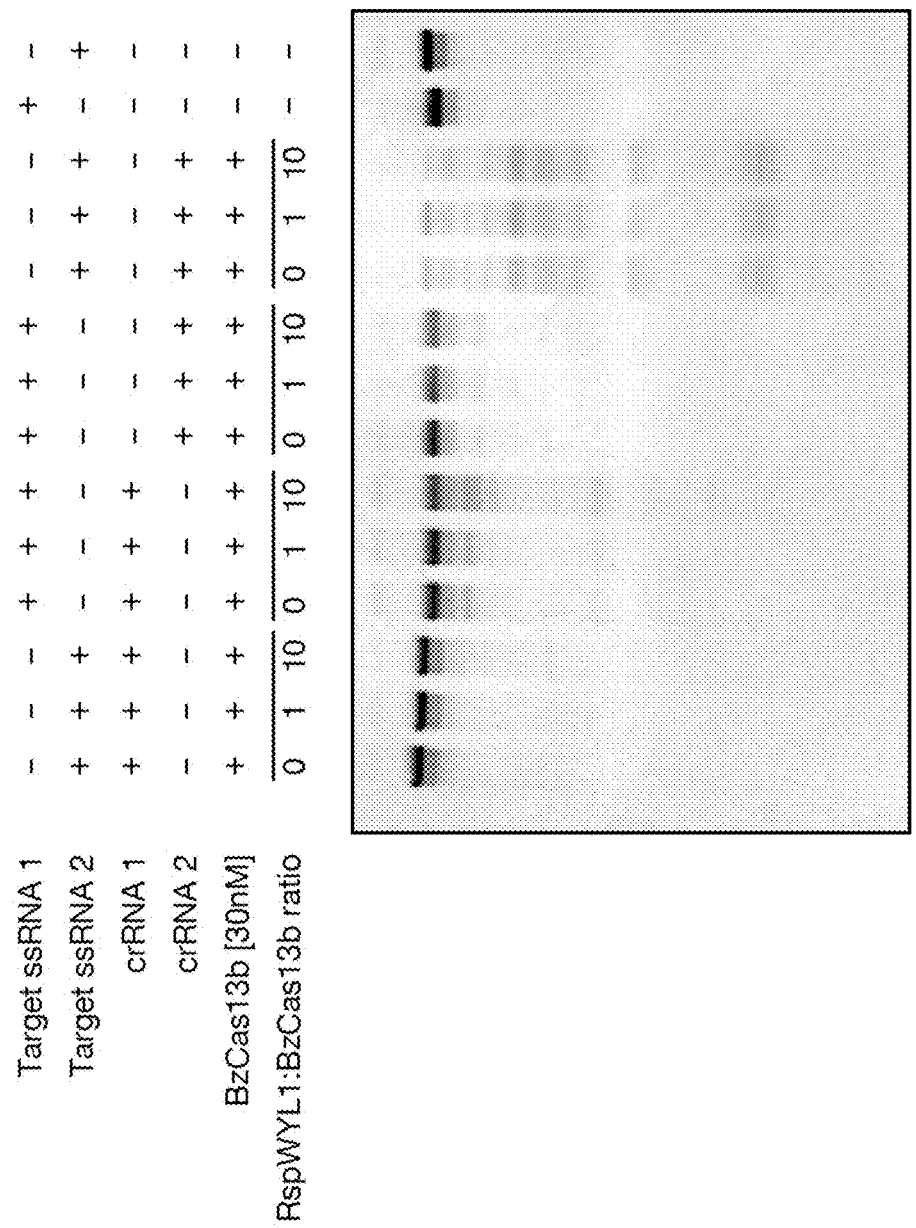

FIG. 31 shows that RspWYL1 enhances the activity of type VI-B effector BzCas13b. Representative gel displaying the ability of RspWYL1 to enhance target cleavage and collateral activity for Cas13 enzymes of subtype VI-B, demonstrating modularity beyond Type VI-D. In this reaction RspWYL1 was pre-incubated along with the pre-crRNA and BzCas13b effector for 5 minutes at 37 C before incubation with substrate RNA.

Figure 32:
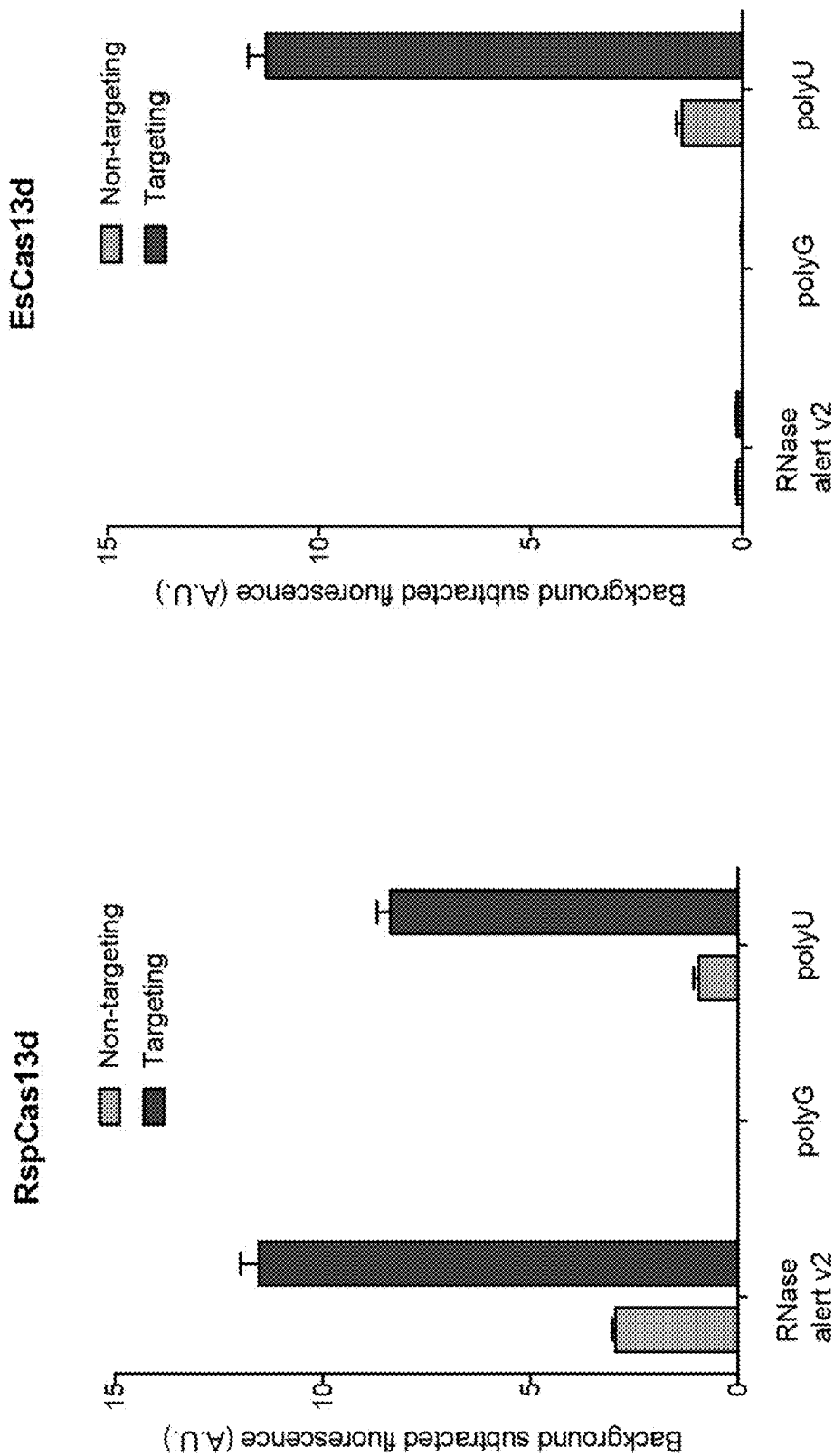

FIG. 32 shows that EsCas13d and RspCas13d are capable of specific detection of RNA species using the collateral effect of the enzymes, and additionally, demonstrate differential activity over short ribonucleotide oligomer substrates. The poly-G and poly-U labels refer to substrates containing 5 identical ribonucleotide bases, with the 5' end modified with a FAM labeled fluorescent ribonucleotide and the 3' end modified with an Iowa Black FQ fluorescent quencher. These data were collected 60 minutes after incubation at 37° C. The error bars represent S.E.M. of four technical replicates.

Figure 33A:
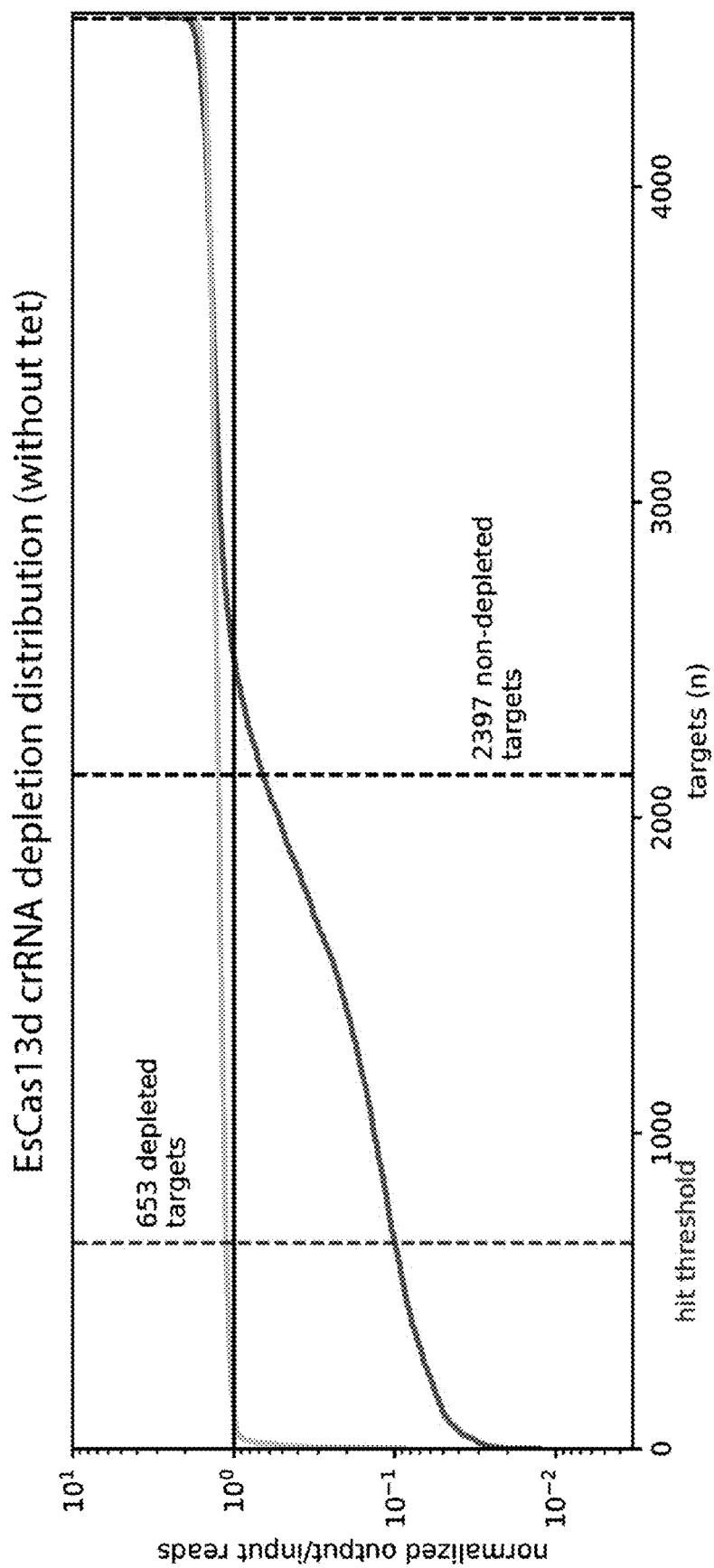
Figure 33B:
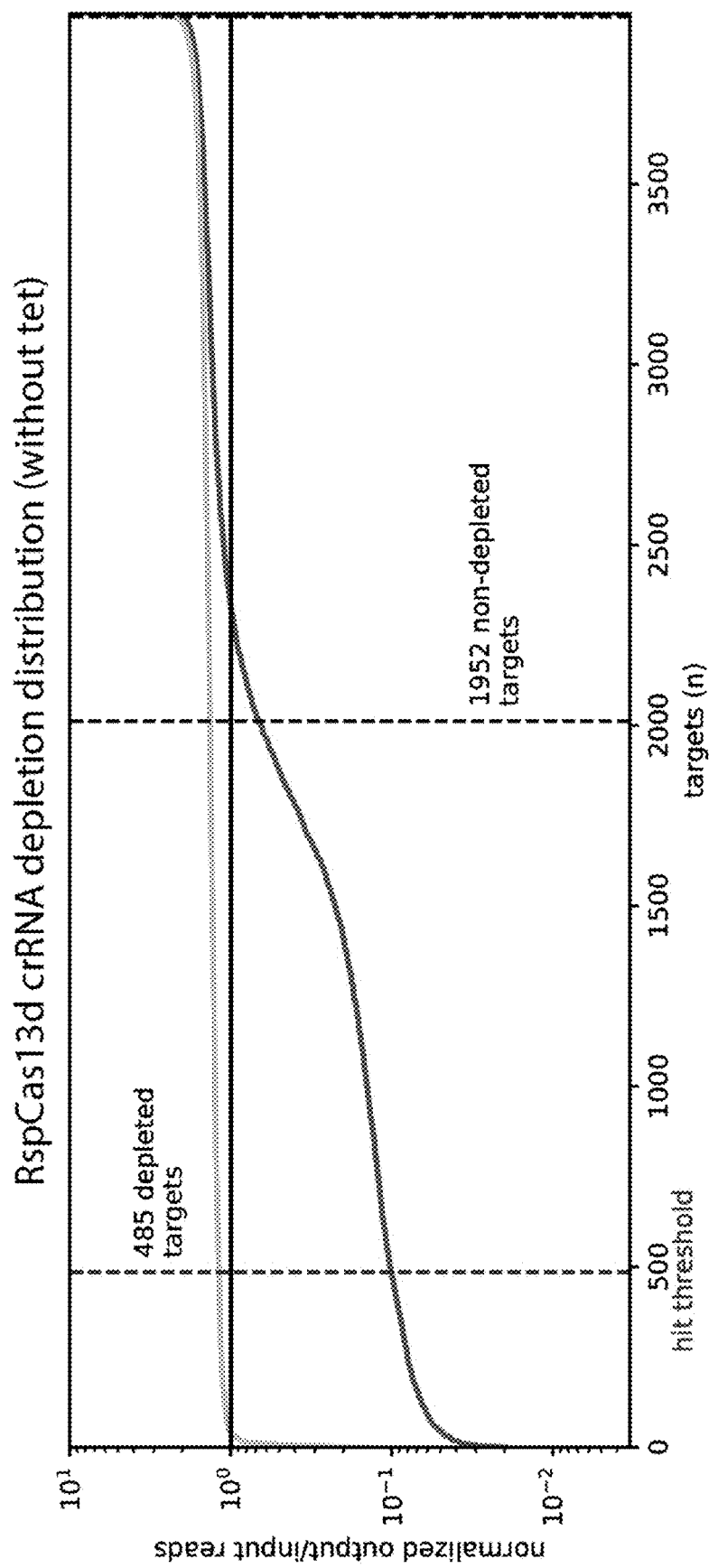

FIGS. 33A and 33B depict the distribution and magnitude of crRNA depletion for primary screening of EsCas13d and RspCas13d (effector only), respectively, in the absence of tetracycline. The value of crRNA depletion was calculated by normalized sequencing reads from the screen output divided by normalized reads from the pre-transformation screen input library for each crRNA spacer and orientation. The blue dashed lines demarcate the intersection of the ranked screen hits with the depletion fraction of 0.1, below which we define as strongly depleted.

Figure 34A:
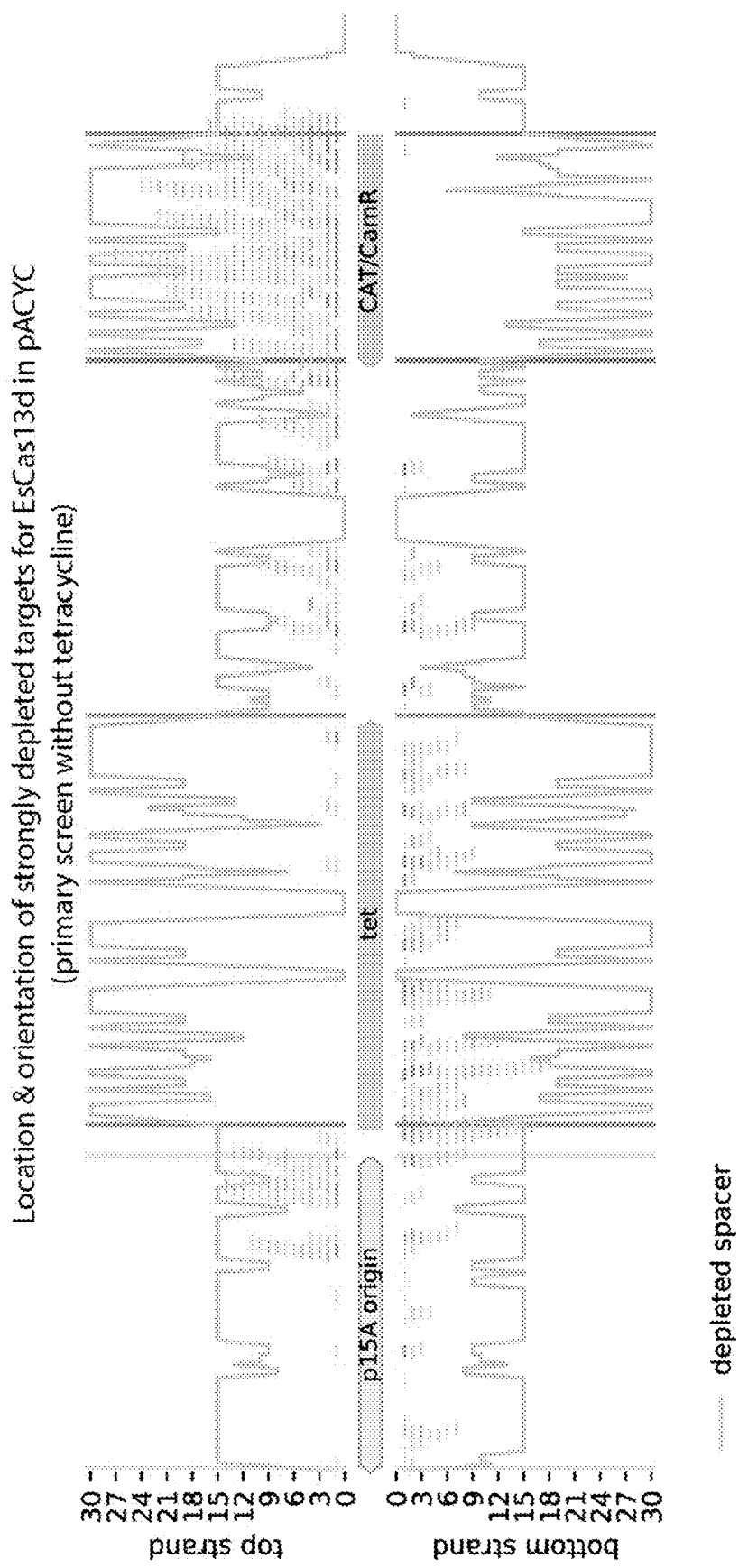
Figure 34B:
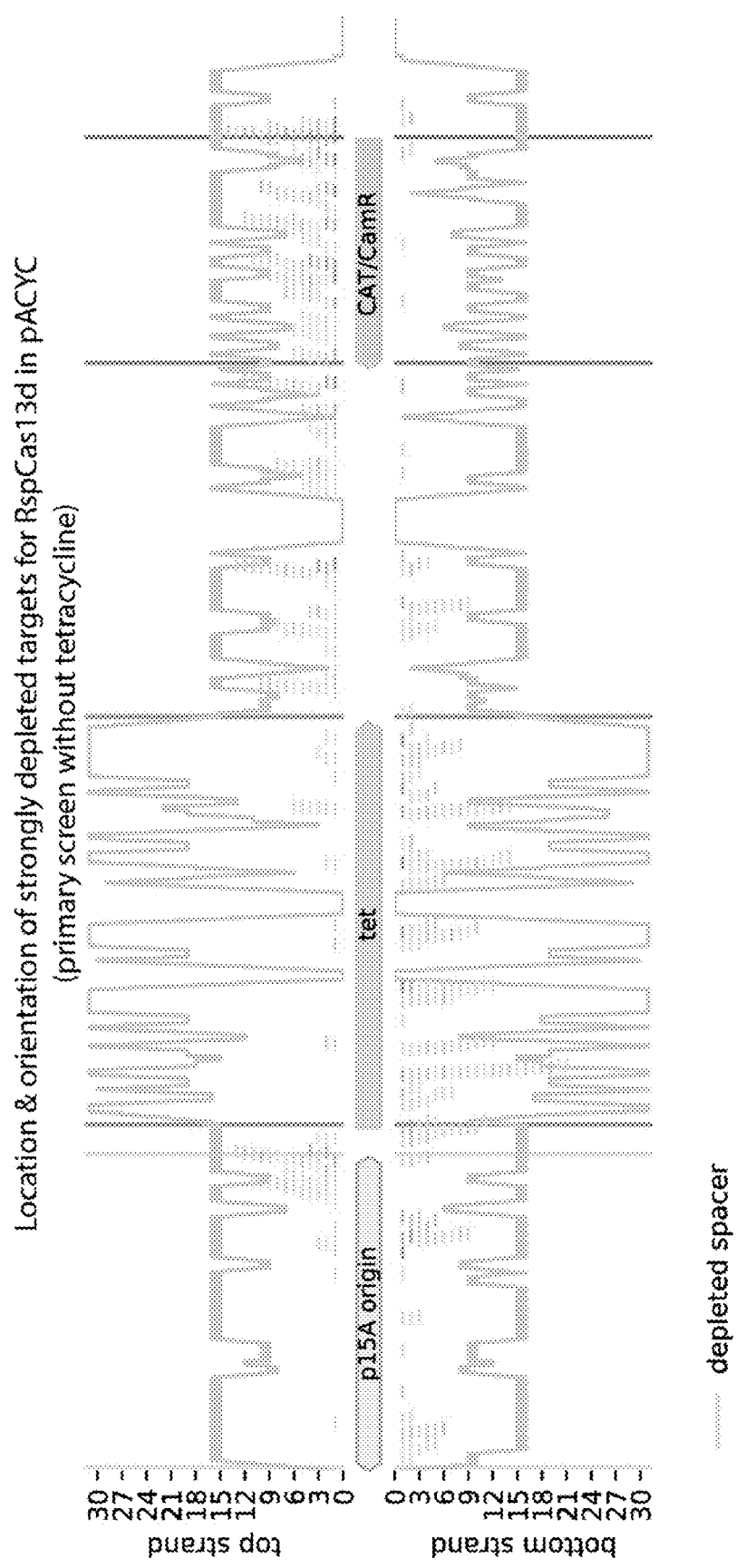

FIGS. 34A and 34B depict the location of strongly depleted targets of the active DR orientation over the strands and genetic features of the pACYC184 plasmid for EsCas13d and RspCas13d (effector only), respectively. Gray outlines represent the total number of spacers (y-axis) targeting a location, while red bars depict the locations of strongly depleted spacers with heatmap color proportional to magnitude of depletion.

DETAILED DESCRIPTION

In one aspect, the disclosure relates to the use of computational methods and algorithms to search for and identify novel protein families that exhibit a strong co-occurrence pattern with certain other features within naturally occurring genome sequences. In certain exemplary embodiments, these computational methods are directed to identifying protein families that co-occur in close proximity to CRISPR arrays. However, the methods disclosed herein are useful in identifying proteins that naturally occur within close proximity to other features, both non-coding and protein-coding (for example, CRISPR Cas1 proteins). It should be understood that the methods and calculations described herein may be performed on one or more computing devices.

In some embodiments, a set of genomic sequences may be obtained from genomic or metagenomic databases. The databases comprise short reads, or contig level data, or assembled scaffolds, or complete organisms. Likewise, the database may comprise genomic sequence data from prokaryotic organisms, or eukaryotic organisms, or may include data from metagenomic environmental samples. Exemplary database repositories include NCBI RefSeq, NCBI GenBank, NCBI Whole Genome Shotgun (WGS), and JGI Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the size of the protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the size of the CRISPR associated cluster against the size(s) of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self-discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein can be used to discover additional mechanisms and parameters within single subunit Class 2 effector systems that can be more effectively harnessed for programmable biotechnologies.

Pooled-Screening

To efficiently validate the activity of the engineered novel CRISPR-Cas systems and simultaneously evaluate in an unbiased manner different activity mechanisms and functional parameters, a new pooled-screening approach was developed in E. coli. First, from the computational identification of the conserved protein and noncoding elements of the novel CRISPR-Cas system, these separate components were assembled into an engineered locus, which in one embodiment is on a single artificial expression vector based on the pET-28a+ backbone; in another embodiment, multiple compatible expression plasmids were used to recapitulate the engineered locus. To construct the vector, in one embodiment, DNA synthesis was used to assemble the components together; in another embodiment, molecular cloning was used for assembly, in another embodiment, the proteins and noncoding elements are transcribed on a single mRNA transcript, and different ribosomal binding sites are used to translate individual proteins.

Second, a library of unprocessed crRNAs consisting of the direct repeat::spacer::direct repeat sequence was cloned into the engineered locus. In one embodiment, the spacers were targeting a second plasmid, pACYC184, and the spacers were of the length found in the natural CRISPR array. This crRNA library was cloned into the vector backbone containing the proteins and noncoding elements (e.g. pET-28a+), and then subsequently transformed the library into E. coli along with the second target plasmid (e.g., pACYC184). It is important to have the plasmid(s) containing the engineered loci be on compatible origin(s) of replication with respect to the target plasmid to enable bacterial co-transformation. Consequently, each resulting E. coli cell contains no more than one targeting spacer.

Third, the E. coli were grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the proteins, noncoding elements, and specific active elements of the crRNA library. Using deep sequencing (e.g., next-generation sequencing), examining the population of surviving cells at a later time point compared to an earlier time point results in a depleted signal specifically for the active elements compared to the inactive crRNAs.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

The key advantages of the in vivo pooled-screen described herein include:

(1) Versatility—engineered locus design allows multiple proteins and/or noncoding elements to be expressed; the library cloning strategy enables both transcriptional directions of the computationally predicted crRNA to be expressed;

(2) Comprehensive tests of activity mechanisms & functional parameters—Evaluates diverse interference mechanisms, including DNA or RNA cleavage; examines co-occurrence of features such as transcription, plasmid DNA replication; and flanking sequences for crRNA library can be used to reliably determine PAMs with complexity equivalence of 4N's;

(3) Sensitivity—pACYC184 is a low copy plasmid, enabling high sensitivity for CRISPR-Cas activity since even modest interference rates can eliminate the antibiotic resistance encoded by the plasmid; and (4) Efficiency—Optimized molecular biology steps to enable greater speed and throughput RNA-sequencing and protein expression samples can be directly harvested from the surviving cells in the screen.

The novel CRISPR-Cas families described herein were evaluated using this in vivo pooled-screen to evaluate their operational elements, mechanisms and parameters, as well as their ability to be active and reprogrammed in an engineered system outside of their natural cellular environment.

CRISPR Class 2 RNA-Guided RNases

In one aspect, provided herein is a novel family of CRISPR Class 2 effectors having two strictly conserved RX4-6H motifs, characteristic of Higher Eukaryotes and Prokaryotes Nucleotide-binding (HEPN) domains. CRISPR Class 2 effectors that contain two HEPN domains have been previously characterized and include, for example, CRISPR Cas13a (C2c2), Cas13b, and Cas13c.

HEPN domains have been shown to be RNAse domains and confer the ability bind to and cleave any target RNA molecule. The target RNA may be any suitable form of RNA, including but not limited to mRNA, tRNA, ribosomal RNA, non-coding RNA, lincRNA, and nuclear RNA. For example, in some embodiments, the CRISPR-associated protein recognizes and cleaves targets located on the coding strand of open reading frames (ORFs).

In one embodiment, the disclosure provides a family of CRISPR Class 2 effectors, referred to herein generally as Type VI-D CRISPR-Cas effector proteins, Cas13d or Cas13e. Direct comparison of the Type VI-D CRISPR-Cas effector proteins with the effector of these other systems shows that Type VI-D CRISPR-Cas effector proteins are significantly smaller (e.g., 20% fewer amino acids), and have less than 10% sequence similarity in multiple sequence alignments to other previously described effector proteins. This newly-identified family of CRISPR Class 2 effectors can be used in a variety of applications, and are particularly suitable for therapeutic applications since they are significantly smaller than other effectors (e.g., CRISPR Cas13a, Cas13b, or Cas13c effectors) which allows for the packaging of the effectors and/or nucleic acids encoding the effectors into delivery systems having size limitations.

In bacteria, the Type VI-D CRISPR-Cas systems include a single effector (approximately 920 amino acids in length), and one or none accessory proteins (approximately 380 amino acids in length) within close proximity to a CRISPR array. The CRISPR array includes direct repeat sequences typically 36 nucleotides in length, which are generally well conserved, especially on the 3' end which ends with TNT-NAAAC (SEQ ID NO: 154). Reduced consensus of the nucleotide sequence in the 5' end of the direct repeats suggests that the crRNA is processed from the 5' end. With few exceptions, the 21 nucleotide sequence immediately upstream of the 3' end TNTNAAAC (SEQ ID NO: 154) starts with a highly conserved A and exhibits sequence complementarity that suggests strong base pairing for a RNA loop structure. The spacers contained in the Cas13d CRISPR arrays are most commonly 30 nucleotides in length, with the majority of variation in length contained in the range of 28 to 36 nucleotides.

Exemplary Type VI-D CRISPR-Cas effector proteins are provided below in Table 2. In some embodiments, a Type VI-D CRISPR-Cas effector proteins include an amino acid sequence having at least about 80% identity to the amino acid sequence of any one of Table 2 (e.g., 81%, 82%, 83%, 84%, 85%, 86%, 87% 88%, 89%, 90%, 91%, 92%, 93%, 94%, 95%, 96%, 97%, 98%, 99%, or 100%). In some embodiments, a Type VI-D CRISPR-Cas effector proteins includes the amino acid sequence of any one of Table 2. In some embodiments, the Type VI-D CRISPR-Cas effector proteins is DS499551 (SEQ ID NO: 1; also referred to herein as EsCas13d) or LARF01000048 (SEQ ID NO: 2; also referred to herein as RspCas13d), the amino acid sequences of each are provided below:

```
>WP_005358205.1 (EsCas13d)
[Eubacterium siraeum DSM 15702]
                                          (SEQ ID NO: 1)
MGKKIHARDLREQRKTDRTEKFADQNKKREAERAVPKKDAAVSVKSVSSV

SSKKDNVTKSMAKAAGVKSVFAVGNTVYMTSFGRGNDAVLEQKIVDTSHE

PLNIDDPAYQLNVVTMNGYSVTGHRGETVSAVTDNPLRRFNGRKKDEPEQ

SVPTDMLCLKPTLEKKFFGKEFDDNIHIQLIYNILDIEKILAVYSTNAIY

ALNNMSADENIENSDFFMKRTTDETFDDFEKKKESTNSREKADFDAFEKF

IGNYRLAYFADAFYVNKKNPKGKAKNVLREDKELYSVLTLIGKLRHWCVH

SEEGRAEFWLYKLDELKDDFKNVLDVVYNRPVEEINNRFIENNKVNIQIL

GSVYKNTDIAELVRSYYEFLITKKYKNMGFSIKKLRESMLEGKGYADKEY

DSVRNKLYQMTDFILYTGYINEDSDRADDLVNTLRSSLKEDDKTTVYCKE

ADYLWKKYRESIREVADALDGDNIKKLSKSNIEIQEDKLRKCFISYADSV

SEFTKLIYLLTRFLSGKEINDLVTTLINKFDNIRSFLEIMDELGLDRTFT

AEYSFFEGSTKYLAELVELNSFVKSCSFDINAKRTMYRDALDILGIESDK

TEEDIEKMIDNILQIDANGDKKLKKNNGLRNFIASNVIDSNRFKYLVRYG

NPKKIRETAKCKPAVRFVLNEIPDAQIERYYEACCPKNTALCSANKRREK

LADMIAEIKFENFSDAGNYQKANVTSRTSEAEIKRKNQAIIRLYLTVMYI

MLKNLVNVNARYVIAFHCVERDTKLYAESGLEVGNIEKNKTNLTMAVMGV

KLENGIIKTEFDKSFAENAANRYLRNARWYKLILDNLKKSERAVVNEFRN

TVCHLNAIRNININIKEIKEVENYFALYHYLIQKHLENRFADKKVERDTG

DFISKLEEHKTYCKDFVKAYCTPFGYNLVRYKNLTIDGLFDKNYPGKDDS

DEQK

>WP_046441786.1 (RspCas13d)
[Ruminococcus sp. N15.MGS-57]
                                          (SEQ ID NO: 2)
MAKKNKMKPRELREAQKKARQLKAAEINNNAAPAIAAMPAAEVIAPVAEK

KKSSVKAAGMKSILVSKNKMYITSFGKGNSAVLEYEVDNNDYNQTQLSSK

GSSNIELRGVNEVNITFSSKHGFESGVEINTSNPTHRSGESSPVRGDMLG

LKSELEKRFFGKTFDDNIHIQLIYNILDIEKILAVYVTNIVYALNNMLSI

KDSESYDDFMGYLSARNTYEVFTHPDKSNLSDKAKGNIKKSFSTFNDLLK

TKRLGYFGLEEPKTKDTRVSQAYKKRVYHMLAIVGQIRQSVFHDKSSKLD

EDLYSFIDIIDSEYRETLDYLVDERFDSINKGFIQGNKVNISLLIDMMKG

-continued
YEADDIIRLYYDFIVLKSQKNLGFSIKKLREKMLDEYGFRFKDKQYDSVR

SKMYKLMDFLLFCNYYRNDVVAGEALVRKLRFSMTDDEKEGIYADEASKL

WGKFRNDFENIADHMNGDVIKELGKADMDFDEKILDSEKKNASDLLYFSK

MIYMLTYFLDGKEINDLLTTLISKFDNIKEFLKIMKSSAVDVECELTAGY

KLFNDSQRITNELFIVKNIASMRKPASSAKLTMFRDALTILGIDDNITDD

RISEILKLKEKGKGIHGLRNFITNNVIESSRFVYLIKYANAQKIRKVAKN

EKVVMFVLGGIPDTQIERYYKSCVEFPDMNSSLEVKRSELARMIKNISFD

DFKNVKQQAKGRENVAKERAKAVIGLYLTVMYLLVKNLVNVNARYVIAIH

CLERDFGLYKEIIPELASKNLKNDYRILSQTLCELCDKSPNLFLKKNERL

RKCVEVDINNADSSMTRKYRNCIAHLTVVRELKEYIGDIRTVDSYFSIYH

YVMQRCITKRENDTKQEEKIKYEDDLLKNHGYTKDFVKALNSPFGYNIPR

FKNLSIEQLFDRNEYLTEK
```

In some embodiments, the CRISPR-associated proteins described herein (e.g., Type VI-D CRISPR-Cas effector proteins) are from about 800 to about 1150 amino acids long, such as about 850 to about 1100 amino acids in length, e.g., about 850 to about 1050, about 850 to about 1000 amino acids long, or about 850 to about 950 amino acids long.

In some embodiments, the CRISPR-associated proteins (e.g., Type VI-D CRISPR-Cas effector proteins) have RNAse activity (e.g., collateral RNAse activity). In some embodiments, the CRISPR-associated proteins have DNAse activity. In some embodiments, the DNAse and/or RNAse activity is mediated by a single or both HEPN domains present in the CRISPR-associated proteins.

In some embodiments, a CRISPR-associated protein (e.g., Type VI-D CRISPR-Cas effector protein) is derived from a *Ruminococcus* or *Eubacterium* bacterium. In some embodiments, the CRISPR associated protein is derived from a human stool sample bacterial source.

Collateral RNase Activity

In some embodiments, a complex comprised of (but not limited to) a CRISPR-associated protein and a crRNA is activated upon binding to a target nucleic acid (e.g., a target RNA). Activation induces a conformational change, which results in the complex acting as a non-specific RNase, cleaving and/or degrading nearby RNA molecules (e.g., ssRNA or dsRNA molecules) (i.e., "collateral" effects).

Collateral-Free RNA Cleavage

In other embodiments, a complex comprised of (but not limited to) the CRISPR-associated protein and a crRNA does not exhibit collateral RNase activity subsequent to target recognition. This "collateral-free" embodiment may comprise wild-type or engineered effector proteins.

PAM/PFS-Independent Targeting

In some embodiments, a CRISPR-associated protein (e.g., a Type VI-D CRISPR-Cas effector protein described herein) recognizes and cleaves the target nucleic acid without any additional requirements adjacent to or flanking the protospacer (i.e., protospacer adjacent motif "PAM" or protospacer flanking sequence "PFS" requirements).

Deactivated/Inactivated CRISPR Associated Proteins

Where the CRISPR-associated proteins described herein have nuclease activity, the CRISPR-associated proteins can be modified to have diminished nuclease activity, e.g., nuclease inactivation of at least 50%, at least 60%, at least 70%, at least 80%, at least 90%, at least 95%, at least 97%, or 100% as compared with the wild type CRISPR-associated proteins. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity. In some embodiments, the amino acid substitution is a conservative amino acid substitution. In some embodiments, the amino acid substitution is a non-conservative amino acid substitution.

In some embodiments, the CRISPR-associated proteins described herein (e.g., a Type VI-D CRISPR-Cas effector protein) are modified to comprise one or more mutations (e.g., amino acid deletions, insertions, or substitutions) in at least one HEPN domain. In some embodiments, the CRISPR associate protein comprises one, two, three, four, five, six, seven, eight, nine, or more amino acid substitutions in at least one HEPN domain. For example, in some embodiments, the one or more mutations comprise a substitution (e.g., an alanine substitution) at an amino acid residue corresponding to R295, H300, R849, H854 of SEQ ID NO: 1, or R288, H293, R820, or H825 of SEQ ID NO: 2. The presence of at least one of these mutations results in a CRISPR-associated protein having reduced nuclease activity (e.g., RNAse activity) as compared to the nuclease activity of the CRISPR-associated protein from which the protein was derived (i.e., lacking the mutation).

The inactivated CRISPR-associated proteins can be fused or associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, base-editing activity, and switch activity (e.g., light inducible). In some embodiments, the functional domains are Krüppel associated box (KRAB), VP64, VP16, Fok1, P65, HSF1, MyoD1, Adenosine Deaminase Acting on RNA (ADAR) 1, ADAR2, APOBEC, cytidine deaminase (AID), mini-SOG, APEX, and biotin-APEX. In some embodiments, the functional domain is a base editing domain (e.g., ADAR1, ADAR2, APOBEC, or AID). In some embodiments, the CRISPR-associated protein is fused to one functional domain. In some embodiments, the CRISPR-associated protein is fused to multiple (e.g., two, three, four, five, six, seven, eight, or more) functional domains. In some embodiments, the functional domain (e.g., a base editing domain) is further fused to an RNA-binding domain (e.g., MS2). In some embodiments, the CRISPR-associated protein is associated to or fused to a functional domain via a linker sequence (e.g., a flexible linker sequence or a rigid linker sequence). Exemplary linker sequences and functional domain sequences are provided in Table 10.

The positioning of the one or more functional domains on the inactivated CRISPR-associated proteins is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR-associated protein. In some embodiments, the functional domain is positioned at the C-terminus of the CRISPR-associated protein. In some embodiments, the inactivated CRISPR-associated protein is modified to comprise a first functional domain at the N-terminus and a second functional domain at the C-terminus.

Various examples of inactivated CRISPR-associated proteins fused with one or more functional domains and methods of using the same are described, e.g., in International Publication No. WO 2017/219027, which is incorporated herein by reference in its entirety, and in particular with respect to the features described herein.

Split Enzymes

The present disclosure also provides a split version of the CRISPR-associated proteins described herein (e.g., a Type VI-D CRISPR-Cas effector protein). The split version of the CRISPR-associated protein may be advantageous for delivery. In some embodiments, the CRISPR-associated proteins are split into two parts of the enzyme, which together substantially comprise a functioning CRISPR-associated protein.

The split can be done in a way that the catalytic domain(s) are unaffected. The CRISPR-associated protein may function as a nuclease or may be an inactivated enzyme, which is essentially a RNA-binding protein with very little or no catalytic activity (e.g., due to mutation(s) in its catalytic domains). Split enzymes are described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the nuclease lobe and α-helical lobe are expressed as separate polypeptides. Although the lobes do not interact on their own, the crRNA recruits them into a ternary complex that recapitulates the activity of full-length CRISPR-associated proteins and catalyzes site-specific DNA cleavage. The use of a modified crRNA abrogates split-enzyme activity by preventing dimerization, allowing for the development of an inducible dimerization system.

In some embodiments, the split CRISPR-associated protein can be fused to a dimerization partner, e.g., by employing rapamycin sensitive dimerization domains. This allows the generation of a chemically inducible CRISPR-associated protein for temporal control of the activity of the protein. The CRISPR-associated protein can thus be rendered chemically inducible by being split into two fragments and rapamycin-sensitive dimerization domains can be used for controlled re-assembly of the protein.

The split point is typically designed in silico and cloned into the constructs. During this process, mutations can be introduced to the split CRISPR-associated protein and non-functional domains can be removed. In some embodiments, the two parts or fragments of the split CRISPR-associated protein (i.e., the N-terminal and C-terminal fragments), can form a full CRISPR-associated protein, comprising, e.g., at least 70%, at least 80%, at least 90%, at least 95%, or at least 99% of the sequence of the wild-type CRISPR-associated protein.

Self-Activating or Inactivating Enzymes

The CRISPR-associated proteins described herein (e.g., a Type VI-D CRISPR-Cas effector protein) can be designed to be self-activating or self-inactivating. For example, the target sequence can be introduced into the coding construct of the CRISPR-associated protein. Thus, the CRISPR-associated protein can cleave the target sequence, as well as the construct encoding the protein thereby self-inactivating their expression. Methods of constructing a self-inactivating CRISPR system are described, e.g., in Epstein, and Schaffer, *Mol. Ther.* 24 (2016): S50, which is incorporated herein by reference in its entirety.

In some other embodiments, an additional crRNA, expressed under the control of a weak promoter (e.g., 7SK promoter), can target the nucleic acid sequence encoding the CRISPR-associated protein to prevent and/or block its expression (e.g., by preventing the transcription and/or translation of the nucleic acid). The transfection of cells with vectors expressing the CRISPR-associated protein, the crRNAs, and crRNAs that target the nucleic acid encoding the CRISPR-associated protein can lead to efficient disruption of the nucleic acid encoding the CRISPR-associated protein and decrease the levels of CRISPR-associated protein, thereby limiting the genome editing activity.

In some embodiments, the genome editing activity of the CRISPR-associated protein can be modulated through endogenous RNA signatures (e.g., miRNA) in mammalian cells. A CRISPR-associated protein switch can be made by using a miRNA-complementary sequence in the 5'-UTR of mRNA encoding the CRISPR-associated protein. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (see, e.g., Hirosawa et al. *Nucl. Acids Res.*, 2017, 45(13): e118).

Inducible CRISPR-Associated Proteins

The CRISPR-associated proteins (e.g., Type VI-D CRISPR-Cas effector proteins) can be inducibly expressed, e.g., their expression can be light-induced or chemically-induced. This mechanism allows for activation of the functional domain in the CRISPR-associated proteins. Light inducibility can be achieved by various methods known in the art, e.g., by designing a fusion complex wherein CRY2 PHR/CIBN pairing is used in split CRISPR-associated proteins (see, e.g., Konermann et al. "Optical control of mammalian endogenous transcription and epigenetic states," *Nature,* 500.7463 (2013): 472). Chemical inducibility can be achieved, e.g., by designing a fusion complex wherein FKBP/FRB (FK506 binding protein/FKBP rapamycin binding domain) pairing is used in split CRISPR-associated proteins. Rapamycin is required for forming the fusion complex, thereby activating the CRISPR-associated proteins (see, e.g., Zetsche, Volz, and Zhang, "A split-Cas9 architecture for inducible genome editing and transcription modulation," *Nature Biotech.,* 33.2 (2015): 139-142).

Furthermore, expression of the CRISPR-associated proteins can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," *Nucl. Acids Res.,* 40.9 (2012): e64-e64).

Various embodiments of inducible CRISPR-associated proteins and inducible CRISPR systems are described, e.g., in U.S. Pat. No. 8,871,445, US Publication No. 2016/0208243, and International Publication No. WO 2016/205764, each of which is incorporated herein by reference in its entirety.

Functional Mutations

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 135); the NLS from nucleoplasmin (e.g., the nucleoplasmin bipartite NLS with the sequence KRPAATKKAGQAKKKK (SEQ ID NO: 136)); the c-myc NLS having the amino acid sequence PAAKRVKLD (SEQ ID NO: 137) or RQRRNELKRSP (SEQ ID NO: 138); the hRNPA1 M9 NLS having the sequence NQSSNFGPMKGGNFGGRSSGPYGGGGQYFAKPRNQGGY (SEQ ID NO: 139); the sequence RMRIZFKNKGKDTAELRRRRVEVSVELRKAKKDEQILKRRNV (SEQ ID NO: 140) of the IBB domain from importin-alpha; the sequences VSRKRPRP (SEQ ID NO: 141) and PPKKARED (SEQ ID NO: 142) of the myoma T protein; the sequence PQPKKKPL (SEQ ID NO: 143) of human p53; the sequence SALIKKKKKMAP (SEQ ID NO: 144) of mouse c-abl IV; the sequences DRLRR (SEQ ID NO: 145) and PKQKKRK (SEQ ID NO: 146) of the influenza virus NS1; the sequence RKLKKKIKKL (SEQ ID NO: 147) of the Hepatitis virus delta antigen; the sequence REKKKFLKRR (SEQ ID NO: 148) of the mouse Mx1 protein; the sequence KRKGDEVDGVDEVAKKKSKK (SEQ ID NO: 149) of the human poly(ADP-ribose) polymerase; and the sequence RKCLQAGMNLEARKTKK (SEQ ID NO: 150) of the human glucocorticoid receptor. In some embodiments, the CRISPR-associated protein comprises at least one (e.g., 1, 2, 3, 4, 5, 6, 7, 8, 9, or 10) Nuclear Export Signal (NES) attached the N-terminal or C-terminal of the protein. In a preferred embodiment a C-terminal and/or N-terminal NLS or NES is attached for optimal expression and nuclear targeting in eukaryotic cells, e.g., human cells.

In some embodiments, the CRISPR-associated proteins described herein are mutated at one or more amino acid residues to alter one or more functional activities. For example, in some embodiments, the CRISPR-associated protein is mutated at one or more amino acid residues to alter its helicase activity. In some embodiments, the CRISPR-associated protein is mutated at one or more amino acid residues to alter its nuclease activity (e.g., endonuclease activity or exonuclease activity). In some embodiments, the CRISPR-associated protein is mutated at one or more amino acid residues to alter its ability to functionally associate with a guide RNA. In some embodiments, the CRISPR-associated protein is mutated at one or more amino acid residues to alter its ability to functionally associate with a target nucleic acid.

In some embodiments, the CRISPR-associated proteins described herein are capable of cleaving a target nucleic acid molecule. In some embodiments, the CRISPR-associated protein cleaves both strands of the target nucleic acid molecule. However, in some embodiments, the CRISPR-associated protein is mutated at one or more amino acid residues to alter its cleaving activity. For example, in some embodiments, the CRISPR-associated protein may comprise one or more mutations that render the enzyme incapable of cleaving a target nucleic acid. In other embodiments, the CRISPR-associated protein comprise one or more mutations such that the enzyme is capable of cleaving a single strand of the target nucleic acid (i.e., nickase activity). In some embodiments, the CRISPR-associated protein is capable of cleaving the strand of the target nucleic acid that is complementary to the strand to which the guide RNA hybridizes. In some embodiments, the CRISPR-associated protein is capable of cleaving the strand of the target nucleic acid to which the guide RNA hybridizes.

In some embodiments, a CRISPR-associated protein described herein can be engineered to have a deletion in one or more amino acid residues to reduce the size of the enzyme while retaining one or more desired functional activities (e.g., nuclease activity and the ability to interact functionally with a guide RNA). The truncated CRISPR-associated protein can be advantageously used in combination with delivery systems having load limitations.

Nucleic acids encoding the proteins and guide RNAs (e.g., a crRNA) described herein (e.g., a CRISPR-associated protein or an accessory protein) are also provided. In some embodiments, the nucleic acid is a synthetic nucleic acid. In some embodiments, the nucleic acid is a DNA molecule. In some embodiments, the nucleic acid is an RNA molecule (e.g., an mRNA molecule). In some embodiments, the nucleic acid is an mRNA. In some embodiments, the mRNA is capped, polyadenylated, substituted with 5-methylcytidine, substituted with pseudouridine, or a combination thereof. In some embodiments, the nucleic acid (e.g., DNA) is operably linked to a regulatory element (e.g., a promoter) in order to control the expression of the nucleic acid. In some embodiments, the promoter is a constitutive promoter. In some embodiments, the promoter is an inducible promoter. In some embodiments, the promoter is a cell-specific promoter. In some embodiments, the promoter is an organism-specific promoter. Suitable promoters are known in the art and include, for example, a pol I promoter, a pol II promoter, a pol III promoter, a T7 promoter, a U6 promoter, a H1 promoter, retroviral Rous sarcoma virus LTR promoter, a cytomegalovirus (CMV) promoter, a SV40 promoter, a dihydrofolate reductase promoter, and a β-actin promoter. For example, a U6 promoter can be used to regulate the expression of a guide RNA molecule described herein.

In some embodiments, the nucleic acid(s) are present in a vector (e.g., a viral vector or a phage). The vectors can include one or more regulatory elements that allow for the propagation of the vector in a cell of interest (e.g., a bacterial cell or a mammalian cell). In some embodiments, the vector includes a nucleic acid encoding a single component of a CRISPR-associated (Cas) system described herein. In some embodiments, the vector includes multiple nucleic acids, each encoding a component of a CRISPR-associated (Cas) system described herein.

In one aspect, the present disclosure provides nucleic acid sequences that are at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequences described herein. In another aspect, the present disclosure also provides amino acid sequences that are at least 50%, 55%, 60%, 65%, 70%, 75%, 80%, 85%, 90%, 91%, 92%, 93%, 94%, 95%, 96%, 97%, 98%, 99%, or 100% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

In some embodiments, the CRISPR-associated proteins and accessory proteins described herein can be fused to one or more peptide tags, including a His-tag, GST-tag, or myc-tag. In some embodiments, the CRISPR-associated proteins or accessory proteins described herein can be fused to a detectable moiety such as a fluorescent protein (e.g., green fluorescent protein or yellow fluorescent protein).

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at kazusa.orjp/codon/ and these tables can be adapted in a number of ways. See Nakamura et al. Nucl. Acids Res. 28:292 (2000), which is incorporated herein by reference in its entirety. Computer algorithms for codon optimizing a particular sequence for expression in a particular host cell are also available, such as Gene Forge (Aptagen; Jacobus, P A).

RNA Guides

In some embodiments, the CRISPR systems described herein include at least RNA guide (e.g., a gRNA or a crRNA). The architecture of multiple RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., one, two, three, four, five, six, seven, eight, or more RNA guides). In some embodiments, the RNA guide includes a crRNA. In some embodiments, the RNA guide includes a crRNA and a tracrRNA. In some embodiments, the RNA guide is an engineered construct that comprises a tracrRNA and a crRNA (in a single RNA guide). Sequences for guide RNAs from multiple CRISPR systems are known in the art and can be searched using public databases (see, e.g., Grissa et al. (2007) Nucleic Acids Res. 35 (web server issue): W52-7; Grissa et al. (2007) BMC Bioinformatics 8: 172; Grissa et al. (2008) Nucleic Acids Res. 36 (web server issue): W145-8; and Moller and Liang (2017) PeerJ 5: e3788; see also the CRISPR database available at: crispr.i2bc.paris-saclayfr/crispr/BLAST/CRISPRsBlast.php; and MetaCRAST available at: github.com/molleraj/MetaCRAST).

In some embodiments, the CRISPR systems described herein include at least one crRNA or a nucleic acid encoding at least one crRNA. In some embodiments, the crRNA includes a direct repeat sequence, a spacer sequence, and a direct repeat sequence, which is typical of precursor crRNA (pre-crRNA) configurations in other CRISPR systems. In some embodiments, the crRNA includes a truncated direct repeat sequence and a spacer sequence, which is typical of processed or mature crRNA. The CRISPR-associated protein is capable of cleaving pre-crRNA to form processed or mature crRNA. The CRISPR-associated protein forms a complex with the mature crRNA, and the spacer sequence directs the complex to a sequence-specific binding with the target nucleic acid that is complementary to the spacer sequence. The resulting complex comprises the CRISPR-associated protein and the mature crRNA bound to the target RNA.

In some embodiments, the CRISPR systems described herein include a mature crRNA. In some embodiments, the CRISPR systems described herein include a pre-crRNA.

In some embodiments, the CRISPR systems described herein include a plurality of crRNAs (e.g., 2, 3, 4, 5, 10, 15, or more) or a plurality of nucleic acids encoding a plurality of crRNAs. Generally, the crRNAs described herein include a direct repeat sequence and a spacer sequence. In certain embodiments, the crRNA includes, consists essentially of, or consists of a direct repeat sequence linked to a guide sequence or spacer sequence.

In some embodiments, the CRISPR system described herein includes an RNA guide (e.g., a crRNA) or a nucleic acid encoding the RNA guide. In some embodiments, the RNA guide comprises or consists of a direct repeat sequence and a spacer sequence capable of hybridizing to a target nucleic acid, wherein the direct repeat sequence comprises 5'-$X_1X_2X_3X_4TX_5TX_6$AAAC-3' (SEQ ID NO: 151) at the 3' terminal end of the RNA guide, and wherein $X_1$ is A or C or G, $X_2$ is G or T, $X_3$ is A or G, $X_4$ is C or G or T, $X_5$ is C or T, and $X_6$ is A or G.

In some embodiments, the direct repeat sequence comprises or consists of a nucleic acid sequence listed in Table 3 (SEQ ID NOs: 32-77). In some embodiments, the direct repeat sequence comprises or consists of a nucleic acid having a nucleic acid sequence listed in Table 3 with a truncation of the initial three 5' nucleotides. In some embodiments, the direct repeat sequence comprises or consists of a nucleic acid having a nucleic acid sequence listed in Table 3 with a truncation of the initial four 5' nucleotides. In some embodiments, the direct repeat sequence comprises or consists of a nucleic acid having a nucleic acid sequence listed in Table 3 with a truncation of the initial five 5' nucleotides. In some embodiments, the direct repeat sequence comprises or consists of a nucleic acid having a nucleic acid sequence listed in Table 3 with a truncation of the initial six 5' nucleotides. In some embodiments, the direct repeat sequence comprises or consists of a nucleic acid having a nucleic acid sequence listed in Table 3 with a truncation of the initial seven 5' nucleotides. In some embodiments, the direct repeat sequence comprises or consists of a nucleic acid having a nucleic acid sequence listed in Table 3 with a truncation of the initial eight 5' nucleotides.

In some embodiments, the direct repeat sequence comprises or consists of the nucleic acid sequence 5'-GAAC-TACACCCGTGCAAAATTGCAGGGGTCTAAAAC-3' (SEQ ID NO: 34) or 5'-CTACTACACTGGTGCAAAT-TTGCACTAGTCTAAAAC-3' (SEQ ID NO: 72). In some embodiments, the direct repeat sequence comprises or consists of the nucleic acid sequence

```
                                         (SEQ ID NO: 152)
    5'-CACCCGTGCAAAATTGCAGGGGTCTAAAAC-3'
    or
                                         (SEQ ID NO: 153)
    5'-CACTGGTGCAAATTTGCACTAGTCTAAAAC-3'.
```

In some embodiments, the CRISPR-associated protein comprises the amino acid sequence of SEQ ID NO: 1 and the crRNA comprises a direct repeat sequence, wherein the direct repeat sequence comprises or consists of the nucleic acid sequence 5'-GAACTACACCCGTGCAAAAT-TGCAGGGGTCTAAAAC-3' (SEQ ID NO: 34) or 5'-CACCCGTGCAAAATTGCAGGGGTCTAAAAC-3' (SEQ ID NO: 152). In some embodiments, the CRISPR-associated protein comprises the amino acid sequence of SEQ ID NO: 2 and the crRNA comprises a direct repeat sequence, wherein the direct repeat sequence comprises or consists of the nucleic acid sequence 5'-CTACTA-CACTGGTGCAAATTTGCACTAGTCTAAAAC-3' (SEQ ID NO: 72) or 5'-CACTGGTGCAAAT-TTGCACTAGTCTAAAAC-3' (SEQ ID NO: 153).

Multiplexing RNA Guides

Type VI CRISPR-Cas effectors have been demonstrated to employ more than one RNA guide, thus enabling the ability of these effectors, and systems and complexes that include them, to target multiple nucleic acids. In some embodiments, the CRISPR systems described herein include multiple RNA guides (e.g., two, three, four, five, six, seven, eight, nine, ten, fifteen, twenty, thirty, forty, or more) RNA guides. In some embodiments, the CRISPR systems described herein include a single RNA strand or a nucleic acid encoding a single RNA strand, wherein the RNA guides are arranged in tandem. The single RNA strand can include multiple copies of the same RNA guide, multiple copies of distinct RNA guides, or combinations thereof. The processing capability of the Type VI-D CRISPR-Cas effector proteins described herein enables these effectors to be able to target multiple target nucleic acids (e.g., target RNAs) without a loss of activity. In some embodiments, the Type VI-D CRISPR-Cas effector proteins may be delivered in complex with multiple RNA guides directed to different target nucleic acids. In some embodiments, the Type VI-D CRISPR-Cas effector proteins may be co-delivered with multiple RNA guides, each specific for a different target nucleic acid. Methods of multiplexing using CRISPR-associated proteins are described, for example, in U.S. Pat. No. 9,790,490 B2, and EP 3009511 B1, the entire contents of each of which are expressly incorporated herein by reference.

Spacer Lengths

The spacer length of crRNAs can range from about 15 to 50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides (e.g., 15, 16, or 17 nucleotides), from 17 to 20 nucleotides (e.g., 17, 18, 19, or 20 nucleotides), from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 36, 37, 38, 39, 40, 41, 42, 43, 44, or 45 nucleotides), from 30 or 35 to 40 nucleotides, from 41 to 45 nucleotides, from 45 to 50 nucleotides (e.g., 45, 46, 47, 48, 49, or 50 nucleotides), or longer. In some embodiments, the direct repeat length of the guide RNA is at least 16 nucleotides, or is from 16 to 20 nucleotides (e.g., 16, 17, 18, 19, or 20 nucleotides). In some embodiments, the spacer length is from about 15 to about 42 nucleotides. In some embodiments, the direct repeat length of the guide RNA is 19 nucleotides.

The crRNA sequences can be modified in a manner that allows for formation of a complex between the crRNA and CRISPR-associated protein and successful binding to the target, while at the same time not allowing for successful nuclease activity (i.e., without nuclease activity/without causing indels). These modified guide sequences are referred to as "dead crRNAs," "dead guides," or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR-associated protein as described herein, and a crRNA, wherein the crRNA comprises a dead crRNA sequence whereby the crRNA is capable of hybridizing to a target sequence such that the CRISPR system is directed to a genomic locus of interest in a cell without detectable nuclease activity (e.g., RNAse activity).

A detailed description of dead guides is described, e.g., in International Publication No. WO 2016/094872, which is incorporated herein by reference in its entirety.

Inducible Guides

Guide RNAs (e.g., crRNAs) can be generated as components of inducible systems. The inducible nature of the systems allows for spatio-temporal control of gene editing or gene expression. In some embodiments, the stimuli for the inducible systems include, e.g., electromagnetic radiation, sound energy, chemical energy, and/or thermal energy.

In some embodiments, the transcription of guide RNA (e.g., crRNA) can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical Modifications

Chemical modifications can be applied to the crRNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," Nucl. Acid Ther., 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," J. Med. Chem., 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," Front. Genet., 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized crRNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the crRNA includes one or more phosphorothioate modifications. In some embodiments, the crRNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," J. Biotechnol. 2016 Sep. 10; 233:74-83; WO 2016205764; and U.S. Pat. No. 8,795,965 B2; each which is incorporated by reference in its entirety.

Sequence Modifications

The sequences and the lengths of the RNA guides (e.g., crRNAs) described herein can be optimized. In some embodiments, the optimized length of an RNA guide can be determined by identifying the processed form of crRNA (i.e., a mature crRNA), or by empirical length studies for crRNA tetraloops.

The crRNAs can also include one or more aptamer sequences. Aptamers are oligonucleotide or peptide molecules have a specific three-dimensional structure and can bind to a specific target molecule. The aptamers can be specific to gene effectors, gene activators, or gene repressors. In some embodiments, the aptamers can be specific to a protein, which in turn is specific to and recruits and/or binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φkCb5, φkCb8r, φkCb12r, φkCb23r, 7s, and PRR1. Accordingly, in some embodiments, the aptamer is selected from binding proteins specifically binding any one of the adaptor proteins as described herein. In some embodiments, the aptamer sequence is a MS2 binding loop (5'-ggcccAACAUGAGGAUCACC-CAUGUCUGCAGgggcc-3' (SEQ ID NO: 169)). In some embodiments, the apatamer sequence is a QBeta binding loop (5'-ggcccAUGCUGUCUAAGACAGCAUgggcc-3' (SEQ ID NO: 170)). In some embodiments, the aptamer sequence is a PP7 binding loop (5'-ggcccUAAGG-GUUUAUAUGGAAACCCUUAgggcc-3' (SEQ ID NO: 173)). A detailed description of aptamers can be found, e.g., in Nowak et al., "Guide RNA engineering for versatile Cas9 functionality," *Nucl. Acid. Res.*, 2016 Nov. 16; 44(20):9555-9564; and WO 2016205764, which are incorporated herein by reference in their entirety.

Target Nucleic Acids

The target nucleic acids can be a DNA molecule or a RNA molecule. As described above, in some embodiments, the CRISPR-associated proteins described herein have RNAse activity. Thus, the target nucleic acids can be any RNA molecule of interest, including naturally-occurring and engineered RNA molecules. The target RNA can be an mRNA, a tRNA, a ribosomal RNA (rRNA), a microRNA (miRNA), an interfering RNA (siRNA), a ribozyme, a riboswitch, a satellite RNA, a microswitch, a microzyme, or a viral RNA.

In some embodiments, the target nucleic acid is associated with a condition or disease (e.g., an infectious disease or a cancer). Thus, in some embodiments, the systems described herein can be used to treat a condition or disease by targeting these nucleic acids. For instance, the target nucleic acid associated with a condition or disease may be an RNA molecule that is overexpressed in a diseased cell (e.g., a cancer or tumor cell). The target nucleic acid may also be a toxic RNA and/or a mutated RNA (e.g., an mRNA molecule having a splicing defect or a mutation). The target nucleic acid may also be an RNA that is specific for a particular microorganism (e.g., a pathogenic bacteria).

Guide: Target Sequence Matching Requirements

In classic CRISPR systems, the degree of complementarity between a guide sequence (e.g., a crRNA) and its corresponding target sequence can be about 50%, 60%, 75%, 80%, 85%, 90%, 95%, 97.5%, 99%, or 100%. In some embodiments, the degree of complementarity is 100%. The guide RNAs can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Target Nucleic Acids to Regulate Collateral RNAse Activity Activation

In some embodiments, the CRISPR systems described herein further comprise a target nucleic acid (e.g., a linear or circular nucleic acid) which may advantageously be used to activate the collateral RNAse activity of a Type VI-D CRISPR-Cas effector protein in a controlled manner. By regulating the expression and/or delivery of the target nucleic acid, the activation of the collateral RNAse activity of the effector protein may be controlled. For example, exogenous target nucleic acid may be included in the system to increase the activation rate of the collateral RNAse activity of a Type VI-D CRISPR-Cas effector protein. In some embodiments, the target nucleic acid is a DNA molecule. In some embodiments, the target nucleic acid is an RNA molecule (e.g., a mRNA molecule). In some embodiments, when the target nucleic acid is an RNA, the system includes a DNA molecule (e.g., a plasmid DNA) that codes for the target nucleic acid that is specifically targeted by the Type VI-D CRISPR-Cas effector protein and crRNA complex, operably linked to a promoter. In some embodiments, the promoter is an inducible promoter. In some embodiments, the promoter is a constitutive promoter.

Accessory Proteins

In one aspect, the CRISPR systems described herein includes at least one accessory protein. As shown in Example 4, the inventors have surprisingly discovered that the accessory proteins described herein enhance the nuclease activity of CRISPR-associated proteins (e.g., Type VI-D CRISPR-Cas effector proteins) as compared to the nuclease activity of the CRISPR associated protein in the absence of the accessory protein. The ability of the accessory proteins described herein to enhance the nuclease activity of CRISPR-associated proteins is particularly desirable in clinical and therapeutic applications. Therefore, CRISPR systems including at least one accessory protein are provided herein. For example, an accessory protein described herein may be used in combination with CRISPR-associated proteins known in the art in order to enhance their nuclease activity. Alternatively, an accessory protein may be used in combination with a Type VI-D CRISPR-Cas effector protein described herein to enhance its nuclease activity (e.g., collateral RNAse activity or targeted RNAse activity).

In some embodiments, the accessory protein includes a WYL domain (PFAM: PF13280), which has been predicted to be a ligand-sensing domain, which can regulate CRISPR-Cas systems. WYL domains are SH3 beta-barrel fold containing domains named for three conserved amino acids found in some domains belonging to the WYL-like superfamily. One WYL domain protein, sll7009, has been found to be a negative regulator of the *Synechocystis* sp. I-D CRISPR-Cas system (see, e.g., Hein et al. (2013) *RNA Biol.* 10: 852-64).

In some embodiments, the accessory protein includes at least one WYL domain. In some embodiments, the accessory protein includes two WYL domains. In some embodiments, the accessory protein includes a helix-turn-helix (HTH) fold. In some embodiments, the accessory protein includes a ribbon-helix-helix (RHH) fold.

In some embodiments, the accessory proteins describe herein modulate the RNAse activity of a CRISPR-associated protein. In some embodiments, the accessory protein modulates (e.g., increases or decreases) the collateral RNAse activity of a CRISPR-associated protein. In some embodiments, the accessory protein modulates (e.g., increases or decreases) the RNA-binding activity of a CRISPR-associated protein. In some embodiments, the accessory protein modulates (e.g., increases or decreases) the crRNA processing activity of a CRISPR-associated protein. In some embodiments, the accessory protein modulates (e.g., increases or decreases) the targeted RNAse activity of a CRISPR-associated protein.

In some embodiments, the accessory proteins described herein enhances the RNAse activity of a CRISPR-associated protein (e.g., a Cas13a protein, a Cas13b protein, a Cas13c protein, a Cas12a protein, a Cas9 protein). In some embodiments, the accessory protein enhances the collateral RNAse activity of a CRISPR-associated protein. In some embodiments, the accessory protein enhances the crRNA processing activity of a CRISPR-associated protein. In some embodiments, the accessory protein enhances the RNA-binding activity of a CRISPR-associated protein. In some embodiments, the accessory protein enhances the targeted RNAse activity of a CRISPR-associated protein. CRISPR systems comprising an accessory protein described herein are particularly useful in applications where increased sequence-specific or collateral RNA degradation is desirable. For example, in diagnostic applications, enhanced RNAse activity provides a greater degree of sensitivity, allowing the detection of lower concentrations of a target RNA. In some embodiments, an accessory protein described herein enhances the RNAse activity of the ternary complex of multiple CRISPR Type VI effectors. The ability of the accessory protein to enhance the RNAse of multiple effectors is particularly useful in applications where combinations of Type VI effectors of different sub-types are used together, for example in a multi-channel diagnostic applications. In some embodiments, the accessory protein can enhance the RNAse activity of Type VI effectors outside the Cas13d family thereby providing a valuable tool for screening the activity of uncharacterized Type VI effectors.

Exemplary accessory proteins are provided below in Tables 4, 5 and 6. In some embodiments, the accessory proteins include an amino acid sequence having at least about 80% identity to the amino acid sequence of any one of Tables 4, 5 and 6 (e.g., 81%, 82%, 83%, 84%, 85%, 86%, 87%, 88%, 89%, 90%, 91%, 92%, 93%, 94%, 95%, 96%, 97%, 98%, 99%, or 100% identity). In some embodiments, the accessory protein includes the amino acid sequence of any one of the proteins in Tables 4, 5 and 6. In some embodiments, the accessory protein is RspWYL1 (SEQ ID NO: 81).

Methods of Using CRISPR Systems

The CRISPR systems described herein have a wide variety of utilities including modifying (e.g., deleting, inserting, translocating, inactivating, or activating) a target polynucleotide or nucleic acid in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), controlling interfering RNA or miRNA, detecting circulating tumor DNA, preparing next generation library, drug screening, disease diagnosis and prognosis, and treating various genetic disorders.

DNA/RNA Detection

In one aspect, the CRISPR systems described herein can be used in DNA or RNA detection. CRISPR-associated proteins can be reprogrammed with CRISPR RNAs (crRNAs) to provide a platform for specific RNA sensing. Upon recognition of its RNA target, activated CRISPR-associated proteins engage in "collateral" cleavage of nearby non-targeted RNAs. This crRNA-programmed collateral cleavage activity allows the CRISPR systems to detect the presence of a specific RNA by triggering programmed cell death or by nonspecific degradation of labeled RNA.

The SHERLOCK method (Specific High Sensitivity Enzymatic Reporter UnLOCKing) provides an in vitro nucleic acid detection platform with attomolar sensitivity based on nucleic acid amplification and collateral cleavage of a reporter RNA, allowing for real-time detection of the target. To achieve signal detection, the detection can be combined with different isothermal amplification steps. For example, recombinase polymerase amplification (RPA) can be coupled with T7 transcription to convert amplified DNA to RNA for subsequent detection. The combination of amplification by RPA, T7 RNA polymerase transcription of amplified DNA to RNA, and detection of target RNA by collateral RNA cleavage-mediated release of reporter signal is referred as SHERLOCK. Methods of using CRISPR in SHERLOCK are described in detail, e.g., in Gootenberg, et al. "Nucleic acid detection with CRISPR-Cas13a/C2c2," *Science,* 2017 Apr. 28; 356(6336):438-442, which is incorporated herein by reference in its entirety.

The CRISPR-associated proteins can further be used in Northern blot assays, which use electrophoresis to separate RNA samples by size. The CRISPR-associated proteins can be used to specifically bind and detect the target RNA sequence. The CRISPR-associated proteins can also be fused to a fluorescent protein (e.g., GFP) and used to track RNA localization in living cells. More particularly, the CRISPR-associated proteins can be inactivated in that they no longer cleave RNAs as described above. Thus, CRISPR-associated proteins can be used to determine the localization of the RNA or specific splice variants, the level of mRNA transcripts, up- or down-regulation of transcripts and disease-specific diagnosis. The CRISPR-associated proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in International Publication No. WO 2017/070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science,* 2015 Apr. 24; 348(6233):aaa6090, which is incorporated herein by reference herein in its entirety.

In some embodiments, the CRISPR systems described herein can be used to detect a target RNA in a sample (e.g., a clinical sample, a cell, or a cell lysate). The collateral RNAse activity of the Type VI-D CRISPR-Cas effector proteins described herein is activated when the effector proteins bind to a target nucleic acid. Upon binding to the target RNA of interest, the effector protein cleaves a labeled detector RNA to generate a signal (e.g., an increased signal or a decreased signal) thereby allowing for the qualitative and quantitative detection of the target RNA in the sample. The specific detection and quantification of RNA in the sample allows for a multitude of applications including diagnostics. In some embodiments, the methods include contacting a sample with: i) an RNA guide (e.g., crRNA) and/or a nucleic acid encoding the RNA guide, wherein the RNA guide consists of a direct repeat sequence and a spacer sequence capable of hybridizing to the target RNA; (ii) a Type VI-D CRISPR-Cas effector protein and/or a nucleic acid encoding the effector protein; and (iii) a labeled detector RNA; wherein the effector protein associates with the RNA guide to form a complex; wherein the RNA guide hybridizes to the target RNA; and wherein upon binding of the complex to the target RNA, the effector protein exhibits collateral RNAse activity and cleaves the labeled detector RNA; and b) measuring a detectable signal produced by cleavage of the labeled detector RNA, wherein said measuring provides for detection of the single-stranded target RNA in the sample. In some embodiments, the methods further comprise comparing the detectable signal with a reference signal and determining the amount of target RNA in the sample. In some embodiments, the measuring is performed using gold nanoparticle detection, fluorescence polarization, colloid phase transition/dispersion, electrochemical detection, and semiconductor based-sensing. In some embodiments, the labeled detector RNA includes a fluorescence-emitting dye pair, a fluorescence resonance energy transfer (FRET) pair, or a quencher/fluor pair. In some embodiments, upon cleavage of the labeled detector RNA by the effector protein, an amount of detectable signal produced by the labeled detector RNA is decreased or increased. In some embodiments, the labeled detector RNA produces a first detectable signal prior to cleavage by the effector protein and a second detectable signal after cleavage by the effector protein. In some embodiments, a detectable signal is produced when the labeled detector RNA is cleaved by the effector protein. In some embodiments, the labeled detector RNA comprises a modified nucleobase, a modified sugar moiety, a modified nucleic acid linkage, or a combination thereof. In some embodiments, the methods include the multi-channel detection of multiple independent target RNAs in a sample (e.g., two, three, four, five, six, seven, eight, nine, ten, fifteen, twenty, thirty, forty, or more target RNAs) by using multiple Type VI-D CRISPR-Cas systems, each including a distinct orthologous effector protein and corresponding RNA guides, allowing for the differentiation of multiple target RNAs in the sample. In some embodiments, the methods include the multi-channel detection of multiple independent target RNAs in a sample, with the use of multiple instances of Type VI-D CRISPR-Cas systems, each containing an orthologous effector protein with differentiable collateral RNAse substrates. Methods of detecting an RNA in a sample using CRISPR-associated proteins are described, for example, in U.S. Patent Publication No. 2017/0362644, the entire contents of which are incorporated herein by reference.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The CRISPR-associated proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965, WO 2016205764, and WO 2017070605; each of which is incorporated herein by reference herein in its entirety.

RNA Isolation, Purification, Enrichment, and/or Depletion

The CRISPR systems (e.g., CRISPR-associated proteins) described herein can be used to isolate and/or purify the RNA. The CRISPR-associated proteins can be fused to an affinity tag that can be used to isolate and/or purify the RNA-CRISPR-associated protein complex. These applications are useful, e.g., for the analysis of gene expression profiles in cells.

In some embodiments, the CRISPR-associated proteins can be used to target a specific noncoding RNA (ncRNA) thereby blocking its activity. In some embodiments, the CRISPR-associated proteins can be used to specifically enrich a particular RNA (including but not limited to increasing stability, etc.), or alternatively, to specifically deplete a particular RNA (e.g., particular splice variants, isoforms, etc.).

These methods are described, e.g., in U.S. Pat. No. 8,795,965, WO 2016205764, and WO 2017070605; each of which is incorporated herein by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR-associated protein transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics*, 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, crRNAs that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of Saccharomyces cerevisiae," Yeast, 2017 Sep. 8. doi: 10.1002/yea.3278; and Hlavova et al., "Improving microalgae for biotechnology—from genetics to synthetic biology," Biotechnol. Adv., 2015 Nov. 1; 33:1194-203, both of which are incorporated herein by reference in the entirety.

In some embodiments, the CRISPR systems provided herein can be used to induce death or dormancy of a cell (e.g., a microorganism such as an engineered microorganism). These methods can be used to induce dormancy or death of a multitude of cell types including prokaryotic and eukaryotic cells, including, but not limited to mammalian cells (e.g., cancer cells, or tissue culture cells), protozoans, fungal cells, cells infected with a virus, cells infected with an intracellular bacteria, cells infected with an intracellular protozoan, cells infected with a prion, bacteria (e.g., pathogenic and non-pathogenic bacteria), protozoans, and unicellular and multicellular parasites. For instance, in the field of synthetic biology it is highly desirable to have mechanisms of controlling engineered microorganisms (e.g., bacteria) in order to prevent their propagation or dissemination. The systems described herein can be used as "kill-switches" to regulate and/or prevent the propagation or dissemination of an engineered microorganism. Further, there is a need in the art for alternatives to current antibiotic treatments. The systems described herein can also be used in applications where it is desirable to kill or control a specific microbial population (e.g., a bacterial population). For example, the systems described herein may include an RNA guide (e.g., a crRNA) that targets a nucleic acid (e.g., an RNA) that is genus-, species-, or strain-specific, and can be delivered to the cell. Upon complexing and binding to the target nucleic acid, the collateral RNAse activity of the Type VI-D CRISPR-Cas effector proteins is activated leading to the cleavage of non-target RNA within the microorganisms, ultimately resulting in dormancy or death. In some embodiments, the methods comprise contacting the cell with a system described herein including a Type VI-D CRISPR-Cas effector proteins or a nucleic acid encoding the effector protein, and a RNA guide (e.g., a crRNA) or a nucleic acid encoding the RNA guide, wherein the spacer sequence is complementary to at least 15 nucleotides (e.g., 16, 17, 18, 19, 20, 21, 22, 23, 24, 25, 26, 27, 28, 29, 30, 35, 40, 45, 50 or more nucleotides) of a target nucleic acid (e.g., a genus-, strain-, or species-specific RNA guide). Without wishing to be bound by any particular theory, the cleavage of non-target RNA by the Type VI-D CRISPR-Cas effector proteins may induce programmed cell death, cell toxicity, apoptosis, necrosis, necroptosis, cell death, cell cycle arrest, cell anergy, a reduction of cell growth, or a reduction in cell proliferation. For example, in bacteria, the cleavage of non-target RNA by the Type VI-D CRISPR-Cas effector proteins may be bacteriostatic or bacteriocidal.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," Curr. Opin. Allergy Clin. Immunol., 2011 June; 11(3):222-8, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector Anopheles gambiae," Nat. Biotechnol., 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," Nat. Methods., 2017 March; 14(3):297-301, which is incorporated herein by reference in its entirety.

Saturation Mutagenesis (Bashing)

The CRISPR systems described herein can be used for in situ saturating mutagenesis. In some embodiments, a pooled guide RNA library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577):192-7, which is incorporated herein by reference in its entirety.

RNA-Related Applications

The CRISPR systems described herein can have various RNA-related applications, e.g., modulating gene expression, degrading a RNA molecule, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016/205764 A1, which is incorporated herein by reference in its entirety. In different embodiments, the methods described herein can be performed in vitro, in vivo, or ex vivo.

For example, the CRISPR systems described herein can be administered to a subject having a disease or disorder to target and induce cell death in a cell in a diseased state (e.g., cancer cells or cells infected with an infectious agent). For instance, in some embodiments, the CRISPR systems described herein can be used to target and induce cell death in a cancer cell, wherein the cancer cell is from a subject having a Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, or urinary bladder cancer.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the CRISPR-associated proteins and suitable crRNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins in combination with suitable guide RNAs to target the riboswitches. This may be achieved through cleavage of, or binding to, the riboswitch. Methods of using CRISPR systems to control riboswitches are described, e.g., in WO 2016205764 and WO 2017070605, both of which are incorporated herein by reference in their entireties.

RNA Modification

In some embodiments, the CRISPR-associated proteins described herein can be fused to a base-editing domain, such as ADAR1, ADAR2, APOBEC, or activation-induced cytidine deaminase (AID), and can be used to modify an RNA sequence (e.g., an mRNA). In some embodiments, the CRISPR-associated protein includes one or more mutations (e.g., in a catalytic domain), which renders the CRISPR-associated protein incapable of cleaving RNA.

In some embodiments, the CRISPR-associated proteins can be used with an RNA-binding fusion polypeptide comprising a base-editing domain (e.g., ADAR1, ADAR2, APOBEC, or AID) fused to an RNA-binding domain, such as MS2 (also known as MS2 coat protein), Qbeta (also known as Qbeta coat protein), or PP7 (also known as PP7 coat protein). The amino acid sequences of the RNA-binding domains MS2, Qbeta, and PP7 are provided below:

```
MS2 (MS2 coat protein)
                              (SEQ ID NO: 171)
MASNFTQFVLVDNGGTGDVTVAPSNFANGVAEWISSNSRSQAYKVTCSVR
QSSAQKRKYTIKVEVPKVATQTVGGVELPVAAWRSYLNMELTIPIFATNS
DCELIVKAMQGLLKDGNPIPSAIAANSGIY Qbeta (Qbeta coat protein)
                              (SEQ ID NO: 172)
MAKLETVTLGNIGKDGKQTLVLNPRGVNPTNGVASLSQAGAVPALEKRVT
VSVSQPSRNRKNYKVQVKIQNPTACTANGSCDPSVTRQAYADVTFSFTQY
STDEERAFVRTELAALLASPLLIDAIDQLNPAY
```

-continued

PP7 (PP7 coat protein)
(SEQ ID NO: 155)
MSKTIVLSVGEATRTLTEIQSTADRQIFEEKVGPLVGRLRLTASLRQNGA
KTAYRVNLKLDQADVVDCSTSVCGELPKVRYTQVWSHDVTIVANSTEASR
KSLYDLTKSLVVQATSEDLVVNLVPLGR In some embodiments, the RNA binding domain can bind to a specific sequence (e.g., an aptamer sequence) or secondary structure motifs on a crRNA of the system described herein (e.g., when the crRNA is in an effector-crRNA complex), thereby recruiting the RNA binding fusion polypeptide (which has a base-editing domain) to the effector complex. For example, in some embodiments, the CRISPR system includes a CRISPR associated protein, a crRNA having an aptamer sequence (e.g., an MS2 binding loop, a QBeta binding loop, or a PP7 binding loop), and a RNA-binding fusion polypeptide having a base-editing domain fused to an RNA-binding domain that specifically binds to the aptamer sequence. In this system, the CRISPR-associated protein forms a complex with the crRNA having the aptamer sequence. Further the RNA-binding fusion polypeptide binds to the crRNA (via the aptamer sequence) thereby forming a tripartite complex that can modify a target RNA.

Methods of using CRISPR systems for base editing are described, e.g., in International Publication No. WO 2017/219027, which is incorporated herein by reference in its entirety, and in particular with respect to its discussion of RNA modification.

RNA Splicing

In some embodiments, an inactivated CRISPR-associated protein described herein (e.g., a CRISPR associated protein having one or more mutations in a catalytic domain) can be used to target and bind to specific splicing sites on RNA transcripts. Binding of the inactivated CRISPR-associated protein to the RNA may sterically inhibit interaction of the spliceosome with the transcript, enabling alteration in the frequency of generation of specific transcript isoforms. Methods of using CRISPR systems to alter splicing are described, e.g., in International Publication No. WO 2017/219027, which is incorporated herein by reference in its entirety, and in particular with respect to its discussion of RNA splicing.

Therapeutic Applications

The CRISPR systems described herein can have various therapeutic applications. In some embodiments, the new CRISPR systems can be used to treat various diseases and disorders, e.g., genetic disorders (e.g., monogenetic diseases), diseases that can be treated by nuclease activity (e.g., Pcsk9 targeting, Duchenne Muscular Dystrophy (DMD), BCL11a targeting), and various cancers, etc.

In some embodiments, the CRISPR systems described herein can be used to edit a target nucleic acid to modify the target nucleic acid (e.g., by inserting, deleting, or mutating one or more nucleic acid residues). For example, in some embodiments the CRISPR systems described herein comprise an exogenous donor template nucleic acid (e.g., a DNA molecule or a RNA molecule), which comprises a desirable nucleic acid sequence. Upon resolution of a cleavage event induced with the CRISPR system described herein, the molecular machinery of the cell will utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to alter a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double stranded or single stranded nucleic acid molecules (e.g., DNA or RNA). Methods of designing exogenous donor template nucleic acids are described, for example, in International Publication No. WO 2016/094874 A1, the entire contents of which are expressly incorporated herein by reference.

In one aspect, the CRISPR systems described herein can be used for treating a disease caused by overexpression of RNAs, toxic RNAs, and/or mutated RNAs (e.g., splicing defects or truncations). For example, expression of toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," Hum. Mol. Genet., 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," Cell, 136.4 (2009): 777-793, and WO 2016/205764 A1, both of which are incorporated herein by reference in the entirety. Those of skill in this field will understand how to use the new CRISPR systems to treat these diseases.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can further be used for antiviral activity, in particular against RNA viruses. The CRISPR-associated proteins can target the viral RNAs using suitable guide RNAs selected to target viral RNA sequences.

The CRISPR systems described herein can also be used to treat a cancer in a subject (e.g., a human subject). For example, the CRISPR-associated proteins described herein can be programmed with crRNA targeting a RNA molecule that is aberrant (e.g., comprises a point mutation or are alternatively-spliced) and found in cancer cells to induce cell death in the cancer cells (e.g., via apoptosis).

Further, the CRISPR systems described herein can also be used to treat an infectious disease in a subject. For example, the CRISPR-associated proteins described herein can be programmed with crRNA targeting a RNA molecule expressed by an infectious agent (e.g., a bacteria, a virus, a parasite or a protozoan) in order to target and induce cell death in the infectious agent cell. The CRISPR systems may also be used to treat diseases where an intracellular infectious agent infects the cells of a host subject. By programming the CRISPR-associated protein to target a RNA molecule encoded by an infectious agent gene, cells infected with the infectious agent can be targeted and cell death induced.

Furthermore, in vitro RNA sensing assays can be used to detect specific RNA substrates. The CRISPR-associated proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605; each of which is incorporated herein by reference in its entirety.

Delivery

Through this disclosure and the knowledge in the art, the CRISPR systems described herein, or components thereof, nucleic acid molecules thereof, and/or nucleic acid molecules encoding or providing components thereof, can be delivered by various delivery systems such as vectors, e.g., plasmids and viral delivery vectors. The CRISPR-associated proteins and/or any of the RNAs (e.g., guide RNAs or crRNAs) and/or accessory proteins can be delivered using suitable vectors, e.g., plasmids or viral vectors, such as adeno-associated viruses (AAV), lentiviruses, adenoviruses, and other viral vectors, or combinations thereof. The proteins and one or more crRNAs can be packaged into one or more vectors, e.g., plasmids or viral vectors. For bacterial applications, the nucleic acids encoding any of the components of the CRISPR systems described herein can be delivered to the bacteria using a phage. Exemplary phages, include, but are not limited to, T4 phage, Mu, λ phage, T5 phage, T7 phage, T3 phage, Φ29, M13, MS2, Qβ, and ΦX174.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least $1\times10^5$ particles (also referred to as particle units, pu) of adenoviruses. In some embodiments, the dose preferably is at least about $1\times10^6$ particles, at least about $1\times10^7$ particles, at least about $1\times10^8$ particles, and at least about $1\times10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR-associated proteins and/or an accessory protein, each operably linked to a promoter (e.g., the same promoter or a different promoter); (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofection formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR-associated proteins. In some embodiments, the CRISPR-associated proteins and/or guide RNAs are coupled to one or more CPPs to effectively transport them inside cells (e.g., plant protoplasts). In some embodiments, the CRISPR-associated proteins and/or guide RNA(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hällbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764 A1; each of which is incorporated herein by reference in its entirety.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

EXAMPLES

The invention is further described in the following examples, which do not limit the scope of the invention described in the claims.

Example 1—Building an Expanded Database of CRISPR-Cas Systems, and Searching for Type VI-D RNA-Targeting Systems We developed a computational pipeline to produce an expanded database of class 2 CRISPR-Cas systems from genomic and metagenomic sources. Genome and metagenome sequences were downloaded from NCBI (Benson et al., 2013; Pruitt et al., 2012), NCBI whole genome sequencing (WGS), and DOE JGI Integrated Microbial Genomes (Markowitz et al., 2012). Proteins were predicted (MetaGeneMark (Zhu et al., 2010) using the standard model MetaGeneMark_v1.mod, and Prodigal (Hyatt et al., 2010) in anon mode) on all contigs at least 5 kb in length, and de-duplicated in favor of pre-existing annotations to construct a complete protein database. CRISPR arrays were identified and protein sequences for ORFs located within +/−10 kb from CRISPR arrays were grouped into CRISPR-proximal protein clusters. Clusters of fewer than 4 proteins, or comprising proteins from fewer than 3 contigs were discarded. Each of these remaining protein clusters were considered to be a putative effector of a CRISPR-Cas system. In addition to the CRISPR array and putative effector protein, many CRISPR-Cas systems also include additional proteins that enable adaptation, crRNA processing, and defense. Potential additional CRISPR-Cas system components associated with each of the predicted effectors were identified as clusters of protein-coding genes with high effector co-occurrence, and CRISPR enrichment or CRISPR representation of at least 15%.

Effector co-occurrence was calculated as the percentage of loci containing the effector that also contain the potential co-occurring protein. The high co-occurrence threshold was a function of the cohesiveness of the effector cluster (more homogenous clusters requiring a higher threshold). The CRISPR enrichment was calculated as follows: 1) Up to 20 unique proteins were sampled from each protein cluster, and UBLAST (Edgar, 2010) was used to generate a rank ordered list of proteins by E-value from the complete protein database, 2) An E-value threshold was imposed to recover at least 50% of the members of the cluster, and 3) CRISPR enrichment was calculated by dividing the number of CRISPR-proximal proteins below the E-value threshold by the total number of proteins below the threshold. CRISPR representation was calculated as the percentage of effector-proximal proteins in a CRISPR-proximal protein cluster. All clustering operations were performed using mmseqs2 (Steinegger and Söding, 2017).

This information was incorporated into a database of (predicted) CRISPR-Cas systems, each composed of: 1) a CRISPR array, 2) a putative effector, and optionally, 3) clusters of potential co-acting proteins. Aggregating and processing a collection of more than 10 Tb of prokaryotic genomic and metagenomic sequence data from multiple sources, our pipeline produced a database of 293,985 putative CRISPR-Cas systems. One important difference from previously reported computational pipelines (Shmakov et al., 2015; Smargon et al., 2017) is that we perform minimal filtering (e.g., imposing a minimum size on putative effector) in the intermediate stages of the search in order to expand the range for potential discovery of novel CRISPR-Cas systems. As such, the resulting database of putative CRISPR-Cas loci includes all previously characterized class 2 CRISPR-Cas systems, but also contains a considerable amount of noise, such as degraded, non-functional CRISPR-Cas loci.

For functional characterization of this database of candidate CRISPR-Cas systems, we constructed multiple sequence alignment for each family of putative effectors using MAFFT (Katoh and Standley, 2013) and conducted an HMM search using HMMer (Eddy, 2011) against protein family databases Pfam (Finn et al., 2014) and Uniprot (Bateman et al., 2017), as well as a BLASTN search of CRISPR spacer sequences against a reference set of phages. This analysis led to the detection of protein families corresponding to all previously identified class 2 CRISPR-Cas systems, indicating a minimal false negative rate. To identify novel class 2 CRISPR-Cas systems, features included above for the prediction of the functions of putative CRISPR-Cas systems were used to rank candidate families for follow-up functional evaluation.

Genomic Survey of Type VI-D RNA-Targeting CRISPR-Cas Systems

Figure 4A:
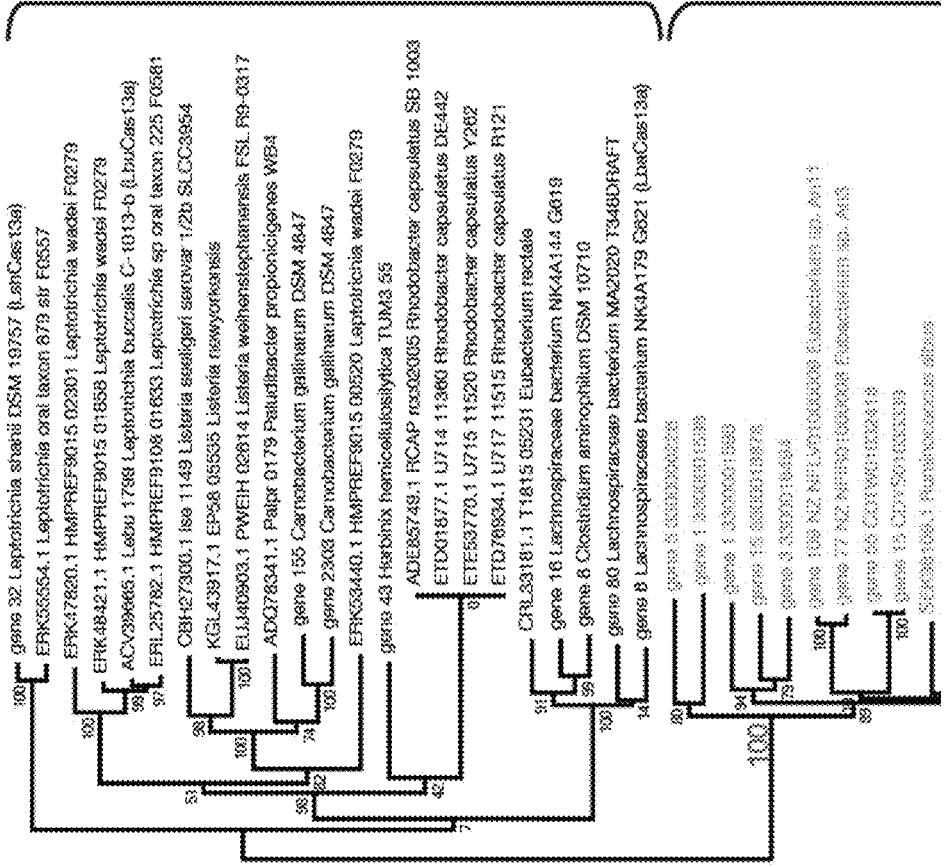
Figure 4B:
Figure 5A:
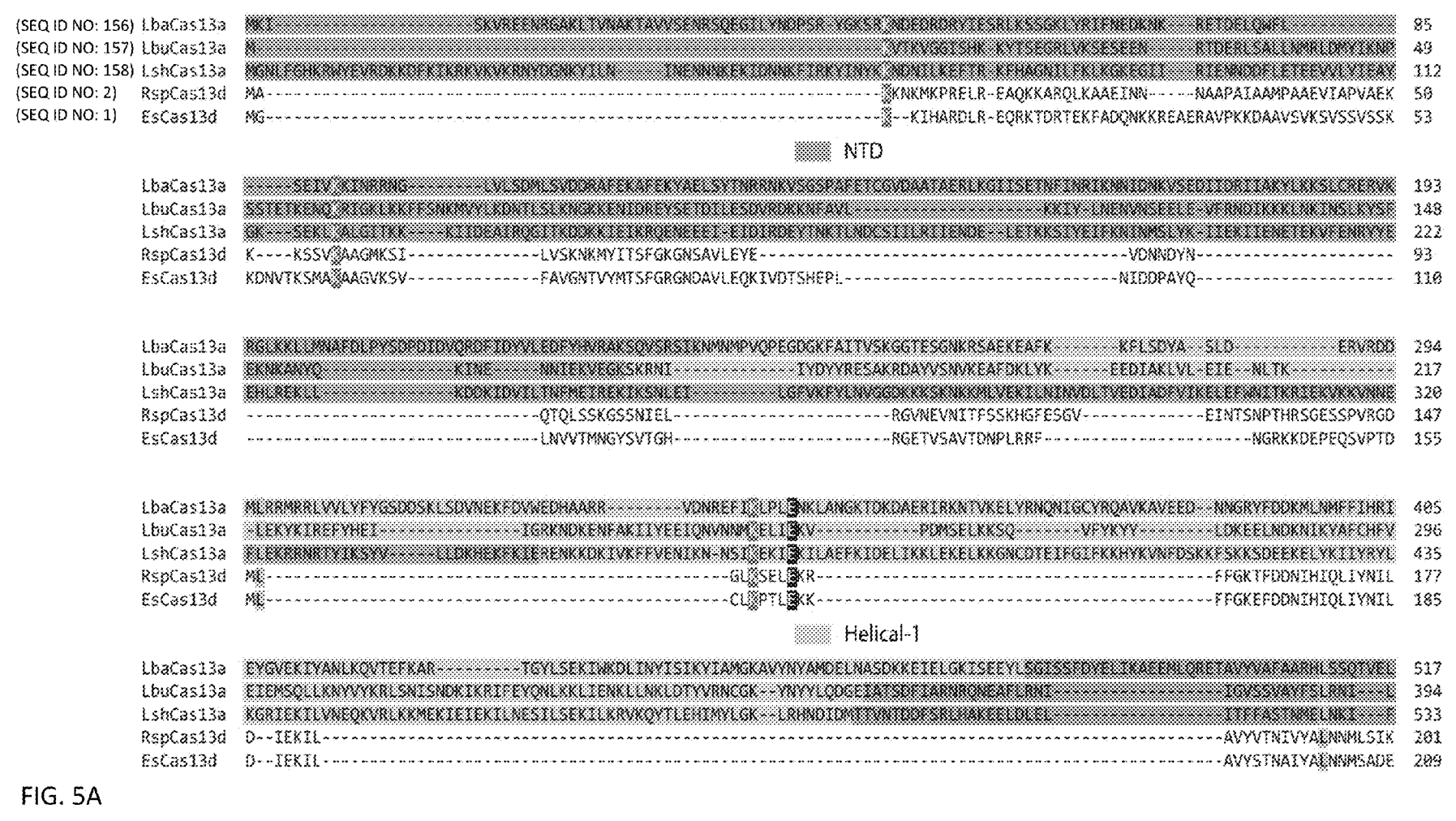
Figure 5B:
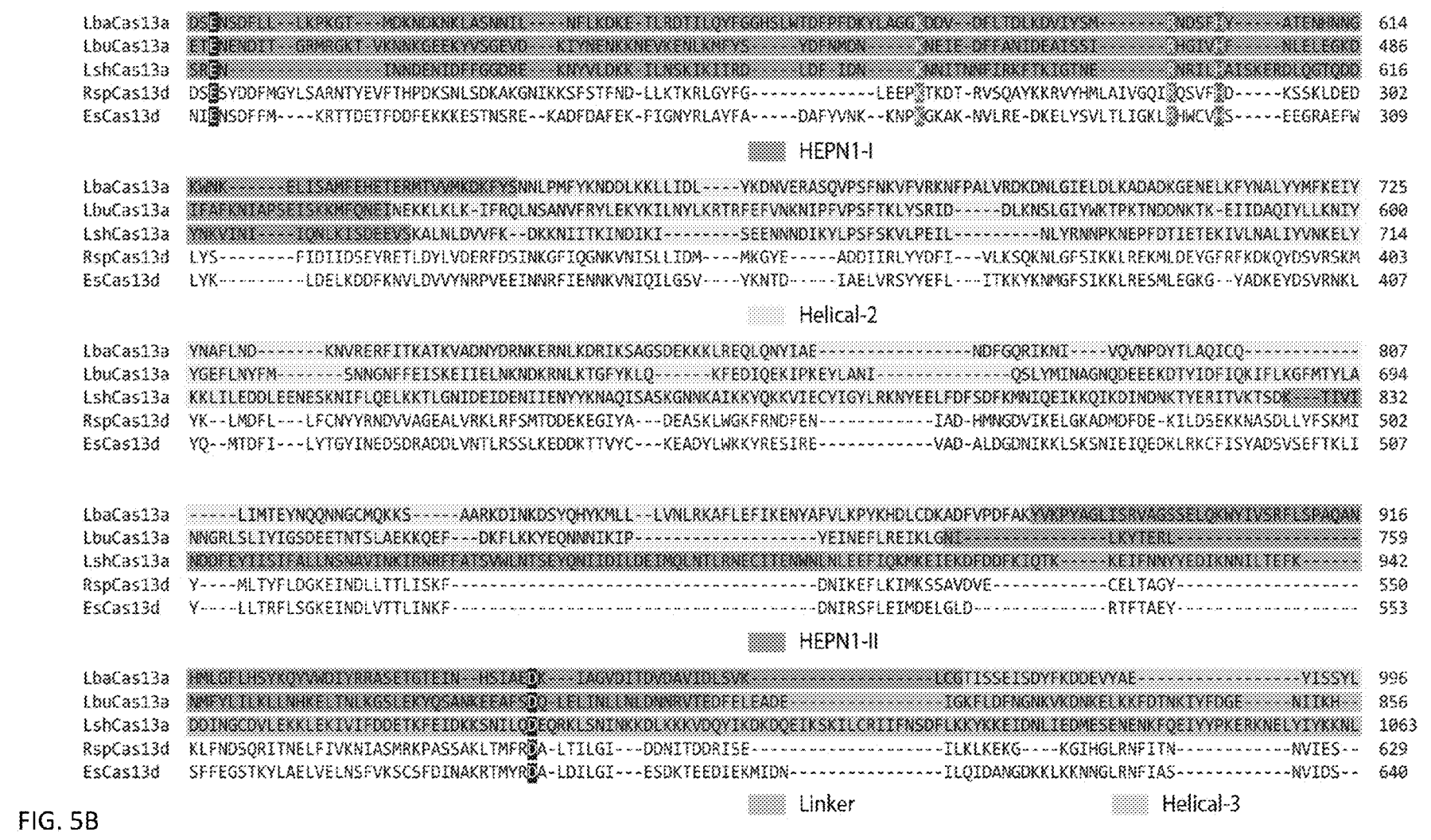
Figure 5C:
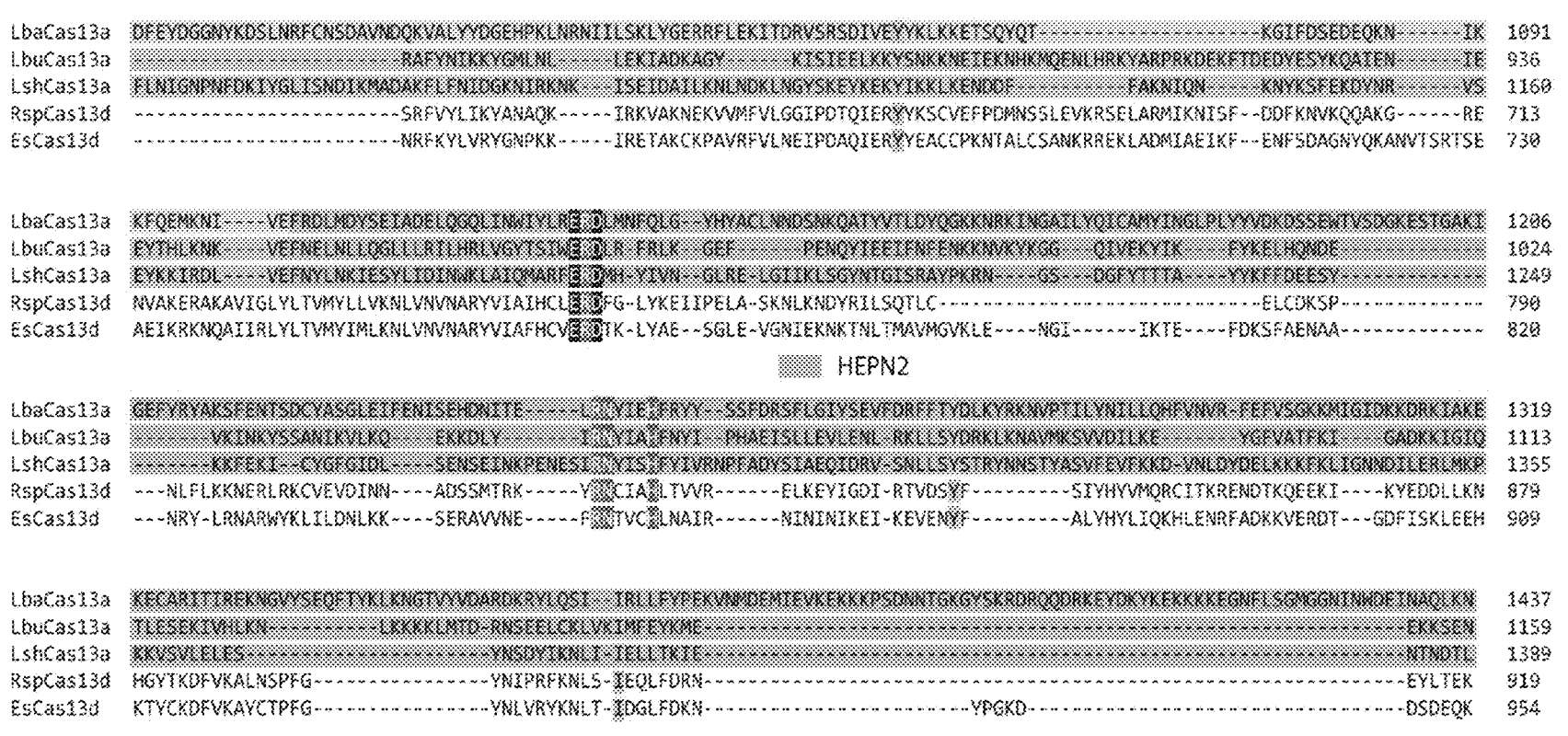

To expand the repertoire of Cas nucleases for RNA manipulation and sensing, we searched our database for type VI CRISPR-Cas systems with effector proteins containing two HEPN-domains each (2-HEPN proteins). In addition to the previously identified 2-HEPN proteins, Cas13a, Cas13b, and Cas13c, we detected a group of 2-HEPN proteins distantly related to Cas13a (effectors of type VI-A), primarily in *Eubacterium* and *Ruminococcus*, which we denote Cas13d. The amino acid sequences of Cas13d proteins show less than 8% identity to the most similar Cas13a sequences; nevertheless, statistically significant sequence similarity between Cas13d and Cas13a can be demonstrated using PSI-BLAST initiated with a profile made from the multiple alignment of Cas13a (E-value=0.002). This significant similarity is primarily due to the conservation of the HEPN domain sequences between Cas13a and Cas13d, whereas the remaining portions of the protein sequences in the two families are highly divergent; in particular, Cas13d proteins lack a counterpart to the Helical-1 domain of Cas13a (FIGS. 5A-C). Phylogenetic analysis of the Cas13 proteins clearly shows that Cas13a and Cas13d form strongly supported clades (FIGS. 4A-B).

Figure 2A:
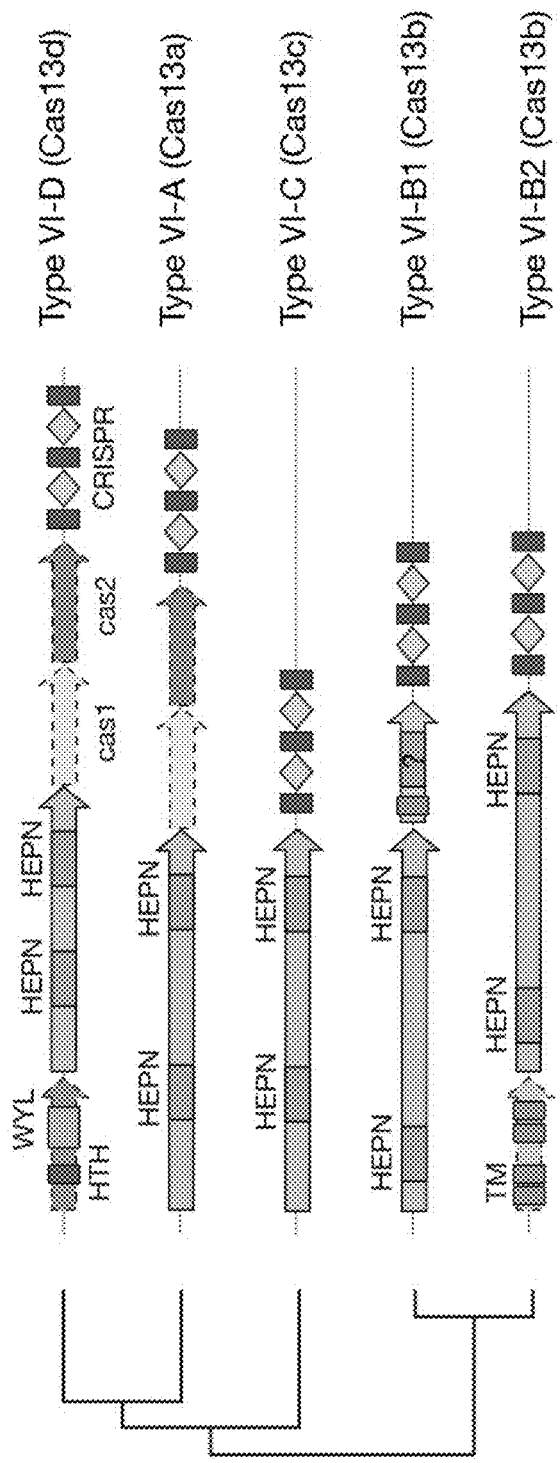
Figure 2B:
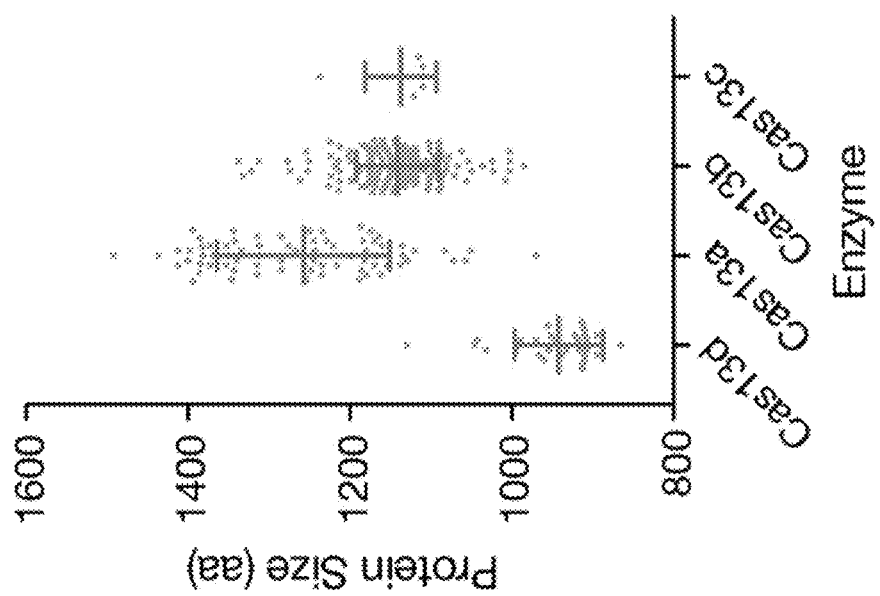

Additionally, Cas13d effectors are notably smaller than previously characterized class 2 CRISPR effectors, with a median size of 928 aa. For comparison, this median size is 190 aa (17%) less than that of Cas13c, more than 200 aa (18%) less than that of Cas13b, and more than 300 aa (26%) less than that of Cas13a (FIG. 2B). Taken together, these lines of evidence suggest that this distinct group of class 2 CRISPR-Cas systems are best classified as Type VI-D, with the effector denoted Cas (FIG. 2A).

Figure 3:
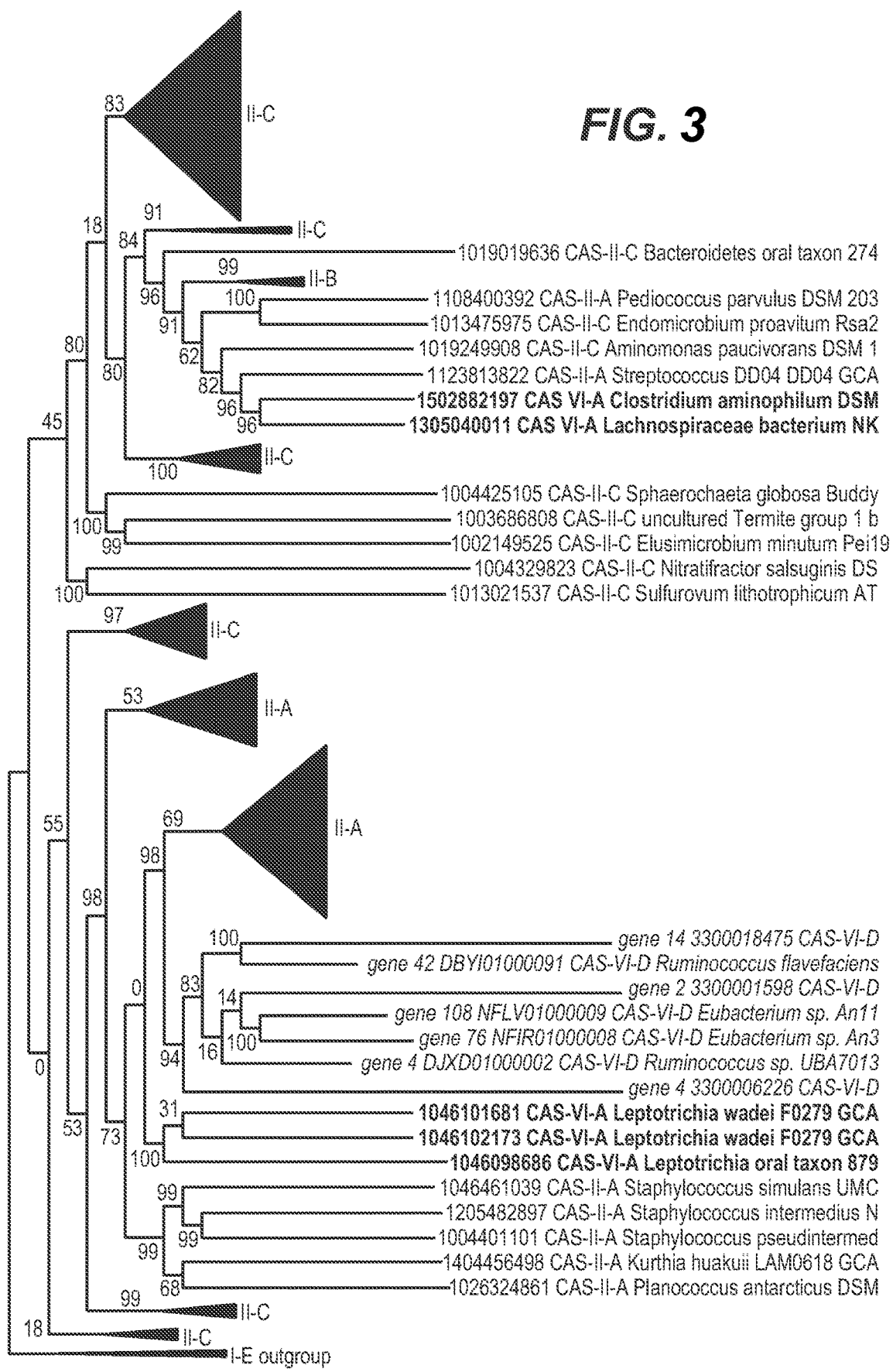

We found that 77% of Cas13d genes occur adjacent to CRISPR arrays, and for 19%, the adaptation module (Cas1 and Cas2 genes) is present in the vicinity (FIG. 1), suggesting that many Type VI-D loci encode CRISPR-Cas systems that are active in both adaptation and interference. Phylogenetic analysis indicates that Cas1 proteins associated with Type VI-D are monophyletic and, in accord with previous observations on other type VI systems, are affiliated with the type II-A clade (FIG. 3). Thus, in the case of type VI, the adaptation module seems to have co-evolved with the effector module.

Spacer sequences from CRISPR arrays within 3 kb of Cas13d effectors were extracted. In the case of multiple contigs containing the same Cas13d sequence (e.g., duplicated locus), only the contig containing the longest CRISPR array was used. Subsequent spacer analysis closely follows the method described previously (Shmakov et al., 2017b). Briefly, the resulting 198 spacers were de-duplicated by comparison of direct and reverse complement sequences, to produce a set of 182 unique spacers. A BLASTN (Camacho et al., 2009) search with the command line parameters- word_size 7-gapopen 5-gapextend 2-reward 1-penalty-3 was performed for the unique spacer set against a database comprising the virus and prokaryotic sequences in NCBI. To identify prophage regions, (i) all ORFs within 3 kb of prokaryotic matches were collected; (ii) a PSI-BLAST search was conducted against the proteins extracted from the virus part of NCBI, using the command line parameters -seg no -evalue 0.000001-dbsize 20000000; and (iii) a spacer hit was classified as prophage if it overlapped with an ORF with a viral match, or if two or more ORFs with viral matches were identified within the neighborhood of the spacer hit.

The CRISPR arrays adjacent to Cas13d genes contain 198 spacers total, of which 182 are unique. A BLASTN search of the unique spacer sequences against a database comprising known phages and NCBI prokaryotic sequences revealed 7 spacers with significant hits (defined as E-value<0.0001, alignment length at least 24, 0 gaps, and no more than one mismatch). One spacer, from *Ruminococcus flavefaciens* FD-1, showed significant matches against the *Arthrobacter* dsDNA phage Gordon (alignment length=28, 1 mismatch) and against a putative prophage region in an uncultured *Flavonifractor* sequence (alignment length=24, 0 mismatches). A different spacer, from a gut metagenome sequence, resulted in a significant match against a putative prophage region in *Bacillus soli* (alignment length=24, 0 mismatches). The remaining five spacer matches targeted ORFs in prokaryotic sequences, but were not classified as being in prophage regions. The presence of spacers homologous to DNA phage genomic sequences in an RNA-targeting CRISPR-Cas system might appear unexpected but is in line with similar observations on type VI-A and type VI-B systems (Smargon et al., 2017). Presumably, type VI systems abrogate the reproduction of DNA phages by cleaving phage mRNAs, but the mechanistic details of the antivirus activity of these systems remain to be characterized experimentally.

Figure 6:
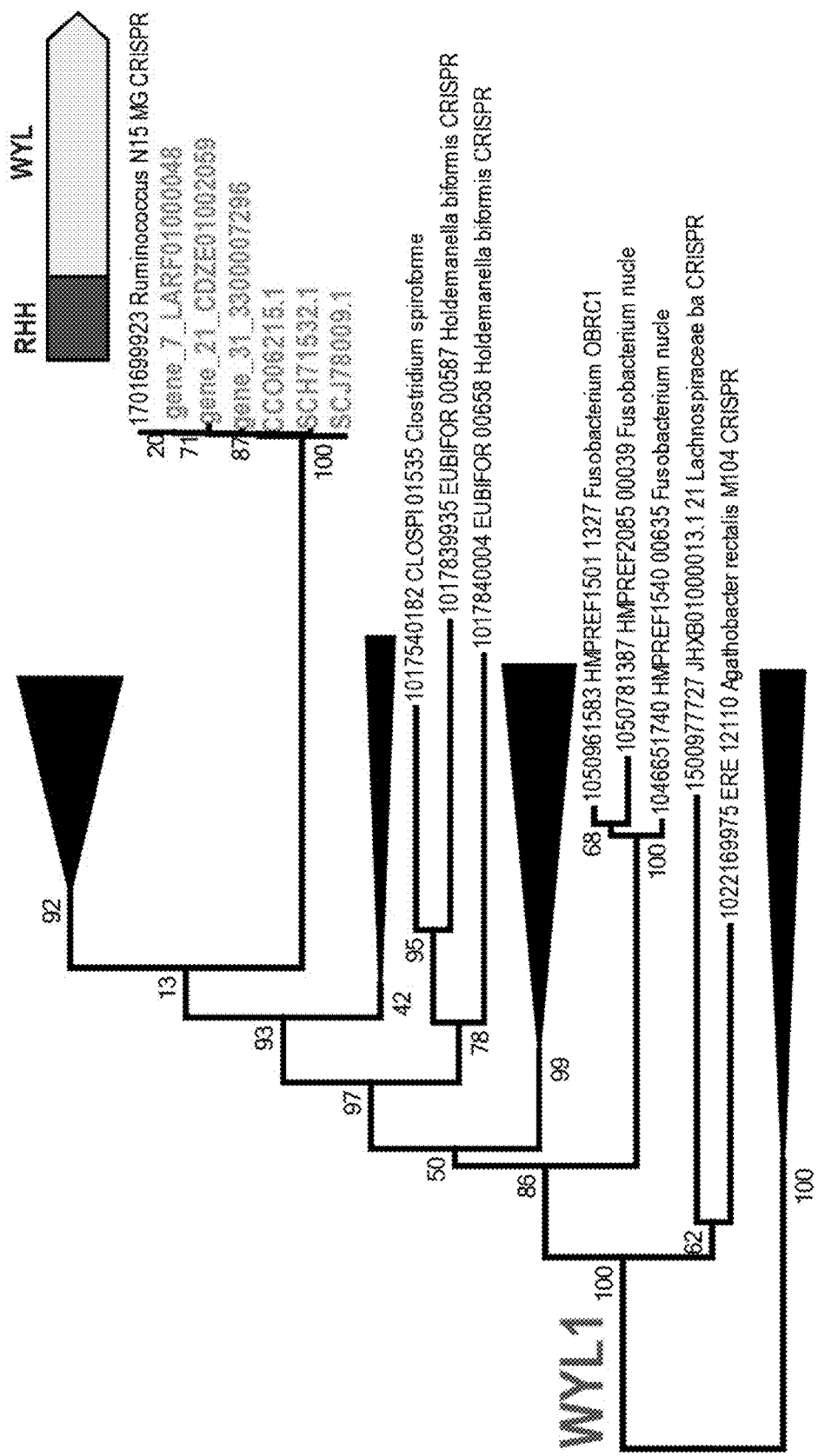

Examination of the additional genes in the vicinity of Cas13d led to the identification in most of the VI-D loci of potential accessory proteins containing WYL domains (so denoted after three amino acids that were conserved in the originally identified group of these domains) and additionally, ribbon-helix-helix (RHH) DNA-binding domains (FIG. 6).

For phylogenetic analysis of these Cas13d-associated WYL-domain containing proteins, we compiled a data set of WYL proteins. In addition to automatically identified WYL proteins, we used PSI-BLAST (Altschul et al., 1997) to search over a local set of NCBI sourced proteins using RspWYL1 as a query. The results with E-value 0.01 or lower were added to the set of WYL proteins. Proteins smaller than 150 aa were discarded from the data set, and UCLUST (Edgar, 2010) with identity threshold 0.90 was used to obtain a non-redundant set. We then added all WYL proteins identified in the vicinity of Cas13d genes to form a set of 3908 WYL sequences for phylogenetic analysis. Multiple alignment and phylogeny of protein sequences were constructed as described previously (Peters et al., 2017).

Figure 7:
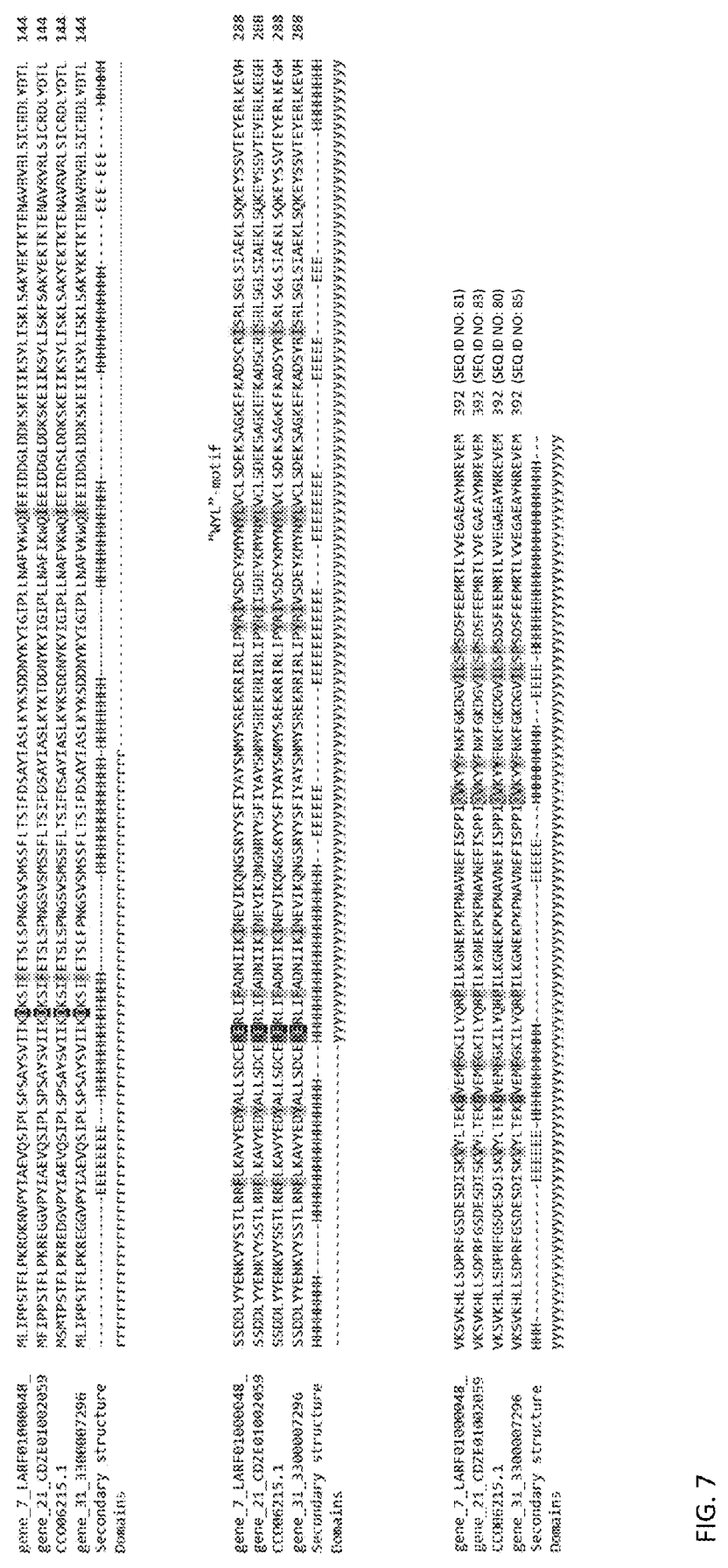

Briefly, the sequences were clustered by similarity, and for each cluster, a multiple alignment was built using MUSCLE (Edgar, 2004). Alignments were combined into larger aligned clusters by HHalign (Yu et al., 2015) if the resulting score between the two alignments was higher than the threshold; otherwise, the scores were recorded in a similarity matrix. The matrix was used to reconstruct a UPGMA tree. For each cluster, the alignment was filtered as follows: the alignment positions with the gap character fraction values of 0.5 and homogeneity values of 0.1 or less were removed. The remaining positions were used for tree reconstruction using FastTree with the WAG evolutionary model and the discrete gamma model with 20 rate categories. The same program was used to compute SH (Shimodaira-Hasegawa)-like node support values The WYL-domain proteins contained in Type VI-D loci fall into six strongly supported branches of the broader phylogenetic tree of WYL-domain proteins. The branch we denote WYL1 is a single WYL-domain protein associated primarily with *Ruminococcus*. Multiple sequence alignment of WYL1 shows an N-terminal RHH domain, as well as a pattern of primarily hydrophobic conserved residues, including an invariant tyrosine-leucine doublet corresponding to the original WYL motif (FIG. 7). Other VI-D loci contain duplicated genes encoding WYL-domain proteins, as in *Ruminococcus flavefaciens*, or a fusion of two WYL-domain proteins, as in *Eubacterium* sp. Although a substantial majority of the VI-D loci encode WYL-domain proteins, phylogenetic analysis indicates that these CRISPR-associated WYL proteins are scattered among different branches of the WYL family tree, i.e., are polyphyletic. Thus, the VI-D CRISPR-Cas systems appear to have acquired WYL-domain proteins on several independent occasions, suggesting a role for this protein in modulating the CRISPR-Cas function.

Exemplary Type VI-D CRISPR-Cas effector proteins are provided in TABLES 1 and 2. Exemplary Type VI-D CRISPR-Cas direct repeat sequences are provided in TABLE 3. Exemplary Type VI-D CRISPR-Cas associated WYL accessory proteins are provided in TABLES 1, 4, 5, and 6. In some embodiments, a Type VI-D CRISPR-Cas effector protein comprises an exemplary motif provided in TABLE 7.

TABLE 1

Representative Cas13d Effector and WYL1 Accessory Proteins

| Species | Cas13d Accession | WYL1 Accession | # spacers | cas1 | cas2 | Effector size |
|---|---|---|---|---|---|---|
| [*Eubacterium*] *siraeum* DSM 15702 (DS499551) | WP_005358205.1 | N/A | 18 | N | N | 954 |
| animal-digestive system-orangutan individual fecal (3300010266\|Ga0129314_1001134) | 3300010266\|Ga0129314_1001134_19 | N/A | 6 | N | N | 981 |
| arthropoda-digestive system-*cubitermes* and *nasutitermes* termite gut (3300006226\|Ga0099364_10024192) | 3300006226\|Ga0099364_10024192_5 | N/A | 13 | Y | Y | 1054 |
| *Eubacterium* sp. An11 (NZ_NFLV01000009) | NFLV01000009_111 | N/A | 9 | Y | Y | 1006 |

TABLE 1-continued

Representative Cas13d Effector and WYL1 Accessory Proteins

| Species | Cas13d Accession | WYL1 Accession | # spacers | cas1 | cas2 | Effector size |
|---|---|---|---|---|---|---|
| Eubacterium sp. An3 (NZ_NFIR01000008) | NFIR01000008_78 | N/A | 2 | Y | Y | 1001 |
| gut metagenome (CDYS01033339) | CDYS01033339_14 | CDYS01033339_20 | 5 | N | N | 906 |
| gut metagenome (CDYU01004315) | CDYU01004315_2 | CDYU01004315_3 | 2 | N | N | 925 |
| gut metagenome (CDZE01002059) | CDYX01024884_4 | CDYX01024884_5 | 8 | N | N | 923 |
| gut metagenome (CDZF01043927) | CDTW01032418_55 | CDTW01032418_59 | 4 | N | N | 906 |
| gut metagenome (CDZV01031905) | CDZU01022944_3 | WP_041337479.1 | 4 | N | N | 929 |
| human-digestive system-*homo sapiens* (3300007296\|Ga0104830_100502) | 3300007296\|Ga0104830_100502_31 | 3300007296\|Ga0104830_100502_30 | 5 | N | N | 919 |
| human-digestive system-*homo sapiens* (3300007299\|Ga0104319_1000623) | 3300007299\|Ga0104319_1000623_29 | 3300007299\|Ga0104319_1000623_27 | 8 | N | N | 924 |
| human-digestive system-*homo sapiens* (3300008496\|Ga0115078_100057) | 3300008496\|Ga0115078_100057_49 | 3300008496\|Ga0115078_100057_48 | 3 | N | N | 922 |
| human-digestive system-*homo sapiens* (CDZK01015063) | CDZK01015063_14 | N/A | 3 | N | N | 923 |
| mammals-digestive system-asian elephant fecal (3300001598\|EMG_10000232) | 3300001598\|EMG_10000232_1 | N/A | 2 | N | N | 963 |
| mammals-digestive system-asian elephant fecal (3300001598\|EMG_10003641) | 3300001598\|EMG_10003641_1 | N/A | 11 | Y | N | 1057 |
| mammals-digestive system-feces (3300018493\|Ga0187909_10005433) | 3300018493\|Ga0187909_10005433_18 | N/A | 18 | Y | Y | 977 |
| mammals-digestive system-feces (3300018494\|Ga0187911_10005861) | 3300018494\|Ga0187911_10005861_18 | N/A | 18 | Y | Y | 971 |
| mammals-digestive system-feces (3300018494\|Ga0187911_10069260) | 3300018494\|Ga0187911_10069260_3 | N/A | 2 | N | N | 900 |
| mammals-digestive system-feces (3300018494\|scaffold19634) | 3300018494\|scaffold19634_7 | N/A | 11 | N | N | 927 |
| mammals-digestive system-feces (3300018878\|Ga0187910_10015336) | 3300018878\|Ga0187910_10015336_4 | N/A | 4 | N | N | 1141 |
| *Ruminococcus albus* (NZ_FOAT01000009) | WP_074833651.1 | N/A | 6 | N | N | 944 |
| *Ruminococcus bicirculans* (NZ_HF545617) | WP_041337480.1 | WP_041337479.1 | 6 | N | N | 918 |
| *Ruminococcus flavefaciens* (DBYI01000091) | DBYI01000091_43 | N/A | 11 | Y | Y | 958 |
| *Ruminococcus flavefaciens* (NZ_FPJT01000005) | WP_075424065.1 | N/A | 4 | N | N | 967 |
| *Ruminococcus flavefaciens* FD-1 (NZ_ACOK01000100) | WP_009985792.1 | N/A | 5 | N | N | 933 |
| *Ruminococcus sp.* CAG: 57 (FR890758) | CDC65743.1 | CDC65744.1 | 2 | N | N | 922 |
| *Ruminococcus sp.* N15.MGS-57 (LARF01000048) | WP_046441786.1 | WP_046441785.1 | 3 | N | N | 919 |
| *Ruminococcus sp.* UBA7013 (DJXD01000002) | DJXD01000002_3 | N/A | 9 | Y | Y | 877 |
| uncultured *Ruminococcus sp.* (FMEA01000016) | SCH71549.1 | CDC65744.1 | 2 | N | N | 922 |
| uncultured *Ruminococcus sp.* (FMFL01000053) | SCJ27598.1 | SCJ78009.1 | 10 | N | N | 919 |

TABLE 2

Amino Acid Sequences of Cas13d Effector Proteins

>WP_005358205.1 (EsCas13d)
[*Eubacterium siraeum* DSM 15702]
MGKKIHARDLREQRKTDRTEKFADQNKKREAERAVPKKDAAVSVKSVSSVSSKKDNVTKSMAKAAGVKSVFAVGNTVYMTSFGR
GNDAVLEQKIVDTSHEPLNIDDPAYQLNVVTMNGYSVTGHRGETVSAVTDNPLRRFNGRKKDEPEQSVPTDMLCLKPTLEKKFF
GKEFDDNIHIQLIYNILDIEKILAVYSTNAIYALNNMSADENIENSDFFMKRTTDETFDDFEKKKESTNSREKADFDAFEKFIG
NYRLAYFADAFYVNKKNPKGKAKNVLREDKELYSVLTLIGKLRHWCVHSEEGRAEFWLYKLDELKDDFKNVLDVVYNRPVEEIN
NRFIENNKVNIQILGSVYKNTDIAELVRSYYEFLITKKYKNMGFSIKKLRESMLEGKGYADKEYDSVRNKLYQMTDFILYTGYI
NEDSDRADDLVNTLRSSLKEDDKTTVYCKEADYLWKKYRESIREVADALDGDNIKKLSKSNIEIQEDKLRKCFISYADSVSEFT
KLIYLLTRFLSGKEINDLVTTLINKFDNIRSFLEIMDELGLDRTFTAEYSFFEGSTKYLAELVELNSFVKSCSFDINAKRTMYR
DALDILGIESDKTEEDIEKMIDNILQIDANGDKKLKKNNGLRNFIASNVIDSNRFKYLVRYGNPKKIRETAKCCKPAVRFVLNEI
PDAQIERYYEACCPKNTALCSANKRREKLADMIAEIKFENFSDAGNYQKANVTSRTSEAEIKRKNQAIIRLYLTVMYIMLKNLV
NVNARYVIAFHCVERDTKLYAESGLEVGNIEKNKTNLTMAVMGVKLENGIIKTEFDKSFAENAANRYLRNARWYKLILDNLKKS
ERAVVNEFRNTVCHLNAIRNININIKEIKEVENYFALYHYLIQKHLENRFADKKVERDTGDFISKLEEHKTYCKDFVKAYCTPF
GYNLVRYKNLTIDGLFDKNYPGKDDSDEQK (SEQ ID NO: 1)

>3300010266|Ga0129314_1001134_19
[animal-digestive system-orangutan individual fecal]
MGKKIHARDLREQRKNDRTTKFAEQNKKREAQMAVQKKDAAVSAKSVSSVSSKKGNVTKSMAKAAGVKSVFAVGKNTVYMTSFG
RGNDAVLEQKIVDTSHEPLNIDDPAYQLNVVTMNGYSVTGHRGETVSAITDNPLRRFNGGKKDKPEQSVPADMLCLKPTLEKKF

TABLE 2-continued

Amino Acid Sequences of Cas13d Effector Proteins

FGKEFDDNIHIQLIYNILDIEKILAVYSTNAVYALNNTIADENNENWDLFANFSTDNTYGELINAATYKESTDDVSTDDEKRRE
AEKKKREAKIAEKILADYEKFRKNNRLAYFADAFYIEKNKSKSKSQNKAEGIKRGKKEIYSILALIAKLRHWCVHSEDGRAEFW
LYKLDELEDDFKNVLDVVYNRPVEEINDDFVERNKVNIQILHSKCENSDIAELTRSYYEFLITKKYKNMGFSIKKLREIILEGT
EYNDNKYDTVRNKLYQMVDFILYRGYINENSERAEALVNALRSTLNEDDKTKLYSSEAAFLRKKYMKIIREVTDSLDVKKLKEL
KKNAFTIPDNELRKCFISYADSVSEFTKLIYLLTRFLSGKEINDLVTTLINKFDNIRSFLEIMDELGLERTFTDEYSFFEGSTK
YLAELIELNSFVKSCSPDMSAKRPMYRDALDILGIESDKSEDDIKRMIDNILQVDANGKKLPNKNHGLRNFIASNVVESNRFEY
LVRYGNPKKIRETAKCCKPAVRFVLNEIPDAQIERYYKAYYLDEKSLCLANMQRDKLAGVIADIKFDDFSDAGSYQKANATSTKI
TSEAEIKRKNQAIIRLYLTVMYIMLKNLVNVNARYVIAFHCLERDTKLYAESGLEVGNIEKNKTNLTMAVMGVKLENGIIKTEF
DKSLAENAANRYLRNARWYKLILDNLKMSERAVVNEFRNTVCHLNAIRNININIDGIKEVENYFALYHYLIQKHLENRFADNGG
STGDYIGKLEEHKTYCKDFVKAYCTPFGYNLVRYKNLTIDGLFDKNYPGKDDSDKQK (SEQ ID NO: 3)

>3300006226|Ga0099364_10024192_5
[arthropoda-digestive system-cubitermes and nasutitermes termite gut]
MSQSTKTKAKRMGVKSVLAHGKDEKGHIKLAITAFGKGNKAELAIQTDEKGSNLAKTYKERNITANKIVSEGIQTSGTIAGEGH
ATFLNNPAEHVGTDYLKLKETLEMEFFGKSFPGDSVRIQIIHQILDQKLLGIYITDIIYCINNLRDETHLDHESDIVGLSMSN
TNVNLALNQMRPYFGFFGEAFRPVGDDKVKEITLSDEVRKNIEKIIALEEQKRNPSTPRFKQENINLEIENAMGKFKSKDAFET
AKKKYNRIVADETNAKTLRILGAMRQITAHFKDQATLFMSDVELPKILKKEFSKADWQTVEDYYAKLVDRINEGFCKNAATNVH
FLTELLPEESKKQLTEDYFRFAILKEGKNLGVNMKRLREVMFALFVPELTAPETKKRYDSYRAKIYGLTDFLLFKHIHNTKQLE
EWVAVLRETSNEDAKENLYDEFARTAWNTVGDSAKQLIENMQSYFTKKEKEITKTAQPVLSTSSIAHTSKKITQFSSFAKLLAF
LCNFWEGKEINELLSAYIHKFENIQEFINLLEKLEGKKPQFTENYALFNEAAGQRAGEIAQNLRILASIGKMKPDLGDAKRQLY
KAAIEMLGIDTEEYISDEWLEPNMLLAQPPKEPKKDNEKYRKEPHKYSYEKDMETYRKKLREYEETWRSLIDYEYLMPETNPFR
NFVAKQVIESRRFMYLVRYTKPKTVRALMSNRAIVHYVLSRIADIQDHHMTESQIDRYYQNLPQYNEQQHKNVSLETKIDALAD
YLCKYTFEKNVLKQKNGIVLNTKSATKNVEIEHLKALTGLYLTYAVIAVKNLVKANARYYIAFSIFERDYALFEKKLGKDTLEK
YVKPFKYIDKGEEKEGKNNFFALTEYLLDKDNSLRYQWNNDLSDEENKQALRKHLDKKEIRSQRHFSQYWLDIFARQIENAKKT
SESGYLLTAARNCALHLNVLTALPEFVGEFRKTGDKMTSYFELYHPLLQKLMLAEAGLNLDEYRERIDTYQTACKDLINITYVS
LGYNLPRYKNLTCEPLFDEESATGKERQTRLDEKSKEKKQRKGGQK (SEQ ID NO: 4)

>NFLV01000009_111
[Eubacterium sp. An11]
MSKKQRPKDIRKRQEEEKREKYKKQEELRKKQEELRKEQEQRREDQKELEKIKKEVGEEGEKKKSRAKALGLKSTFILDRDEQK
VLMTSFGQGNKAVRDKYIIGDKVSDINDDRKNKKAALLVEVCGKSFNISKKENDDCDPVKVNNPVVSRNKKDDDLIHCRKKLEE
LYFGEQFKDNIHIQLIYNILDIEKILAVQVNNIVFALNNLLSWSGEEKFDLIGYLGVNDTYEKFRDAKGKRKGLYEKFSTLIEK
KRMRYFGSTFYPLNEKGEEITSNDKKEWEQFEKKCYHLLAVLGMMRQATAHGDSKRRAEIYKLGKEFDKSEARGCRQEEARKELD
DLYRKKIHEMNQSFLKNSKRDILMLFRIYDAESKEAKRKLAQEYYEFIMLKSYKNTGFSIKHLRETVIDKMDEDIKEKIKDDKY
NPIRRKLYRIMDFVIYQYYQESEQQEEAMELVRKLRNAETKVEKELTYRKEAEKLKEELEKIIRRNSILSVCDRILAEMNEKRHK
KVNQESSDTDSEEPLDPEISEGITFIKETAHSFSEMIYLLTVFLDGKEINILLTQLIHCFDNISSFMDTMKEENLLTKLKEDYE
IFEESKEISKELRIINSFARMTEPVPKTEKTMFIDAAQILGYSNDEKELEGYVDALLDTKNKTKDKERKGFEKYIWNNVIKSTR
FRYLVRYADPKKVRAFAANKKVVAFVLKDIPDEQIKAYYNSCFSQNSDSSSNMSIAFQDGDSNKKGTSVHDMMRKALTEKITGL
NFGDFEEESKKGIRREESDKNIIRLYLTVLYLVQKNLIYVNSRYFLAFHCAERDEVLYNGETIDNNKEKGSEKDWKKFAKEFII
EHPPKKKVKDYLAKNFEYSNKWSLRVFRNSVQHLNVIRDAYKYIKCIDDNKDVQSYFALYHYLVQRYISEMAENLTDKGELSEG
RLQYYLSQVENYRTYCKDFVKALNVPFAYNLPRYKNLSIDELFDRNNYLPNKAKKWISEKKENGEYVMEDCGNKGAGQVENA
(SEQ ID NO: 5)

>NFIR01000008_78
[Eubacterium sp. An3]
MAKKLRPKELREKRRMAEKEEHKKQEKLRKEQEELRKKQEKQREDQKELEKIKKEEGGEGEKKKSGAKALGLKSTFILDRDEQK
MLMTSFGRGNKAVRDKYIIGDKVSDIDDSWENKKAALSVEVCGKSFNISKKENDDCEPVKVNNPVLSGNKKDDDLIHCRKNLEE
MYFGQQFKDNIHIQLIYNILDIEKILAVQINNIVFILNNLLRWSGEEEFDLIGYLGVNDTYEKFRDAKGKRKNYGKFSELIKQSOMR
YFGSTFCLFNENEERITSENKKEWKRFEKKCYHLLAVLGMMRQATAHGDSKRRAEIYKLGKEFDRLEARGCRPEARKELDELYK
KKIHEMNQGFLKNSKSDILMLFRIYNAESKEARKLAQEYYEFIMLKSYKNTGFSIKHLRETMIDKMDEDKKEKLKDDKYNPIR
RKIYRIMDFMIYQYYQEPEHQEEAEELVRKLRNAEIEAKKELAYRKEAEKLKKELEKIIFNSVLPSCDRILSEMDERRNKKVNQ
ESSDTDKEEPLDSEIAEGITFIKETAHSFSEMIYLLTVFLDGKEINILLTQLIHCFDNISSFMDTMEEENLLTKLKEDYEIFEE
SKEISRELRIINSFARMTEPVPKTERIMFIEAAQILGYSNGEKELEGYVDALLDTKNKTNDKKKKGFVRYIWNNVIKSTRFRYL
VRYADPKKVRAFAANKKVVAFVLKDIPDDQIRAYYNSCFRQNSDSSSNNSNASWDADSNKRDISVSDMRKALTEKITGLNFGDF
EEESKKGIRKEESDKNIIRLYLTVLYLVQKNLIYVNSRYFLAFHCAERDEMLYNGETIDNNKEKGSEKDWRKFAKQFIMEHSPK
KKVKDYLAKNFEYSNKWSLKEFRNSVQHLNVIRDAHKYIKYINDNKDVQSYFALYHYLVQRYISERAANRTDKESLSEGRLQYY
LSQVKEYRTYCKDFVKALNVPFAYNLPRYKNLSIDELFDRNNYLPNKAKKWIPEKKENGEYVMEDCGNKDAGQVENA (SEQ
ID NO: 6)

>CDYS01033339_14
[gut metagenome]
MEREVKKPPKKSLAKAAGLKSTFVISPQEKELAMTAFGRGNDALLQKRIVDGVVRDVAGEKQQFQVQRQDESRFRLQNSRLADR
TVTADDPLHRAETPRRQPLGAGMDQLRRKAILEQKYFGRTFDDNIHQLIYNILDIHKMLAVPANHIVHTLNLLGGYGETDFVG
MLPAGLPYDKLRVVKKKNGDTVDIKADIAAYAKRPQLAYLGAAFYDVTPGKSKRDAARGRVKREQDVYTILSLMSLLRQFCAHD
SVRIWGQNTPAALYGLQALPQDMKDLLDDGWRRALGGVNDHFLDTNKVNLLTLFEYYGAETKQERVALTQDFYRFVVLKEQKNM
GFSLRRLREELLKLPDAAYLTGQEYDSVRQKLYMLLDFLLCRLYAQERADRCEELVSALRCALSDEEKDAVYQAEAAALWQALG
DTLRRELLPLLKGKKLQDKDKKKLDELGLSRDVLDGVLFRPAQQGSRANADYFCRLMHLSTWFMDGKEINTLLTTLISKLENID
SLRSVLESMGLAYSFVPAYAMFDHSRYIAGQLRVVNNIARMRKPAIGAKREMYRAAVVLLGVDSPEAAAITDDLLQIDPETGK
VRPRGDSARDTGLRNFVANNVVESRRFTYLLRYMTPEQARVLAQNEKLIAFVLSTVPSAQLERYCRTCGREDITGRPAQIRYLT
AQIMGVRYESFTDVEQRGRGDNPKKERYKALIGLYLTVLYLAVKNMVNCNARYVIAFYCRDRDTALYQKEVCWYDLEEDKKSGK
QRQVEDTYALTRYFVSQGYLNRHACGYLRSNMNGISNGLLAAYRNAVDHLNVIPPLGSLCRDIGRVDSYFALYHYAVQQYLNGR
YYRKTPREQELFAAMAQHRTWCSDLVKALNTPFGYNLARYKNLSIDGLFDREGDHVVREDGEKPAE (SEQ ID NO: 7)

>CDYU01004315_2
[gut metagenome]
MAKKNKMKPRELREAQKKARQLKAAEIKNNAVPAIAAMPAAEAAAPAVEKKKSSVKAAGMKSILVSENKMYITSFGKGNSAVLE
YEVDKKVDNNNYNKTQLSSKDNSNIELGDVNEVNITFSSKRGNESGVEINTSNPTHRSGESSPVRWDMLGLKSELEKRFFGKTFD
DNIHIQLIYNILDIEKILAVYVTNIVYALNNMLGIKGSESYDDFMGYLSARNTYEVFTHPDKSNLSDKVKGNIKKSLSKFNDLL TABLE 2-continued Amino Acid Sequences of Cas13d Effector Proteins KTKRLGYFGLEEPKTKDTRVSQAYKKRVYHMLAIVGQIRQCVFHDKSGAKRFDLYSFINNIDPEYRDTLDYLVEERLKSINKDF
IEGNKVNISLLIDMMKGYEADDIIRLYYDFIVLKSQKNLGFSIKKLREKMLEEYGYRFKDKQYDSVRSKMYKLMDFLLFCNYYR
NDVVAGEALVRKLRFSMTDDEKEGIYADEASKLWGKFRNDFENIADHMNGDVIKELGKADMDFDEKILDSEKKNASDLLYFSKM
IYMLTYFLDGKEINDLLTTLISKFDNIKEFLKIMKSSAVDVECELTAGYKLFNDSQRITNELFIVKNIASMRKPAASAKLTMFR
DALTILGIDDKITDDRISEILKLKEKGKGIHGLRNFITNNVIESSRFVYLIKYANAQKIREVAKNEKVVMFVLGGIPDTQIERY
YKSCVEFPDMNSSLEAKRSELARMIKNIRFDDFKNVKQQAKGRENVAKERAKAVIGLYLTVMYLLVKNLVNVNARYVIAIHCLE
RDFGLYKEIIPELASKNLKNDYRILSQTLCELCDDRDESPNLFLKKNKRLRKCVEVDINNADSSMTRKYRNCIAHLTVVRELKE
YIGDIRTVDSYFSIYHYVMQRCITKREDDTKQEEKIKYEDDLLKNHGYTKDFVKALNSPFGYNIPRFKNLSIEQLFDRNEYLTE
K (SEQ ID NO: 8)

>CDYX01024884_4
[gut metagenome]
MAKKNKMKPRELREAQKKARQLKAAEINNNAVPAIAAMPAAEVIAPAAEKKKSSVKAAGMKSILVSENKMYITSFGKGNSAVLE
YEVDKVDDNDYNKTQLSSKDNSNIELGNVNEVNITFSSRRGFESGVEINTSNPTHRSGESSSVRGDMLGLKSELEKRFFGKTFD
DNIHIQLIYNILDIEKILAVYVTNIVYALNNMLGVKGSESYDDFMGYLSAQNTYYIFTHPDKSNLSDKVKGNIKSLSKFNDLL
KTKRLGYFGLEEPKTKDKRVSEAYKKRVYHMLAIVGQIRQSVFHDKSNELDEYLYSFIDIIDSEYRDTLDYLVDERFDSINKGF
IQGNKVNISLLIDMMKDDYEADDIIRLYYDFIVLKSQKNLGFSIKKLREKMLEEYGFRFKDKQYDSVRSKMYKIMDFLLFCNYY
RNDVVAGEALVRKLRFSMTDDEKEGIYADEAAKLWGKFRNDFENIADHMNGDVIKELGKADMDFDEKILDSEKKNASDLLYFSK
MIYMLTYFLDGKEINDLLTTLISKFDNIKEFLKIMKSSAVDVECELTAGYKLFNDSQRITNELFIVKNIASMRKPAASAKLTMF
RDALTILGIDDNITDDRISEILKLKEKGKGIHGLRNFITNNVIESSRFVYLIKYANAQKIREVAKNEKVVMFVLGGIPDTQIER
YYKSCVEFPDMNSSLEVKRSELARMIKNICFDDFKNVKQQAKGRENVAKERAKAVIGLYLTVMYLLVKNLVNVNARYVIAIHCL
ERDFGLYKEIVSELASKNLKNDYRILSQTLCELCDKSPNLFLKKNERLRKCVEVDINNADSSMTRKYRNCIAHLTVVRELKEYI
GDIRAVDSYFSIYHYVMQRCITKRGNDTKQEDKIKYEDDLLKNHGYTKDFVKALNSPFGYNIPRFKNLSIEQLFDRNEYLTEK
(SEQ ID NO: 9)

>CDTW01032418_55
[gut metagenome]
MEREVKKPPPKKSLAKAAGLKSTFVISPQEKELAMTAFGRGNDALLQKRIVDGVVRDVAGEKQQFQVQRQDESRFRLQNSRLADR
TVTADDPLHRAETPRRQPLGAGMDQLRRKAILEQKYFGRTFDDNIHIQLIYNILDIHKMLAVPANHIVHTLNLLGGYGETDFVG
MLPAGLPYDKLRVVKKKNGDTVDIKADIAAYAKRPQLAYLGAAFYDVTPGKSKRDAARGRVKREQDVYAILSLMSLLRQFCAHD
SVRIWGQNTTAALYHLQALPQDMKDLLDDGWRRALGGVNDHFPLDTNKVNLLTLFEYYGAETKQARVALTQDFYRFVVLKEQKNM
GFSLRRLREELLKLPDAAYLTGQEYDSVRQKLYMLLLDFLLCRLYAQERADRCEELVSALRCALSDEEKDTVYQAEAAALWQALG
DTLRRKLLPLLKGKKLQDKDKKKSDELGLSRDVLDGVLFRPAQQGSRANADYFCRLMHLSTWFMDGKEINTLLTTLISKLENID
SLRSVLESMGLAYSFVPAYAMFDHSRYIAGQLRVVNNIARMRKPAIGAKREMYRAAVVLLGVDSPEAAAAITDDLLQIDPETGK
VRPRSDSARDTGLRNFIANNVVESRRFTYLLRYMTPEQARVLAQNEKLIAFVLSTVPDTQLERYCRTCGREDITGRPAQIRYLT
AQIMGVRYESFTDVEQRGRGDNPKKERYKALIGLYLTVLYAKNVMVNCNARYVIAFYCRDRDTALYQKEVCWYDLEEDKKSGK
QRQVEDYTALTRYFVSQGYLNRHACGYLRSNMNGISNSLLTAYRNAVDHLNAIPPLGSLCRDIGRVDSYFALYHYAVQQYLNGR
YYRKTPREQELFAAMAQHRTWCSDLVKALNTPFGYNLARYKNLSIDGLFDREGDHVVREDGEKPAE (SEQ ID NO: 10)

>CDZU01022944_3
[gut metagenome]
MAKKNKMKPRELREAQKKARQLKAAEINNNAAPAIAAMPAAQVIAPAAEKKKSSVKAAGMKSILVSENKMYITSFGKGNSAVLE
YEVDKVDNNNYNKTQLSSKDNSNIELGDVNEVNITFSSKHGFESGVEINTSNPTHRSGESSPVRWDMLGLKSELEKRFFGKTFD
DNIHIQLIYNILDIEKILAVYVTNIVYALNNMLGIKGSESYDDFMGYLSARNTYEVFTHPDKSNLSDKVKGNIKSFSTFNDLL
KTKRLGYFGLEEPKTKDTRVSEAYKKRVYHMLAIVGQIRQCVFHDLSEHSEYDLYSFIDNSKKVYRECRETLNYLVDERFDSIN
KGFIQGNKVNISLLIDMMKDDYEADDIIHLYYDFIVLKSQKNLGFSIKKLREKMLDEYGFRFKDKQYDSVRSKMYKLMDFLLFC
NYYRNDVVAGEALVRKLRFSMTDDEKEGIYADEAEKLWGKFRNDFENIADHMNGDVIKELGKADMDFDEKILDSEKKNASDLLY
FSKMIYMLTYFLDGKEINDLLTTLISKFDNIKEFLKIMKSSAVDVECELTAGYKLFNDSQRITNELFIVKNIASMRKPAASAKL
TMFRDALTILGIDDKITDDRISEILKLKEKGKGIHGLRNFITNNVIESSRFVYLIKYANAQKIREVAKNEKVVMFVLGGIPDTQ
IERYYKSCVEFPDMNSSLKVKRSELARMIKNIRFDDFKNVKQQAKGRENVAKERAKAVIGLYLTVMYLLVKNLVNVNARYVIAI
HCLERDFGLYKEIIPELASKNLKNDYRILSQTLCELCDDRDESPNLFLKKNRRLRKCVEVDINNADSSMTRKYRNCIAHLTVVR
ELKEYIGDIRTVDSYFSIYHYVMQRCITKREDDTKQEEKIKYEDDLLKNHGYTKDFVKALNSPFGYNIPRFKNLSIEQLFDRNE
YLTEK (SEQ ID NO: 11)

>3300007296|Ga0104830_100502_31
[human-digestive system-*homo sapiens*]
MAKKNKMKPRELREAQKKARQLKAAEINNNAAPAIAAMPAAEVIAPAAEKKKSSVKAAGMKSILVSENKMYITSFGKGNSAVLE
YEVDNNDYNKTQLSSKDSSNIELRGVNEVNITFSSKHGFGSGVEINTSNPTHRSGESSPVRWDMLGLKSELEKRFFGKTFDDNI
HIQLIYNILDIEKILAVYVTNIVYALNNMLGIKKSESHDDFMGYLSAKNTYDVFTNPNGSTLSDDKKKNIRKSLRKFNDLLKTK
RLGYFGLEEPKTKDTRVSQAYKKRVYHMLAIVGQIRQSVFHDKSSKLHEDLYSFIDIIDSEYRETLDYLVDERFDSINKGFIQG
NKVNISLLIDMMKGYEADDIIRLYYDFIVLKSQKNLGFSIKKLREKMLDEYGFRFKDKQYDSVRSKMYKLMDFLLFCNYYRNDV
AAGEALVRKLRFSMTDDEKEGIYADEAAKLWGKFRNDFENIADHMNGDVIKELGKADMDFDEKIIDSEKKNASDLLYFSKMIYM
LTYFLDGKEINDLLTTLISKFDNIKEFLKIMKSSAVDVECELTAGYKLFNDSQRITNELFIVKNIASMRKPAASAKLTMFRDAL
TILGIDDNITDDRISEILKLKEKGKGIHGLRNFITNNVIESSRFVYLIKYANAQKIRVAKNEKVVMFVLGGIPDTQIERYYKS
CVEFPDMNSSLEVKRSELARMIKNISFDDFKNVKQQAKGRENVAKERAKAVIGLYLTVMYLLVKNLVNVNARYVIAIHCLERDF
GLYKEIIPELASKNLKNDYRILSQTLCELCDKSPNLFLKKNRRLRKCVEVDINNADSSMTRKYRNCIAHLTVVRELKEYIGDIR
TVDSYFSIYHYVMQRCITKRENDTKQEEKIKYEDDLLKNHGYTKDFVKALNSPFGYNIPRFKNLSIEQLFDRNEYLTEK (SEQ
ID NO: 12)

>3300007299|Ga0104319_1000623_29
[human-digestive system-*homo sapiens*]
MAKKNKMKPRELREAQKKARQLKAAEINNNAAPAIAAMPAAEVIAPAAEKKKSSVKAAGMKSILVSENKMYITSFGKGNSAVLE
YEVDNNDYNKTQLSSEDSSNIELCGVNKVNITFSSKHGFESGVEINTSNPTHRSGESSPVRWDMLGLKSELEKRFFGKTFDDNI
HIQLIYNILDIEKILAVYVTNIVYALNNMLGEGDESNYDFMGYLSTFNTYKVFTNPNGSTLSDDKKENIRKSLSKFNALLKTKR
LGYFGLEEPKTKDTNALEAYKKRVYYMLAIVGQIRQCVFHDLSEHSEYDLYSFIDNSKKVYRECRETLDYLVDERFDSINKGFI
QGNKVNISLLIDMMKGYEADDIIRLYYDFIVLKSQKNLGFSIKKLREKMLDEYGFRFKDKQYDPVRSKMYKLMDFLLFCNYYRN
DVVAGEALVRKLRFSMTDDEKEGIYADEAAKLWGKFRNDFENIADHMNGDVIKELGKADMDFDEKILDSEKKNASDLLYFSKMI
YMLTYFLDGKEINDLLTTLISKFDNIKEFLKIMKSSAVNVECELTAGYKLFNDSQRITNELFIVKNIASMRKPAASAKLTMFRD TABLE 2-continued Amino Acid Sequences of Cas13d Effector Proteins ALTILGIDDKITDDRISEILKLKEKGKGIHGLRNFITNNVIESSRFVYLIKYANAQKIREVAKNEKVVMFVLGGIPDTQIERYY
KSCVEFPDMNSSLEAKRSELARMIKNISFDDPKNVKQQAKGRENVAKERAKAVIGLYLTVMLLVENLVNVNARYVIAIHCLER
DFGLYKEIISELASKNLKNDYRILSQTLCELCDNCDESPNLFLKKNERLRKCVEVDINNADSNMTRKYRNCIAHLTVVRELNKY
IKDIRTVDSYFSIYHYVMQRCITKREDDKKQEEKIKYEDDLLKNHGYTKDFVKALNSPFGYNIPRFKNLSIEQLFDRNEYLTEK
(SEQ ID NO: 13)

>3300008496|Ga0115078_100057_49
[human-digestive system-*homo sapiens*]
MAKKNKMKPRELREAQKKARQLKAAEINNNAAPAIAAMPAAEAAAPAAEKKKSSVKAAGMKSILVSENKMYITSFGKGNSAVLE
YEVDNNDYNKTQLSSKDNSNIELGDVDEVNITFSSKHGFGSGVEINTSNPTHRSGESSPVRWDMLGLKSELEKRFFGKTFDDNI
HIQLIYNILDIEKILAVYVTNIVYALNNMLGEGGDESHDDIMGYLSAKNTYDVFTDPDESDLSKNIKGNIKKSLSKFNDLLKTK
RLGYFGLEEPKTKDKRASEAYKKRVYHMLAIVGQIRQSVFHDKSNELDEYLYSFIDIIDSEYRDTLDYLVDERFDSINKGFIQG
NKVNISLLIDMMKGYEADDIIRLYYDFIVLKSQKNLGFSIKKLREKMLDEYGFRFKDKQYDSVRSKMYKLMDFLLFCNYYRNDV
LAGEALVRKLRFSMTDDEKEGIYADEAAKLWGKFRNDFENIADHMNGDVIKELGKADMDFDEKILDSEKKNASDLLYFSKMIYM
LTYFLDGKEINDLLTTLISKFDNIKEFLKIMKSSAVDVECELTAGYKLFNDSQRITNELFIVKNIASMRKPAASAKLTMFRDAL
TILGIDDNITDDRISEILKLKEKGKGIHGLRNFITNNVIESSRFVYLIKYANAQKIREVAKNEKVVMFVLGGIPDTQIERYYKS
CVEFPDMNSSMGAKRRELAKMIKSISFEDFKDVKQQAKGRENVAKERAKAVIGLYLTVMYLLVKNLVNVNARYVIAIHCLERDF
GLYKEIIPELASKNLKNDYRILSQTLCELCDNGDESPNLFLKKNKRLRKCVEVDINNADSNMTRKYRNCIAHLTVVRELNKYIK
DIRTVDSYFSIYHYVMQRCITKRENDTKQEEKINYEDDLLKNHGYTKDFVKALNSPFGYNIPRFKNLSIEQLFDRNEYLTEK
(SEQ ID NO: 14)

>CDZK01015063_14
[human-digestive system-*homo sapiens*]
MFMAKKNKMKPRERREAQKKARQLKAAEINNNAVPAIAAMHAAEVIAPAAEKKKSSVKAAGMKSILVSENKMYITSFGKGNSAV
LEYEVDNNDYNQTQLSSKDNSNIELCGVTKVNITFSSKHGFESGVEINTSNPTHRSGESSPVRGDMLGLKSELEKRFFGKTFDD
NIHIQLIYNILDIEKILAVYVTNIVYALNNMLGEGDESNYDFMGYLSTFNTYKVFTNPNGSTLSDDKKENIRKSLSKFNALLKT
KRLGYFGLEEPKTKDTRASEAYKKRVYHMLAIVGQIRQCVFHDKSGAKRFDLYSFINNIYPEYRDTLDYLVEERLKSINKDFIQ
GNKVNISLLIDMMKGYEADDIIRLYYDFIVLKSQKNLGFSIKKLREKMLDEYGFRFKDKQYDSVRSKMYKLMDFLLFCNYYRND
VVAGEALVRKLRFSMTDDEKEGIYADEAAKLWGKFRNDFENIADHMNGDVIKELGKADMDFDEKILDSEKKNASDLLYFSKMIY
MLTYFLDGKEINDLLTTLISKFDNIKEFLKIMKSSAVDVECELTAGYKLFNDSQRITNELFIVKNIASMRKPAASAKLTMFRDA
LTILGIDDKITDDRISEILKLKEKGKGIHGLRNFITNNVIESSRFVYLIKYANAQKIREVAKNEKVVMFVLGGIPDTQIERYYK
SCVEFPDMNSSLEAKRSELARMIKNISFDDFKNVKQQAKGRENVAKERAKAVIGLYLTVMYLLVKNLVNVNARYVIAIHCLERD
FGLYKEIIPELASKNLKNDYRILSQTLCELCDDRDESPNLFLKKNKRLRKCVEVDINNADSSMTRKYRNCIAHLTVVRELKKYI
GDIRTVDSYFSIYHYVMQRCITKREDDTKQEEKIKYEDDLLKNHGYTKDFVKALNSPFGYNIPRFKNLSIEQLFDRNEYLTEK
(SEQ ID NO: 15)

>3300001598|EMG_10000232_1
[mammals-digestive system-asian elephant fecal-*elephas maximus*]
MYNIDKLWLTHILFVSLTAGKKNETILEQEINKDSNKKNILVNPTKFDANIKEVRMVSIKPEKYNETVVNNPYYVKDGQVVGQD
YLGIKDKLEDTFFGKTYDDNIHIQIAYKLLDIRKIMGMSVGSAVFSLNNLQQRPVGENPDIVGQIKTDTSFDEIPDNYAKADK
DFIDILLDYTRYFDNVFEKQSISVDDKTKDILNNLKECETVSVKTVGTIDRINKNDPNNNNYTIFKIGGLKIKLKGILSNVDVG
TKLNIEGQIRRNNDYRDKKGKLCRSYSLLTGAKYSISHEVYNPDTYTFNYDILRLVSYLRQAVVHNNNDDYIDWLYSIDNKKET
KDILNAANKVFESQLEAFNKDFNANAQKNVYMIASVLNDSPKTMFKEEIKDIYEKYYNFVLFKENRNVGINLRNIRNNIFYEDI
KPNYDEKELSRERAKINTLLDYFIYQDFNNNEKLAEDVIARLQPTKQEVDKVQVYADVTKEFKVRNPKLVDRILSTVKNTIEAK
IENFIPDNCVPSSSIKVSSLAKYVYVLAKFLDTKEVNNLLTSLINSFENIGSLVKVLKDEKGYSIYKDRFALLNQKNPFDLAND
FILVKNLATMKTKLAKANVKDVKNKVGKRLYCSAINLFKDKNDEVILDNQEFEDIMSEFSSNVGNKKNRRGTAGSKIRNFLINN
VIDSRRFYFIIKYYDTRRCHEIIQNENLVRFILGREDMPTDQLIRYYKTITGNECNNRNQIIDTLVKKLKEVSFRKLLLKGERL
KEIGNDQDNQEVESLKSLIGLYLTICYLIVKGIVNVNSVYLLAWSAYERDMYYLYNEDMEDKNTNHDYLKAATDFYNNKSCYQK
RHKYLIKDIEEARQNSNNLNYKDYRNKVCHYNICTSFMDYANNIGKVSCYFDIYNYCFQRYFAKKNDNLSTLLDTYNCYNKDYL
KLLNMPFAYNMARYKNLTIADLFNDKYPSENKEATASND (SEQ ID NO: 16)

>3300001598|EMG_10003641_1
[mammals-digestive system-asian elephant fecal-*elephas maximus*]
MEETKVTKETTIEKQSTKRHKQKSKKTATKMSGLKSALVINNHEMLLTSFGKGNNAIAEKRYILDGDIETINNKNKKFDANNDS
KVVVIKGISNPNGQLTNPLFDQSPTAIQPNRTSGNDMIGIRRMLERKYFVHNEENKEFQDNIRIQIAYCILDIEKILMPHINNI
CFEINNMLRLEGYQEDSFMGSFNLYKPYDAFIATTDDKESSRRDNFAKLMTSKQVRYLGNALYSDSLSNLTKDEILDGKRSKEL
KKYYQELCLLGMVRQSMIHSNQFNSSIYTLDSSYDSTMNTAELLGKGDDSSLVALATDARVEARAILDEIYKKGVDSINNSFLS
NSINDLENLFKIYKCDSSEKKTELIKQYYDFCIRKPQMNMGFSITTIREGMFTRCSEANTLLLCDEGSTVKLNVHDTMKSKPYK
NLDFMIYKYYKYENPEKGEKLIEDLRSKIKGKKKEDEDKKQRYAEESACILKAKRDIIKKDLTEAANKDLFADLVKSNKNEKQK
FKNEYEELLKPFMIPVKVDYFSELIYLVTRFLSGKEINDLLTQLINKFENIAAFIRMYQNDQGKLEFTANYKMFEIDPQKDIPK
DGKRVLSGSAKIAYYLRTINYIARMESFEIKSDKTAINDAISLLGYNSNEHRDEFITYTMAKHVVDKYQNTDYQKIVKDFLSAN
KTLDCKSKNMQAFVSELKNAHLSENYEQREKEIYELADTNLPAYFSEEDKEKLARYIVHSDGTYKKFLKESFYAIEELPNEGFR
NPFISNNVINSRRFNYIMRFCNPEKIANIGKNKVLISPALSSLAEKTDMIAKYYRVFCDRIDDQKTMEDYLVNKLTKISYTEFLN
VNQKANAEKNKEKDRSQKLIGLYITLLYEIVKNLVNINSRYNIAFQRCDNDSIMILQGQYDERAVQESKLTKKFISNQKLNSYS
CRYLTHNISQLDRCNDFIRQYRNKVAHLEVVSNIDEYLSGIKHIESYYALYHYLMQKCLLKNYRIEDHSQNEYKNLNDFSSKLD
KHGTYVKDFVKALNVPFGYNLPRYKNLSIDELFDRNKLKTGGTIEMKGE (SEQ ID NO: 17)

>3300018493|Ga0187909_10005433_18
[mammals-digestive system-feces]
MKERIDMIEKKKSYAKGMGLKSTLVSDSKVYMTSFGNGNDARLEKVVENNAISCLVDKKEAFVAEITDKNAGYKIINKKFGHPK
GYDVVANNPLYTGPVQQDMLGLKETLEKRYFGSSVSGNDNICIQVIHNILDIEKILAEYITNAAYAVNNIAGLDKDIIGFKFS
TVYTFDEFAEPDRHKERFIKDGKLDTKLINQLKNQYDEFDAFLDDTRFGYFGKAFFCKEGDKYLNKQDNERYHILALLSGLRNW
VHNNEVESKIDRKWLYNLDEKLYITTLDYMYSDIADELTKSNAANVNYIAEILNIDSKTFAEQYFRFSIMKEQKNL
GFTLTKLRECMLDREELSDIRDNHKVFDSIRSKLYTMMDFVIYRYYIEEAAKIENENKTLSDDKKKLSEKDIFIISLRGSFSEE
QDKLYSDEAERLWAKLGKLMLEIKKFRGQMTRDYKKSDTPTLNRILPESEDVSTFSKLMYALTMFLDGKEINELLTTLINKFD
NIQSMLKIMPLIGVNAKFSSDYAFFNNSEKIADELKLIKSFARMGEPVANAKRDMMIDAIKILGTDLDDNEIKKLADSFFKDSN
GKLLHKGKHGMRNFIINNVVNNKRFHYIIRYGDPAHLHEIAKNEVVVRFVLGRIADIQKKQGKGGKNQIDRYYEICIGNGYGKS
VSEKIDALTKVIINMNYDQFEAKRKVIENTGRDNAEREKYKKIISLYLTVIYQILKNLVNVNSRYVIGFHCVERDAQLYKEKGY TABLE 2-continued Amino Acid Sequences of Cas13d Effector Proteins DINTNNLESKGFTSVTKLCVGIADDDPVKYKNVEIELKERALASFDALEKENPELYEKYNMYSEKQKEAELEKQINREKAKTAL
NAHLRNTKWNVIIRENIRNTEKDACKQFRNKADHLEVARYAYKYINDISEVNSYFQLYHYIMQRIIIDSSGNNANGMIKKYYES
VISDKKYNDRLLKLLCVPFGYCIPRFKNLSIEALFDKNEAAKYDKIKKKVAVR (SEQ ID NO: 18)

>3300018494|Ga0187911_10005861_18
[mammals-digestive system-feces]
MIEKKKSYAKGMGLKSTLVSDSKVYMTSFGNGNDARLEKVVENNAISCLVDKKEAFVAEITDKNAGYKIINKKFGHPKGYDVVA
NNPLYTGPVQQDMLGLKETLEKRYFGSSVSGNDNICIQVIHNILDIEKILAEYITNAAYAVNNIAGLDKDIIGFGKFSTVYTFD
EFAEPDRHKERFIKDGKLDTKLINQLKNQYDEFDAFLDDTRFGYFGKAFFCKEGDKYLNKQDNERYHILALLSGLRNWVVHNNE
VESKIDRKWLYNLDKNLDKEYITTLDYMYSDIADELTKSFSKNSAANVNYIAEILNIDSKTFAEQYFRFSIMKEQKNLGFTLTK
LRECMLDREELSDIRDNHKVFDSIRSKLYTMMDFVIYRYYIEEAKKIENENKTLSDDKKKLSEKDIFIISLRGSFSEEQKDKLY
SDEAERLWAKLGKLMLEIKKFRGQMTRDYKKSDTPTLNRILPESEDVSTFSKLMYALTMFLDGKEINELLTTLINKFDNIQSML
KIMPLIGVNAKFSSDYAFFNNSEKIADELKLIKSFARMGEPVANAKRDMMIDAIKILGTDLDDNEIKKLADSFFKDSNGKLLHK
GKHGMRNFIINNVVNNKRFHYIIRYGDPAHLHEIAKNEVVVRFVLGRIADIQKKQGKGGKNQIDRYYEICIGNGYGKSVSEKID
ALTKVIINMNYDQFEAKRKVIENTGRDNAEREKYKKIISLYLTVIYQILKNLVNVNSRYVIGFHCVERDAQLYKEKGYDINTNN
LESKGFTSVTKLCVGIADDDPVKYKNVEIELKERALASFDALEKENPELYEKYNMYSEKQKEAELEKQINREKAKTALNAHLRN
TKWNVIIRENIRNTEKDACKQFRNKADHLEVARYAYKYINDISEVNSYFQLYHYIMQRIIDSSGNNANGMIKKYYESVISDKK
YNDRLLKLLCVPFGYCIPRFKNLSIEALFDKNEAAKYDKIKKKVAVR (SEQ ID NO: 19)

>3300018494|Ga0187911_10069260_3
[mammals-digestive system-feces]
MSTKKRFRYSVAAKAAGLKSSLAVDTDRTVMTSFGHGNAAILEKEIVDGEISVLNIENPAFDAVINDKKYALTGHHAGVHALVD
QPQNRSDAVHIRGALEKKYFGDTFADNIHVQIAYNILDITKILTVYANNLVHADDDTQADELDSLGNFSAGTSYAKS
KSKSKSKQQDFVELFIKKKEIHGYFGDTFAFLDKRIADADKEKQVYAMLACLGSLRQACSHYRIRYSVNGKNVDADADTWLFSS
AQLDQTDPLFSEMLNRIYSHKIKTVNQNFFENNRKANFPILKKMYPETTLKVLMNEYYDFSIRKGYKNFGFSIKSLREALLSPQ
YESLIGVQIKDNKEYDTVRSKLYQLFDFALTRYFNQHPDMVDAFVVELRSLAKDEDAKNAVYEKYAKAVWNDVKQPIAVMLSYM
NGSAIKNIKAFELKPDQKELNGIMNSNALDVPHFCKLVYFLTRFLDGKEINDLLTTLVNKFDNIHSFNQVLTALGLSASYEADY
KIFEDSGRVVEYLREINSFARMTVDMEKIKRSAYKKALLILGSSKYSDEDLDARVDEMLGVDYNQNGEKIKVRVDTGFRNFIAN
NVVESSRFHYLIRYCHPRKIRNLAGNAALIEYQLRRLPELQILRYYEACTEPIKRTARTMDEKIGTLIDLIVKMDFSQFEDVQQ
NDRVRVFSDAEKKEKIRKMREKQRYQSIISLYLTMLYLIVKNLVNINARYVMAFQAWERDNYLLLQLSGKEAEAEYLNLTRHFI
EPLDGAKPYLKKRPVEYLKKDMAMVGNSSIRHFRNATVHLNVIMEAHRYTKDIKYIGSYYALYHYILQRHLLDKIEEDSYAEKT
VSEKLWESQISQYGTYSKDFVKALCCPFGYNLPRFKNLSIEQLFDRNESKEITDATAPRQ (SEQ ID NO: 20)

>3300018494|scaffold19634_7
[mammals-digestive system-feces]
MAKKKKAKQRREEQEAARMNKIQSAVKAKAETAPAVSSAFVEKRKDKQSKKTFAKASGLKSTLAVDNSAVMTVFGRGNEAKLDH
RINADLQSESLHPQAALKNVHAPNKQKIHFIGRMQDMNLTADHPLHSHDGERAVGADLLCAKDKLEQLYFGRTFNDNIHIQLIY
QILDIQKILALHANNIIFALDNLLHKKNDELSDDFVGMGRMRATIGYDAFRNSTNQKVQETYREFQEFVRRKELLYFGSAFYNG
DTRRDEKVIYHILSLAASVRQFCFHNDYTSDDGKGFIKADWMYRLEEALPAEYKDTLDALYLEGVEGLDQSFLKNNTVNIQILC
SIFNHDDPNKIAEEYYGFLMTKEYKNMGFSIKKLRECMLELPELSGYKEDQYNVSRSKLYKLFDFIIAHYFRKHPEKGEEMVDC
LRLCMTEDEKDSHYEGTAKKLVRELAYDMQEAAEQANGSNITQMQKNEQQGKTKGMFAIRDEIRVSRKPVSYFSKVIYVMTLLL
DGKEINDLLTTLINKFENIVSFEDVLRQLNVDCTFKPEFAFFGYDRCRNISGELRLINSFARMQKPSAKAKHVMYRDALRILGL
DNGMSEEALDQEVRRILQIGADGKPIKNANKGFRNFIASNVIESSRFRYLVRYNNPHKTRMIAQNEAIVRFVLSEIPDEQIRRY
YDVCRDPKLPRSSSREAQVDILTGIITDVNYRIFEDVPQSKKINKDRPDANDRMTLKKQRYQAIVSLYLTVMYLVTKNLVYVNS
RYVMAFRALERDAYLYGITNIKGDYRKLTDNLLADENYKKFGHFKNKKWRGIAEQNLRNSDVPVIKSFRNMAAHISVIRNIDLY
IGDIQKVDSYFALYHFLMQKLIQRVVPENTKGLSDQTKKYYDALEQYNTYCKDFVKAYCTPFAYVTPRYKNLTIDGLFDRNRPG
EDK (SEQ ID NO: 21)

>3300018878|Ga0187910_10015336_4
[mammals-digestive system-feces]
MGVEKNKVFESVIMNFDQERKYGFIEYKETNNLFFHMENVKNPKEIVKGAKVRFEIYENPKPKKQNQRFSAINVEVITDETHKE
AKIQKNEFKTFDQFTKELQETQKVNGETKKEHITKNKHTNVKAAGVKSVFAVDDGNVLITSFGRGNAADIETLKSDDDKTINLT
ETENQKKYVVTNKRSNVKGLADNPTKVESIIPGETQIGFKSILEKHFFGRTFNDNIHIQIIHNILDIKKILAVHTNNIVYALDN
IHERGRENSAEKPIDMIGAGGISTSKEYEQYCSEKSDYEDNFLKQLINNERIAYFGNAFFKDEGNKKVMRTEKEIYYILGMLNE
VRNVSTHFTEEDNRDWAKANLYNLSNRLKVGSKEVLNQLYEKIDLKTQRDLKQDNVEKQKQLAIMSLYLNILYQIAKN
LVYVNSRYVMAFHSLERDSQMLFDAYYDVKRGYCDLSTVLLFGVDDLQNRNRGSYKYLRDNRRSNKDVIETFGDFKGKVSKVVE
KKNQGLTNEIYDSLCNVAGTTKTEVQNEIKSILKSNGLDESASSYLSHKLVNKVHSYKYLKQNLDCADNTMINQFRNNVAHLNT
IRNMDGIENVTGITSYFQIYHYLMQKALYKEFKKCRENAVRKWIPYITENAEPKYVVWNKKEQQEVEVSFNPKIFGYMENIKNH
SNTYCKDFVKALCAPFAYNLPRFKNLSIEELFDMHELSEEPKESMKLTD (SEQ ID NO: 22)

>WP_074833651.1
[Ruminococcus albus]
MAKKSKGMSLREKRELEKQKRIQKAAVNSVNDTPEKTEEANVVSVNVRTSAENKHSKKSAAKALGLKSGLVIGDELYLTSFGRG
NEAKLEKKISGDTVEKLGIGAFEVAERDESTLTLESGRIKDKTARPKDPRHITVDTQGKFKEDMLGIRSVLEKKIFGKTFDDNI
HVQLAYNILDVEKIMAQYVSDIVYMLHNTDKTERNDNLMGYMSINRTYKTFCDTSNLPDDTKQKVENQKREFDKIIKSGRLGYF
GEAFMVNSGNSTKLRPEKEIYHIFALMASLRQSYFHGYVKDTDYQGTTWAYTLEDKLKGPSHEFRETIDKIFDEGFSKISKDFG
KMNKVNLQILEQMIGELYGSIERQNLTCDYYDFIQLKKHKYLGFSIKRLRETMLETTPAECYKAECYNSERQKLYKLIDFLIYD
LYYNRKPARIEEIVDKLRESVNDEEKESIYSVEAKYVYESLSKVLDKSLKNSVSGETIKDLQKRYDDETANRIWDISQHSISGN
VNCFCKLIYIMTLMLDGKEINDLLTTLVNKFDNIASFIDVMDELGLEHSFTDNYKMFADSKAICLDLQFINSFARMSKIDDEKS
KRQLFRDALVILDIGNKDETWINNYLDSDIFKLDKEGNKLKGARHDFRNFIANNVIKSSRFKYLVKYSSADGMIKLKTNEKLIG
FVLDKLPETQIDRYYESCGLDNAVVDKKVRIEKLSGLIRDMKFDDFSGVKTSNKAGDNDKQDKAKYQAIISLYLMVLYQIVKNM TABLE 2-continued Amino Acid Sequences of Cas13d Effector Proteins IYVNSRYVIAFHCLERDFGMYGKDFGKYYQGCRKLTDHFIEEKYMKEGKLGCNKKVGRYLKNNISCCTDGLINTYRNQVDHFAV
VRKIGNYAAYIKSIGSWFELYHYVIQRIVFDEYRFALNNTESNYKNSIIKHHTYCKDMVKALNTPFGYDLPRYKNLSIGDLFDR
NNYLNKTKESIDANSSIDSQ (SEQ ID NO: 23)

>WP_041337480.1
[Ruminococcus bicirculans]
MAKKNKMKPRELREAQKKARQLKAAEINNNAVPAIAAMPAAEAAAPAAEKKKSSVKAAGMKSILVSENKMYITSFGKGNSAVLE
YEVDNNDYNKTQLSSKDNSNIELCDVGKVNITFSSRRGFESGVEINTSNPTHRSGESSSVRGDMLGLKSELEKRFFGKNFDDNI
HIQLIYNILDIEKILAVYVTNIVYALNNMLGEGDESNYDFMGYLSTFNTYKVFTNPNGSTLSDDKKENIRKSLSKFNALLKTKR
LGYFGLEEPKTKDTRASEAYKKRVYHMLAIVGQIRQCVFHDKSGAKRFDLYSFINNIDPEYRETLDYLVDERFDSINKGFIQGN
KVNISLLIDMMKGYEADDIIRLYYDFIVLKSQKNLGFSIKKLREKMLDEYGFRFKDKQYDSVRSKMYKLMDFLLFCNYYRNDIA
AGESLVRKLRFSMTDDEKEGIYADEAAKLWGKFRNDFENIADHMNGDVIKELGKADMDFDEKILDSEKKNASDLLYFSKMIYML
TYFLDGKEINDLLTTLISKFDNIKEFLKIMKSSAVDVECELTAGYKLFNDSQRITNELFIVKNIASMRKPAASAKLTMFRDALT
ILGIDDKITDDRISEILKLKEKGKGIHGLRNFITNNVIESSRFVYLIKYANAQKIREVAKNEKVVMFVLGGIPDTQIERYYKSC
VEFPDMNSSLGVKRSELARMIKNISFDDFKNVKQQAKGRENVAKERAKAVIGLYLTVMYLLVKNLVNVNARYVIAIHCLERDFG
LYKEIIPELASKNLKNDYRILSQTLCELCDKSPNLFLKKNERLRKCVEVDINNADSSMTRKYRNCIAHLTVVRELKEYIGDICT
VDSYFSIYHYVMQRCITKRENDTKQEEKIKYEDDLLKNHGYTKDFVKALNSPFGYNIPRFKNLSIEQLFDRNEYLTEK (SEQ
ID NO: 24)

>DBYI01000091_43
[Ruminococcus flavefaciens]
MKKKKIKARDLREAKKQEKLAAFSAKANTVYENEDKNVEAFPEALNLRSIKKSMNKAAGLKSTLIDGKSLYLTAFGKGNNAVVEH
MIATDDSYSLKTLENEPSLKVKAADELKVTFMSRRPFVQESELSAVNPLHSGLDKPNKSAGQDMLGLKSELEKRYFGKIFDDNL
HIQIIHNILDIEKIIAVYATNITAAIDHMVDDDNEQYLQGDFIGYMNTLNTYEVFMEPSKNPRLDSNARKNIENSREKFEYLLD
TQRLGYLSLEYDKRSKDKRKSEEIKKRLYHLVAFAGQLRQWSFHSVEGLPRTWIYQLDNPKLAQEYRDTLDYFFNERFDAINKD
FIETNNINLHILKEVFPAEDFQKLAALYYDFIVKKTFKNIGFSIKNLREQMLECDEAEKIRSKDMNSVRSKLYKLFDFCIFYQY
FIDEERSRENVNYLRSTLNDEQKDAFYEEEGKRLWSENRKKFYLFIDNINKWVKDYSDEVAKCIDLNEFRVNSNVSYFSKLLY
AMSFFFLDGKEINDLLTTLINKFDNIRSFIDTANFLNIDVKFTKDYDFFNIICDYAGELNIIKNIARMKKPSPSAKKNMYRDALT
ILGIPTEMSDEQLDAEIDKILEKKINPVTGKTEKGKNPFRNFIANNVIENKRFIYVIKFCNPKNVRKLVNNTKVTEFVLKRMPE
TQIDRYFESCIEGNLNPTTEKKIEKLAEMIKNIKFEEFRNVKQKVRDNSQEAVEKERFKAIIGLYLTVIYLLVKNLVNVNSRYV
MAFHCLERDAKLYGVQNIGGDYLALTAKLCAEGDDYGKKLSEAKQNINQDKVQMPKNYFLARNKRWREAIEQDIDNAKKWFIGE
KFNNVKNYRNNVAHLTAIRNCAEFIGEITKIDSYFALYHYLIQRQLAGRLDPNHPGFEKNYPQYAPLFKWNTYVKDMVKALNSP
FGYNIPRFKDLSIDALFDRNEMKEETDDEKKIQT (SEQ ID NO: 25)

>WP_075424065.1
[Ruminococcus flavefaciens]
MIEKKKSFAKGMGVKSTLVSGSKVYMTTFAEGSDARLEKIVEGDSIRSVNEGEAFSAEMADKNAGYKIGNAKFSHPKGYAVVAN
NPLYTGPVQQDMLGLKETLEKRYFGESADGNDNICIQVIHNILDIEKILAEYITNAAYAVNNISGLDKDIIGFGKFSTVYTYDE
FKDPEHHRAAFNNNDKLINAIKAQYDEFDNFLDNPRLGYFGQAFFSKEGRNYIINYGNECYDILALLSGLRHWVVHNNEEESRI
SRTWLYNLDKNLDNEYISTLNYLYDRITNELTNSFSKNSAANVNYIAETLGINPAEFAEQYFRFSIMKEQKNLGFNITKLREVM
LDRKDMSEIRKNHKVFDSIRTKVYTMMDFVIYRYYIEEDAKVAAANKSLPDNEKSLSEKDIFVINLRGSFNDDQKDALYYDEAN
RIWRKLENIMHNIKEFRGNKTREYKKKDAPRLPRILPAGRDVSAFSKLMYALTMFLDGKEINDLLTTLINKFDNIQSFLKVMPL
IGVNAKFVEEYAFFKDSAKIADELRLIKSFARMGEPIADARRAMYIDAIRILGTNLSYDELKALADTFSLDENGNKLKKGKHGM
RNFIINNVISNKRFHYLIRYGDPAHLHEIAKNEAVVKFVLGRIADIQKKQGQNGKNQIDRYYETCIGKDKGKSVSEKVDALTKI
ITGMNYDQFDKKRSVIEDTGRENAEREKFKKIISLYLTVIYHILKNIVNINARYVIGFHCVERDAQLYKEKGYDINLKKLEEKG
FSSVTKLCAGIDETAPDKRKDVEKEMAERAKESIDSLESANPKLYANYIKYSDEKKAEEFTRQINREKAKTALNAYLRNTKWNV
IIREDLLRIDNKTCTLFRNKAVHLEVARYVHAYINDIAEVNSYFQLYHYIMQRIIMNERYEKSSGKVSEYFDAVNDEKKYNDRL
LKLLCVPFGYCIPRFKNLSIEALFDRNEAAKFDKEKKKVSGNS (SEQ ID NO: 26)

>WP_009985792.1
[Ruminococcus flavefaciens FD-1]
MKKKMSLREKREAEKQAKKAAYSAASKNTDSKPAEKKAETPKPAEIISDNSRNKTAVKAAGLKSTIISGDKLYMTSFGKGNAAV
IEQKIDINDYSFSAMKDTPSLEVDKAESKEISFSSHHPFVKNDKLTTYNPLYGGKDNPEKPVGRDMLGLKDKLEERYFGCTFND
NLHIQIIYNILDIEKILAVHSANITTALDHMVDEDDEKYLNSDYIGYMNTINTYDVFMDPSKNSSLSPKDRKNIDNSRAKFEKL
LSTKRLGYFGFDYDANGKDKKKNEEIKKRLYHLTAFAGQLRQWSFHSAGNYPRTWLYKLDSLDKEYLDTLDHYFDKRFNDINDD
FVTKNATNLYILKEVFPEANFKDIADLYYDFIVIKSHKNMGFSIKKLREKMLECDGARNIKEQDMDSVRSKLYKLIDFCIFKYY
HEFPELSEKNVDILRAAVSDTKKDNLYSDEAARLWSIFKEKFLGFCDKIVVWVTGEHEKDITSVIDKDAYRNRSNVSYFSKLMY
AMCFFLDGKEINDLLTTLINKFDNIANQIKTAKELGINTAFVKNYDFFNHSEKYVDELNIVKNIARMKKPSSNAKKAMYHDALT
ILGIPEDMDEKALDEELDLILEKKTDPVTGKPLKGKNPLRNFIANNVIENSRFIYLIKFCNPENVRKIVNNTKVTEFVLKRIPD
AQIERYYKSCTDSEMNPPTEKKITELAGKLKDMNFGNFRNVRQSAKENMEKERFKAVIGLYLTVVYRVVKNLVDVNSRYIMAFH
SLERDSQLYNVSVDNDYLALTDLVKEGDNSRSRYLAGNKRLRDCVKQDIDNAKKWFVSDKYNSITKYRNNVAHLTAVRNCAEF
IGDITKIDSYFALYHYLIQRQLAKGLDHERSGFDRNYPQYAPLFKWHTYVKDVVKALNAPFGYNIPRFKNLSIDALFDRNEIKK
NDGEKKSDD (SEQ ID NO: 27)

>CDC65743.1
[Ruminococcus sp. CAG:57]
MAKKNKMKPRELREAQKKARQLKAAEINNNAAPAIAAMPAAEVIAPVAEKKKSSVKAAGMKSILVSENKMYITSFGKGNSAVLE
YEVDNNDYNKTQLSSKDNSNIELGDVNEVNITFSSKHGFGSGVEINTSNPTHRSGESSPVRGDMLGLKSELEKRFFGKTFDDNI
HIQLIYNILDIEKILAVYVTNIVYALNNMLGIKDSESYDDFMGYLSARNTYEVFTHPDKSNLSDKVKGNIKKSLSKFNDLLKTK
RLGYFGLEEPKTKDTRASEAYKKRVYHMLAIVGQIRQCVFHDKSGAKRFDLYSFINNIDPEYRDTLDYLVEERLKSINKDFIEG
NKVNISLLIDMMKGYEADDIIRLYYDFIVLKSQKNLGFSIKKLREKMLEEYGFRFKDKQYDSVRSKMYKLMDFLLFCNYYRNDV
AAGEALVRKLRFSMTDDEKEGIYADEAAKLWGKFRNDFENIADHMNGDVIKELGKADMDFDEKILDSEKKNASDLLYFSKMIYM
LTYFLDGKEINDLLTTLISKFDNIKEFLKIMKSSAVDVECELTAGYKLFNDSQRITNELFIVKNIASMRKPAASAVDKLTMFRD
TILGIDDNITDDRISEILKLKEKGKGIHGLRNFITNNVIESSRFVYLIKYANAQKIREVAKDEKVVMFVLGGIPDTQIERYYKS
CVEFPDMNSSLEAKRSELARMIKNISFDDFKNVKQQAKGRENVAKERAKAVIGLYLTVMYLLVKNLVNVNARYVIAIHCLERDF
GLYKEIIPELASKNLKNDYRILSQTLCELCDDRNESSNLFLKKNKRLRKCVEVDINNADSSMTRKYRNCIAHLTVVRELKEYIG
DIRTVDSYFSIYHYVMQRCITKRGDDTKQEEKIKYEDDLLKNHGYTKDFVKALNSPFGYNIPRFKNLSIEQLFDRNEYLTEK
(SEQ ID NO: 28)

TABLE 2-continued

Amino Acid Sequences of Cas13d Effector Proteins

>WP_046441786.1 (RspCas13d)
[*Ruminococcus* sp. N15.MGS-57]
MAKKNKMKPRELREAQKKARQLKAAEINNNAAPAIAAMPAAEVIAPVAEKKKSSVKAAGMKSILVSKNKMYITSFGKGNSAVLE
YEVDNNDYNQTQLSSKGSSNIELRGVNEVNITFSSKHGFESGVEINTSNPTHRSGESSPVRGDMLGLKSELEKRFFGKTFDDNI
HIQLIYNILDIEKILAVYVTNIVYALNNMLSIKDSESYDDFMGYLSARNTYEVFTHPDKSNLSDKAKGNIKKSFSTFNDLLKTK
RLGYFGLEEPKTKDTRVSQAYKKRVYHMLAIVGQIRQSVFHDKSSKLDEDLYSFIDIIDSEYRETLDYLVDERFDSINKGFIQG
NKVNISLLIDMMKGYEADDIIRLYYDFIVLKSQKNLGFSIKKLREKMLDEYGFRFKDKQYDSVRSKMYKLMDFLLFCNYYRNDV
VAGEALVRKLRFSMTDDEKEGIYADEASKLWGKFRNDFENIADHMNGDVIKELGKADMDFDEKILDSEKKNASDLLYFSKMIYM
LTYFLDGKEINDLLTTLISKFDNIKEFLKIMKSSAVDVECELTAGYKLFNDSQRITNELFIVKNIASMRKPASSAKLTMFRDAL
TILGIDDNITDDRISEILKLKEKGKGIHGLRNFITNNVIESSRFVYLIKYANAQKIRVAKNEKVVMFVLGGIPDTQIERYYKS
CVEFPDMNSSLEVKRSELARMIKNISFDDFKNVQQAKGRENVAKERAKAVIGLYLTVMYLLVKNLVNVNARYVIAIHCLERDF
GLYKEIIPELASKNLKNDYRILSQTLCELCDKSPNLFLKKNERLRKCVEVDINNADSSMTRKYRNCIAHLTVVRELKEYIGDIR
TVDSYFSIYHYVMQRCITKRENDTKQEEKIKYEDDLLKNHGYTKDFVKALNSPFGYNIPRFKNLSIEQLFDRNEYLTEK (SEQ
ID NO: 2)

>DJXD01000002_3
[*Ruminococcus* sp. UBA7013]
MKKQKSKKTVSKTSGLKEALSVQGTVIMTSFGKGNMANLSYKIPSSQKPQNLNSSAGLKNVEVSGKKIKFQGRHPKIATTDNPL
FKPQPGMDLLCLKDKLEMHYFGKTFDDNIHIQLIYQILDIEKILAVHVNNIVFTLDNVLHPQKEELTEDFIGAGGWRINLDYQT
LRGQTNKYDRFKNYIKRKELLYFGEAFYHENERRYEEDIFAILTLLSALRQFCFHSDLSSDESDHVNSFWLYQLEDQLSDEFKE
TLSILWEEVTERIDSEFLKTNTVNLHILCHVFPKESKETIVRAYYEFLIKKSFKNMGFSIKKLREIMLEQSDLKSFKEDKYNSV
RAKLYKLFDFIITYYYDHHAFEKEALVSSLRSSLTEENKEEIYIKTARTLASALGADFKKAAADVNAKNIRDYQKKANDYRISF
EDIKIGNTGIGYFSELIYMLTLLLDGKEINDLLTTLINKFDNIISFIDILKKLNLEFKFKPEYADFFNMTNCRYTLEELRVINS
IARMQKPSADARKIMYRDALRILGMDNRPDEEIDRELERTMPVGADGKFIKGKQGFRNFIASNVIESSRFHYLVRYNNPHKTRT
LVKNPNVVKFVLEGIPETQIKRYFDVCKGQEIPPTSDKSAQIDVLARIISSVDYKIFEDVPQSAKINKDDPSRNFSDALKKQRY
QAIVSLYLTVMYLITKNLVYVNSRYVIAFHCLERDAFLHGVTLPKMNKKIVYSQLTTHLLTDKNYTTYGHLKNQKGHRKWYVLV
KNNLQNSDITAVSSFRNIVAHISVVRNSNEYISGIGELHSYFELYHYLVQSMIAKNNWYDTSHQPKTAEYLNNLKKHHTYCKDF
VKAYCIPFGYVVPRYKNLTINELFDRNNPNPEPKEEV (SEQ ID NO: 29)

>SCH71549.1
[uncultured *Ruminococcus* sp.]
MAKKNKMKPRELREAQKKARQLKAAEINNNAAPAIAAMPAAEVIAPVAEKKKSSVKAAGMKSILVSENKMYITSFGKGNSAVLE
YEVDNNDYNKTQLSSKDNSNIELGDVNEVNITFSSKHGFGSGVEINTSNPTHRSGESSPVRGDMLGLKSELEKRFFGKTFDDNI
HIQLIYNILDIEKILAVYVTNIVYALNNMLGIKDSESYDDFMGYLSARNTYEVFTHPDKSNLSDKVKGNIKKSLSKFNDLLKTK
RLGYFGLEEPKTKDTRASEAYKKRVYHMLAIVGQIRQCVFHDKSGAKRFDLYSFINNIDPEYRDTLDYLVEERLKSINKDFIEG
NKVNISLLIDMMKGYEADDIIRLYYDFIVLKSQKNLGFSIKKLREKMLEEYGFRFKDKQYDSVRSKMYKLMDFLLFCNYYRNDV
AAGEALVRKLRFSMTDDEKEGIYADEAAKLWGKFRNDFENIADHMNGDVIKELGKADMDFDEKILDSEKKNASDLLYFSKMIYM
LTYFLDGKEINDLLTTLISKFDNIKEFLKIMKSSAVDVECELTAGYKLFNDSQRITNELFIVKNIASMRKPAASAKLTMFRDAL
TILGIDDNITDDRISEILKLKEKGKGIHGLRNFITNNVIESSRFVYLIKYANAQKIREVAKNEKVVMFVLGGIPDTQIERYYKS
CVEFPDMNSSLEAKRSELARMIKNISFDDFKNVQQAKGRENVAKERAKAVIGLYLTVMYLLVKNLVNVNARYVIAIHCLERDF
GLYKEIIPELASKNLKNDYRILSQTLCELCDDRNESSNLFLKKNKRLRKCVEVDINNADSSMTRKYRNCIAHLTVVRELKEYIG
DIRTVDSYFSIYHYVMQRCITKRGDDTKQEEKIKYEDDLLKNHGYTKDFVKALNSPFGYNIPRFKNLSIEQLFDRNEYLTEK
(SEQ ID NO: 30)

>SCJ27598.1
[uncultured *Ruminococcus* sp.]
MAKKNKMKPRELREAQKKARQLKAAEINNNAAPAIAAMPAAEVIAPAAEKKKSSVKAAGMKSILVSENKMYITSFGKGNSAVLE
YEVDNNDYNQTQLSSKDNSNIQLGGVNEVNITFSSKHGFESGVEINTSNPTHRSGESSPVRGDMLGLKSELEKRFFGKTFDDNI
HIQLIYNILDIEKILAVYVTNIVYALNNMLGVKSESHDDFIGYLSTNNIYDVFIDPDNSSLSDDKKANVRKSLSKFNALLKTK
RLGYFGLEEPKTKDNRVSQAYKKRVYHMLAIVGQIRQCVFHDKSGAKRFDLYSFINNNIDPEYRDTLDYLVEERLKSINKDFIED
NKVNISLLIDMMKGYEADDIIRLYYDFIVLKSQKNLGFSIKKLREKMLDEYGFRFKDKQYDSVRSKMYKLMDFLLFCNYYRNDI
AAGESLVRKLRFSMTDDEKEGIYADEAAKLWGKFRNDFENIADHMNGDVIKELGKADMDFDEKILDSEKKNASDLLYFSKMIYM
LTYFLDGKEINDLLTTLISKFDNIKEFLKIMKSSAVDVECELTAGYKLFNDSQRITNELFIVKNIASMRKPAASAKLTMFRDAL
TILGIDDKITDDRISGILKLKEKGKGIHGLRNFITNNVIESSRFVYLIKYANAQKIREVAKNEKVVMFVLGGIPDTQIERYYKS
CVEFPDMNSSLGVKRSELARMIKNISFDDFKNVQQAKGRENVAKERAKAVIGLYLTVMYLLVKNLVNVNARYVIAIHCLERDF
GLYKEIIPELASKNLKNDYRILSQTLCELCDKSPNLFLKKNERLRKCVEVDINNADSSMTRKYRNCIAHLTVVRELKEYIGDIC
TVDSYFSIYHYVMQRCITKRENDTKQEEKIKYEDDLLKNHGYTKDFVKALNSPFGYNIPRFKNLSIEQLFDRNEYLTEK (SEQ
ID NO: 31)

TABLE 3

Representative Type VI-D DirectRepeatNucleotide Sequences

| | |
|---|---|
| DS499551 | GAACTACACCCGTGCAAAAATGCAGGGGTCTAAAAC (SEQ ID NO: 32) |
| NZ_KB907524 | GAATTACACCCGTGCAAAAATGCAGGGGTCTAAAAC (SEQ ID NO: 33) |
| NZ_KB907524 | GAACTACACCCGTGCAAAATTGCAGGGGTCTAAAAC (SEQ ID NO: 34) |
| 3300001598\|EMG_10003641 | GAACTACACCCCTGCAGAAATGCTGGGGTCTAAAC (SEQ ID NO: 35) |
| 3300001598\|EMG_10000232 | GGACAATAACCTGCGAATTTTGGCAGGTTCTATGAC (SEQ ID NO: 36) |
| 3300006226\|Ga0099364_10024192 | GTGCAGTAGCCTTACAGATTCGTAGGGTTCTGAGAC (SEQ ID NO: 37) |

TABLE 3-continued

Representative Type VI-D Direct Repeat Nucleotide Sequences

| | |
|---|---|
| 3300007296\|Ga0104830_100502 | CTACTACACTGGTGCGAATTTGCACTAGTCTAAAAC (SEQ ID NO: 38) |
| 3300007299\|Ga0104319_1000623 | CTACTACACTAGTGCAAATTTGCACTAGTCTAAAAC (SEQ ID NO: 39) |
| 3300007361\|Ga0104787_100954 | CTACTACACAGGTGCAATTTTGCACTAGTCTAAAAC (SEQ ID NO: 40) |
| 3300007361\|Ga0104787_100954 | CTACTACACTGGTGCGAATTTGCACTAGTCTAAAAC (SEQ ID NO: 41) |
| 3300008496\|Ga0115078_100057 | CTACTATACTGGTGCGAATTTGCACTAGTCTAAAAC (SEQ ID NO: 42) |
| 3300010266\|Ga0129314_1001134 | GAACTACACCCGTGCAAAAATGCAGGGGTCTAAAAC (SEQ ID NO: 43) |
| 3300018475\|Ga0187907_10006632 | CATGTAAACCCCTAACAAATGATAGGGGGTTGAAAC (SEQ ID NO: 44) |
| 3300018493\|Ga0187909_10005433 | CTACTACCCTGTTATTTGACAGGGTTCAAAAAC (SEQ ID NO: 45) |
| 3300018494\|Ga0187911_10005861 | GAACTACAGCCCTGTGAAATAACGGGGTTCTAAAAC (SEQ ID NO: 46) |
| 3300018494\|Ga0187911_10005861 | GAACTACAGCCCTGTGAAATAACAGGGTTCTAAAAC (SEQ ID NO: 47) |
| 3300018495\|Ga0187908_10013323 | GAACGACGTCACTACACACCGAGAGGTGTCTAAAAC (SEQ ID NO: 48) |
| 3300018878\|Ga0187910_10015336 | CAACTACCCTGCCAAATGGCAGGGTTCAGAAAC (SEQ ID NO: 49) |
| LSQX01212483 | GACCAACACCTCTGCAAAACTGCAGGGGTCTAAAAC (SEQ ID NO: 50) |
| NFIR01000008 | GAACTACACTCTGGCTGAAAGTCAGGGTCTAAAAC (SEQ ID NO: 51) |
| NFIR01000008 | GAACTACACTCTGGCTGAAAGTCAGGGTCTAAAAC (SEQ ID NO: 52) |
| NFLV01000009 | GAACTACACCCTGGCTGAAAGTCAGGGTCTAAAAC (SEQ ID NO: 53) |
| CDYU01004315 | CTACTACACTGGTGCAAATTTGCACTAGTCTAAAAC (SEQ ID NO: 54) |
| CDYU01004315 | CTACTACACTAGTGCGAATTTGCACTAGTCTAAAAC (SEQ ID NO: 55) |
| CDYU01023067 | CAGCACTACACCCCCCTGAAACAGGAGGGGTCTAAAAC (SEQ ID NO: 56) |
| CDZR01037537 | CTACTACACTAGTGCGAATTTGCACTAGTCTAAAAT (SEQ ID NO: 57) |
| CDZR01037537 | CTACTACACTAGTGCGAATTTGCGCTAGTCTAAAAC (SEQ ID NO: 58) |
| CDZI01047721 | CTACTATACTGGTGCGAATTTGCACTAGTCTAAAAT (SEQ ID NO: 59) |
| FOAT01000009 | CCCTTTGTACTATACCTGTTTTACACAGGTCTAAAAC (SEQ ID NO: 60) |
| FOAT01000009 | GTACTATACCTGTTTTACACAGGATAATAACCAAAAT (SEQ ID NO: 61) |
| HF545617 | CTACTACACTGGTGCGAATTTGCACTAGTCTAAAAC (SEQ ID NO: 62) |
| HF545617 | CTACTACACTAGTGCGAATTTGCACTAGTCTAAAAC (SEQ ID NO: 63) |
| DBYI01000091 | GAACTATACCCCTACCAAATGGTCGGGGTCTGAAAC (SEQ ID NO: 64) |
| FPJT01000005 | CAAGTAAACCCCTACCAACTGGTCGGGGTTTGAAAC (SEQ ID NO: 65) |
| FPJT01000005 | CAAGTAAACCCTTACCAACTGGTCGGGGTTTGAAAC (SEQ ID NO: 66) |
| NZ_ACOK01000100 | GAACTATAGTAGTGTAAATTTGCACTACTATAAAAC (SEQ ID NO: 67) |
| CBFS010000062 | CTACTACACTAGTGCGAATTTGCACTAGTCTAAAAC (SEQ ID NO: 68) |
| CBFS010000062 | CTACTACACTAGTGCGAATTTGCGCTAGTCTAAAAC (SEQ ID NO: 69) |
| FR890758 | CTACTACACTAGTGCGAATTTGCACTAGTCTAAAAC (SEQ ID NO: 70) |
| FR890758 | CTACTACACTGGTGCAAATTTGCACTAGTCTAAAAC (SEQ ID NO: 71) |

TABLE 3-continued

Representative Type VI-D DirectRepeat Nucleotide Sequences

| LARF01000048 | CTACTACACTGGTGCAAATTTGCACTAGTCTAAAAC (SEQ ID NO: 72) |
| --- | --- |
| DJXD01000002 | CAACTACAACCCCGTAAAAATACGGGGTTCTGAAAC (SEQ ID NO: 73) |
| FMEA01000016 | CTACTACACTAGTGCGAATTTGCACTAGTCTAAAAC (SEQ ID NO: 74) |
| FMEA01000016 | CTACTACACTGGTGCAAATTTGCACTAGTCTAAAAC (SEQ ID NO: 75) |
| FMFL01000053 | CTACTACACTGGTGCAAATTAGCACTAGTCTAAAAC (SEQ ID NO: 76) |
| FMGZ01000034 | CTACTACACTGGTGCAAATTAGCACTAGTCTAAAAC (SEQ ID NO: 77) |

TABLE 4

Amino Acid Sequences of Cas13d Accessory Proteins WYL1

>CDC65744.1
[*Ruminococcus* sp. CAG:57]
MLIPPSTFLPKRDKNVPYIAEVQSIPLSPSAYSVIIKDKSIFETSLSPNGSVSMSSFLTSIFDSAYIASLKYKSDDNYKYIGIP
LLNAFVEWQIEEIDDSLDDKSKEIIKSYLISKLSAKYEKTKTENAVRVRLSICRDLYDTLSSDDLYYENKVYSLTLRRFLKAVY
EDYALLSDCERERLIFADNIIKINEVIKQNGSRYYSFIYAYSNMYSREKRRIRLIPYRIVSDEYKMYNYLVCLSDEKSAGKEFK
ADSYRISRLSGLSIAEKLSQKEYSSVTEYERLKEGHVKSVKHLLSDPRFGSDESDISKVYLTEKGVEMFGKILYQRPILKGNEK
PKPNTVNEFISPPIQVKYYFNKFGKDGVILSPSDSFEEMRTLYVEGAEAYNREVEM (SEQ ID NO: 78)

>SCJ78009.1
[uncultured *Ruminococcus* sp.]
MLILPSTFLPKRDKNVPYIAEVQSIPLSPSAYSVIIKDKSIFETSLSPNGSVSMSSFLTSIFDSAYIASLKYKSEKYNGIPLLN
AFVKWQIEEINDGLDDKSKEIIKSYLISKLSAKYEKTKTENAVRVRLSICRDLYDTLSSDDLYYENKVYSSTLRRFLKAVYEDY
ALLSDCERERLIFADNIIKINEVIKQNGSRYYSFIYAYSNMYSREKRRIRLIPYRIVSDEYKMYNYLVCLSDEKSAGKEFKADS
YRISRLSGLSIAEKLSQKEYSSVTEYERLKEGHVKSVKHLLSDPRFGSDESDISKVYLTEKGVEMFGKILYQRPILKGNEKPKP
NAVNEFISPPIQVKYYFNKFGKDGVILSPSDSFEEMRTLYVEGAEAYNREVEM (SEQ ID NO: 79)

>WP_041337479.1
[*Ruminococcus bicirculans*]
MSMTPSTFLPKREDGVPYIAEVQSIPLSPSAYSVIIKDKSIFETSLSPNGSVSMSSFLTSIFDSAYIASLKYKSDDNYKYIGIP
LLNAFVKWQIEEIDDSLDDKSKEIIKSYLISKLSAKYEKTKTENAVRVRLSICRDLYDTLSSDDLYYENKVYSSTLRRFLKAVY
EDYALLSDCERERLIFADNIIKINEVIKQNGSRYYSFIYAYSNMYSREKRRIRLIPYRIVSDEYKMYNYLVCLSDEKSAGKEFK
ADSYRISRLSGLSIAEKLSQKEYSSVTEYERLKEGHVKSVKHLLSDPRFGSDESDISKVYLTEKGVEMFGKILYQRPILKGNEK
PKPNAVNEFISPPIQVKYYFNKFGKDGVILSPSDSFEEMRTLYVEGAEAYNREVEM (SEQ ID NO: 80)

>WP_046441785.1 (RspCsx29 or RspWYL1)
[*Ruminococcus* sp. N15.MGS-57]
MLIPPSTFLPKRDKNVPYIAEVQSIPLSPSAYSVIIKDKSIFETSLSPNGSVSMSSFLTSIFDSAYIASLKYKSDDNYKYIGIP
LLNAFVKWQIEEIDDGLDDKSKEIIKSYLISKLSAKYEKTKTENAVRVRLSICRDLYDTLSSDDLYYENKVYSSTLRRFLKAVY
EDYALLSDCERERLIFADNIIKINEVIKQNGSRYYSFIYAYSNMYSREKRRIRLIPYRIVSDEYKMYNYLVCLSDEKSAGKEFK
ADSCRISRLSGLSIAEKLSQKEYSSVTEYERLKEVHVKSVKHLLSDPRFGSDESDISKVYLTEKGVEMFGKILYQRPILKGNEK
PKPNAVNEFISPPIQVKYYFNKFGKDGVILSPSDSFEEMRTLYVEGAEAYNREVEM (SEQ ID NO: 81)

>CDYU01004315_3
[gut metagenome]
MSMTPSTFLPKRDKNATYIAEVQSIPLSPSAYSVIIKDKSIFETSLSPNGSVSMSSFLTSIFDSAYIASLKYKSEKYNGIPLLN
AFVKWQIEEIDDGLDDKSKEIIKSYLISKLSAKYEKTKTENAVRVRLSICRDLYDTLSSDDLYYENKVYSSTLRRFLKAVYEDY
ALLSDCERERLIFADNIIKINEIIKQNGSRYYSFIYAYSNMYSREKRRIRLIPYRIVSDEYKMYNYLVCLSDEKSAGKEFKADS
YRISRLSGLSIAEKLSQKEYSSVTEYERLKEGHVKSVKHLLSDPRFGSDESDISKVYLTEKGVEMFGKILYQRPILKGNEKPKP
NTVNEFISPPIQVKYYFNKFGKDGVILSPSDSFEEMRTLYVEGAEAYNREVEM (SEQ ID NO: 82)

>CDYX01024884_5
[gut metagenome]
MFIPPSTFLPKREGGVPYIAEVQSIPLSPSAYSVIIKDKSIFETSLSPNGSVSMSSFLTSIFDSAYIASLKYKTDDNYKYIGIP
LLNAFIKWQIEEIDDGLDDKSKEIIKSYLISKFSAKYEKTKTENAVRVRLSICRDLYDTLSSDDLYYENKVYSSTLRRFLKAVY
EDYALLSDCERERLIFADNIIKINEVIKQNGNRYYSFIYAYSNMYSREKRRIRLIPYRIISDEYKMYNYLVCLSDEKSAGKEFK
ADSCRISRLSGLSIAEKLSQKEYSSVTEYERLKEGHVKSVKHLLSDPRFGSDESDISKVYLTEKGVEMFGKILYQRPILKGNEK
PKPNAVNEFISPPIQVKYYFNKFGKDGVILSPSDSFEEMRTLYVEGAEAYNREVEM (SEQ ID NO: 83)

>3300008496|Ga0115078_100057_48
[human-digestive system-*homo sapiens*]
MSMTPSTFLPKRDTNIPYIAEVQSIPLSPSAYAVIVKDKSIFETSLFPNGGSVSMSSFLTRIFDSAYIASLKYKSEEYNGIPLL
NAFVQWQIEEIDDSLDDKSKEIIKSYLISKLSAKYEKTKTENAVRVRLSICRDLYDTLSSDDLYYENKVYSSTLRRFLKAVYED

TABLE 4-continued

Amino Acid Sequences of Cas13d Accessory Proteins WYL1

YALLSDCERERLIFADNIIKINEVIKQNGSRYYSFIYAYSNMYSREKRRIRLIPYRIVSDEYKMYNYLVCLSDEKSAGKEFKAD
SYRISRLSGLSIAEKLSQKEYSSVTEYERLKEGHVKSVKHLLSDPRFGSDESDISKVYLTEKGVEMFGKILYQRPILKGNEKPK
PNAVNEFISPPIQVKYYFNKFGKDGVILSPSDSFEEMRTLYVEGAEAYNREVEM (SEQ ID NO: 84)

>3300007296|Ga0104830_100502_30
[human-digestive system-*homo sapiens*]
MLIPPSTFLPKREGGVPYIAEVQSIPLSPSAYSVIIKDKSIFETSLFPNGSVSMSSFLTSIFDSAYIASLKYKSDDNYKYIGIP
LLNAFVKWQIEEIDDGLDDKSKEIIKSYLISKLSAKYKKTKTENAVRVRLSICRDLYDTLSSDDLYYENKVYSSTLRRFLKAVY
EDYALLSDCERERLIFADNIIKINEVIKQNGSRYYSFIYAYSNMYSREKRRIRLIPYRIVSDEYKMYNYLVCLSDEKSAGKEFK
ADSYRISRLSGLSIAEKLSQKEYSSVTEYERLKEVHVKSVKHLLSDPRFGSDESDISKVYLTEKGVEMFGKILYQRPILKGNEK
PKPNAVNEFISPPIQVKYYFNKFGKDGVILSPSDSFEEMRTLYVEGAEAYNREVEM (SEQ ID NO: 85)

>3300007299|Ga0104319_1000623_27
[human-digestive system-*homo sapiens*]
MLIPPSTFLPKRKDGVPYIAEVQSIPLSPSAYAVIVKDKSIFETSLSPNSSVSMSSFLTRIFDSAYRASLKYKSEEYNGIPLLN
AFVQWQIEEIDGSLDDKSKEIIRSYLISKLSAKYKKTKTENAVRVRLSICRDLYDTLSRVDLCYENKVYGSTLRRFLKAVYEDY
ALLSDCERERLIFADNIIKINEVIKQNSNRYDNFIYAYSSMYSREKCRIRLIPYRIVSDEYKMYNYLVCLSDEKSVGKEFKADS
YRISRLSGLSIAEKLSQKEYSSVTEYERLKEGHVKSVKHLLSDPRFGSDESDISKVYLTEKGVEMFGKILYQRPILKGNEKPKP
NAVNEFISPPIQVKYYFNKFGKDGVILSPSDSFEEMRTLYVEGAEAYNREVEM (SEQ ID NO: 86)

>CDYS01033339_20
[gut metagenome]
MGTENSSNEYQEARQHLSLSDAAWAVLQDDRQDFGGGRSWAGILNYVFAEYRDKADASISVAVERRRAQYEEKLVGVAAPAVRK
AVLEALLADYTEELIKKAAQNGATPPDKESFKFRLDRDNYAFREQWLDSPDAQYYGGRFSRYLRAVLEEYAAKTVYQREAIYFD
PQMRLIQASAANGELLRIRLKKGSEFEVRPYGVLGDRQETYHYLVGLSRPDGTREPEKASSFRLSNIVKLEVSFRRSGRLTEKE
RTDIESSIRGKGVQFLVQQRETIRIRLTEDGRQNYGRQLHLRPAARERAEVDDGLYRWEYTFYCTEFQAKAYFLKFCGDAKVVE
PQSLRETFAQEYRSGLRACGEEP (SEQ ID NO: 87)

>CDTW01032418_59
[gut metagenome]
MGTENSSNEYQEARQHLSLSDAAWAVLQDDRRDFGGGRSWAGILNYVFTMYRDKADASVSVAVSRRREQLEEQLGGVVSPAARD
AVLDRLMEVYAGELAEKAMSDGAVAQQKEVFKFRLDRDNYAFREQWLDSPDAARYYGNRFSRYLRAVLEEYAAKTVYQREAIYF
DPQMRLIRAAAANGELLRIRMKTGSSFEVRPYGVLGDRQETYHYLVGLSRPDGTRGPEKEFNFRLSKIIKLDVSFRRSGRLTEK
ERTDIESSIRGKGVQFLAQQRETIRIRLTEEGRRDYGSQMHLRPPAQTRTAVDDGAYRWEYTFFCTEFQARAYFLKFCGEAKVV
EPQSLRDTLAQEYRSGLRACGEEP (SEQ ID NO: 88)

TABLE 5

Amino Acid Sequences of Cas13d Accessory Proteins WYL-b1

>DBYI01000091_50
[*Ruminococcus flavefaciens*]
MENKGKQREFIKDYNKIVPFLEKVFYYGTFSSEDYEKMDMMKKSKYSDYKRILEFAFRDVLYEKKNINGKKALGLRIDHFYDPH
RAFLRFFTLKSFVSIERLFLTCYILKRISKKGKCTINDICIGLDEVSVDDEVKDRKSTISRIIKNMVDYGFLIKKGSAYSINTG
AKTLNNVALLNLIDICTNAYPISICGSCIQNKIDQNYQSPFLIKHLHLGQIFNDELIWKLLIYANEKKQLCIELKKGIKLRELL
PYRIITNRETGRQYLFAIYVGTNNFDEYLMLRLDKISDIKIEASECEIPDDTVLKEKYDTAFRYSFNGTTFLKRDQQPESGILV
YDKSFEWNIKKHFPYSDAVSVDEKHNKVSIKVNTLTELKPWLRRNYDKVSLVESSDDTVDKMCDELKKWRKMYGII (SEQ ID
NO: 89)

>SFX39521.1
[*Ruminococcus flavefaciens*]
MANEEKNRSFFKITTYENFRRFLKTNFYYCSLSQGQQGMFIKSIGTTKYNEYKNIIELIAGGKIEFPKINKRLAFRYNISQLES
DYNELANSFQLRTLTSLDACLTLYILLFLSDKEMGSSDIYNRIGDIDFDIDEKTIRGKLKNMCEYGMISYKNKKYSLNECSLYS
VDTSIMLSLLNMADFMKNLVYPEVLGYDLFAALKKIYEERTGNEYISPFQFKYSHLANILDDNVLWTLIEAIDNRQHVAFEYGG
KIKERLIPVKIFTENEYNRCYLFAVKRFRNKLKFFVFRLSKIYNLKITNSDEDITEADFKEYSELYDSEKKCSFFGKIDSSAQN
DTVELKYKRGIRSQLERDFSCIEFRKNYTAIVTVKSKKMMIPYLRANMGLIRTTDDELSGILNEDIEEMKKNYGII (SEQ ID
NO: 90)

>3300018494|Ga0187911_10005861_21
[mammals-digestive system-feces]
MNVIIKQGDIFMGNEERNRSFFKEDTYETFRKFLKTNFYYCTLSQKQQSEYVKYIGTTQYNHYRGIIERISEGKISFKKYNKKK
APFKYDVSQFASDYNVLANSFQLKTITASQTCLTIYILCVLAKSSLTRKGIVAAIADGIDEKTIVSRIKSMKEAGLISYDGEKYF
IEESIFYSMDESLLLRLLNMVDFMKNLVYPEALGYNLFDIIKKIYDDRLCVDYYSPFQLKYSHLANILDDNVLWSLIEAIEERQ
YISFIYKNEKKERIIPVKLFTENEYARRYLFAVKKFGNNYKKFIFRLSEIYNIKVMEKEVSVSKEEFGKLLEMYETESGYSFSG
KIAPSSKTVSIKLRYKGRLKNQIERDFSNVKFEKGNTAEILIKNKKMIIPYLRSNMQLIQSTDEELSQKINSEIMEMKKLYGII
(SEQ ID NO: 91)

TABLE 6

Amino Acid Sequences of Cas13d Accessory Proteins WYL-b2

```
>SFX39545.1
[Ruminococcus flavefaciens]
MELFNEYRNKSLRAFLKLAERISYGEELSIDEFEAEYYRLSGDNKKITSVFYKNTLYNDKLPIFDTREGKVRLFGEPDKCSNKH
ISDTLLKSEITWLHNALNDKLSKLFLSDEERISIDAKLSDYTEYYKNIDDMWRSNEDISEEVEKNFKIILKAINEKQALSYTFK
NKNCEGFPVRIEYDERTCRIYMIIYDGNRFVKSDISKLSDIYITENSIDTIPEIKDDMLNKKAYLPVVFTVTDDKNRKAIDRAL
LAFSVYDHVVEPIDEKTARFTIQYYTMDLDLLIKDILAFGSDIKVESPRYVVKRITDILRKV (SEQ ID NO: 92)

>3300018494|Ga0187911_10005861_20
[mammals-digestive system-feces]
MELFNEFRNKSFNAFITLAERIANDNAVFSKTEFETEYYRLSGDENRITSIFYNNVINNEKYQIFTIPKDSKDKVQLSIEFDNK
DDINIANIPITSEKKWLHSALHDKLSKLFLSDEEISYIDETISEFPLYYEHIDDSWRKGENISEESVINFRIILQAINEKKSLS
YKYNGKDSEGSPVKIEYDERTCKIYMILYNGSRFIKSDISGLSDICIKEQLYEKIPDIKEGMLEKKARHPIVFTVTDNKNRKSI
ERALLAFSVYEHYVEPIDKNTAKFTIHYYTMDLDILIKDILAFGADIKVEAPQFVVKKIINILENV (SEQ ID NO: 93)
```

TABLE 7

Amino acid sequences of motifs in Type VI-DCRISPR-Cas Effector Proteins

```
>MOTIF_1
RXXXXH (SEQ ID NO: 94)

>MOTIF_2
DXXXQXXXXJLDXXK (SEQ ID NO: 95)

>MOTIF_3
FXXXXXXXXXGXXXXXJR (SEQ ID NO: 96)

>MOTIF_4
KEXNXXXXXXXXXXXNI (SEQ ID NO: 97)

>MOTIF_5
YXXXRXKBLXXXXLF (SEQ ID NO: 98)
```

REFERENCES

Altschul, S. F., Madden, T. L., Schäffer, A. A., Zhang, J., Zhang, Z., Miller, W., and Lipman, D. J. (1997). Gapped BLAST and PSI-BLAST: a new generation of protein database search programs. Nucleic Acids Res. 25, 3389-3402.

Bateman, A., Martin, M. J., O'Donovan, C., Magrane, M., Alpi, E., Antunes, R., Bely, B., Bingley, M., Bonilla, C., Britto, R., et al. (2017). UniProt: the universal protein knowledgebase. Nucleic Acids Res. 45, D158-D169.

Benson, D. A., Cavanaugh, M., Clark, K., Karsch-Mizrachi, I., Lipman, D. J., Ostell, J., and Sayers, E. W. (2013). GenBank. Nucleic Acids Res. 41, D36-42.

Eddy, S. R. (2011). Accelerated Profile HMM Searches. PLoS Comput. Biol. 7, e1002195.

Edgar, R. C. (2004). MUSCLE: multiple sequence alignment with high accuracy and high throughput. Nucleic Acids Res. 32, 1792-1797.

Edgar, R. C. (2010). Search and clustering orders of magnitude faster than BLAST. Bioinformatics 26, 2460-2461.

Finn, R. D., Bateman, A., Clements, J., Coggill, P., Eberhardt, R. Y., Eddy, S. R., Heger, A., Hetherington, K., Holm, L., Mistry, J., et al. (2014). Pfam: the protein families database. Nucleic Acids Res. 42, D222-D230.

Hein, S., Scholz, I., Voß, B., and Hess, W. R. (2013). Adaptation and modification of three CRISPR loci in two closely related cyanobacteria. RNA Biol. 10, 852-864.

Hyatt, D., Chen, G.-L., LoCascio, P. F., Land, M. L., Larimer, F. W., and Hauser, L. J. (2010). Prodigal: prokaryotic gene recognition and translation initiation site identification. BMC Bioinformatics 11, 119.

Makarova, K. S., Anantharaman, V., Grishin, N. V., Koonin, E. V., and Aravind, L. (2014). CARF and WYL domains: ligand-binding regulators of prokaryotic defense systems. Front. Genet. 5.

Peters, J. E., Makarova, K. S., Shmakov, S., and Koonin, E. V. (2017). Recruitment of CRISPR-Cas systems by Tn7-like transposons. Proc. Natl. Acad. Sci. U.S.A. 114, E7358-E7366.

Pruitt, K. D., Tatusova, T., Brown, G. R., and Maglott, D. R. (2012). NCBI Reference Sequences (RefSeq): current status, new features and genome annotation policy. Nucleic Acids Res. 40, D130-135.

Shmakov, S., Abudayyeh, O. O., Makarova, K. S., Wolf, Y. I., Gootenberg, J. S., Semenova, E., Minakhin, L., Joung, J., Konermann, S., Severinov, K., et al. (2015). Discovery and Functional Characterization of Diverse Class 2 CRISPR-Cas Systems. Mol. Cell 60, 385-397.

Shmakov, S., Smargon, A., Scott, D., Cox, D., Pyzocha, N., Yan, W., Abudayyeh, O. O., Gootenberg, J. S., Makarova, K. S., Wolf, Y. I., et al. (2017). Diversity and evolution of class 2 CRISPR-Cas systems. Nat. Rev. Microbiol. 15, 169-182.

Smargon, A. A., Cox, D. B. T., Pyzocha, N. K., Zheng, K., Slaymaker, I. M., Gootenberg, J. S., Abudayyeh, O. A., Essletzbichler, P., Shmakov, S., Makarova, K. S., et al. (2017). Cas13b Is a Type VI-B CRISPR-Associated RNA-Guided RNase Differentially Regulated by Accessory Proteins Csx27 and Csx28. Mol. Cell 65, 618-630.e7.

Steinegger, M., and Söding, J. (2017). MMseqs2 enables sensitive protein sequence searching for the analysis of massive data sets.

Yu, J., Picord, G., Tuffery, P., and Guerois, R. (2015). HHalign-Kbest: exploring sub-optimal alignments for remote homology comparative modeling. Bioinforma. Oxf. Engl. 31, 3850-3852.

Zhu, W., Lomsadze, A., and Borodovsky, M. (2010). Ab initio gene identification in metagenomic sequences. Nucleic Acids Res. 38, e132-e132.

Figure 1:
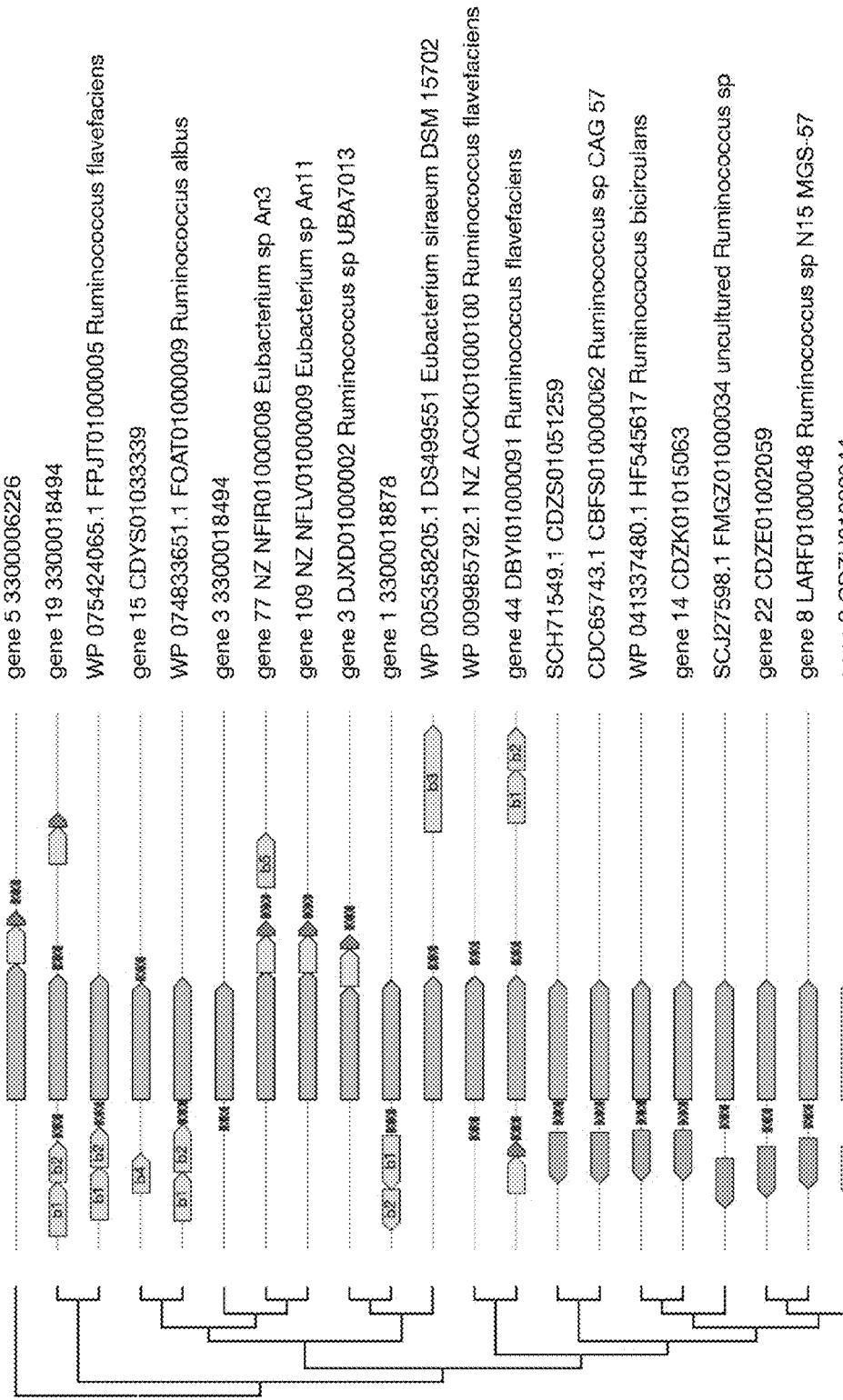

Example 2. Accelerated In Vivo Functional Screening of Type VI-D CRISPR-Cas Systems Having identified the minimal suite of Type VI-D CRISPR-Cas system components, we selected two loci for functional validation, those from *Eubacterium siraeum* DSM 15702 (EsCas13d) and *Ruminococcus* sp. N15.MGS-57 (RspCas13d). RspCas13d is a member of the largest subgroup of Cas13d proteins which contains 13 of the 31 unique members of the family and shows co-conservation with a putative WYL1 accessory protein (FIGS. 1, 6, 7). In contrast, there are no WYL-domain proteins (or other putative accessory proteins) encoded within 3 kb of the EsCas13d effector.

DNA Synthesis and Effector Library Cloning

Figure 8:
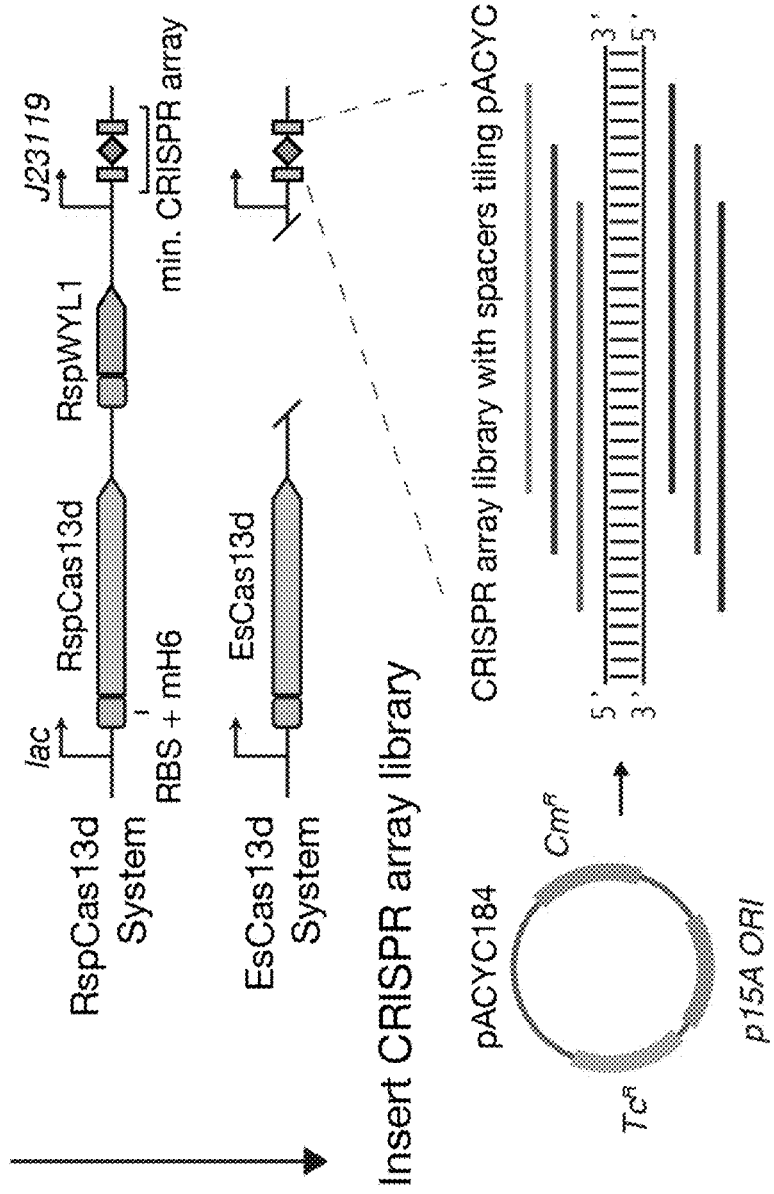
FIG. 8 depicts a design of minimal engineered CRISPR-Cas systems for the Rsp and Es type VI-D CRISPR loci (referred to as RspCas13d and EsCas13d systems), with a spacer library tiling pACYC184 (both top strand and bottom strand).

To test the activity of Type VI-D CRISPR-Cas, we designed and synthesized minimal systems containing RspCas13d or EsCas13d into the pET28a(+) vector. The synthesized *Ruminococcus* sp. RspCas13d system included RspCas13d and RspWYL1, codon optimized for *E. coli* expression under the control of a lac promoter and separated by an *E. coli* ribosome binding sequence (FIG. 8). Following the open reading frames for RspCas13d and RspWYL1, we included an acceptor site for a CRISPR array library driven by a J23119 promoter. The *Eubacterium siraeum* system was prepared similarly but included no gene for a WYL-domain containing protein.

The *E. coli* codon-optimized genes representing the minimal CRISPR effectors and accessory proteins were synthesized (Genscript) into a custom expression system derived from the pET-28a(+) (EMD-Millipore). Briefly, the *Ruminococcus* sp. synthesis product included Cas13d and WYL1 codon optimized for *E. coli* expression under the control of a Lac promoter and separated by an *E. coli* ribosome binding sequence. Following the open reading frames for Cas13d and WYL1, we included an acceptor site for a CRISPR array library driven by a J23119 promoter (Registry of Standard Biological Parts: parts.igem.org/Part:BBa_J23119). Our *Eubacterium siraeum* system was similarly constructed, but with only the effector protein.

In tandem with the effector gene synthesis, we first computationally designed an oligonucleotide library synthesis (OLS) pool containing "repeat-spacer-repeat" sequences, where "repeat" represents the consensus direct repeat sequence found in the CRISPR array associated with the effector, and "spacer" represents sequences tiling the pACYC184 plasmid. The spacer length was determined by the mode of the spacer lengths found in the endogenous CRISPR array. The repeat-spacer-repeat sequence was appended with restriction sites enabling the bidirectional cloning of the fragment into the aforementioned CRISPR array library acceptor site, as well as unique PCR priming sites to enable specific amplification of a specific repeat-spacer-repeat library from a larger pool. The library synthesis was performed by Agilent Genomics.

We next cloned the repeat-spacer-repeat library into the plasmid containing the minimal engineered locus using the Golden Gate assembly method. In brief, we first amplified each repeat-spacer-repeat from the OLS pool (Agilent Genomics) using unique PCR primers, and pre-linearized the plasmid backbone using BsaI to reduce potential background. Both DNA fragments were purified with Ampure XP (Beckman Coulter) prior to addition to Golden Gate Assembly Master Mix (New England Biolabs) and incubated as per manufacturer's instructions. We further purified and concentrated the Golden Gate reaction to enable maximum transformation efficiency in the subsequent steps of the bacterial screen.

Accelerated Functional Screening for Cas13d

To accelerate functional screening of Type VI-D systems, we developed a strategy to derive the following functional information in a single screen: 1) crRNA expression direction and processing, 2) nucleic acid substrate type, and 3) targeting requirements such as protospacer adjacent motif (PAM), protospacer flanking sequence (PFS), or target secondary structure. We designed minimal CRISPR array libraries consisting of two consensus direct repeats, each flanking a unique natural-length spacer sequence targeting either the pACYC184 vector or an absent GFP sequence as a negative control. The CRISPR array libraries for EsCas13d and RspCas13d systems consisted of 4549 and 3972 pACYC184-targeting spacers respectively, in addition to 452 and 450 spacers targeting the GFP negative control sequence, respectively. We also designed a bidirectional array library cloning strategy to test both possible CRISPR array expression directions in parallel.

Figure 9:
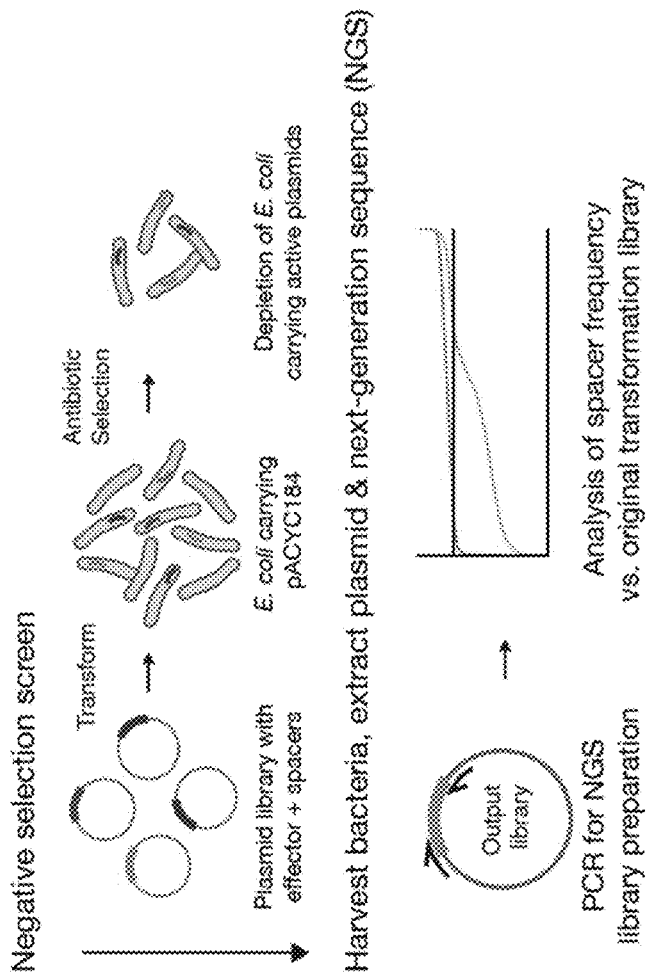
FIG. 9 depicts a schematic of the bacterial negative selection screen used to evaluate functional parameters of RspCas13d and EsCas13d systems.

The CRISPR array libraries for RspCas13d and EsCas13d were cloned into acceptor sites on respective Type VI-D expression plasmids such that each plasmid contained a single library element and orientation (FIG. 8). The resulting plasmid libraries were transformed with pACYC184 into Stbl3 *E. coli* using electroporation, yielding a maximum of one plasmid library element per cell. Transformed *E. coli* cells were plated on bioassay plates containing Kanamycin (selecting for the library plasmid), Chloramphenicol (CAM; selecting for intact pACYC184 CAM expression), and Tetracycline (TET; selecting for intact pACYC184 TET expression), such that interruption of pACYC184 plasmid DNA or antibiotic resistance gene expression by the CRISPR-Cas system results in bacterial cell death. Screens were harvested 12 h after plating, and plasmid DNA was extracted (FIG. 9). We PCR amplified the CRISPR array region of the input plasmid library prior to transformation and the output plasmid library after bacterial selection on antibiotic plates.

The plasmid library containing the distinct repeat-spacer-repeat elements and Cas proteins was electroporated into Endura electrocompetent *E. coli* (Lucigen) using a Gene Pulser Xcell® (Bio-rad) following the protocol recommended by Lucigen. The library was either co-transformed with purified pACYC184 plasmid, or directly transformed into pACYC184-containing Endura electrocompetent *E. coli* (Lucigen), plated onto agar containing Chloramphenicol® (Fisher), Tetracycline (Alfa Aesar), and Kanamycin (Alfa Aesar) in BioAssay® dishes (Thermo Fisher), and incubated for 10-12 h. After estimation of approximate colony count to ensure sufficient library representation on the bacterial plate, the bacteria were harvested and DNA plasmid extracted using a QIAprep Spin Miniprep® Kit (Qiagen) to create the "output library." By performing a PCR using custom primers containing barcodes and sites compatible with Illumina sequencing chemistry, we generated a barcoded next generation sequencing library from both the pre-transformation "input library" and the post-harvest "output library," which were then pooled and loaded onto a Nextseq 550 (Illumina) to evaluate the effectors. At least two independent biological replicates were performed for each screen to ensure consistency.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source plasmid pACYC184 or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR of the input and output plasmid libraries. We defined the array depletion ratio as the normalized output read count divided by the normalized input read count. An array was considered to be strongly depleted if the depletion ratio was less than 0.1 (more than 10-fold depletion). When calculating the array depletion ratio across biological replicates, we took the maximum depletion ratio value for a given CRISPR array across all experiments (i.e. a strongly depleted array must be strongly depleted in all biological replicates). We generated a matrix including array depletion ratios and the following features for each spacer target: target strand, transcript targeting, ORI targeting, target sequence motifs, flanking sequence motifs, and target secondary structure. We investigated the degree to which different features in this matrix explained target depletion for RspCas13d and EsCas13d systems, thereby yielding a broad survey of functional parameters within a single screen.

Distribution of Bacterial Screening Targets Indicates that Cas13d Targets ssRNA Transcripts To identify the targeted substrate for Cas13d, we first identified a set of minimal CRISPR arrays that were strongly depleted in 2 screen biological replicates. For both RspCas13d and EsCas13d systems, these strongly depleted arrays primarily targeted pACYC184, with minimal depletion of the negative control (FIGS. 10 and 11). We observed 1119 and 806 strongly depleted arrays for the RspCas13d and EsCas13d systems, respectively (FIGS. 12A-B). The spatial distribution and strand preference of the strongly depleted target sites along pACYC184 (FIGS. 13A-B) indicate a preference for transcript targeting, suggesting that Cas13d targets single-stranded RNA transcripts. Additionally, the presence of strongly depleted targets within the non-coding region of pACYC184 between the Tet and CAM ORFs corresponds to the extension of RNA transcripts coding for these genes beyond the end of the open reading frame.

These results indicate that targeting of non-essential regions of transcripts might trigger additional catalytic activities of Cas13d enzymes resulting in toxicity and cell death Lack of PFS for Cas13d and a New Model for Analysis of Sequence Constraints Previous RNA targeting CRISPR-Cas systems from subtypes VI-A-C have shown varying dependence on a protospacer flanking sequence (PFS) for efficient RNA targeting (Abudayyeh et al., 2016, 2017; Cox et al., 2017; East-Seletsky et al., 2016, 2017; Gootenberg et al., 2017; Smargon et al., 2017). Here we present evidence that RspCas13d and EsCas13d have no such flanking sequence requirements. For each enzyme, WebLogos® (Crooks et al., 2004) show that at each of 30 positions before and after the target sequences for strongly depleted arrays the nucleotide frequencies do not appreciably differ from a uniform distribution (FIGS. 14A-B).

To investigate possible flanking sequence requirements further, we developed a combinatorial model to search for up to 3 nucleotide locations distributed across the target or flanking sequences that might explain the observed strongly depleted arrays. We calculated a bit score to measure the degree to which the selected locations correspond to strongly biased outcomes (e.g. all hits or all non-hits). More specifically, we defined a targeting requirement to comprise a set of locations relative to a target sequence and the corresponding nucleotide sequences at those locations. For a given targeting requirement, we define the hit ratio (hr) as the ratio of the number of strongly depleted CRISPR arrays to the total number of library targets satisfying the requirement. When searching for a PAM or PFS of length k, we consider $\binom{n}{k}$ potential targeting requirement locations, where n=spacer length+2·flank length. The bit score for a potential targeting requirement is calculated as bitscore=Σ-hr log(hr) over all nucleotide sequences at the specified targeting requirement locations. For CRISPR-Cas systems with known PAM or PFS requirements, such as BzCas13b, high bit scores for targeting requirements of length 2 or 3 within 15 nt flanks of the target were obtained, and accurately recapitulate the location of the known PFS (FIG. 14C). Conversely, for RspCas13d and EsCas13d, our analysis shows no evidence of flanking or spacer sequences contributing to the targeting efficiency of strongly depleted arrays (FIG. 14C).

Explaining Strongly Depleted Arrays for RspCas13d and EsCas13d

Cumulatively, transcript targeting explained 86% and 66% of the strongly depleted arrays for RspCas13d and EsCas13d, respectively (FIG. 15). Accordingly, little if any targeting was observed for the ORF template strand. Non-coding and origin of replication (ORI) targeting correspond to actively transcribed regions of the ORI and the extension of coding transcripts into the intergenic region, as corroborated by RNA sequencing of Stbl3 *E. coli* containing pACYC184 (FIGS. 14A-B). Secondary structure analysis of the transcripts further enhanced the explanation of targeting for Cas13d. We predicted RNA secondary structure (Lorenz et al., 2011) for all sub-sequences within 30 nt of transcript target sites, and found that sequences with no predicted stable secondary structure corresponded to a higher percentage of strongly depleted targets (FIGS. 16A-B). Accordingly, we selected several sub-sequence ranges around the target site (FIGS. 16A-B), and defined a minimal secondary structure targeting requirement to be satisfied if the target site exhibited no predicted stable secondary structure for any of the selected sequence ranges. Among the transcript target sites that satisfy the minimal secondary structure requirement, we can explain 93% and 84% of all strongly depleted arrays for RspCas13d and EsCas13d, respectively (FIG. 16C). Together, our results indicate that RspCas13d and EsCas13d are RNA-targeting effectors with no flanking sequence requirements and a preference for minimal secondary structure for RNA targeting in *E. coli*.

RNA-Sequencing Mature crRNA from In Vivo Bacterial Screen

Sequencing the small RNA from the in vivo bacterial screen began by extracting total RNA from harvested screen bacteria using the Direct-zol RNA MiniPrep® Plus w/TRI Reagent (Zymo Research). Ribosomal RNA was removed using a Ribo-Zero® rRNA Removal Kit for Bacteria, followed by cleanup using a RNA Clean and Concentrator-5 kit. The resultant ribosomal RNA depleted total RNA was treated with T4 PNK, RNA 5' polyphosphatase, prepared for sequencing using the NEBNext® Small RNA Library Prep Set, and analyzed as described above.

We analyzed the pre-crRNA processing in the screen output samples for the direct repeat orientation that demonstrated successful targeting of pACYC184 and identified a mature 53 nt crRNA consisting of a 5' direct repeat truncated by 6 nt (FIG. 17). The most common spacer length observed for EsCas13d was 23 nt, with length variation between 20 nt and 30 nt (length of the native spacer for EsCas13d).

REFERENCES

Abudayyeh, O. O., Gootenberg, J. S., Konermann, S., Joung, J., Slaymaker, I. M., Cox, D. B. T., Shmakov, S., Makarova, K. S., Semenova, E., Minakhin, L., et al. (2016). C2c2 is a single-component programmable RNA-guided RNA-targeting CRISPR effector. Science 353, aaf5573.

Abudayyeh, O. O., Gootenberg, J. S., Essletzbichler, P., Han, S., Joung, J., Belanto, J. J., Verdine, V., Cox, D. B. T., Kellner, M. J., Regev, A., et al. (2017). RNA targeting with CRISPR-Cas13. Nature 550, 280-284.

Cox, D. B. T., Gootenberg, J. S., Abudayyeh, O. O., Franklin, B., Kellner, M. J., Joung, J., and Zhang, F. (2017). RNA editing with CRISPR-Cas13. Science 358, 1019-1027.

Crooks, G. E., Hon, G., Chandonia, J.-M., and Brenner, S. E. (2004). WebLogo: a sequence logo generator. Genome Res. 14, 1188-1190.

East-Seletsky, A., O'Connell, M. R., Knight, S. C., Burstein, D., Cate, J. H. D., Tjian, R., and Doudna, J. A. (2016). Two distinct RNase activities of CRISPR-C2c2 enable guide-RNA processing and RNA detection. Nature 538, 270-273.

East-Seletsky, A., O'Connell, M. R., Burstein, D., Knott, G. J., and Doudna, J. A. (2017). RNA Targeting by Functionally Orthogonal Type VI-A CRISPR-Cas Enzymes. Mol. Cell 66, 373-383.e3.

Gootenberg, J. S., Abudayyeh, O. O., Lee, J. W., Essletzbichler, P., Dy, A. J., Joung, J., Verdine, V., Donghia, N., Daringer, N. M., Freije, C. A., et al. (2017). Nucleic acid detection with CRISPR-Cas13a/C2c2. Science 356, 438-442.

Lorenz, R., Bernhart, S. H., Honer zu Siederdissen, C., Tafer, H., Flamm, C., Stadler, P. F., and Hofacker, I. L. (2011). ViennaRNA Package 2.0. Algorithms Mol. Biol. 6, 26.

Smargon, A. A., Cox, D. B. T., Pyzocha, N. K., Zheng, K., Slaymaker, I. M., Gootenberg, J. S., Abudayyeh, O. A., Essletzbichler, P., Shmakov, S., Makarova, K. S., et al. (2017). Cas13b Is a Type VI-B CRISPR-Associated RNA-Guided RNase Differentially Regulated by Accessory Proteins Csx27 and Csx28. Mol. Cell 65, 618-630.e7.

Example 3. Validation of Type VI-D Effector Activity In Vitro (Biochemically)

Effector and Accessory Protein Purification

The effector or accessory protein expression construct was transformed into an *E. coli* T7 expression strain, NiCo21(DE3)® (New England Biolabs). 1 mL of overnight culture was inoculated into 1 liter of Luria-Bertani broth growth media (10 g/L tryptone, 5 g/L yeast extract, 5 g/L NaCl, Sigma) supplemented with 50 µg/mL Kanamycin. Cells were grown at 37° C. to a cell density of 0.5-0.8 $OD_{600}$. Protein expression was then induced by supplementing with IPTG to a final concentration of 0.2 mM and the culture continued to grow for 14-18 hours at 20° C. The cells were harvested by centrifugation and cell paste was resuspended in 80 ml of freshly prepared Lysis Buffer (50 mM Hepes pH 7.6, 0.5M NaCl, 10 mM imidazole, 14 mM 2-mercaptoethanol and 5% glycerol) supplemented with protease inhibitors (cOmplete, EDTA-free, Roche Diagnostics Corporation). The resuspended cells were broken by passing through a cell disruptor (Constant System Limited). Lysate was cleared by centrifugation twice at 28,000 g for 30 min each. The clarified lysate was applied to a 5 ml HisTrap FF chromatography column (GE Life Sciences).

Protein purification was performed via FPLC (AKTA Pure, GE Healthcare Life Sciences). After washing with Lysis Buffer, protein was eluted with a gradient of 10 mM to 250 mM of imidazole. Fractions containing protein of the expected size were pooled, concentrated in Vivaspin 20 ultrafiltration unit (Sartorius) and either used directly for biochemical assays or frozen at –80° C. for storage. Protein purity was determined by SDS-PAGE analysis and protein concentration was determined by Qubit® protein assay kit (Thermo Fisher). FIG. 17 shows a Coomassie blue stained polyacrylamide gel of the purified recombinant proteins EsCas13d, RspCas13d, and RspWYL1 respectively.

crRNA and Substrate RNA Preparation

DNA oligo templates for crRNA and substrate RNA in vitro transcription were ordered from IDT (TABLES 8 and 9). Templates for crRNAs were annealed to a short T7 primer (final concentrations 4 µM) and incubated with T7 RNA polymerase overnight at 37° C. using the Hiscribe® T7 Quick High Yield RNA Synthesis kit (New England Biolabs). Annealing was performed by incubating T7 primer with templates for 2 minutes at 95° C. followed by a –5° C./s ramp down to 23° C. Templates for substrate RNA were PCR amplified to yield dsDNA and then incubated with T7 RNA polymerase at 37° C. overnight using the same T7 Quick High Yield RNA Synthesis kit. After in vitro transcription, samples were treated with DNase I (Zymo Research) and then purified using RNA Clean & Concentrator kit (Zymo Research).

5' end labeling was accomplished using the 5' end labeling kit (VectorLabs) and with a IR800® dye-maleimide probe (LI-COR Biosciences). Body labeling of RNA was performed during in vitro transcription using the Hiscribe® T7 Quick High Yield RNA Synthesis kit (New England Biolabs). The in vitro transcription reactions contained 2.5 mM Fluorescein-12-UTP (Sigma Aldrich). Labeled RNA was purified to remove excess dyes using RNA Clean & Concentrator kit (Zymo Research). The RNA concentration was measured on Nanodrop® 2000 (Thermo Fisher).

The effectors were then incubated with their respective in vitro transcribed pre-crRNAs consisting of a minimal CRISPR array with the repeat-spacer-repeat construction used in the bacterial screening library, but with a single spacer instead of a library. Pre-crRNA cleavage assays were performed at 37° C. in processing buffer (20 mM Tris pH8.0, 50 mM KCl, 1 mM EDTA, 10 mM MgCl2, and 100 ug/ml BSA) unless otherwise indicated, with a final reaction concentration of 200 nM of pre-crRNA and varying enzyme concentrations and EDTA as indicated. Reactions were incubated for 30 minutes, and quenched with the addition of 1 ug/uL of proteinase K (Ambion) incubated for 10 minutes at 37° C. Afterwards, 50 mM of EDTA was added to the reaction, which was then mixed with equal parts 2×TBE-Urea Sample Buffer (Invitrogen) prior to denaturing at 65 C for 3 minutes. Samples were analyzed by denaturing gel electrophoresis on 15% TBE-Urea gels (Invitrogen) and stained using SYBR Gold nucleic acid stain (Invitrogen) for 10-20 minutes prior to imaging on a Gel Doc EZ (Biorad). We found that EsCas13d and RspCas13d effectors process pre-crRNAs to form mature crRNAs in the absence of any accessory proteins (FIGS. 20A-D).

RNA-Sequencing of In Vitro Cleaved Pre-crRNA

Sequencing of in vitro cleaved pre-crRNA began with performing and quenching the cleavage assays as described above. The reactions were then column purified using a RNA Clean and Concentrator-5 kit (Zymo Research). The RNA samples were then PNK treated for 3 hours without ATP to enrich for 3'-P ends, after which ATP was added and the reaction incubated for another hour to enrich for 5'-OH ends. The samples were then column purified, incubated with RNA 5' polyphosphatase (Lucigen) and column purified again prior to preparation for next-generation sequencing using the NEBNext® Multiplex Small RNA Library Prep Set for Illumina (New England Biolabs). The library was paired-end sequenced on a Nextseq 550® (Illumina), and the resulting paired end alignments were analyzed using Geneious 11.0.2 (Biomatters).

Performing next-generation sequencing of the in vitro cleaved RNA fragments enabled the exact identification of the processing intermediates and mature crRNA (FIG. 19) visualized by denaturing gel. For both EsCas13d and RspCas13d, sequencing the mature crRNA corroborated the Ent truncation from the 5' end of the first direct repeat found in the in vivo small RNA sequencing. For the 3' end, 6 nt of the second direct repeat remained attached to the 3' end of the spacer, yielding a total product of 66 nt consistent with the mature crRNA visualized by denaturing gel. The difference between the well-defined 3' end of the mature crRNA forms observed in vitro versus the various lengths identified in vivo may be the result of further truncation in vivo by endogenous RNases following the initial pre-crRNA cleavage. The effector's ability to cleave pre-crRNA at the same location relative to the predicted stem loop structure of either direct repeat (FIG. 19 intermediates 1 and 2) indicates that the Type VI-D CRISPR-Cas effectors are able to process pre-crRNAs containing multiple DRs and spacers.

Effect of EDTA on crRNA Processing

We next examined the dependence of pre-crRNA cleavage on divalent metal ions. We observed that the generation of mature crRNA for both EsCas13d and RspCas13d is substantially inhibited by the addition of EDTA (FIGS. 20A-D), while Cas13a from *Leptotrichia wadei* (LwaCas13a) is still able to generate mature crRNAs in the presence of EDTA (FIG. 21). This dependence of Cas13d on divalent cations to generate mature crRNA is a notable functional distinction from Cas13a crRNA processing (East-Seletsky et al., 2016; Knott et al., 2017).

Validation of ssRNA Cleavage Activities

We next sought to biochemically validate the RNA-guided ssRNA cleavage activities of the Cas13d enzymes observed in our bacterial screens. Target cleavage assays were performed at 37° C. in cleavage buffer (20 mM HEPES pH 7.1, 50 mM KCl, 5 mM MgCl2 and 5% glycerol). Cas13-crRNA complex formation was performed in cleavage buffer by incubating a 2:1 molar ratio of protein to crRNA at 37° C. for 5 minutes, and RspWYL1 was added to the Cas13-crRNA pre-incubation according to the experimental conditions. For the cleavage reactions at different Cas13 concentrations, the pre-formed Cas13-crRNA complexes were diluted on ice, keeping the Cas13-crRNA ratio constant at 2:1. The 5' IR800 labeled target ssRNA and/or additional unlabeled and fluorescent body-labeled ssRNAs were then added to the pre-formed complex and incubated at 37° C. for 30 minutes. The final concentration of short substrate RNAs was 100 nM and the fluorescent body-labeled ssRNA for collateral effect visualization was 50 nM, unless otherwise indicated. Reactions were quenched by adding 1 ug/uL of proteinase K (Ambion) and incubating for 10 minutes at 37° C.

Afterwards, 50 mM of EDTA was added to the reaction, which was then mixed with equal parts 2×TBE-Urea Sample Buffer (Invitrogen) prior to denaturing at 65° C. for 3 minutes. Samples were analyzed by denaturing gel electrophoresis on 6% or 15% TBE-Urea gels (Invitrogen). Fluorescence images were obtained using a Gel Doc EZ® (Biorad), and near-infrared images were obtained using an Odyssey® CLx scanner (LI-COR Biosciences). Afterwards, the gels were stained for 10-20 minutes using SYBR Gold nucleic acid stain (Invitrogen) and imaged on the Gel Doc EZ® to verify the results from the fluorescence and IR images.

We titrated Apo EsCas13d and RspCas13d (100-0.4 nM) over a non-targeted ssDNA substrate (100 nM), with the denaturing gel (FIGS. 22A-B) showing minimal cleavage products. We then titrated EsCas13d and RspCas13d in complex with crRNA (100-0.4 nM) over non-targeted ssDNA substrates (100 nM), with the resulting denaturing gel (FIGS. 23A-B) showing minimal cleavage products.

We identified spacer sequences for several strongly depleted arrays from bacterial screens for each CRISPR-Cas system and generated pre-crRNAs with the repeat-spacer-repeat arrangement for each effector. We then titrated EsCas13d and RspCas13d in complex with crRNA (100-0.4 nM) over targeted ssDNA substrates (100 nM), with the resulting denaturing gel (FIGS. 24A-B) showing saturation of target cleavage activity at approx. 50 nM RspCas13d-crRNA complex and 100 nM EsCas13d-crRNA complex. In an additional experiment, we targeted EsCas13d and RspCas13d enzyme-crRNA complexes to 130 nt ssRNA substrates containing target sequences complementary to the crRNA spacer and demonstrated targeted RNA cleavage activity for both enzymes (FIGS. 25A-B).

To evaluate the collateral RNA cleavage activity, identical reactions were prepared and supplemented with 800 nt fluorescent body-labeled ssRNA fragments that did not contain the target sequence. Both EsCas13d and RspCas13d showed substantial collateral activity that occurs with the target cleavage (FIGS. 26A-B). We further demonstrated that both EsCas13d and RspCas13d show robust sequence-specific targeted and collateral RNA cleavage activities across multiple crRNAs with and without complementary substrates (FIGS. 26C-D).

TABLE 8 ssRNA Oligos Used in This Study

| ID | Type | Source | Description | Sequence | Figures |
|---|---|---|---|---|---|
| cr_F1 | ssRNA | IDT IVT | EsCas13d pre-crRNA #1 | GAACUACACCCGUGCAAAAUUGCAGGGGUCUAAAAACUCAUCCGCUUAUUAUCACUAUUCAGGCGUGAACUACACCCG UGCAAAAUUGCAGGGGUCUAAAAC (SEQ ID NO: 99) | 20A-B, 23A, 24A, 25A, 26A, 26C, 30A-B |
| cr_F4 | ssRNA | IDT IVT | EsCas13d pre-crRNA #2 | GAACUACACCCGUGCAAAAUUGCAGGGGUCUAAAAACAUUAGGUACAUUGAGCAACUGAAAUGCGAACUACACCCG UGCAAAAUUGCAGGGGUCUAAAAC (SEQ ID NO: 100) | 20B, 26C |
| cr_F7 | ssRNA | IDT IVT | RspCas13d pre-crRNA #1 | CUACUACACUGGUGCAAAAUUGCACUAGUCUAAAAACCAAGGGGUGAACACUAUCCCAUAUCACCAGCUCUACACACUG GUGCCGAAUUGCACUAGUCUAAAAC (SEQ ID NO: 101) | 20C-D, 23B, 24B, 25B, 26B, 26D, 29A-C |
| cr_F10 | ssRNA | IDT IVT | RspCas13d pre-crRNA #2 | CUACUACACUGGUGCAAAAUUGCACUAGUCUAAAAACCCUGUGACAACCUACACUCGUAUUAACGAACUACACACUG GUGCCGAAUUGCACUAGUCUAAAAC (SEQ ID NO: 102) | 20D, 26D |
| cr_3 | ssRNA | IDT IVT | LwaCas13a pre-crRNA #1 | GAUUUAGACUACUCCCAAAAACGAAGGGGACUAAAAACAUUUUUUCUCCAUUUUAGCUCCCUUAGAGAUUUAGACUACCC CAAAAACGAAGGGGACUAAAAC (SEQ ID NO: 103) | 21 |
| cr_4 | ssRNA | IDT IVT | LwaCas13a pre-crRNA #2 | GAUUUAGACUACUCCCAAAAACGAAGGGGACUAAAAACAGAAACUAAAAUCACUAUAAUGGGGAAGGCCAUCCAGCGAUUUAGACUACCC CAAAAACGAAGGGGACUAAAAC (SEQ ID NO: 104) | 21 |
| sub_F1 | ssRNA | PCR IVT | EsCas13d substrate #1; "target ssRNA" in FIGS. 24, 25, 26, 30; "A" in FIG. 26C | AUACGCCUGUGGUUCCCAAGAGUCCCAAUGGCAUCGUAAAGAACAUUUGAGGAACAUUUCAGUCAGUCUCAAUGUACCU AUAACCAGACCGUUCAGCUGGAUAUUACGCCAAGAGAGCACGAAAGUGUUG (SEQ ID NO: 105) | 24A, 25A, 26A, 26C, 30A-B |
| sub_F4 | ssRNA | PCR IVT | EsCas13d substrate #2; "non target ssRNA" in FIGS. 22, 23, 25, 26, 30; "B" in FIG. 26C | AUACGCCUGUGGUUCCCAAGAGUUAUUGGUGCCCUGAAACGCCUGGGCUACGCCUGAUAAAGUGAUAAUAAGCGGAU GAAUGGCAGAAAUUCGAAAGCAAAUUCGACCCAAGAGAGCACGAAAGUGUUG (SEQ ID NO: 106) | 22A, 23A, 25A, 26A, 26C, 30A-B |
| sub_F7 | ssRNA | PCR IVT | RspCas13d substrate #1; "target ssRNA" in FIGS. 24, 25, 26, 29; "A" in FIG. 26D | AUACCGCUGUGGUUCGCCAAGCGGAAUUCCGUAUGGCAAUGAGAGCUGGUGAUAUGGGAUAGUGUUCACCG UUGGUUACACCGUUUUCCGUUUUCCAUGAGCAAACAAGAGCACGAAAGUGUUG (SEQ ID NO: 107) | 24B, 25B, 26B, 26D, 29A-C |
| sub_F10 | ssRNA | PCR IVT | RspCas13d substrate #2; "non target ssRNA" in FIGS. 22, 23, 25, 26, 29; "B" in FIG. 26D | AUACGCCUGUGGUUCGCCAAGCUCCCAGAGCCUGAUAAACACAGAUGUAGGUGUCCAC AGGGUAGCCAGCAGCAUCCUGCGAUGCAGAUCCAAGAGCACGAAAGUGUUG (SEQ ID NO: 108) | 22B, 23B, 25B, 26B, 26D, 29A-C |
| GFP | ssRNA | PCR IVT | Collateral ssRNA; when IVT completed with Fluorescein-12-UTP, produces body labeled ssRNA | GGGAAUUGUGAGCGGAUAAACAAUUCCCUCUAGAAAUAAUUUGUUUAACUUUAAGAAGGAGAUAUAAAUGAAAAU CGAAGAAGGUAAAGUCACGACGUAAAGCACGAUGAACGGCCAUGAGGUGCAAAACUGUUUGAGAA AGAGAUCCCGUAUAUCACCCGAACUGGAAGCCGCUCGAAGGUAUGAAAUUAUCAUUAAAGCGAAGGUACCGGUGA CGCGACCACGGGUACCACGGGUACCAGGGAAAUACAUCUGCAACAUGCACGGGCGACCCUGGGCAACCCUGUCGAG CACCCUGAGCUACACGGUGUUCAGUGGUCUUCGCCAAGACCCGAGCCACGCAAGGAGAUUUCUUUAAGAGCGCAUCCGGA | 26A-D, 29B-C, 30B |

TABLE 8-continued ssRNA Oligos Used in This Study

| ID | Type | Source | Description | Sequence | Figures |
|----|------|--------|-------------|----------|---------|
| | | | | AGGUAUACCCAAGAGAGCGUACCAUCAGCUUCGAAGGCGACGGCCGUGUACAAGACGCGUGCUAUGGUUACCUACGAACG CGGUUCUAUCUACAAUCGUGUCACGCUGACUGGUGAGAACGUUAAGAAGACGUCACAUUCUGCGUAAGAACGUUGC AUUCCAAUGCCCGCCAAGCAUUCGUAUAUCUGCCUGACACCGUUAACAAUGGCAUCCGCGUUGAGUUCAACCAGGC GUACGAUAUUGAAGGUGACCGAAAAACUGGUUACUGAAUGCAGCCAAAUGAUCCGUCCGUUGGCGGGCUCCGCGGC AGUGCAUAUCCGCGUAUCAUCACAUUACCUACCACACAAUCGAGCAAAGACCGACGAGGCGCCUGAUCACAU GUGUCUGGUAGAGGUCGUGAAAGCGGUUGAUCUGGACACGGUUAUCAGUAGGACACGGUAAUAAAAGCCCGAAAAGAUGAGUGGC UGCUGCCACCGCUGAGCAAUAA (SEQ ID NO: 109) | |

TABLE 9 ssDNA Primers Used to Generate the ssRNA Targets Using in Vitro Transcription

| ID | Type | Source | Description | Sequence |
|---|---|---|---|---|
| T7_primer | ssDNA | IDT | annealing to different IVT rev primers to create double-stranded T7 promoter region for IVT | CCTCGAGTAATACGACTCACTATAGGG (SEQ ID NO: 110) |
| cr_F1_IVT_rev | ssDNA | IDT | For IVT of cr_F1 | GTTTTAGACCCCTGCAATTTGCACGGGTGTAGTTCGCATTTCAGTCAGTTGCTCAATGTACCTATGTTTTAGACCCCTGCAATTTGCACGGGTGTAGTTCCCCTATAGTGAGTCGTATTACTCGAGGAATTCTTATTATTCT (SEQ ID NO: 111) |
| cr_F4_IVT_rev | ssDNA | IDT | For IVT of cr_F4 | GTTTTAGACCCCTGCAATTTGCACGGGTGTAGTTCACGCCTGAATAAGTGATAATAAGCGATGAGTTTAGACCCCTGCAATTTGCACGGGTGTAGTTCCCCTATAGTGAGTCGTATTACTCGAGGAATTCTTATTATTCT (SEQ ID NO: 112) |
| cr_F7_IVT_rev | ssDNA | IDT | For IVT of cr_F7 | GTTTTAGACTAGTGCAAATTCGCACCAGTGTAGTAGAGCTGTGTAATGGATAGTGTTCACCCTTGGTTTAGACTAGTGCAAATTGCACCAGTGTAGTAGCCCTATAGTGAGTCGTATTACTCGAGGGATCCTTATTACATTT (SEQ ID NO: 113) |
| cr_F10_IVT_rev | ssDNA | IDT | For IVT of cr_F10 | GTTTTAGACTAGTGCAAATTCGCACCAGTGTAGTTCGTTAATACAGATAGTTCGAGGGATCCTTATTACATTTGACTAGTGCAAATTGCACCAGTGTAGTAGCCCTATAGTGAGTCGTATTACTCGAGGGATCCTTATTACATTT (SEQ ID NO: 114) |
| cr_3_IVT_rev | ssDNA | IDT | For IVT of cr_3 | GTTTTAGTCCCCCTCGTTTTGGGGTAGTCTAAATCCTAAGGAAGCTAAATGGAGAAAATGTTTAGTCCCTTCGTTTTGGGGTAGTCTAAATCCCTATAGTGAGTCGTATTACTCGAGGGATCCTTATTACATTT (SEQ ID NO: 115) |
| cr_4_IVT_rev | ssDNA | IDT | For IVT of cr_4 | GTTTTAGTCCCCCTCGTTTTGGGGTAGTCTAAATCGTCGATGGCCTTCCCCATTATGATTCGTTTAGTCCCTTCGTTTTGGGGTAGTCTAAATCCCTATAGTGAGTCGTATTACTCGAGGGATCCTTATTACATTT (SEQ ID NO: 116) |
| sub_F1_rev | ssDNA | IDT | For IVT of sub_F1 | ATACGCTGTGGTTCGCCAAGTCCCAATGCATCGTAAGAACATTTTGAGCATTTCAGTCAGTTGCTCAATGTACCTATAACCAGACCCGTTCAGCTGAATTATTACGGCCAAGAGCACGAAAGTGTTG (SEQ ID NO: 117) |
| sub_F4_rev | ssDNA | IDT | For IVT of sub_F4 | ATACGCTGTGGTTCGCCAAGAGTTATTGGTGCCCTAAACGCCTGGTCTACCCTGAATAAGTGATAATAAGCGGATGAATGGCAGAATTCGAAAGCAAATTCGACCCAAGAGCACGAAAGTGTTG (SEQ ID NO: 118) |
| subJ7_rev | ssDNA | IDT | For IVT of sub_F7 | ATACGCTGTGGTTCGCCAAGCGAATTCCGTATGGCAATGAAAGACGGTGAGCTGGTGATATGGATAGTGTTCACCCTTGTTACCCGTTTTCATGAGCAAACTGAAACAAGAGAGCACGAAAGTGTTG (SEQ ID NO: 119) |
| sub_F10_rev | ssDNA | IDT | For IVT of sub_F10 | ATACGCTGTGGTTCGCCAAGCTCCAGAGCCTTAGCGCTTCGTTAATACAGATAGTAGGTGTTCCACAGGGTAGCCAGCAGCATCCTGCGATGCAGATCCAAGAGCACGAAAGTGTTG (SEQ ID NO: 120) |

TABLE 9-continued ssDNA Primers Used to Generate the ssRNA Targets Using in Vitro Transcription

| ID | Type | Source | Description | Sequence |
|---|---|---|---|---|
| PT7_Sub_fw | ssDNA | IDT | For PCR all target substrates for IVT | CGAAATTAATACGACTCACTATAGGGATACGCTGTGGTTCGCCAAG (SEQ ID NO: 121) |
| Sub_rv | ssDNA | IDT | For PCR all target substrates for IVT | CGAAATTATTTCGACTGAGATTATTCCCCAACACTTTCGTGCTCTCTT (SEQ ID NO: 122) |
| GFP_PCR_fwd | ssDNA | IDT | For PCR GFP gene for IVT | GATGCGTCCGGCGTAGAGGATCGAGATCTC (SEQ ID NO: 123) |

Notes:
IDT IVT: ssDNA primers from IDT were directly annealed with the T7_primer and transcribed
PCR IVT: a PCR using the IDT oligo or GFP as a template was used first to create the dsDNA with the T7 promoter sequence, on which IVT was then performed
IDT: primers ordered from Integrated DNA Technologies

REFERENCES

East-Seletsky, A., O'Connell, M. R., Knight, S. C., Burstein, D., Cate, J. H. D., Tjian, R., and Doudna, J. A. (2016). Two distinct RNase activities of CRISPR-C2c2 enable guide-RNA processing and RNA detection. Nature 538, 270-273.

Knott, G. J., East-Seletsky, A., Cofsky, J. C., Holton, J. M., Charles, E., O'Connell, M. R., and Doudna, J. A. (2017). Guide-bound structures of an RNA-targeting A-cleaving CRISPR-Cas13a enzyme. Nat. Struct. Mol. Biol. 24, 825-833.

Example 4. Validation of Type VI-D CRISPR-Cas Systems Comprising Cas13d and WYL1 Activity In Vitro (Biochemically)

Putative accessory proteins containing WYL domains and additional predicted DNA-binding domains are present in the great majority of the Type VI-D loci (FIG. 1). We initially synthesized and screened the predicted minimal CRISPR-Cas system for RspCas13d including both the RspCas13d effector and RspWYL1 accessory protein. To investigate the modulation of Cas13d by WYL1, we screened both the RspCas13d effector and RspWYL1 accessory protein separately. Comparison of screening results for RspCas13d effector alone versus the RspCas13d system, including RspWYL1, shows that RspCas13d targeted RNA cleavage is increased in the presence of RspWYL1 (FIGS. 27A-B). Bacterial screening with RspWYL1 alone yielded a minimal number of hits, indicating that RspWYL1 has no individual activity (FIG. 28). Cumulatively, these results suggest that RspCas13d enzymatic activity is modulated either directly or indirectly by WYL1.

We further investigated whether WYL1 could modulate RspCas13d in vitro by purifying recombinant RspWYL1 for use in ssRNA cleavage biochemical assays. To enable high resolution of enhanced or decreased complex activity in the presence of WYL, we selected doses of Cas13d-crRNA complex resulting in approximately 50% cleavage of the target substrates based on a dose titration curve (FIGS. 24A-B). We pre-incubated Cas13d-crRNA with no RspWYL1, an equimolar ratio of RspWYL1 to Cas13d, or a molar excess of RspWYL1 over Cas13d, and the resulting samples were incubated with target and collateral ssRNA under the same conditions as in the target cleavage assays. We observed that RspWYL1 increases both the targeted and collateral ssRNA cleavage activity of RspCas13d in a dose-dependent manner, with a molar excess of RspWYL1 yielding the greatest increase in Cas13d activity (FIGS. 29A-C).

Given that Type VI-D CRISPR-Cas systems appear to have acquired WYL-domain containing accessory proteins on multiple, independent occasions (FIGS. 1, 6, 8, 9), we tested the specificity of RspWYL1 in modulating the cleavage activity of orthologous Cas13d effectors. We observed that RspWYL1 enhanced the targeted and collateral ssRNA nuclease activities of EsCas13d to a similar extent as observed for RspCas13d (FIG. 30A-B). Thus, the effects of WYL1 orthologs appear not to be limited to their native effectors, but instead reflect a modular regulatory mechanism for Cas13d effectors.

To test whether RspWYL1 could modulate the activity of a type VI-B Cas13b effector, in vitro ssRNA cleavage biochemical assays were performed using recombinant RspWYL1 and *Bergeyella zoohelcum* Cas13b (BzCas13b). As shown in FIG. 31, RspWYL1 enhanced the activity of BzCas13b, demonstrating that this accessory protein is also capable of enhancing the activity of Cas13b effectors.

Example 5. Type VI-D CRISPR-Cas Systems can be Used with a Fluorescent Reporter for the Specific Detection of Nucleic Acid Species The dual nuclease activities of Cas13 effectors (i.e., target-specific and non-specific collateral RNase activity) make these effectors promising candidates for use in the detection of nucleic acid species. Some of these methods have been previously described (see, e.g., East—Seletsky et al. (2016), Gootenberg et al. (2017), and Gootenberg et al. (2018) "Multiplexed and portable nucleic acid detection platform with Cas13, Cas12a, and Csm6" *Science* 15 Feb. 2018: eaaq0179), describing the general principle of RNA detection using Cas13a (East-Seletsky et al. (2016)), supplemented by amplification to increase the detection sensitivity and optimization of additional Cas13a enzymes (Gootenberg et al. (2017)), and most recently, the inclusion of additional RNA targets, orthologous and paralogous enzymes, and Csm6 activator to enable multiplexed detection of nucleic acids along with an increase in detection sensitivity (Gootenberg et al. (2018)). The addition of Cas13d to this toolkit not only provides an additional channel of orthogonal activity for nucleic acid detection, but the nuclease activity-enhancing effect of the WYL1 proteins across orthologous and paralogous effectors suggests that WYL1 proteins can play an activity-enhancing role.

We tested the ability of EsCas13D or RspCas13d to cleave RNaseAlert® v2 (Thermo Fisher) substrate under different buffer conditions. Using a buffer of 50 mM potassium acetate, 20 mM Tris-acetate, 10 mM magnesium acetate, 100 µg/ml BSA, pH 7.9 provided key improvements from the described cleavage or processing buffers in the following: 1) maximum differentiation of targeting vs. non-targeting, 2) total fluorescence signal intensity, and 3) sufficient stability to support enzyme activity for the duration of the measurement.

We next tested different short fluorescent-quencher RNA substrates for the fluorescent detection of the collateral effect. These included RNase alert v2, a poly-G, and a poly-U substrate. We performed this experiment using a final reaction concentration of 40 nM of the Cas effector, 20 nM of crRNA, 5 nM of the target or nontarget RNA, and 160 nM of the fluorescent-quencher substrate along with 0.5 µL of the murine RNase inhibitor (in 50 uL) in the optimized buffer condition as described above. The reaction was incubated for 3 hours at 37° C. and the fluorescence read out using a Lightcycler 480 II at one-minute intervals. This demonstrated that both RspCas13d and EsCas13d can differentiate between a targeting vs. a non-targeting RNA using a poly-U substrate (FIG. 32). Furthermore, the differences between the activity of the two Cas13d effectors on the different substrate identities suggests the possibility of having multiple channels for the reporter.

Example 6. Type VI-D CRISPR-Cas Systems can be Used to Provide Genotype-Gated Control of Cell Death or Dormancy Hybridization of the Type VI-D CRISPR-Cas effector protein and crRNA with an RNA target complementary to the crRNA spacer forms an active complex that may exhibit nonspecific, "collateral" RNase activity. Such collateral RNAse activity can be used to provide genotype-gated control of cell death or dormancy. The dependence of such activity on the presence of a specific RNA target in a cell is valuable since it enables targeting of specific cell populations based on specific underlying transcriptional states or genotypes. Numerous applications exist in both eukaryotic and prokaryotic settings for such control of cell death or dormancy.

For prokaryotic applications, a Type VI-D CRISPR-Cas system (e.g., including a Type VI-D effector and a crRNA) can be delivered (e.g., in vitro or in vivo) in order to induce cell death or dormancy of specific prokaryote populations (e.g., bacterial populations) in a genotype and transcriptome-specific way. For instance, the Type VI-D CRISPR-Cas system can include one or more crRNAs that specifically target a particular prokaryotic genus, species, or strain. This specific targeting has many therapeutic benefits as it may be used to induce death or dormancy of undesirable bacteria (e.g., pathogenic bacteria such as *Clostridium difficile*). In addition, the Type VI-D systems provided herein may be used to target prokaryotic cells having specific genotypes or transcriptional states. Within the microbial diversity that colonizes humans, only a small number of bacterial strains can induce pathogenesis. Further, even within pathogenic strains such as *Clostridium difficile*, not all members of the bacterial population exist continuously in active, disease-causing states. Thus, using RNA-targeting to control the activity of an Type VI-D effector based on the genotype and transcriptional state of a prokaryotic cell allows for specific control of which cells are targeted without disrupting the entire microbiome.

Additionally, bacterial strains can be readily engineered with genetic circuits or environmentally-controlled expression elements to generate genetic kill switches that limit the growth, colonization, and/or shedding of the engineered bacterial strains. For example, the expression of a Type VI-D effectors, specific crRNA, or specific target RNA, can be controlled using promoters derived from the regulatory regions of genes encoding proteins expressed in response to external stimuli, such as cold sensitive proteins (PcspA), heat shock proteins (Hsp), chemically inducible systems (Tet, Lac, AraC). The controlled expression of one or more elements of the Type VI-D system allows for the full functional system to be expressed only upon exposure to an environmental stimulus, which in turn activates the nonspecific RNase activity of the system and thereby induces cell death or dormancy. Kill switches including Cas13d effectors as those described herein may be advantageous over traditional kill switch designs such as toxin/antitoxin systems (e.g., CcdB/CcdA Type II toxin/antitoxin systems), since they are not dependent on relative protein expression ratios which may be affected by leaky expression from a promoter (e.g., an environmental-stimulus dependent promoter), and thus allow for more precise control of the kill-switch.

To assess the ability of Cas13d to directly induce the dormancy or death of bacteria cells upon recognition of a target RNA, a variation of the in vivo functional screening described in Example 2 was performed, in which the antibiotic tetracycline was removed from the culture plate. Removing tetracycline selection meant that the survival of the host *E. coli* was no longer dependent on the successful natural expression of the tetracycline resistance protein by pACYC184. However, the targeting library still contained crRNAs with spacers to the tetracycline resistance gene, $Tc^R$. When the dependence of *E. coli* survival on successful $Tc^R$ expression is removed, one would expect that there would be no impact on *E. coli* survival if the Cas13d effector directly cleaved $Tc^R$ mRNA, and thus no $Tc^R$ targeting spacers should register as strong depletion event on the in vivo screen. Nevertheless, the screening data without tetracycline selection still showed strongly depleted spacers on the $Tc^R$ gene (FIGS. 33A-B, 34A-B), suggesting that the effect of Cas13d targeting RNA alone can mediate a growth disadvantage or cell death, even without antibiotic selection.

For eukaryotic applications, many diseases result from specific genotypes or transcriptional states in the diseased cells that distinguish them from healthy cells. Disease related genotypes are often contained in regions of the genome that are expressed, generating transcripts that can be targeted by a Type VI-D effector using a crRNA that specifically targets the genotype. Such targeting can provide cell dormancy or cell death in a population of cells with a specific disease related mutations. An exemplary application is the targeted depletion of cancer cells containing specific mutations, such as driver mutations that occur spontaneously in the tumor microenvironment. In addition, the Type VI-D CRISPR-Cas systems described herein can be used as kill-switch mechanisms to induce the death or dormancy of recombinant eukaryotic cells, such as chimeric antigen receptor-expressing T-cells, to limit their activity in inappropriate environments or when no longer desired.

Additionally, in a therapeutic context, numerous disease processes often involve dysregulation of cellular pathways that result in transcriptional states that are different from the normal baseline. A Type VI-D CRISPR-Cas system can be used to specifically induce the death or dormancy of cells that have an altered transcriptome. For example, the system can be used to induce the death or dormancy of cells having a temporally altered transcriptome, such as cells involved in an anti-inflammatory response during an autoimmune disease flare that are differentiated from normal cells.

The expression of the Type VI-D CRISPR-Cas systems described herein can be controlled and expressed using synthetic biology to induced or trigger cell death or dormancy. For example, the expression of genes encoding each of the components of the Type VI-D CRISPR-Cas systems can be controlled using genetic elements including, but are not limited to, promoters that are regulated by environmental stimuli, such as hypoxia (hif), neuronal activity (fos, arc), heat-shock (HSF-1), or exogenous controls such as light (FixJ), steroids (LexA), alcohol (AlcA), tetracycline (Tet). These promoters can be used to control the expression of components of the Type VI-D CRISPR-Cas system and/or of a specific RNA target to activate the system, thereby inducing the death or dormancy of targeted cells in response to the particular environmental stimuli to which the promoters respond.

Example 7. Adaptation of Type VI-D CRISPR Cas System Effectors for Eukaryotic and Mammalian Activity Beyond the biochemical and diagnostic applications described herein, programmable RNA-modifying CRISPR-Cas systems such as Type VI-D, e.g., Cas13d, systems described herein have important applications in eukaryotic cells, ranging from therapeutic uses such as disease transcript correction, to research and development advances, such as for transcriptome engineering and RNA visualization.

To develop Type VI-D CRISPR Cas systems for eukaryotic applications, the constructs encoding the protein effectors are first codon-optimized for expression in mammalian cells, and specific localization tags are optionally appended to either or both the N-terminus or C-terminus of the effector protein. These localization tags can include sequences such as nuclear localization signal (NLS) sequences, which localize the effector to the nucleus for modification of nascent RNAs, as well as nuclear export signal (NES) sequences, which target the effector to the cytoplasm in order to modify mature RNAs. These sequences are described above in the "Functional Mutations" section. Other accessory proteins, such as fluorescent proteins, may be further appended. It has been demonstrated that the addition of robust, "superfolding" proteins such as superfolding green fluorescent protein (GFP) can increase the activity of Cas13 enzymes in mammalian cells when appended to the effector (Abudayyeh et al. (2017) *Nature* 550(7675): 280-4, and Cox et al. (2017) *Science* 358(6366): 1019-27).

The codon-optimized sequence coding for the Cas13d effector and appended accessory proteins and localization signals is then cloned into a eukaryotic expression vector with the appropriate 5' Kozak eukaryotic translation initiation sequence, eukaryotic promoters, and polyadenylation signals. In mammalian expression vectors, these promoters can include, e.g., general promoters such as CMV, EF1a, EFS, CAG, SV40, and cell-type specific RNA polymerase II promoters such as Syn and CamKIIa for neuronal expression, and thyroxine binding globulin (TBG) for hepatocyte expression to name a few. Similarly, useful polyadenylation signals include, but are not limited to, SV40, hGH, and BGH. For expression of the pre-crRNA or mature crRNA, RNA polymerase III promoters such as H1 or U6 can be used.

Depending on the application and mode of packaging, the eukaryotic expression vector can be a lentiviral plasmid backbone, adeno-associated viral (AAV) plasmid backbone, or similar plasmid backbone capable of use in recombinant viral vector production. Notably, the small size of Type VI-D CRISPR Cas effector proteins, e.g., Cas13d effector proteins, make them ideally suited for packaging along with its crRNA and appropriate control sequences into a single adeno-associated virus particle; the packaging size limit of 4.7 kb for AAV may preclude the use of larger Cas13 effectors.

After adapting the sequences, delivery vectors, and methods for eukaryotic and mammalian use, different Cas13d constructs as described herein are characterized for performance. For efficient testing of the mammalian activity levels of various constructs, we use a dual-luciferase reporter expressing both *Gaussia* luciferase (Gluc) and *Cypridinia* luciferase (Cluc) (Abudayyeh et al. (2017) *Nature* 550 (7675): 280-4). Targeting the Gluc transcript and comparing the relative activity versus the internal control of the Cluc activity enables an estimation of Cas13d effectiveness in a mammalian context. This activity is corroborated on the reporter through knockdown of endogenous transcripts, such as from the well-characterized KRAS genetic locus. The dual-luciferase reporter construct along with plasmids expressing the type VI-D CRISPR-Cas system and cognate crRNA are delivered using transient transfection (e.g., Lipofectamine® 2000) into model cell lines such as HEK 293T cells.

In addition to testing various construct configurations and accessory sequences on individual targets, pooled library-based approaches are used to determine 1) any targeting dependency of specific Cas13d effector proteins in mammalian cells as well as 2) the effect of mismatch locations and combinations along the length of the targeting crRNA. Briefly, the pooled library includes a plasmid that expresses a target RNA containing different flanking sequences as well as mismatches to the guide or guides used in the screening experiment, such that the successful target recognition and cleavage results in depletion of the sequence from the library. Furthermore, mRNA sequencing can be used to determine the off-target RNA cleavage effects of the type VI-D CRISPR-Cas system.

Complementary to the possibilities of transcriptome modification using the RNA cleavage activity of Cas13d, we can also explore the applications of catalytically-inactive Cas13d effector proteins in which the conserved residues of the two HEPN domains are mutated from the arginine and histidine to alanine. Like other Cas13 enzymes, catalytically inactive Cas13d (known as dCas13d) likely will retain its programmable RNA binding activity, though it will no longer be able to cleave target or collateral RNA.

In addition to direct uses of dCas13d such as in RNA immunoprecipitation, transcript labeling (when dCas13d effector is fused with fluorescent protein), and translation modification through site-specific targeted disruption of native translational machinery, other domains can be appended onto the dCas13d protein to provide further functionality. Activities of these domains include, but are not limited to, RNA base modification (ADAR1, ADAR2, APOBEC), RNA methylation ($m^6A$ methyltransferases and demethylases), splicing modifiers (hnRNPA1), localization factors (KDEL retention sequence, mitochondrial targeting signal, peroxisomal targeting signal), translation modification factors (EIF4G translation initiation factor, GLD2 poly (A) polymerase, transcriptional repressors). Additionally, domains can be appended to provide additional control, such as light-gated control (cryptochromes) and chemically inducible components (FKBP-FRB chemically inducible dimerization).

Optimizing the activity of such fusion proteins requires a systematic way of comparing linkers that connect the dCas13d with the appended domain. These linkers may include, but are not limited to, flexible glycine-serine (GS) linkers in various combinations and lengths, rigid linkers such as the alpha-helix forming EAAAK (SEQ ID NO: 124) sequence, XTEN linker (Schellenberger V, et al. *Nat. Biotechnol.* 2009; 27:1186-1190), as well as different combinations thereof (see TABLE 10). The various designs are then assayed in parallel over the same crRNA target complex and functional readout to determine which one yields the desired properties.

For adapting Cas13d for use in targeted RNA base modification (see, e.g., Cox D B T et al., *Science* 2017 10.1126/science.aaq0180), we begin with the Cas13d ortholog and NES combination that yielded the highest endogenous mammalian RNA knockdown activity and mutate the conserved residues of the two HEPN domains to create a catalytically inactive enzyme. Next, a linker is used to create the fusion protein between Cas13d-NES and the base editing domain. Initially, this domain will consist of the $ADAR2_{DD}$(E488Q/T375G) mutant engineered previously for hyperactivity and greater specificity when used with Cas13b in REPAIRv2, but alternate deaminases such as ADAR1 and APOBEC1, among others, can be engineered and assayed in parallel (TABLE 10). Given the likely structural differences between the smaller Cas13d versus the previously characterized Cas13 effectors, alternate linker designs and lengths may yield the optimal design of the base editing fusion protein.

To evaluate the activity of the dCas13d-derived base editors, the HEK 293T cells are transiently transfected with the dCas13d-ADAR construct, a plasmid expressing the crRNA, and optionally, a reporter plasmid if targeting the reporter and not an endogenous locus. The cells are harvested 48 hours after transient transfection, the RNA is extracted and reverse-transcribed to yield a cDNA library that is prepared for next generation sequencing. Analysis of the base composition of loci of samples containing the targeting vs. negative control non-targeting crRNAs provide information about the editing efficiency, and analysis of broader changes to the transcriptome will yield information about the off-target activity.

One particular advantage of developing an RNA base editing system using Cas13d is that the small size, on average 20% smaller than the existing Cas13 effectors, enables more ready packaging in AAV of dCas13d-ADAR along with its crRNA and control elements without the need for protein truncations. This all-in-one AAV vector enables greater efficacy of in vivo base editing in tissues, which is particularly relevant as a path towards therapeutic applications of Cas13d. In base editing and other applications, the small size, the lack of a biochemical PFS, and robust activity of Cas13d effectors make it a valuable addition to the toolbox of programmable RNA modifying enzymes.

Multiplexing of Cas13d with multiple crRNAs targeting different sequences enables the manipulation of multiple RNA species for therapeutic applications requiring manipulation of multiple transcripts simultaneously.

TABLE 10

Amino Acid Sequences of Motifs and Functional Domainsin Engineered Variants of Type VI-DCRISPR-Cas Effector Proteins

```
>LINKER_1
GS

>LINKER_2
GSGGGGS (SEQ ID NO: 125)

>LINKER_3
GGGGSGGGGSGGGGS (SEQ ID NO: 126)

>LINKER_4
GGSGGSGGSGGSGGSGGS (SEQ ID NO: 127)

[ADAR1, ADAR2: C-term fusion (or optionally N-term)]
>ADAR1DD-WT
SLGTGNRCVKGDSLSLKGETVNDCHAEIISRRGFIRFLYSELMKYNSQTAKDSIFEPAKGGEKLQIKKTVSFHLYISTAPCGDG
ALFDKSCSDRAMESTESRHYPVFENPKQGKLRTKVENGEGTIPVESSDIVPTWDGIRLGERLRTMSCSDKILRWNVLGLQGALL
THFLQPIYLKSVTLGYLFSQGHLTRAICCRVTRDGSAFEDGLRHPFIVNHPKVGRVSIYDSKRQSGKTKETSVNWCLADGYDLE
ILDGTRGTVDGPRNELSRVSKKNIFLLFKKLCSFRYRRDLLRLSYGEAKKAARDYETAKNYFKKGLKDMGYGNWISKPQEEKNF
(SEQ ID NO: 128)

>ADAR1DD-E1008Q (Cox et al., 2017)
SLGTGNRCVKGDSLSLKGETVNDCHAEIISRRGFIRFLYSELMKYNSQTAKDSIFEPAKGGEKLQIKKTVSFHLYISTAPCGDG
ALFDKSCSDRAMESTESRHYPVFENPKQGKLRTKVENGEGTIPVESSDIVPTWDGIRLGERLRTMSCSDKILRWNVLGLQGALL
THFLQPIYLKSVTLGYLFSQGHLTRAICCRVTRDGSAFEDGLRHPFIVNHPKVGRVSIYDSKRQSGKTKETSVNWCLADGYDLE
ILDGTRGTVDGPRNELSRVSKKNIFLLFKKLCSFRYRRDLLRLSYGEAKKAARDYETAKNYFKKGLKDMGYGNWISKPQEEKNF
(SEQ ID NO: 129)

>ADAR2DD-WT
QLHLPQVLADAVSRLVLGKFGDLTDNFSSPHARRKVLAGVVMTTGTDVKDAKVISVSTGTKCINGEYMSDRGLALNDCHAEIIS
RRSLLRFLYTQLELYLNNKDDQKRSIFQKSERGGFRLKENVQFHLYISTSPCGDARIFSPHEPILEEPADRHPNRKARGQLRTK
IESGEGTIPVRSNASIQTWDGVLQGERLLTMSCSDKIARWNVVGIQGSLLSIFVEPIYFSSIILGSLYHGDHLSRAMYQRISNI
EDLPPLYTLNKPLLSGISNAEARQPGKAPNFSVNWTVGDSAIEVINATTGKDELGRASRLCKHALYCRWMRVHGKVPSHLLRSK
ITKPNVYHESKLAAKEYQAAKARLFTAFIKAGLGAWVEKPTEQDQFSLT (SEQ ID NO: 130)

>ADAR2DD-E488Q (Cox et al., 2017)
QLHLPQVLADAVSRLVLGKFGDLTDNFSSPHARRKVLAGVVMTTGTDVKDAKVISVSTGTKCINGEYMSDRGLALNDCHAEIIS
RRSLLRFLYTQLELYLNNKDDQKRSIFQKSERGGFRLKENVQFHLYISTSPCGDARIFSPHEPILEEPADRHPNRKARGQLRTK
IESGQGTIPVRSNASIQTWDGVLQGERLLTMSCSDKIARWNVVGIQGSLLSIFVEPIYFSSIILGSLYHGDHLSRAMYQRISNI
EDLPPLYTLNKPLLSGISNAEARQPGKAPNFSVNWTVGDSAIEVINATTGKDELGRASRLCKHALYCRWMRVHGKVPSHLLRSK
ITKPNVYHESKLAAKEYQAAKARLFTAFIKAGLGAWVEKPTEQDQFSLT (SEQ ID NO: 131)

[Cytidine deaminase, AID, APOBEC1: N-term fusion (or optionally C-term)]
>AID-APOBEC1 (Dickerson et al., 2003, Komor et al., 2017)
MDSLLMNRRKFLYQFKNVRWAKGRRETYLCYVVKRRDSATSFSLDFGYLRNKNGCHVELLFLRYISDWDLDPGRCYRVTWFTSW
SPCYDCARHVADFLRGNPNLSLRIFTARLYFCEDRKAEPEGLRRLHRAGVQIAIMTFKDYFYCWNTFVENHERTFKAWEGLHEN
SVRLSRQLRRILLPLYEVDDLRDAFRTLGL (SEQ ID NO: 132)

>Lamprey_AID-APOBEC1 (Rogozin et al., 2007, Komor et al., 2017)
MTDAEYVRIHEKLDIYTFKKQFFNNKKSVSHRCYVLFELKRRGERRACFWGYAVNKPQSGTERGIHAEIFSIRKVEEYLRDNPG
QFTINWYSSWSPCADCAEKILEWYNQELRGNGHTLKIWACKLYYEKNARNQIGLWNLRDNGVGLNVMVSEHYQCCRKIFIQSSH
NQLNENRWLEKTLKRAEKRRSELSIMIQVKILHTTKSPAV (SEQ ID NO: 133)

>APOBEC1_BE1 (Komor et al., 2016)
MSSETGPVAVDPTLRRRIEPHEFEVFFDPRELRKETCLLYEINWGGRHSIWRHTSQNTNKHVEVNFIEKFTTERYFCPNTRCSI
TWFLSWSPCGECSRAITEFLSRYPHVTLFIYIARLYHHADPRNRQGLRDLISSGVTIQIMTEQESGYCWRNFVNYSPSNEAHWP
RYPHLWVRLYVLELYCIILGLPPCLNILRRKQPQLTFFTIALQSCHYQRLPPHILWATGLK (SEQ ID NO: 134)
```

REFERENCES

Abudayyeh, O. O., Gootenberg, J. S., Essletzbichler, P., Han, S., Joung, J., Belanto, J. J., Verdine, V., Cox, D. B. T., Kellner, M. J., Regev, A., et al. (2017). RNA targeting with CRISPR-Cas13. Nature 550, 280-284.

Cox, D. B. T., Gootenberg, J. S., Abudayyeh, O. O., Franklin, B., Kellner, M. J., Joung, J., and Zhang, F. (2017). RNA editing with CRISPR-Cas13. Science 358, 1019-1027.

Schellenberger V., Wang C. W., Geething N. C., Spink, B. J., Campbell, A., To, W., Scholle, M. D., Yin, Y., Yao, Y., Bogin, O., et al. (2009). A recombinant polypeptide extends the in vivo half-life of peptides and proteins in a tunable manner. Nat Biotechnol 2009; 27: 1186-1190.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An engineered, non-naturally occurring Clustered Regularly Interspaced Short Palindromic Repeat (CRISPR) associated (Cas) system comprising:
   (a) an RNA guide or a nucleic acid encoding the RNA guide, wherein the RNA guide comprises a direct repeat sequence and a spacer sequence; and
   (b) a CRISPR-Cas effector protein or a nucleic acid encoding the CRISPR-Cas effector protein, wherein the CRISPR-Cas effector protein comprises the amino acid sequence set forth in SEQ ID NO: 2,
   wherein the CRISPR-Cas effector protein binds to the RNA guide, and wherein the spacer sequence binds to a target nucleic acid.

2. The system of claim 1, wherein the direct repeat sequence comprises a nucleotide sequence with at least 95% sequence identity to SEQ ID NO: 72 or SEQ ID NO: 153.

3. The system of claim 2, wherein the direct repeat sequence comprises the nucleotide sequence set forth in SEQ ID NO: 72 or SEQ ID NO: 153.

4. The system of claim 1, wherein the spacer sequence comprises between 15 and 42 nucleotides in length.

5. The system of claim 1, wherein the target nucleic acid is an RNA molecule.

6. The system of claim 1, wherein the target nucleic acid comprises a sequence complementary to a nucleotide sequence in the spacer sequence.

7. The system of claim 1, wherein the CRISPR-Cas effector protein cleaves the target nucleic acid.

8. The system of claim 1, wherein the system further comprises an accessory protein.

9. The system of claim 8, wherein the accessory protein comprises at least one WYL domain.

10. The system of claim 8, wherein the accessory protein comprises at least one DNA binding domain.

11. The system of claim 8, wherein the accessory protein comprises an amino acid sequence with at least 95% identity to SEQ ID NO: 81.

12. The system of claim 11, wherein the accessory protein comprises the amino acid sequence set forth in SEQ ID NO: 81.

13. The system of claim 1, wherein the CRISPR-Cas effector protein further comprises at least one nuclear localization signal (NLS), at least one nuclear export signal (NES), or at least one NLS and at least one NES.

14. The system of claim 1, wherein the CRISPR-Cas effector protein further comprises a peptide tag, a fluorescent protein, a base-editing domain, an RNA methyltransferase, an RNA demethylase, a splicing modifier, a localization factor, or a translation modification factor.

15. The system of claim 1, wherein the nucleic acid encoding the CRISPR-Cas effector protein is codon-optimized for expression in a cell.

16. The system of claim 1, wherein the nucleic acid encoding the CRISPR-Cas effector protein is operably linked to a promoter.

17. The system of claim 1, wherein the nucleic acid encoding the CRISPR-Cas effector protein is in a vector.

18. The system of claim 17, wherein the vector comprises a retroviral vector, a lentiviral vector, a phage vector, an adenoviral vector, an adeno-associated vector, or a herpes simplex vector.

19. The system of claim 1, wherein the system is present in a delivery system comprising a nanoparticle, a liposome, an exosome, a microvesicle, or a gene-gun.

20. A cell comprising the system of claim 1.

21. A method of binding the system of claim 1 to the target nucleic acid in a cell comprising:
   (a) providing the system; and
   (b) delivering the system to the cell,
   wherein the cell comprises the target nucleic acid, wherein the CRISPR-Cas effector protein binds to the RNA guide, and wherein the spacer sequence binds to the target nucleic acid.

* * * * *